US008168651B2

(12) United States Patent
Chua et al.

(10) Patent No.: US 8,168,651 B2
(45) Date of Patent: *May 1, 2012

(54) PROTEIN KINASE MODULATORS

(75) Inventors: Peter C. Chua, Maple Ridge (CA); Mustapha Haddach, San Diego, CA (US); Johnny Y. Nagasawa, San Diego, CA (US); Fabrice Pierre, La Jolla, CA (US); Jeffrey P. Whitten, Santee, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 12/396,084

(22) Filed: Mar. 2, 2009

(65) Prior Publication Data

US 2009/0239859 A1 Sep. 24, 2009

Related U.S. Application Data

(60) Provisional application No. 61/067,845, filed on Feb. 29, 2008, provisional application No. 61/103,908, filed on Oct. 8, 2008.

(51) Int. Cl.
*A61K 31/44* (2006.01)
*C07D 471/02* (2006.01)

(52) U.S. Cl. ........................................ 514/300; 546/122

(58) Field of Classification Search .................. 546/122; 514/300

See application file for complete search history.

(56) References Cited

U.S. PATENT DOCUMENTS

| | | | | |
|---|---|---|---|---|
| 3,991,064 | A | 11/1976 | Brown et al. | |
| 5,624,677 | A | 4/1997 | El-Rashidy et al. | |
| 2006/0155128 | A1 | 7/2006 | Jones et al. | |
| 2009/0105233 | A1 * | 4/2009 | Chua et al. | 514/228.5 |

FOREIGN PATENT DOCUMENTS

| | | |
|---|---|---|
| WO | WO-2005/105814 | 11/2005 |
| WO | WO-2007/007152 | 1/2007 |
| WO | WO-2007/022268 | 2/2007 |
| WO | WO-2007/070319 | 6/2007 |
| WO | WO-2008/042282 | 4/2008 |

OTHER PUBLICATIONS

Aho et al., FEBS Letters (2004) 571:43-49.
Alessi et al., J. Org. Chem. (2007) 72:1588-1594.
Bachmann and Moroy, Int. J. Biochem. Cell Biol. (2005) 37:726-730.
Bachmann et al., JBC (2004) 279:48319-48348.
Edwan et al., J. Immunology (2004) 5016-23.
Fedorov et al., PNAS USA (2007) 104(51):20523-20528.
Gaidano and Dalla-Favera, Current Opinion Oncology (1993) 5(5):776-784.
Gourley et al., "A potent small molecule PIM kinase inhibitor with activity in cell lines from the hematological and solid malignancies" 2008 AACR Annual Meeting (Abstract No. 4974).
Hirano et al., Oncogene (2000) 19:2548-2556.
Li et al., Cancer Res. (2006) 66(13):6741-6747.
Li et al., Pain (2005) 115(1-2):182-90.
Losman et al., JBC (2003) 278:4800-4805.
Parhar et al., Int. J. Colorectal Dis. (2006) 22(6):601-609.
Ruzzene et al., Biochem. J. (2002) 364(Pt. 1):41-47.
Smith et al., Blood (2004) 103(10):3669-76.
Wang et al., Biochim. Biophys. Act. (2002) 1593:45-55.
International Search Report and Written Opinion for PCT/US09/35609, mailed Jun. 18, 2009, 8 pages.

* cited by examiner

*Primary Examiner* — Rebecca Anderson
(74) *Attorney, Agent, or Firm* — Cooley LLP

(57) ABSTRACT

The invention relates in part to molecules having certain biological activities that include, but are not limited to, inhibiting cell proliferation, modulating protein kinase activity and modulating polymerase activity. Molecules of the invention can modulate Pim kinase activity and/or FMS-like tyrosine kinase (Flt) activity. The invention also relates in part to methods for using such molecules.

11 Claims, 9 Drawing Sheets

PROTEIN KINASE MODULATORS

RELATED APPLICATIONS

This application claims benefit of priority to U.S. Provisional Application Ser. No. 61/067,845, filed 29 Feb. 2008, and U.S. Provisional Application Ser. No. 61/103,908, filed 8 Oct. 2008, the contents of each of which are incorporated herein by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 532232004400Seqlist.txt | May 19, 2009 | 10,002 bytes |

FIELD OF THE INVENTION

The invention relates in part to molecules having certain biological activities that include, but are not limited to, inhibiting cell proliferation, modulating serine-threonine protein kinase activity and modulating tyrosine kinase activity. Molecules of the invention can modulate casein kinase (CK) activity (e.g., CK2 activity), Pim kinase activity (e.g., PIM-1, PIM-2 and/or PIM-3 activity) and/or Fms-like tyrosine kinase (Flt) activity (e.g., Flt-3 activity). The invention also relates in part to methods for using such molecules.

BACKGROUND ART

The PIM protein kinases which include the closely related PIM-1, -2, and -3, have been implicated in diverse biological processes such as cell survival, proliferation, and differentiation. PIM-1 is involved in a number of signaling pathways that are highly relevant to tumorigenesis [reviewed in Bachmann & Moroy, *Internat. J. Biochem. Cell Biol.,* 37, 726-730 (2005)]. Many of these are involved in cell cycle progression and apoptosis. It has been shown that PIM-1 acts as an anti-apoptotic factor via inactivation of the pro-apoptotic factor BAD (Bc12 associated death promoter, an apoptosis initiator). This finding suggested a direct role of PIM-1 in preventing cell death, since the inactivation of BAD can enhance Bcl-2 activity and can thereby promote cell survival [Aho et al., *FEBS Letters,* 571, 43-49 (2004)]. PIM-1 has also been recognized as a positive regulator of cell cycle progression. PIM-1 binds and phosphorylates Cdc25A, which leads to an increase in its phosphatase activity and promotion of G1/S transition [reviewed in Losman et al., *JBC,* 278, 4800-4805 (1999)]. In addition, the cyclin kinase inhibitor $p21^{Waf}$ which inhibits G1/S progression, was found to be inactivated by PIM-1 [Wang et al., *Biochim. Biophys. Act.* 1593, 45-55 (2002)]. Furthermore, by means of phosphorylation, PIM-1 inactivates C-TAK1 and activates Cdc25C which results in acceleration of G2/M transition [Bachman et al., *JBC,* 279, 48319-48 (2004)].

PIM-1 appears to be an essential player in hematopoietic proliferation. Kinase active PIM-1 is required for the gp130-mediated STAT3 proliferation signal [Hirano et al., *Oncogene* 19, 2548-2556, (2000)]. PIM-1 is overexpressed or even mutated in a number of tumors and different types of tumor cell lines and leads to genomic instability. Fedorov, et al., concluded that a Phase III compound in development for treating leukemia, LY333'531, is a selective PIM-1 inhibitor. O. Fedorov, et al., *PNAS* 104(51), 20523-28 (December 2007). Evidence has been published to show that PIM-1 is involved in human tumors including prostate cancer, oral cancer, and Burkitt lymphoma (Gaidano & Dalla Faver, 1993). All these findings point to an important role of PIM-1 in the initiation and progression of human cancers, including various tumors and hematopoietic cancers, thus small molecule inhibitors of PIM-1 activity are a promising therapeutic strategy.

Additionally, PIM-2 and PIM-3 have overlapping functions with PIM-1 and inhibition of more than one isoform may provide additional therapeutic benefits. However, it is sometimes preferable for inhibitors of PIM to have little or no in vivo impact through their inhibition of various other kinases, since such effects are likely to cause side effects or unpredictable results. See, e.g., O. Fedorov, et al., *PNAS* 104(51), 20523-28 (December 2007), discussing the effects that non-specific kinase inhibitors can produce. Accordingly, in some embodiments, the invention provides compounds that are selective inhibitors of at least one of PIM-1, PIM-2, and PIM-3, or some combination of these, while having substantially less activity on certain other human kinases, as described further herein.

The implication of a role for PIM-3 in cancer was first suggested by transcriptional profiling experiments showing that PIM3 gene transcription was upregulated in EWS/ETS-induced malignant transformation of NIH 3T3 cells. These results were extended to show that PIM-3 is selectively expressed in human and mouse hepatocellular and pancreatic carcinomas but not in normal liver or pancreatic tissues. In addition, PIM-3 mRNA and protein are constitutively expressed in multiple human pancreatic and hepatocellular cancer cell lines.

The link between PIM-3 overexpression and a functional role in promoting tumorigenesis came from RNAi studies in human pancreatic and hepatocellular cancer cell lines overexpressing PIM-3. In these studies the ablation of endogenous PIM-3 protein promoted apoptosis of these cells. The molecular mechanism by which PIM-3 suppresses apoptosis is in part carried out through the modulation of phosphorylation of the pro-apoptotic protein BAD. Similar to both PIM-1 & 2 which phosphorylate BAD protein, the knockdown of PIM-3 protein by siRNA results in a decrease in BAD phosphorylation at Ser112. Thus, similar to PIM-1 and 2, PIM-3 acts a suppressor of apoptosis in cancers of endodermal origin, e.g., pancreatic and liver cancers. Moreover, as conventional therapies in pancreatic cancer have a poor clinical outcome, PIM-3 could represent a new important molecular target towards successful control of this incurable disease.

At the 2008 AACR Annual Meeting, SuperGen announced that it has identified a lead PIM kinase inhibitor, SGI-1776, that causes tumor regression in acute myelogenous leukemia (AML) xenograft models (Abstract No. 4974). In an oral presentation entitled, "A potent small molecule PIM kinase inhibitor with activity in cell lines from hematological and solid malignancies," Dr. Steven Warner detailed how scientists used SuperGen's CLIMB™ technology to build a model that allowed for the creation of small molecule PIM kinase inhibitors. SGI-1776 was identified as a potent and selective inhibitor of the PIM kinases, inducing apoptosis and cell cycle arrest, thereby causing a reduction in phospho-BAD levels and enhancement of mTOR inhibition in vitro. Most notably, SGI-1776 induced significant tumor regression in MV-4-11 (AML) and MOLM-13 (AML) xenograft models. This demonstrates that inhibitors of PIM kinases can be used to treat leukemias.

Fedorov, et al., in *PNAS* vol. 104(51), 20523-28, showed that a selective inhibitor of PIM-1 kinase (Ly5333'531) suppressed cell growth and induced cell death in leukemic cells from AML patients. PIM-3 has been shown to be expressed in pancreatic cancer cells, while it is not expressed in normal pancreas cells, demonstrating that it should be a good target for pancreatic cancer. Li, et al., *Cancer Res.* 66(13), 6741-47 (2006).

Another kinase shown to be a useful target for certain cancers, including leukemia, is Flt3 kinase (FMS-like tyrosine kinase 3). Flt3 is prevalent in refractory AML patients, so inhibitors of Flt3 are useful to treat such patients. Smith, et al., reported an alkaloid called CEP-701 that is a potent inhibitor of Flt3 and provided clinical responses in tested subjects with minimal dose-related toxicity. *Blood*, vol. 103(10), 3669-76 (2004). Dual inhibitors that are active against both PIM and Flt3 may be advantageous over inhibitors of either target alone. In particular, excessive Flt3 activity is associated with refractory AML, so dual inhibitors of PIM and Flt3 such as compounds disclosed herein are useful to treat refractory AML.

In addition, Flt3 inhibitors are useful to treat inflammation. Inhibitors of Flt3 have been shown to be effective to treat airway inflammation in mice, using a murine asthma model. Edwan, et al., *J. Immunologoy,* 5016-23 (2004). Accordingly, the compounds of the invention, are useful to treat conditions associated with excessive activity of Flt3, including inflammation such as airway inflammation and asthma.

Collectively, these results demonstrate that inhibitors of PIM kinases and Flt3 kinase are useful for treating certain types of cancers. Accordingly, the identification of compounds that specifically inhibit, regulate and/or modulate the signal transduction of PIM-1, PIM-2, PIM-3, and/or Flt3 is desirable as a means to treat or prevent disease states associated with abnormal cell proliferation, such as cancer. The invention provides compounds, compositions and methods that address this need and are useful for treating cancers, inflammation and pain.

DISCLOSURE OF THE INVENTION

The present invention in part provides chemical compounds having certain biological activities that include, but are not limited to, inhibiting cell proliferation, inhibiting angiogenesis, and modulating protein kinase activity. These molecules can modulate casein kinase 2 (CK2) activity, Pim kinase activity, and/or Fms-like tyrosine kinase 3 (Flt) activity and thus affect biological functions that include but are not limited to, inhibiting gamma phosphate transfer from ATP to a protein or peptide substrate, inhibiting angiogenesis, inhibiting cell proliferation and inducing cell apoptosis, for example. The present invention also in part provides methods for preparing novel chemical compounds, and analogs thereof, and methods of using the foregoing. Also provided are compositions comprising the above-described molecules in combination with other agents, and methods for using such molecules in combination with other agents.

The compounds of the invention have the general formula (A):

(A)

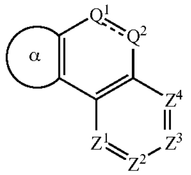

wherein the group labeled α represents a 5-6 membered aromatic or heteroaromatic ring fused onto the ring containing $Q^1$, wherein α is a 6-membered aryl ring optionally containing one or more nitrogen atoms as ring members, or a five membered aryl ring selected from thiophene and thiazole;

$Q^1$ is C═X, $Q^2$ is $NR^5$, and the bond between $Q^1$ and $Q^2$ is a single bond; or $Q^1$ is C—X—$R^5$, $Q^2$ is N, and the bond between $Q^1$ and $Q^2$ is a double bond; and wherein X represents O, S or $NR^4$, and $Z^1$-$Z^8$ and $R^4$ and $R^5$ are as defined below;

provided that when $Q^1$ in Formula (A) is C—NHΦ, where Φ is optionally substituted phenyl:

if the ring labeled α is a six-membered ring containing at least one N as a ring member, at least one $R^3$ present must be a polar substituent, or if each $R^3$ is H, then Φ must be substituted; and if the ring labeled α is phenyl, and three of $Z^1$-$Z^4$ represent CH, then $Z^2$ cannot be C—OR", and $Z^3$ cannot be $NH_2$, $NO_2$, NHC(═O)R" or NHC(═O)—OR", where R" is C1-C4 alkyl.

The invention also includes the pharmaceutically acceptable salts of compounds of formula (A). Thus in each compound of the invention, Formula (A) represents a fused tricyclic ring system which is linked through either Q1 or Q2 to a group R5, which is further described below.

Thus, provided herein are compounds of Formulae I, II, III and IV:

Formula I

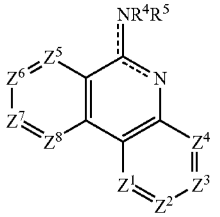

Formula II

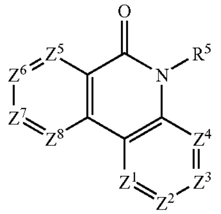

Formula III

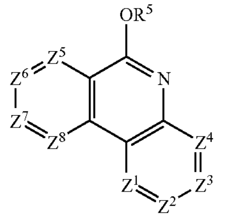

-continued

Formula IV

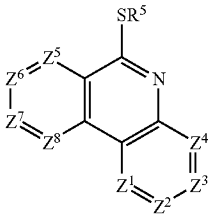

and pharmaceutically acceptable salts, esters, prodrugs and tautomers thereof; wherein:

each $Z^1$, $Z^2$, $Z^3$, and $Z^4$ is N or $CR^3$;

each of $Z^5$, $Z^6$, $Z^7$ and $Z^8$ is $CR^6$ or N;

each $R^3$ and each $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ and each $R^6$ can be halo, OR, $NR_2$, NROR, $NRNR_2$, SR, SOR, $SO_2R$, $SO_2NR_2$, $NRSO_2R$, $NRCONR_2$, $NRCSNR_2$, NRC(=NR)$NR_2$, NRCOOR, NRCOR, CN, COOR, $CONR_2$, OOCR, COR, polar substituent, carboxy bioisostere, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR, =NR', OR', $NR'_2$, SR', $SO_2R'$, $SO_2NR'_2$, $NR'SO_2R'$, $NR'CONR'_2$, $NR'CSNR'_2$, NR'C(=NR') $NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, $R^4$ is H or optionally substituted member selected from the group consisting of $C_1$-$C_6$ alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member;

provided that when —$NR^4R^5$ in Formula (I) is —NHΦ, where Φ is optionally substituted phenyl:

if at least one of $Z^5$-$Z^8$ is N, at least one $R^3$ present must be a polar substituent, or if each $R^3$ is H, then Φ must be substituted; and if each of $Z^5$-$Z^8$ is $CR^6$, and three of $Z^1$-$Z^4$ represent CH, then $Z^2$ cannot be C—OR, and $Z^3$ cannot be $NH_2$, $NO_2$, NHC(=O)R" or NHC(=O)—OR", where R" is C1-C4 alkyl.

In certain embodiments, provided are compounds having the structure of Formulae I, II, III, and IV, and pharmaceutically acceptable salts, esters and tautomers thereof; wherein:

each $Z^1$, $Z^2$, $Z^3$, and $Z^4$ is N or $CR^3$;

each of $Z^5$, $Z^6$, $Z^7$ and $Z^8$ is N or $CR^6$;

none, one or two of $Z^1$-$Z^4$ are N and none, one or two of $Z^5$-$Z^8$ are N;

each $R^3$ and each $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ and each $R^6$ is independently halo, OR, $NR_2$, NROR, $NRNR_2$, SR, SOR, $SO_2R$, $SO_2NR_2$, $NRSO_2R$, $NRCONR_2$, $NRCSNR_2$, NRC(=NR)$NR_2$, NRCOOR, NRCOR, CN, COOR, $CONR_2$, OOCR, COR, polar substituent, carboxy bioisostere, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR, =NR', OR, $NR'_2$, SR', $SO_2R'$, $SO_2NR'_2$, $NR'SO_2R'$, $NR'CONR'_2$, $NR'CSNR'_2$, NR'C(=NR') $NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

$R^4$ is H or an optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member;

provided that when $-NR^4R^5$ in Formula (I) is $-NH\Phi$, where $\Phi$ is optionally substituted phenyl:

if all of $Z^5$-$Z^8$ are CH or one of $Z^5$-$Z^8$ is N, at least one of $Z^1$-$Z^4$ is $CR^3$ and at least one $R^3$ must be a non-hydrogen substituent; or if each $R^3$ is H, then $\Phi$ must be substituted; or if all of $Z^5$-$Z^8$ are CH or one of $Z^5$-$Z^8$ is N, then $Z^2$ is not C—OR, and $Z^3$ is not $NH_2$, $NO_2$, NHC(═O)R" or NHC(═O)—OR", where R" is C1-C4 alkyl.

In certain embodiments of Formulae I, II, III, and IV, one, two, three or four of $Z^5$, $Z^6$, $Z^7$ and $Z^8$ are N. For embodiments in which two of $Z^5$, $Z^6$, $Z^7$ and $Z^8$ are N, the ring nitrogen atoms may be adjacent (e.g., nitrogen atoms at $Z^5$ and $Z^6$, $Z^6$ and $Z^7$, or $Z^7$ and $Z^8$) or may be separated by one or two ring positions (e.g., nitrogen atoms at $Z^5$ and $Z^7$, $Z^6$ and $Z^8$ or $Z^5$ and $Z^8$). In frequent embodiments, at least one $R^3$ substituent is a polar substituent, such as a carboxylic acid or a salt, an ester or a bioisostere thereof. In some embodiments, at least one $R^3$ is a carboxylic acid-containing substituent or a carboxylate bioisostere, or a salt or ester thereof, for example. In some embodiments, at least one $R^3$ is a carboxylic acid-containing substituent or a salt thereof. In certain embodiments, at least one $R^3$ is a carboxamide. In other embodiments, at least one $R^3$ is a $C_{1-3}$ alkyl substituted with $SO_2NR_2$, $NRSO_2R$, $NRCONR_2$, $NRCSNR_2$, NRC(═NR)$NR_2$, NRCOOR, NRCOR, or $CONR_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl.

The term "polar substituent" as used herein refers to any substituent having an electric dipole, and optionally a dipole moment (e.g., an asymmetrical polar substituent has a dipole moment and a symmetrical polar substituent does not have a dipole moment). Polar substituents include substituents that accept or donate a hydrogen bond, and groups that would carry at least a partial positive or negative charge in aqueous solution at physiological pH levels. In certain embodiments, a polar substituent is one that can accept or donate electrons in a non-covalent hydrogen bond with another chemical moiety. In certain embodiments, a polar substituent is selected from a carboxy, a carboxy bioisostere or other acid-derived moiety that exists predominately as an anion at a pH of about 7 to 8. Other polar substituents include, but are not limited to, groups containing an OH or NH, an ether oxygen, an amine nitrogen, an oxidized sulfur or nitrogen, a carbonyl, a nitrile, and a nitrogen-containing or oxygen-containing heterocyclic ring whether aromatic or non-aromatic. In some embodiments, the polar substituent represented by $R^3$ is a carboxylate or a carboxylate bioisostere.

"Carboxylate bioisostere" or "carboxy bioisostere" as used herein refers to a moiety that is expected to be negatively charged to a substantial degree at physiological pH. In certain embodiments, the carboxylate bioisostere is a moiety selected from the group consisting of:

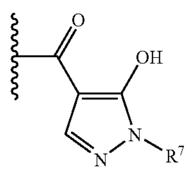
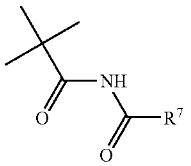

-continued

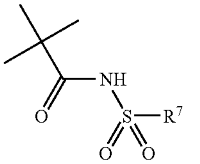
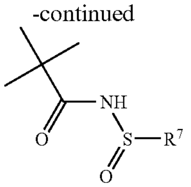
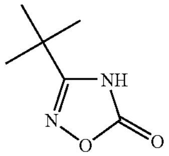
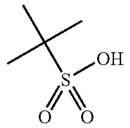
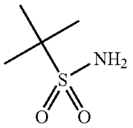
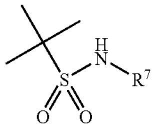
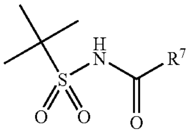
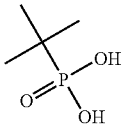
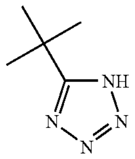
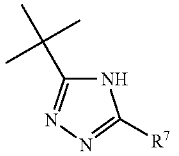
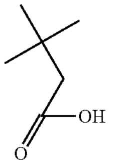
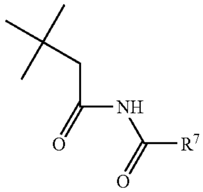
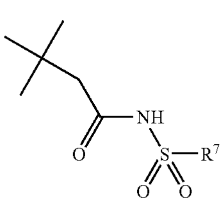
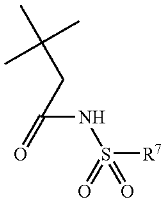
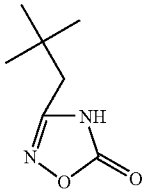
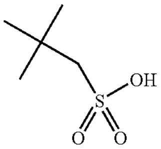
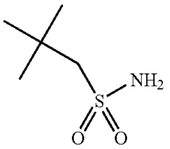
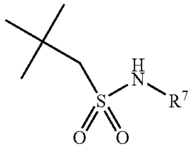
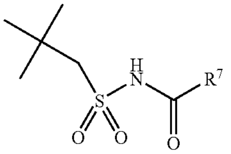
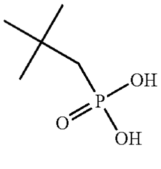
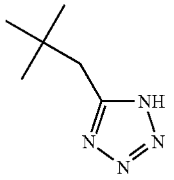
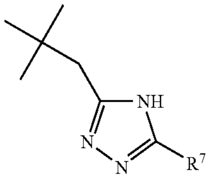

and salts and prodrugs of the foregoing, wherein each $R^7$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic ring; or $R^7$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring. In certain embodiments, the polar substituent (e.g., $R^{3P}$) is selected from the group consisting of carboxylic acid, carboxylic ester, carboxamide, tetrazole, triazole, imidazole, carboxymethanesulfonamide, oxadiazole, oxothiadiazole, thiazole, aminothiazole and hydroxythiazole. In some embodiments, at least one $R^3$ present is a carboxylic acid or a salt, or ester or a bioisostere thereof. In certain embodiments, at least one $R^3$ present is a carboxylic acid-containing substituent or a salt, ester or bioisostere thereof. In the latter embodiments, the $R^3$ substituent may be a C1-C10 alkyl or C1-C10 alkenyl linked to a carboxylic acid (or salt, ester or bioisostere thereof), for example, and in some embodiments, the $R^3$ substituent is not —$NHCOOCH_2CH_3$.

In some preferred embodiments of the present invention, $R^{3P}$ is a triazole or imidazole ring, which can be substituted or unsubstituted, and is preferably bonded through a carbon atom of the triazole or imidazole ring to the fused tricyclic moiety. $R^{3P}$ is frequently a 2-imidazolyl ring or a 3-triazolyl ring, each of which can be unsubstituted or substituted. If these rings are substituted on N, they are typically substituted with C1-C6 alkyl or C1-C6 acyl, or, if substituted on a carbon atom of the ring, with halo. Unsubstituted 3-triazole is a preferred group for $R^{3P}$.

In certain embodiments, at least one of $Z^1$-$Z^4$ and $Z^5$-$Z^8$ is a nitrogen atom, and one or more ring nitrogen atoms can be positioned in the ring containing $Z^1$-$Z^4$ or in the ring containing $Z^5$-$Z^8$ such that each ring is independently an optionally substituted pyridine, pyrimidine, pyridazine or pyrazine ring. For example, one or more ring nitrogen atoms within the ring containing $Z^5$-$Z^8$ may be arranged as follows:

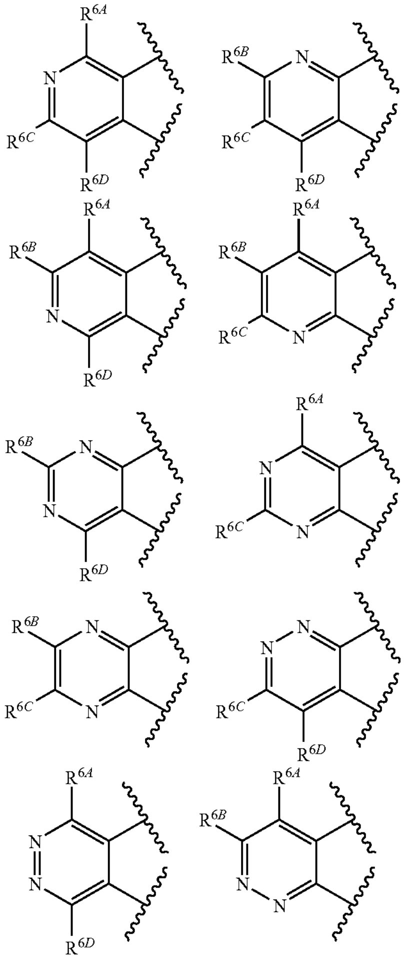

where each $R^{6A}$, $R^{6B}$, $R^{6C}$ and $R^{6D}$ independently is selected from $R^6$ substituents defined above with respect to compounds of Formula I, II, III or IV.

In certain embodiments, no two adjacent $Z^1$-$Z^4$ or $Z^5$-$Z^8$ both are N.

A polar substituent may be at any position on the ring containing $Z^1$-$Z^4$ in Formula I, II, III or IV, and the ring may include one, two, three or four polar substituents. In certain embodiments, each of $Z^1$-$Z^4$ may be $CR^3$ and one of the $R^3$ substituents may be a polar substituent (e.g., a carboxylate or carboxylic acid ester, carboxamide or a tetrazole) arranged at any one of the positions in the ring containing $Z^1$-$Z^4$:

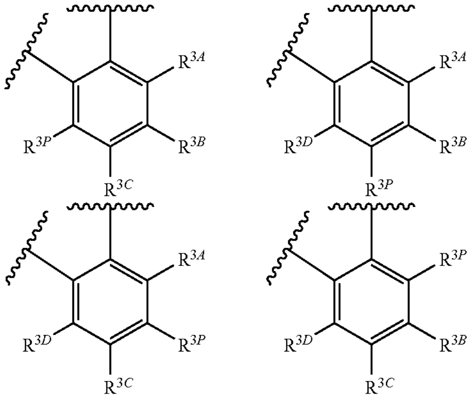

where $R^{3P}$ is a polar substituent and each $R^{3A}$, $R^{3B}$, $R^{3C}$ and $R^{3D}$ independently is selected from $R^3$ substituents, as defined above with respect to compounds of Formula I, II, III or IV.

In certain embodiments of the compounds in the foregoing Formulae, $R^4$ is H. In some embodiments, $R^4$ is H or $CH_3$ and $R^5$ is an optionally substituted 3-8 membered ring, which can be aromatic, nonaromatic, and carbocyclic or heterocyclic, or $R^5$ is a $C_{1-10}$ alkyl group substituted with such an optionally substituted 3-8 membered ring. In specific embodiments, $R^5$ is an optionally substituted five-, six-, or seven-membered carbocyclic or heterocyclic ring, and sometimes is an optionally substituted phenyl ring.

In some embodiments pertaining to compounds of Formula I, $R^4$ is H or $CH_3$ and $R^5$ is a phenyl substituted with one or more halogen (e.g., F, Cl), fluoroalkyl (e.g., $CF_3$) or acetylene substituents, which substituents sometimes are on the phenyl ring at the 3-position, 4-position or 5-position, or combinations thereof (e.g., the 3- and 5-positions).

$R^5$ in certain embodiments is a $C_{1-3}$ alkyl substituted with an optionally substituted phenyl, pyridyl, morpholino, piperidinyl or pyrrolidinyl ring substituent, or is substituted with hydroxyl or —$NR^4R^4$ where $R^4$ is as defined above (e.g., $R^5$ may be $C_{1-3}$ alkyl substituted with —$N(CH_3)_2$). In other embodiments, $R^5$ is a $C_{1-3}$ alkyl substituted with $SO_2NR_2$, $NRSO_2R$, $NRCONR_2$, NRCOOR, NRCOR, or $CONR_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl. The polar group represented by $R^3$ in some embodiments is a carboxy, carboxyalkyl (e.g., carboxymethyl), tetrazole or carboxamide (e.g., —$CONH_2$) substituent. In other embodiments, $R^3$ represents a carboxylate bioisostere.

An $R^6$ substituent in certain embodiments, such as $R^{6B}$, sometimes is a —$NR^4R^5$ substituent, such as a —NH—(C1-C6 alkyl) moiety (e.g., —NH—$CH_3$), for example. In some embodiments, the compound has the structure of Formula I;

$R^4$ is H or $CH_3$; $R^5$ is an optionally substituted five-, six-, or seven-membered carbocyclic or heterocyclic ring, and sometimes is an optionally substituted phenyl ring; and one $R^3$ is a carboxylic acid or a salt, an ester, carboxamide or a carboxylate bioisostere. In some embodiments, the compound has the structure of Formula I; $R^4$ is H or $CH_3$; $R^5$ is an optionally substituted five-, six-, or seven-membered carbocyclic or heterocyclic ring, and sometimes is an optionally substituted phenyl ring; and one or two of $Z^5$, $Z^6$, $Z^7$ and $Z^8$ are N.

In some embodiments of compounds of Formulae I, II, III or IV, each of $Z^1$, $Z^2$, $Z^3$, and $Z^4$ is $CR^3$, and at least one $R^3$ is H, or at least two $R^3$ are H. Often, at least one $R^6$ is H, or at least two $R^6$ are H. In some embodiments, (i) each $Z^1$, $Z^2$, $Z^3$, $Z^4$, $Z^5$, $Z^6$ and $Z^8$ is $CR^3$ and $Z^7$ is nitrogen; or (ii) each $Z^1$, $Z^2$, $Z^3$, $Z^4$, $Z^6$, $Z^7$ and $Z^8$ is $CR^3$ and $Z^5$ is nitrogen; or (iii) each $Z^1$, $Z^2$, $Z^3$, $Z^4$, $Z^6$, and $Z^8$ is $CR^3$ and each of $Z^5$ and $Z^7$ is nitrogen. Each $R^3$ and/or each $R^6$ present in certain embodiments is hydrogen, except that at least one $R^3$ present is a polar substituent. In some embodiments, each $R^{3A}$, $R^{3C}$, $R^{3D}$, $R^{6A}$, $R^{6B}$, $R^{6C}$ and $R^{6D}$ is H and $R^{3B}$ is a polar substituent (e.g., carboxylate, carboxylic acid, tetrazole).

Also provided herein are compounds of Formulae V, VI, VII or VIII:

Formula V

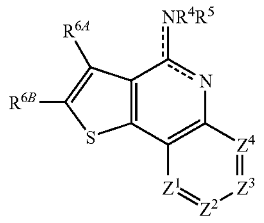

Formula VI

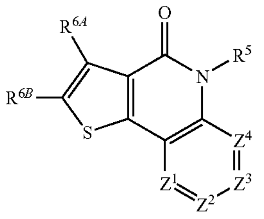

Formula VII

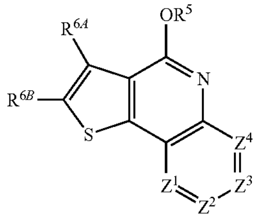

Formula VIII

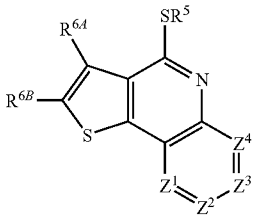

and pharmaceutically acceptable salts, esters, prodrugs and tautomers thereof; where $Z^1$, $Z^2$, $Z^3$, $Z^4$, $R^4$ and $R^5$ are defined above with respect to compounds of Formulae I, II, III and IV, and each $R^{6A}$ and $R^{6B}$ is independently selected from an $R^6$ substituent defined above with respect to compounds of Formulae I, II, III and IV.

As with compounds of Formulae I, II, III and IV, in preferred embodiments at least one $R^3$ present is a polar substituent, such as a polar substituent described above. In frequent embodiments, at least one $R^3$ substituent is a polar substituent, such as a carboxylic acid or a salt, an ester or a bioisostere thereof. In some embodiments, at least one $R^3$ is a carboxylic acid-containing substituent or a carboxylate bioisostere, or a salt or ester thereof, for example. In some embodiments, at least one $R^3$ is a carboxylic acid-containing substituent or a salt thereof. In other embodiments, at least one $R^3$ is a carboxamide. Embodiments described with respect to compounds of Formulae I, II, III and IV also may be applied to compounds of Formulae V, VI, VII and VIII.

In certain embodiments, provided are compounds having a structure of Formulae V, VI, VII and VIII, and pharmaceutically acceptable salts, esters and tautomers thereof; wherein:

each $Z^1$, $Z^2$, $Z^3$, and $Z^4$ independently is N or $CR^3$ and none, one or two of $Z^1$, $Z^2$, $Z^3$, and $Z^4$ is N;

each $R^3$, $R^{6A}$ and $R^{6B}$ independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$, $R^{6A}$ and $R^{6B}$ independently is halo, OR, $NR_2$, NROR, $NRNR_2$, SR, SOR, $SO_2R$, $SO_2NR_2$, $NRSO_2R$, $NRCONR_2$, $NRCSNR_2$, $NRC({=}NR)NR_2$, NRCOOR, NRCOR, CN, COOR, polar substituent, carboxy bioisostere, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, $NR'C({=}NR')NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, $R^4$ is H or optionally substituted member selected from the group consisting of $C_1$-$C_6$ alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member.

In some embodiments pertaining to compounds of Formulae V, VI, VII and VIII, each of $Z^1$, $Z^2$, $Z^3$, and $Z^4$ is $CR^3$, and at least one $R^3$ is H, or at least two $R^3$ are H. Often, at least one of $R^{6A}$ and $R^{6B}$ is H, and sometimes each of $R^{6A}$ and $R^{6B}$ is H. In certain embodiments, each $R^3$ and/or each of $R^{6A}$ and $R^{6B}$ present is H, except that at least one $R^3$ present is a polar substituent. In some embodiments, each $R^{3A}$, $R^{3C}$, $R^{3D}$, $R^{6A}$ and $R^{6B}$ is H and $R^{3B}$ is a polar substituent (e.g., carboxylate bioisostere, carboxylic acid, carboxamide or tetrazole).

In certain embodiments pertaining to compounds of Formula V, $R^4$ is H or $CH_3$ and $R^5$ is an optionally substituted five-, six- or seven-membered carbocyclic or heterocyclic ring (e.g., optionally substituted phenyl ring). In some embodiments pertaining to compounds of Formula V, $R^4$ is H or $CH_3$ and $R^5$ is a phenyl ring substituted with one or more halogen (e.g., F, Cl), trifluoroalkyl (e.g., $CF_3$), or acetylene substituents, which substituents sometimes are at the 3-position, 4-position or 5-position, or a combination thereof (e.g., the 3- and 5-positions). $R^5$ in certain embodiments is a $C_{1-3}$ alkyl substituted with an optionally substituted phenyl, pyridyl, morpholino, pyrrolyl, piperidinyl or pyrrolidinyl substituent, or a $C_{1-3}$ alkyl substituted with a hydroxyl or with a substituent —$NR^4R^4$, where $R^4$ is as defined above (e.g., $R^5$ can be $C_{1-3}$ alkyl substituted with —$N(CH_3)_2$). In other embodiments, $R^5$ is a $C_{1-3}$ alkyl substituted with $SO_2NR_2$, $NRSO_2R$, $NRCONR_2$, $NRCSNR_2$, $NRC(=NR)NR_2$, NRCOOR, NRCOR, or $CONR_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl. An $R^6$ substituent in certain embodiments, such as $R^{6A}$ or $R^{6B}$, sometimes is a —$NR^4R^5$ substituent, such as a —NH—(C1-C6 alkyl) moiety (e.g., —NH—$CH_3$), for example. In other embodiments, each of $R^{6A}$ and $R^{6B}$ is H.

Provided also are compounds of Formulae IX, X, XI and XII:

Formula IX

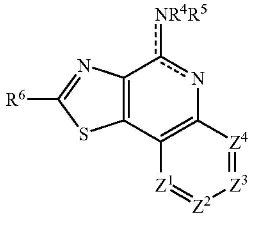

Formula X

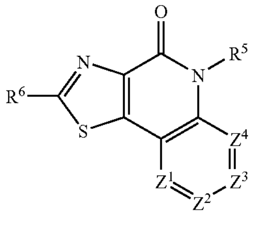

-continued

Formula XI

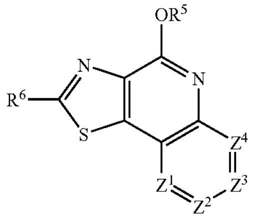

Formula XII

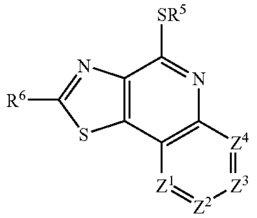

and pharmaceutically acceptable salts, esters, prodrugs and tautomers thereof; where $Z^1$, $Z^2$, $Z^3$, $Z^4$, $R^4$, $R^5$ and $R^6$ are defined above with respect to compounds of Formulae I, II, III and IV.

As with compounds of Formulae I, II, III and IV, in frequent embodiments, at least one $R^3$ present is a polar substituent, such as a polar substituent described above (e.g., carboxylic acid, carboxylate, carboxamide tetrazole). For compounds of Formula IX, $R^4$ and $R^5$ are not both hydrogen, and independently are H, —$Y^0$ or -$LY^1$, where $Y^0$ is an optionally substituted 5-membered ring or optionally substituted 6-membered ring (e.g., heterocyclic ring or carbocyclic ring each being aryl or non-aryl), $Y^1$ is an optionally substituted 5-membered aryl ring or optionally substituted 6-membered aryl ring, and L is a C1-C20 alkyl linker or C1-C20 alkylene linker.

In some embodiments, provided are compounds having a structure of Formulae IX, X, XI and XII, and pharmaceutically acceptable salts, esters and tautomers thereof; wherein:

each $Z^1$, $Z^2$, $Z^3$, and $Z^4$ is N or $CR^3$ and none, one or two of $Z^1$, $Z^2$, $Z^3$, and $Z^4$ is N;

each $R^3$ and $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ and $R^6$ can be halo, OR, $NR_2$, NROR, $NRNR_2$, SR, SOR, $SO_2R$, $SO_2NR_2$, $NRSO_2R$, $NRCONR_2$, $NRCSNR_2$, $NRC(=NR)NR_2$, NRCOOR, NRCOR, CN, COOR, polar substituent, carboxy bioisostere, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, $NR'C(=NR')NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

$R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member.

Embodiments described with respect to compounds of Formulae I, II, III, IV, V, VI, VII and VIII also may be applied to compounds of Formulae IX, X, XI and XII. In some embodiments pertaining to compounds of Formulae IX, X, XI and XII, each of $Z^1$, $Z^2$, $Z^3$, and $Z^4$ is $CR^3$, and at least one $R^3$ is H, or at least two $R^3$ are H. $R^6$ often is H, and in certain embodiments, each $R^6$ and $R^3$ present is H, except that at least one $R^3$ present is a polar substituent. In some embodiments, each $R^{3A}$, $R^{3C}$, $R^{3D}$ and $R^6$ is H and $R^{3B}$ is a polar substituent (e.g., carboxylate, carboxylic acid, carboxamide, or tetrazole).

In certain embodiments pertaining to compounds of Formula IX, $R^4$ is H or $CH_3$ and $R^5$ is an optionally substituted five-, six- or seven-membered carbocyclic or heterocyclic ring (e.g., optionally substituted phenyl ring). In some embodiments pertaining to compounds of Formula IX, $R^4$ is H or $CH_3$ and $R^5$ is a phenyl ring substituted with one or more halogen (e.g., F, Cl) or acetylene substituents, which substituents sometimes are at the 3-position, 4-position or 5-position, or a combination thereof (e.g., the 3- and 5-positions). $R^5$ in certain embodiments is a $C_{1-3}$ alkyl substituted with an optionally substituted phenyl, pyridyl, morpholino, pyrrolyl, piperidinyl or pyrrolidinyl substituent, or a $C_{1-3}$ alkyl substituted with a hydroxyl substituent or substituted with a —$NR^4R^4$ (e.g., —$N(CH_3)_2$) substituent. In other embodiments, $R^5$ is a $C_{1-3}$ alkyl substituted with $SO_2NR_2$, $NRSO_2R$, $NRCONR_2$, $NRCSNR_2$, $NRC(=NR)NR_2$, NRCOOR, NRCOR, or $CONR_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl. $R^6$ in certain embodiments sometimes is a —$NR^4R^5$ substituent, such as a —NH—(C1-C6 alkyl) moiety (e.g., —NH—$CH_3$), for example.

Also provided herein are compounds of Formulae XIII, XIV, XV and XVI:

Formula XIII

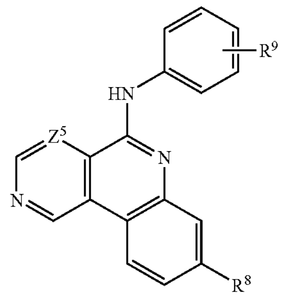

Formula XIV

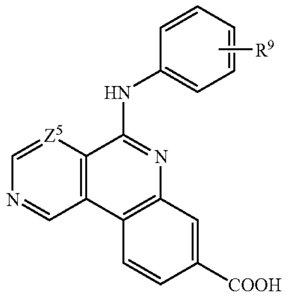

Formula XV

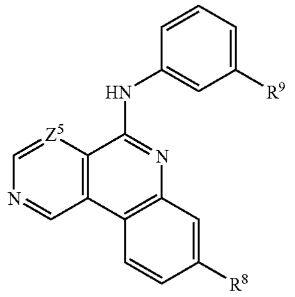

Formula XVI

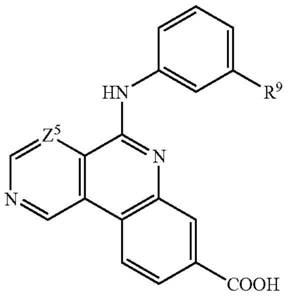

and pharmaceutically acceptable salts, esters, prodrugs and tautomers thereof; wherein:

Z5 is N or CR6A;

each R6A, R6B, R6C and R8 independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each R6A, R6B, R6C and R8 independently is halo, CF3, CFN, OR, NR2, NROR, NRNR2, SR, SOR, SO2R, SO2NR2, NRSO2R, NRCONR2, NRCSNR2, NRC(=NR)NR2, NRCOOR, NRCOR, CN, COOR, carboxy bioisostere, CONR2, OOCR, COR, or NO2, R9 is independently an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or R9 is independently halo, OR, NR2, NROR, NRNR2, SR, SOR, SO2R, SO2NR2, NRSO2R, NRCONR2, NRCOOR, NRCOR, CN, COOR, CONR2, OOCR, COR, or NO2, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', NR'2, SR', SO2R', SO2NR'2, NR'SO2R', NR'CONR'2, NR'CSNR'2, NR'C(=NR')NR'2, NR'COOR', NR'COR', CN, COOR', CONR'2, OOCR', COR', and NO2, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

n is 0 to 4; and p is 0 to 4.

In certain embodiments for compounds of Formulae XIII, XIV, XV and XVI, $Z^5$ is N. In some embodiments, $R^8$ is a carboxy moiety, such as a carboxylate or carboxylic acid. In certain embodiments, $R^9$ is selected from —C≡CR, —C≡CH, $—CH_3$, $—CH_2CH_3$, $—CF_3$, —CFN, —C≡N, —OR or halogen. In some embodiments $R^9$ is selected from halogen, —C≡CR or —C≡CH. In certain embodiments $R^9$ is selected from halogen or —C≡CH, and in some embodiments $R^9$ is halogen, is chloro, is bromo or is —C≡CH Also provided herein are compounds of Formulae XVII, XVIII, XIX or XX:

Formula XVII

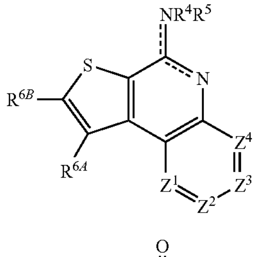

Formula XVIII

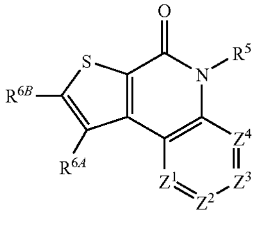

-continued

Formula XIX

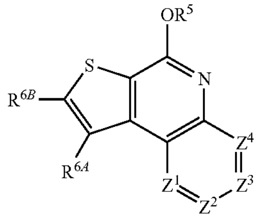

Formula XX

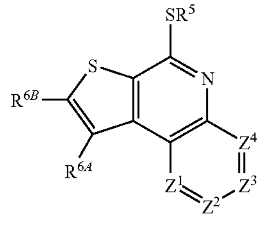

and pharmaceutically acceptable salts, esters, prodrugs and tautomers thereof; where $Z^1$, $Z^2$, $Z^3$, $Z^4$, $R^4$ and $R^5$ are defined above with respect to compounds of Formulae I, II, III and IV, and each $R^{6A}$ and $R^{6B}$ is independently selected from an $R^6$ substituent defined above with respect to compounds of Formulae I, II, III and IV.

As with compounds of Formulae I, II, III and IV, in frequent embodiments at least one $R^3$ present is a polar substituent, such as a polar substituent described above. Embodiments described with respect to compounds of Formulae I, II, III and IV also may be applied to compounds of Formulae XVII, XVIII, XIX or XX.

In certain embodiments, provided are compounds having a structure of Formulae XVII, XVIII, XIX or XX, and pharmaceutically acceptable salts, esters and tautomers thereof; wherein:

each $Z^1$, $Z^2$, $Z^3$, and $Z^4$ independently is N or $CR^3$ and none, one or two of $Z^1$, $Z^2$, $Z^3$, and $Z^4$ is N;

each $R^3$, $R^{6A}$ and $R^{6B}$ independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$, $R^{6A}$ and $R^{6B}$ independently is halo, OR, $NR_2$, NROR, $NRNR_2$, SR, SOR, $SO_2R$, $SO_2NR_2$, $NRSO_2R$, $NRCONR_2$, $NRCSNR_2$, $NRC(=NR)NR_2$, NRCOOR, NRCOR, CN, COOR, polar substituent, carboxy bioisostere, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 LLalkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, $NR'C(=NR')NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

$R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each —$NR^4R^5$, $R^4$ and $R^5$ together with N may form an optionally substituted 3-8 membered ring, which may optionally contain an additional heteroatom selected from N, O and S as a ring member.

In some embodiments pertaining to compounds of Formulae XVII, XVIII, XIX or XX, each of $Z^1$, $Z^2$, $Z^3$, and $Z^4$ is $CR^3$, and at least one $R^3$ is H, or at least two $R^3$ are H. Often, at least one of $R^{6A}$ and $R^{6B}$ is H, and sometimes each of $R^{6A}$ and $R^{6B}$ is H. In certain embodiments, each $R^3$ and/or each of $R^{6A}$ and $R^{6B}$ present is H, except that at least one $R^3$ present is a polar substituent. In some embodiments, each $R^{3A}$, $R^{3C}$, $R^{3D}$, $R^{6A}$ and $R^{6B}$ is H and $R^{3B}$ is a polar substituent (e.g., carboxylate bioisostere, carboxylic acid, carboxamide, or tetrazole).

In certain embodiments pertaining to compounds of Formula XVII, $R^4$ is H or $CH_3$ and $R^5$ is an optionally substituted five-, six- or seven-membered carbocyclic or heterocyclic ring (e.g., optionally substituted phenyl ring). In some embodiments pertaining to compounds of Formula XVII, $R^4$ is H or $CH_3$ and $R^5$ is a phenyl ring substituted with one or more halogen (e.g., F, Cl), fluoroalkyl (e.g., $CF_3$) or acetylene substituents, which substituents sometimes are at the 3-position, 4-position or 5-position, or a combination thereof (e.g., the 3- and 5-positions). $R^5$ in certain embodiments is a $C_{1-3}$ alkyl substituted with an optionally substituted phenyl, pyridyl, morpholino, pyrrolyl, piperidinyl or pyrrolidinyl substituent, or a $C_{1-3}$ alkyl substituted with a hydroxyl substituent or substituted with a substituent —$NR^4R^4$, where $R^4$ is as defined above (e.g., —$N(CH_3)_2$). In other embodiments, $R^5$ is a $C_{1-3}$ alkyl substituted with $SO_2NR_2$, $NRSO_2R$, $NRCONR_2$, $NRCSNR_2$, NRC(=NR)$NR_2$, NRCOOR, NRCOR, or $CONR_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl. An $R^6$ substituent in certain embodiments, such as $R^{6A}$ or $R^{6B}$, sometimes is a halo, or —$NR^4R^5$ substituent, such as a —NH—(C1-C6 alkyl) moiety (e.g., —NH—$CH_3$), for example.

Also provided herein are compounds of Formulae XXI, XXII, XXIII or XXIV:

Formula XXI

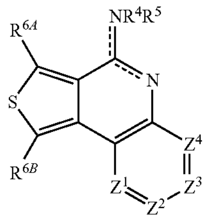

Formula XXII

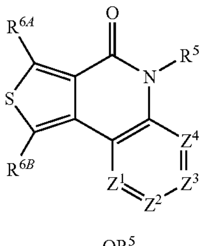

Formula XXIII

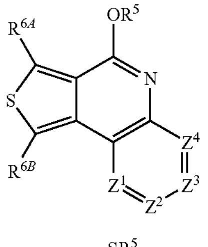

Formula XXIV

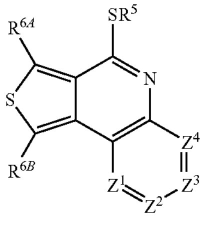

and pharmaceutically acceptable salts, esters, prodrugs and tautomers thereof; where $Z^1$, $Z^2$, $Z^3$, $Z^4$, $R^4$ and $R^5$ are defined above with respect to compounds of Formulae I, II, III and IV, and each $R^{6A}$ and $R^{6B}$ is independently selected from an $R^6$ substituent defined above with respect to compounds of Formulae I, II, III and IV. As with compounds of Formulae I, II, III and IV, in frequent embodiments at least one $R^3$ present is a polar substituent, such as a polar substituent described above. Embodiments described with respect to compounds of Formulae I, II, III and IV also may be applied to compounds of Formulae XXI, XXII, XXIII or XXIV.

In certain embodiments, provided are compounds having a structure of Formulae XXI, XXII, XXIII or XXIV, and pharmaceutically acceptable salts, esters and tautomers thereof; wherein:

each $Z^1$, $Z^2$, $Z^3$, and $Z^4$ independently is N or $CR^3$ and none, one or two of $Z^1$, $Z^2$, $Z^3$, and $Z^4$ is N;

each $R^3$, $R^{6A}$ and $R^{6B}$ independently is H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$, $R^{6A}$ and $R^{6B}$ independently is halo, OR, $NR_2$, NROR, $NRNR_2$, SR, SOR, $SO_2R$, $SO_2NR_2$, $NRSO_2R$, $NRCONR_2$, $NRCSNR_2$, NRC(=NR)$NR_2$, NRCOOR, NRCOR, CN, COOR, polar substituent, carboxy bioisostere, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, NR'COOR', $NR'CSNR'_2$, $NR'C(=NR')NR'_2$, NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S;

$R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each $—NR^4R^5$, $R^4$ and $R^5$ together with N may form an optionally substituted 3-8 membered ring, which may optionally contain an additional heteroatom selected from N, O and S as a ring member.

In some embodiments pertaining to compounds of Formulae XXI, XXII, XXIII or XXIV, each of $Z^1$, $Z^2$, $Z^3$, and $Z^4$ is $CR^3$, and at least one $R^3$ is H, or at least two $R^3$ are H. Often, at least one of $R^{6A}$ and $R^{6B}$ is H, and sometimes each of $R^{6A}$ and $R^{6B}$ is H. In certain embodiments, each $R^3$ and/or each of $R^{6A}$ and $R^{6B}$ present is H, except that at least one $R^3$ present is a polar substituent. In some embodiments, each $R^{3A}$, $R^{3C}$, $R^{3D}$, $R^{6A}$ and $R^{6B}$ is H and $R^{3B}$ is a polar substituent (e.g., carboxylate bioisostere, carboxylic acid, carboxamide, or tetrazole).

In certain embodiments pertaining to compounds of Formula XXI, $R^4$ is H or $CH_3$ and $R^5$ is an optionally substituted five-, six- or seven-membered carbocyclic or heterocyclic ring (e.g., optionally substituted phenyl ring). In some embodiments pertaining to compounds of Formula $XX^1$, $R^4$ is H or $CH_3$ and $R^5$ is a phenyl ring substituted with one or more halogen (e.g., F, Cl), fluoroalkyl (e.g., $CF_3$), or acetylene substituents, which substituents sometimes are at the 3-position, 4-position or 5-position, or a combination thereof (e.g., the 3- and 5-positions). $R^5$ in certain embodiments is a $C_{1-3}$ alkyl substituted with an optionally substituted phenyl, pyridyl, morpholino, pyrrolyl, piperidinyl or pyrrolidinyl substituent, or a $C_{1-3}$ alkyl substituted with a hydroxyl substituent or substituted with a substituent $—NR^4R^4$, where $R^4$ is as defined above (e.g., $—N(CH_3)_2$). In other embodiments, $R^5$ is a $C_{1-3}$ alkyl substituted with $SO_2NR_2$, $NRSO_2R$, $NRCONR_2$, $NRCSNR_2$, $NRC(=NR)NR_2$, NRCOOR, NRCOR, or $CONR_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl. An $R^6$ substituent in certain embodiments, such as $R^{6A}$ or $R^{6B}$, sometimes is a halo, or a $—NR^4R^5$ substituent, such as a —NH—(C1-C6 alkyl) moiety (e.g., $—NH—CH_3$), for example.

Also provided herein are compounds of Formulae XXV, XXVI and XXVII:

Formula XXV

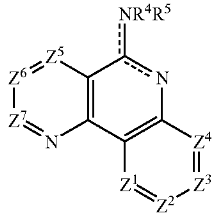

Formula XXVI

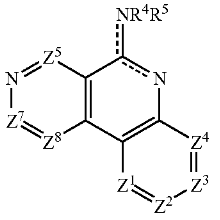

Formula XXVI

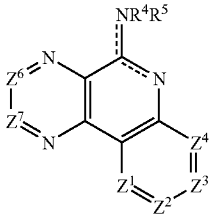

and pharmaceutically acceptable salts, esters, prodrugs and tautomers thereof; wherein:

each $Z^1$, $Z^2$, $Z^3$, and $Z^4$ is N or $CR^3$;

each of $Z^5$, $Z^6$, $Z^7$ and $Z^8$ is $CR^6$;

each $R^3$ and each $R^6$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^3$ and each $R^6$ can be halo, OR, $NR_2$, NROR, $NRNR_2$, SR, SOR, $SO_2R$, $SO_2NR_2$, $NRSO_2R$, $NRCONR_2$, $NRCSNR_2$, $NRC(=NR)NR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, $NR'C(=NR')NR'_2$, $NR'COOR'$, $NR'COR'$, CN, $COOR'$, $CONR'_2$, $OOCR'$, $COR'$, and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, $R^4$ is H or optionally substituted member selected from the group consisting of C1-C6 alkyl, C2-C6 heteroalkyl, and C1-C6 acyl;

each $R^5$ is independently H or an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic; or $R^5$ is a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring; and in each $—NR^4R^5$, $R^4$ and $R^5$ together with N may form an optionally substituted 3-8 membered ring, which may optionally contain an additional heteroatom selected from N, O and S as a ring member;

provided that when $—NR^4R^5$ is —NHΦ, where Φ is optionally substituted phenyl:

at least one $R^3$ present must be a polar substituent, or if each $R^3$ is H, then Φ must be substituted.

In some embodiments pertaining to compounds of Formulae XXV, XXVI, or XXVII, each of $Z^1$, $Z^2$, $Z^3$, and $Z^4$ is $CR^3$, and at least one $R^3$ is H, or at least two $R^3$ are H. Often, at least one of $R^6$ is H, and sometimes each of $R^6$ is H. In certain embodiments, each $R^3$ and/or each of $R^6$ present is H, except that at least one $R^3$ present is a polar substituent. In some embodiments, each $R^{3A}$, $R^{3C}$, $R^{3D}$, and $R^6$ is H and $R^{3B}$ is a polar substituent (e.g., carboxylate bioisostere, carboxylic acid, carboxamide, or tetrazole). Embodiments described with respect to compounds of Formulae I, II, III and IV also may be applied to compounds of Formulae XXV, XXVI, or XXVII.

In certain embodiments pertaining to compounds of Formulae XXV, XXVI, or XXVII, $R^4$ is H or $CH_3$ and $R^5$ is an optionally substituted five-, six- or seven-membered carbocyclic or heterocyclic ring (e.g., optionally substituted phenyl ring). In some embodiments, $R^4$ is H or $CH_3$ and $R^5$ is a phenyl ring substituted with one or more halogen (e.g., F, Cl), fluoroalkyl (e.g., $CF_3$), or acetylene substituents, which substituents sometimes are at the 3-position, 4-position or 5-position, or a combination thereof (e.g., the 3- and 5-positions). $R^5$ in certain embodiments is a $C_{1-3}$ alkyl substituted with an optionally substituted phenyl, pyridyl, morpholino, pyrrolyl, piperidinyl or pyrrolidinyl substituent, or a $C_{1-3}$ alkyl substituted with a hydroxyl substituent or substituted with a substituent $—NR^4R^4$, where $R^4$ is as defined above (e.g., $—N(CH_3)_2$). In other embodiments, $R^5$ is a $C_{1-3}$ alkyl substituted with $SO_2NR_2$, $NRSO_2R$, $NRCONR_2$, $NRCSNR_2$, $NRC(=NR)NR_2$, NRCOOR, NRCOR, or $CONR_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl. An $R^6$ substituent in certain embodiments sometimes is a halo, or a $—NR^4R^5$ substituent, such as a —NH—(C1-C6 alkyl) moiety (e.g., $—NH—CH_3$), for example.

In some embodiments of compounds of Formula I, the invention provides compounds having activity on Pim kinases, particularly Pim1 and/or Pim2 kinase. Compounds of Formula IA (and IB and IC) are inhibitors of at least one of these Pim kinases, and are accordingly useful to treat conditions characterized by or associated with excessive Pim activity. This aspect of the invention provides compounds having the Formula IA, IB and IC, pharmaceutical compositions comprising at least one such compound admixed with one or more pharmaceutically acceptable excipients and/or carriers, and methods of using these compounds to treat conditions such as the cancers described herein, as well as pain and inflammation. The compounds have this formula:

(IA)

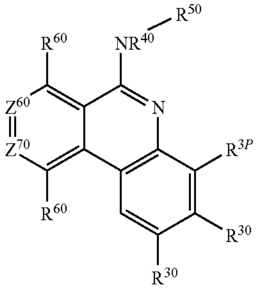

or a pharmaceutically acceptable salt thereof.

In certain preferred embodiments, the compounds of Formula IA include compounds of Formula IB or IC:

IB

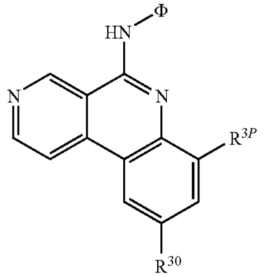

IC

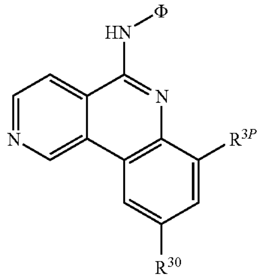

or a pharmaceutically acceptable salt thereof.

In compounds of Formula IA, IB, and IC:

$Z^{60}$ and $Z^{70}$ are independently N or $CR^{60}$, provided at least one of them is N;

each $R^{30}$ and each $R^{60}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^{30}$ and each $R^{60}$ can be halo, OR, $NR_2$, NROR, $NRNR_2$, SR, SOR, $SO_2R$, $SO_2NR_2$, $NRSO_2R$, $NRCONR_2$, $NRCSNR_2$, NRC(=NR)$NR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, NR'C(=NR')$NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, each $R^{40}$ is H or optionally substituted member selected from the group consisting of C1-C6 alkyl, C2-C6 heteroalkyl, and C1-C6 acyl;

each $R^{50}$ is independently an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic;

or $R^{50}$ can be a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring;

in each —$NR^{40}R^{50}$, $R^{40}$ and $R^{50}$ together with N may form an optionally substituted 3-8 membered ring, which may optionally contain an additional heteroatom selected from N, O and S as a ring member;

each $R^{3P}$ represents a polar substituent;

and each Φ independently represents an optionally substituted phenyl.

Pharmaceutically acceptable salts and tautomers of the compounds of Formulae IA, IB and IC are also included within the scope of the invention.

In some compounds of Formula IA, $Z^{60}$ can be N while $Z^{70}$ is CH, or $Z^{70}$ can be N while $Z^{60}$ is CH. In some of these compounds, $R^{40}$ is H or a C1-C6 acyl group, or a C1-C6 alkyl group. In some of these compounds, $R^{50}$ is an optionally substituted phenyl group, or $R^{50}$ can be —$(CH_2)_q$—RG, where q is an integer from 0-2 and RG represents an optionally substituted ring selected from phenyl, 2-pyridyl, 3-pyridyl, 4-pyridyl, morpholine, piperizine, piperidine, pyrrolidine, and cyclopropane. A preferred embodiment of Formula IA includes compounds wherein $R^{50}$ is optionally substituted phenyl (i.e., Φ).

In some compounds of Formula IA, each $R^{30}$ is independently H or halo or C1-C6 alkyl. Preferably at least one $R^{30}$ is H in these compounds.

$R^{3P}$ is a polar substituent, and can be any of the polar substituents described above for compounds of Formula I. In some embodiments of the compounds of Formula IA, $R^{3P}$ is a triazole or imidazole ring, which can be substituted or unsubstituted, and is preferably bonded through a carbon atom of the triazole or imidazole ring to the fused tricyclic moiety in Formula IA. In other embodiments, $R^{3P}$ is a carboxylic acid or a salt, an ester or a bioisostere thereof. In some embodiments, at least one $R^3$ is a carboxylic acid-containing substituent or a carboxylate bioisostere, or a salt or ester thereof, for example. In some embodiments, at least one $R^3$ is a carboxylic acid-containing substituent or a salt thereof. In other embodiments, $R^{3P}$ represents an amide group of the formula —C(O)$NR^{40}R^{50}$, where $NR^{40}R^{50}$ is as defined above. In other embodiments, $R^{3P}$ represents an ester group —$COOR^{80}$, wherein $R^{80}$ is H or an optionally substituted C1-C6 alkyl. Embodiments of $R^{3P}$ described with respect to compounds of Formula I are also useful herein for compounds of formula IA, IB, and IC. Embodiments of $R^{3P}$ described with respect to compounds of Formula I, IA, IB, and IC are also useful for compounds of Formula L, L-A and L-B.

In compounds of formula IB or IC, $R^{30}$ is typically H or halo. $R^{3P}$ is frequently a 2-imidazolyl ring or a 3-triazolyl ring, each of which can be unsubstituted or substituted. If these rings are substituted on N, they are typically substituted with C1-C6 alkyl or C1-C6 acyl, or, if substituted on a carbon atom of the ring, with halo. Unsubstituted 3-triazole is a preferred group for $R^{3P}$.

In the compounds of Formula IB or IC, Φ is an optionally substituted phenyl, which can be unsubstituted phenyl or a phenyl substituted with 1-3 substituents. In some embodiments, the substituents on the phenyl ring are selected from halo, cyano, $CF_3$, —$OCF_3$, $COOR^{40}$, and $SO_2NR^{40}R^{50}$, and one or more of these substituents can be an optionally substituted group selected from C1-C6 alkyl, C1-C6 alkoxy, C2-C6 alkenyl, and C2-C6 alkynyl.

In some embodiments of the invention, the compound has the structure of Formula L, L-A and L-B. This aspect of the invention provides compounds having the Formula L, pharmaceutical compositions comprising at least one such compound admixed with one or more pharmaceutically acceptable excipients and/or carriers, and methods of using these compounds to treat conditions such as cancers, inflammation or pain, as described herein. The compounds have this formula:

(L)

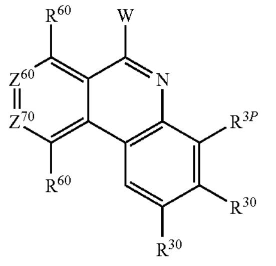

or a pharmaceutically acceptable salt thereof.

In certain preferred embodiments, the compounds of Formula L include compounds of Formula L-A or L-B:

(L-A)

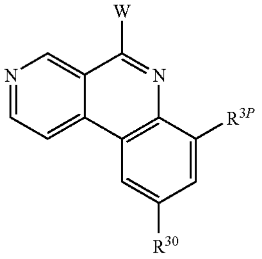

(L-B)

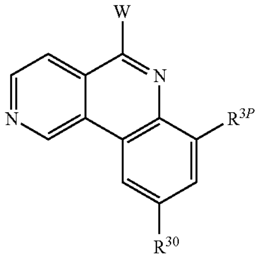

or a pharmaceutically acceptable salt thereof.

In compounds of Formula L, L-A and L-B:

$Z^{60}$ and $Z^{70}$ are independently N or $CR^{60}$, provided at least one of them is N;

each $R^{30}$ and each $R^{60}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^{30}$ and each $R^{60}$ can be halo, OR, $NR_2$, NROR, $NRNR_2$, SR, SOR, $SO_2R$, $SO_2NR_2$, $NRSO_2R$, $NRCONR_2$, $NRCSNR_2$, NRC(=NR)$NR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, NR'C(=NR')$NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, each $R^{3P}$ represents a polar substituent;

and each W represents an optionally substituted aryl, heteroaryl, or $C_{3-8}$ cycloalkyl ring.

Pharmaceutically acceptable salts and tautomers of the compounds of Formulae L, L-A and L-B are also included within the scope of the invention.

In some embodiments of formula L, L-A and L-B, each R3P represents an optionally substituted imidazole or triazole ring.

In some compounds of Formula L, Z60 can be N while Z70 is CH, or Z70 can be N while Z60 is CH.

In some embodiments of formula L, L-A and L-B, W represents a monocyclic 6-membered aromatic or 5-6 membered heteroaromatic ring, or a fused bicyclic 8-10 membered aromatic or heteroaromatic ring, each of which may be optionally substituted. In some such embodiments, W represents an optionally substituted aromatic or heteraromatic ring selected from the group consisting of phenyl, naphthyl, pyridine, pyrimidine, pyridazine, thiophene, oxazole, isoxazole, imidazole, pyrazole, pyrrole, thiazole, and isothiazole.

A preferred embodiment of Formula L includes compounds wherein W is optionally substituted phenyl ring. In other embodiments, W represents an optionally substituted C3-8 cycloalkyl ring; sometimes W is cyclopropyl.

In some embodiments of Formula L, each R30 is independently H, halo or C1-C6 alkyl. Preferably at least one R30 is H in these compounds.

R3P is a polar substituent, and can be any of the polar substituents described above for compounds of Formula IA, IB and IC. In some embodiments of Formula L, R3P is a triazole or imidazole ring, which can be substituted or unsubstituted, and is preferably bonded through a carbon atom of the triazole or imidazole ring to the fused tricyclic moiety in Formula L.

In compounds of formula L-A or L-B, R30 is typically H or halo. R3P is frequently a 2-imidazolyl ring or a 3-triazolyl ring, each of which can be unsubstituted or substituted. If these rings are substituted on N, they are typically substituted with C1-C6 alkyl or C1-C6 acyl, or, if substituted on a carbon atom of the ring, with halo. Unsubstituted 3-triazole is a preferred group for R3P.

In some embodiments of Formula L-A or L-B, W is an optionally substituted phenyl, which can be unsubstituted phenyl or a phenyl substituted with 1-3 substituents. In some embodiments, the substituents on the phenyl ring are selected from halo, cyano, CF3, —OCF3, COOR40, and SO2NR40R50, and one or more of these substituents can be an optionally substituted group selected from C1-C6 alkyl, C1-C6 alkoxy, C2-C6 alkenyl, and C2-C6 alkynyl, wherein each of R40 and R50 are defined as for formula IA.

Also provided herein is a pharmaceutical composition comprising a compound of any of the Formulae described herein, including Formula IA, IB, IC, L, L-A and L-B, and at least one pharmaceutically acceptable carrier or excipient, or two or more pharmaceutically acceptable carriers and/or excipients. It is understood that the compounds of Formula I can include compounds of Formula IA, IB and IC. Pharmaceutical compositions can be utilized in treatments described herein.

Provided also are methods for identifying a candidate molecule that interacts with a CK2, Pim or Flt protein, which comprise: contacting a composition containing a CK2, Pim or Flt protein kinase and a compound described herein with a candidate molecule under conditions in which the compound and the protein kinase interact, and determining whether the amount of the compound that interacts with the protein kinase is modulated relative to a control interaction between the compound and the protein kinase without the candidate molecule, whereby a candidate molecule that modulates the amount of the compound interacting with the protein kinase relative to the control interaction is identified as a candidate molecule that interacts with the protein kinase.

In certain embodiments the protein is in a cell or in a cell-free system. The protein, the compound or the molecule in some embodiments is in association with a solid phase. In certain embodiments, the interaction between the compound and the protein is detected via a detectable label, where in some embodiments the protein comprises a detectable label and in certain embodiments the compound comprises a detectable label. The interaction between the compound and the protein sometimes is detected without a detectable label.

In certain embodiments, the protein is a CK2 protein, such as a CK2 protein comprising the amino acid sequence of SEQ ID NO: 1, 2 or 3 or a substantially identical variant thereof, for example.

cell-free system. The protein or the compound may be in association with a solid phase in certain embodiments.

Provided also are methods for inhibiting cell proliferation, which comprise contacting cells with a compound described herein in an amount effective to inhibit proliferation of the cells. The cells sometimes are in a cell line, such as a cancer cell line (e.g., breast cancer, prostate cancer, pancreatic cancer, lung cancer, hemopoietic cancer, colorectal cancer, skin cancer, ovary cancer cell line), for example. In some embodiments, the cancer cell line is a breast cancer, prostate cancer or pancreatic cancer cell line. The cells sometimes are in a tissue, can be in a subject, at times are in a tumor, and sometimes are in a tumor in a subject. In certain embodiments, the method further comprises inducing cell apoptosis. Cells sometimes are from a subject having macular degeneration.

```
(NP_001886; casein kinase II alpha 1 subunit isoform a
[Homo sapiens])
                                                           SEQ ID NO: 1
   1msgpvpsrar vytdvnthrp reywdyeshv vewgnqddyq lvrklgrgky sevfeainit

  61nnekvvvkil kpvkkkkikr eikilenlrg gpniitladi vkdpvsrtpa lvfehvnntd

 121fkqlyqtltd ydirfymyei lkaldychsm gimhrdvkph nvmidhehrk lrlidwglae

 181fyhpgqeynv rvasryfkgp ellvdyqmyd ysldmwslgc mlasmifrke pffhghdnyd

 241qlvriakvlg tedlydyidk ynieldprfn dilgrhsrkr werfvhsenq hlvspealdf

 301ldkllrydhq srltareame hpyfytvvkd qarmgsssmp ggstpvssan mmsgissvpt

 361psplgplags pviaaanplg mpvpaaagaq q

(NP_808227: casein kinase II alpha 1 subunit isoform a
[Homo sapiens])
                                                           SEQ ID NO: 2
   1msgpvpsrar vytdvnthrp reywdyeshv vewgnqddyq lvrklgrgky sevfeainit

  61nnekvvvkil kpvkkkkikr eikilenlrg gpniitladi vkdpvsrtpa lvfehvnntd

 121fkqlyqtltd ydirfymyei lkaldychsm gimhrdvkph nvmidhehrk lrlidwglae

 181fyhpgqeynv rvasryfkgp ellvdyqmyd ysldmwslgc mlasmifrke pffhghdnyd

 241qlvriakvlg tedlydyidk ynieldprfn dilgrhsrkr werfvhsenq hlvspealdf

 301ldkllrydhq srltareame hpyfytvvkd qarmgsssmp ggstpvssan mmsgissvpt

 361psplgplags pviaaanplg mpvpaaagaq q

(NP_808228: casein kinase II alpha 1 subunit isoform b
[Homo sapiens])
                                                           SEQ ID NO: 3
   1myeilkaldy chsmgimhrd vkphnvmidh ehrklrlidw glaefyhpgq eynvrvasry

  61fkgpellvdy qmydysldmw sigomlasmi frkepffhgh dnydqlvria kvlgtedlyd

 121yidkynield prfndilgrh srkrwerfvh senqhlvspe aldfldkllr ydhqsrltar

 181eamehpyfyt vvkdqarmgs ssmpggstpv ssanmmsgis svptpsplgp lagspviaaa

 241nplgmpvpaa agaqq
```

Also provided are methods for modulating the activity of a CK2 protein, Pim protein, or Flt protein which comprise contacting a system comprising the protein with a compound described herein in an amount effective for modulating the activity of the protein. In certain embodiments the activity of the protein is inhibited, and sometimes the protein is a CK2 protein, such as a CK2 protein comprising the amino acid sequence of SEQ ID NO: 1, 2 or 3 or a substantially identical variant thereof, for example. In other embodiments the protein is a Pim protein or a Flt protein. In certain embodiments, the system is a cell, and in other embodiments the system is a Also provided are methods for treating a condition related to aberrant cell proliferation, which comprise administering a compound described herein to a subject in need thereof in an amount effective to treat the cell proliferative condition. In certain embodiments the cell proliferative condition is a tumor-associated cancer. The cancer sometimes is of the breast, prostate, pancreas, lung, colorectum, skin, or ovary. In some embodiments, the cell proliferative condition is a non-tumor cancer, such as a hematopoietic cancer, for example. In other embodiments, the cell proliferative condition is macular degeneration in some embodiments.

Provided also are methods for treating cancer or an inflammatory disorder in a subject in need of such treatment, comprising: administering to the subject a therapeutically effective amount of a therapeutic agent useful for treating such disorder; and administering to the subject a molecule that inhibits CK2, Pim or Flt in an amount that is effective to enhance a desired effect of the therapeutic agent. In certain embodiments, the molecule that inhibits CK2, Pim or Flt is a compound of Formula I, IA, IB, IC, L, L-A or L-B as described herein, or a pharmaceutically acceptable salt thereof. In some embodiments, the molecule that inhibits CK2, Pim or Flt is a known compound shown above, or a compound in one of the Tables provided herein, or a pharmaceutically acceptable salt of one of these compounds. In some embodiments, the desired effect of the therapeutic agent that is enhanced by the molecule that inhibits CK2, Pim or Flt is a reduction in cell proliferation. In certain embodiments, the desired effect of the therapeutic agent that is enhanced by the molecule that inhibits CK2, Pim or Flt is an increase in apoptosis in at least one type of cell.

In some embodiments, the therapeutic agent and the molecule that inhibits CK2, Pim or Flt are administered at substantially the same time. The therapeutic agent and molecule that inhibits CK2, Pim or Flt sometimes are used concurrently by the subject. The therapeutic agent and the molecule that inhibits CK2, Pim or Flt are combined into one pharmaceutical composition in certain embodiments.

Also provided are compositions of matter comprising a compound described herein and an isolated protein. The protein sometimes is a CK2 protein, such as a CK2 protein comprising the amino acid sequence of SEQ ID NO: 1, 2 or 3 or a substantially identical variant thereof, for example. In some embodiments, the protein is a Pim protein. In other embodiments, the protein is a Flt protein. Certain compositions comprise a compound described herein in combination with a cell. The cell may be from a cell line, such as a cancer cell line. In the latter embodiments, the cancer cell line is sometimes a breast cancer, prostate cancer, pancreatic cancer, lung cancer, hemopoietic cancer, colorectal cancer, skin cancer, ovary cancer cell line.

These and other embodiments of the invention are described in the description that follows.

MODES OF CARRYING OUT THE INVENTION

Figure 1:
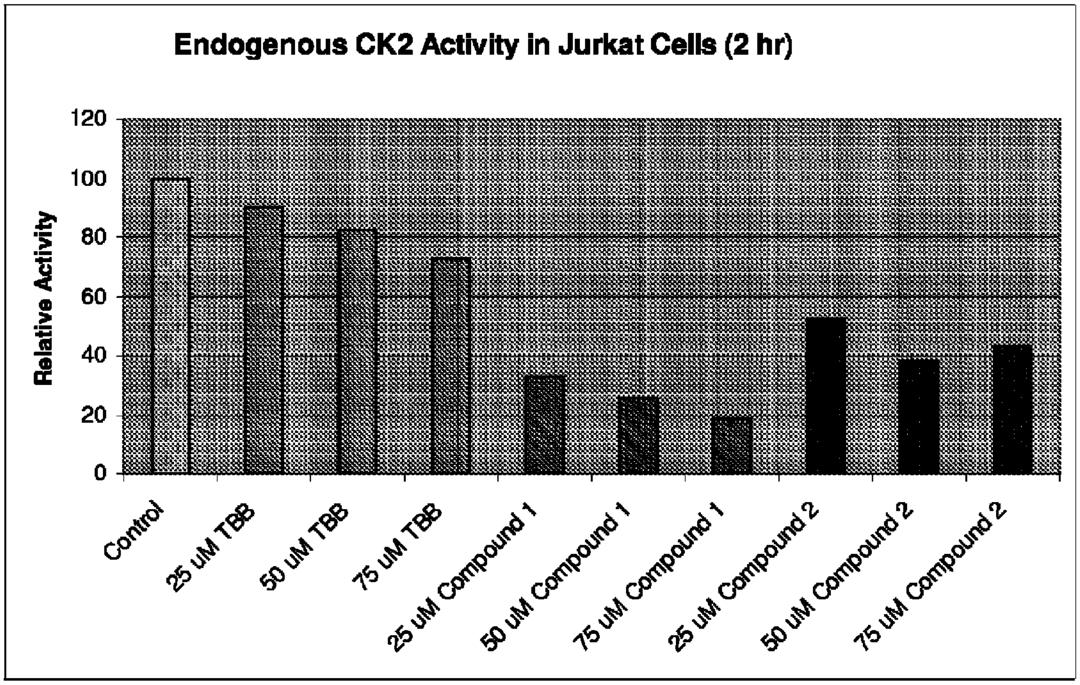
FIG. 1 depicts assay data showing inhibition of CK2 activity.

Compounds of the Formulae provided herein, including compounds of Formulae IA, IB, IC, L, L-A or L-B, can exert biological activities that include, but are not limited to, inhibiting cell proliferation. Compounds of such Formulae can modulate CK2 activity, Pim activity and/or Flt activity, for example. Such compounds therefore can be utilized in multiple applications by a person of ordinary skill in the art. For example, compounds described herein may find uses that include, but are not limited to, (i) modulation of protein kinase activity (e.g., CK2 activity), (ii) modulation of Pim activity (e.g., PIM-1 activity), (iii) modulation of FMS-like tyrosine kinase (Flt) activity (e.g., Flt-3 activity), (iv) modulation of cell proliferation, (v) modulation of apoptosis, and (vi) treatments of cell proliferation related disorders, pain or inflammation (e.g., administration alone or co-administration with another molecule).

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

The compounds of the invention often have ionizable groups so as to be capable of preparation as salts. In that case, wherever reference is made to the compound, it is understood in the art that a pharmaceutically acceptable salt may also be used. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed. The compounds of the invention may also exist in more than one tautomeric form; the depiction herein of one tautomer is for convenience only, and is also understood to encompass other tautomers of the form shown.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as 1-10C or as C1-C10 or C1-10. When heteroatoms (N, O and S typically) are allowed to replace carbon atoms as in heteroalkyl groups, for example, the numbers describing the group, though still written as e.g. C1-C6, represent the sum of the number of carbon atoms in the group plus the number of such heteroatoms that are included as replacements for carbon atoms in the backbone of the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often optionally substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, $NRCSNR_2$, NRC(=NR)$NR_2$, NRCOOR, NRCOR, CN, C≡CR, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, NR'C(=NR')$NR'_2$, NR'COOR', NR'COR', CN, C≡CR', COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Acetylene" substituents are 2-10C alkynyl groups that are optionally substituted, and are of the formula —C≡C—$R^a$, wherein $R^a$ is H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and each Ra group is optionally substituted with one or more substituents selected from halo, =O, =N—CN, =N—OR', =NR', OR', NR'2, SR', SO2R', SO2NR'2, NR'SO2R', NR'CONR'2, NR'CSNR'2, NR'C(=NR')NR'2, NR'COOR', NR'COR', CN, COOR', CONR'2, OOCR', COR', and NO2, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O; and wherein two R' can be linked to form a 3-7 membered ring optionally containing up to three heteroatoms selected from N, O and S. In some embodiments, $R^a$ of —C≡C—$R^a$ is H or Me.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)$NR_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic aryls contain 6 ring members and monocylic heteroaryls contain 5-6 ring members, and the bicyclic aryls and heteroaryls contain 8-10 ring members.

Aryl and heteroaryl moieties may be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, $NR_2$, SR, $SO_2R$, $SO_2NR_2$, $NRSO_2R$, $NRCONR_2$, $NRCSNR_2$, $NRC(=NR)NR_2$, NRCOOR, NRCOR, CN, C≡CR, COOR, $CONR_2$, OOCR, COR, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to $-(CH_2)_n-$ where n is 1-8 and preferably n is 1-4, though where specified, an alkylene can also be substituted by other groups, and can be of other lengths, and the open valences need not be at opposite ends of a chain. Thus —CH(Me)- and $-C(Me)_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Halo", as used herein includes fluoro, chloro, bromo and iodo. Fluoro and chloro are often preferred.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems. Carbocyclic and heterocyclic rings may be saturated, partially unsaturated, or aromatic.

As used herein, the term "heteroatom" refers to any atom that is not carbon or hydrogen, such as nitrogen, oxygen or sulfur.

Illustrative examples of heterocycles include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4 b]pyridine, piperazine, pyrazine, morpholine, thiomorpholine, imidazole, imidazolidine 2,4-dione, 1,3-dihydrobenzimidazol-2-one, indole, thiazole, benzothiazole, thiadiazole, thiophene, tetrahydro thiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

As used herein, the term "inorganic substituent" refers to substituents that do not contain carbon or contain carbon bound to elements other than hydrogen (e.g., elemental carbon, carbon monoxide, carbon dioxide, and carbonate). Examples of inorganic substituents include but are not limited to nitro, halogen, azido, cyano, sulfonyls, sulfinyls, sulfonates, phosphates, etc.

The terms "treat" and "treating" as used herein refer to ameliorating, alleviating, lessening, and removing symptoms of a disease or condition. A candidate molecule or compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus. Thus the invention provides methods for treating protozoal disorders such as protozoan parasitosis, including infection by parasitic protozoa responsible for neurological disorders such as schizophrenia, paranoia, and encephalitis in immunocompromised patients, as well as Chagas' disease. It also provides methods to treat various viral diseases, including human immunodeficiency virus type 1 (HIV-1), human papilloma viruses (HPVs), herpes simplex virus (HSV), Epstein-Barr virus (EBV), human cytomegalovirus, hepatitis C and B viruses, influenza virus, Borna disease virus, adenovirus, coxsackievirus, coronavirus and varicella zoster virus. The methods for treating these disorders comprises administering to a subject in need thereof an effective amount of a CK2 inhibitor of Formula A.

"Treating" or "treatment" as used herein with respect to cancers or cell proliferative disorders also covers the treatment of a disease-state in a human, which disease-state is characterized by abnormal, excessive and/or undesired cellular proliferation, and includes at least one of: (i) preventing the disease-state from occurring in a human, in particular, when such human is predisposed to the disease-state but has not yet been diagnosed as having it; (ii) inhibiting the disease-state, i.e., arresting its development; (iii) inhibiting spread of the disease state to new loci, e.g., slowing or preventing metastasis of a tumor; and (iv) relieving the disease-state, i.e., causing regression of the disease-state.

'Treating' or 'treatment' with regard to inflammatory conditions includes prevention of inflammation in a subject where inflammation is expected to occur, or reduction of the extent or duration of one or more of the symptoms of inflammation in a subject having symptoms of inflammation such as redness, swelling, pain associated with these, or elevated temperature.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

The invention in part provides pharmaceutical compositions comprising at least one compound within the scope of the invention as described herein, and methods of using compounds described herein. For example, the invention in part provides methods for identifying a candidate molecule that interacts with a CK2, Pim or Flt protein, which comprises contacting a composition containing a CK2, Pim or Flt protein and a molecule described herein with a candidate molecule and determining whether the amount of the molecule described herein that interacts with the protein is modulated, whereby a candidate molecule that modulates the amount of the molecule described herein that interacts with the protein is identified as a candidate molecule that interacts with the protein.

Provided also are methods for modulating a protein kinase activity. Protein kinases catalyze the transfer of a gamma phosphate from adenosine triphosphate to a serine or threonine amino acid (serine/threonine protein kinase), tyrosine amino acid (tyrosine protein kinase), tyrosine, serine or threonine (dual specificity protein kinase) or histidine amino acid (histidine protein kinase) in a peptide or protein substrate. Thus, included herein are methods which comprise contacting a system comprising a protein kinase protein with a compound described herein in an amount effective for modulating (e.g., inhibiting) the activity of the protein kinase. In some embodiments, the activity of the protein kinase is the catalytic activity of the protein (e.g., catalyzing the transfer of a gamma phosphate from adenosine triphosphate to a peptide or protein substrate). In certain embodiments, provided are methods for identifying a candidate molecule that interacts with a protein kinase, which comprise: contacting a composition containing a protein kinase and a compound described herein with a candidate molecule under conditions in which the compound and the protein kinase interact, and determining whether the amount of the compound that interacts with the protein kinase is modulated relative to a control interaction between the compound and the protein kinase without the candidate molecule, whereby a candidate molecule that modulates the amount of the compound interacting with the protein kinase relative to the control interaction is identified as a candidate molecule that interacts with the protein kinase. Systems in such embodiments can be a cell-free system or a system comprising cells (e.g., in vitro). The protein kinase, the compound or the molecule in some embodiments is in association with a solid phase. In certain embodiments, the interaction between the compound and the protein kinase is detected via a detectable label, where in some embodiments the protein kinase comprises a detectable label and in certain embodiments the compound comprises a detectable label. The interaction between the compound and the protein kinase sometimes is detected without a detectable label.

Provided also are compositions of matter comprising a protein kinase and a compound described herein. In certain embodiments, the compound in the composition is not compound A2, compound A1 or compound A3. In some embodiments, the protein kinase in the composition is a serine-threonine protein kinase or a tyrosine protein kinase. In certain embodiments, the protein kinase is a protein kinase fragment having compound-binding activity. In some embodiments, the protein kinase in the composition is, or contains a subunit (e.g., catalytic subunit, SH2 domain, SH3 domain) of, CK2, Pim subfamily protein kinase (e.g., PIM1, PIM2, PIM3) or Flt subfamily protein kinase (e.g., FLT1, FLT3, FLT4). In certain embodiments the composition is cell free and sometimes the protein kinase is a recombinant protein.

The protein kinase can be from any source, such as cells from a mammal, ape or human, for example. Examples of serine-threonine protein kinases that can be inhibited, or may potentially be inhibited, by compounds disclosed herein include without limitation human versions of CK2, CK2α2, Pim subfamily kinases (e.g., PIM1, PIM2, PIM3), CDK1/cyclinB, c-RAF, Mer, MELK, HIPK3, HIPK2 and ZIPK. A serine-threonine protein kinase sometimes is a member of a sub-family containing one or more of the following amino acids at positions corresponding to those listed in human CK2: leucine at position 45, methionine at position 163 and isoleucine at position 174. Examples of such protein kinases include without limitation human versions of CK2, STK10, HIPK2, HIPK3, DAPK3, DYK2 and PIM-1. Examples of tyrosine protein kinases that can be inhibited, or may potentially be inhibited, by compounds disclosed herein include without limitation human versions of Flt subfamily members (e.g., FLT1, FLT2, FLT3, FLT3 (D835Y), FLT4). An example of a dual specificity protein kinase that can be inhibited, or may potentially be inhibited, by compounds disclosed herein includes without limitation DYRK2. Nucleotide and amino acid sequences for protein kinases and reagents are publicly available (e.g., World Wide Web URLs ncbi.nlm.nih.gov/sites/entrez/ and Invitrogen.com). For example, various nucleotide sequences can be accessed using the following accession numbers: NM_002648.2 and NP_002639.1 for PIM1; NM_006875.2 and NP_006866.2 for PIM2; XM_938171.2 and XP_943264.2 for PIM3; NM_004119.2 and NP_004110.2 for FLT3; NM_002020.3 and NP_002011.2 for FLT4; and NM_002019.3 and NP_002010.2 for FLT1.

The invention also in part provides methods for treating a condition related to aberrant cell proliferation. For example, provided are methods of treating a cell proliferative condition in a subject, which comprises administering a compound described herein to a subject in need thereof in an amount effective to treat the cell proliferative condition. The subject may be a research animal (e.g., rodent, dog, cat, monkey), optionally containing a tumor such as a xenograft tumor (e.g., human tumor), for example, or may be a human. A cell proliferative condition sometimes is a tumor or non-tumor cancer, including but not limited to, cancers of the colorectum, breast, lung, liver, pancreas, lymph node, colon, prostate, brain, head and neck, skin, liver, kidney, blood and heart (e.g., leukemia, lymphoma, carcinoma). In some embodiments, the cell proliferative condition is a non-tumor cancer. In some such embodiments, the non-tumor cancer is a hematopoietic cancer. In specific embodiments, it is acute myelogenous leukemia. In some such embodiments, the leukemia is refractory AML or wherein the AML is associated with a mutated Flt3.

Also provided are methods for treating a condition related to inflammation or pain. For example, provided are methods of treating pain in a subject, which comprise administering a compound described herein to a subject in need thereof in an amount effective to treat the pain. Provided also are methods of treating inflammation in a subject, which comprises administering a compound described herein to a subject in need thereof in an amount effective to treat the inflammation. The subject may be a research animal (e.g., rodent, dog, cat, monkey), for example, or may be a human.

Conditions associated with inflammation and pain include, without limitation, acid reflux, heartburn, acne, allergies and sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, glomerulonephritis (GN), juvenile cystic kidney disease, and type I nephronophthisis (NPHP), osteoporosis, Parkinson's disease, Guam-Parkinson dementia, supranuclear palsy, Kuf's disease, and Pick's disease, as well as memory impairment, brain ischemia, and schizophrenia, periodontal disease, polyarteritis, polychondritis, psoriasis, scleroderma, sinusitis, Sjögren's syndrome, spastic colon, systemic candidiasis, tendonitis, urinary track infections, vaginitis, inflammatory cancer (e.g., inflammatory breast cancer) and the like.

Methods for determining effects of compounds herein on pain or inflammation are known. For example, formalin-stimulated pain behaviors in research animals can be monitored after administration of a compound described herein to assess treatment of pain (e.g., Li et al., *Pain* 115(1-2): 182-90 (2005)). Also, modulation of pro-inflammatory molecules (e.g., IL-8, GRO-alpha, MCP-1, TNFalpha and iNOS) can be monitored after administration of a compound described herein to assess treatment of inflammation (e.g., Parhar et al., *Int J Colorectal Dis.* 22(6): 601-9 (2006)), for example. Thus, also provided are methods for determining whether a compound herein reduces inflammation or pain, which comprise contacting a system with a compound described herein in an amount effective for modulating (e.g., inhibiting) the activity of a pain signal or inflammation signal.

Provided also are methods for identifying a compound that reduces inflammation or pain, which comprise: contacting a system with a compound of one of the Formulae described herein, including a compound of Formula IA, IB, IC, L, L-A or L-B, and detecting a pain signal or inflammation signal, whereby a compound that modulates the pain signal relative to a control molecule is identified as a compound that reduces inflammation of pain. Non-limiting examples of pain signals are formalin-stimulated pain behaviors and examples of inflammation signals include without limitation a level of a pro-inflammatory molecule.

The invention thus in part pertains to methods for modulating angiogenesis in a subject, and methods for treating a condition associated with aberrant angiogenesis in a subject, proliferative diabetic retinopathy.

CK2 has also been shown to play a role in the pathogenesis of atherosclerosis, and may prevent atherogenesis by maintaining laminar shear stress flow. CK2 plays a role in vascularization, and has been shown to mediate the hypoxia-induced activation of histone deacetylases (HDACs). CK2 is also involved in diseases relating to skeletal muscle and bone tissue, including, e.g., cardiomyocyte hypertrophy, heart failure, impaired insulin signaling and insulin resistance, hypophosphatemia and inadequate bone matrix mineralization.

Thus in one aspect, the invention provides methods to treat these conditions, comprising administering to a subject in need of such treatment an effect amount of a CK2 inhibitor, such as a compound of Formula A.

Thus, provided are methods for determining whether a compound herein modulates angiogenesis, which comprise contacting a system with a compound described herein in an amount effective for modulating (e.g., inhibiting) angiogenesis or a signal associated with angiogenesis. Signals associated with angiogenesis are levels of a pro-angiogenesis growth factor such as VEGF. Methods for assessing modulation of angiogenesis also are known, such as analyzing human endothelial tube formation (BD BioCoat™ Angiogenesis System from BD Biosciences). Provided also are methods for identifying a compound that modulates angiogenesis, which comprise contacting a system with a compound of one of the Formulae described herein, including a compound of Formulae IA, IB, IC, L, L-A or L-B; and detecting angiogenesis in the system or an angiogenesis signal, whereby a compound that modulates the angiogenesis or angiogenesis signal relative to a control molecule is identified as a compound that modulates angiogenesis. Also provided are methods for treating an angiogenesis condition, which comprise administering a compound described herein to a subject in need thereof in an amount effective to treat the angiogenesis condition. Angiogenesis conditions include without limitation solid tumor cancers, varicose disease and the like.

The invention also in part pertains to methods for modulating an immune response in a subject, and methods for treating a condition associated with an aberrant immune response in a subject. Thus, provided are methods for determining whether a compound herein modulates an immune response, which comprise contacting a system with a compound described herein in an amount effective for modulating (e.g., inhibiting) an immune response or a signal associated with an immune response. Signals associated with immunomodulatory activity include, e.g., stimulation of T-cell proliferation, suppression or induction of cytokines, including, e.g., interleukins, interferon-γ and TNF. Methods of assessing immunomodulatory activity are known in the art. Provided also are methods for identifying a compound that modulates an immune response, which comprise contacting a system with a compound of one of the Formulae described herein, including a compound of Formulae IA, IB, IC, L, L-A or L-B, or a pharmaceutically acceptable salt thereof; and detecting immunomodulatory activity in a system, or a signal associated with immunomodulatory activity, whereby a compound that modulates the immune response relative to a control molecule is identified as an immune response modulatory compound.

Also provided are methods for treating a condition associated with an aberrant immune response in a subject, which comprise administering a compound described herein to a subject in need thereof in an amount effective to treat the condition. Conditions characterized by an aberrant immune response include without limitation, organ transplant rejection, asthma, autoimmune disorders, including rheumatoid arthritis, multiple sclerosis, myasthenia gravis, systemic lupus erythematosus, scleroderma, polymyositis, mixed connective tissue disease (MCTD), Crohn's disease, and ulcerative colitis. In certain embodiments, an immune response may be modulated by administering a compound herein in combination with a molecule that modulates (e.g., inhibits) the biological activity of an mTOR pathway member or member of a related pathway (e.g., mTOR, PI3 kinase, AKT). In certain embodiments the molecule that modulates the biological activity of an mTOR pathway member or member of a related pathway is rapamycin. In certain embodiments, provided herein is a composition comprising a compound described herein in combination with a molecule that modulates the biological activity of an mTOR pathway member or member of a related pathway, such as rapamycin, for example.

In preferred embodiments of the present invention, the compound is a compound of Formula IA, IB, IC, L, L-A or L-B in one of the Tables provided herein, or a pharmaceutically acceptable salt of one of these compounds.

Any suitable formulation of a compound described above can be prepared for administration. Any suitable route of administration may be used, including, but not limited to, oral, parenteral, intravenous, intramuscular, transdermal, topical and subcutaneous routes. Depending on the subject to be treated, the mode of administration, and the type of treatment desired—e.g., prevention, prophylaxis, therapy; the compounds are formulated in ways consonant with these parameters. Preparation of suitable formulations for each route of administration are known in the art. A summary of such formulation methods and techniques is found in *Remington's Pharmaceutical Sciences*, latest edition, Mack Publishing Co., Easton, Pa., which is incorporated herein by reference. The formulation of each substance or of the combination of two substances will generally include a diluent as well as, in some cases, adjuvants, buffers, preservatives and the like. The substances to be administered can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised, and can be applied to compounds of the invention. See, for example, U.S. Pat. No. 5,624,677, the methods of which are incorporated herein by reference.

Systemic administration may also include relatively noninvasive methods such as the use of suppositories, transdermal patches, transmucosal delivery and intranasal administration. Oral administration is also suitable for compounds of the invention. Suitable forms include syrups, capsules, tablets, as is understood in the art.

For administration to animal or human subjects, the appropriate dosage of the a compound described above often is 0.01-15 mg/kg, and sometimes 0.1-10 mg/kg. Dosage levels are dependent on the nature of the condition, drug efficacy, the condition of the patient, the judgment of the practitioner, and the frequency and mode of administration; however, optimization of such parameters is within the ordinary level of skill in the art.

Therapeutic Combinations

Compounds of the invention may be used alone or in combination with another therapeutic agent. The invention provides methods to treat conditions such as cancer, inflammation and immune disorders by administering to a subject in need of such treatment a therapeutically effective amount of a therapeutic agent useful for treating said disorder and administering to the same subject a a therapeutically effective amount of a modulator of the present invention. A CK2, Pim or Flt modulator is an agent that inhibits or enhances a biological activity of a CK2 protein, a Pim protein or a Flt protein, and is generically referred to hereafter as a "modulator." The therapeutic agent and the modulator may be administered together, either as separate pharmaceutical compositions or admixed in a single pharmaceutical composition. The therapeutic agent and the modulator may also be administered separately, including at different times and with different frequencies. The modulator may be administered by any known route, such as orally, intravenously, intramuscularly, nasally, and the like; and the therapeutic agent may also be administered by any conventional route. In many embodiments, at least one and optionally both of the modulator and the therapeutic agent may be administered orally.

When used in combination, in some embodiments the compounds of the invention may be administered as a single pharmaceutical dosage formulation that contains both a compound of the invention and another therapeutic agent. In other embodiments, separate dosage formulations are administered; the compound of the invention and the other therapeutic agent may be, administered at essentially the same time, for example, concurrently, or at separately staggered times, for example, sequentially. In certain examples, the individual components of the combination may be administered separately, at different times during the course of therapy, or concurrently, in divided or single combination forms. The present invention provides, for example, simultaneous, staggered, or alternating treatment. Thus, the compound of the invention may be administered at the same time as another therapeutic agent, in the same pharmaceutical composition; the compound of the invention may be administered in separate pharmaceutical compositions; the compound of the invention may be administered before the other therapeutic agent, or the other therapeutic agent may be administered before the compound of the invention, for example, with a time difference of seconds, minutes, hours, days, or weeks. In examples of a staggered treatment, a course of therapy with the compound of the invention may be administered, followed by a course of therapy with the other therapeutic agent, or the reverse order of treatment may be used, more than one series of treatments with each component may be used. In certain examples of the present invention, one component, for example, the compound of the invention or the other therapeutic agent agent, is administered to a mammal while the other component, or its derivative products, remains in the bloodstream of the mammal. In other examples, the second component is administered after all, or most of the first component, or its derivatives, have left the bloodstream of the mammal.

Compounds of the invention are useful when used in combination with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids, plant alkaloids, topoisomerase inhibitors and the like.

Compounds of the invention are useful when used in combination with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids, plant alkaloids, topoisomerase inhibitors and the like.

Alkylating agents include altretamine, AMD-473, AP-5280, apaziquone, bendamustine, brostallicin, busulfan, carboquone, carmustine (BCND), chlorambucil, VNP 40101M, cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include BMS-354825, imatinib and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC202, R-roscovitine), ZK-304709 and the like.

COX-2 inhibitors include ABT-963, etoricoxib, valdecoxib, BMS347070, celecoxib, COX-189 (lumiracoxib), CT-3, deracoxib, JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, rofecoxib and the like.

EGFR inhibitors include ABX-EGF, anti-EGFr immunoliposomes, EGFvaccine, EMD-7200, cetuximab, HR3, IgA antibodies, gefitinib, erlotinib, TP-38, EGFR fusion protein, (lapatinib and the like.

ErbB2 receptor inhibitors include CP-724-714, CI-1033 (canertinib), trastuzumab, lapatinib, pertuzumab, TAK-165, GW-572016 (ionafarnib), GW-282974, EKB-569, PI-166, dHER2 (HER2 vaccine), APC-8024 (HER-2 vaccine), anti- HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCI, PU-3, radicicol, SNX-2112, STA-9090, VER49009 and the like.

MEK inhibitors include ARRY-142886, ARRY-438162, PD-325901, PD-98059 and the like.

mTOR inhibitors include AP-23573, CCI-779, everolimus, RAD-001, rapamycin, temsirolimus and the like.

Non-steroidal anti-inflammatory drugs include salsalate, diflunisal, ibuprofen, ketoprofen, nabumetone, piroxicam, ibuprofin cream, naproxen, diclofenac, indomethacin, sulindac, tolmetin, etodolac, ketorolac, oxaprozin and the like.

PDGFR inhibitors include C-451, CP-673, CP-868596 and the like.

Platinum chemotherapeutics include cisplatin, oxaliplatin, eptaplatin, lobaplatin, nedaplatin, carboplatin, satraplatin and the like.

Polo-like kinase inhibitors include B1-2536 and the like.

Thrombospondin analogs include ABT-510, ABT-567, ABT-898, TSP-1 and the like.

VEGFR inhibitors include bevacizumab, ABT-869, AEE-788, RPI.4610, axitinib (AG-13736), AZD-2171, CP-547, 632, 1M-862, pegaptanib, sorafenib, pazopanib, PTK-787/ZK-222584, sunitinib, VEGF trap, vatalanib, vandetanib and the like.

Antimetabolites include pemetrexed, 5-azacitidine, capecitabine, carmofur, cladribine, clofarabine, cytarabine, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, gemcitabine, hydroxyurea, melphalan, mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, bleomycin, daunorubicin, doxorubicin, liposomal doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and the like.

Topoisomerase inhibitors include aclarubicin, 9-aminocamptothecin, amonafide, amsacrine, becatecarin, belotecan, BN-80915, irinotecan, camptothecin, dexrazoxine, diflomotecan, edotecarin, epirubicin, etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include bevacizumab, CD40-specific antibodies, chTNT-1/B, denosumab, cetuximab, zanolimumab, IGF1R-specific antibodies, lintuzumab, edrecolomab, WX-G250, rituximab, ticilimumab, trastuzimab and the like.

Hormonal therapies include anastrozole, exemestane, arzoxifene, bicalutamide, cetrorelix, degarelix, deslorelin, trilostane, dexamethasone, flutamide, raloxifene, fadrozole, toremifene, fulvestrant, letrozole, formestane, glucocorticoids, doxercalciferol, lasofoxifene, leuprolide acetate, megesterol, mifepristone, nilutamide, tamoxifen citrate, abarelix, predisone, finasteride, rilostane, buserelin, triptorelin, luteinizing hormone releasing hormone (LHRH), vantas, trilostane, fosrelin (goserelin) and the like.

Deltoids and retinoids include seocalcitol (EB 1089, CB 1093), lexacalcitrol (KH1060), fenretinide, aliretinoin, liposomal tretinoin, bexarotene, LGD-1550 and the like.

Plant alkaloids include, but are not limited to, vincristine, vinblastine, vindesine, vinorelbine and the like.

Proteasome inhibitors include bortezomib, MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, interferon gamma-1b, or interferon gamma-n1, combinations thereof and the like.

Other agents include ALFAFERONE®, BAM-002, tasonermin, tositumomab, alemtuzumab, CTLA4 (cytotoxic lymphocyte antigen 4), decarbazine, denileukin, epratuzumab, lenograstim, lentinan, leukocyte alpha interferon, imiquimod, MDX-010, melanoma vaccine, mitumomab, molgramostim, gemtuzumab ozogamicin, filgrastim, OncoVAC-CL, oregovomab, pemtumomab (Y-muHMFG1), sipuleucel-T, sargaramostim, sizofilan, teceleukin, TheraCys® (BCG live), ubenimex, VIRULIZIN®, Z-100, WF-10, aldesleukin, thymalfasin, daclizumab, Ibritumomab tiuxetan and the like.

Biological response modifiers are agents that modify defense mechanisms of living organisms or biological responses, such as survival, growth, or differentiation of tissue cells to direct them to have anti-tumor activity and include include krestin, lentinan, sizofuran, picibanil PF-3512676 (CpG-8954), ubenimex and the like.

Pyrimidine analogs include cytarabine (ara C), cytosine arabinoside, doxifluridine, fludarabine, 5-FU (5-fluorouracil), floxuridine, gemcitabine, ratitrexed, triacetyluridine troxacitabine and the like.

Purine analogs include thioguanine and mercaptopurine.

Antimitotic agents include batabulin, epothilone D, N-(2-((4hydroxyphenyl)amino)pyridin-3-yl)-4-methoxybenzenesulfonamide, ixabepilone (BMS 247550), paclitaxel, docetaxel, PNUI00940 (109881), patupilone (epothilone B), XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds of the invention may be combined with other chemotherapeutic agents such as ABI-007, ABT-100 (farnesyl transferase inhibitor), lovastatin, poly I:poly CI2U, exisulind, pamidronic acid, arglabin, L-asparaginase, atamestane (1-methyl-3,17-dione-androsta-1,4-diene), tazarotne, AVE-8062, BEC2 (mitumomab), cachectin or cachexin (tumor necrosis factor), canvaxin (vaccine), CeaVac™ (cancer vaccine), celmoleukin, histamine dihydrochloride, human papillomavirus vaccine, cyclophosphamide; doxorubicin; Vincristine; prednisone, Cyproterone Acetate, combrestatin A4P, DAB(389)EGF or TransMID-107R™ (diphtheria toxins), dacarbazine, dactinomycin, 5,6-dimethylxanthenone-4-acetic acid (DMXAA), eniluracil, squalamine lactate, T4N5 liposome lotion, discodermolide, DX-8951f (exatecan mesylate), enzastaurin, EP0906, quadrivalent human papillomavirus (Types 6, 11, 16, 18) recombinant vaccine, gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, mifamurtide, lonafamib, 5,10-methylenetetrahydrofolate, miltefosine (hexadecylphosphocholine), AE-941, trimetrexate glucuronate, pentostatin, ONCONASE® (a ribonuclease enzyme), ONCOPHAGE® (melanoma vaccine treatment), OncoVAX (IL-2 Vaccine), rubitecan, OSIDEM® (antibody-based cell drug), OvaRex® MAb (murine monoclonal antibody), paclitaxel, aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, catumaxomab, lenalidomide, RSR13 (efaproxiral), lanreotide, acitretin, staurosporine (Streptomyces staurospores), talabostat (PTI00), bexarotene, DHA-paclitaxel, TLK286, temilifene, temozolomide, tesmilifene, thalidomide, STn-KLH, thymitaq (2-amino-3,4-dihydro-6-methyl-4-oxo-5-(4pyridylthio)-quinazoline dihydrochloride), TNFerade™ (adenovector: DNA carrier containing the gene for tumor necrosis factor-α), bosentan, tretinoin (Retin-A), tetrandrine, arsenic trioxide, VIRULIZIN®, ukrain (derivative of alkaloids from the greater celandine plant), vitaxin (anti-alphavbeta3 antibody), motexafin gadolinium, atrasentan, paclitaxel poliglumex, trabectedin, ZD-6126, dexrazoxane, zometa (zolendronic acid), zorubicin and the like.

In certain embodiments, a modulator compound of the invention may be used in combination with a therapeutic agent that can act by binding to regions of DNA that can form certain quadruplex structures. In such embodiments, the therapeutic agents have anticancer activity on their own, but their activity is enhanced when they are used in combination with a modulator. This synergistic effect allows the therapeutic agent to be administered in a lower dosage while achieving equivalent or higher levels of at least one desired effect.

A modulator may be separately active for treating a cancer. For combination therapies described above, when used in combination with a therapeutic agent, the dosage of a modulator will frequently be two-fold to ten-fold lower than the dosage required when the modulator is used alone to treat the same condition or subject. Determination of a suitable amount of the modulator for use in combination with a therapeutic agent is readily determined by methods known in the art.

The following examples illustrate and do not limit the invention.

Example 1

Processes for Synthesizing Compounds of Formulae I, II, III and IV

Process 1

3-bromo-4-pyridine carboxylic acid (3.0 g, 14.9 mmol) in ethanol (100 mL) was treated with concentrated sulfuric acid (5 mL).

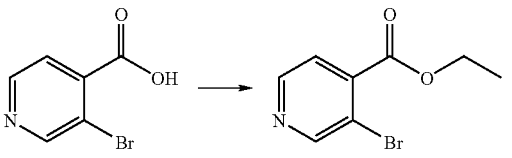

The mixture was brought to reflux at which time everything went into solution. After 12 hours at reflux, LCMS indicated that the reaction was complete. The reaction mixture was cooled to room temperature and concentrated on a rotary evaporator to a third of its original volume. The mixture was then diluted with 250 mL of ethyl acetate and washed twice with saturated aqueous sodium bicarbonate. Concentration on a rotary evaporator yielded 3.25 g of the ethyl ester as a yellowish oil which was sufficiently pure enough for subsequent chemical transformations. LCMS (ESI) 216.2 $(M+1)^+$.

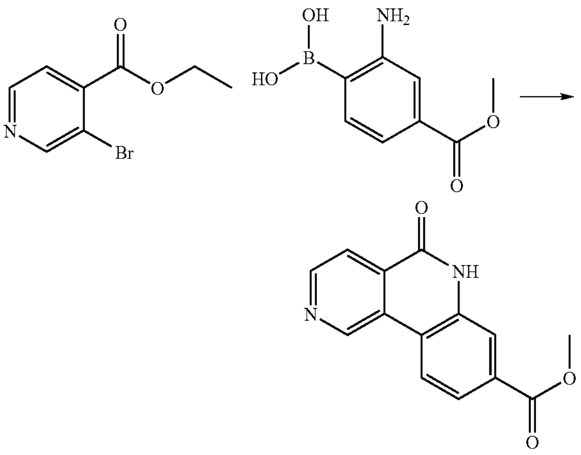

Ethyl 3-bromo-4-pyridine carboxylate 1.15 g, 5.0 mmol), 2-amino-4-methoxycarbonyl-phenylboronic acid (1.04 g, 4.5 mmol), sodium acetate (1.64 g, 20 mmol), 1,1'-bis(diphenylphosphino)ferrocene palladium (II) chloride (complexed with dichloromethane) (182 mg, 0.25 mmol) and dimethylformamide (7.5 mL) were combined in a flask. The flask was evacuated and filled with nitrogen twice and heated to 125° C. with stirring for 12 hours or until LCMS indicated the absence of any starting material. The mixture was cooled to room temperature and water (100 mL) was added to form a brown precipitate. The precipitate was filtered to yield 637 mg of methyl 5-oxo-5,6-dihydrobenzo[c][2,6]naphthyridine-8-carboxylate. LCMS (ESI) 255.4 $(M+1)^+$.

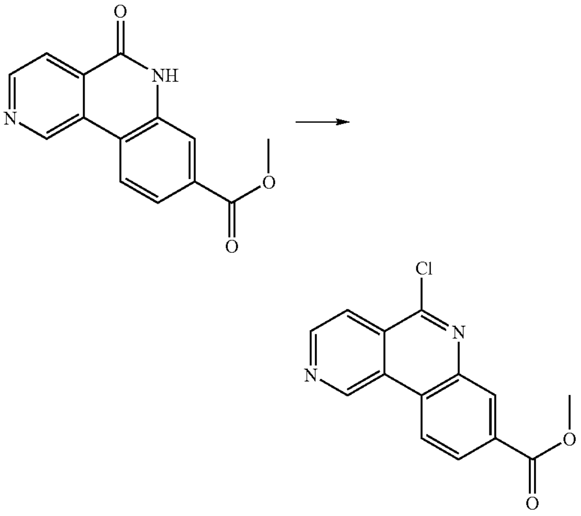

Methyl 5-oxo-5,6-dihydrobenzo[c][2,6]naphthyridine-8-carboxylate (200 mg, 0.787 mmol) was combined with phosphorus oxychloride (1 mL) and heated to reflux. After 2 hours, LCMS indicated the absence of any starting material. The volatiles were removed under reduced pressure. The residue was taken up in dichloromethane (50 mL) and washed twice with saturated aqueous sodium bicarbonate. The organic phase was dried over sodium sulfate and concentrated on a rotary evaporator to give methyl 5-chlorobenzo[c][2,6]naphthyridine-8-carboxylate (140 mg) as a grayish solid. LCMS (ESI) 273.3 $(M+1)^+$.

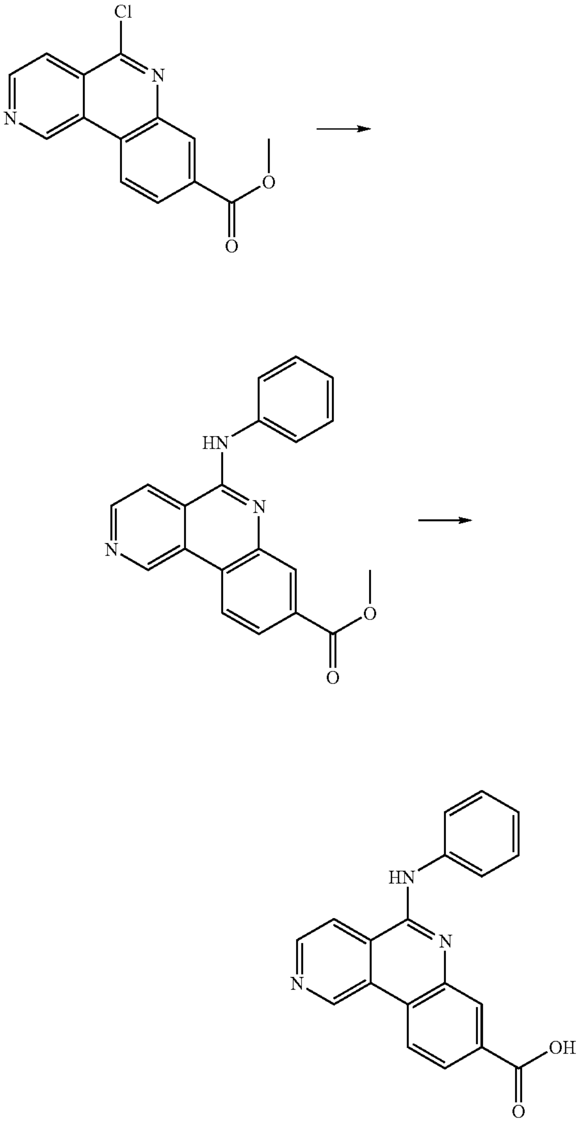

Methyl 5-chlorobenzo[c][2,6]naphthyridine-8-carboxylate (20 mg, 0.074 mmol) was combined with aniline (60 mg, 0.65 mmol) and N-methylpyrrolidinone (0.2 mL) in a microwave tube and the mixture was heated to 120° C. for 10 minutes at which time LCMS indicated that the reaction was complete as indicated by the absence of any starting material. The mixture was then purified by HPLC to yield the ester (22 mg) or it could be treated with 6N sodium hydroxide to yield the acid (19 mg). LCMS (ESI) 316.3 $(M+1)^+$. $^1$HNMR (400 MHz, $CD_3OD$) 10.17 (1H, s), 9.67 (1H, br), 8.99 (1H, d, 5.9 Hz), 8.83 (1H, d, 8.6 Hz), 8.62 (1H, d, 5.9 Hz), 8.24 (1H, d, 1.6 Hz), 8.04 (1H, s), 8.02 (1H, s), 7.93 (1H, dd, 8.2, 1.6 Hz), 7.43 (1H, d, 7.4 Hz), 7.41 (1H, d, 7.4 Hz), 7.10 (1H, m).

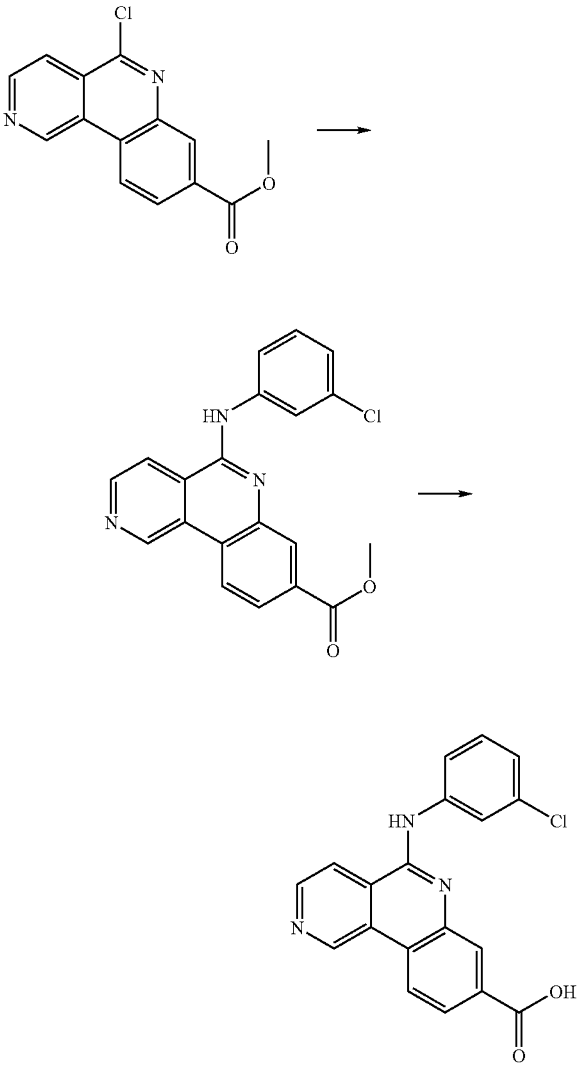

Methyl 5-chlorobenzo[c][2,6]naphthyridine-8-carboxylate (232 mg, 0.853 mmol) was combined with meta-chloroaniline (217 mg, 1.71 mmol) and N-methylpyrrolidinone (1 mL) in a flask and the mixture was heated to 80° C. for 2 hours at which time LCMS indicated that the reaction was complete as indicated by the absence of any starting material. The mixture was dissolved in $CH_2Cl_2$, washed with saturated aqueous sodium bicarbonate and dried over $Na_2SO_4$. The material was purified by flash chromatography ($SiO_2$, 1:1 to 9:1 gradient of EtOAc/Hexanes) to obtain the ester. The material was dissolved in methanol and 6N aqueous NaOH and the mixture stirred at 50° C. for 30 minutes. The volatiles were removed in vacuo. The residue was triturated from acetic acid/THF/methanol using a mixture of hexanes and ethylacetate. Filtration and drying provided 147 mg of 5-(3-chlorophenylamino)benzo[c][2,6]naphthyridine-8-carboxylic acid. LCMS (ESI) 350 $(M+1)^+$. $^1$HNMR (400 MHz, DMSO-$d_6$) δ 10.21 (s, 1H), 9.72 (br s, 1H), 9.02 (d, J=5.6, 1H), 8.89 (d, J=8.8, 1H), 8.62 (d, J=5.6, 1H), 8.31 (br s, 1H), 8.28 (d, J=1.6, 1H), 8.10 (br d, J=8, 1H), 7.99 (dd, J=2, J=8.4, 1H), 7.46 (t, J=8.0, 1H), 7.16 (br d, J=7.2, 1H) ppm.

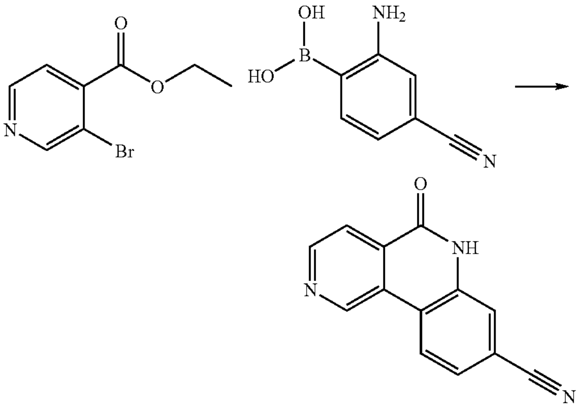

Sodium acetate (410 mg, 5 mmol) and 1,1'-bis(diphenylphosphino)ferrocene palladium (II) chloride (complexed with dichloromethane) (36 mg, 0.05 mmol) were added to a mixture of ethyl 3-bromo-4-pyridine carboxylate (230 mg, 1.0 mmol) and 2-amino-4-cyanophenylboronic acid hydrochloric acid salt (179 mg, 0.9 mmol). The mixture was connected to an exit bubbler and heated to 120° C. for 18 hours at which time LCMS analysis indicated that the reaction was done based on the disappearance of starting material. After cooling to room temperature, water was added and the dark solids were filtered and washed with dichloromethane to give 5-oxo-5,6-dihydrobenzo[c][2,6]naphthyridine-8-carbonitrile (156 mg) as a gray solid which was sufficiently pure enough for subsequent chemical transformations. LCMS (ESI) 222.4 $(M+1)^+$. $^1$HNMR (400 MHz, DMSO-$d_6$) 12.2 (1H, s), 9.96 (1H, s), 8.90 (1H, d, 5.1 Hz), 8.77 (1H, d, 8.2 Hz), 8.13 (1H, d, 5.1 Hz), 7.73 (1H, dd 8.2, 1.6 Hz), 7.70 (1H, d, 1.6 Hz).

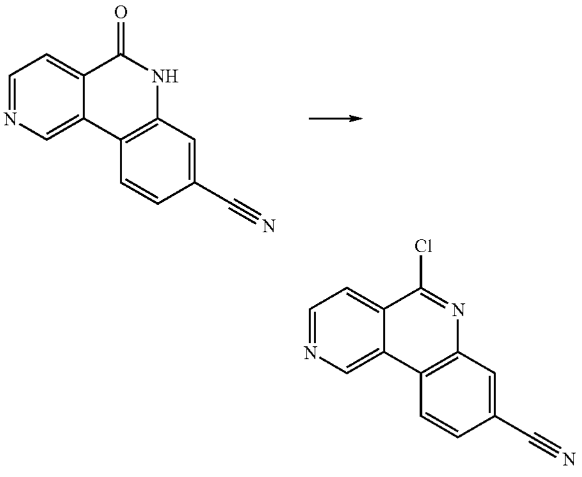

Phosphorus oxychloride (2 mL) was added to the 5-oxo-5,6-dihydrobenzo[c][2,6]naphthyridine-8-carbonitrile (150 mg, 0.66 mmol). The mixture was heated reflux for 3 hours at which time LCMS analysis indicated the absence of any starting material. Volatiles were removed under vacuum and the crude product was dissolved in dichloromethane, washed with brine and saturated aqueous sodium bicarbonate and dried over sodium sulfate. After concentrating under vacuum, the crude product was triturated with ethyl acetate and hexanes to give 5-chlorobenzo[c][2,6]naphthyridine-8-carbonitrile (125 mg). LCMS (ESI) 240.3 $(M+1)^+$.

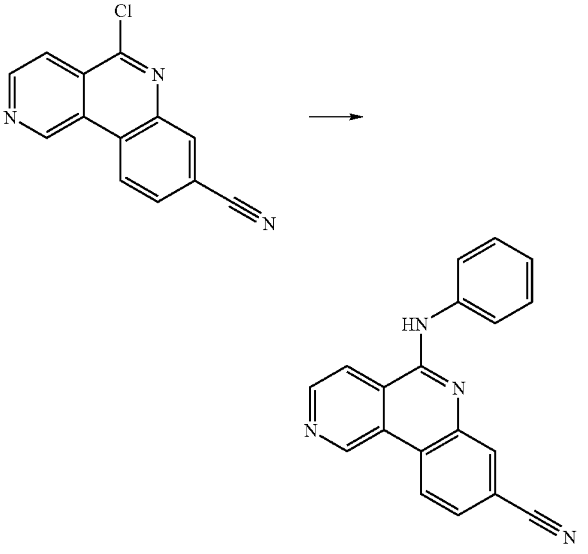

A mixture of the 5-chlorobenzo[c][2,6]naphthyridine-8-carbonitrile (30 mg, 0.13 mmol), aniline (60 mg, 0.65 mmol) and dimethylformamide (0.2 mL) was heated to 120° C. in a microwave reactor for 10 minutes. LCMS indicated that absence of starting material. The mixture was diluted with water and left to stand for a few minutes as 5-(phenylamino)benzo[c][2,6]naphthyridine-8-carbonitrile (25 mg) precipitated as an off-white solid. LCMS (ESI) 297.3 $(M+1)^+$.

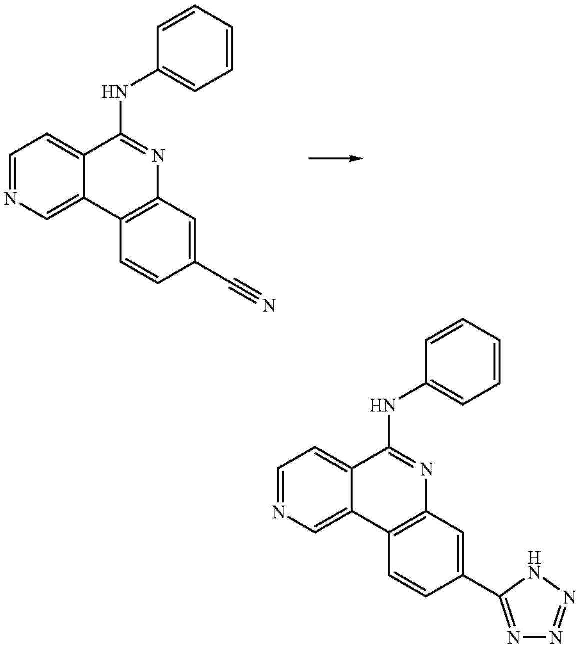

Sodium azide (65 mg, 1 mmol) and ammonium chloride (53 mg, 1 mmol) were added to a crude mixture of the 5-(phenylamino)benzo[c][2,6]naphthyridine-8-carbonitrile (25 mg, 0.084 mmol) in dimethylformamide (0.2 mL). The mixture was heated for 18 h at 120° C. at which time LCMS analysis indicated the absence of any starting material. The mixture was diluted with water and purified by preparative HPLC to give N-phenyl-8-(1H-tetrazol-5-yl)benzo[c][2,6]naphthyridin-5-amine (14 mg). LCMS (ESI) 340.3 $(M+1)^+$. $^1$HNMR (400 MHz, $CD_3OD$) 10.11 (1H, s), 8.96 (1H, d, 5.9 Hz), 8.85 (1H, d, 8.2 Hz), 8.53 (1H, d, 5.5 Hz), 8.47 (1H, s), 8.16 (1H, d, 8.6 Hz), 7.88 (1H, s), 7.86 (1H, d, 0.8 Hz), 7.57-7.51 (3H, m), 7.36-7.31 (2H, m).

Representative compounds are set forth hereafter in Table 1.

TABLE 1

| Compound | Molecular Weight | LCMS (ES) m/z |
|---|---|---|
| 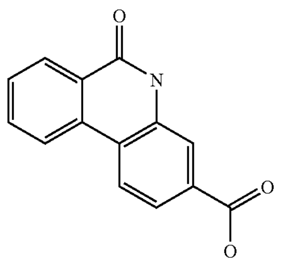 | 239.2 | 240 $[M+1]^+$ |
| 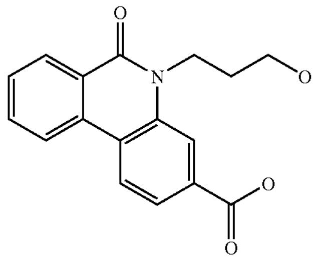 | 297.3 | 298 $[M+1]^+$ |
| 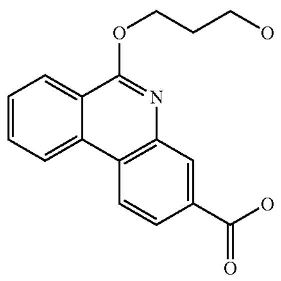 | 297.3 | 298 $[M+1]^+$ |
| 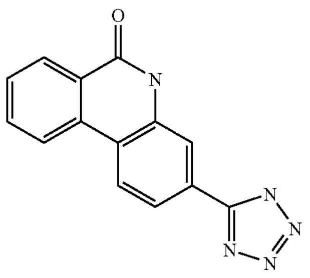 | 263.3 | 264 $[M+1]^+$ |

TABLE 1-continued

| | | |
|---|---|---|
| 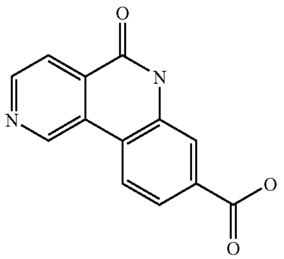 | 240.2 | 241 $[M+1]^+$ |
| 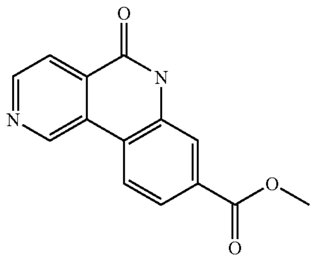 | 254.2 | 255 $[M+1]^+$ |
| 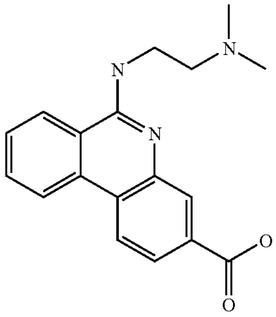 | 309.4 | 310 $[M+1]^+$ |
| 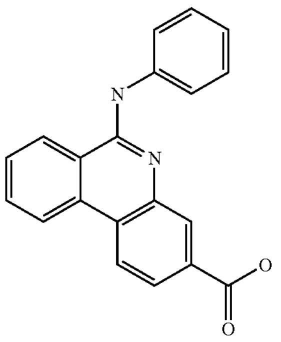 | 314.3 | 315 $[M+1]^+$ |
| 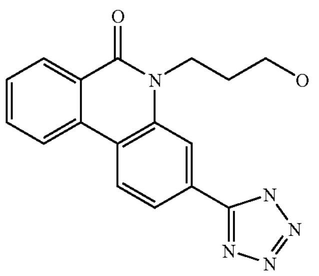 | 321.3 | 322 $[M+1]^+$ |

TABLE 1-continued
| | | |
|---|---|---|
| 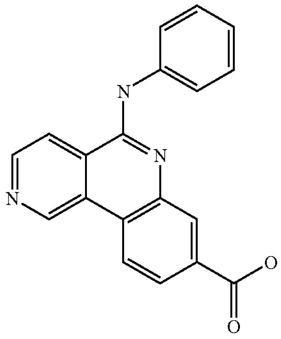 | 315.3 | 316 $[M+1]^+$ |
| 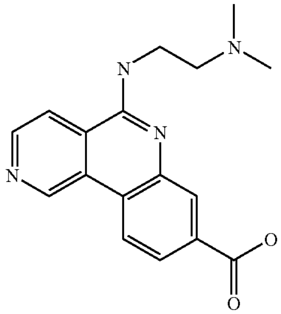 | 310.4 | 311 $[M+1]^+$ |
| 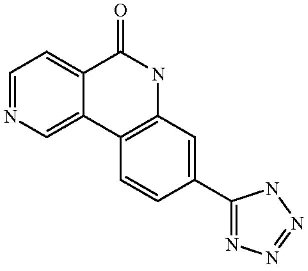 | 264.3 | 265 $[M+1]^+$ |
| 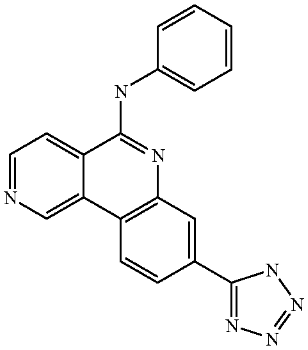 | 339.4 | 340 $[M+1]^+$ |
| 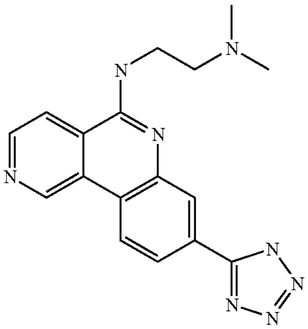 | 334.4 | 335 $[M+1]^+$ |
| 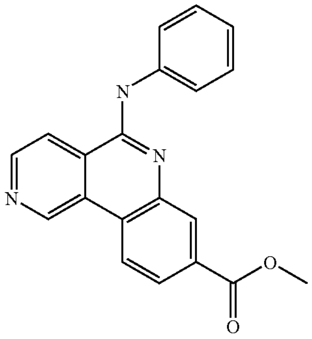 | 329.4 | 330 $[M+1]^+$ |
| 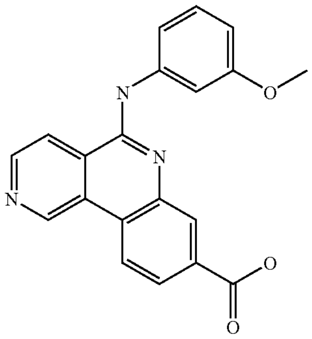 | 345.4 | 346 $[M+1]^+$ |
| 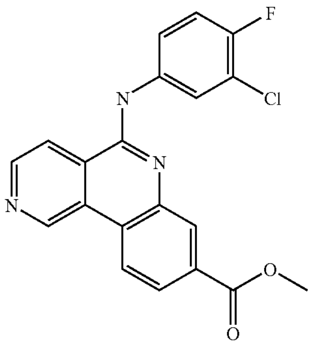 | 367.8 | 368 $[M+1]^+$ |
| Structure | MW | LCMS (ES) m/z [M + 1]+ |
|---|---|---|
| 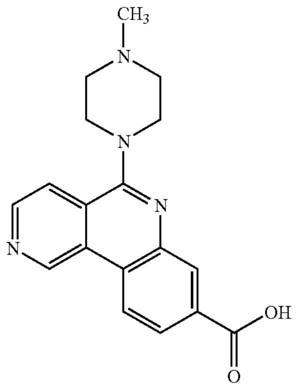 | 322.36 | 323 |

TABLE 1-continued
| | | |
|---|---|---|
| 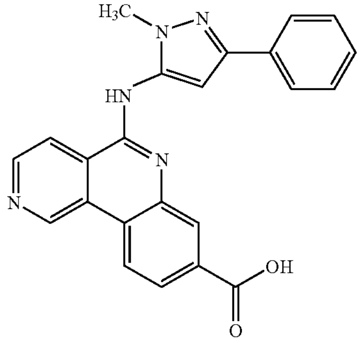 | 395.41 | 396 |
| 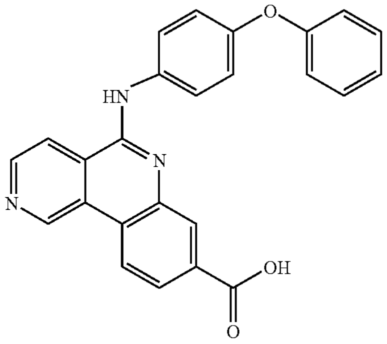 | 407.42 | 408 |
| 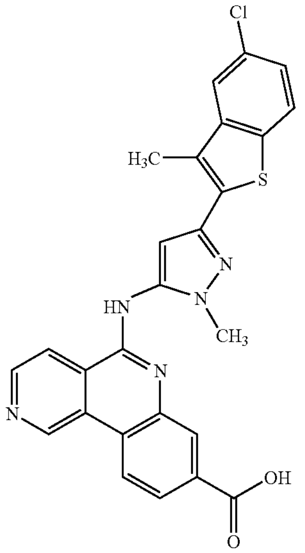 | 499.97 | 500 |
| 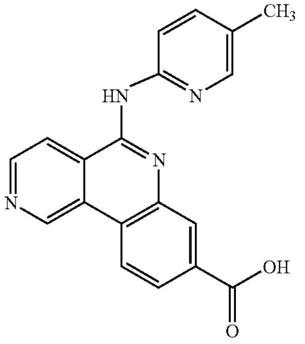 | 330.34 | 331 |
TABLE 1-continued
| | | |
|---|---|---|
| 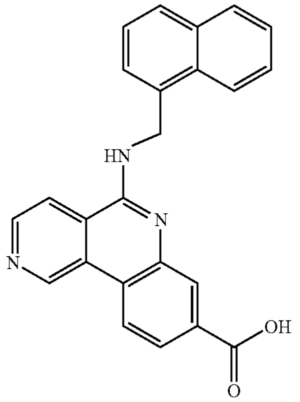 | 379.41 | 380 |
| 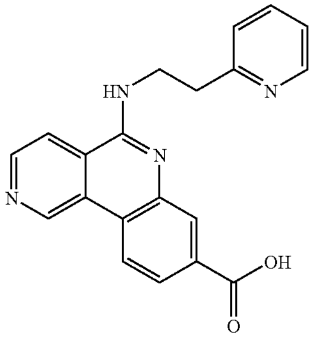 | 344.37 | 345 |
| 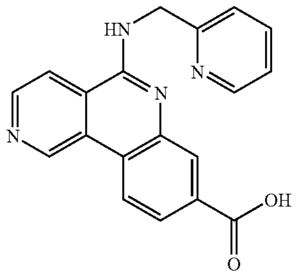 | 330.34 | 331 |
| 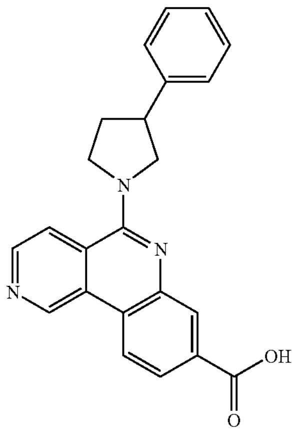 | 369.42 | 370 |

TABLE 1-continued
| | | |
|---|---|---|
| 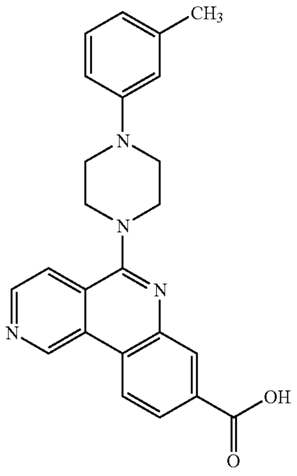 | 398.46 | 399 |
| 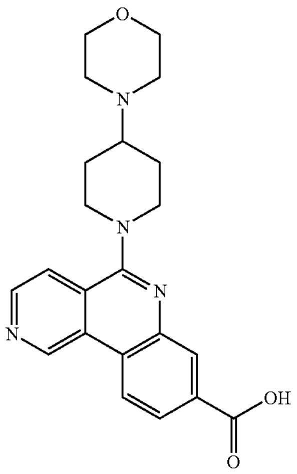 | 392.45 | 393 |
| 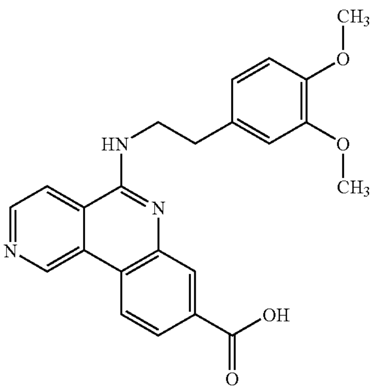 | 403.43 | 404 |
TABLE 1-continued
| | | |
|---|---|---|
| 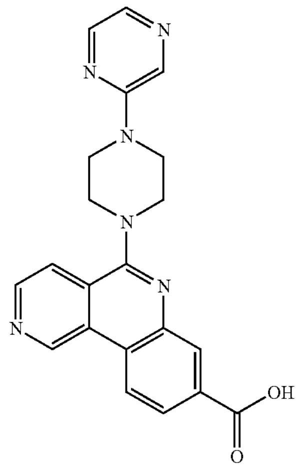 | 386.41 | 387 |
| 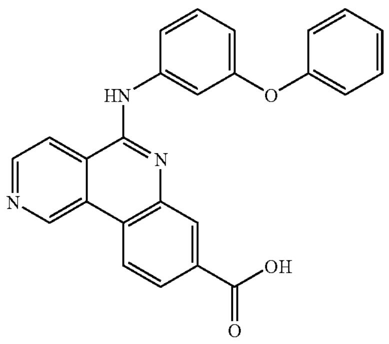 | 407.42 | 408 |
| 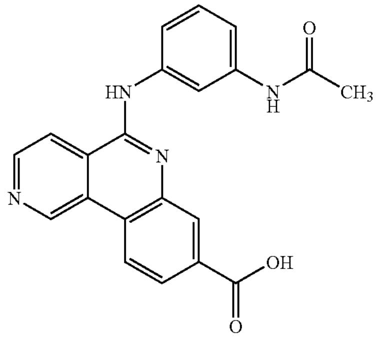 | 372.38 | 373 |
| 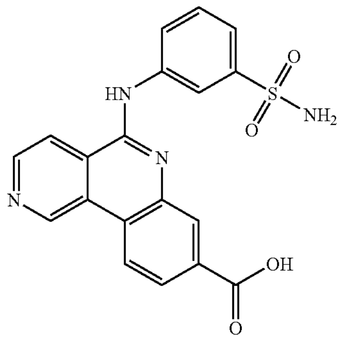 | 394.40 | 395 |

TABLE 1-continued
| | | |
|---|---|---|
| 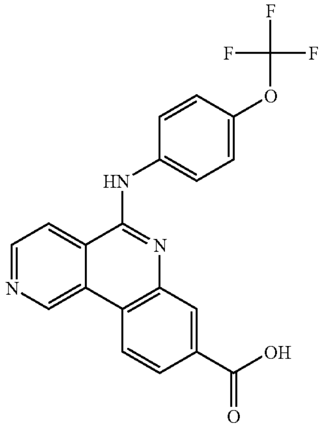 | 399.32 | 400 |
| 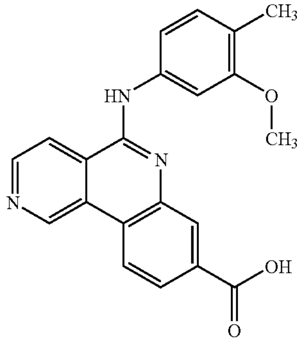 | 359.38 | 360 |
| 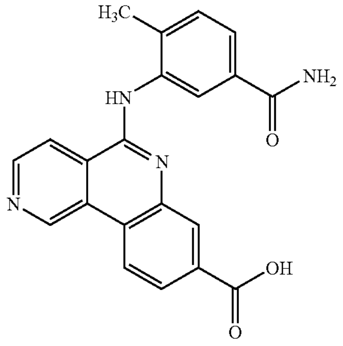 | 372.38 | 373 |
| 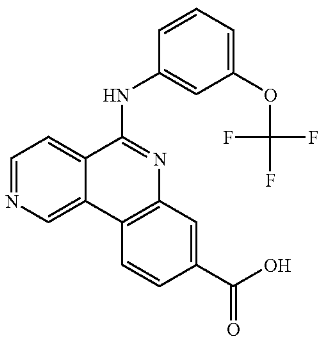 | 399.32 | 400 |
| 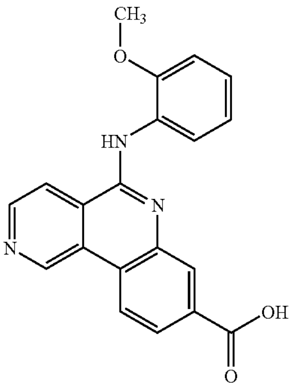 | 345.35 | 346 |
| 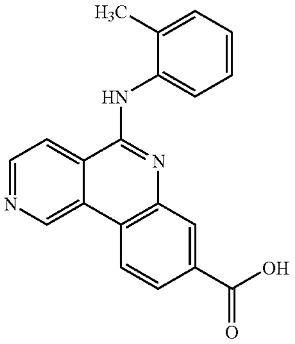 | 329.35 | 330 |
| 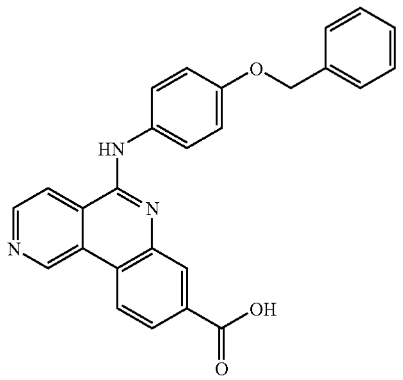 | 421.45 | 422 |
| 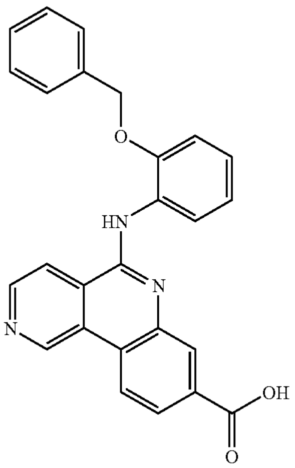 | 421.45 | 422 |

TABLE 1-continued
| | | |
|---|---|---|
| 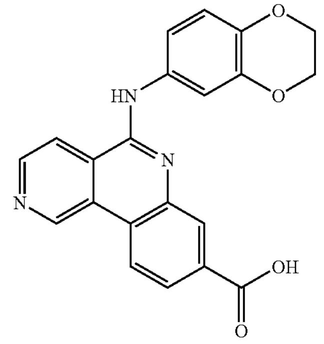 | 373.36 | 374 |
| 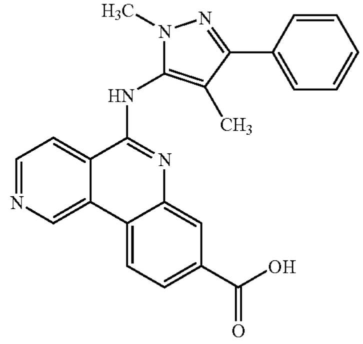 | 409.44 | 410 |
| 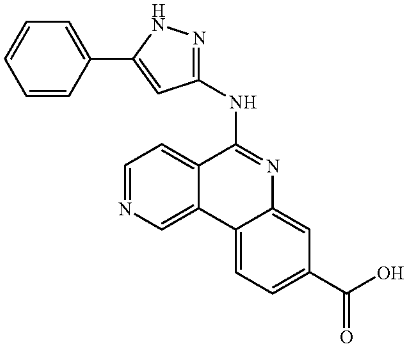 | 381.39 | 382 |
| 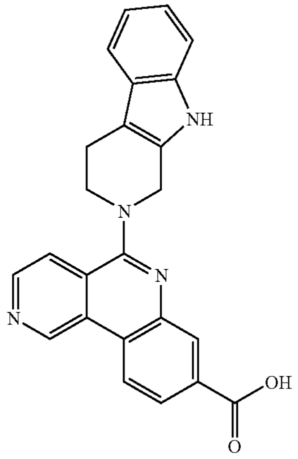 | 394.43 | 395 |
TABLE 1-continued
| | | |
|---|---|---|
| 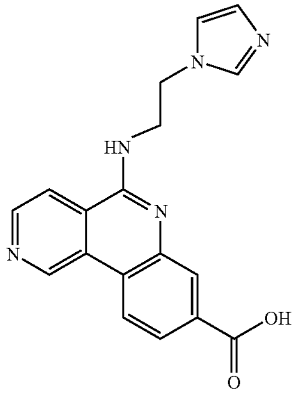 | 333.34 | 334 |
| 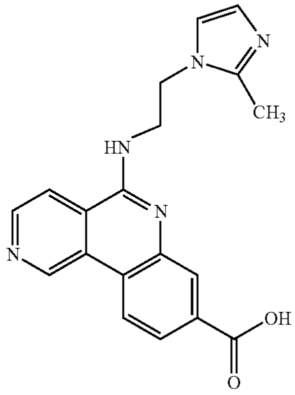 | 347.37 | 348 |
| 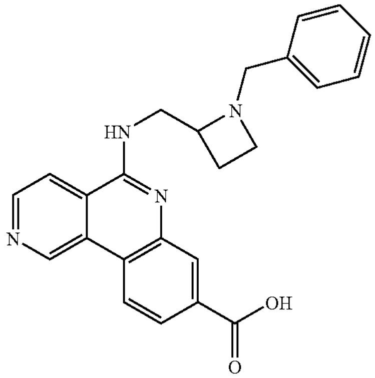 | 398.46 | 399 |
| 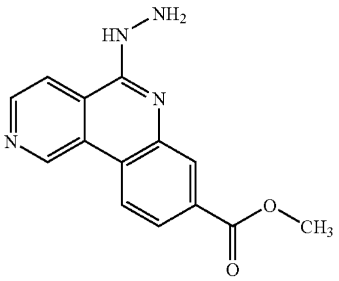 | 268.27 | 269 |

TABLE 1-continued
| | | |
|---|---|---|
| 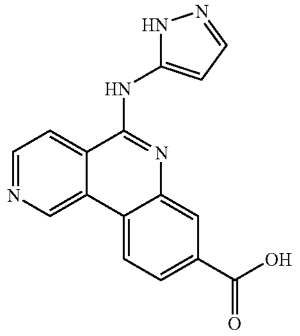 | 305.29 | 306 |
| 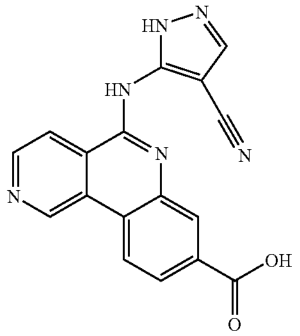 | 330.30 | 331 |
| 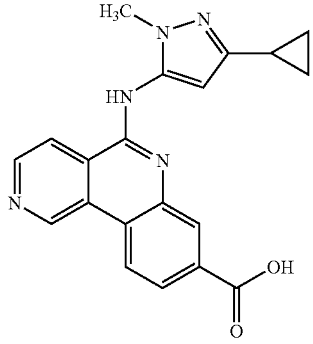 | 359.38 | 360 |
| 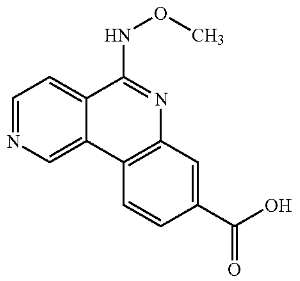 | 269.26 | 270 |
| 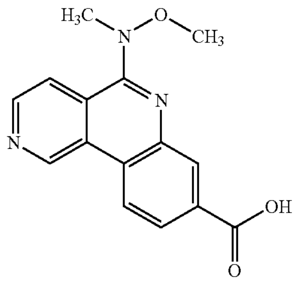 | 283.28 | 284 |
TABLE 1-continued
| | | |
|---|---|---|
| 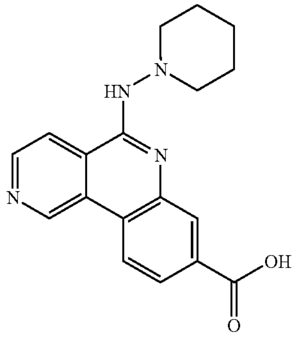 | 322.36 | 323 |
| 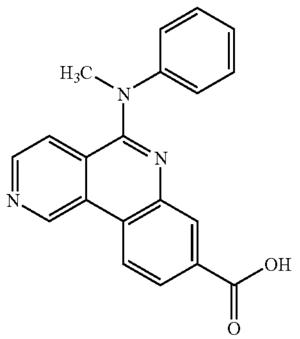 | 329.35 | 330 |
| 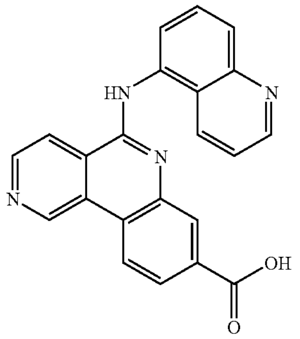 | 366.37 | 367 |
| 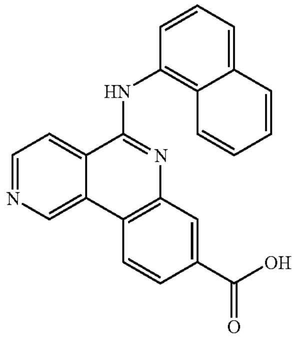 | 365.38 | 366 |

TABLE 1-continued
| | | |
|---|---|---|
| 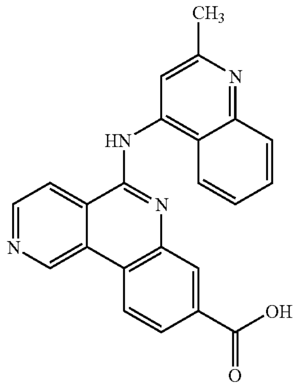 | 380.40 | 381 |
| 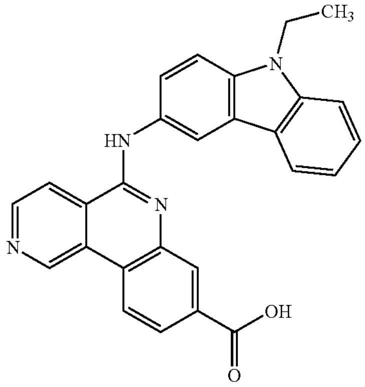 | 432.47 | 433 |
| 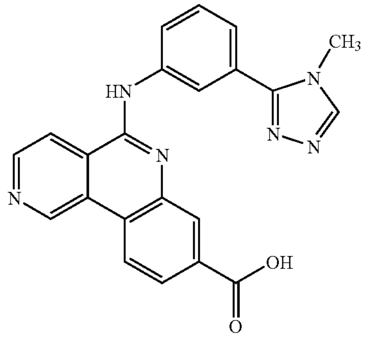 | 396.40 | 397 |
| 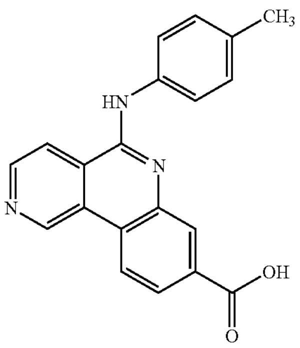 | 329.35 | 330 |
TABLE 1-continued
| | | |
|---|---|---|
| 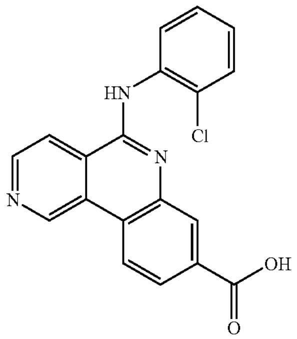 | 349.77 | 350 |
| 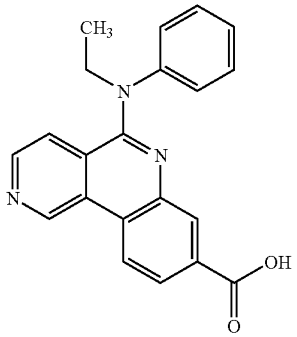 | 343.38 | 344 |
| 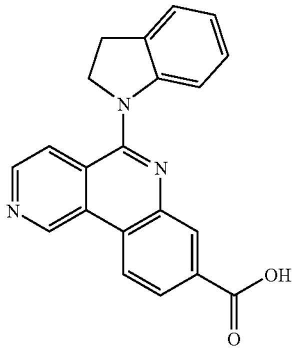 | 341.36 | 342 |
| 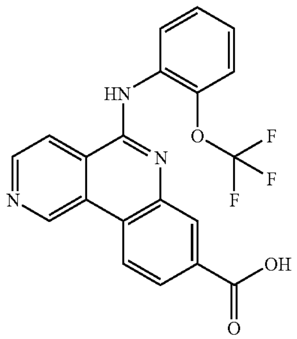 | 399.32 | 400 |

TABLE 1-continued
| | | |
|---|---|---|
| 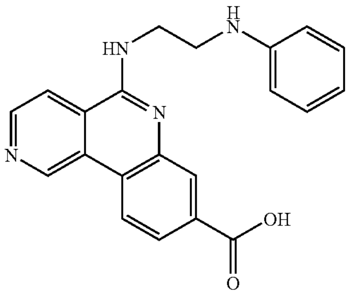 | 358.39 | 359 |
| 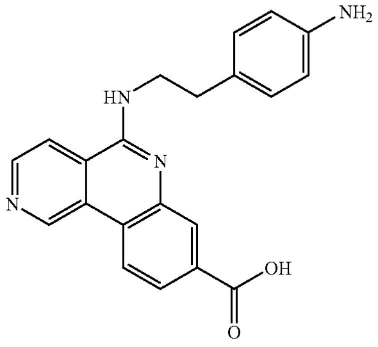 | 358.39 | 359 |
| 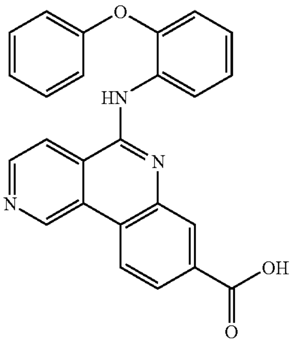 | 407.42 | 408 |
| 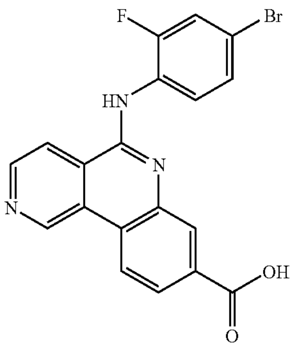 | 412.21 | 413 |
TABLE 1-continued
| | | |
|---|---|---|
| 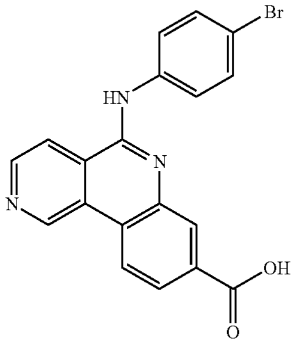 | 394.22 | 395 |
| 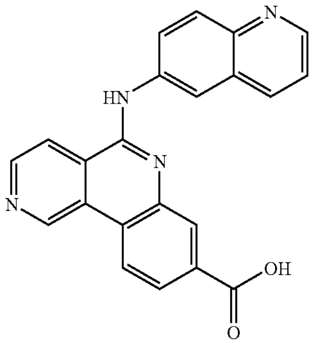 | 366.37 | 367 |
| 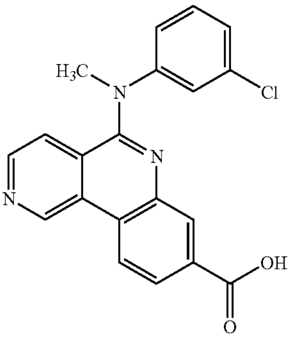 | 363.80 | 364 |
| 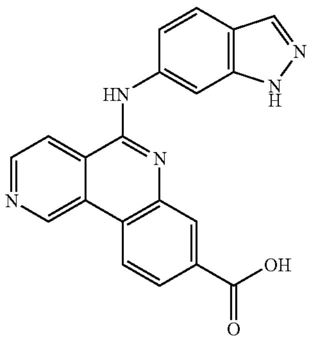 | 355.35 | 356 |

TABLE 1-continued
| | | |
|---|---|---|
| 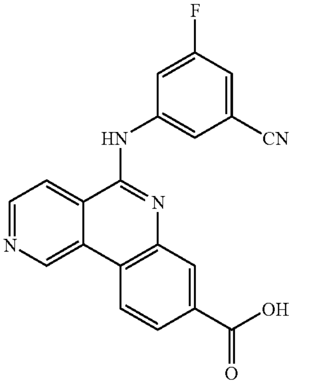 | 358.33 | 359 |
| 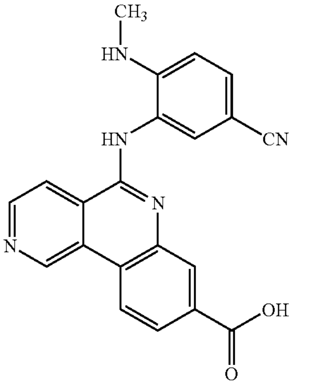 | 369.38 | 370 |
| 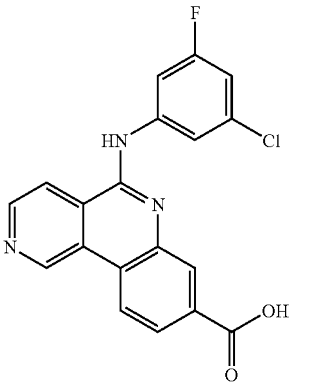 | 367.76 | 367 |
| 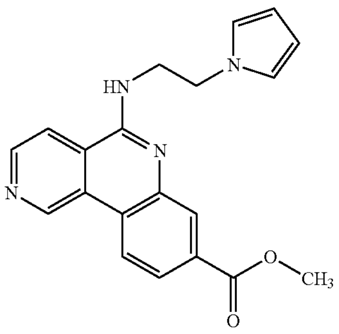 | 346.38 | 347 |
| 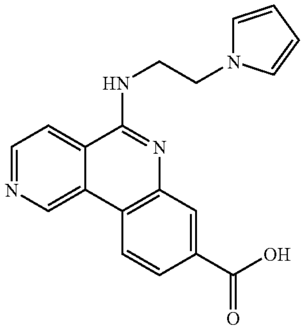 | 332.36 | 333 |
| 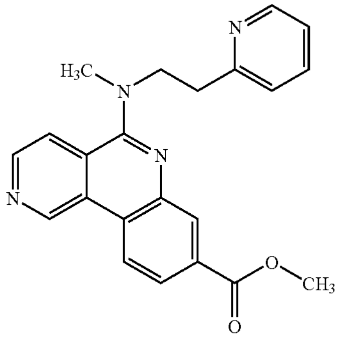 | 372.42 | 373 |
| 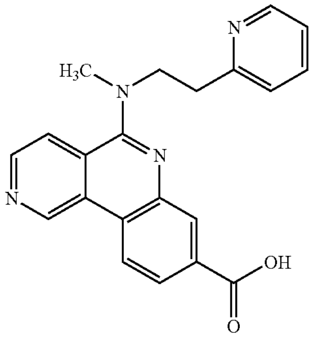 | 358.39 | 359 |
| 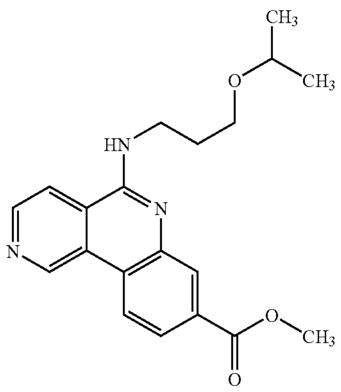 | 353.41 | 354 |

TABLE 1-continued
| | | |
|---|---|---|
| 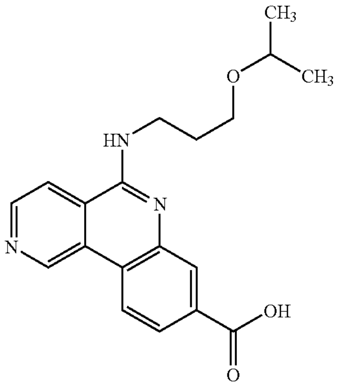 | 339.39 | 340 |
| 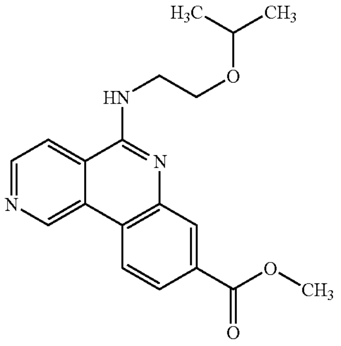 | 339.39 | 340 |
| 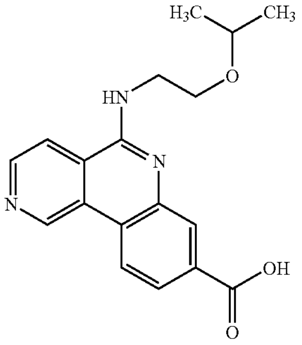 | 325.36 | 326 |
| 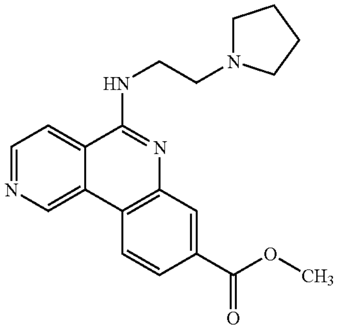 | 350.41 | 351 |
TABLE 1-continued
| | | |
|---|---|---|
| 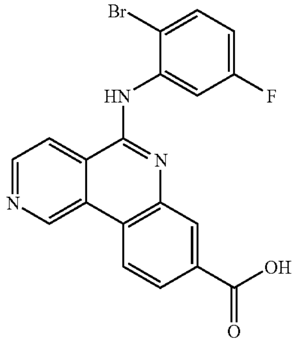 | 412.21 | 413 |
| 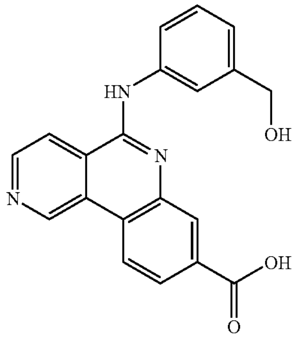 | 345.35 | 346 |
| 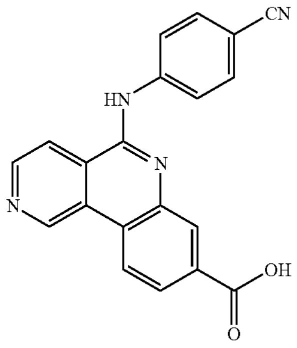 | 340.33 | 341 |
| 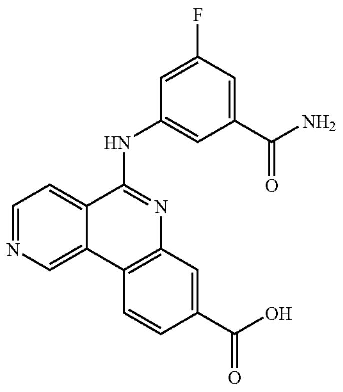 | 376.34 | 377 |

TABLE 1-continued
| | | |
|---|---|---|
| 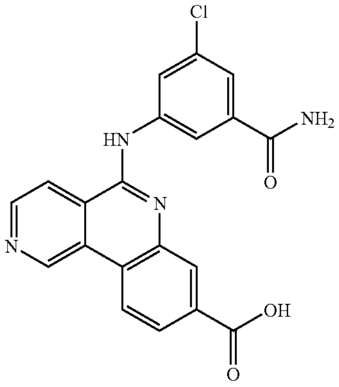 | 392.80 | 394 |
| 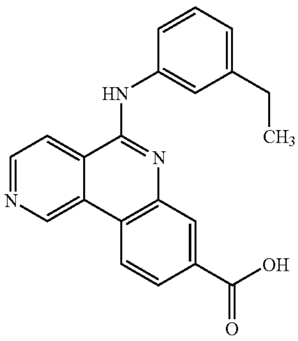 | 343.38 | 344 |
| 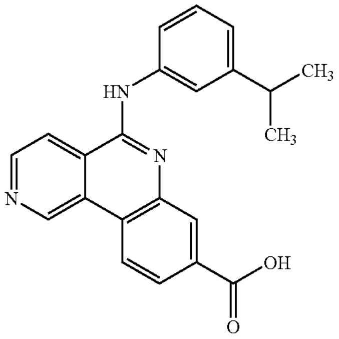 | 357.41 | 358 |
| 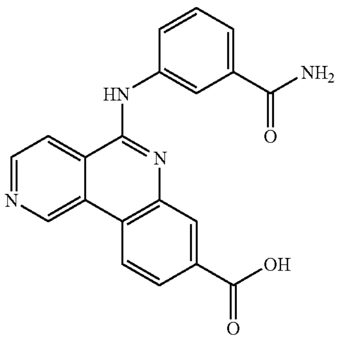 | 358.35 | 359 |
TABLE 1-continued
| | | |
|---|---|---|
| 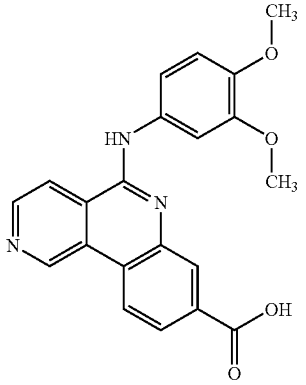 | 375.38 | 376 |
| 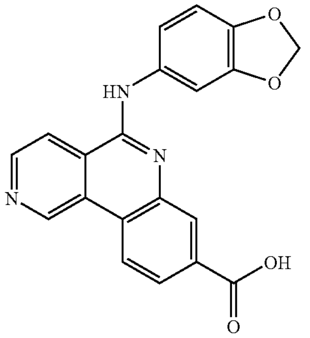 | 359.33 | 360 |
| 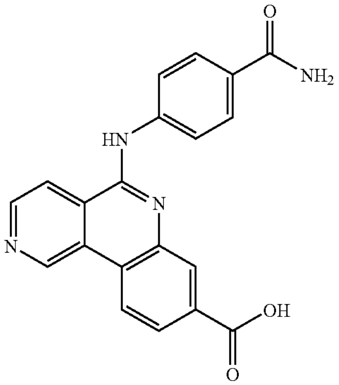 | 358.35 | 359 |
| 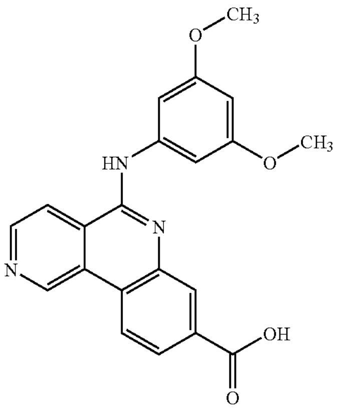 | 375.38 | 376 |

TABLE 1-continued

| | | |
|---|---|---|
| 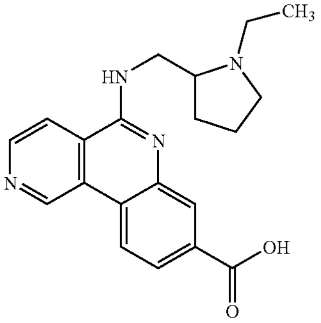 | 350.41 | 351 |
| 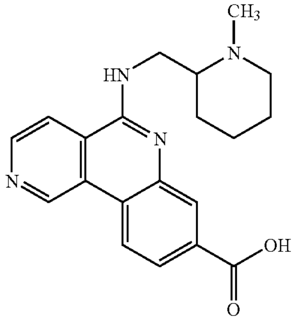 | 350.41 | 351 |
| 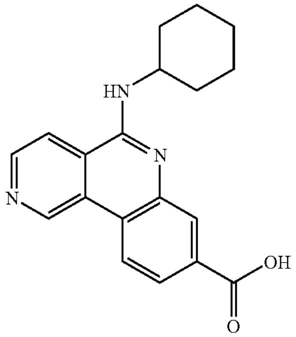 | 321.37 | 322 |
| 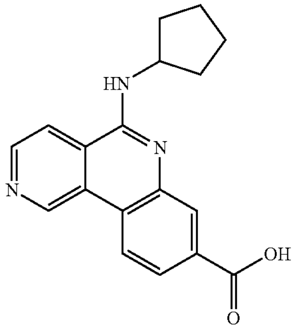 | 307.35 | 308 |
| 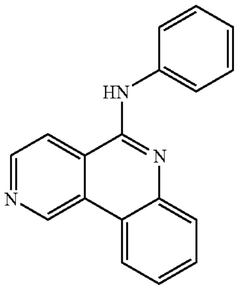 | 271.32 | 272 |
| 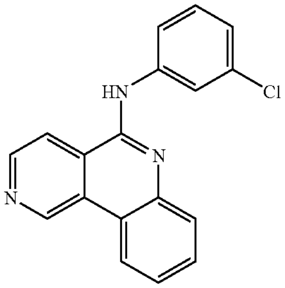 | 305.76 | 306 |
| 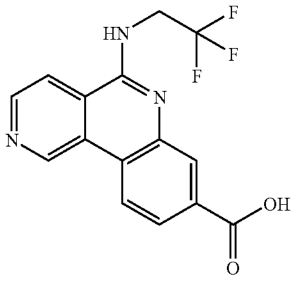 | 321.1 | 322 |
| 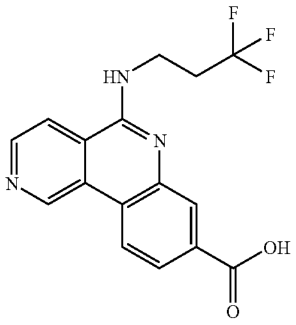 | 335.1 | 336 |
| 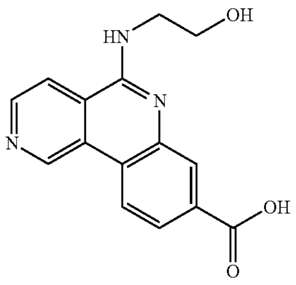 | 283.1 | 284 |

Process 2

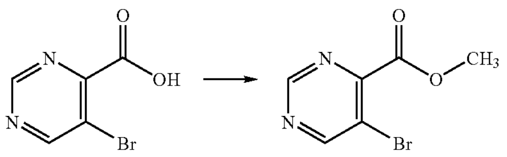

5-bromopyrimidine-4-carboxylic acid (prepared according to the procedure described in U.S. Pat. No. 4,110,450) (1.0 eq, 6.14 g, 30.2 mmol) was suspended in $CH_2Cl_2$ (100 ml). Oxalylchloride (1.1 eq, 2.9 ml, 33.0 mmol) was added followed by 2 drops of DMF. The mixture was stirred at room temperature overnight and the volatiles were removed in vacuo. The residue was taken in MeOH (50 ml) and heated. After evaporation of MeOH in vacuo the compound was dissolved in $CH_2Cl_2$ and poured on a prepacked silica gel column. The material was eluted using 20% Ethyl acetate in hexanes. Evaporation of the solvent provided methyl-5-bromopyrimidine-4-carboxylate as a light orange crystalline solid (2.54 g, 39% yield). LCMS (ES): 95% pure, m/z 217 $[M]^+$; 219 $[M+2]^+$; $^1H$ NMR ($CDCl_3$, 400 MHz) δ 4.04 (s, 3H), 9.02 (s, 1H), 9.21 (s, 1H) ppm.

Process 3

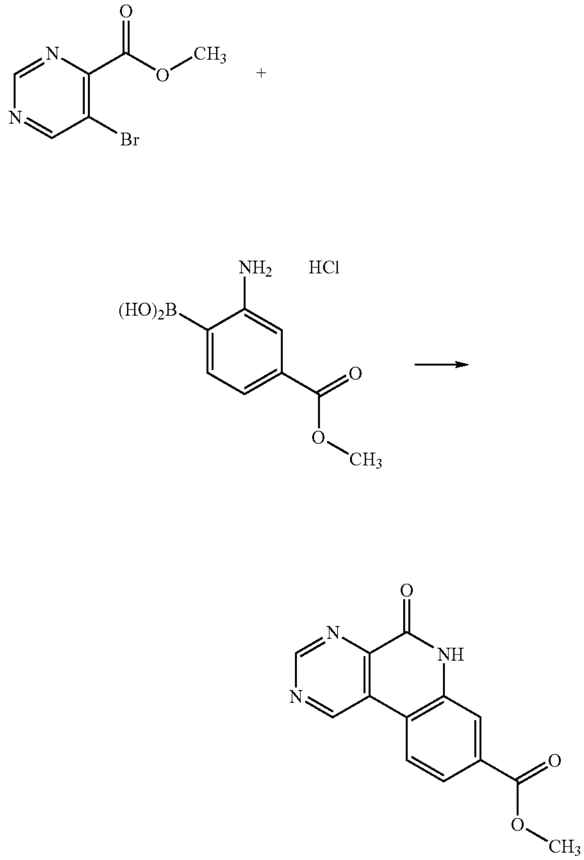

Sodium acetate (4.0 eq, 1.92 g, 23.41 mmol) and 1,1'-bis (diphenylphosphino)ferrocene palladium (II) chloride (complexed with dichloromethane) (0.05 eq, 214 mg, 0.29 mmol) were added to a mixture of methyl-5-bromopyrimidine-4-carboxylate (1.0 eq, 1.27 g, 5.85 mmol), and 2-amino-4-(methoxycarbonyl)phenylboronic acid hydrochloride (1.0 eq, 1.35 g, 5.85 mmol) in anhydrous DMF (10 ml). The Mixture was stirred under nitrogen atmosphere at 120° C. for 18 hours. Water and brine were added and the resulting solid impurities filtered off. The material was extracted with $CH_2Cl_2$ (4×) and the combined extracts dried over $Na_2SO_4$. After evaporation of $CH_2Cl_2$, the remaining DMF was evaporated by heating the residue in vacuo. The resulting solid was triturated in $CH_2Cl_2$, filtered and dried to provide methyl 5-oxo-5,6-dihydropyrimido[4,5-c]quinoline-8-carboxylate as a beige solid (127 mg, 8.5% yield). LCMS (ES): >80% pure, m/z 256 $[M+1]^+$; $^1H$ NMR (DMSO-$d_6$, 400 MHz) δ 3.79 (s, 3H), 7.81 (d, J=8.0, 1H), 8.68 (d, J=8.8, 1H), 9.49 (s, 1H), 10.19 (s, 1H), 12.37 (s, 1H) ppm.

Process 4

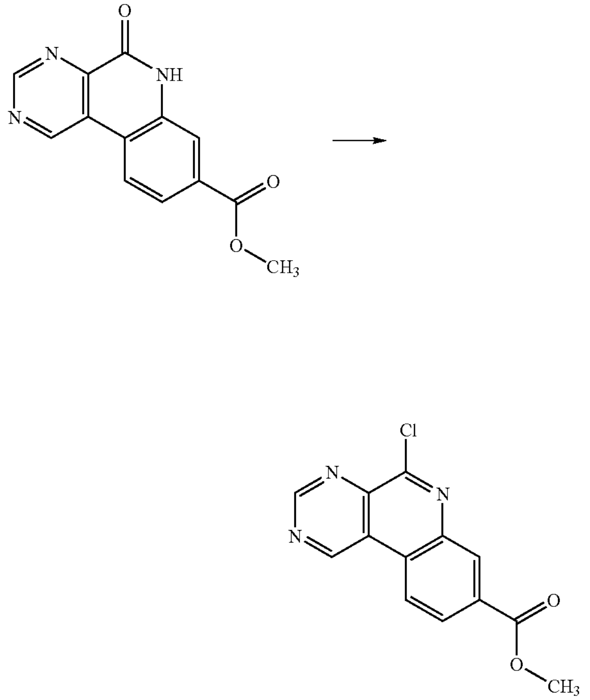

In a vial, methyl 5-oxo-5,6-dihydropyrimido[4,5-c]quinoline-8-carboxylate (1.0 eq, 151 mg, 0.59 mmol) was mixed in toluene (1 ml) with DIEA (1.5 eq, 155 ul, 0.89 mmol) and $POCl_3$ (5 eq, 270 ul, 3.0 mmol). The mixture was stirred at 120° C. for 1 hour and cooled down to room temperature. After adding ice and water the compound was extracted with $CH_2Cl_2$ (4×). The solution was filtered over $Na_2SO_4$ and filtered through a pad of celite. After evaporation of the volatiles, the material was triturated in a mixture of ethyl acetate and hexanes, filtered and dried to afford methyl 5-chloropyrimido[4,5-c]quinoline-8-carboxylate as a light brown fluffy solid (115 mg, 71% yield). LCMS (ES): 95% pure, m/z 274 $[M+1]^+$. $^1H$ NMR (DMSO-$d_6$, 400 MHz) δ 3.96 (s, 3H), 8.37 (dd, J=1.6, J=8.4, 1H), 8.60 (d, J=1.6, 1H), 9.15 (d, J=8.8, 1H), 9.74 (s, 1H), 10.61 (s, 1H) ppm Process 5

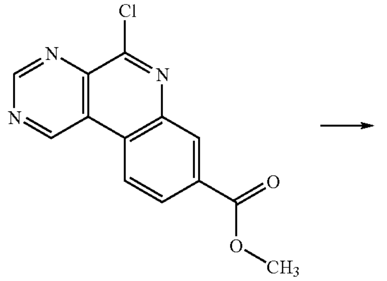

-continued

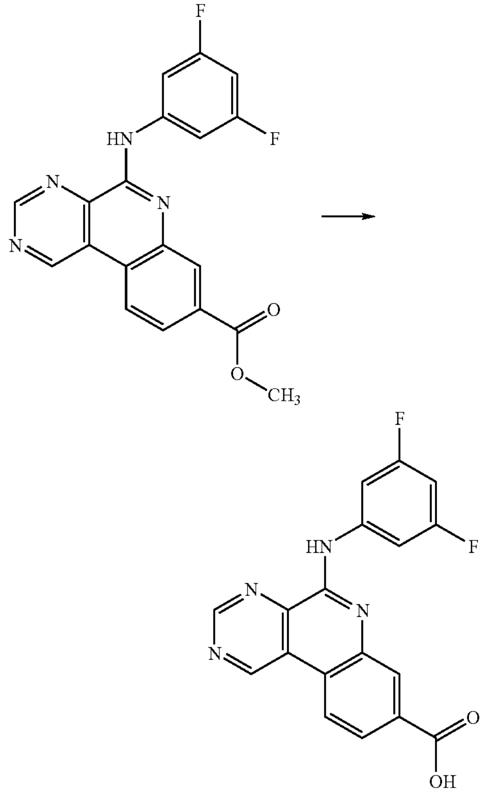

methyl 5-chloropyrimido[4,5-c]quinoline-8-carboxylate (10 mg) was mixed with 3,5-difluoroaniline (100 mg) in NMP (0.1 ml). The mixture was heated under microwaves at 120° C. for 10 minutes. Water was added and the material extracted with $CH_2Cl_2$. The solvent was removed. Trituration in a mixture of ethylacetate and hexanes and filtration provided methyl 5-(3,5-difluorophenylamino)pyrimido[4,5-c]quinoline-8-carboxylate. This material was suspended in a 1:1 mixture of THF and MeOH (2 ml) and a 5N aqueous solution of Lithium Hydroxide was added. The mixture was vigorously stirred at room temperature for 5 hours. Water and 6N hydrochloric acid were added to induce precipitation of the expected material. The solid was filtered, washed with water, dried and suspended in MeOH. Filtration and drying gave 5-(3,5-difluorophenylamino)pyrimido[4,5-c]quinoline-8-carboxylic acid as a yellow solid (4 mg, 31% yield). LCMS (ES): 95% pure, m/z 353 $[M+1]^+$. $^1H$ NMR (DMSO-$d_6$, 400 MHz) δ 6.90 (br t, J=9.6, 1H), 8.02 (dd, J=1.6, J=8.0, 1H), 8.18 (br d, J=10.8, 2H), 8.34 (d, J=1.6, 1H), 8.86 (d, J=8.4, 1H), 9.65 (s, 1H), 10.40 (s, 1H), 10.44 (s, 1H) ppm.

Process 6

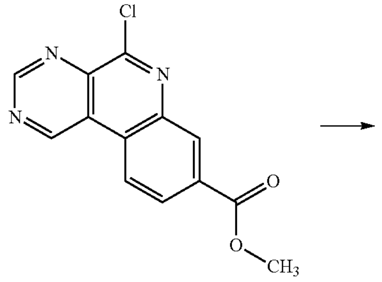

-continued

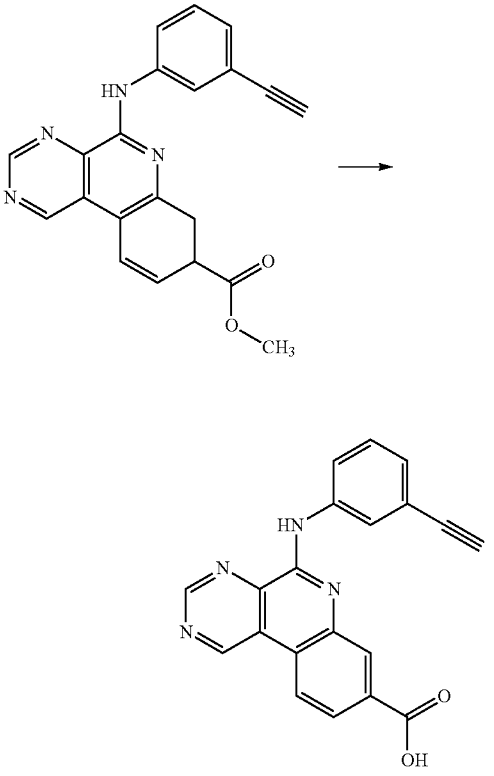

5-(3-ethynylphenylamino)pyrimido[4,5-c]quinoline-8-carboxylic acid was prepared using the same method, starting from methyl 5-chloropyrimido[4,5-c]quinoline-8-carboxylate and 3-ethynylaniline. LCMS (ES): 95% pure, m/z 341 $[M+1]^+$. $^1H$ NMR (DMSO-$d_6$, 400 MHz) δ 4.20 (s, 1H), 7.19 (d, J=7.6, 1H), 7.42 (t, J=8.0, 1H), 7.99 (dd, J=1.6, J=8.4, 1H), 8.30 (d, J=1.6, 1H), 8.34 (dd, J=1.6, J=8.0, 1H), 8.49 (br s, 1H), 8.85 (d, J=8.8, 1H), 9.65 (s, 1H), 10.11 (s, 1H), 10.43 (s, 1H) ppm.

Representative analogs (Table 2) were prepared by the same method using methyl 5-chloropyrimido[4,5-c]quinoline-8-carboxylate and appropriate amines.

TABLE 2

| Structure | MW | LCMS (ES) m/z |
|---|---|---|
| 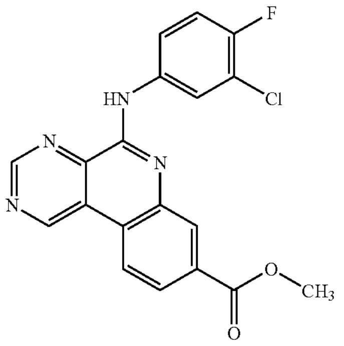 | 382.78 | 383 $[M + 1]^+$ |

TABLE 2-continued

| Structure | MW | LCMS (ES) m/z |
|---|---|---|
| 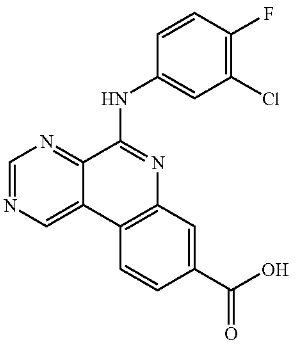 | 368.75 | 369 [M + 1]$^+$ |
| 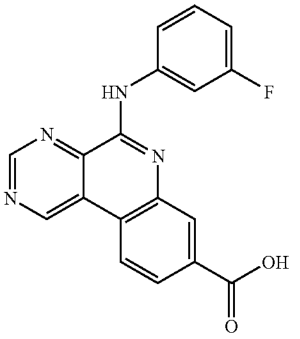 | 334.30 | 335 [M + 1]$^+$ |
| 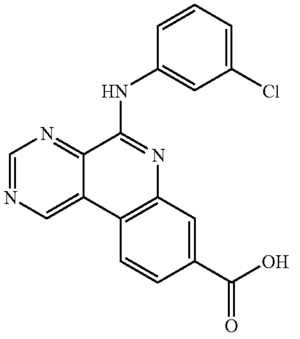 | 350.76 | 351 [M + 1]$^+$ |
| 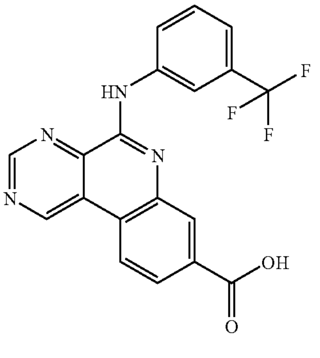 | 384.3114 | 385 [M + 1]$^+$ |

TABLE 2-continued

| Structure | MW | LCMS (ES) m/z |
|---|---|---|
| 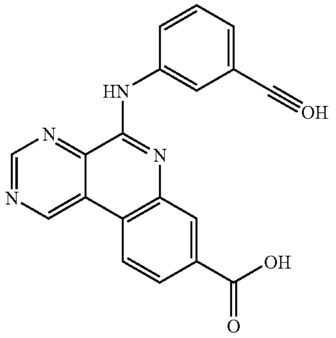 | 339.3501 | 340 [M + 1]$^+$ |

Process 7

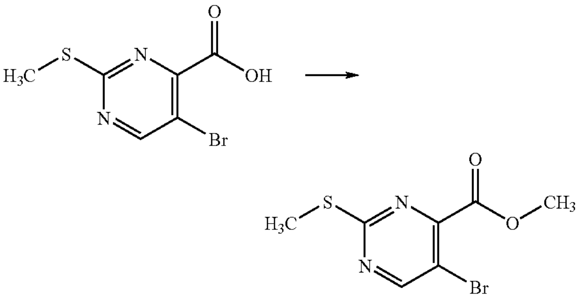

methyl-5-bromo-2-(methylthio)pyrimidine-4-carboxylate was prepared according to the procedure used in process 2 for the preparation of methyl-5-bromopyrimidine-4-carboxylate. LCMS (ES): >90% pure, m/z 263 [M]$^+$, 265 [M+2]$^+$; $^1$H NMR ($CDCl_3$, 400 MHz) δ 2.59 (s, 3H), 4.00 (s, 3H), 8.71 (s, 1H) ppm.

Process 8

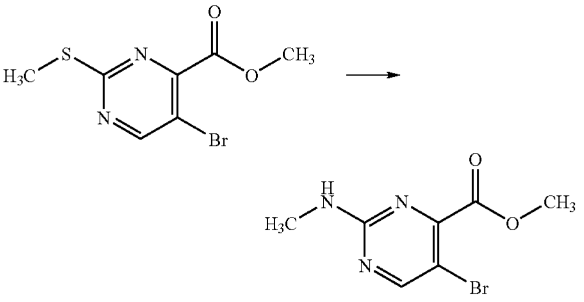

Methyl-5-bromo-2-(methylthio)pyrimidine-4-carboxylate (1.0 eq, 661 mg, 2.52 mmol) was dissolved in $CH_2Cl_2$ (10 ml). meta-chloro perbenzoic acid (m-cpba, 77% pure grade, 2.5 eq, 1.42 g, 6.34 mmol) was added and the mixture was stirred at room temperature for 1 hour. To the resulting suspension was added anhydrous THF (10 ml), methylamine hydrochloride (10 eq, 1.7 g, 25.18 mmol) and DIEA (10 eq, 4.3 ml, 24.69 mmol) and the mixture stirred at room temperature overnight. The solvents were removed in vacuo prior to adding $CH_2Cl_2$ and a saturated aqueous sodium bicarbonate solution. The two phases were decanted and two further $CH_2Cl_2$ extractions were carried out. The combined extracts were dried over $Na_2SO_4$ and the solvents evaporated. Purification by flash chromatography on silica gel (20-30% ethylacetate in hexanes) provided methyl 5-bromo-2-(methylamino)pyrimidine-4-carboxylate as an off-white solid (461 mg, 75% yield). LCMS (ES): >95% pure, m/z 246 $[M]^+$, 248 $[M+2]^+$.

Process 9

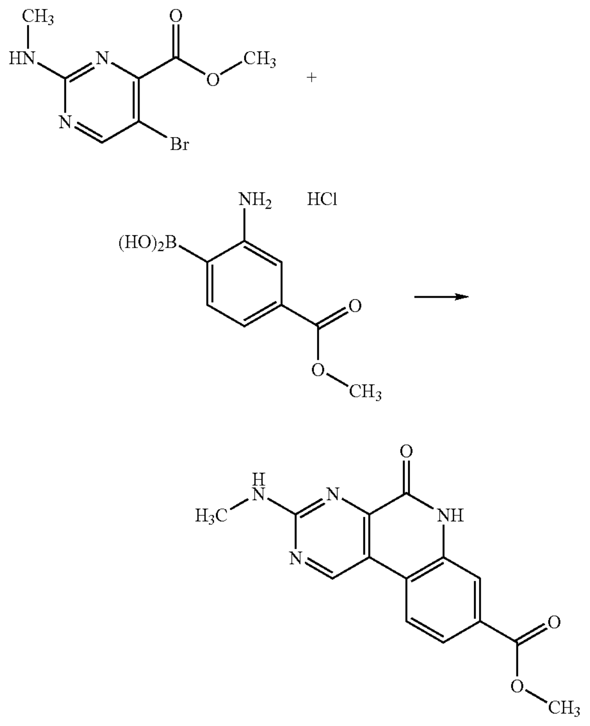

Sodium acetate (3.0 eq, 240 mg, 2.93 mmol) and 1,1'-bis (diphenylphosphino)ferrocene palladium (II) chloride (complexed with dichloromethane) (0.05 eq, 36 mg, 0.049 mmol) were added to a mixture of methyl 5-bromo-2-(methylamino) pyrimidine-4-carboxylate (1.0 eq, 240 mg, 0.975 mmol), and 2-amino-4-(methoxycarbonyl)phenylboronic acid hydrochloride (1.0 eq, 226 mg, 0.98 mmol) in anhydrous DMF (2 ml). The mixture was stirred under microwave heating at 120° C. for 10 min. Addition of water induced precipitation of the expected compound that was filtered and dried. methyl 3-(methylamino)-5-oxo-5,6-dihydropyrimido[4,5-c]quinoline-8-carboxylate (57 mg, 21% yield). LCMS (ES): >80% pure, m/z 285 $[M+1]^+$.

Process 10

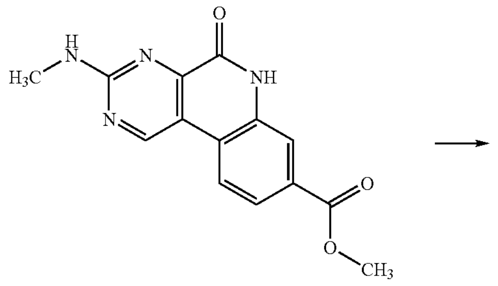

-continued

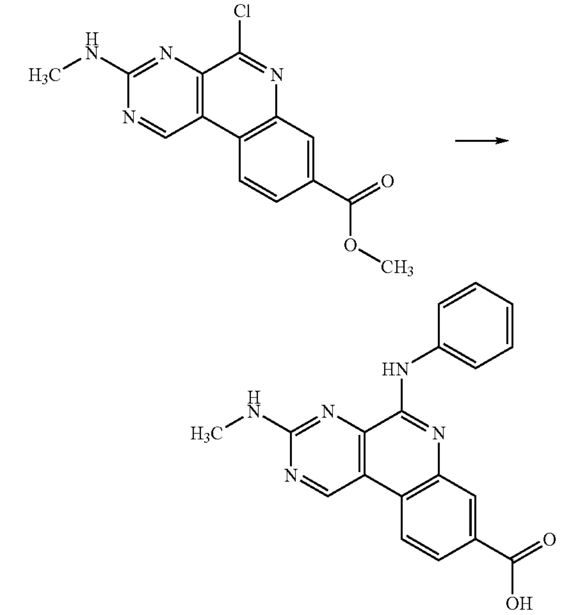

3-(methylamino)-5-(phenylamino)pyrimido[4,5-c]quinoline-8-carboxylic acid was prepared using methods described in process 3 and 4 starting from methyl 3-(methylamino)-5-oxo-5,6-dihydropyrimido[4,5-c]quinoline-8-carboxylate. The final product was purified by flash chromatography and isolated as a yellow solid (0.35 mg). LCMS (ES): >95% pure, m/z 346 $[M+1]^+$.

Process 11

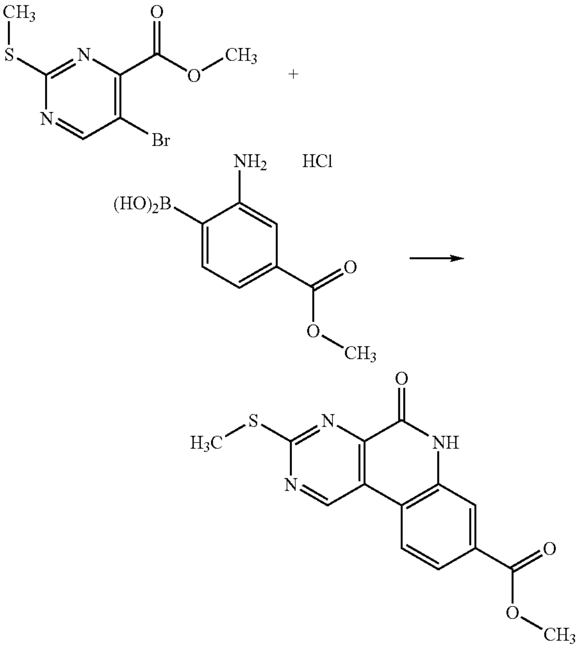

In a microwave vessel, methyl 5-bromo-2-(methylthio)pyrimidine-4-carboxylate (1.0 eq, 274 mg, 1.18 mmol), 2-amino-4-(methoxycarbonyl)phenylboronic acid hydrochloride (1.2 eq, 329 mg, 1.42 mmol), and sodium acetate (3.0 eq, 291 mg, 3.55 mmol) were mixed in anhydrous DMF (2 ml). The mixture was degassed by bubbling nitrogen gas in the solution for 10 min and the reaction heated under microwaves at 120° C. for 30 min. After cooling down the expected material crashed out of NMP. The solid was filtered, suspended in water filtered and dried. The material was triturated in AcOEt and filtered give a yellow solid. The same procedure was repeated 9 times using the same amounts of materials to provide methyl 3-(methylthio)-5-oxo-5,6-dihydropyrimido[4,5-c]quinoline-8-carboxylate (283 mg, 10% yield). LCMS (ES): >95% pure, m/z 302 $[M+1]^+$, $^1H$ NMR (DMSO-$d_6$, 400 MHz) δ 2.71 (s, 3H), 3.89 (s, 3H), 7.80 (dd, J=1.6, J=8.4, 1H), 7.97 (d, J=1.6, 1H), 8.59 (d, J=8.8, 1H), 9.98 (s, 1H), 12.34 (s, 1H) ppm.

Process 12

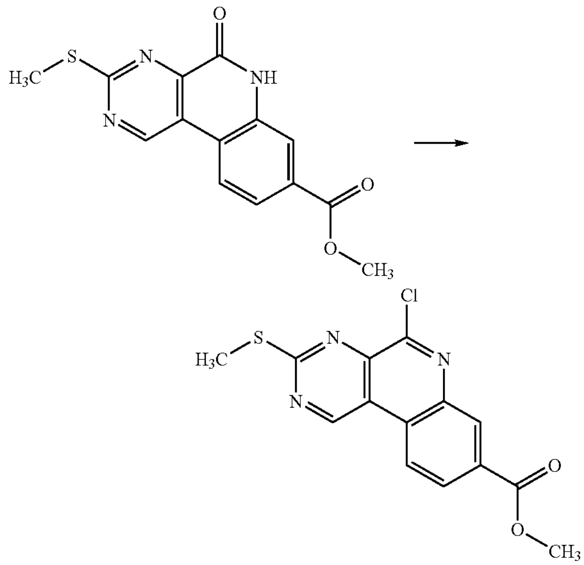

methyl 3-(methylthio)-5-oxo-5,6-dihydropyrimido[4,5-c]quinoline-8-carboxylate (1.0 eq, 279 mg, 0.926 mmol) was suspended in toluene (2 ml). $POCl_3$ (2 ml) and DIEA (0.5 ml) were added and the mixture stirred at 120° C. for 5 hours. The volatiles were removed in vacuo and $CH_2Cl_2$ was added. The organic phase was washed with saturated aqueous sodium bicarbonate, washed with water and dried over $Na_2SO_4$. The solution was filtered through a pad of celite and the solvents removed in vacuo. The material was triturated in hexanes and AcOEt, filtered and dried to provide methyl 5-chloro-3-(methylthio)pyrimido[4,5-c]quinoline-8-carboxylate as a beige solid (184 mg, 63% yield). LCMS (ES): >95% pure, m/z 320 $[M+1]^+$, 322 $[M+3]^+$.

Process 13

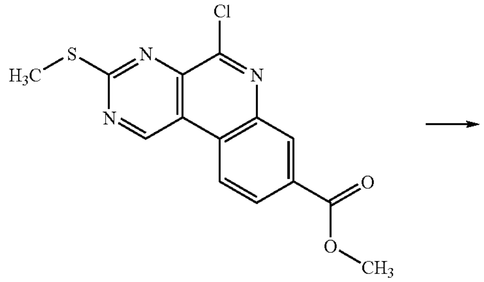

-continued

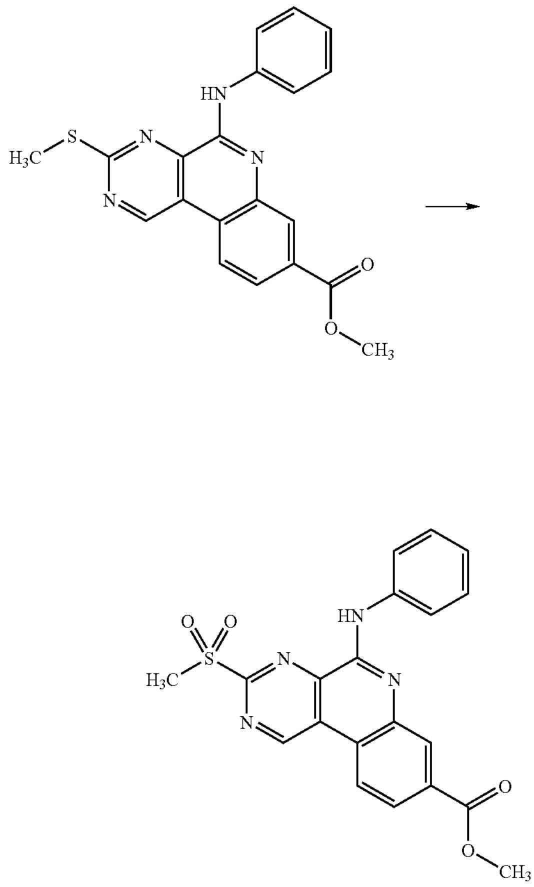

methyl 5-chloro-3-(methylthio)pyrimido[4,5-c]quinoline-8-carboxylate (1.0 eq, 182 mg, 0.57 mmol) was mixed with aniline (0.5 ml) in NMP (1 ml). The mixture was heated under microwave for 10 minutes at 120° C. Water was added and the resulting solid was filtered and dried. The compound was triturated in EtOAc and hexanes and filtered to afford methyl 3-(methylthio)-5-(phenylamino)pyrimido[4,5-c]quinoline-8-carboxylate as a yellow solid. LCMS (ES): >95% pure, m/z 377 $[M+1]^+$. This material was suspended in $CH_2Cl_2$ (4 ml) and meta-chloroperbenzoic acid (77% pure, 2.5 eq, 165 mg, 0.737 mmol) was added in small portions. After one hour, an additional amount (100 mg) of mcpba was added and the mixture stirred for 1.5 hours. After addition of more $CH_2Cl_2$, the organic phase was washed with water (4×), dried over $Na_2SO_4$ and the solution was filtered through a pad of silica gel, eluting with a MeOH/$CH_2Cl_2$ mixture. After evaporation of the solvents, methyl 3-(methylsulfonyl)-5-(phenylamino)pyrimido[4,5-c]quinoline-8-carboxylate was isolated as a yellow solid (166 mg, 72% yield). LCMS (ES): >95% pure, m/z 409 $[M+1]^+$, $^1H$ NMR (DMSO-$d_6$, 400 MHz) δ 3.77 (s, 3H), 3.93 (s, 3H), 7.15 (t, J=7.2, 1H), 7.45 (t, J=7.6, 2H), 7.99 (dd, J=2.0, J=8.4, 1H), 8.16 (d, J=7.6, 2H), 8.28 (d, J=2.0, 1H), 8.89 (d, J=8.8, 1H), 9.76 (s, 1H), 10.61 (s, 1H) ppm.

Process 14

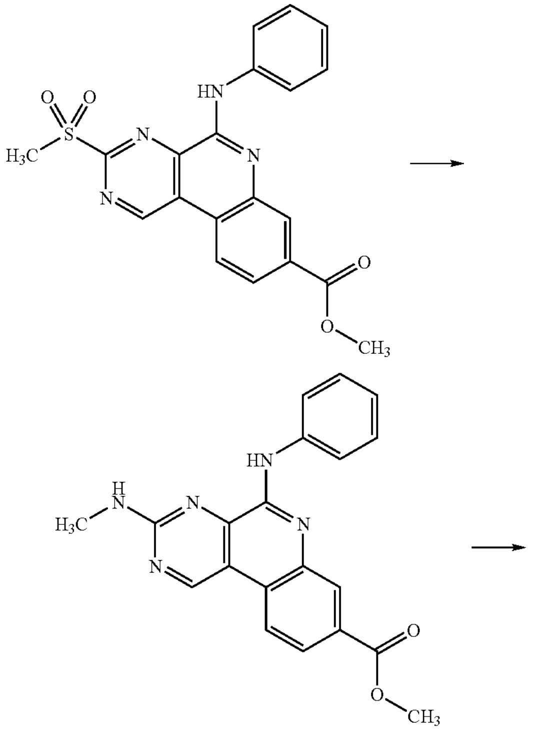

-continued

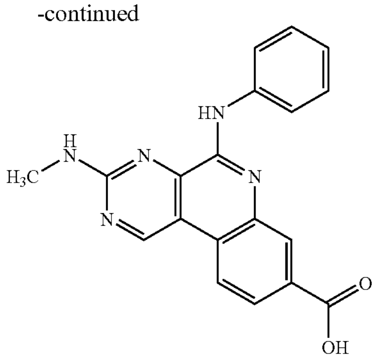

In a closed vial, methyl 3-(methylsulfonyl)-5-(phenylamino)pyrimido[4,5-c]quinoline-8-carboxylate (1.0 eq, 62 mg, 0.152 mmol) was mixed with Methylamine hydrochloride (100 mg), DIEA (260 ul) in DMF (1 ml). The mixture was stirred at 60° C. for 40 min. Addition of water induced precipitation of methyl 3-(methylamino)-5-(phenylamino)pyrimido[4,5-c]quinoline-8-carboxylate which was isolated by filtration. This material was suspended in a 1:1:1 mixture of THF, MeOH and water (4 ml), and vigorously stirred at 60° C. in the presence of LiOH (200 mg) for 1.5 hours. Water aqueous HCl were added and to reach pH=1. The solid was filtered, dried and triturated in AcOEt/hexanes to provide 3-(methylamino)-5-(phenylamino)pyrimido[4,5-c]quinoline-8-carboxylic acid as a yellow solid (40 mg, 74% yield). LCMS (ES): >95% pure, m/z 346 [M+1]+.

The following analogs (table 3) were prepared using the same method. After purification by preparative HPLC and genevac evaporation the material were isolated as solids.

TABLE 3

| Structure | Molecular Weight | LCMS (ES) m/z |
|---|---|---|
| 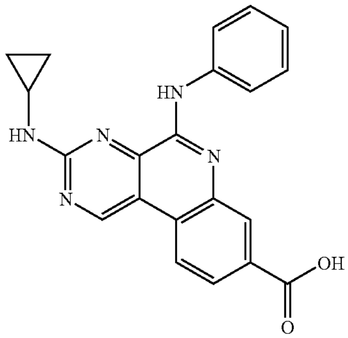 | 371.39 | 372 $[M + 1]^+$ |
| 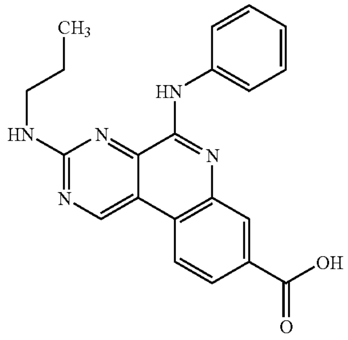 | 373.41 | 374 [M + 1]+ |

TABLE 3-continued
| | | |
|---|---|---|
| 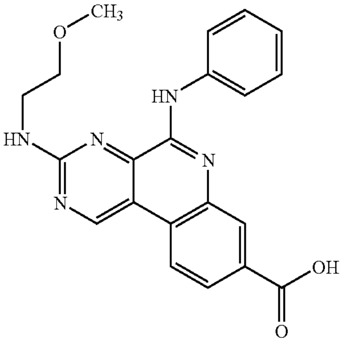 | 389.41 | 390 [M + 1]+ |
| 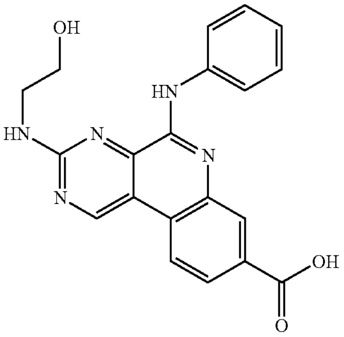 | 375.38 | 376 [M + 1]+ |
| 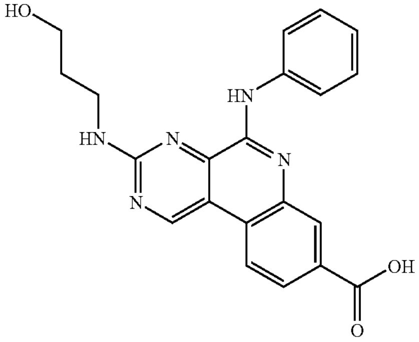 | 389.41 | 390 [M + 1]+ |
| 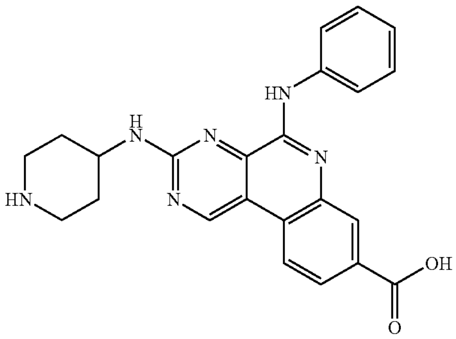 | 414.46 | 415 [M + 1]+ |

TABLE 3-continued
| | | |
|---|---|---|
| 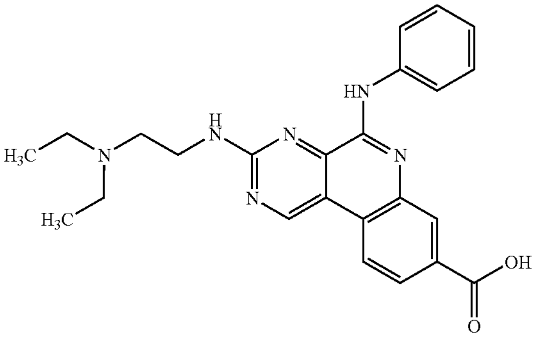 | 430.50 | 431 [M + 1]+ |
| 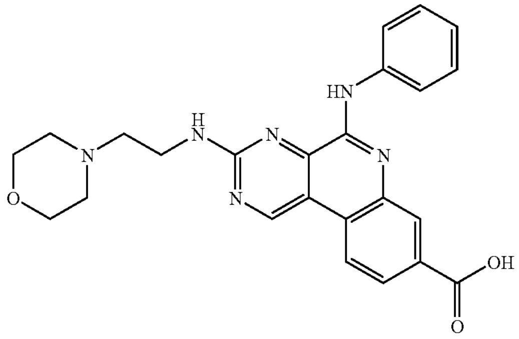 | 444.49 | 445 [M + 1]+ |
| 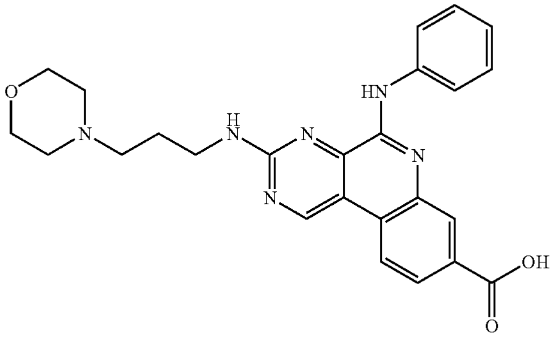 | 458.51 | 459 [M + 1]+ |
| 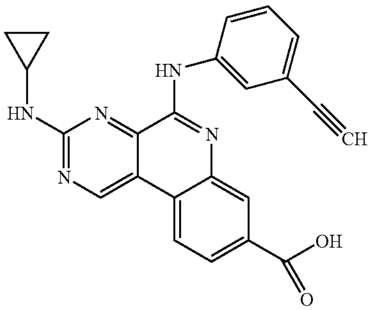 | 395.41 | 396 $[M + 1]^+$ |

TABLE 3-continued
| | | |
|---|---|---|
| 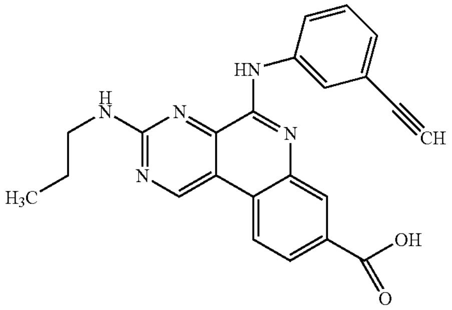 | 397.43 | 398 $[M + 1]^+$ |
| 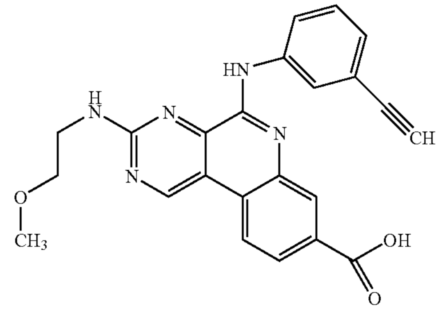 | 413.43 | 414 $[M + 1]^+$ |
| 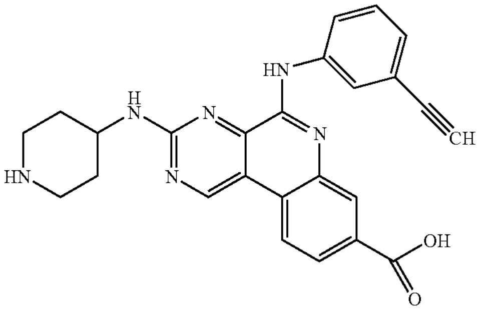 | 438.48 | 439 $[M + 1]^+$ |
| 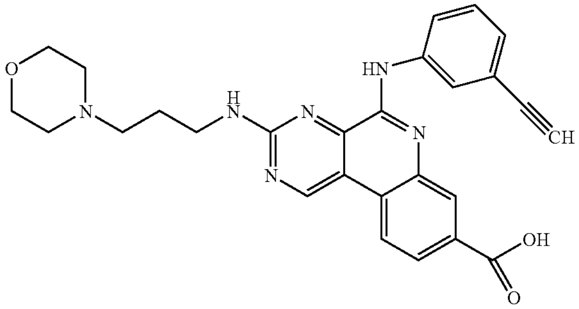 | 482.53 | 483 $[M + 1]^+$ |
| 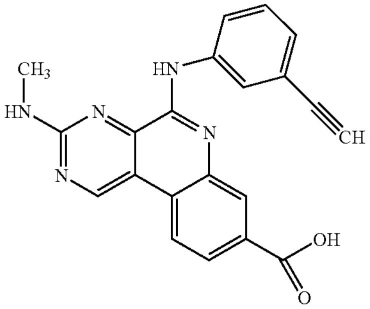 | 369.38 | 370 $[M + 1]^+$ |

TABLE 3-continued
| | | |
|---|---|---|
| 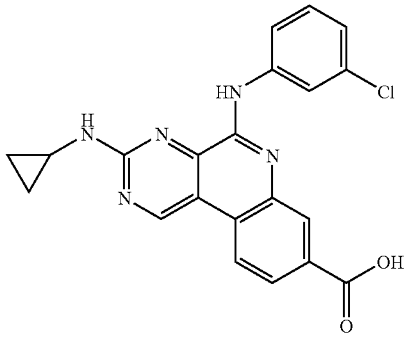 | 405.84 | 406 [M + 1]$^+$ |
| 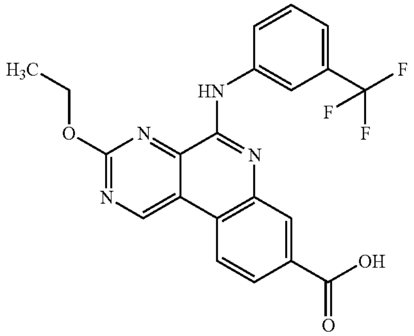 | 428.36 | 429 [M + 1]$^+$ |
| 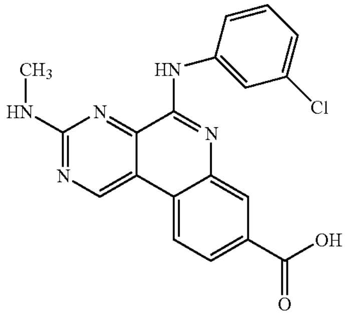 | 379.80 | 380 [M + 1]$^+$ |
| 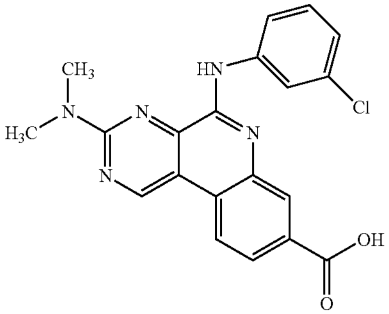 | 393.83 | 394 [M + 1]$^+$ |
| 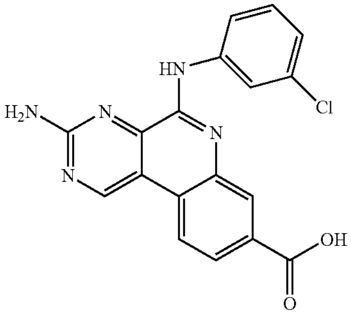 | 365.77 | 366 [M + 1]$^+$ |

TABLE 3-continued
| | | |
|---|---|---|
| 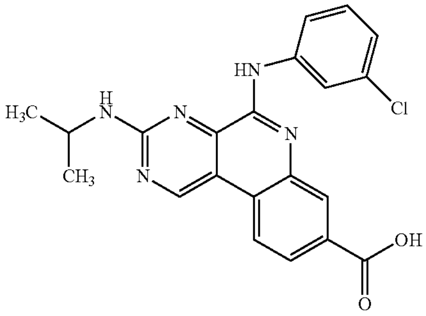 | 407.85 | 408 $[M + 1]^+$ |
| 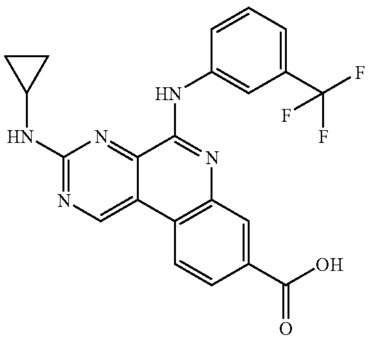 | 439.39 | 440 $[M + 1]^+$ |
| 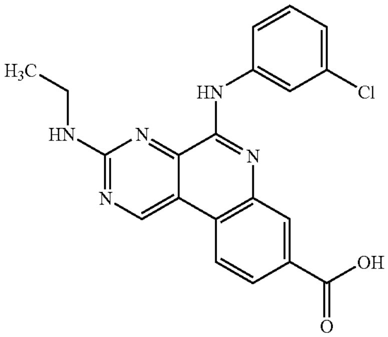 | 393.83 | 397 $[M + 1]^+$ |
| 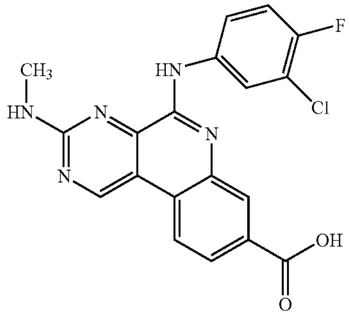 | 397.79 | 398 $[M + 1]^+$ |

TABLE 3-continued
| | | |
|---|---|---|
| 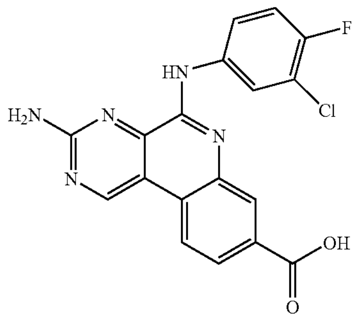 | 383.76 | 384 [M + 1]$^+$ |
| 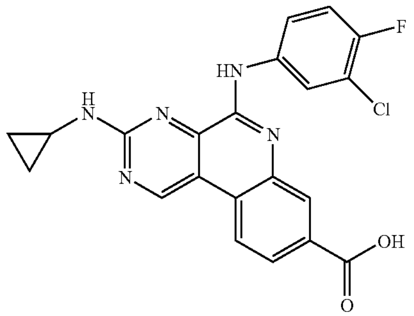 | 423.83 | 424 [M + 1]$^+$ |
| 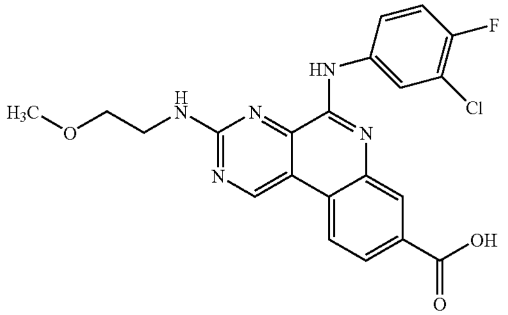 | 441.84 | 442 [M + 1]$^+$ |
| 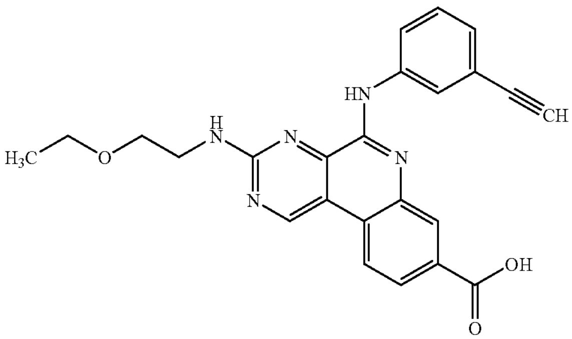 | 427.46 | 428 [M + 1]$^+$ |
| 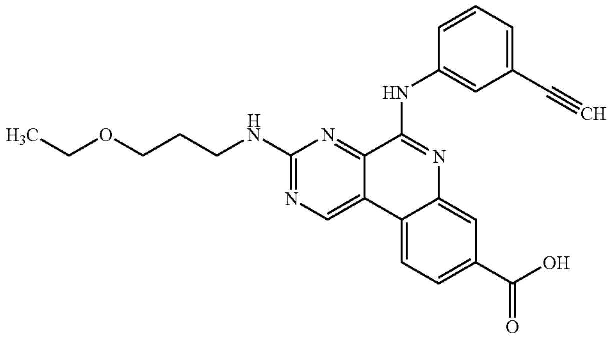 | 441.48 | 442 [M + 1]$^+$ |

TABLE 3-continued
| | | |
|---|---|---|
| 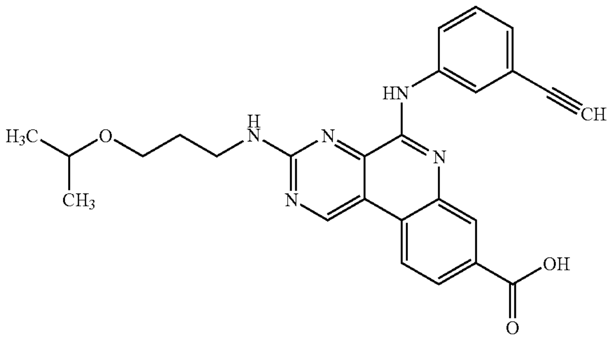 | 455.51 | 456 [M + 1]+ |
| 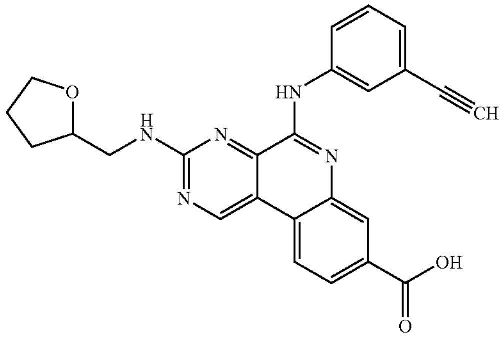 | 439.47 | 440 [M + 1]+ |
| 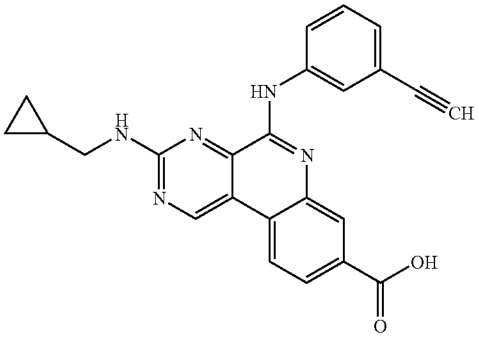 | 409.44 | 410 [M + 1]+ |
| 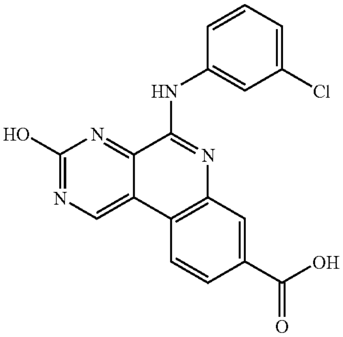 | 366.76 | 367 [M + 1]+ |

TABLE 3-continued
| | | |
|---|---|---|
| 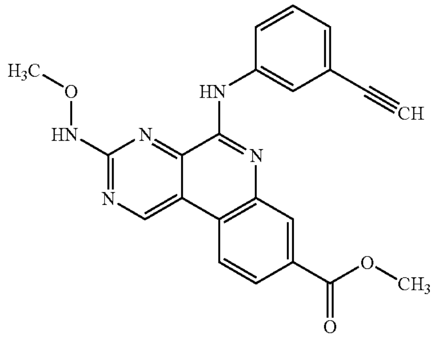 | 399.40 | 400 [M + 1]+ |
| 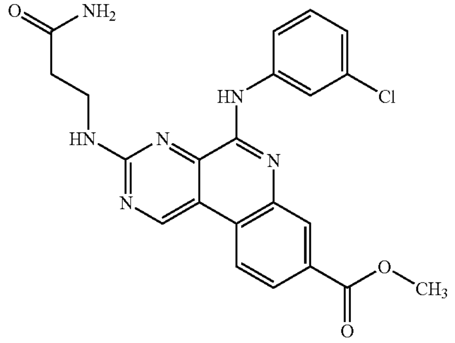 | 450.88 | 451 [M + 1]+ |
| 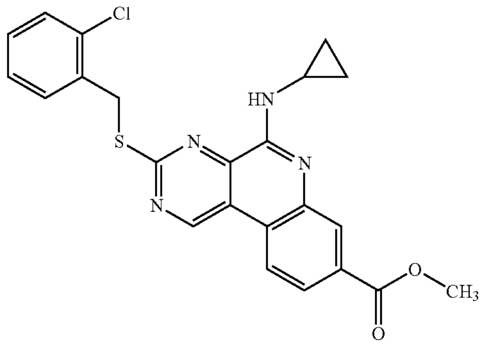 | 450.94 | 451 [M + 1]+ |
| 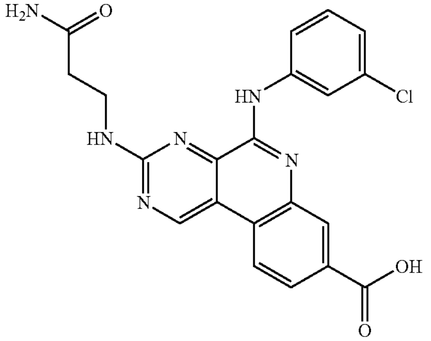 | 436.85 | 437 [M + 1]+ |

TABLE 3-continued
| | | |
|---|---|---|
| 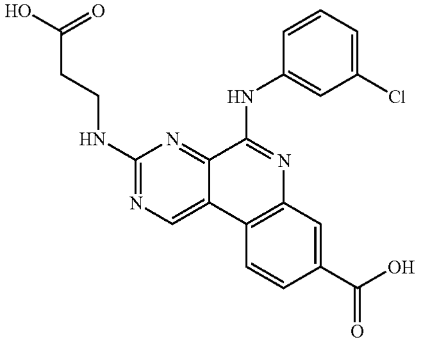 | 437.84 | 438 $[M + 1]^+$ |
| 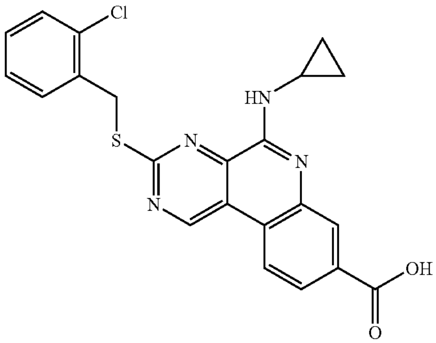 | 436.91 | 437 $[M + 1]^+$ |
| 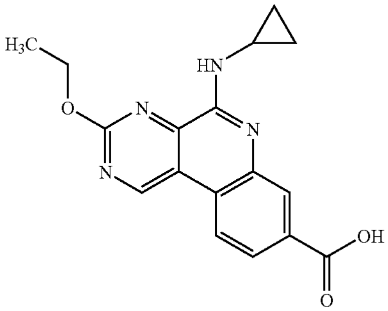 | 324.33 | 325 $[M + 1]^+$ |
| 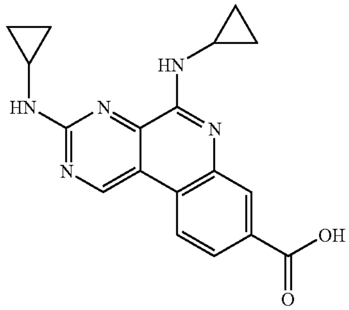 | 335.36 | 336 $[M + 1]^+$ |
| 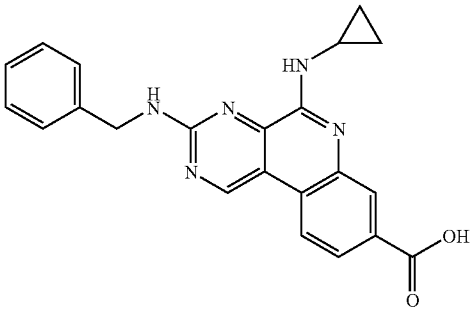 | 385.42 | 386 $[M + 1]^+$ |

TABLE 3-continued
| | | |
|---|---|---|
| 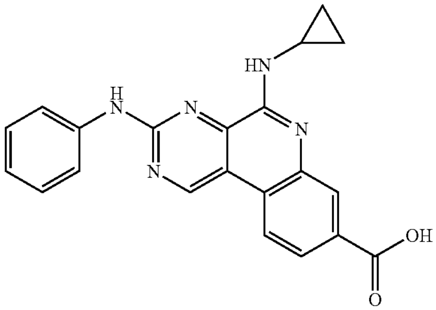 | 371.39 | 372 $[M+1]^+$ |
| 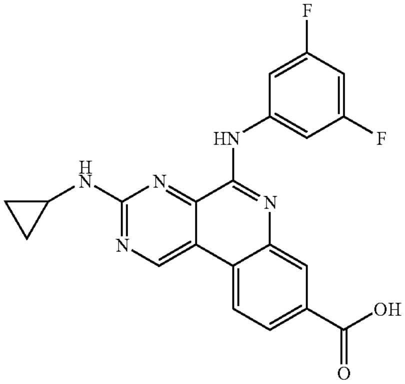 | 407.37 | 408 $[M+1]^+$ |
| 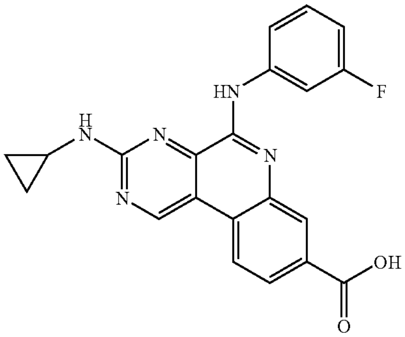 | 389.38 | 390 $[M+1]^+$ |
| 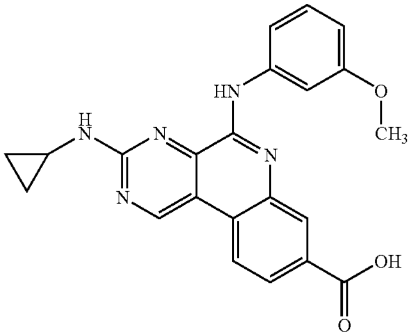 | 401.42 | 402 $[M+1]^+$ |

TABLE 3-continued
| | | |
|---|---|---|
| 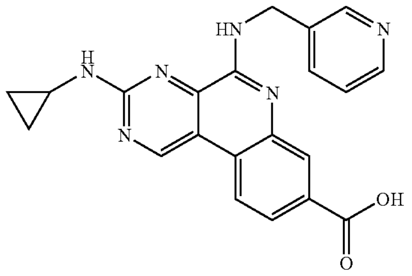 | 386.41 | 387 $[M + 1]^+$ |
| 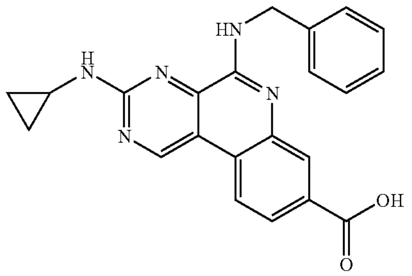 | 385.42 | 386 $[M + 1]^+$ |
| 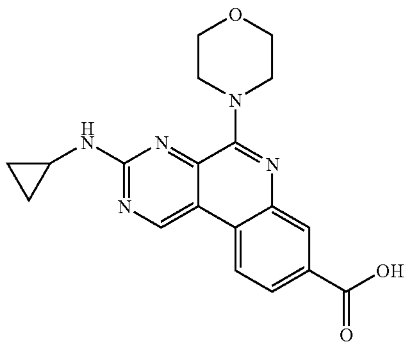 | 365.39 | 366 $[M + 1]^+$ |
| 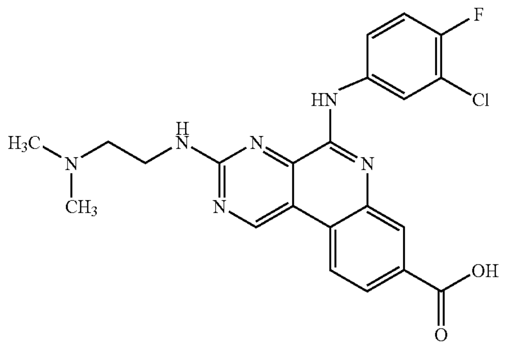 | 454.88 | 455 $[M + 1]^+$ |
| 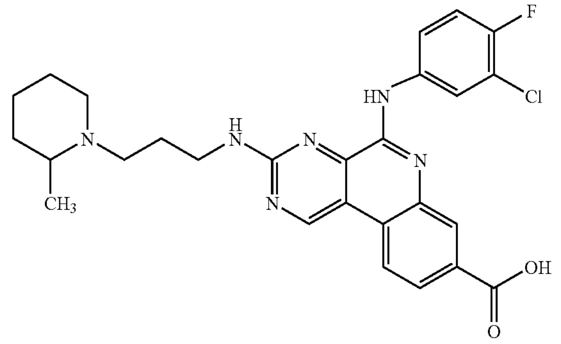 | 523.00 | 524 $[M + 1]^+$ |

TABLE 3-continued
| | | |
|---|---|---|
| 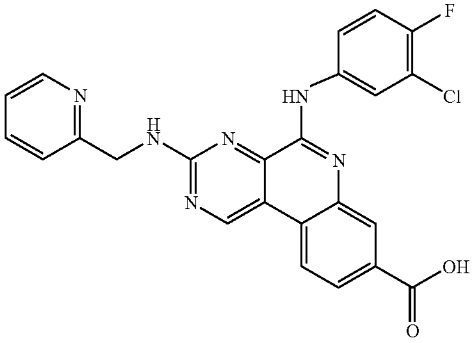 | 474.87 | 475 [M + 1]+ |
| 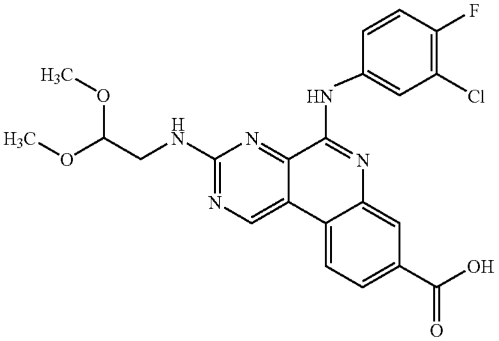 | 471.87 | 472 [M + 1]+ |
| 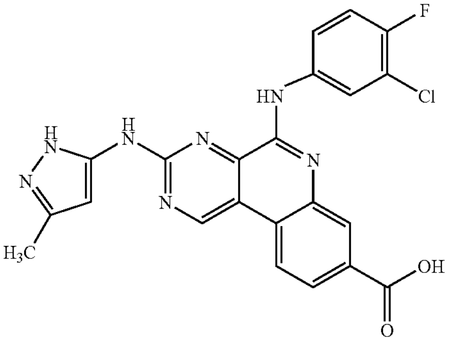 | 463.85 | 464 [M + 1]+ |
| 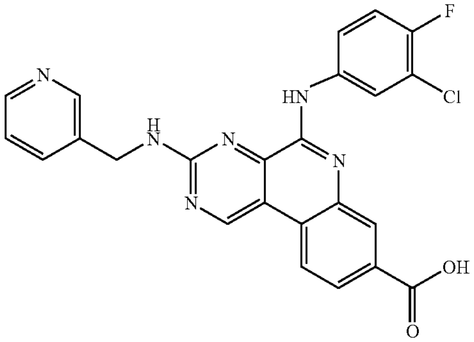 | 474.87 | 475 [M + 1]+ |

TABLE 3-continued
| | | |
|---|---|---|
| 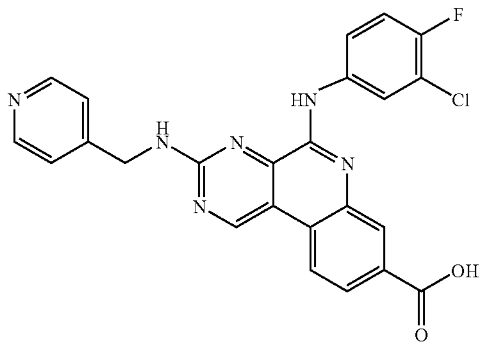 | 474.87 | 475 $[M + 1]^+$ |
| 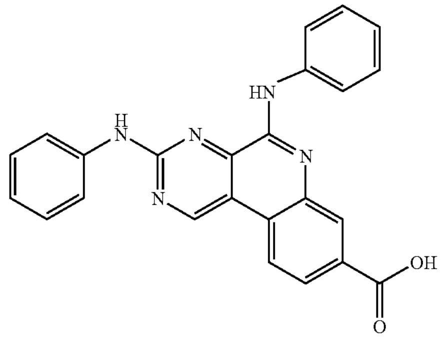 | 407.42 | 408 $[M + 1]^+$ |
| 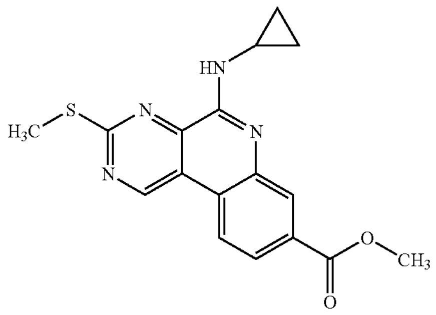 | 340.40 | 341 $[M + 1]^+$ |
| 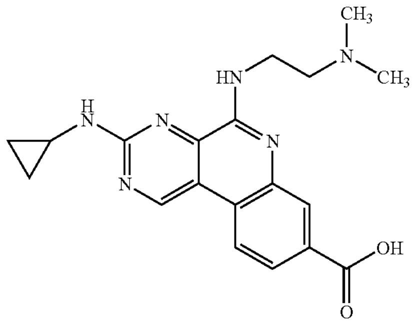 | 366.42 | 367 $[M + 1]^+$ |

TABLE 3-continued
| | | |
|---|---|---|
| 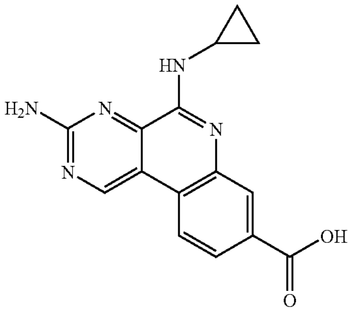 | 295.30 | 296 [M + 1]$^+$ |
| 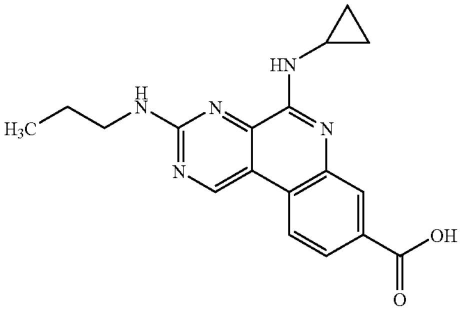 | 337.38 | 338 [M + 1]$^+$ |
| 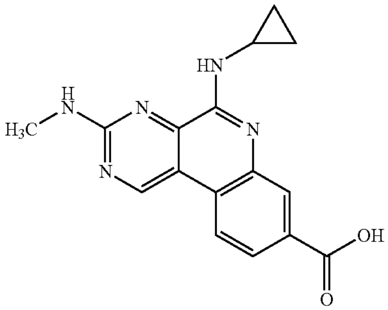 | 309.32 | 310 [M + 1]$^+$ |
| 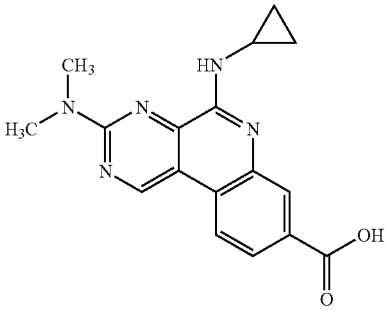 | 323.35 | 324 [M + 1]$^+$ |
| 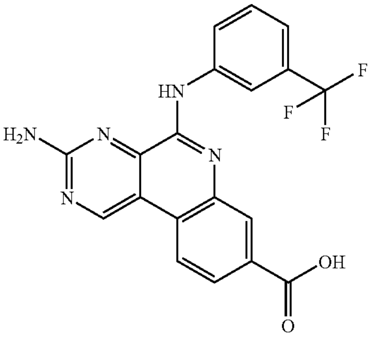 | 399.33 | 400 [M + 1]$^+$ |

TABLE 3-continued
| | | |
|---|---|---|
| 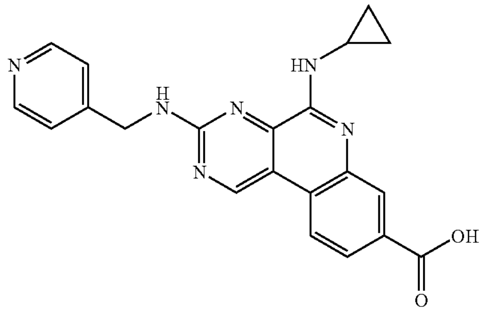 | 386.41 | 387 [M + 1]+ |
| 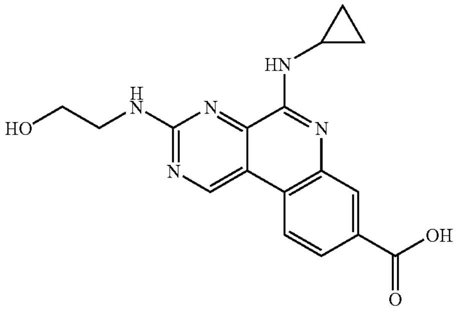 | 339.35 | 340 [M + 1]+ |
| 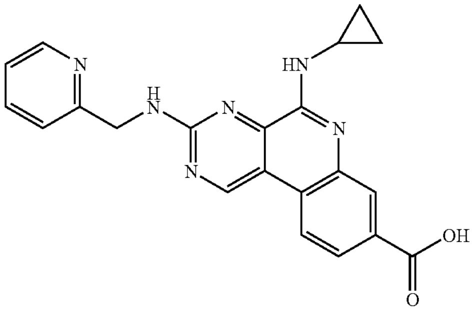 | 386.41 | 387 [M + 1]+ |
| 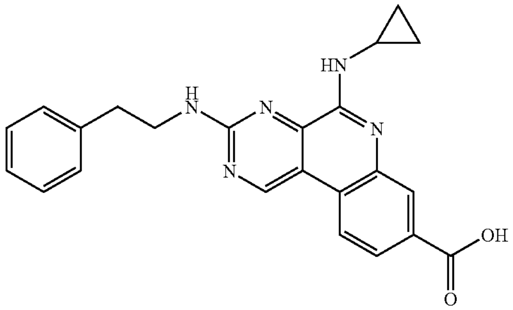 | 399.45 | 400 [M + 1]+ |
| 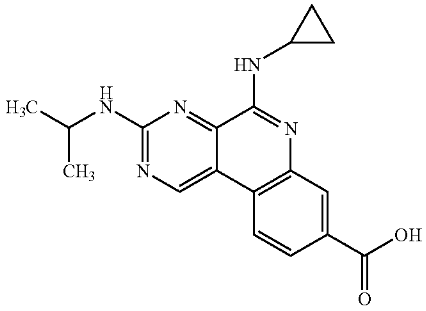 | 337.38 | 338 [M + 1]+ |

TABLE 3-continued
| | | |
|---|---|---|
| 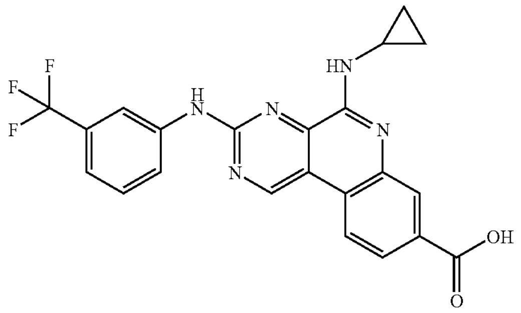 | 439.39 | 440 [M + 1]$^+$ |
| 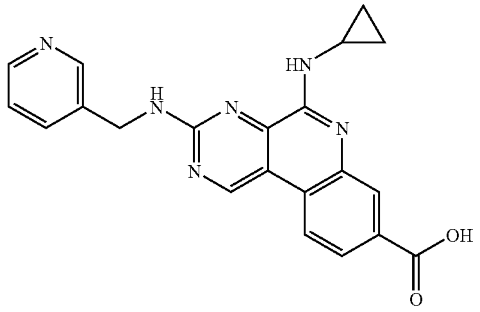 | 386.41 | 387 [M + 1]$^+$ |
| 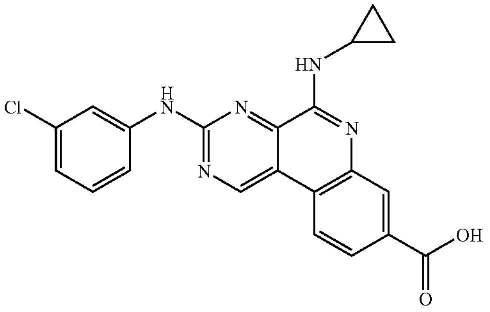 | 405.84 | 406 [M + 1]$^+$ |
| 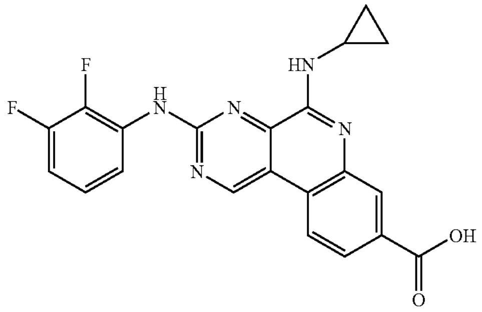 | 407.37 | 408 [M + 1]$^+$ |
| 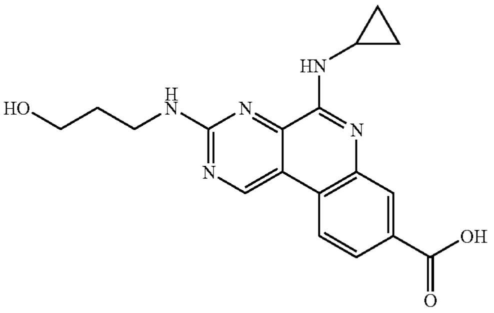 | 353.38 | 354 [M + 1]$^+$ |

TABLE 3-continued
| | | |
|---|---|---|
| 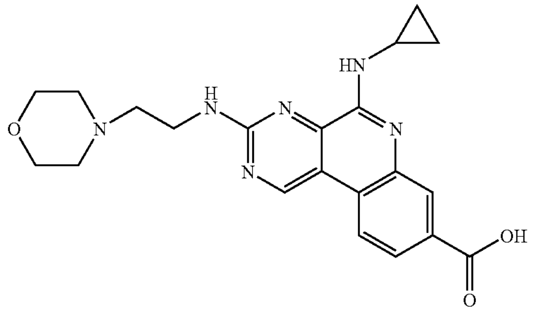 | 408.45 | 409 [M + 1]$^+$ |
| 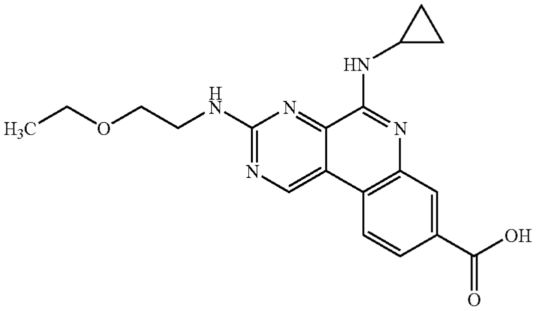 | 367.40 | 368 [M + 1]$^+$ |
| 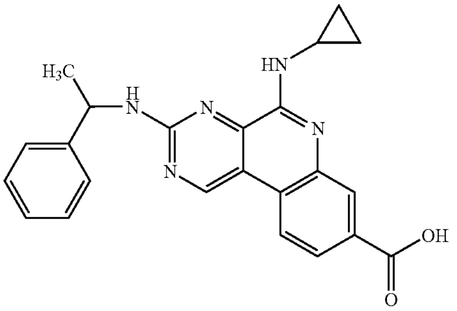 | 399.45 | 400 [M + 1]$^+$ |
| 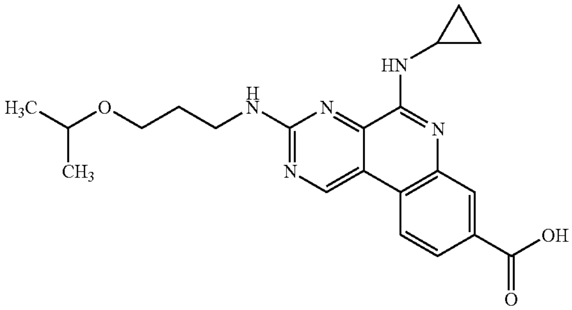 | 395.45 | 396 [M + 1]$^+$ |
| 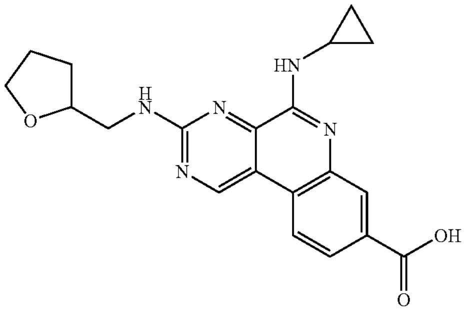 | 379.41 | 380 [M + 1]$^+$ |

TABLE 3-continued
| Structure | MW | LCMS (ES) m/z [M + 1]+ |
|---|---|---|
| 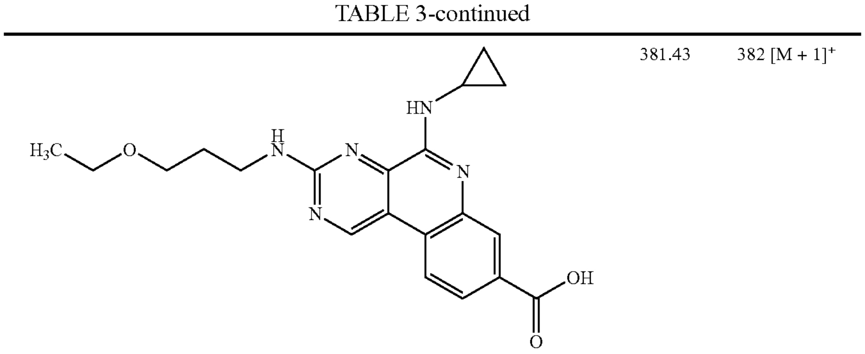 | 381.43 | 382 $[M + 1]^+$ |
| 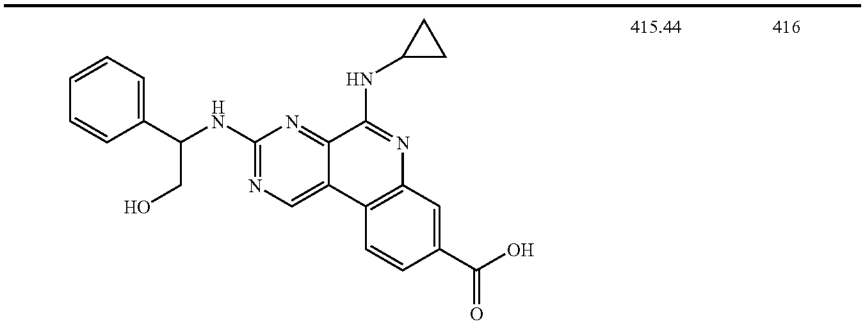 | 415.44 | 416 |
| 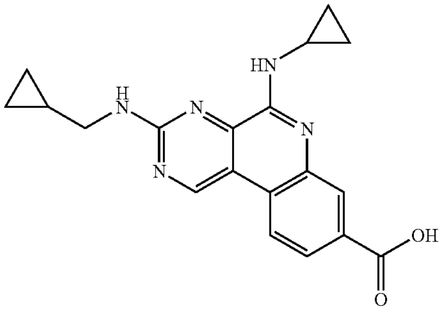 | 349.39 | 350 |
| 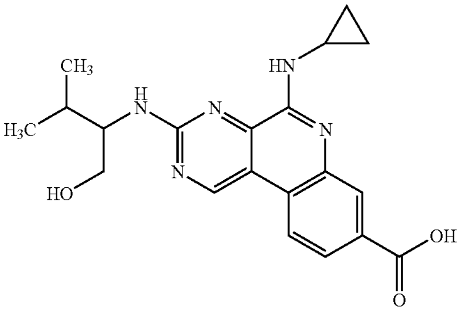 | 381.43 | 382 |
| 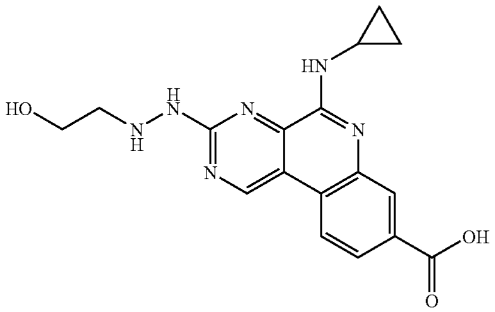 | 354.36 | 355 |

TABLE 3-continued
| | | |
|---|---|---|
| 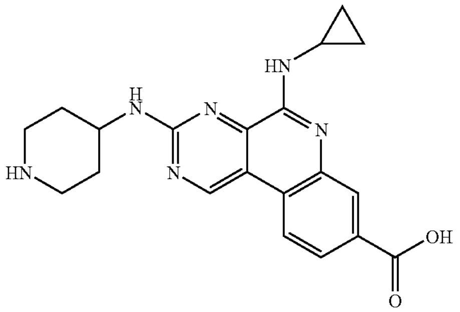 | 378.43 | 379 |
| 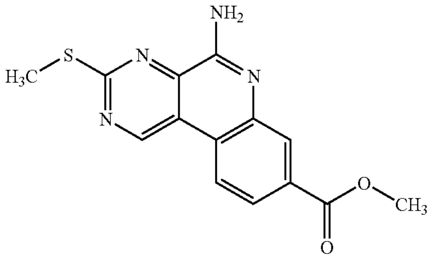 | 300.34 | 301 |
| 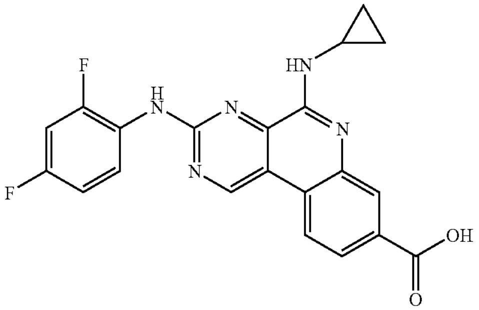 | 407.37 | 408 |
| 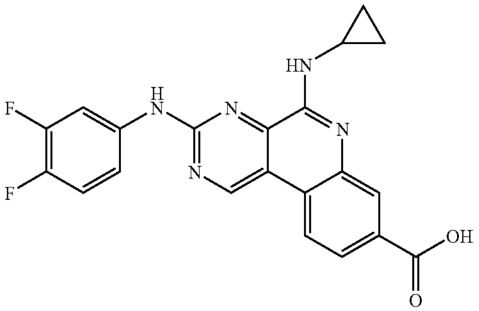 | 407.37 | 408 |
| 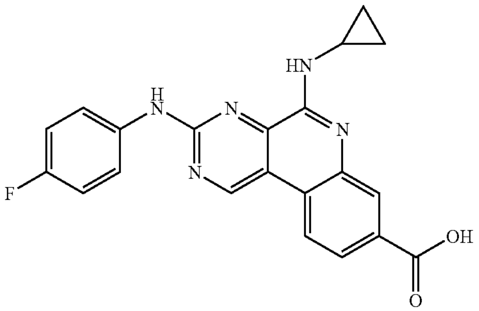 | 389.38 | 390 |

TABLE 3-continued
| | | |
|---|---|---|
| 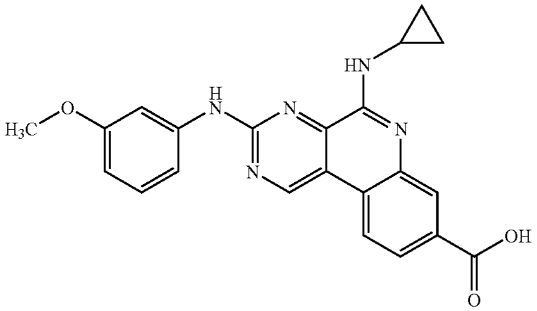 | 401.42 | 402 |
| 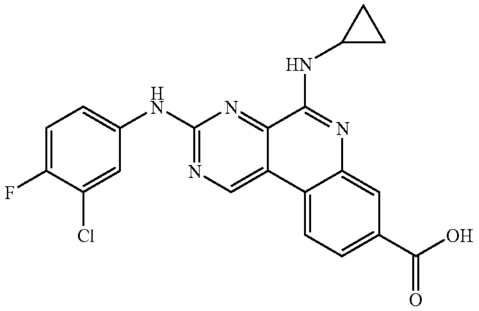 | 423.83 | 424 |
| 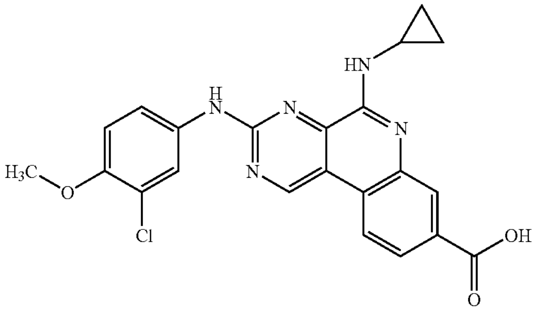 | 435.86 | 436 |
| 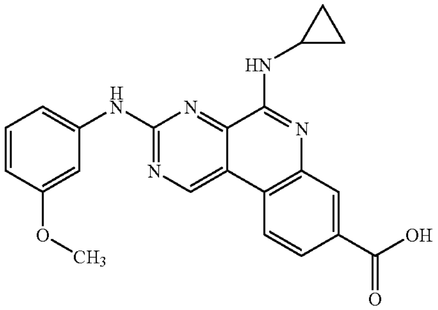 | 401.42 | 402 |
| 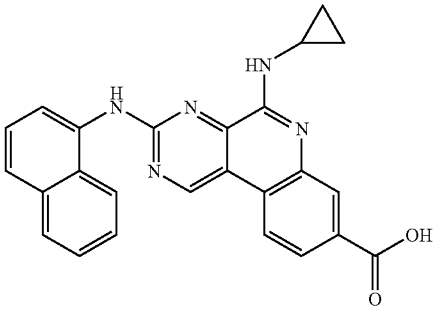 | 421.45 | 422 |

TABLE 3-continued
| | | |
|---|---|---|
| 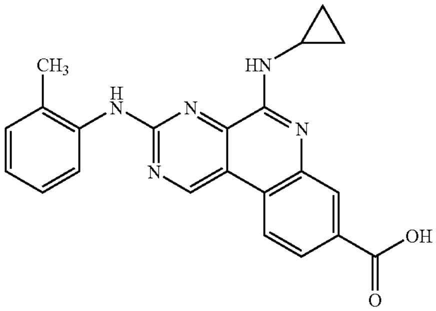 | 385.42 | 386 |
| 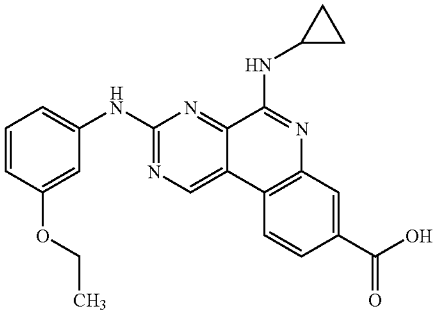 | 415.44 | 416 |
| 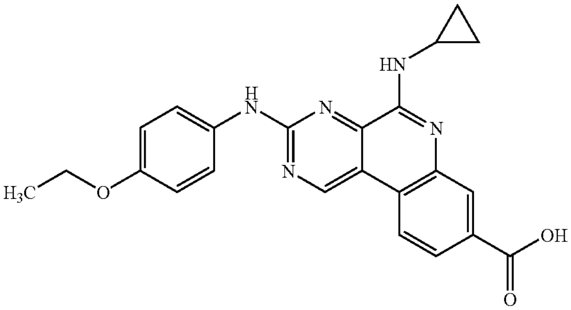 | 415.44 | 416 |
| 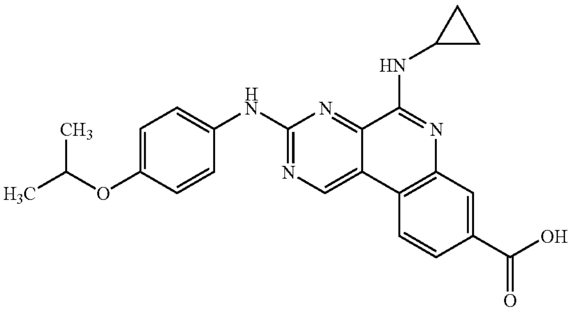 | 429.47 | 430 |
| 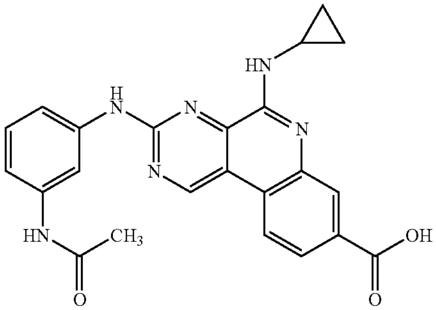 | 428.44 | 429 |

TABLE 3-continued
| | | |
|---|---|---|
| 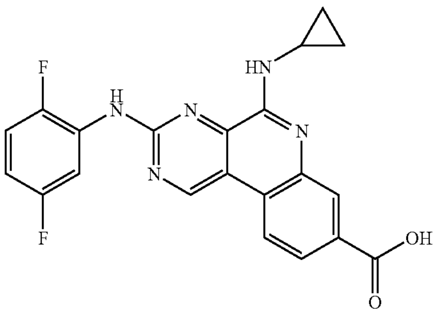 | 407.37 | 408 |
| 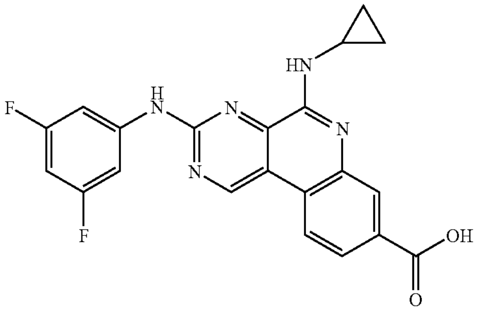 | 407.37 | 408 |
| 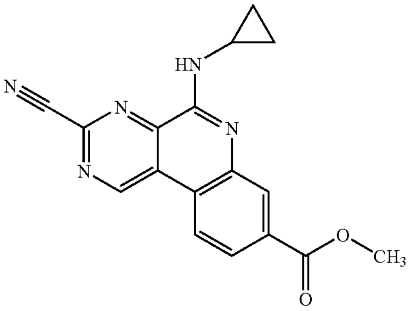 | 319.32 | 320 |
| 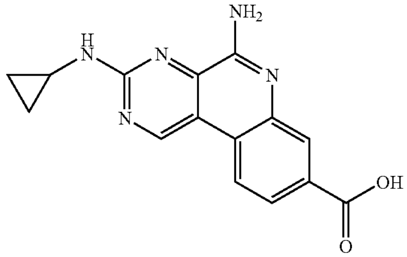 | 295.30 | 296 |
| 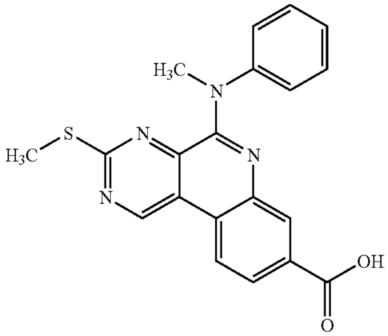 | 376.43 | 377 |

TABLE 3-continued
| | | |
|---|---|---|
| 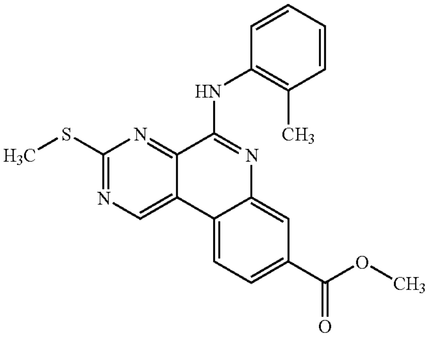 | 390.46 | 391 |
| 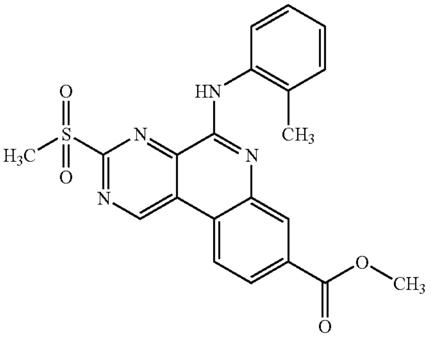 | 422.46 | 423 |
| 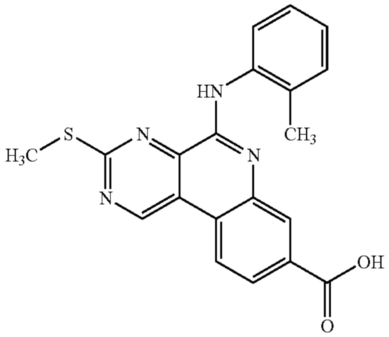 | 376.43 | 377 |
| 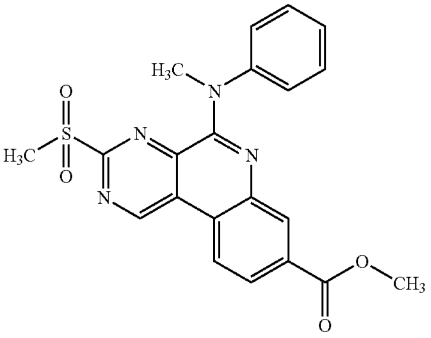 | 422.46 | 423 |

TABLE 3-continued
| | | |
|---|---|---|
| 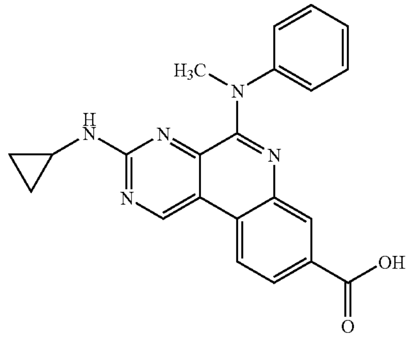 | 385.42 | 386 |
| 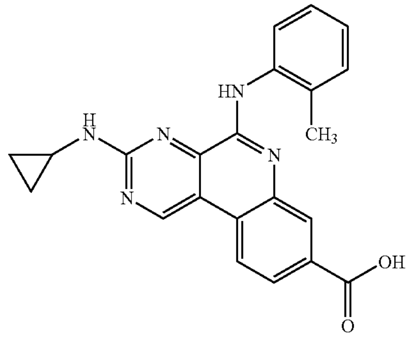 | 385.42 | 386 |
| 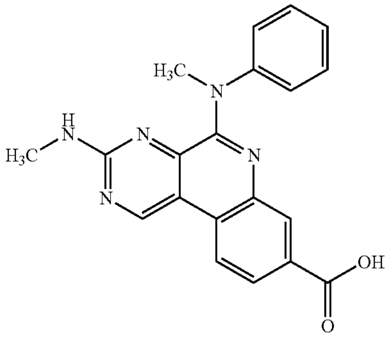 | 359.38 | 360 |
| 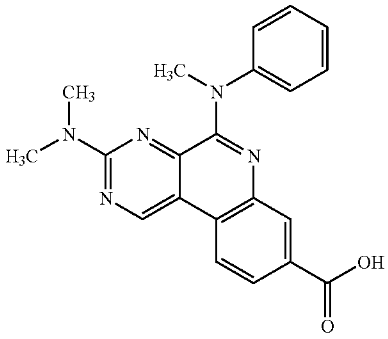 | 373.41 | 374 |

TABLE 3-continued
| | | |
|---|---|---|
| 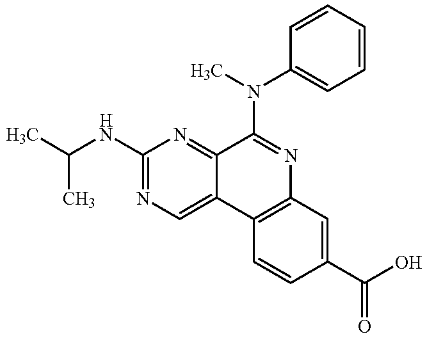 | 387.43 | 388 |
| 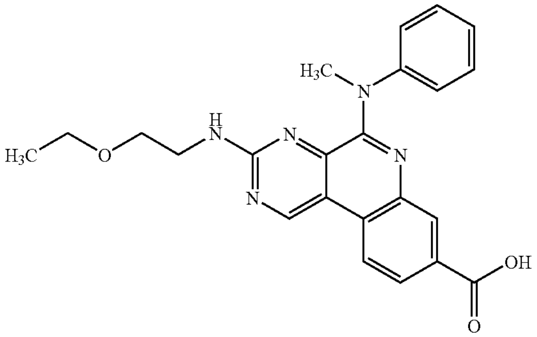 | 417.46 | 418 |
| 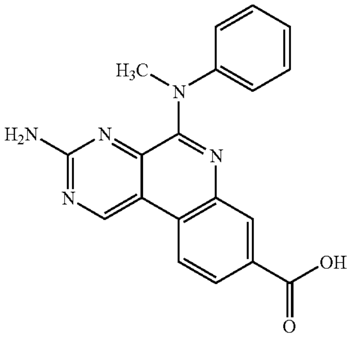 | 345.35 | 346 |
Process 15
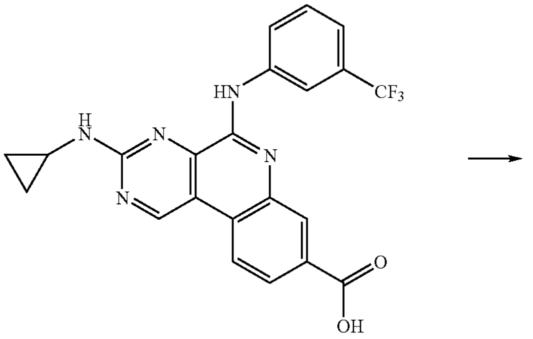
-continued
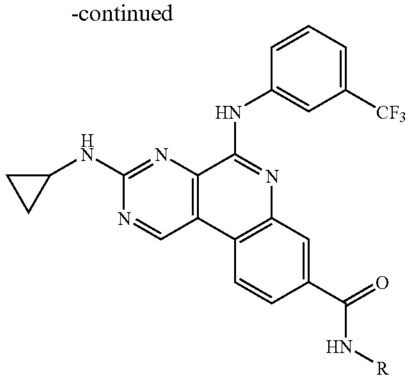
3-(cyclopropylamino)-5-(3-(trifluoromethyl)phenylamino)pyrimido[4,5-c]quinoline-8-carboxylic acid (20 mg) was mixed with 2 equivalent of an appropriate primary amine in NMP (0.5 ml). HOBt (14 mg), triethylamine (13 uL) and EDCI (18 mg) were added and the mixture was stirred at 70° C. for 1 hour. Water and HCl were added and the material was isolated by filtration. This protocol was used to prepare compounds shown in table 4
TABLE 4
| Structure | MW | LCMS (ES) m/z |
|---|---|---|
| 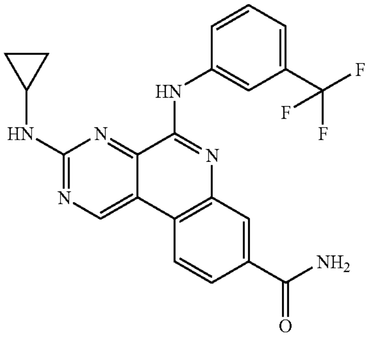 | 438.41 | 439 [M + 1]+ |
| 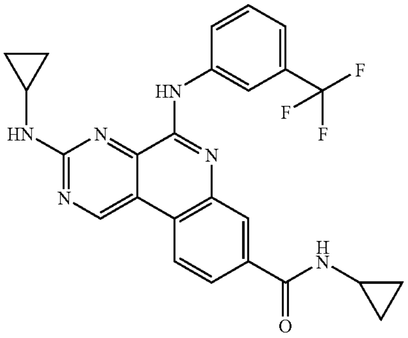 | 478.47 | 479 [M + 1]+ |
| 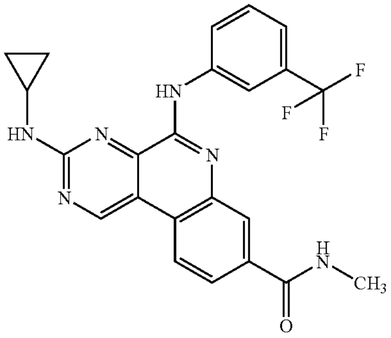 | 452.43 | 453 [M + 1]+ |
| Structure | MW | LCMS (ES) m/z, [M + 1]+ |
|---|---|---|
| 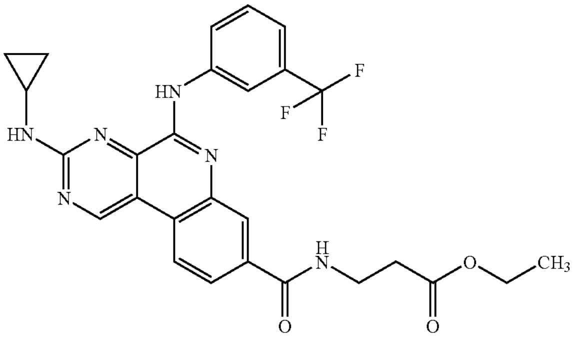 | 538.52 | 539 |

TABLE 4-continued
| | | |
|---|---|---|
| 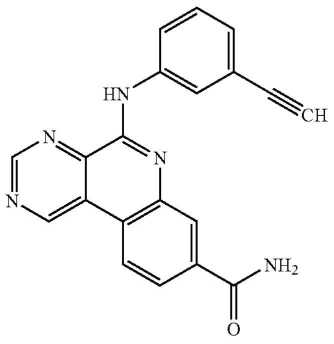 | 339.35 | 340 |
| 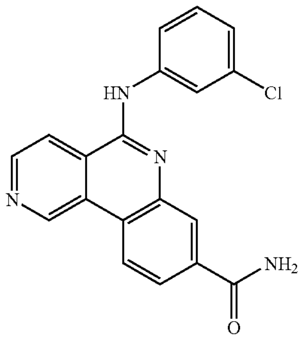 | 348.79 | 349 |
| 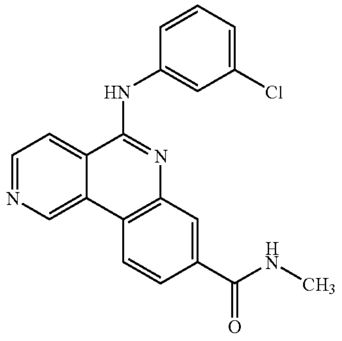 | 362.81 | 363 |
| 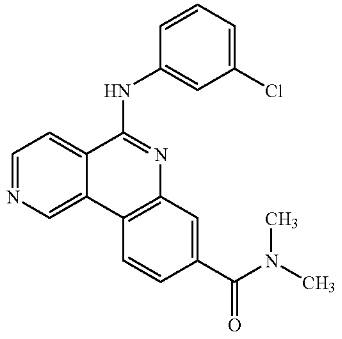 | 376.84 | 377 |

TABLE 4-continued
| | | |
|---|---|---|
| 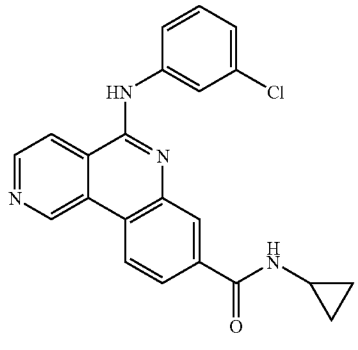 | 388.85 | 389 |
| 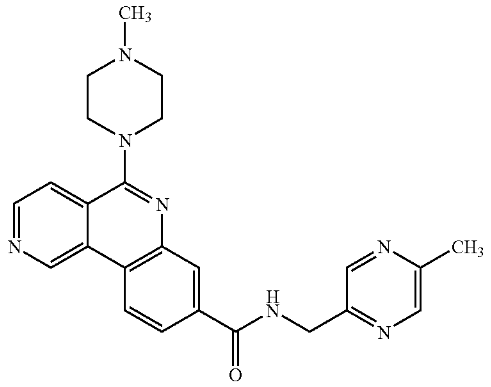 | 427.50 | 428 |
| 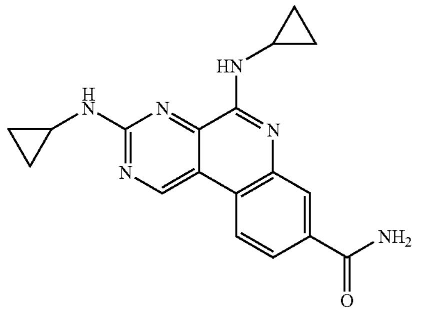 | 334.38 | 335 |
| 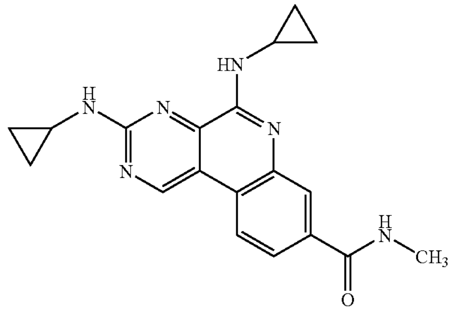 | 348.40 | 349 |

TABLE 4-continued
| | | |
|---|---|---|
| 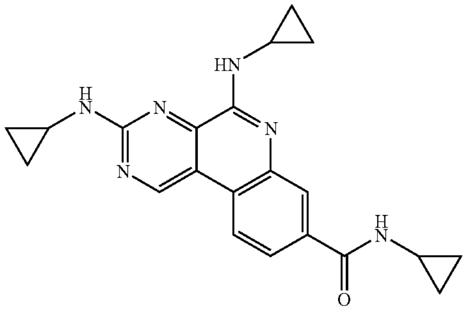 | 374.44 | 375 |
| 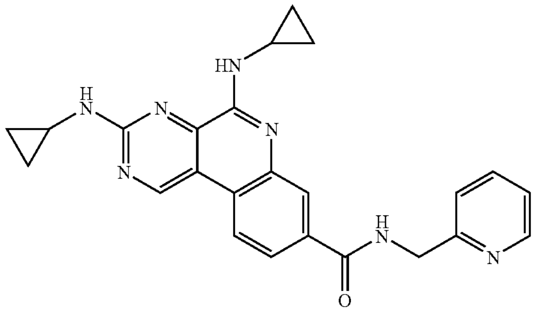 | 425.49 | 426 |
| 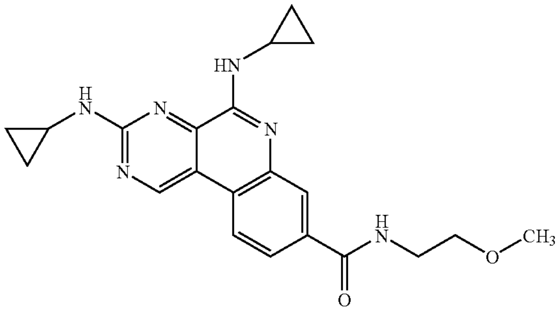 | 392.45 | 393 |
| 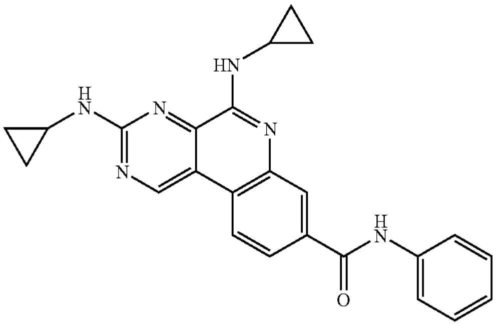 | 410.47 | 411 |
| 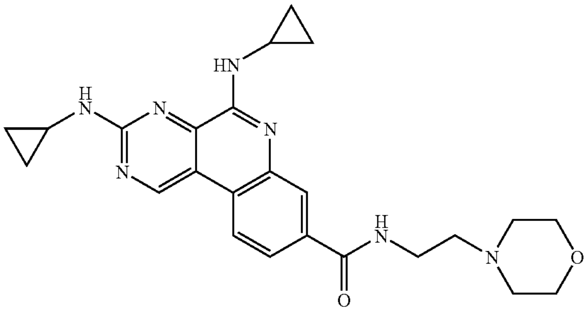 | 447.53 | 448 |

TABLE 4-continued
| | | |
|---|---|---|
| 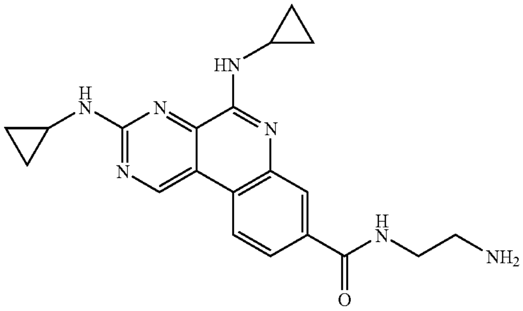 | 377.44 | 378 |
| 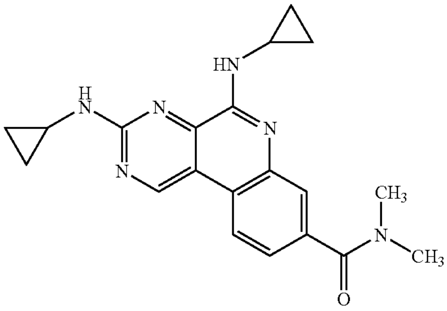 | 362.43 | 363 |
| 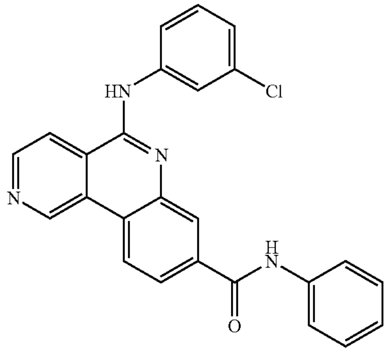 | 424.88 | 425 |
| 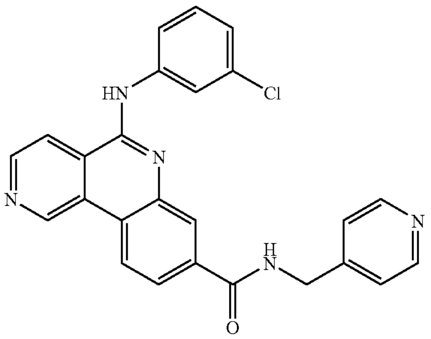 | 439.90 | 440 |

TABLE 4-continued
| | | |
|---|---|---|
| 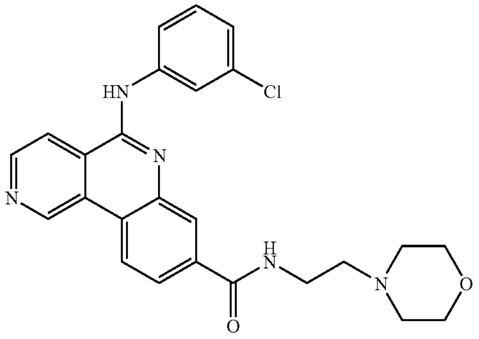 | 461.94 | 462 |
| 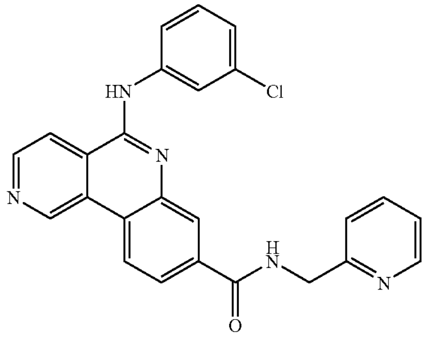 | 439.90 | 440 |
| 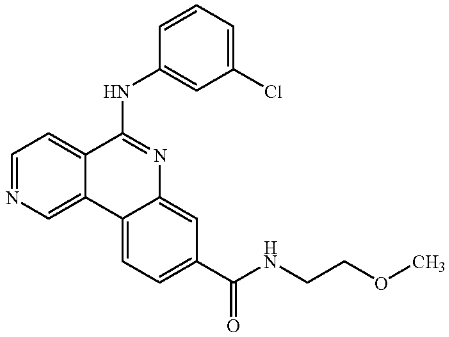 | 406.86 | 407 |
| 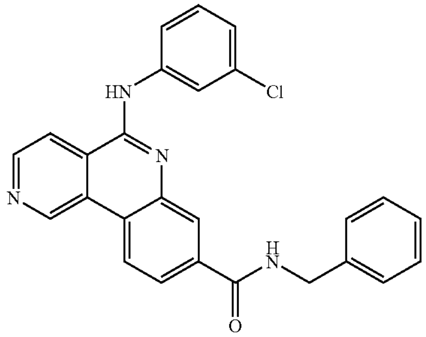 | 438.91 | 439 |

TABLE 4-continued
| | | |
|---|---|---|
| 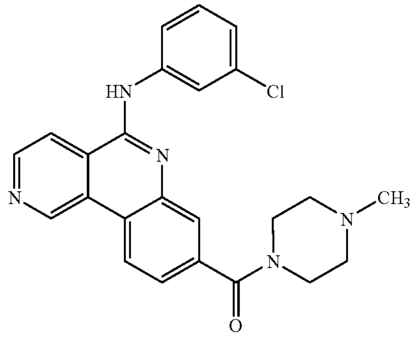 | 431.92 | 432 |
| 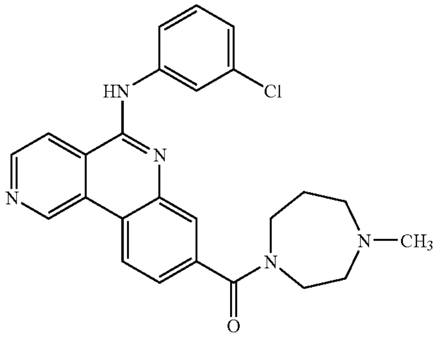 | 445.94 | 446 |
| 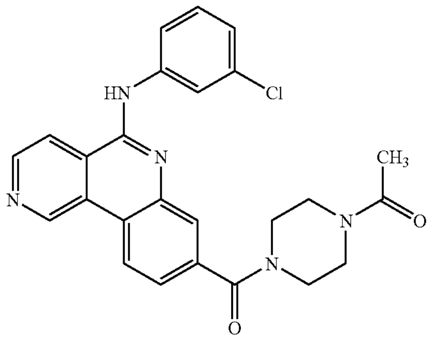 | 459.93 | 460 |
| 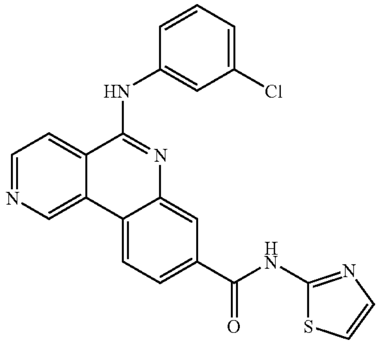 | 431.90 | 432 |

TABLE 4-continued
| | | |
|---|---|---|
| 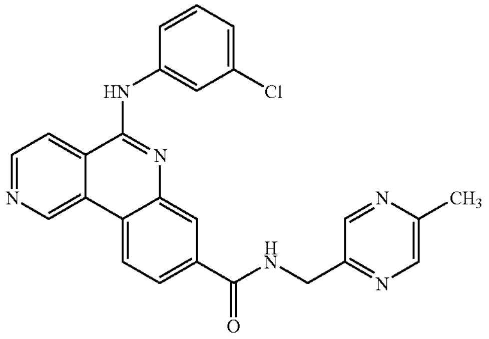 | 454.91 | 455 |
| 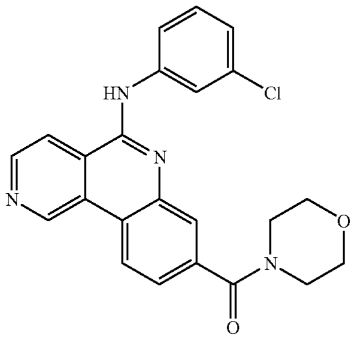 | 418.88 | 419 |
| 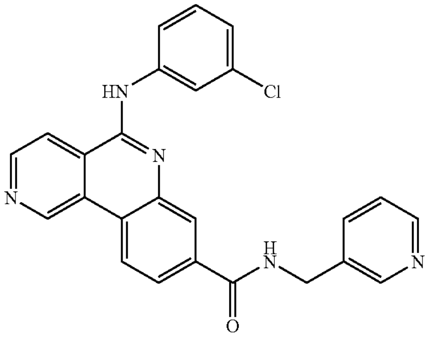 | 439.90 | 440 |
| 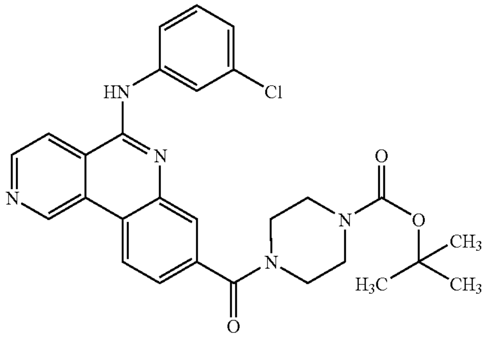 | 518.01 | 519 |

TABLE 4-continued
| | | |
|---|---|---|
| 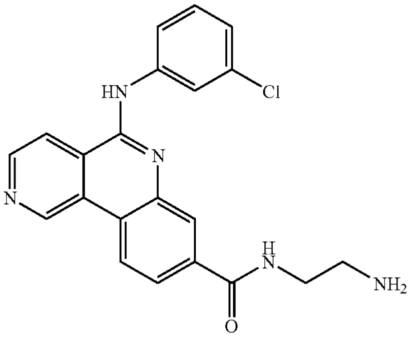 | 391.85 | 392 |
| 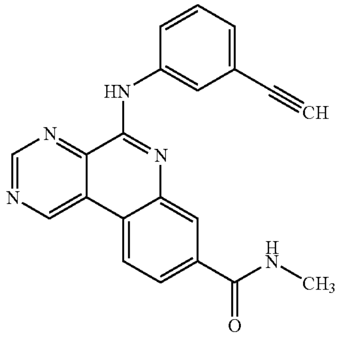 | 353.38 | 354 |
| 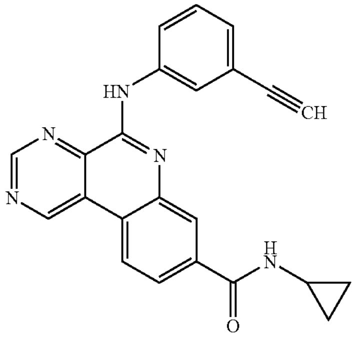 | 379.41 | 380 |
| 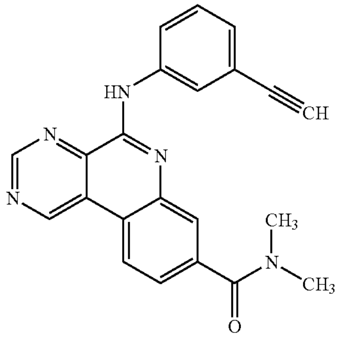 | 367.40 | 368 |

TABLE 4-continued
| | | |
|---|---|---|
| 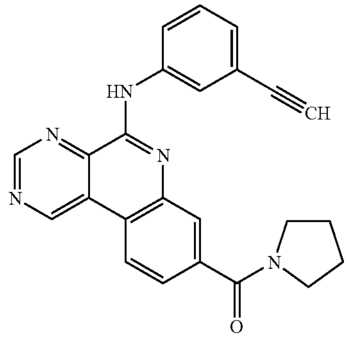 | 393.44 | 394 |
| 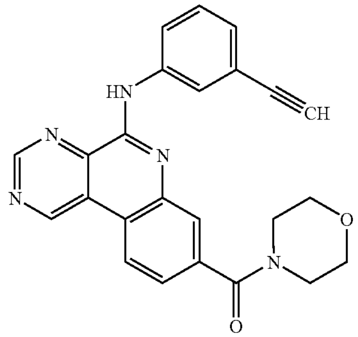 | 409.44 | 410 |
| 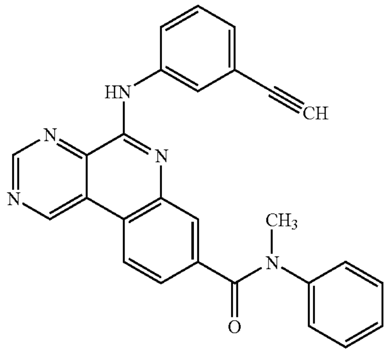 | 429.47 | 430 |
| 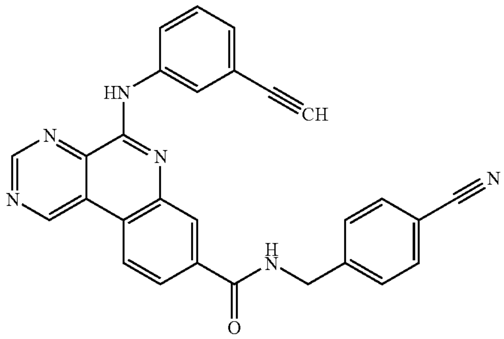 | 454.48 | 455 |

TABLE 4-continued
| | | |
|---|---|---|
| 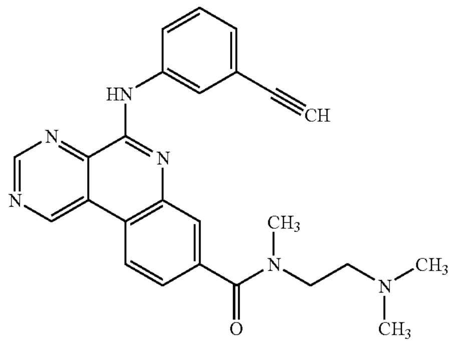 | 424.50 | 425 |
| 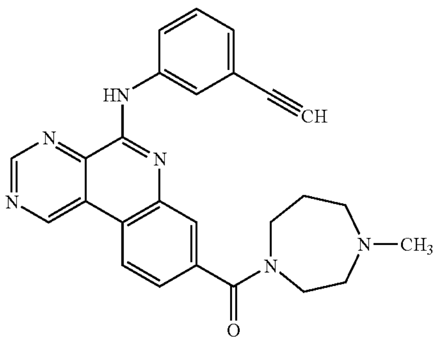 | 436.51 | 437 |
| 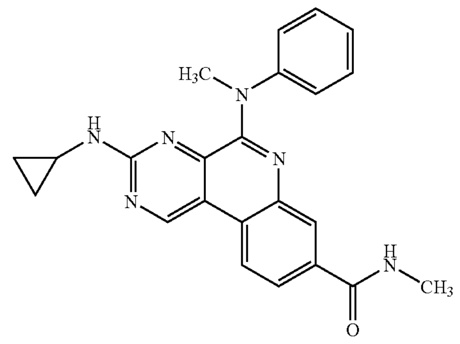 | 398.46 | 399 |
| 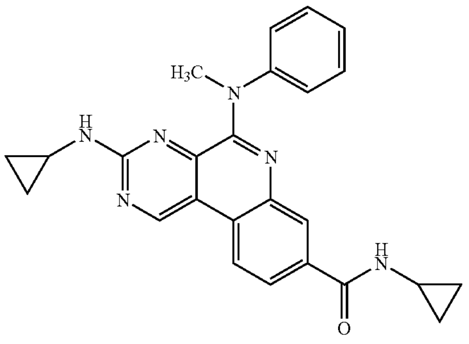 | 424.50 | 425 |

TABLE 4-continued
| | | |
|---|---|---|
| 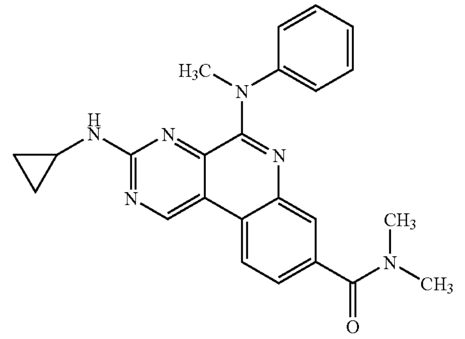 | 412.49 | 413 |
| 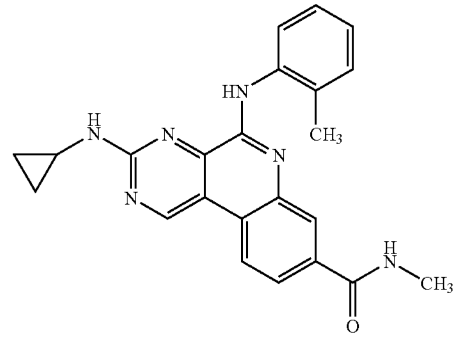 | 398.46 | 399 |
| 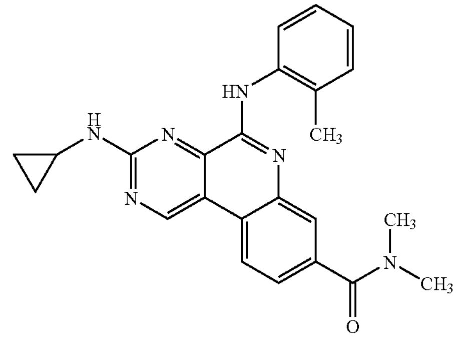 | 412.49 | 413 |
| 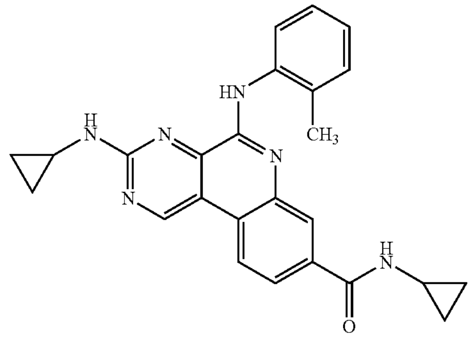 | 424.50 | 425 |

TABLE 4-continued
| | | |
|---|---|---|
| 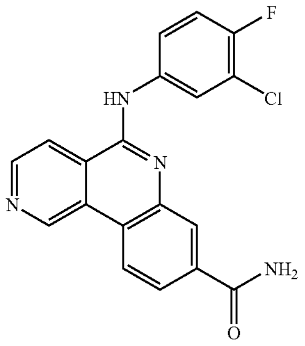 | 366.78 | 368 |
| 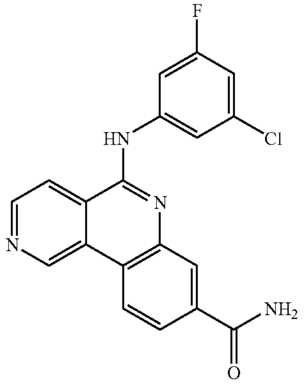 | 366.78 | 368 |
| 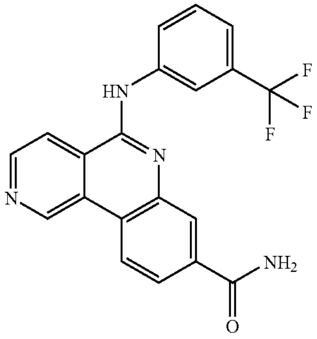 | 382.34 | 383 |
| 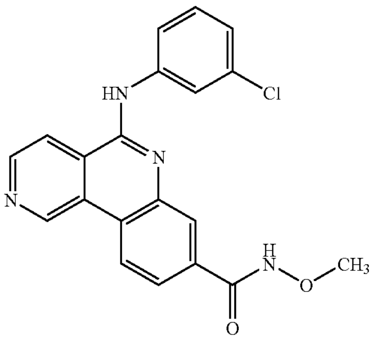 | 378.81 | 380 |

Process 16

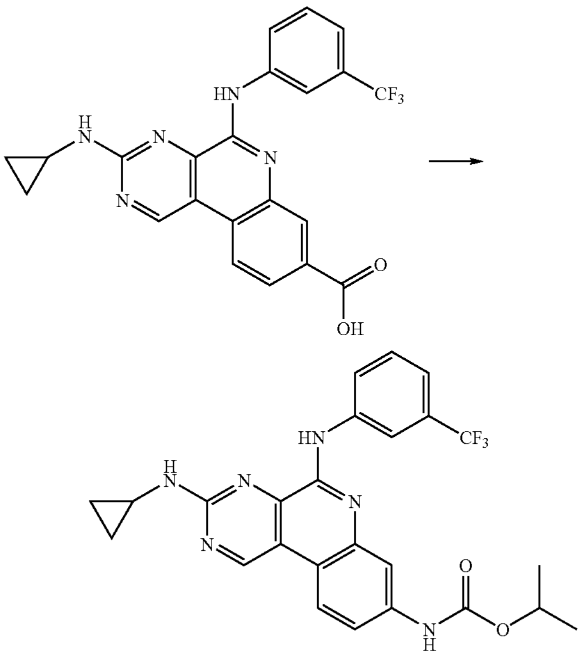

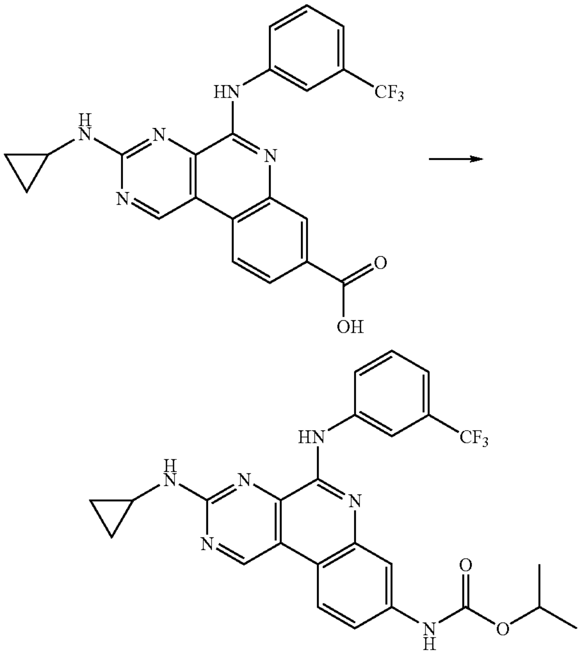

3-(cyclopropylamino)-5-(3-(trifluoromethyl)phenylamino)pyrimido[4,5-c]quinoline-8-carboxylic acid (100 mg, 0.23 mmol) was reacted with diphenylphosphoryl azide (50 ul, 0.23 mmol) and triethylamine (34 ul, 0.23 mmol) in isopropanol (8 ml). The mixture was stirred at 95° C. for 3 hours. The solvents were removed and the residue partitioned between water and ethylacetate. The organic layer was dried over $Na_2SO_4$ and the solvents removed in vacuo. Addition of $CH_2Cl_2$ induced formation of a solid that was filtered off and dried to afford isopropyl 3-(cyclopropylamino)-5-(3-(trifluoromethyl)phenylamino)pyrimido[4,5-c]quinolin-8-ylcarbamate. LCMS (ES): 90% pure, m/z 497 $[M+1]^+$.

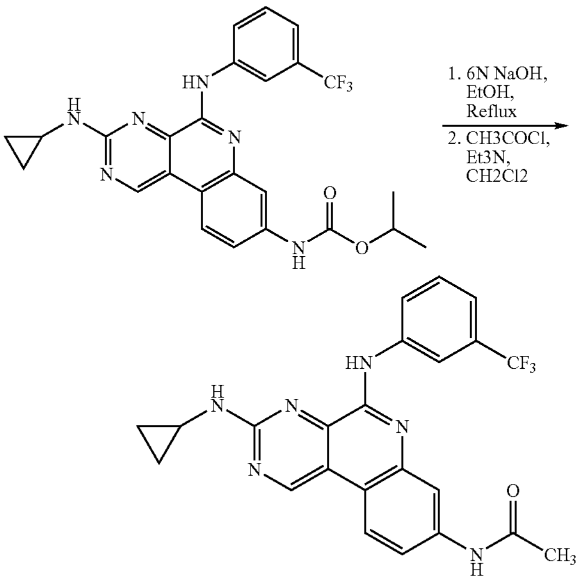

To isopropyl 3-(cyclopropylamino)-5-(3-(trifluoromethyl) phenylamino) pyrimido[4,5-c]quinolin-8-ylcarbamate (60 mg) in EtOH (3 mL) was added 1.5 mL of NaOH solution (6 N) and the mixture was heated at reflux for 3 hrs. EtOH was removed and the residue obtained was partitioned between dichloromethane and water. Organic layer was separated, washed with brine and dried with sodium sulfate. Dichloromethane was removed and the yellow solid obtained was used in the next step without further purification. 19.5 mg of the yellow solid was dissolved in dichloromethane (3 mL) and acetyl chloride (7.4 μL) was added followed by triethyl amine (14.54 μL). The mixture was stirred at room temperature over night. Water and dichloromethane were added and organic layer was isolated, washed with 1N NaOH, Brine, dried with sodium sulfate and concentrate. The residue obtained was purified by preparative TLC eluting with dichloromethane-methanol (9-1) to afford N-(3-(cyclopropylamino)-5-(3-(trifluoromethyl)phenylamino)pyrimido[4,5-c]quinolin-8-yl)acetamide. LCMS (ES) m/z 453 [M+1]+.

Example 2

Processes for Synthesizing Compounds of Formulae V, VI, VII and VIII

Process 1

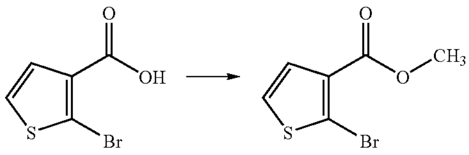

2-bromo-3-thiophene carboxylic acid (1.0 eq, 12.56 g, 60.66 mmol) was suspended in $CH_2Cl_2$ (200 ml). Oxalyl chloride (1.1 eq, 5.9 ml, 67.16 mmol) and 5 drops of DMF were added, inducing formation of gas. The mixture was stirred overnight at room temperature and the volatiles were removed in vacuo. The resulting solid was suspended in dry methanol (150 ml) and the mixture heated to ebullition.

Evaporation of the solvents afforded methyl 2-bromo-3-thiophene carboxylate (13.16 g, 98% yield) as a crude brown oil. LCMS (ES): 99% pure, m/z not detected; $^1H$ NMR ($CDCl_3$, 400 MHz) δ 3.88 (s, 3H), 7.23 (d, J=5.6, 1H), 7.56 (d, J=5.6, 1H) ppm.

Process 2

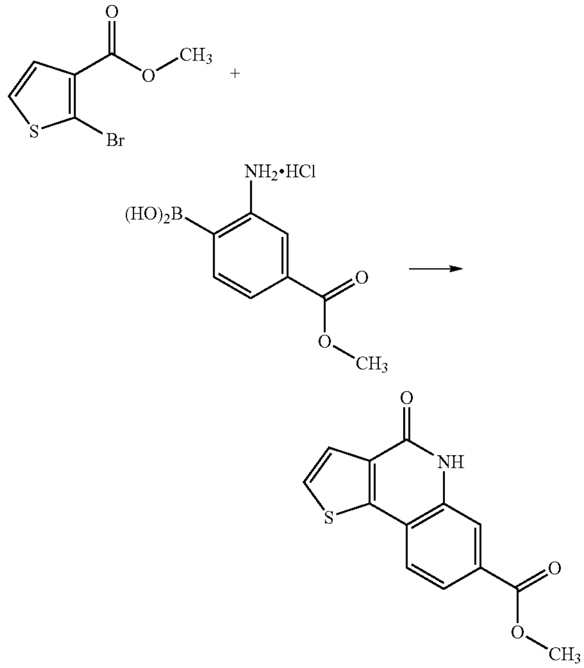

In a microwave vessel, methyl 2-bromo-3-thiophene carboxylate (1.0 eq, 260 mg, 1.18 mmol), 2-amino-4-(methoxycarbonyl)phenylboronic acid hydrochloride (1.1 eq, 300 mg, 1.30 mmol), sodium acetate (3.0 eq, 292 mg, 3.56 mmol) and $PdCl_2$(dppf) (0.05 eq, 31 mg, 0.059 mmol) were mixed together in anhydrous DMF (2 ml). The mixture was heated in a microwave oven at 120° C. for 10 nm. Water was added and the solid filtered and dried. The material was suspended in $CH_2Cl_2$, filtered and dried to afford methyl 4-oxo-4,5-dihydrothieno[3,2-c]quinoline-7-carboxylate as a yellow solid (152 mg, 50% yield). LCMS (ES): 95% pure, m/z 260 $[M+1]^+$; $^1H$ NMR ($CDCl_3$, 400 MHz) δ 3.99 (s, 3H), 7.54 (d, J=5.2, 1H), 7.79 (d, J=4.8, 1H), 7.86 (d, J=8.4, 1H), 7.91 (dd, J=8.4, J=1.6, 1H), 8.03 (d, J=1.2, 1H) ppm.

Process 3

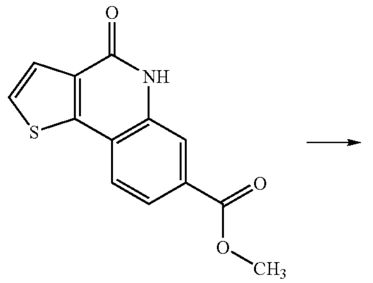

-continued

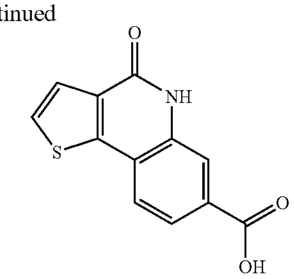

Methyl 4-oxo-4,5-dihydrothieno[3,2-c]quinoline-7-carboxylate (1.0 eq, 618 mg, 2.38 mmol) was suspended in 10 ml of a mixture of MeOH, THF, and water (1:1:1, v:v:v). LiOH (2.0 eq, 114 mg, 4.76 mmol) was added and the mixture was stirred at room temperature for 2 hours. An additional amount of LiOH (114 mg) was added and the mixture was stirred for an hour. LiOH (50 mg) was added and the mixture stirred for an additional 2 hours. Water was added and the solution filtered through a pad of celite. The pad of celite was thoroughly washed with aqueous 1 N NaOH. The solution was acidified with 6 N aqueous HCl to induce precipitation of the expected material. Filtration and drying afforded 4-oxo-4,5-dihydrothieno[3,2-c]quinoline-7-carboxylic acid as a yellow solid (562 mg, 96% yield). LCMS (ES): 95% pure, m/z 246 $[M+1]^+$; $^1H$ NMR (DMSO-$d_6$, 400 MHz) δ 7.61 (d, J=5.2, 1H), 7.73 (dd, J=1.6, J=8.0, 1H), 7.88 (d, J=5.6, 1H), 7.92 (d, J=8.4, 1H), 8.02 (d, J=1.6, 1H), 11.92 (s, 1H), 13.21 (br. s, 1H) ppm.

Process 4

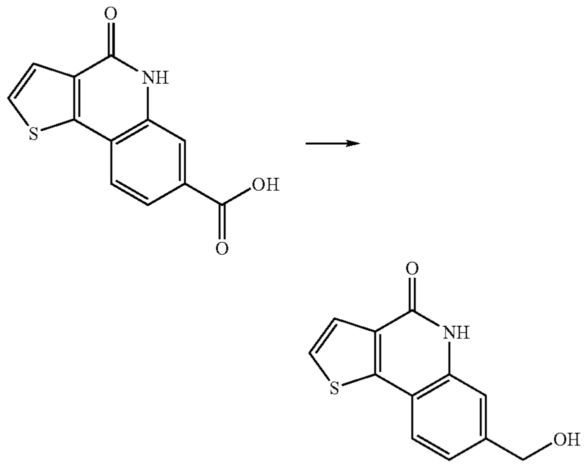

4-oxo-4,5-dihydrothieno[3,2-c]quinoline-7-carboxylic acid (1.0 eq, 38 mg, 0.155 mmol) was suspended in dioxane (1 ml). $LiAlH_4$ (7.0 eq, 40 mg, 1.05 mmol) was added and the mixture stirred at 100° C. for 45 nm. Water was added, then MeOH and $CH_2Cl_2$. The solid salts were filtered off and washed with MeOH and $CH_2Cl_2$. After evaporation of the volatiles in vacuo, the material was dissolved in a mixture of NMP, MeOH and water and was purified by preparative HPLC. Genevac evaporation afforded 7-(hydroxymethyl)thieno[3,2-c]quinolin-4(5H)-one as an off-white solid (12 mg, 34%). LCMS (ES): 95% pure, m/z 232 $[M+1]^+$; $^1H$ NMR (DMSO-$d_6$, 400 MHz) δ 4.56 (s, 2H), 7.15 (d, J=7.6, 1H), 7.39 (br s, 1H), 7.55 (d, J=5.2, 1H), 7.73 (d, J=5.2, 1H), 7.76 (d, J=8.0, 1H), 11.73 (s, 1H) ppm.

Process 5

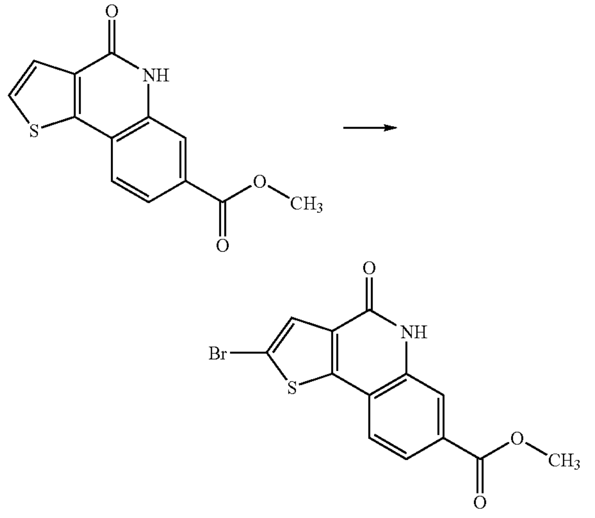

Methyl 4-oxo-4,5-dihydrothieno[3,2-c]quinoline-7-carboxylate (1.0 eq, 17 mg, 0.066 mmol) was suspended in a mixture of chloroform (0.3 ml) and acetic acid (0.1 ml). NBS was added (9.5 eq, 112 mg, 0.63 mmol) and the mixture stirred at 70° C. for 16 hours. Water and aqueous ammonia was added and the material was extracted with $CH_2Cl_2$ (2×). The combined extracts were dried over $Na_2SO_4$ and the solvent removed in vacuo to provide methyl 2-bromo-4-oxo-4,5-dihydrothieno[3,2-c]quinoline-7-carboxylate (17 mg, 76%). LCMS (ES): >85% pure, m/z 338 $[M]^+$, 340 $[M+2]^+$; $^1$H NMR ($CDCl_3/CD_3OD$, 9:1, 400 MHz) δ 3.99 (s, 3H), 7.30 (m, 1H), 7.69 (d, J=8.4, 1H), 7.45 (m, 1H), 7.88 (br d, J=8, 1H), 8.05 (br s, 1H) ppm.

Process 6

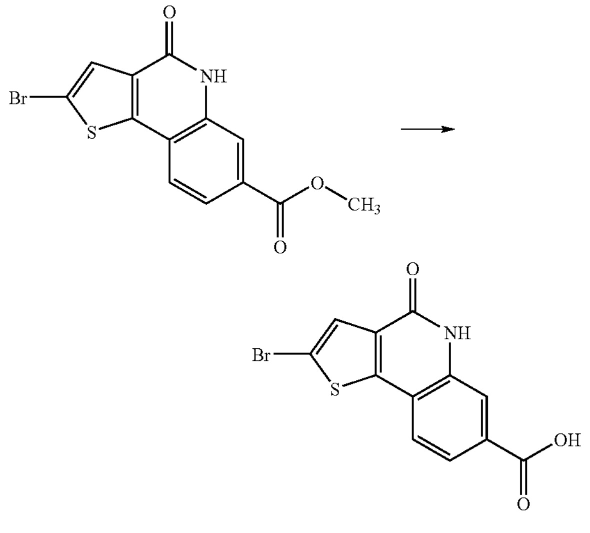

Methyl 2-bromo-4-oxo-4,5-dihydrothieno[3,2-c]quinoline-7-carboxylate (1.0 eq, 17 mg, 0.050 mmol) was suspended in a 1:1:1 mixture of MeOH/THF/water (0.6 ml). LiOH (39 mg) was added and the mixture stirred at room temperature for one hour. Water and 6N HCl was added and the resulting precipitate was filtered. The material was purified by preparative HPLC. Genevac evaporation provided 2-bromo-4-oxo-4,5-dihydrothieno[3,2-c]quinoline-7-carboxylic acid as a solid (2.1 mg, 13% yield). LCMS (ES): >95% pure, m/z 324 $[M]^+$, 326$[M+2]^+$; $^1$H NMR (DMSO-$d_6$, 400 MHz) δ 7.75 (s, 1H), 7.75 (dd, J=1.6, J=8.0, 1H), 7.90 (d, J=8.4, 1H), 8.03 (d, J=1.6, 1H), 12.06 (s, 1H) ppm.

Process 7

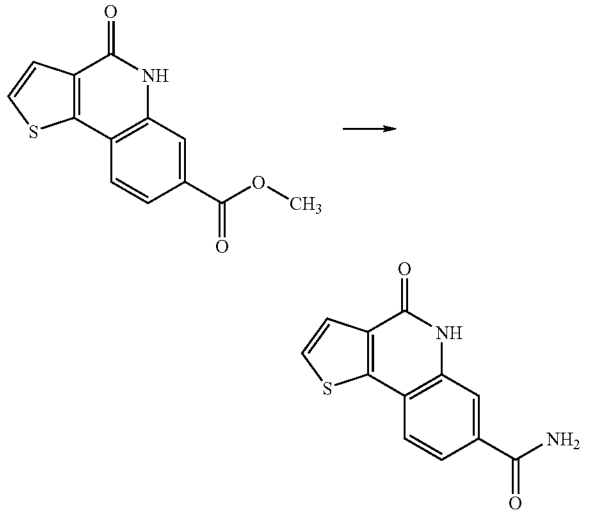

In a closed vessel, Methyl 4-oxo-4,5-dihydrothieno[3,2-c]quinoline-7-carboxylate (44 mg, 0.170 mmol) was suspended in concentrated aqueous ammonia (1 ml). The mixture was stirred at 100° C. overnight. Aqueous 1N NaOH was added and the mixture stirred at room temperature for 2 hours. The solid was filtered and dried to provide 4-oxo-4,5-dihydrothieno[3,2-c]quinoline-7-carboxamide as a brown solid (13 mg, 32% yield). LCMS (ES): 95% pure, m/z 245 $[M+1]^+$.

Process 8

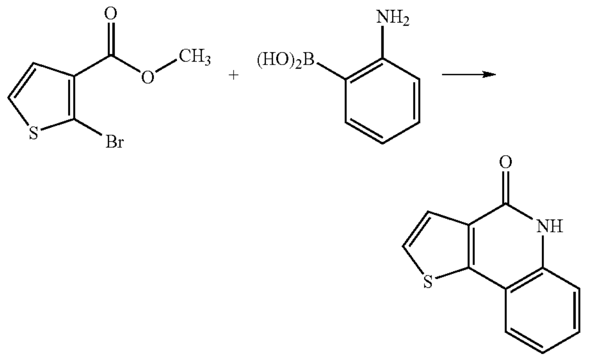

In a microwave vessel, methyl 2-bromo-3-thiophene carboxylate (1.0 eq, 64 mg, 0.29 mmol), 2-amino phenyl boronic acid (1.2 eq, 48 mg, 0.35 mmol), sodium acetate (3.0 eq, 71 mg, 0.86 mmol) and $PdCl_2$(dppf) (0.1 eq, 15 mg, 0.028 mmol) were mixed together in anhydrous DMF (0.2 ml). The mixture was heated in a microwave oven at 120° C. for 5 nm. The material was purified by preparative HPLC. Acetonitrile was evaporated, and the compound was extracted with $CH_2Cl_2$ (3×). The combined extracts were washed with water, dried over $Na_2SO_4$, and the solvents removed in vacuo. Recrystallization in EtOH provided thieno[3,2-c]quinolin-4(5H)-one as a tan crystalline solid (7 mg, 12% yield). LCMS (ES): 95% pure, m/z 202 $[M+1]^+$; $^1H$ NMR ($CDCl_3/CD_3OD$, 9:1, 400 MHz) δ 7.28 (m, 1H), 7.33 (m, 1H), 7.43-7.50 (m, 2H), 7.74 (d, J=4.4, 1H), 7.82 (d, J=7.6, 1H) ppm.

Process 9

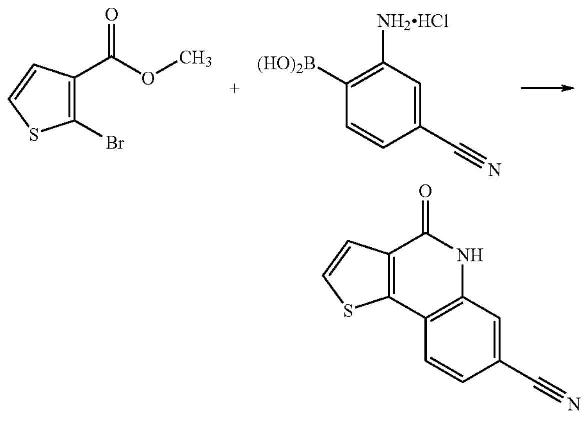

In a microwave vessel, methyl 2-bromo-3-thiophene carboxylate (1.0 eq, 250 mg, 1.13 mmol), 2-amino-3-cyanophenyl boronic acid HCl (1.1 eq, 250 mg, 1.24 mmol), sodium acetate (3.0 eq, 278 mg, 3.39 mmol) and $PdCl_2$(dppf) (0.007 eq, 4.3 mg, 0.0082 mmol) were mixed together in anhydrous DMF (2.5 ml). The mixture was heated in a microwave oven at 120° C. for 10 nm. Water was added and the material extracted with $CH_2Cl_2$. The organic extracts were washed with brine, dried over $Na_2SO_4$ and the solvents removed in vacuo. The resulting solid was sonicated in AcOEt, filtered and dried to afford 4-oxo-4,5-dihydrothieno[3,2-c]quinoline-7-carbonitrile as a beige solid (121 mg, 48% yield). LCMS (ES): 95% pure, m/z 227 $[M+1]^+$.

Process 10

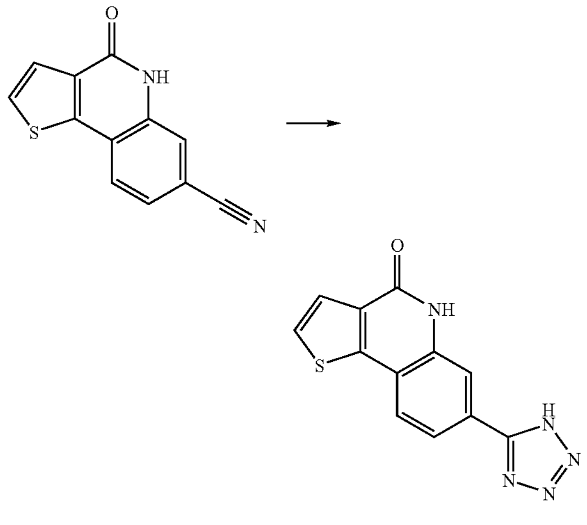

4-oxo-4,5-dihydrothieno[3,2-c]quinoline-7-carbonitrile (1.0 eq, 20 mg, 0.088 mmol) was dissolved in anhydrous DMF (0.15 ml). Sodium azide (4.0 eq, 23 mg, 0.354 mmol) and ammonium chloride (4.0 eq, 19 mg, 0.354 mmol) were added and the mixture stirred at 120° C. overnight. The reaction mixture was cooled down and water was added. Addition of aqueous 6N HCl induced formation of a precipitate. After filtration and drying in vacuo, 7-(1H-tetrazol-5-yl)thieno[3,2-c]quinolin-4(5H)-one was isolated as a greenish solid (18 mg, 76% yield)). LCMS (ES): 95% pure, m/z 270 $[M+1]^+$, 242 $[M+1-N_2]^+$; $^1H$ NMR (DMSO-$d_6$, 400 MHz) δ 7.64 (d, J=5.2, 1H), 7.86 (dd, J=1.6, J=8.4, 1H), 7.89 (d, J=5.2, 1H), 8.09 (d, J=8.0, 1H), 8.16 (d, J=1.6, 1H), 12.03 (s, 1H) ppm.

Process 11

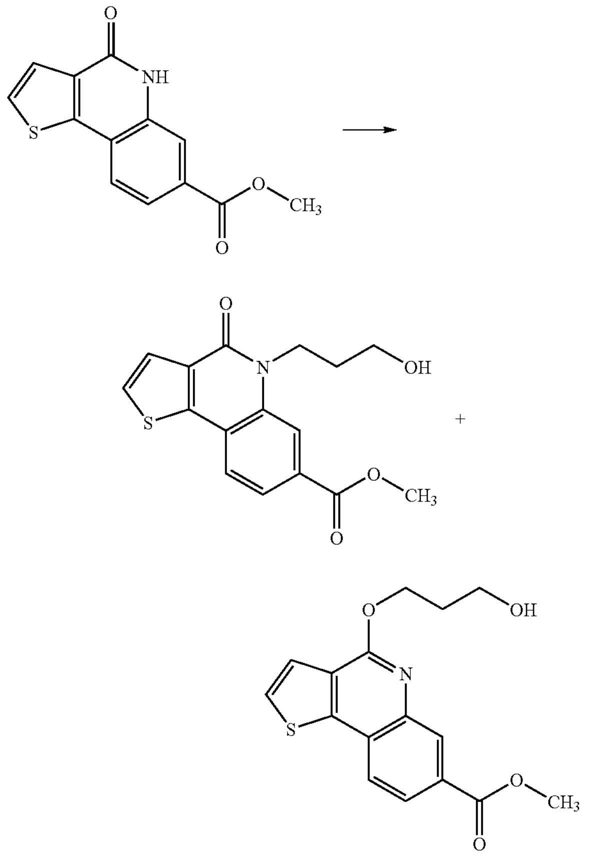

Methyl 4-oxo-4,5-dihydrothieno[3,2-c]quinoline-7-carboxylate (1.0 eq, 18 mg, 0.069 mmol) was dissolved in anhydrous DMF (0.4 ml). $K_2CO_3$ (7.0 eq, 70 mg, 0.506 mmol) and 3-bromo-1-propanol (16 eq, 100 ul, 1.144 mmol) were added and the mixture stirred at 100° C. for 1.5 hour. After adding water, the mixture was extracted with $CH_2Cl_2$. The combined extracts were dried over $Na_2SO_4$ and the solvents removed in vacuo. Compounds 8 and 9 were separated by preparative TLC on silica gel (eluted twice with 30% AcOEt in hexanes, then once with 50% AcOEt in hexanes). The less polar compound is methyl 4-(3-hydroxypropoxy)thieno[3,2-c]quinoline-7-carboxylate (12 mg). LCMS (ES): 80% pure, m/z 318 $[M+1]^+$. The more polar compound is methyl 5-(3-hydroxypropyl)-4-oxo-4,5-dihydrothieno[3,2-c]quinoline-7-carboxylate (19 mg). LCMS (ES): 80% pure, m/z 318 $[M+1]^+$. The two compounds were used for the following step without any further purification.

Process 12

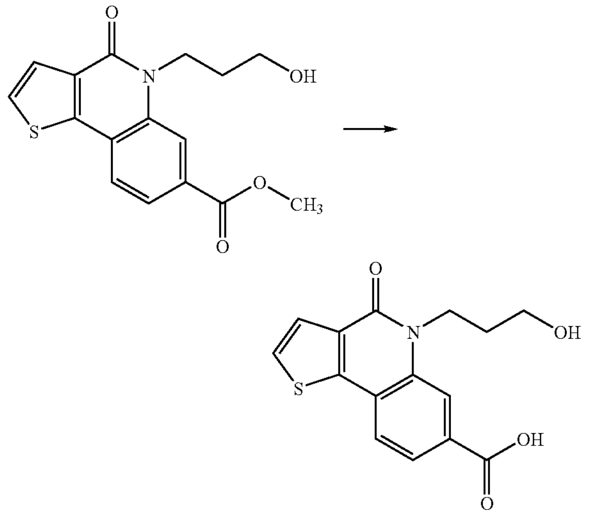

Methyl 5-(3-hydroxypropyl)-4-oxo-4,5-dihydrothieno[3,2-c]quinoline-7-carboxylate (1.0 eq, 19 mg, 0.060 mmol) was dissolved in a 1:1:1 mixture of THF, MeOH and water (0.5 ml). LiOH (40 mg) was added and the resulting mixture stirred at room temperature for 1.5 hours. Water, MeOH and HCl were added and the solution purified by preparative HPLC. Genevac evaporation afforded 5-(3-hydroxypropyl)-4-oxo-4,5-dihydrothieno[3,2-c]quinoline-7-carboxylic acid as a white solid (4 mg, 22% yield). LCMS (ES): 95% pure, m/z 304 $[M+1]^+$. $^1H$ NMR ($CDCl_3/CD_3OD$, 9:1, 400 MHz) δ 2.08 (qi, J=6.0, 2H), 3.61 (t, J=5.2, 2H), 4.62 (t, J=6.0, 2H), 7.53 (d, J=5.2, 1H), 7.77 (d, J=5.2, 1H), 7.93 (d, J=8.0, 1H), 7.99 (dd, J=1.2, J=8.4, 1H), 8.26 (d, J=0.8, 1H) ppm.

Process 13

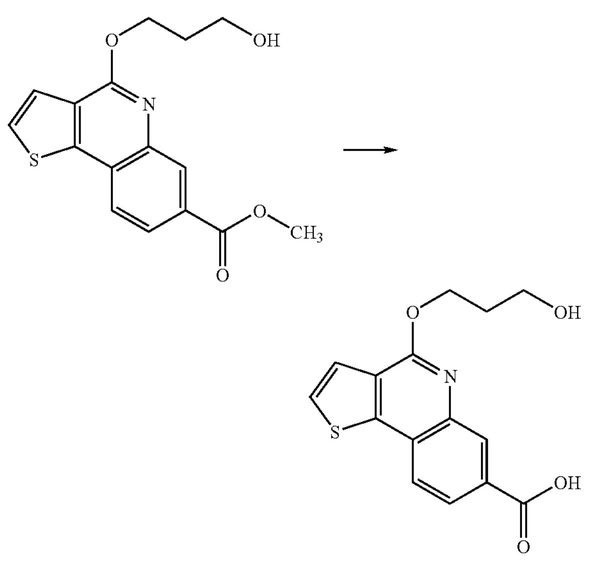

Methyl 4-(3-hydroxypropoxy)thieno[3,2-c]quinoline-7-carboxylate was prepared according to the procedure used in process 12. 4-(3-hydroxypropoxy)thieno[3,2-c]quinoline-7-carboxylic acid was isolated as a solid (3 mg, 26% yield). LCMS (ES): 95% pure, m/z 304 $[M+1]^+$.

Process 14

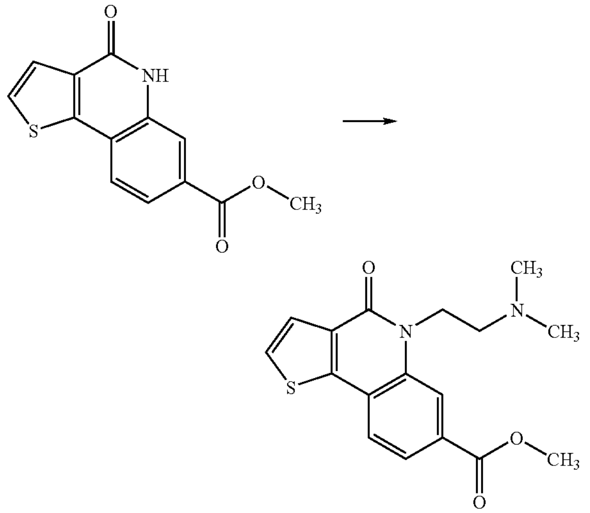

Methyl 5-(2-(dimethylamino)ethyl)-4-oxo-4,5-dihydrothieno[3,2-c]quinoline-7-carboxylate was prepared according to the procedure used in process 11 starting from methyl 4-oxo-4,5-dihydrothieno[3,2-c]quinoline-7-carboxylate and 2-dimethylaminoethyl chloride. LCMS (ES): 95% pure, m/z 331 $[M+1]^+$.

Process 15

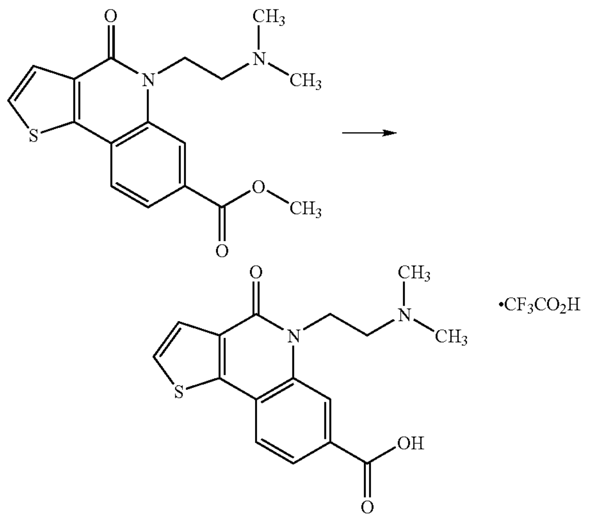

5-(2-(dimethylamino)ethyl)-4-oxo-4,5-dihydrothieno[3,2-c]quinoline-7-carboxylic acid was prepared according to the procedure used in process 12. Preparative HPLC and genevac evaporation provided the material as a TFA salt. LCMS (ES): 95% pure, m/z 317 $[M+1]^+$, $^1H$ NMR ($CDCl_3/CD_3OD$, 9:1, 400 MHz) δ 3.06 (s, 6H), 3.50 (t, J=7.6, 2H), 4.88 (t, J=7.6, 2H), 7.53 (d, J=5.2, 1H), 7.73 (d, J=5.6, 1H), 7.89 (d, J=8.4, 1H), 7.95 (br d, J=8.4, 1H), 8.2 (br s, 1H) ppm.

Process 16

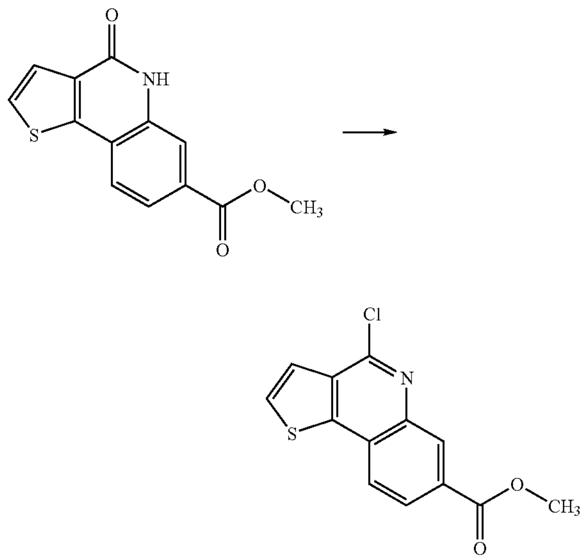

Methyl 4-oxo-4,5-dihydrothieno[3,2-c]quinoline-7-carboxylate (1.0 eq, 1.50 g, 5.79 mmol) was suspended in dry toluene (15 ml). $POCl_3$ (1.2 eq, 0.64 mmol, 6.99 mmol) and DIEA (0.8 eq, 0.81 mmol, 4.65 mmol) were added and the mixture vigorously stirred at 120° C. for 3 hours under nitrogen atmosphere. The mixture was hydrolyzed by addition of ice and water. The compound was extracted with $CH_2Cl_2$ (4×). The combined extracts were dried over $Na_2SO_4$ and the black solution filtered through a pad of celite. After evaporation of the volatiles in vacuo, the resulting solid was triturated in a mixture of AcOEt and hexanes. Filtration and drying provided methyl 4-chlorothieno[3,2-c]quinoline-7-carboxylate as a yellow fluffy solid (1.14 g, 71% yield). LCMS (ES): 95% pure, m/z 278 $[M+1]^+$, $^1H$ NMR ($CDCl_3$, 400 MHz) δ 4.01 (s, 3H), 7.72 (d, J=4.8, 1H), 7.74 (d, J=5.2, 1H), 8.14 (d, J=8.4, 1H), 8.25 (d, J=8.4, 1H), 8.85 (d, J=1.6, 1H) ppm.

Process 17

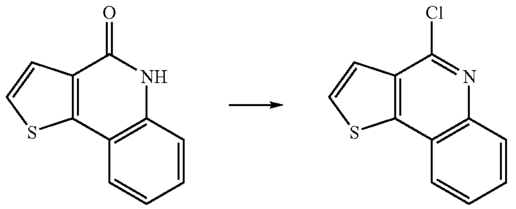

4-chlorothieno[3,2-c]quinoline was prepared according to the procedure used in process 16, starting from thieno[3,2-c]quinolin-4(5H)-one. 4-chlorothieno[3,2-c]quinoline was isolated as a solid (71 mg, 93% yield). LCMS (ES): 95% pure, m/z 220 $[M+1]^+$, 223 $[M+3]^+$.

Process 18

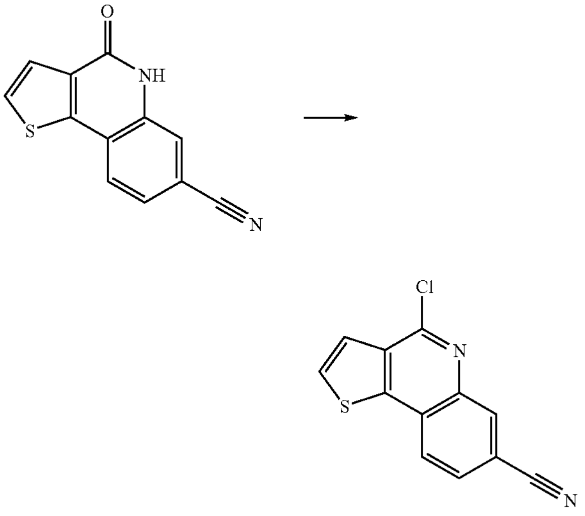

4-chlorothieno[3,2-c]quinoline-7-carbonitrile was prepared according to the procedure used in process 16. 4-chlorothieno[3,2-c]quinoline-7-carbonitrile was isolated as a yellow fluffy solid (833 mg, 77% yield). LCMS (ES): 95% pure, m/z 245 $[M+1]^+$, 247 $[M+3]^+$.

Process 19

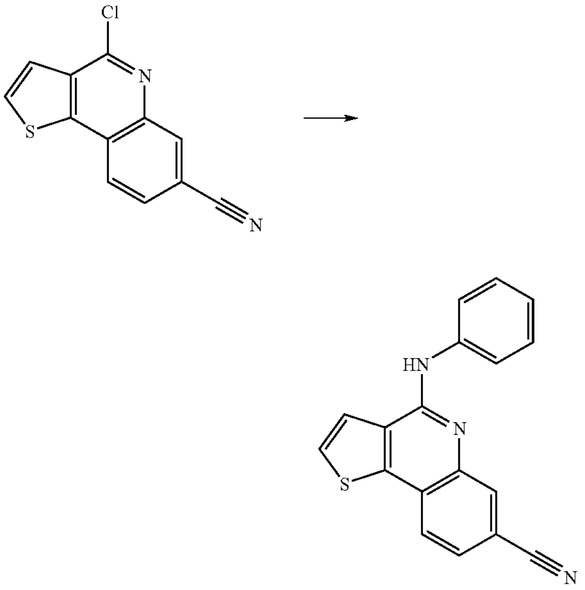

4-chlorothieno[3,2-c]quinoline-7-carbonitrile (1.0 eq, 23 mg, 0.094 mmol), aniline (0.1 ml) and NMP (0.1 ml) were mixed in a vial. The mixture was heated in a microwave oven at 120° C. for 10 nm. Water was added and the resulting solid 4-(phenylamino)thieno[3,2-c]quinoline-7-carbonitrile was filtered and dried. LCMS (ES): 95% pure, m/z 302 $[M+1]^+$.

Process 20

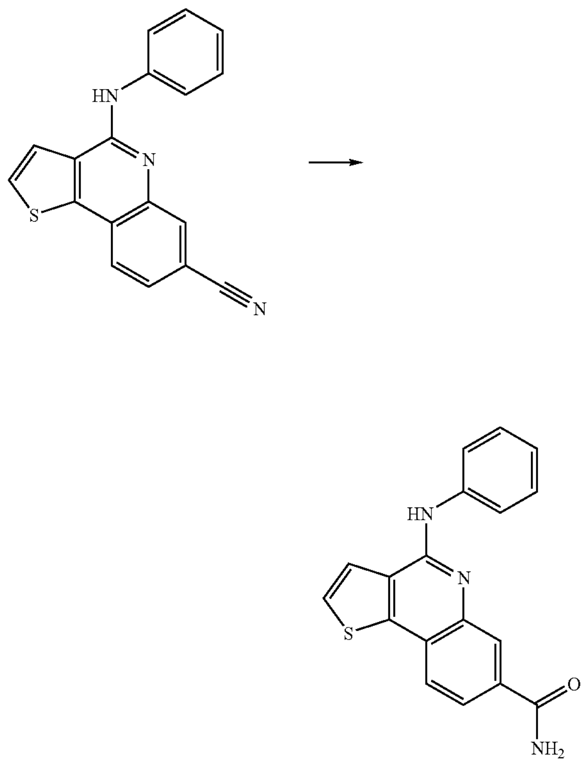

4-(phenylamino)thieno[3,2-c]quinoline-7-carbonitrile (34 mg, 0.113 mmol) was dissolved in NMP (0.3 ml). 30% aqueous $H_2O_2$ (0.2 ml) was added followed by addition of 6N NaOH (50 ul). The mixture was stirred at 50° C. for 2 hours. An extra amount of 30% aqueous $H_2O_2$ (0.3 ml) and 6N NaOH (100 ul) were added and a 70% conversion was achieved after 30 min. Water was added and the solid filtered and dried. The material was further reacted under the same conditions in order to achieve a complete transformation. 4-(phenylamino)thieno[3,2-c]quinoline-7-carboxamide was isolated as solid (30 mg, 83% yield). LCMS (ES): 95% pure, m/z 320 $[M+1]^+$.

Process 21

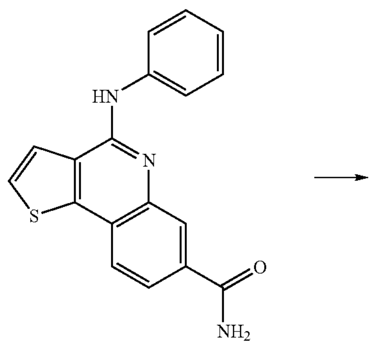

-continued

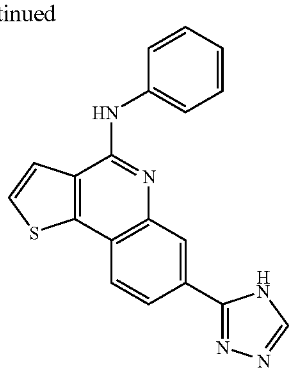

4-(phenylamino)thieno[3,2-c]quinoline-7-carboxamide (28 mg, 0.088 mmol) was suspended in N,N-dimethylformamide dimethylacetal and the mixture stirred at 80° C. under nitrogen atmosphere for 2 hours. The volatiles were removed in vacuo. Acetic acid (0.5 ml) and anhydrous hydrazine (0.1 ml) and the mixture stirred at 115° C. for 1 hour. Water and brine were added and the solid filtered. The material was purified by preparative HPLC. Genevac evaporation and trituration in AcOEt/hexanes afforded N-phenyl-7-(4H-1,2,4-triazol-3-yl)thieno[3,2-c]quinolin-4-amine as an off-white solid (9 mg, 30% yield). LCMS (ES): 94% pure, m/z 344 $[M+1]^+$.

Process 22

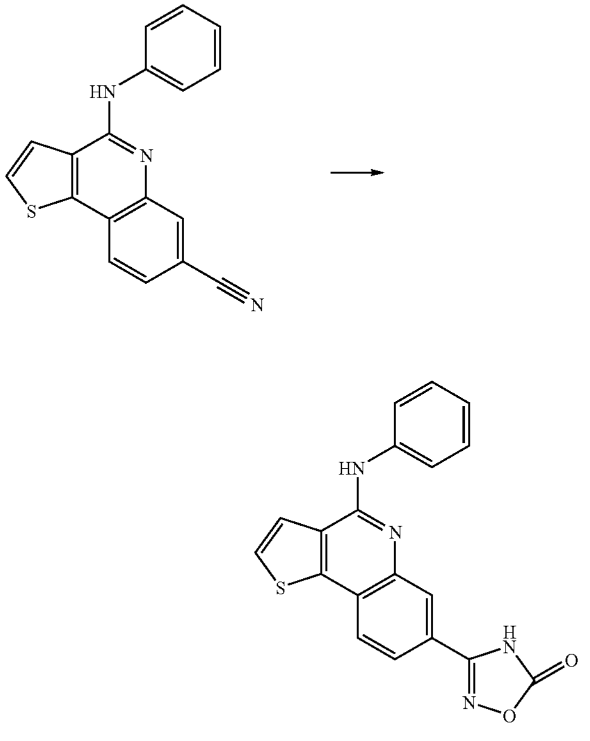

4-(phenylamino)thieno[3,2-c]quinoline-7-carbonitrile (1.0 eq, 27 mg, 0.0897 mmol) and hydroxylamine hydrochloride (10 eq, 62 mg, 0.892 mmol) and $K_2CO_3$ (10 eq, 124 mg, 0.896 mmol) were mixed in EtOH (0.5 ml) and the mixture heated under microwave at 100° C. for 10 min. The solid were removed by filtration and washed with EtOH. The solvents were removed in vacuo. The crude material was suspended in chloroform (0.5 ml). Ethyl chloroformate (20 ul) and triethylamine (20 ul) were added and the mixture stirred at room temperature for 10 min. $CH_2Cl_2$ was added and the organic phase was washed with brine. The organic phase was dried over $Na_2SO_4$ and the solvent removed. The crude material was suspended in NMP (1 ml) and heated under microwave at 160° C. for 10 min. The material was purified by preparative HPLC. Genevac evaporation afforded 3-(4-(phenylamino)thieno[3,2-c]quinolin-7-yl)-1,2,4-oxadiazol-5(4H)-one as an off-white solid (7 mg, 22% yield). LCMS (ES): 95% pure, m/z 361 [M+1]+.

Process 23

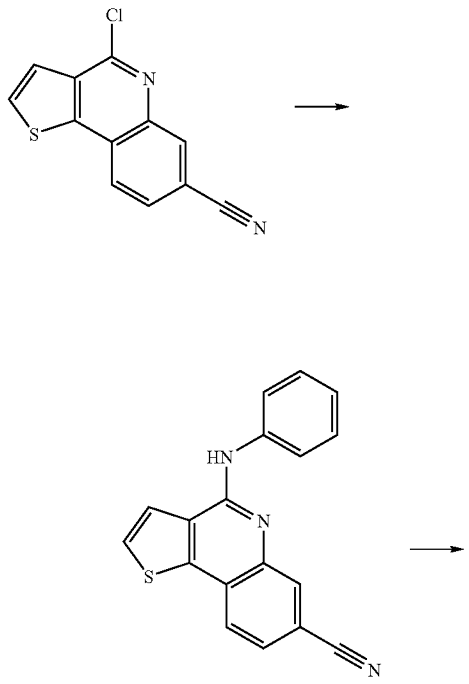

-continued

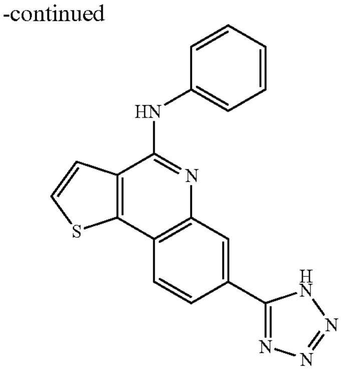

4-chlorothieno[3,2-c]quinoline-7-carbonitrile (1.0 eq, 23 mg, 0.094 mmol), aniline (0.1 ml) and NMP (0.1 ml) were mixed in a vial. The mixture was heated in a microwave oven at 120° C. for 10 nm. Water was added and the resulting solid 4-(phenylamino)thieno[3,2-c]quinoline-7-carbonitrile was filtered and dried. LCMS (ES): 95% pure, m/z 302 [M+1]+. This material was mixed in a vial with DMF (0.5 ml), $NH_4Cl$ (50 mg) and $NaN_3$ (50 mg). The mixture was stirred at 120° C. for 3 hours. After addition of water and filtration, N-phenyl-7-(1H-tetrazol-5-yl)thieno[3,2-c]quinolin-4-amine was isolated as a beige solid (13 mg, 41% yield). LCMS (ES): 95% pure, m/z 345 [M+1]+, 317 [M+1-$N_2$]+. $^1$H NMR (DMSO-$d_6$, 400 MHz) δ 7.07 (t, J=7.2, 1H), 7.40 (t, J=7.6, 2H), 8.00 (dd, J=1.6, J=8.4, 1H), 8.04 (d, J=5.2, 1H), 8.10 (dd, J=1.2, J=8.8, 2H), 8.19 (d, J=8.0, 1H), 8.25 (d, J=5.6, 1H), 8.43 (d, J=1.6, 1H), 9.34 (s, 1H) ppm.

Representative analogs (Table 5) were prepared by the same method using 4-chlorothieno[3,2-c]quinoline-7-carbonitrile and appropriate amines. The reaction temperatures used for the microwave reactions ranged from 120° C. to 180° C. After synthesis of the tetrazoles, the materials were isolated by preparative HPLC/genevac evaporation. In some instances, the materials precipitated after addition of water to the reaction mixture and were isolated by filtration.

TABLE 5

| Structure | M.W. | LCMS (ES) m/z |
|---|---|---|
| 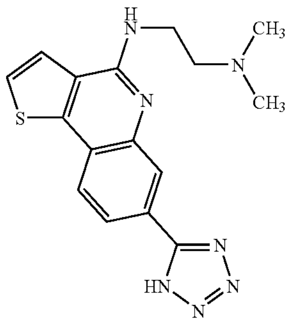 | 339.42 | 340 [M + 1]+ |

TABLE 5-continued
| | | |
|---|---|---|
| 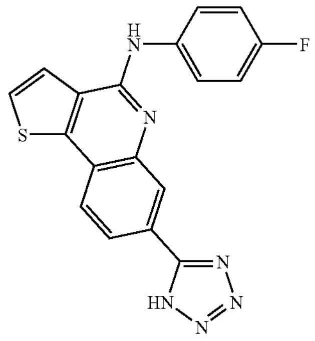 | 362.38 | 363 [M + 1]+ |
| 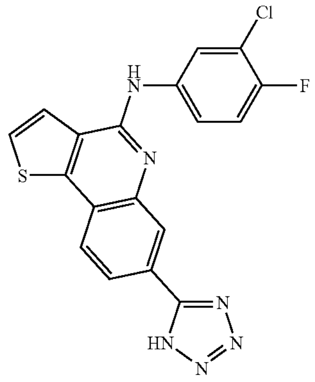 | 396.83 | 397 [M + 1]+ |
| 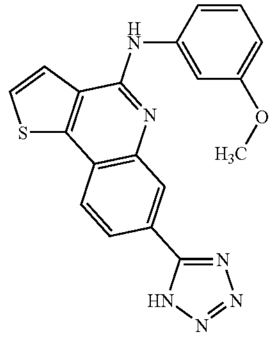 | 374.42 | 375 [M + 1]+ |
| 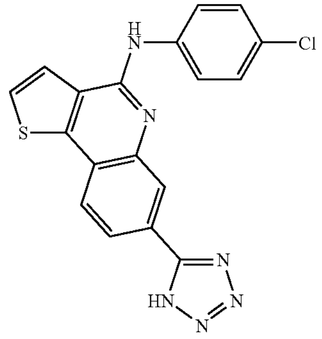 | 378.84 | 379 [M + 1]+ |

TABLE 5-continued
| | | |
|---|---|---|
| 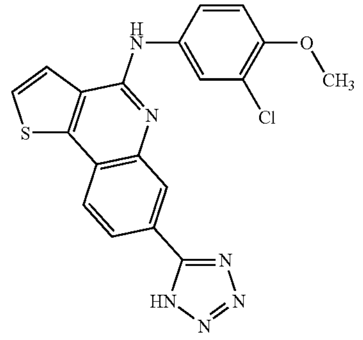 | 408.86 | 409 [M + 1]$^+$ |
| 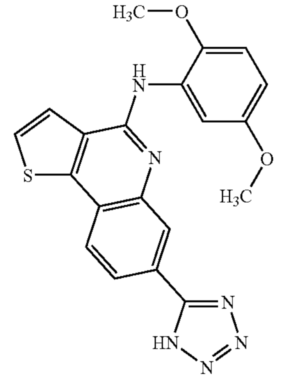 | 404.45 | 405 [M + 1]$^+$ |
| 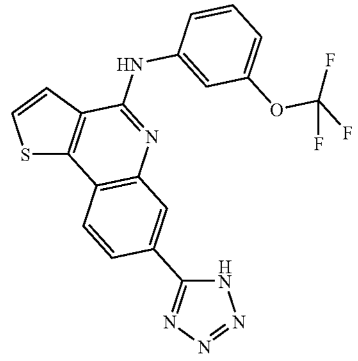 | 428.39 | 429 [M + 1]$^+$ |
| 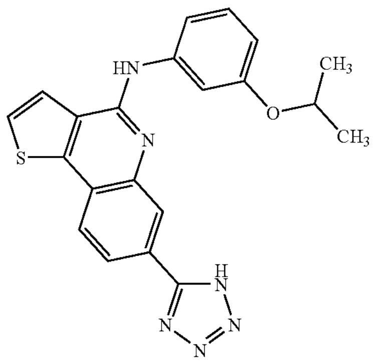 | 402.47 | 403 [M + 1]$^+$ |

TABLE 5-continued
| | | |
|---|---|---|
| 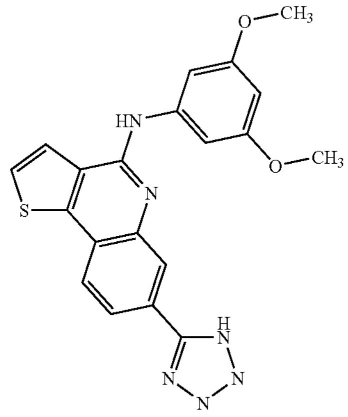 | 404.45 | 405 [M + 1]$^+$ |
| 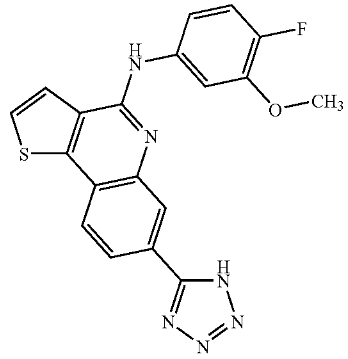 | 392.41 | 393 [M + 1]$^+$ |
| 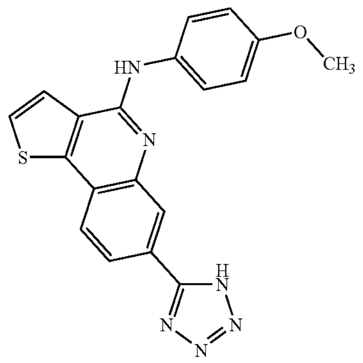 | 374.42 | 375 [M + 1]$^+$ |
| 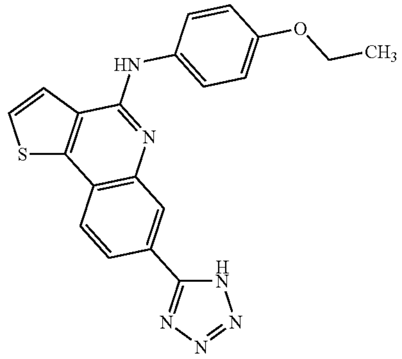 | 388.45 | 389 [M + 1]$^+$ |

TABLE 5-continued
| | | |
|---|---|---|
| 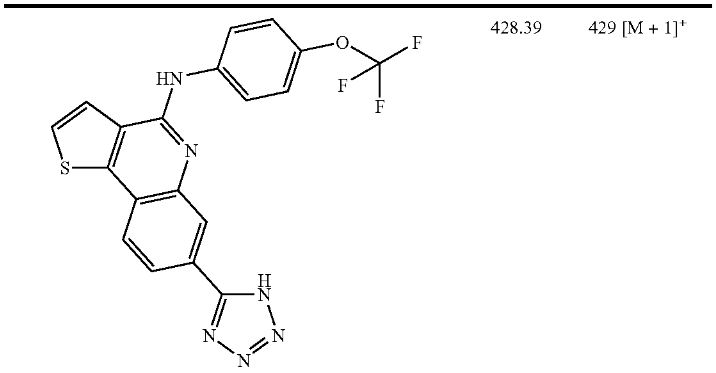 | 428.39 | 429 $[M + 1]^+$ |
| 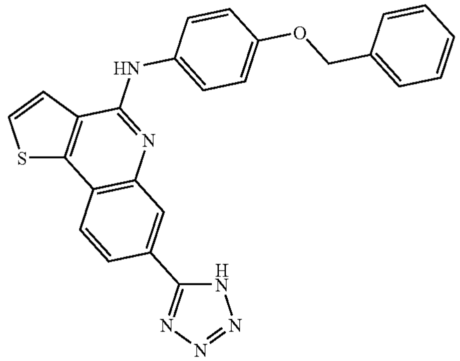 | 450.52 | 451 $[M + 1]^+$ |
| 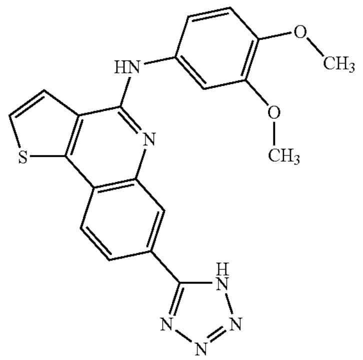 | 404.45 | 405 $[M + 1]^+$ |
| 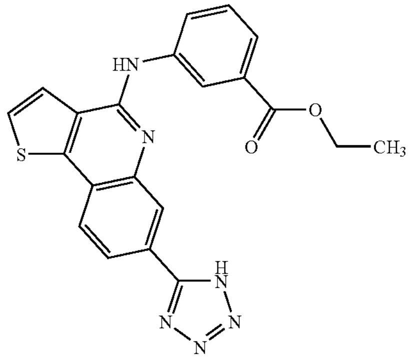 | 416.46 | 417 $[M + 1]^+$ |

TABLE 5-continued
| | | |
|---|---|---|
| 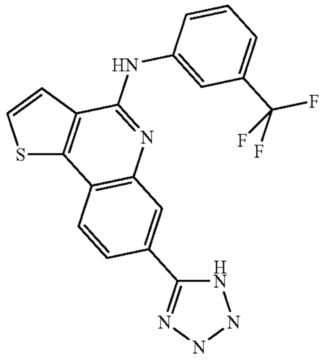 | 412.39 | 413 $[M + 1]^+$ |
| 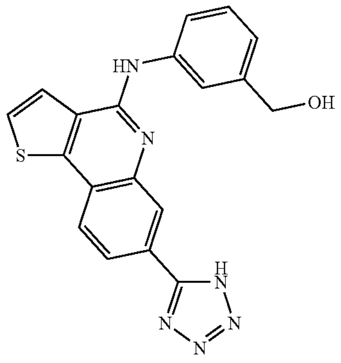 | 374.42 | 375 $[M + 1]^+$ |
| 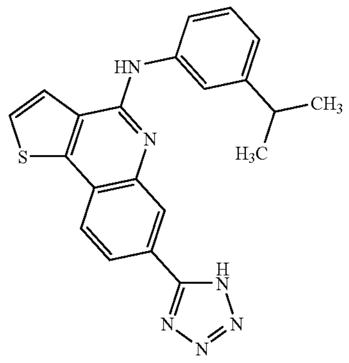 | 386.47 | 387 $[M + 1]^+$ |
| 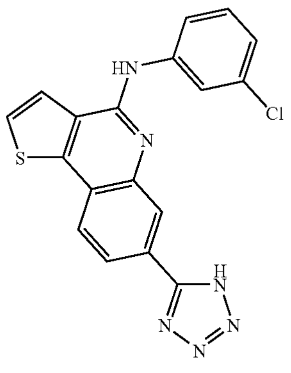 | 378.84 | 379 $[M + 1]^+$ |

TABLE 5-continued
| | | |
|---|---|---|
| 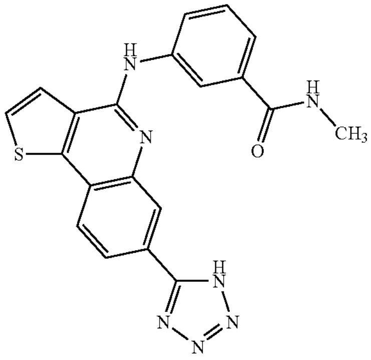 | 401.44 | 402 [M + 1]+ |
| 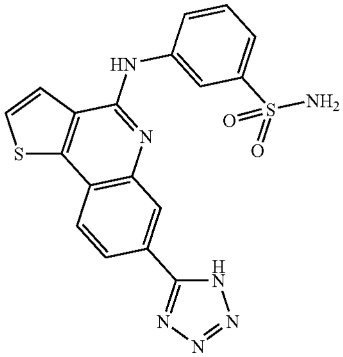 | 423.47 | 424 [M + 1]+ |
| 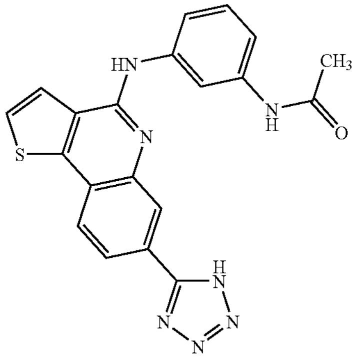 | 401.44 | 402 [M + 1]+ |
| 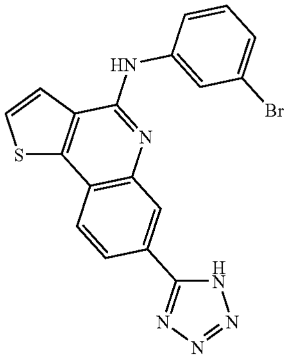 | 423.29 | 424 [M + 1]+ |

TABLE 5-continued
| | | |
|---|---|---|
| 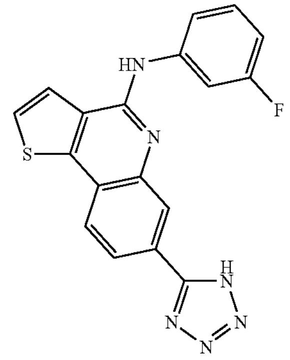 | 362.38 | 363 [M + 1]$^+$ |
| 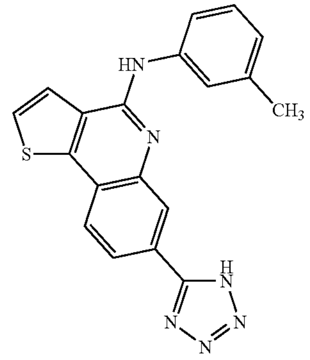 | 358.42 | 359 [M + 1]$^+$ |
| 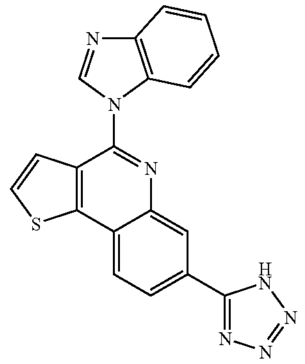 | 369.40 | 370 [M + 1]$^+$ |
| 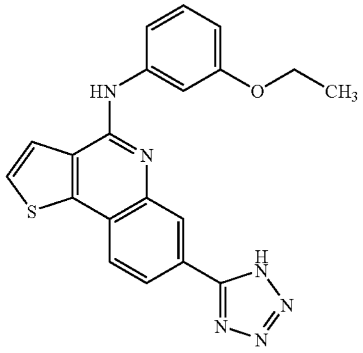 | 388.45 | 389 [M + 1]$^+$ |

TABLE 5-continued
| | | |
|---|---|---|
| 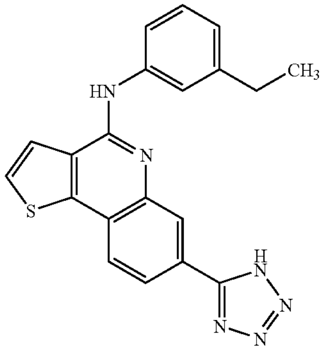 | 372.45 | 373 [M + 1]$^+$ |
| 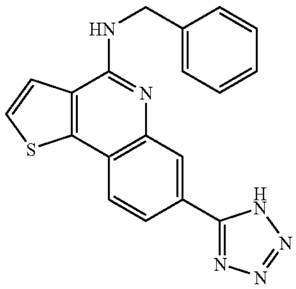 | 358.42 | 359 [M + 1]$^+$ |
| 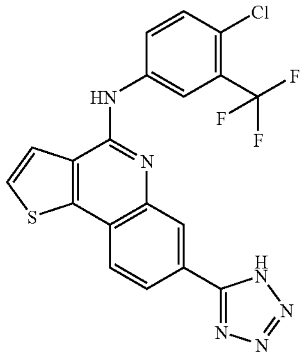 | 446.84 | 447 [M + 1]$^+$ |
| 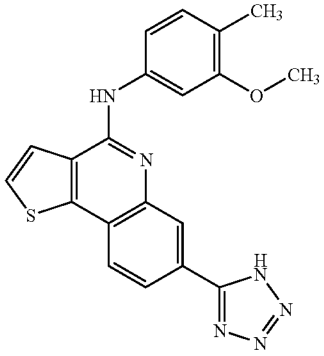 | 388.45 | 389 [M + 1]$^+$ |

TABLE 5-continued
| | | |
|---|---|---|
| 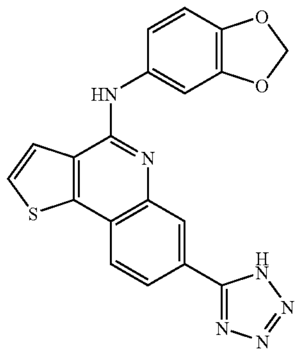 | 388.40 | 389 $[M + 1]^+$ |
| 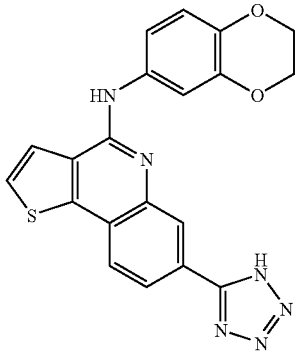 | 402.43 | 403 $[M + 1]^+$ |
| 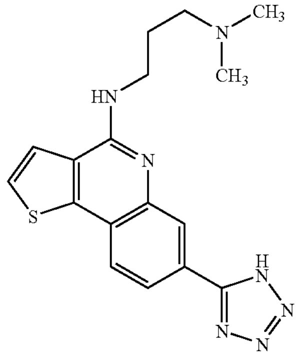 | 353.44 | 354 $[M + 1]^+$ |
| 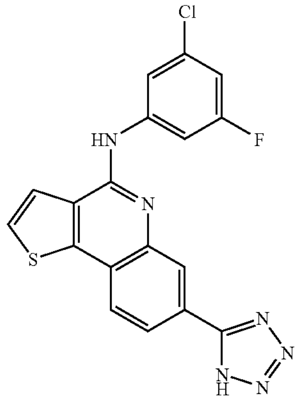 | 396.83 | 397 $[M + 1]^+$ |

TABLE 5-continued
| | | |
|---|---|---|
| 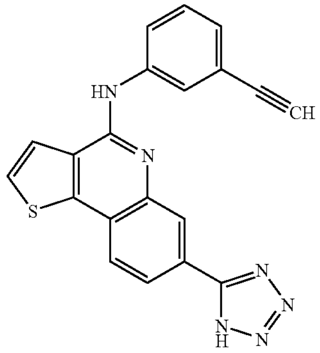 | 368.41 | 369 [M + 1]$^+$ |
| 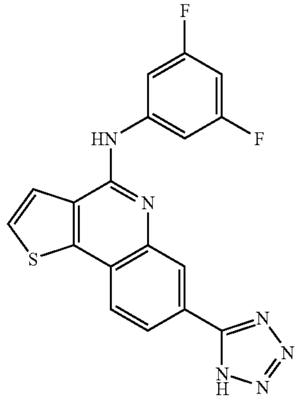 | 380.37 | 381 [M + 1]$^+$ |
| Structure | MW | LCMS (ES) m/z, [M + 1]+ |
|---|---|---|
| 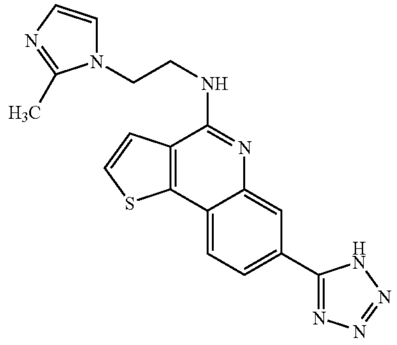 | 376.44 | 377 |
| 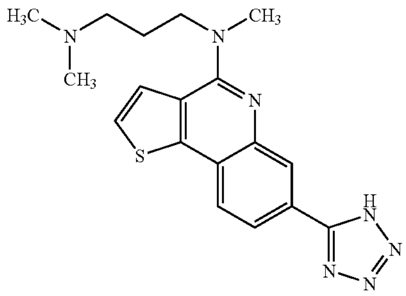 | 367.47 | 368 |

TABLE 5-continued
| | | |
|---|---|---|
| 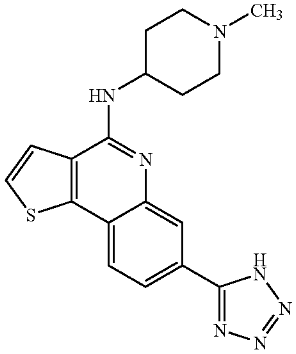 | 365.46 | 366 |
| 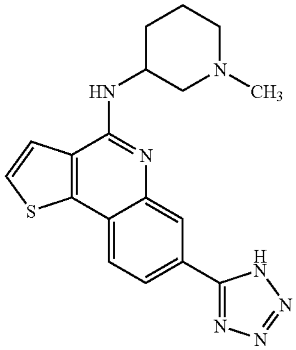 | 365.46 | 366 |
| 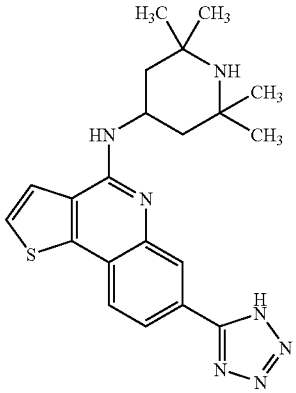 | 407.54 | 408 |
| 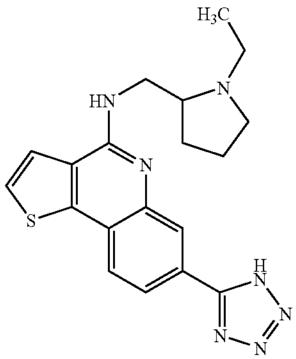 | 379.48 | 380 |

TABLE 5-continued
| | | |
|---|---|---|
| 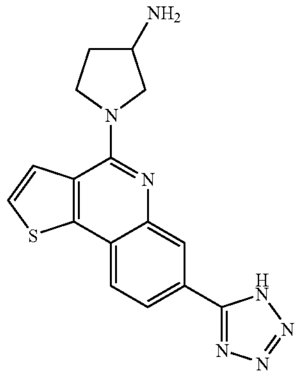 | 337.40 | 338 |
| 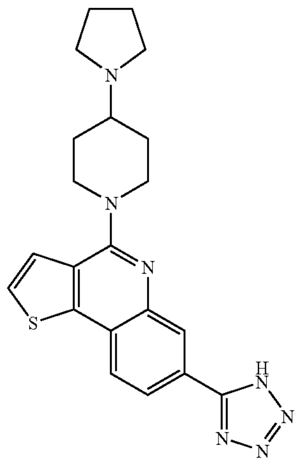 | 405.52 | 406 |
| 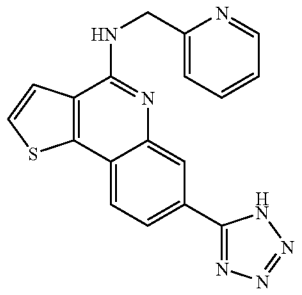 | 359.41 | 360 |
| 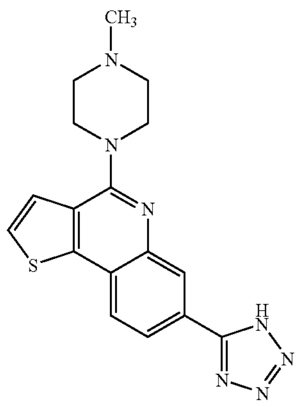 | 351.43 | 352 |

TABLE 5-continued
| | | |
|---|---|---|
| 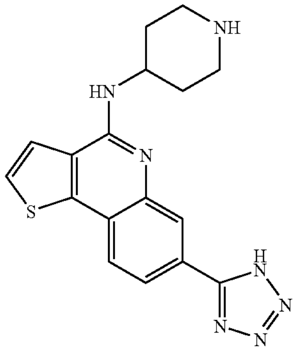 | 351.43 | 352 |
| 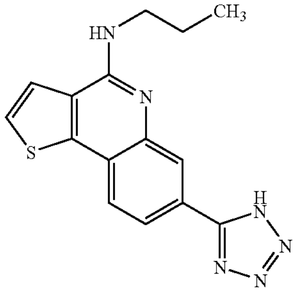 | 310.38 | 311 |
| 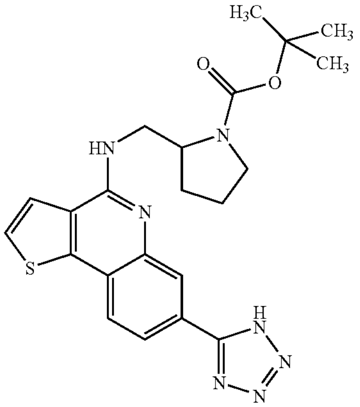 | 451.54 | 452 |
| 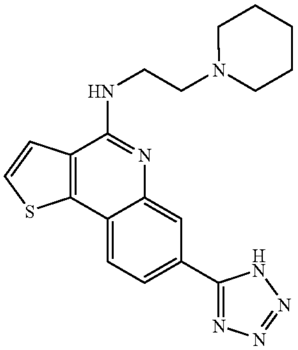 | 379.48 | 380 |

TABLE 5-continued
| | | | |
|---|---|---|---|
| 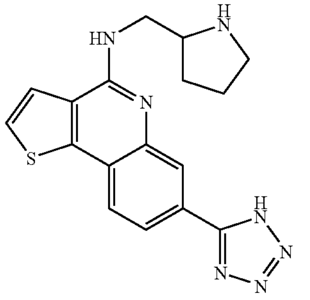 | | 351.43 | 352 |
| 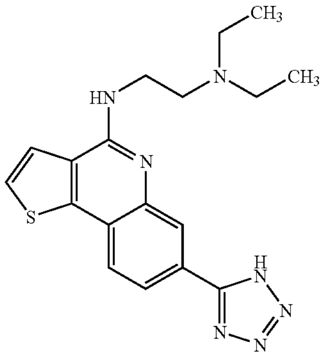 | | 367.47 | 368 |
| 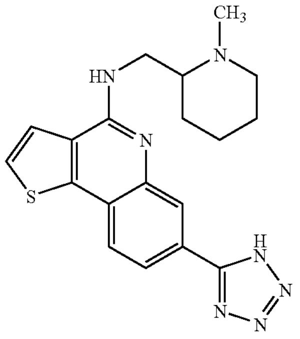 | | 379.48 | 380 |
| 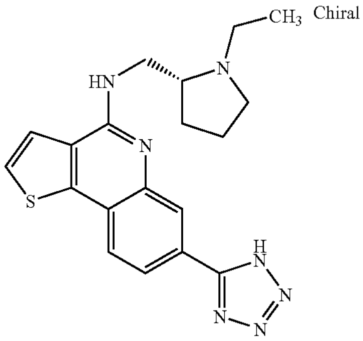 | Chiral | 379.48 | 380 |

TABLE 5-continued
| | | | |
|---|---|---|---|
| 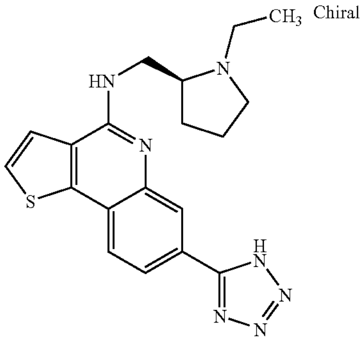 | Chiral | 379.48 | 380 |
| 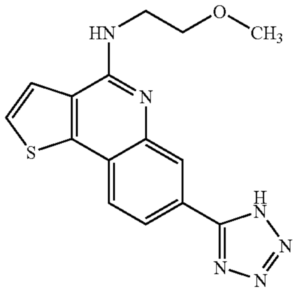 | | 326.38 | 327 |
| 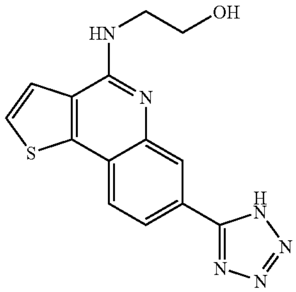 | | 312.35 | 313 |
| 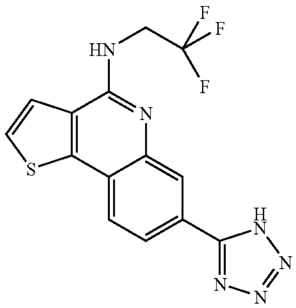 | | 350.32 | 351 |
| 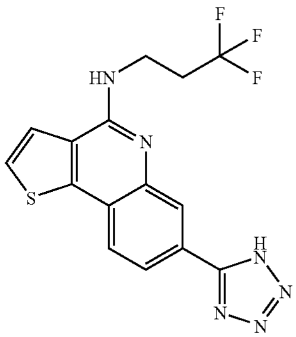 | | 364.35 | 365 |

TABLE 5-continued

| | | |
|---|---|---|
| 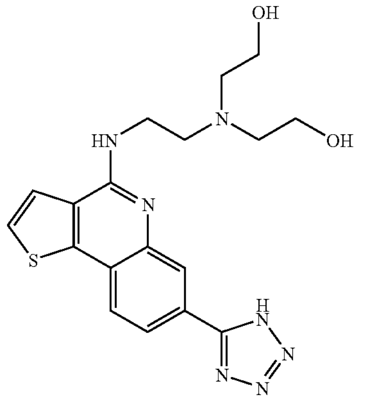 | 399.47 | 400 |

Process 24

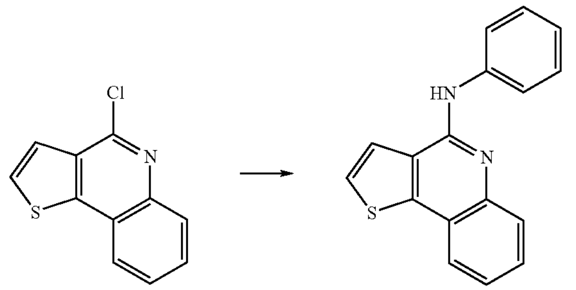

4-chlorothieno[3,2-c]quinoline (23 mg) was mixed with aniline (0.1 ml) and NMP (0.1 ml) and the mixture was heated in a microwave oven at 120° C. for 10 min. NMP (0.8 ml) was added and the compound purified by preparative HPLC. Genevac evaporation afforded N-phenylthieno[3,2-c]quinolin-4-amine as a pinky solid (31 mg, quant.). LCMS (ES): 95% pure, m/z 277 $[M+1]^+$.

Process 25

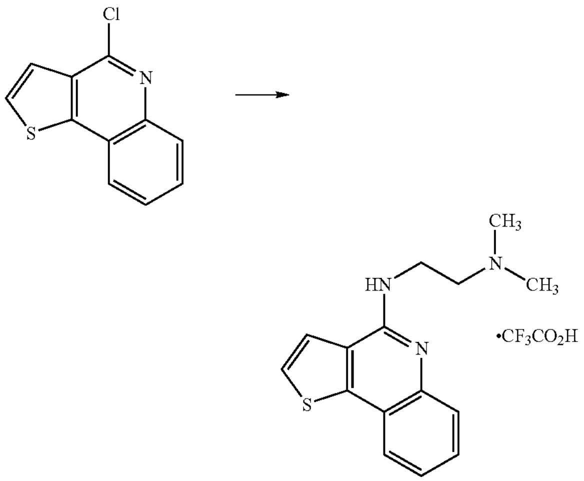

N1,N1-dimethyl-N2-(thieno[3,2-c]quinolin-4-yl)ethane-1,2-diamine was prepared according to the procedure in process 24 using N,N-dimethyl ethylene diamine. Preparative HPLC and genevac evaporation afforded the expected material as a TFA salt. LCMS (ES): 95% pure, m/z 272 $[M+1]^+$.

Process 26

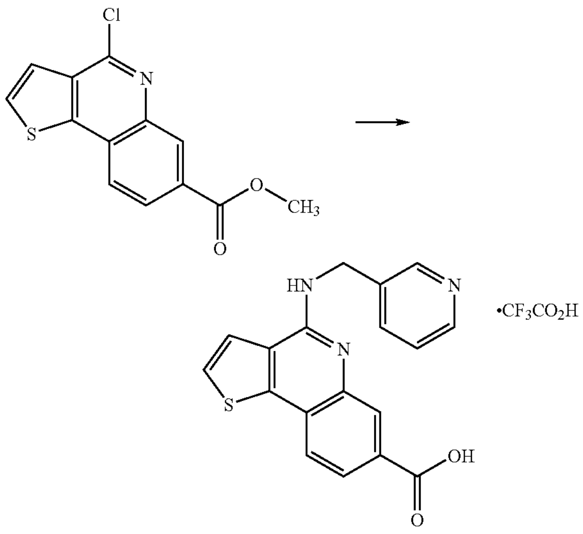

4-chlorothieno[3,2-c]quinoline-7-carboxylate (10 mg, 0.036 mmol) was suspended in NMP (0.1 ml) and 3-aminomethylpyridine (0.1 ml). The mixture was heated in a microwave oven at 120° C. for 10 nm. The reaction mixture was dissolved in a mixture of NMP and MeOH and the ester intermediate purified by preparative HPLC. After genevac evaporation of the solvents, the resulting solid was dissolved in a 1:1 mixture of THF and MeOH (0.6 ml). 5N aqueous LiOH (0.2 ml) was added and the mixture stirred at room temperature for 17 hrs. Water and aqueous HCl were added and the solution of 4-(pyridin-3-ylmethylamino)thieno[3,2-c]quinoline-7-carboxylic acid was purified by preparative HPLC. Removal of the solvents by genevac evaporation provided compound 4-(pyridin-3-ylmethylamino)thieno[3,2-c]quinoline-7-carboxylic acid as a white solid (10 mg, 62% yield). LCMS (ES): 95% pure, m/z 336 $[M+1]^+$. $^1H$ NMR ($CDCl_3$, 400 MHz) δ 5.23 (s, 2H), 7.71-7.78 (m, 4H), 8.11 (d, J=5.6, 1H), 8.47 (d, J=8.0, 1H), 8.49 (d, J=0.8, 1H), 8.62 (d, J=5.2, 1H), 8.97 (s, 1H) ppm.

Representative analogs (Table 6) were prepared by the same method, using 4-chlorothieno[3,2-c]quinoline-7-carboxylate and appropriate amines. The reaction temperatures used for the microwave reactions ranged from 120° C. to 180° C. After hydrolysis of the esters, the materials were isolated by preparative HPLC/genevac evaporation. In some instances, the materials precipitated after acidification of the hydrolysis mixture and were isolated by filtration.

TABLE 6

| Structure | M.W. | LCMS (ES) m/z |
|---|---|---|
| 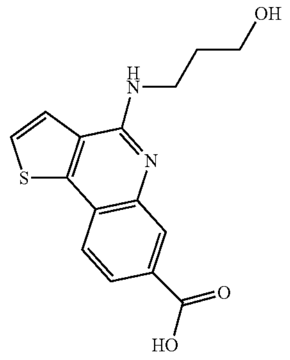 | 302.35 | 303 [M + 1]$^+$ |
| 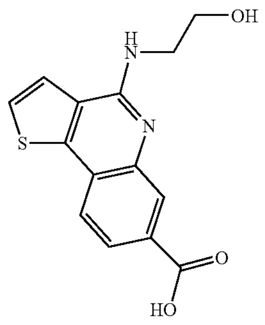 | 288.32 | 289 [M + 1]$^+$ |
| 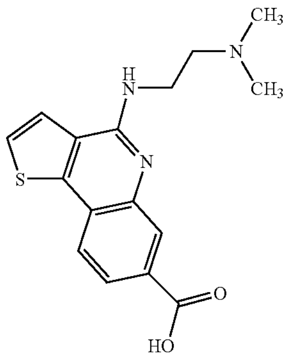 | 315.39 | 316 [M + 1]$^+$ |

TABLE 6-continued

| Structure | M.W. | LCMS (ES) m/z |
|---|---|---|
| 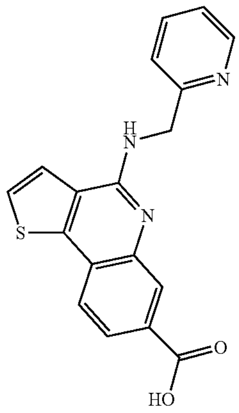 | 335.38 | 336 [M + 1]$^+$ |
| 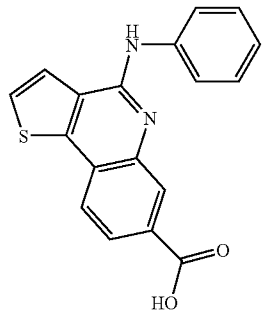 | 320.37 | 321 [M + 1]$^+$ |
| 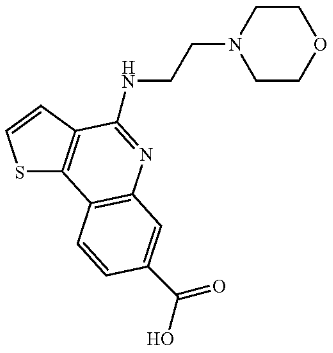 | 357.43 | 358 [M + 1]$^+$ |
| 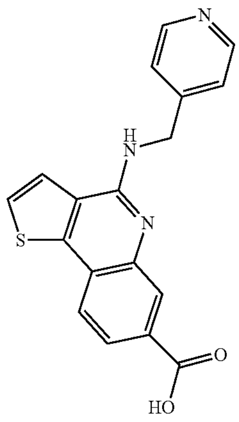 | 335.38 | 336 [M + 1]$^+$ |

TABLE 6-continued
| | | |
|---|---|---|
| 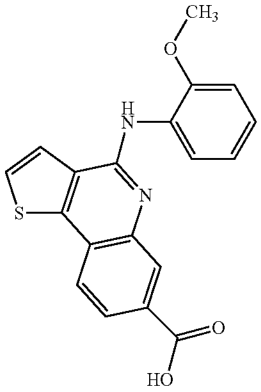 | 350.39 | 351 [M + 1]$^+$ |
| 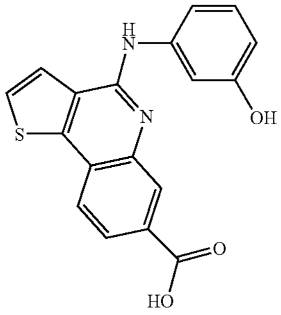 | 336.36 | 337 [M + 1]$^+$ |
| 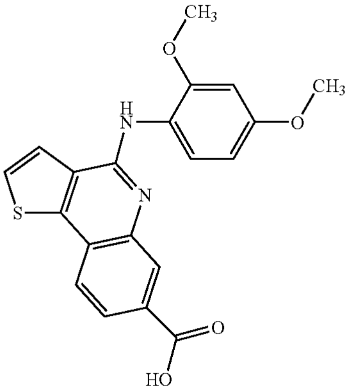 | 380.42 | 381 [M + 1]$^+$ |
| 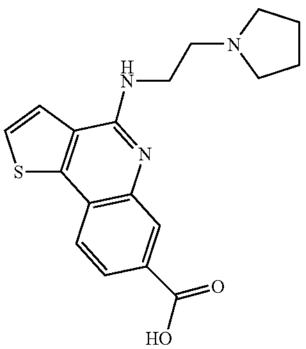 | 341.43 | 342 [M + 1]$^+$ |
| 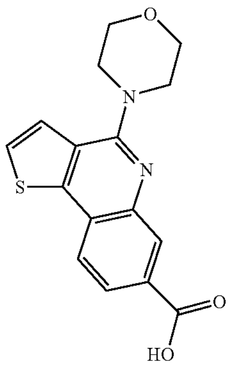 | 314.36 | 315 [M + 1]$^+$ |
| 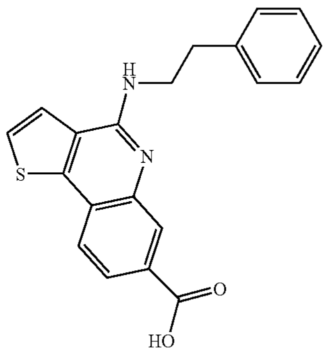 | 348.42 | 349 [M + 1]$^+$ |
| 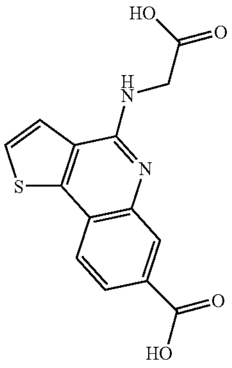 | 302.31 | 303 [M + 1]$^+$ |
| 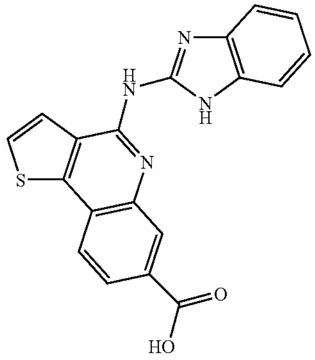 | 360.39 | 361 [M + 1]$^+$ |

TABLE 6-continued
| | | |
|---|---|---|
| 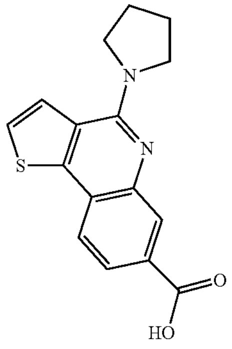 | 298.36 | 299 $[M+1]^+$ |
| 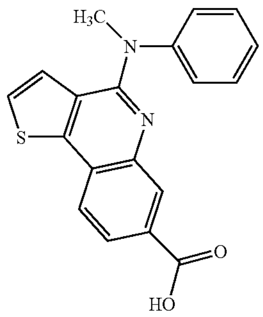 | 334.39 | 335 $[M+1]^+$ |
| 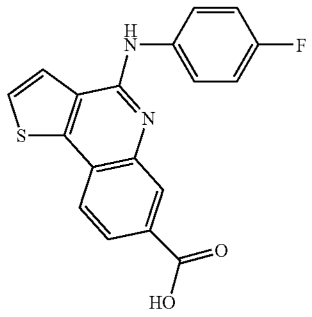 | 338.36 | 339 $[M+1]^+$ |
| 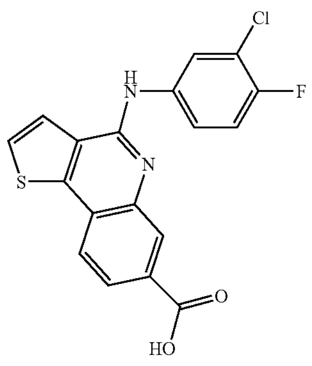 | 372.80 | 373 $[M+1]^+$ |
TABLE 6-continued
| | | |
|---|---|---|
| 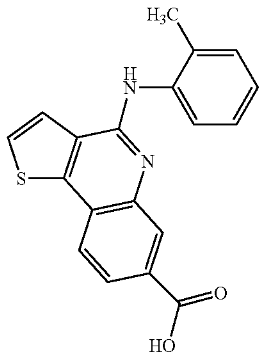 | 334.39 | 335 $[M+1]^+$ |
| 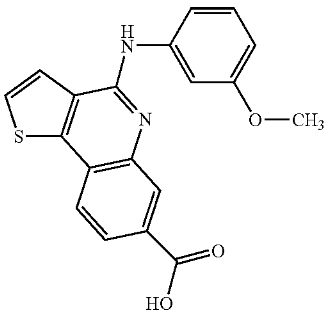 | 350.39 | 351 $[M+1]^+$ |
| 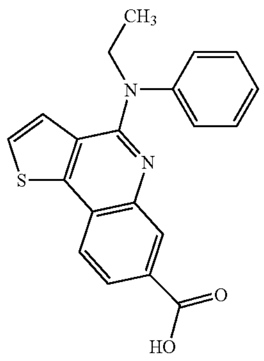 | 348.42 | 349 $[M+1]^+$ |
| 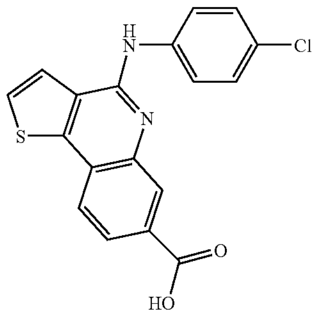 | 354.81 | 355 $[M+1]^+$ |

TABLE 6-continued
| | | |
|---|---|---|
| 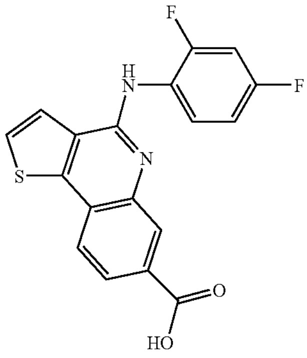 | 356.35 | 357 [M + 1]+ |
| 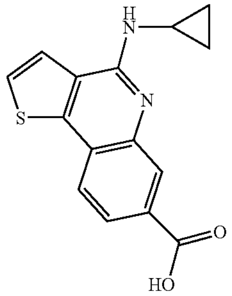 | 284.33 | 285 [M + 1]+ |
| 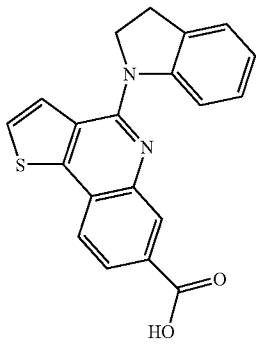 | 346.40 | 347 [M + 1]+ |
| 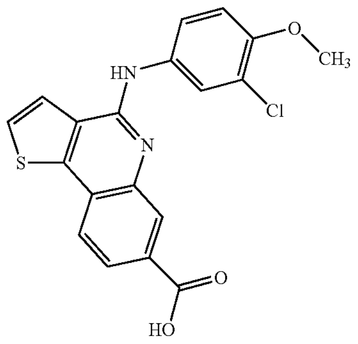 | 384.84 | 385 [M + 1]+ |
TABLE 6-continued
| | | |
|---|---|---|
| 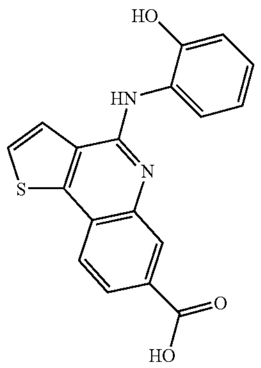 | 336.36 | 337 [M + 1]+ |
| 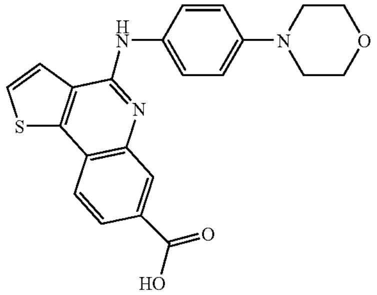 | 405.47 | 406 [M + 1]+ |
| 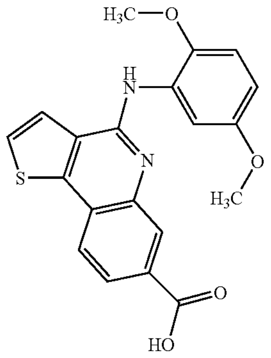 | 380.42 | 381 [M + 1]+ |
| 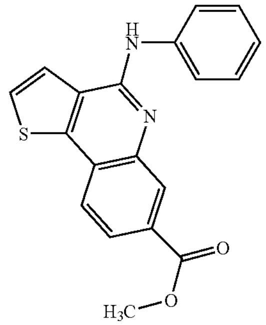 | 334.39 | 335 [M + 1]+ |

TABLE 6-continued
| | | |
|---|---|---|
| 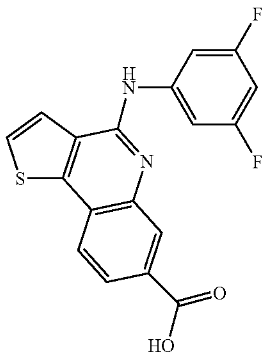 | 356.35 | 357 [M + 1]$^+$ |
| 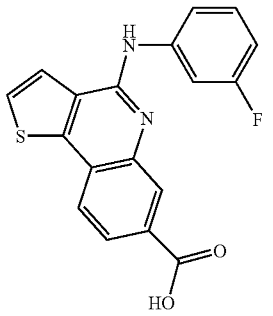 | 338.36 | 339 [M + 1]$^+$ |
| 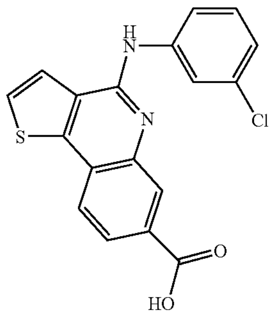 | 354.81 | 355 [M + 1]$^+$ |
| 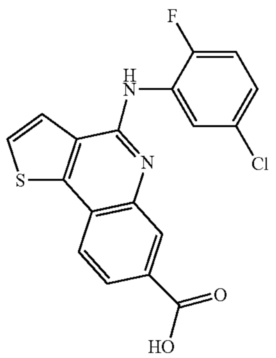 | 372.80 | 373 [M + 1]$^+$ |
TABLE 6-continued
| | | |
|---|---|---|
| 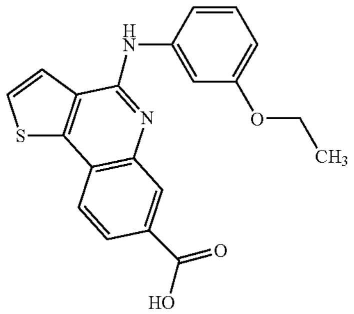 | 364.42 | 365 [M + 1]$^+$ |
| 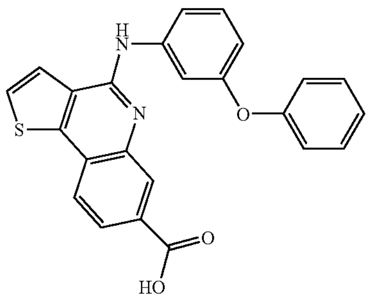 | 412.46 | 413 [M + 1]$^+$ |
| 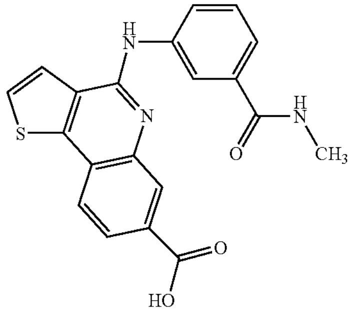 | 377.42 | 378 [M + 1]$^+$ |
| 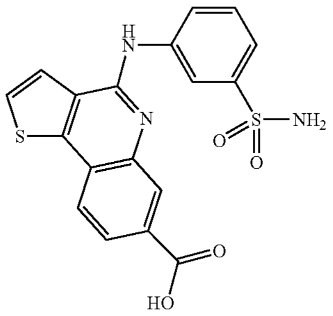 | 399.44 | 400 [M + 1]$^+$ |
| 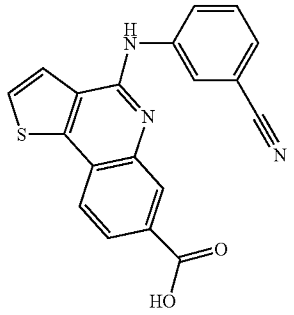 | 345.37 | 346 [M + 1]$^+$ |

TABLE 6-continued
| | | |
|---|---|---|
| 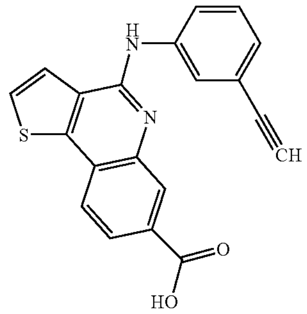 | 344.39 | 345 [M + 1]+ |
| 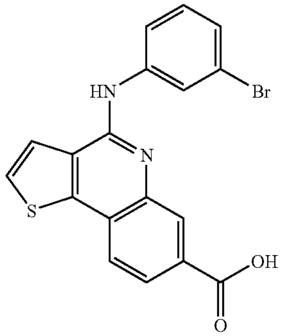 | 399.26 | 400 [M + 1]+ |
| 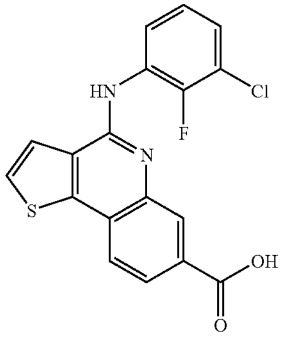 | 372.80 | 373 [M + 1]+ |
| 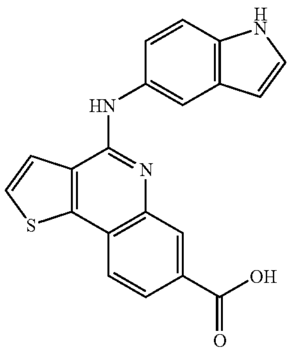 | 359.40 | 360 [M + 1]+ |
TABLE 6-continued
| | | |
|---|---|---|
| 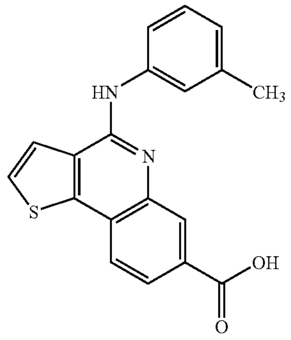 | 334.39 | 335 [M + 1]+ |
| 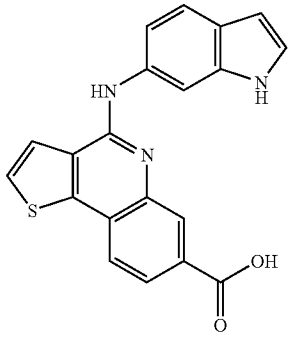 | 359.40 | 360 [M + 1]+ |
| 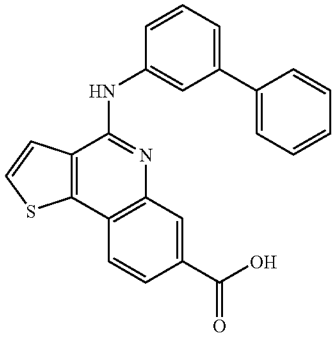 | 396.46 | 397 [M + 1]+ |
| 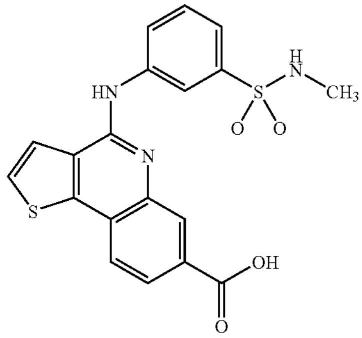 | 413.47 | 414 [M + 1]+ |

TABLE 6-continued
| | | |
|---|---|---|
| 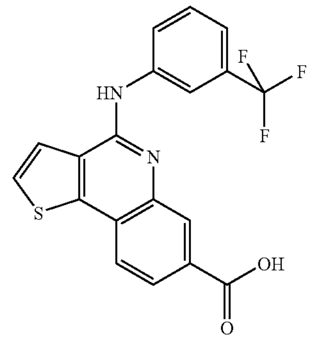 | 388.36 | 389 $[M + 1]^+$ |
| 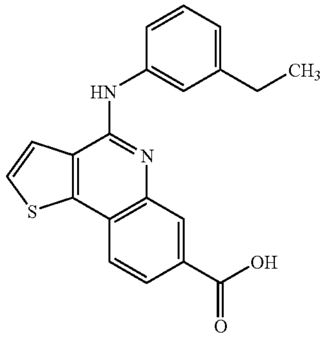 | 348.42 | 349 $[M + 1]^+$ |
| 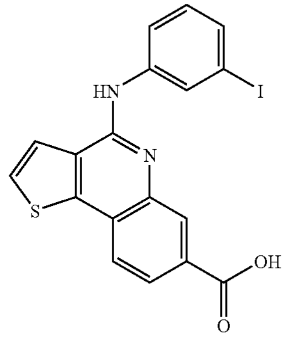 | 446.26 | 447 $[M + 1]^+$ |
| 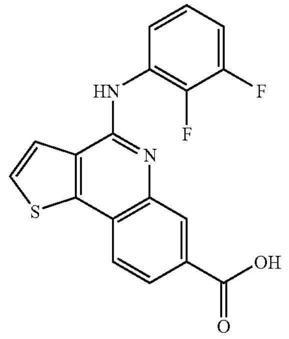 | 356.35 | 357 $[M + 1]^+$ |
TABLE 6-continued
| | | |
|---|---|---|
| 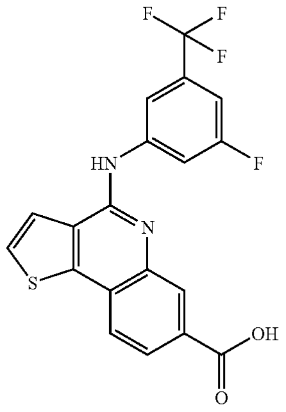 | 406.35 | 407 $[M + 1]^+$ |
| 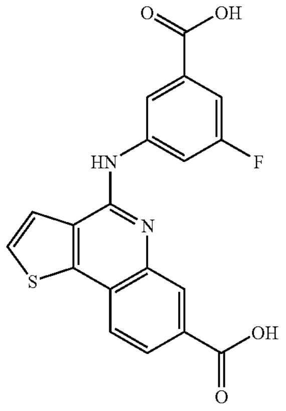 | 382.37 | 383 $[M + 1]^+$ |
| 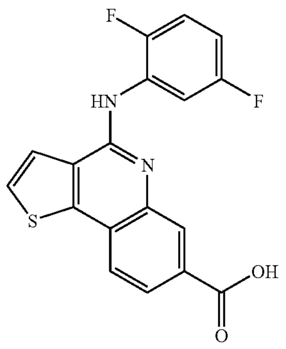 | 356.35 | 357 $[M + 1]^+$ |
| 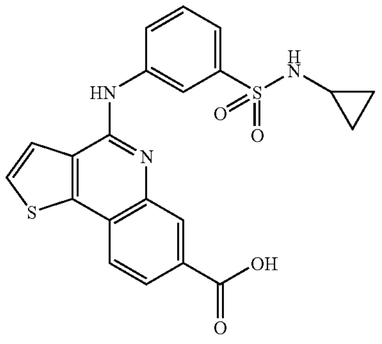 | 439.51 | 440 $[M + 1]^+$ |

TABLE 6-continued
| Structure | MW | LCMS (ES) m/z [M + 1]+ |
|---|---|---|
| 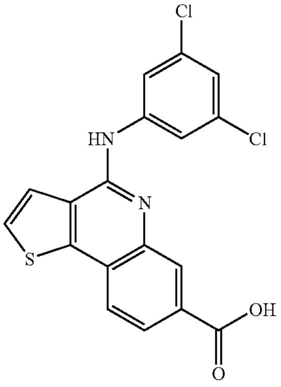 | 389.26 | 390 [M + 1]$^+$ |
| 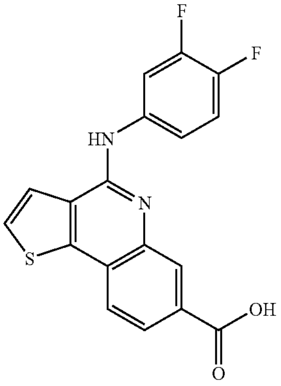 | 356.35 | 357 [M + 1]$^+$ |
| 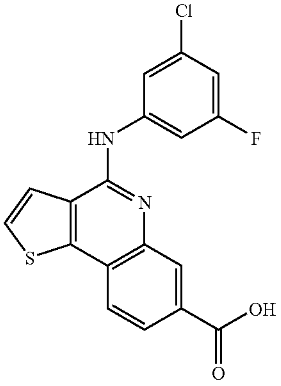 | 372.80 | 373 [M + 1]$^+$ |
| 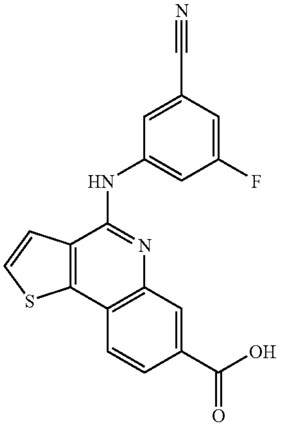 | 363.37 | 364 [M + 1]$^+$ |
TABLE 6-continued
| Structure | MW | LCMS (ES) m/z [M + 1]+ |
|---|---|---|
| 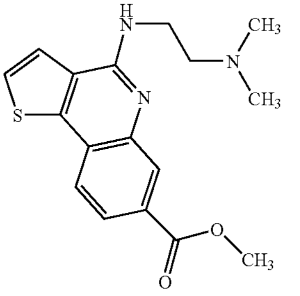 | 329.42 | 330 |
| 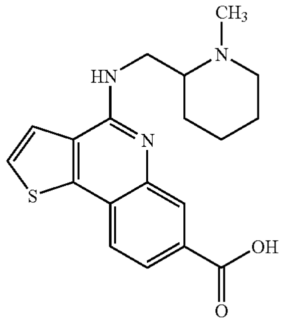 | 355.45 | 356 |
| 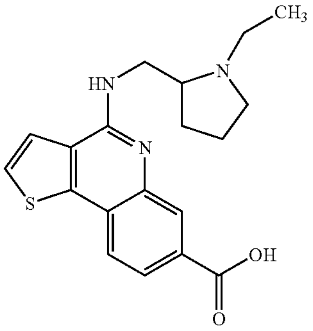 | 355.45 | 356 |
Process 27
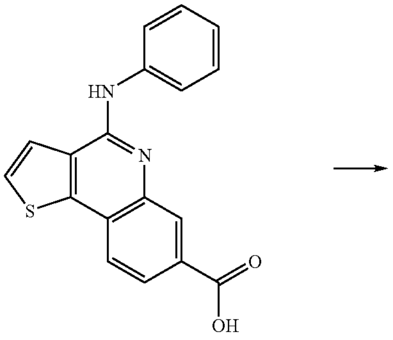

-continued

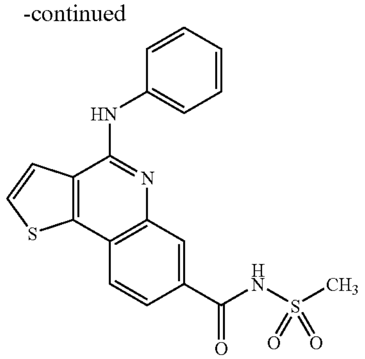

4-(phenylamino)thieno[3,2-c]quinoline-7-carboxylic acid (6 mg) was reacted with methyl sulfonamide (120 mg), EDCI (80 mg) and DMAP (20 mg) in anhydrous DMF (0.5 ml). After 5 hours, water was added and the solution subjected to preparative HPLC. Genevac evaporation provided N-(methylsulfonyl)-4-(phenylamino)thieno[3,2-c]quinoline-7-carboxamide as a solid (6 mg, 81% yield). LCMS (ES): 95% pure, m/z 398 $[M+1]^+$.

Process 28

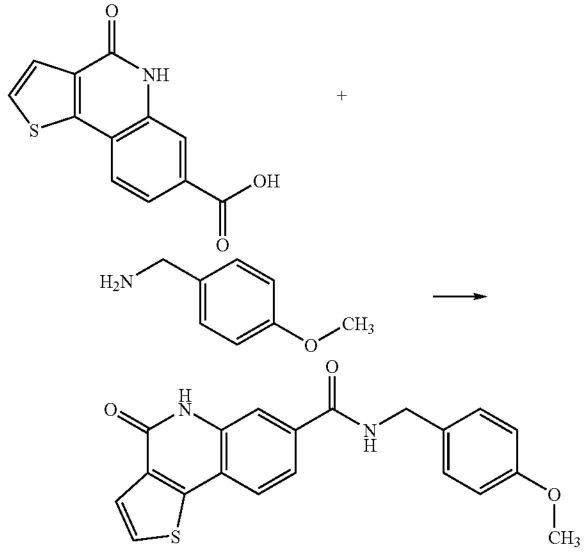

In a vial, 4-oxo-4,5-dihydrothieno[3,2-c]quinoline-7-carboxylic acid (1.0 eq, 20 mg, 0.081 mmol), N-hydroxybenzotriazole monohydrate (2.0 eq, 22 mg, 0162 mmol), para-methoxybenzylamine (2.0 eq, 21 ul, 0.162 mmol) and triethylamine (2.0 eq, 23 ul, 0.165 mmol) were dissolved in anhydrous DMF (0.5 ml). EDCI (2.0 eq 31 mg, 0.162 mmol) was added and the reaction mixture was stirred at 70° C. overnight. MeOH (0.5 ml) and water (2 ml) were added and the resulting precipitate filtered and dried. The material was triturated in AcOEt, filtered and dried to provide an off-white solid (19 mg, 65% yield). LCMS (ES): 95% pure, m/z 365 $[M+1]^+$, $^1H$ NMR (DMSO-$d_6$, 400 MHz) δ 3.71 (s, 3H), 4.40 (d, J=6.0, 2H), 6.88 (d, J=8.8, 2H), 7.24 (d, J=8.8, 2H), 7.60 (d, J=5.6, 1H), 7.69 (dd, J=1.6, J=8.0, 1H), 7.84 (d, J=5.6, 1H), 7.90 (s, 1H), 7.91 (d, J=8.8, 1H), 9.11 (t, J=5.6, 1H) ppm.

The following representative analogs (Table 7) were prepared by these processes, using 4-oxo-4,5-dihydrothieno[3,2-c]quinoline-7-carboxylic acid and appropriate amines. In some instances, the materials were purified by preparative HPLC and were isolated as dry solids after Genevac evaporation.

TABLE 7

| Structure | M.W. | LCMS (ES) m/z |
|---|---|---|
| 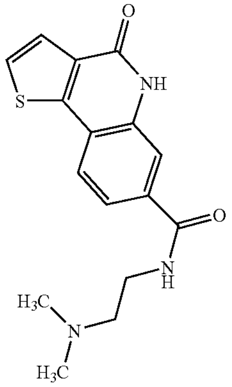 | 315.39 | 316 $[M + 1]^+$ |
| 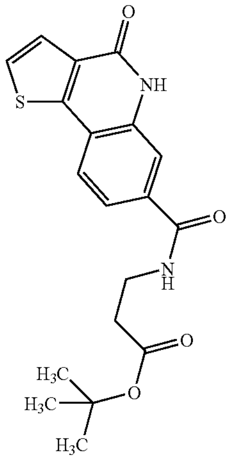 | 372.44 | 373 $[M + 1]^+$ |
| 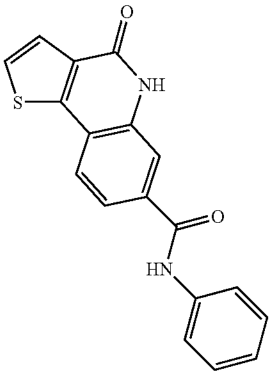 | 320.37 | 321 $[M + 1]^+$ |

TABLE 7-continued
| Structure | M.W. | LCMS (ES) m/z |
|---|---|---|
| 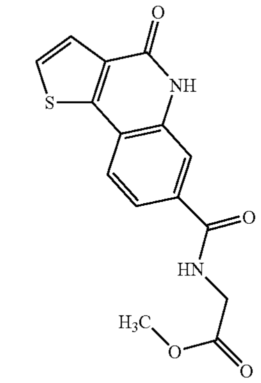 | 316.33 | 316 $[M + 1]^+$ |
| 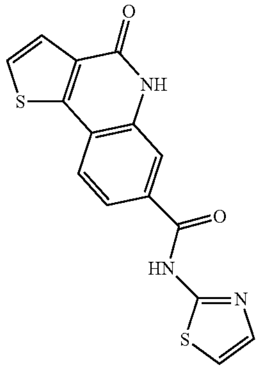 | 327.38 | 328 $[M + 1]^+$ |
| 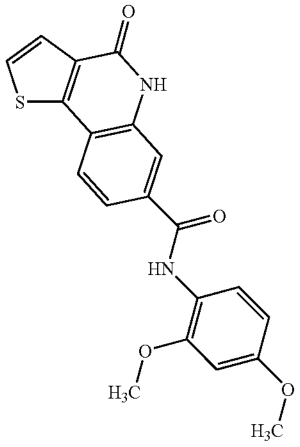 | 380.42 | 381 $[M + 1]^+$ |
| 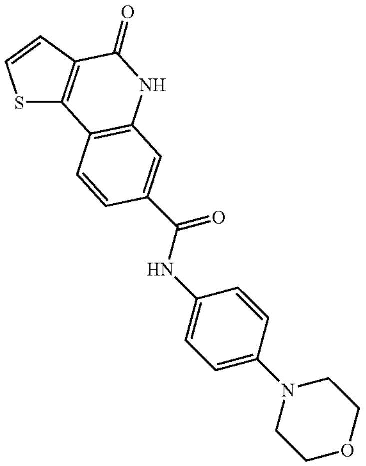 | 405.47 | 406 $[M + 1]^+$ |
| 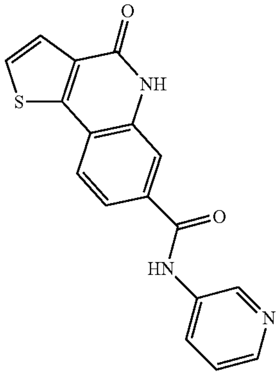 | 321.35 | 322 $[M + 1]^+$ |
| 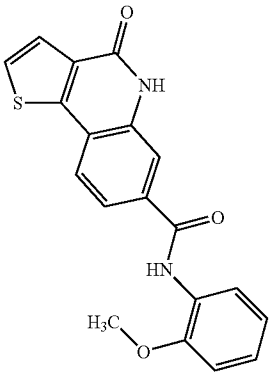 | 350.39 | 351 $[M + 1]^+$ |

TABLE 7-continued
| Structure | M.W. | LCMS (ES) m/z |
|---|---|---|
| 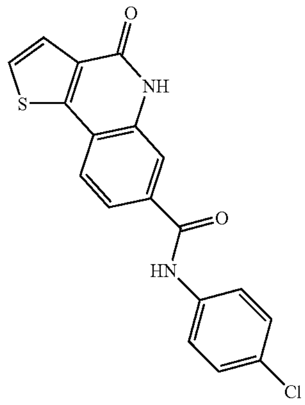 | 354.81 | 355 [M + 1]$^+$ |
| 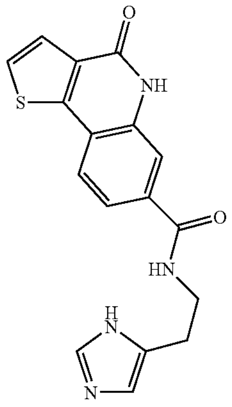 | 338.38 | 339 [M + 1]$^+$ |
| 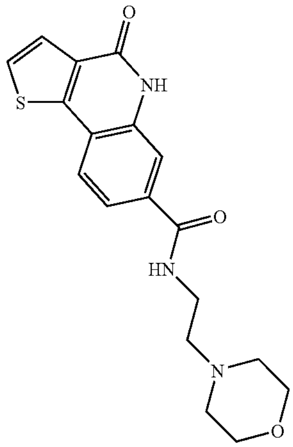 | 357.43 | 358 [M + 1]$^+$ |
TABLE 7-continued
| Structure | M.W. | LCMS (ES) m/z |
|---|---|---|
| 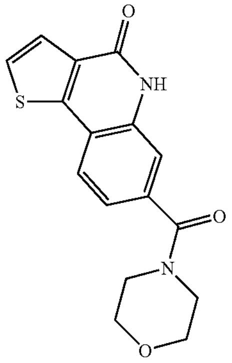 | 314.36 | 315 [M + 1]$^+$ |
| 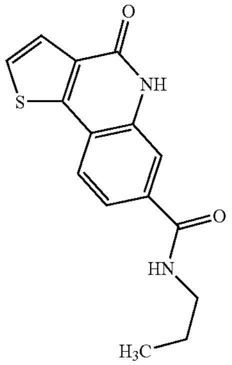 | 286.35 | 287 [M + 1]$^+$ |
| 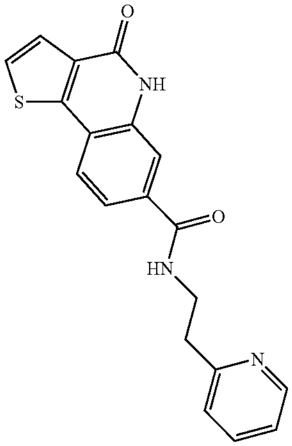 | 349.41 | 350 [M + 1]$^+$ |

TABLE 7-continued
| Structure | M.W. | LCMS (ES) m/z |
|---|---|---|
| 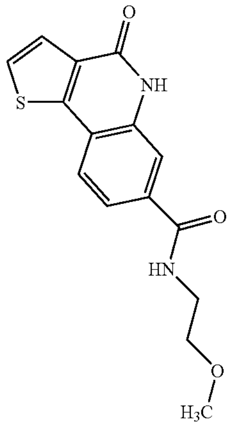 | 302.35 | 303 [M + 1]+ |
| 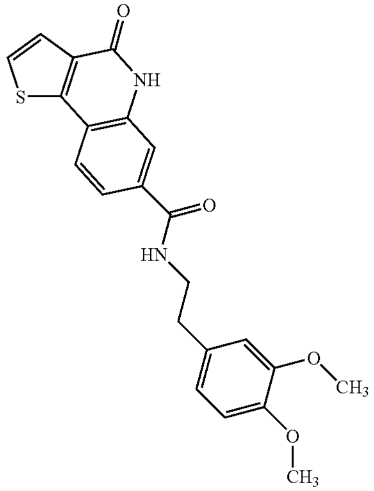 | 408.47 | 409 [M + 1]+ |
| 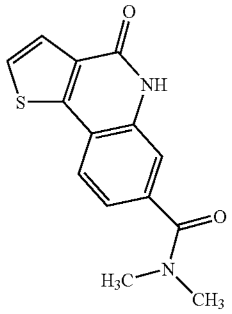 | 272.32 | 273 [M + 1]+ |
| 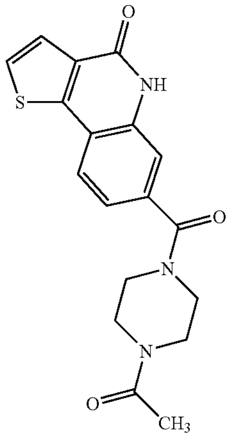 | 355.41 | 356 [M + 1]+ |
| 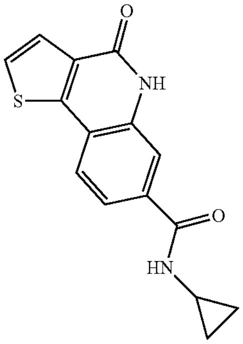 | 284.33 | 285 [M + 1]+ |
| 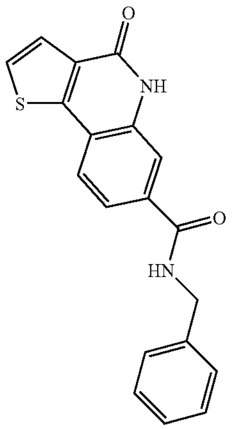 | 334.39 | 335 [M + 1]+ |

TABLE 7-continued
| Structure | M.W. | LCMS (ES) m/z |
|---|---|---|
| 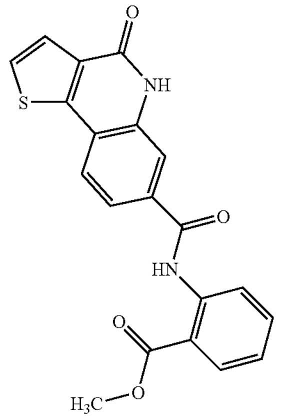 | 378.40 | 379 [M + 1]+ |
| 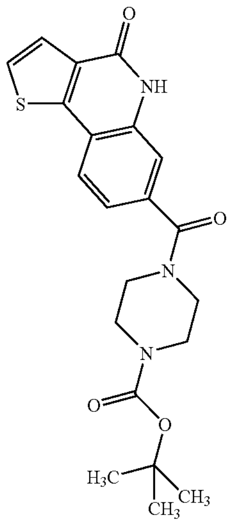 | 413.49 | 414 [M + 1]+ |
| 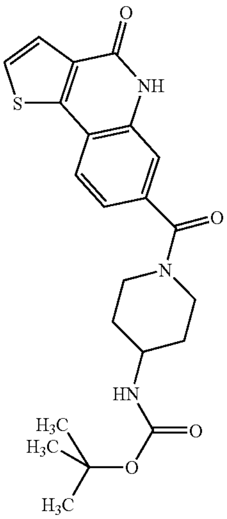 | 427.52 | 428 [M + 1]+ |
TABLE 7-continued
| Structure | M.W. | LCMS (ES) m/z |
|---|---|---|
| 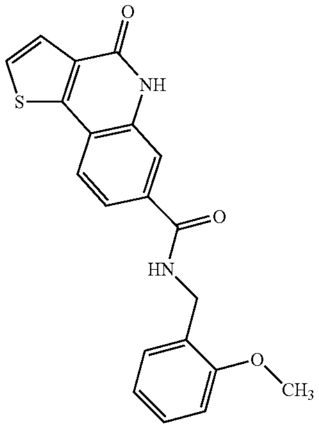 | 364.42 | 365 [M + 1]+ |
| 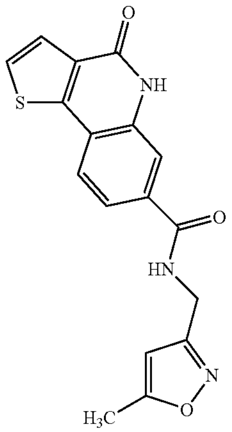 | 339.37 | 340 [M + 1]+ |
| 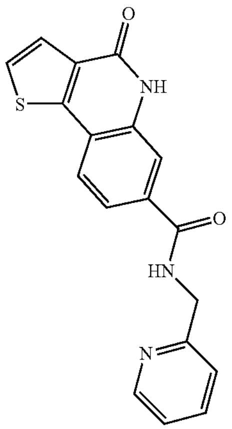 | 335.38 | 336 [M + 1]+ |

TABLE 7-continued
| Structure | M.W. | LCMS (ES) m/z |
|---|---|---|
| 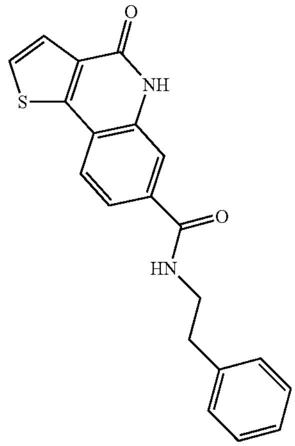 | 348.42 | 349 [M + 1]$^+$ |
| 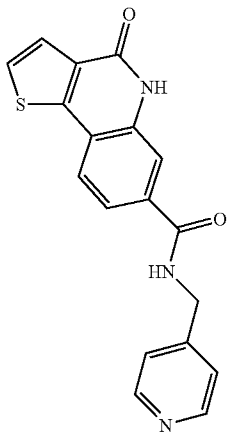 | 335.38 | 336 [M + 1]$^+$ |
| 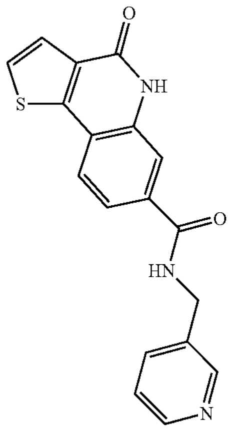 | 335.38 | 336 [M + 1]$^+$ |
| 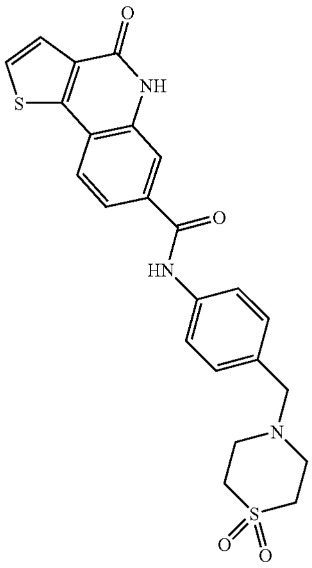 | 467.56 | 468 [M + 1]$^+$ |
The following representative analogs (Table 8) were prepared from their corresponding methyl esters. The compounds were prepared according to the hydrolysis procedure utilized for compound 15.
TABLE 8
| Structure | M.W. | LCMS (ES) m/z |
|---|---|---|
| 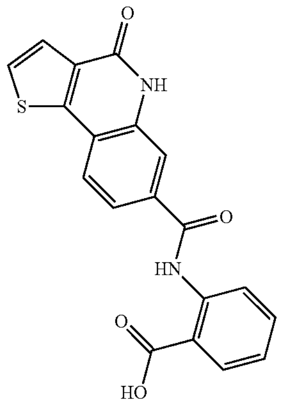 | 364.37 | 365 [M + 1]$^+$ |
| 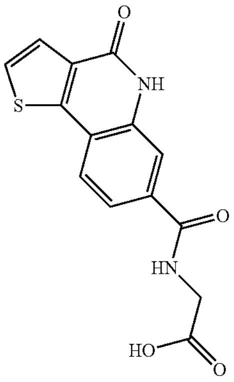 | 302.31 | 303 [M + 1]$^+$ |

The following representative analogs (Table 9) were prepared from their corresponding tert-butyl esters or N-Boc protected precursors. The precursors were treated with 30% trifluoroacetic acid in $CH_2Cl_2$ for 2 hours. Removal of the volatiles in vacuo afforded the expected materials.

TABLE 9

| Structure | M.W. | LCMS (ES) m/z |
|---|---|---|
| 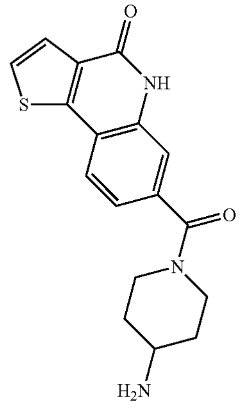 | 327.40 | 328 $[M + 1]^+$ |
| 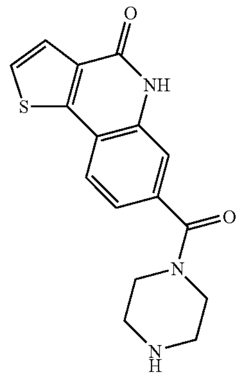 | 313.37 | 314 $[M + 1]^+$ |
| 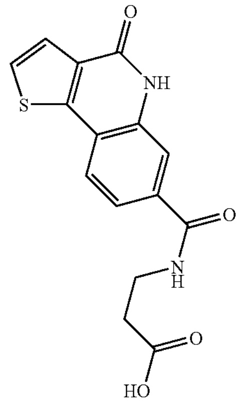 | 316.33 | 317 $[M + 1]^+$ |

Process 29

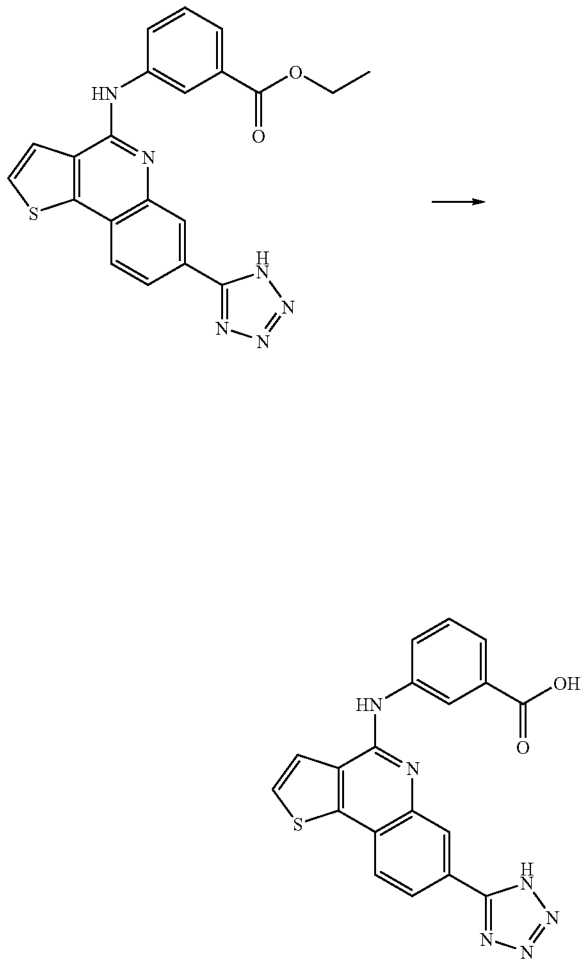

ethyl 3-(7-(1H-tetrazol-5-yl)thieno[3,2-c]quinolin-4-ylamino)benzoate (1.0 eq, 7.6 mg, 0.018 mmol) was suspended in a 1:1:1 mixture of THF, MeOH and water. Lithium Hydroxide was added (40 mg, 1.66 mmol) and the mixture stirred at room temperature for one hour. Water and hydrochloric acid were added and the resulting solid filtered and dried to afford 3-(7-(1H-tetrazol-5-yl)thieno[3,2-c]quinolin-4-ylamino)benzoic acid as a solid. LCMS (ES): 95% pure, m/z 389 $[M+1]^+$.

The following representative analogs (table 10) were prepared by reacting 3-(7-(1H-tetrazol-5-yl)thieno[3,2-c]quinolin-4-ylamino)benzoic acid and appropriate amines using the procedure described in process 28. The materials were purified by preparative HPLC and were isolated as dry solids after Genevac evaporation.

TABLE 10
| Structure | MW | LCMS (ES) m/z |
|---|---|---|
| 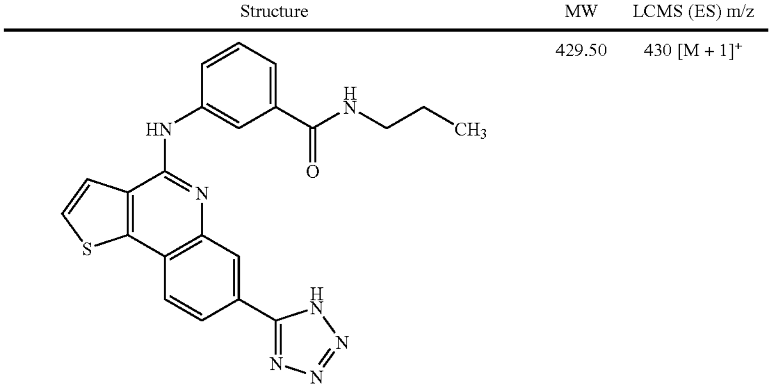 | 429.50 | 430 [M + 1]$^+$ |
| 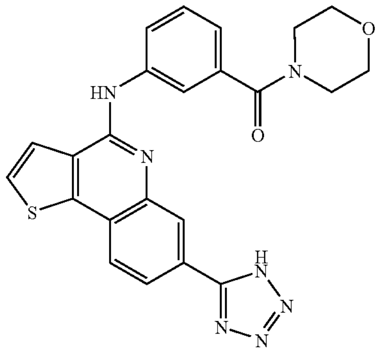 | 457.51 | 458 [M + 1]$^+$ |
| 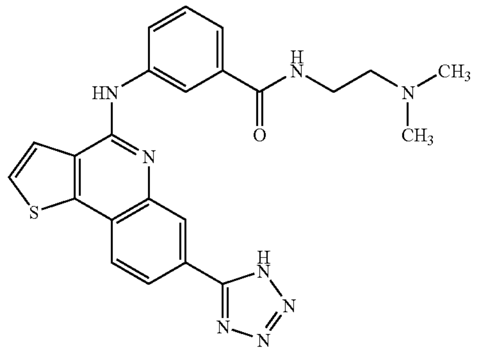 | 458.54 | 459 [M + 1]$^+$ |
| 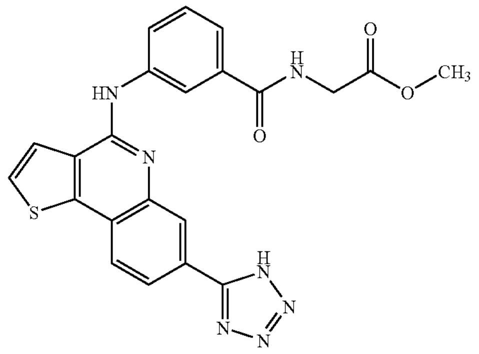 | 459.48 | 460 [M + 1]$^+$ |

TABLE 10-continued
| Structure | MW | LCMS (ES) m/z |
|---|---|---|
| 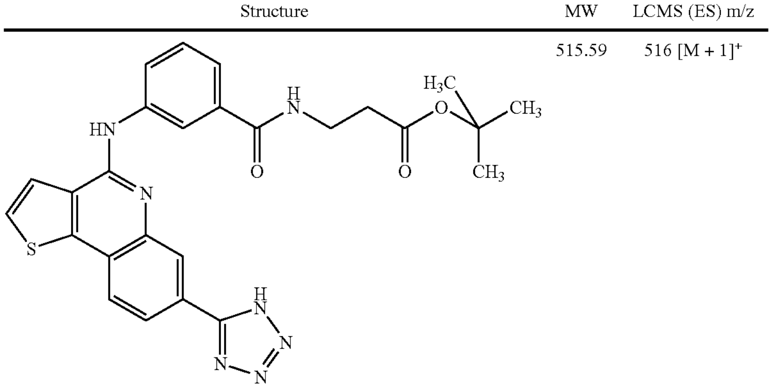 | 515.59 | 516 [M + 1]+ |
| 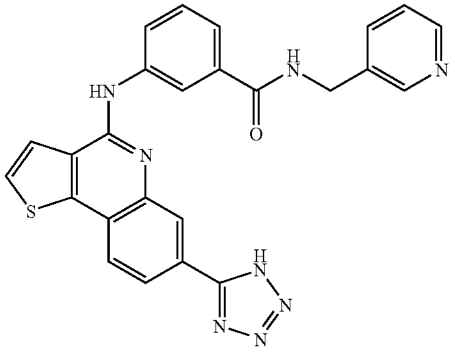 | 478.53 | 479 [M + 1]+ |
| 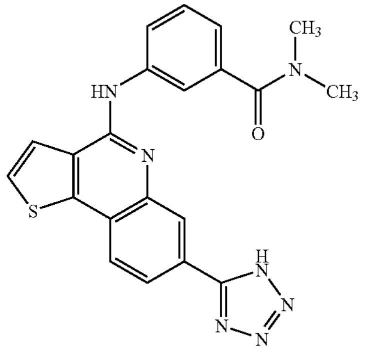 | 415.47 | 416 [M + 1]+ |
| 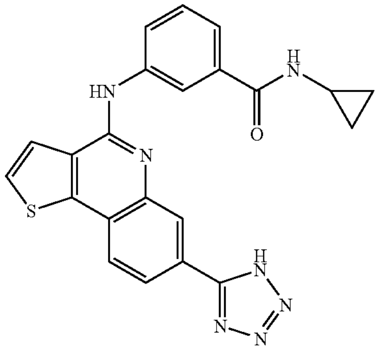 | 427.48 | 428 [M + 1]+ |

TABLE 10-continued
| Structure | MW | LCMS (ES) m/z |
|---|---|---|
| 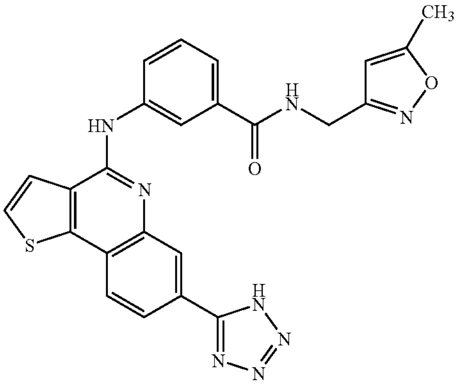 | 482.52 | 483 [M + 1]$^+$ |
| 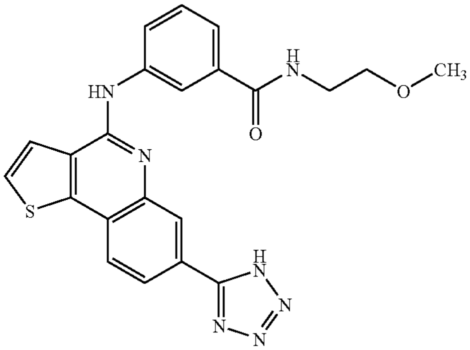 | 445.50 | 446 [M + 1]$^+$ |
| 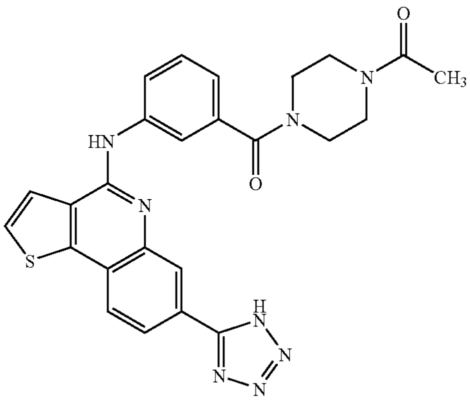 | 498.56 | 499 [M + 1]$^+$ |
Process 30
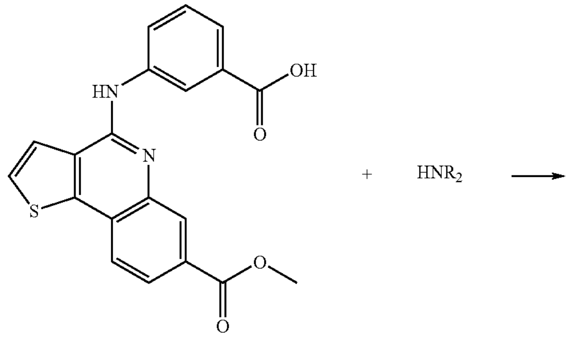
-continued
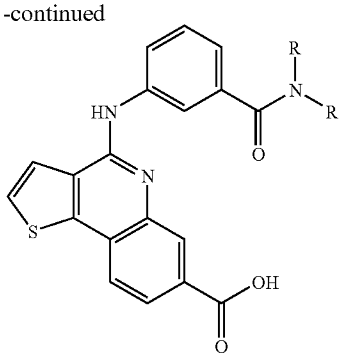
The following representative analogs (table 11) were prepared by reacting 3-(7-(methoxycarbonyl)thieno[3,2-c]

quinolin-4-ylamino)benzoic acid and the appropriate amines using reaction conditions described in process 28. Hydrolysis of the ester using conditions described in process 29 afforded the following analogs.
TABLE 11
| Structure | MW | LCMS (ES) m/z |
|---|---|---|
| 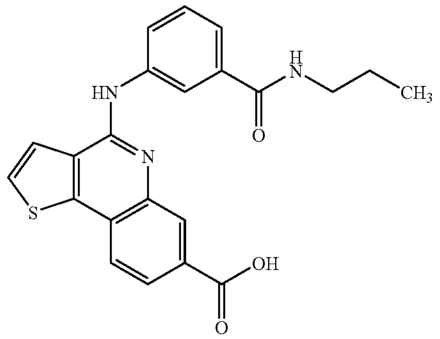 | 405.47 | 406 [M + 1]$^+$ |
| 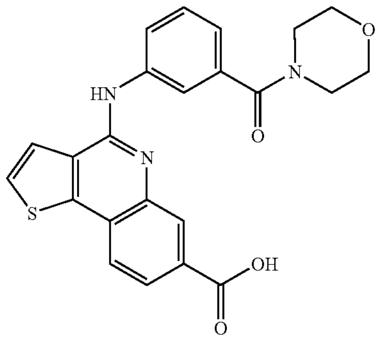 | 433.48 | 434 [M + 1]$^+$ |
| 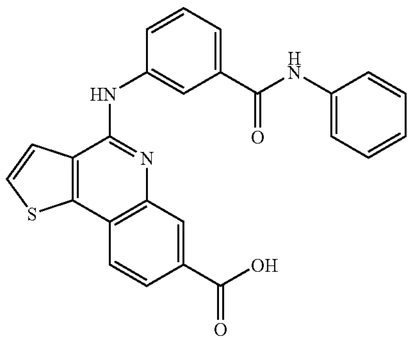 | 439.49 | 440 [M + 1]$^+$ |
| 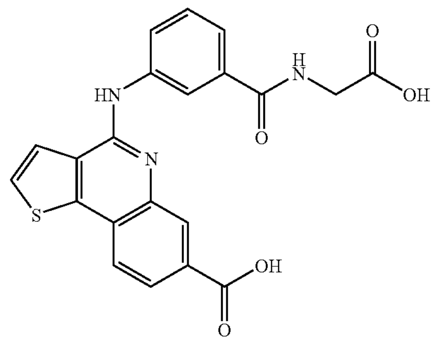 | 421.43 | 422 [M + 1]$^+$ |

TABLE 11-continued
| Structure | MW | LCMS (ES) m/z |
|---|---|---|
| 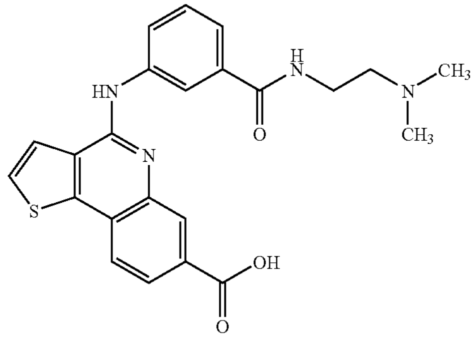 | 434.51 | 435 [M + 1]+ |
| 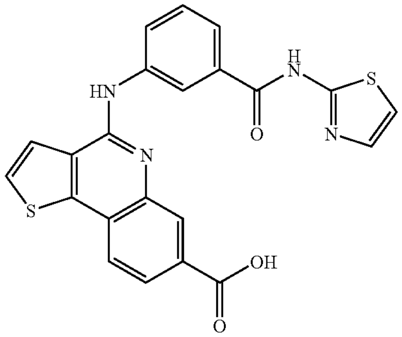 | 446.50 | 447 [M + 1]+ |
| 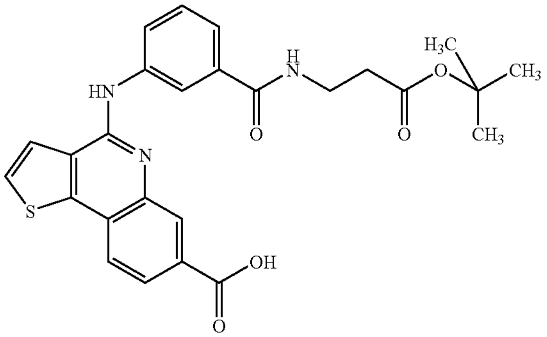 | 491.56 | 492 [M + 1]+ |
| 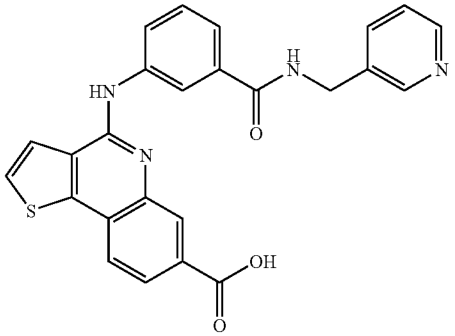 | 454.50 | 455 [M + 1]+ |

TABLE 11-continued
| Structure | MW | LCMS (ES) m/z |
| --- | --- | --- |
| 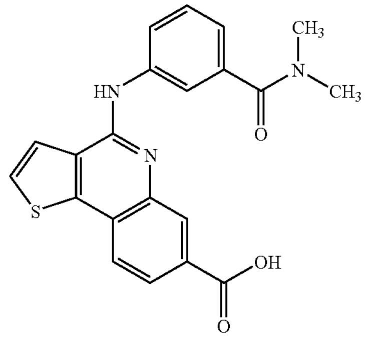 | 391.44 | 392 $[M + 1]^+$ |
| 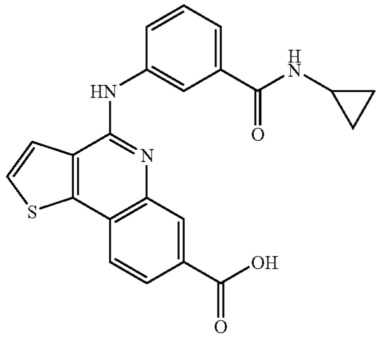 | 403.45 | 404 $[M + 1]^+$ |
| 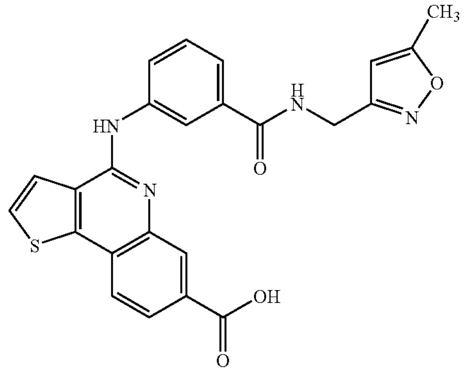 | 458.49 | 459 $[M + 1]^+$ |
| 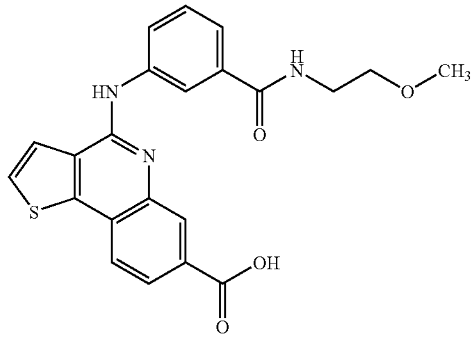 | 421.47 | 422 $[M + 1]^+$ |

TABLE 11-continued
| Structure | MW | LCMS (ES) m/z |
|---|---|---|
| 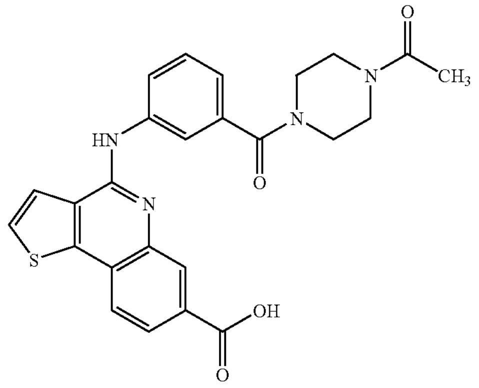 | 474.53 | 475 $[M+1]^+$ |
Process 31
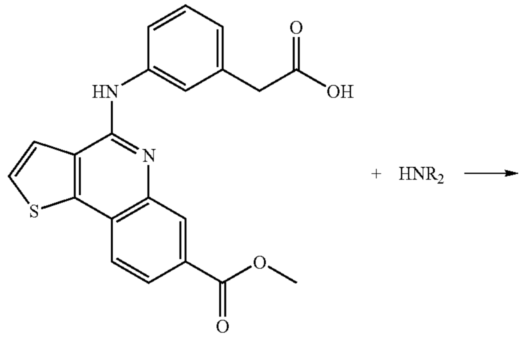
-continued
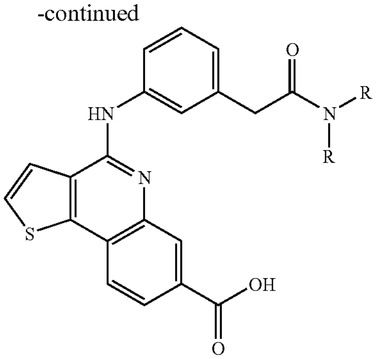
The following representative analogs (table 12) were prepared by reacting 2-(3-(7-(methoxycarbonyl)thieno[3,2-c]quinolin-4-ylamino)phenyl)acetic acid and the appropriate amines using reaction conditions described in process 30.
TABLE 12
| Structure | MW | LCMS (ES) m/z |
|---|---|---|
| 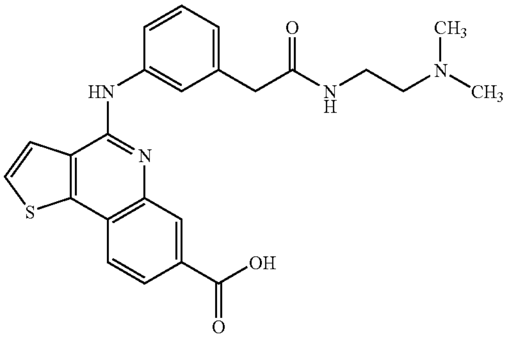 | 448.54 | 449 $[M+1]^+$ |

TABLE 12-continued
| Structure | MW | LCMS (ES) m/z |
|---|---|---|
| 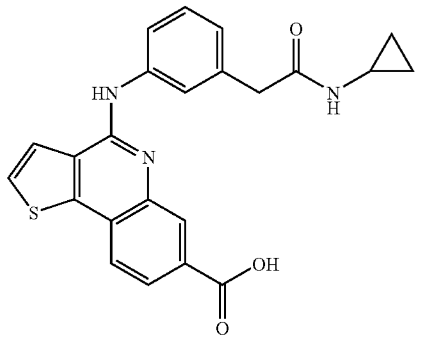 | 417.48 | 418 $[M + 1]^+$ |
| 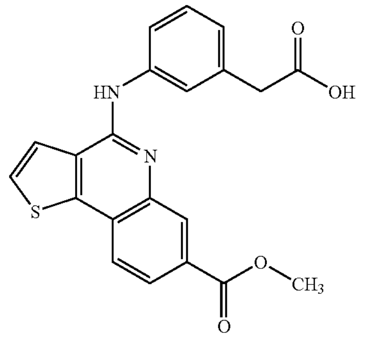 | 392.43 | 393 $[M + 1]^+$ |
| 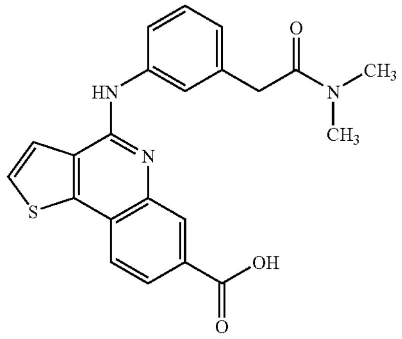 | 405.47 | 406 $[M + 1]^+$ |
| 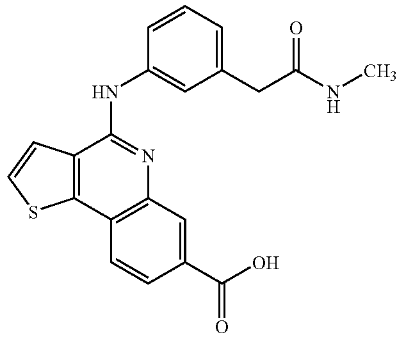 | 391.44 | 392 $[M + 1]^+$ |

Example 3

Processes for Synthesizing Compounds of Formulae IX, X, XI and XII

Process 1

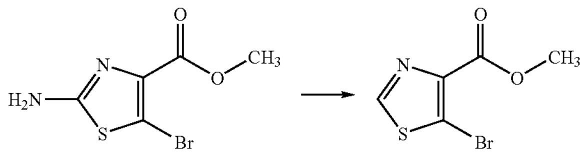

Methyl 2-amino-4-bromothiazole-4-carboxylate (1.0 eq, 100 mg, 0.42 mmol) was dissolved in anhydrous DMF (0.8 ml). The mixture was heated to 80° C. under nitrogen atmosphere. To the hot mixture, a solution of tert-Butyl nitrite (1.2 eq, 60 ul, 0.50 mmol) in DMF (0.8 ml) was added dropwise. After a few minutes, absence of gas evolution indicated completion of the reaction. The mixture was cooled down and poured onto a prepacked silica gel column. Flash chromatography using hexanes, then AcOEt/hexanes (2:8), provided methyl 5-bromothiazole-4-carboxylate as a yellow solid (49 mg, 53% yield). LCMS (ES): 95% pure, m/z 222 $[M]^+$, 224 $[M+2]^+$.

Process 2

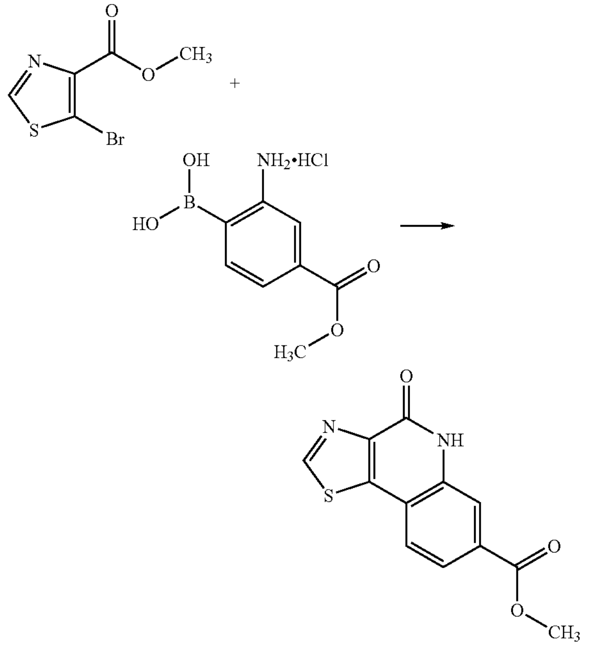

In a microwave vessel, methyl 5-bromothiazole-4-carboxylate (1.0 eq, 97 mg, 0.44 mmol), 2-amino-3-methoxycarbonyl phenyl boronic acid HCl (1.1 eq, 111 mg, 0.48 mmol), sodium acetate (3.0 eq, 107 mg, 1.31 mmol) and $PdCl_2$(dppf) (0.05 eq, 11 mg, 0.022 mmol) were mixed together in anhydrous DMF (1 ml). The mixture was heated in a microwave oven at 120° C. for 10 nm. Water was added and the material extracted with $CH_2Cl_2$. The combined extracts were washed with brine, dried over $Na_2SO_4$ and the solvents removed by evaporation. The material was dissolved in a mixture of $CH_2Cl_2$ and MeOH and the solution filtered through a pad of celite. Evaporation of the volatiles afforded crude methyl 4-oxo-4,5-dihydrothiazolo[4,5-c]quinoline-7-carboxylate as a black solid (44 mg, 39% yield). A small part of the compound was subjected to preparative HPLC for analytical purpose. LCMS (ES): 95% pure, m/z 261 $[M+1]^+$.

Process 3

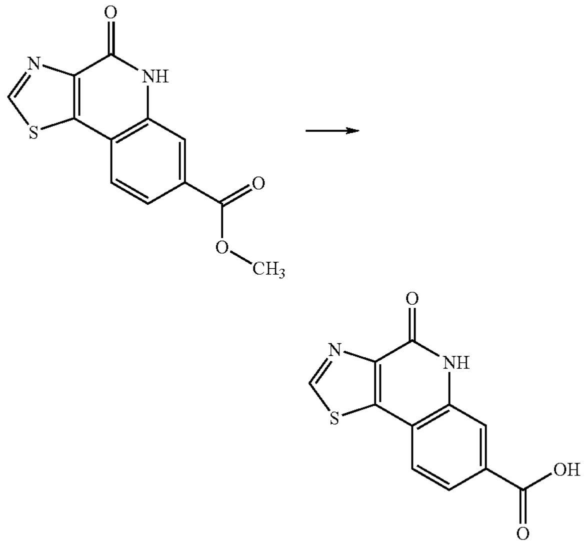

Methyl 4-oxo-4,5-dihydrothiazolo[4,5-c]quinoline-7-carboxylate (35 mg, 0.12 mmol) and LiOH (60 mg, 0.83 mmol) were stirred in a (1:1:1, v:v:v) mixture of THF, MeOH and water (0.6 ml) for 2 hours. 6N aqueous NaOH was added and the solution filtered through celite. The solution was acidified and the resulting solid filtered. Preparative HPLC purification and genevac evaporation provided 4-oxo-4,5-dihydrothiazolo[4,5-c]quinoline-7-carboxylic acid as a white solid (0.8 mg). LCMS (ES): 95% pure, m/z 247 $[M+1]^+$.

Process 4

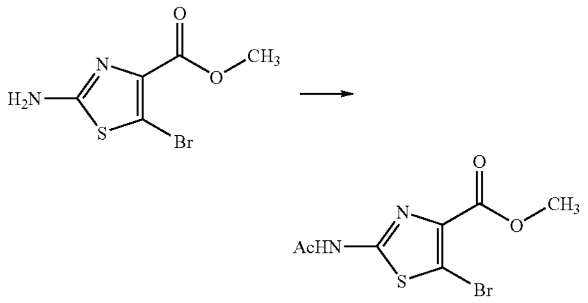

Methyl 2-amino-4-bromothiazole-4-carboxylate (1.0 eq, 2.0 g, 8.44 mmol) was dissolved in $CH_2Cl_2$ (4 ml). Acetic anhydride (1.5 eq, 1.2 ml, 12.66 mmol) and triethylamine (1.1 eq, 1.3 ml, 9.28 mmol) were added and the mixture stirred at 100° C. for one hour. The resulting solid was filtered, triturated in AcOEt and then filtered again. After drying, methyl 2-acetamido-5-bromothiazole-4-carboxylate was isolated as a beige solid (1.81 g, 77% yield). LCMS (ES): 95% pure, m/z 280 $[M+1]^+$. $^1H$ NMR ($CDCl_3$, 400 MHz) δ 2.25 (s, 3H), 3.95 (s, 3H) ppm.

Process 5

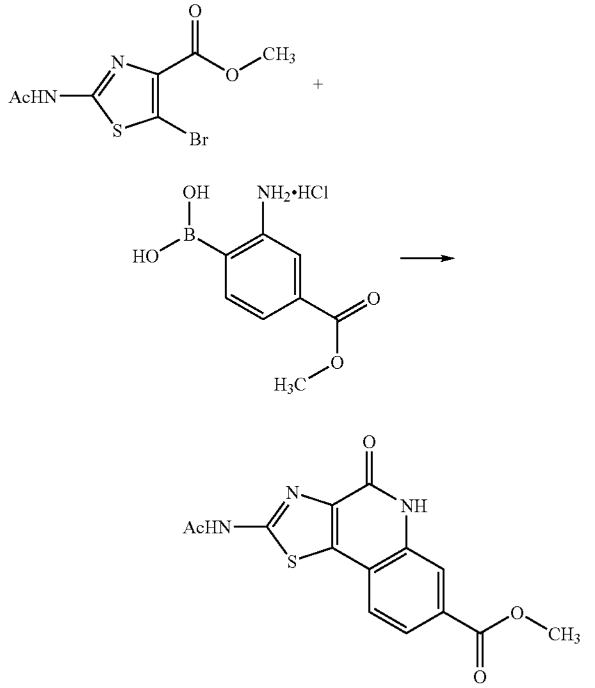

Methyl 2-acetamido-4-oxo-4,5-dihydrothiazolo[4,5-c]quinoline-7-carboxylate was prepared according to the procedure used in process 2, starting from methyl 2-acetamido-5-bromothiazole-4-carboxylate. Methyl 2-acetamido-4-oxo-4,5-dihydrothiazolo[4,5-c]quinoline-7-carboxylate was isolated as a black solid (106 mg, 37% yield). LCMS (ES): 95% pure, m/z 318 $[M+1]^+$.

Process 6

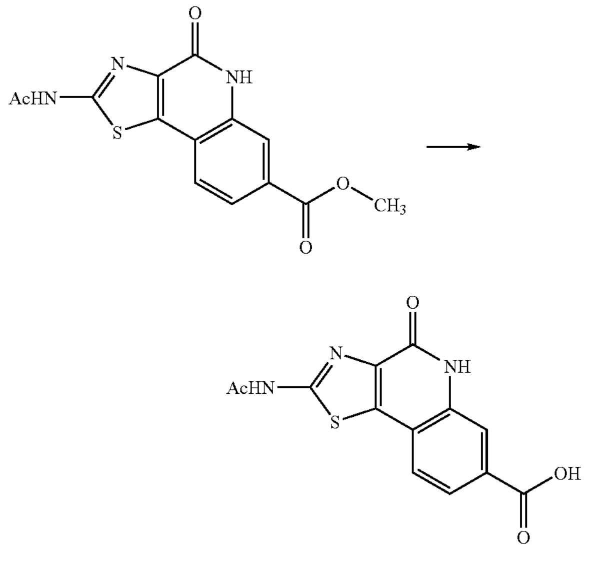

2-acetamido-4-oxo-4,5-dihydrothiazolo[4,5-c]quinoline-7-carboxylic acid was prepared according to the procedure in process 3, starting from. Methyl 2-acetamido-4-oxo-4,5-dihydrothiazolo[4,5-c]quinoline-7-carboxylate. -acetamido-4-oxo-4,5-dihydrothiazolo[4,5-c]quinoline-7-carboxylic acid was isolated as a black solid (14 mg, 44% yield). LCMS (ES): 95% pure, m/z 304 $[M+1]^+$, $^1$H NMR (DMSO-$d_6$, 400 MHz) δ 2.22 (s, 3H), 7.74 (dd, J=1.2, J=8.0, 1H), 7.89 (d, J=8.4, 1H), 8.03 (d, J=1.6, 1H), 12.07 (s, 1H), 12.80 (s, 1H) ppm.

Process 7

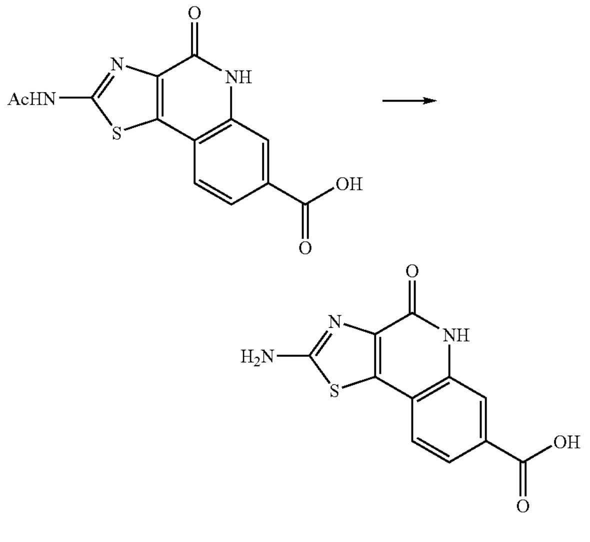

2-acetamido-4-oxo-4,5-dihydrothiazolo[4,5-c]quinoline-7-carboxylic acid (102 mg, 0.34 mmol) was stirred at 120° C. in aqueous 6N HCl overnight. Water was added and the compound was filtered and dried to provide 2-amino-4-oxo-4,5-dihydrothiazolo[4,5-c]quinoline-7-carboxylic acid as a black solid (76 mg, 86% yield). LCMS (ES): 95% pure, m/z 262 $[M+1]^+$, $^1$H NMR (DMSO-$d_6$, 400 MHz) δ 7.60 (d, J=8.4, 1H), 7.70 (dd, J=1.2, J=8.0, 1H), 7.99 (d, J=1.2, 1H), 11.94 (s, 1H) ppm.

Process 8

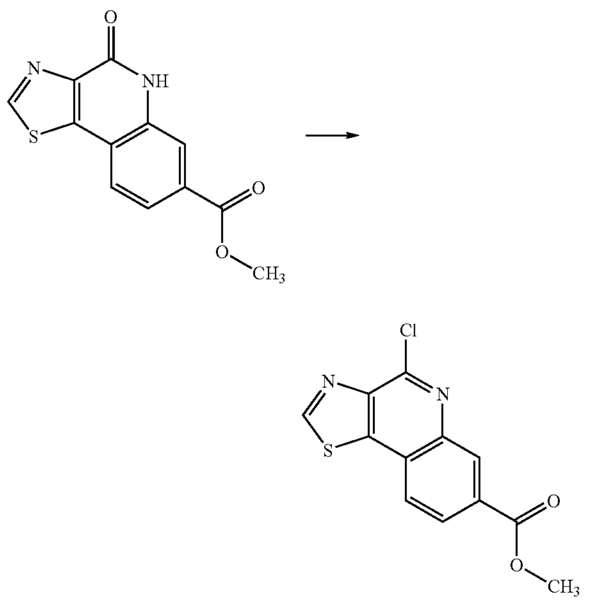

Methyl 4-oxo-4,5-dihydrothiazolo[4,5-c]quinoline-7-carboxylate (1.0 eq, 0.62 g, 2.38 mmol) was suspended in toluene. DIEA (1.5 eq, 122 ul, 3.57 mmol) and $POCl_3$ (2.3 eq, 507 ul, 5.47 mmol) were added and the mixture vigorously stirred at 120° C. for 1 hour. Water, ice and $CH_2Cl_2$ were added and the resulting emulsion filtered through celite. The organic phase was decanted and the aqueous phase further extracted with $CH_2Cl_2$. The combined organic extracts were dried over $Na_2SO_4$ and the solvent removed in vacuo to afford methyl 4-chlorothiazolo[4,5-c]quinoline-7-carboxylate (0.31 g, 47% yield). LCMS (ES): >90% pure, m/z 279[M+1]$^+$.

Process 9

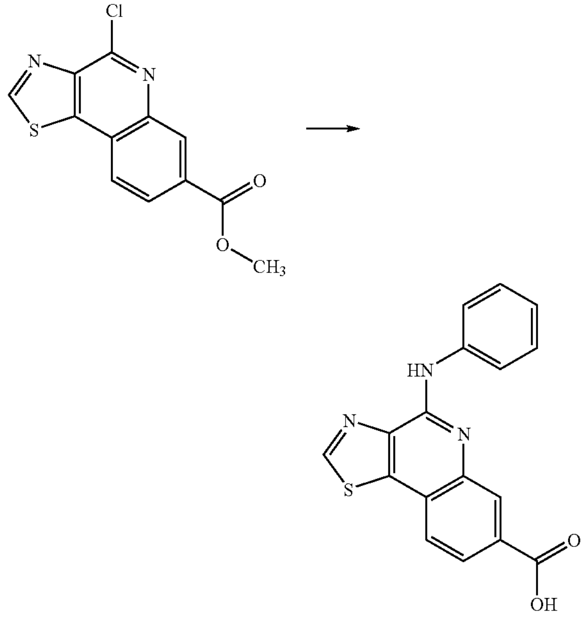

In a microwave vessel, methyl 4-chlorothiazolo[4,5-c]quinoline-7-carboxylate (1.0 eq, 23 mg, 0.084 mmol) and aniline (13 eq, 0.1 ml, 1.1 mmol) were mixed in NMP (0.1 ml). The mixture was heated in a microwave oven at 120° C. for 10 min. The intermediate ester was purified by preparative HPLC and isolated as a solid after genevac evaporation. The solid was stirred in a (1:1:1, v:v:v) mixture of THF, MeOH and water (0.6 ml) with LiOH (41 mg) at room temperature for 2 hours. HCl and water were added, the organic solvents were evaporated and the solution allowed resting for 2 hours. The precipitate that slowly formed was filtered and dried to afford 4-(phenylamino)thiazolo[4,5-c]quinoline-7-carboxylic acid as a solid (8% yield over 2 steps). LCMS (ES): >95% pure, m/z 322 [M+1]$^+$.

Representative analogs (Table 13) were prepared by the same process using methyl 4-chlorothiazolo[4,5-c]quinoline-7-carboxylate and appropriate amines. The reaction temperatures used for the microwave reactions ranged from 120° C. to 180° C. After synthesis of the final compounds, the materials were isolated by preparative HPLC/genevac evaporation. In some instances, the materials precipitated after acidification and were isolated by filtration.

TABLE 13

| Structure | MW | LCMS (ES) m/z |
|---|---|---|
| 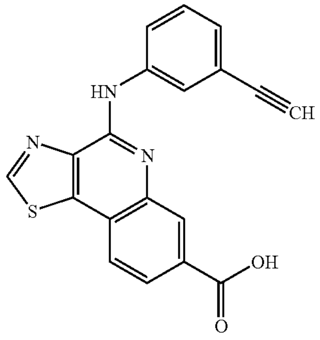 | 345.37 | 346 [M + 1]$^+$ |
| 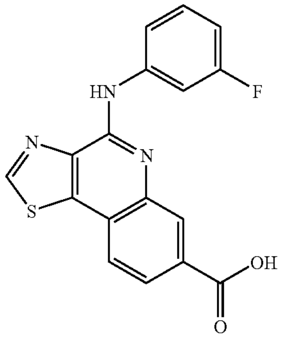 | 339.34 | 340 [M + 1]+ |
| 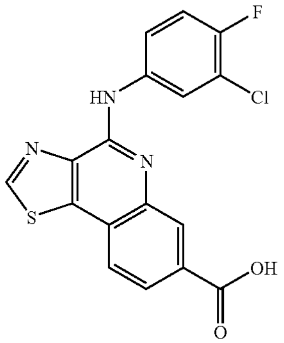 | 373.79 | 374 [M + 1]+ |
| 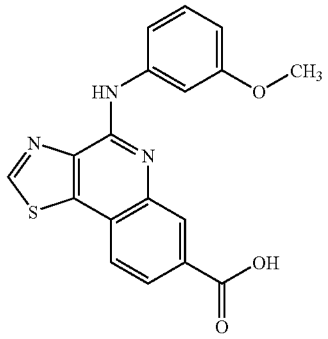 | 351.38 | 352 [M + 1]+ |

Example 4

Modulation of CK2 and PARP Activity in Cell-Free In Vitro Assays

Modulatory activity of compounds described herein was assessed in vitro in cell-free CK2 assays. Modulatory activity of compounds described herein also are assessed in vitro in cell-free PARP assays. These assays are described hereafter.

CK2 Assay

Test compounds in aqueous solution were added at a volume of 10 microliters, to a reaction mixture comprising 10 microliters Assay Dilution Buffer (ADB; 20 mM MOPS, pH 7.2, 25 mM beta-glycerolphosphate, 5 mM EGTA, 1 mM sodium orthovanadate and 1 mM dithiothreitol), 10 microliters of substrate peptide (RRRDDDSDDD (SEQ ID NO:4), dissolved in ADB at a concentration of 1 mM), 10 microliters of recombinant human CK2 (25 ng dissolved in ADB; Upstate). Reactions were initiated by the addition of 10 microliters of ATP Solution (90% 75 mM $MgCl_2$, 75 micromolar ATP dissolved in ADB; 10% [$\gamma$-$^{33}$P]ATP (stock 1 mCi/100 μl; 3000 Ci/mmol (Perkin Elmer) and maintained for 10 minutes at 30 degrees C. The reactions were quenched with 100 microliters of 0.75% phosphoric acid, then transferred to and filtered through a phosphocellulose filter plate (Millipore). After washing each well 5 times with 0.75% phosphoric acid, the plate was dried under vacuum for 5 min and, following the addition of 15 ul of scintilation fluid to each well, the residual radioactivity was measured using a Wallac luminescence counter.

PARP Assay

PARP assays are conducted using a chemiluminescent PARP assay kit (Trevigen). Briefly, reactions are performed in Histone-coated strip wells, by adding 10 microliters test compound dissolved in 1×PARP Buffer (prepared by mixing 20×PARP buffer diluted with high-purity water) and 15 microliters diluted PARP-HSA enzyme (diluted in 1×PARP buffer, 0.1 unit per well) to 25 microliters PARP cocktail (prepared from 10×PARP cocktail and 10× activated DNA, both 2.5 microliters per well and 20 microliters per well of 1×PARP buffer). The reactions are incubated at ambient temperature for 60 minutes, then the liquid was removed. After washing the wells four times with PBS (200 ul), 50 microliters of STREP-HRP (Horseradish Peroxidase) solution (diluted 500-fold in 1× Strep-Diluent) was added and the reactions were allowed to incubate for 30 minutes at ambient temperature. The liquid was removed and, after washing the wells four times with PBS (200 ul), 50 microliters each of PeroxyGlo A and B (Chemiluminescent Horseradish Peroxidase substrates) are added and the resulting chemiluminescence quantified on the SpectraMax M5 plate reader.

Tables 14A, 14B, and 15-18 show modulatory effects of compounds on CK2 and/or PARP activity.

TABLE 14A

| Compound | CK2 Inhibition | PARP Inhibition |
|---|---|---|
| 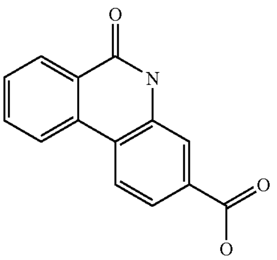 | 28% (at 5 μM) | $IC_{50}$ = 0.070 μM |

TABLE 14A-continued

| Compound | CK2 Inhibition | PARP Inhibition |
|---|---|---|
| 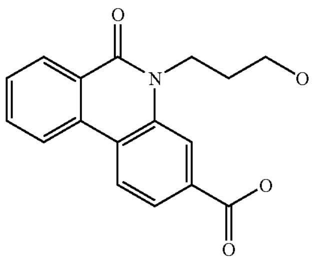 | 29% (at 5 μM) | $IC_{50}$ = 0.060 μM |
| 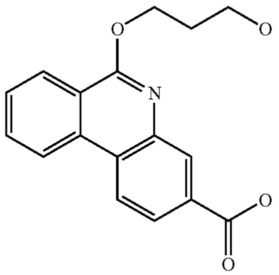 | 38% (at 5 μM) | $IC_{50}$ = 0.40 μM |
| 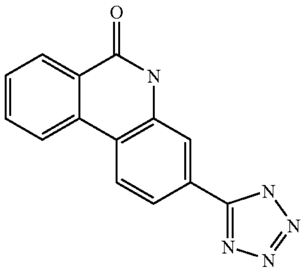 | $IC_{50}$ = 2 μM | $IC_{50}$ = 0.030 μM |
| 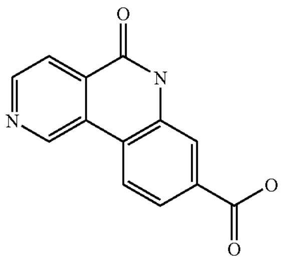 | $IC_{50}$ = 0.18 μM | $IC_{50}$ = 1.0 μM |
| 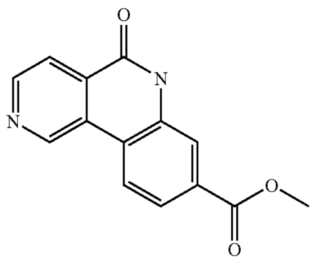 | $IC_{50}$ = 2.5 μM | $IC_{50}$ = 0.80 μM |

TABLE 14A-continued
| Compound | CK2 Inhibition | PARP Inhibition |
|---|---|---|
| 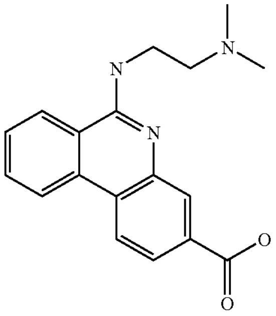 | $IC_{50}$ = 1.0 μM | 15% (at 1 μM) |
| 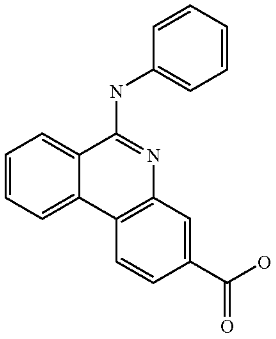 | $IC_{50}$ = 1.6 μM | 9% (at 1 μM) |
| 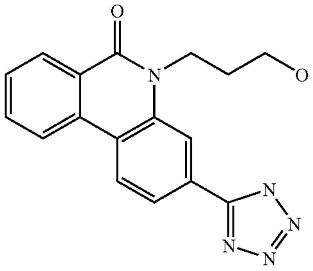 | 16% (at 2.5 μM) | 33% (at 1 μM) |
| 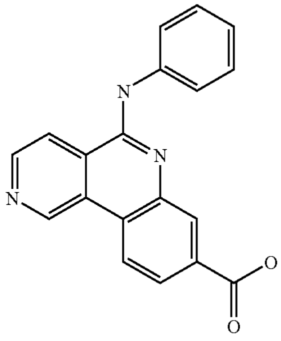 | $IC_{50}$ = 0.013 μM | |
TABLE 14A-continued
| Compound | CK2 Inhibition | PARP Inhibition |
|---|---|---|
| 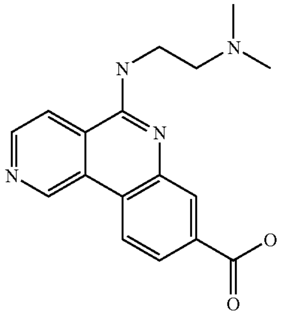 | 96% (at 1 μM) | |
| 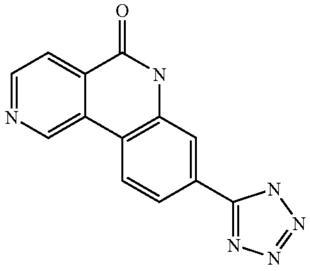 | 46% (at 1 μM) | |
| 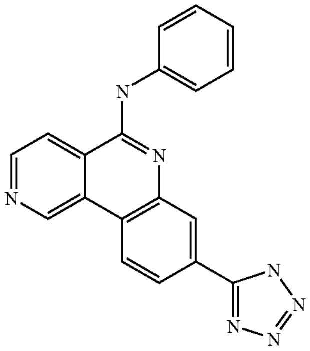 | 78% (at 1 μM) | |
| 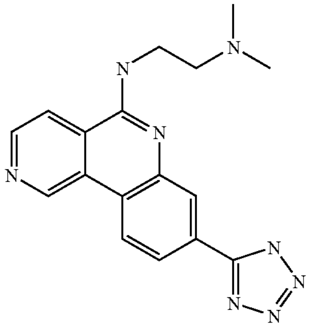 | 62% (at 1 μM) | |

TABLE 14B
| Structure | CK2 IC50 (uM) | CK2 % inhibition 5 uM | 2.5 uM | 1.0 uM |
|---|---|---|---|---|
| 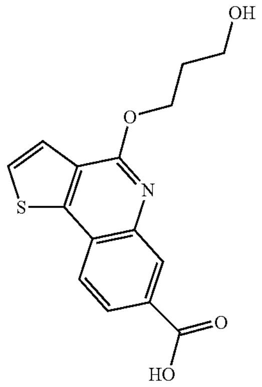 | 1.2 | | | |
| 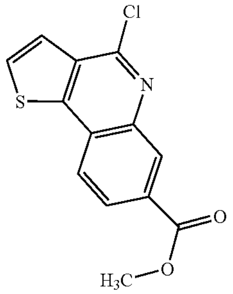 | >10 | | | |
| 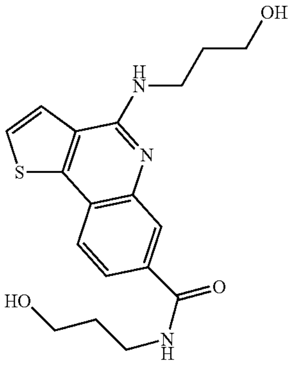 | >10 | | | |
| 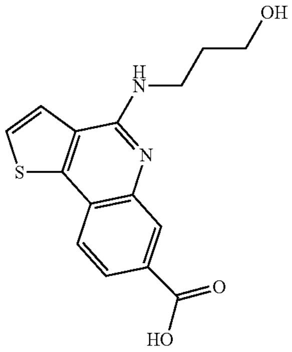 | 0.67 | | | |

TABLE 14B-continued
| Structure | CK2 IC50 (uM) | CK2 % inhibition | | |
|---|---|---|---|---|
| | | 5 uM | 2.5 uM | 1.0 uM |
| 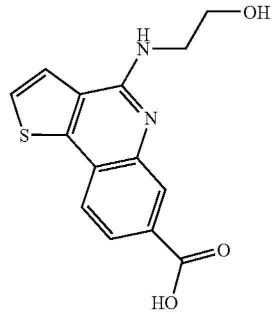 | 1.1 | | | |
| 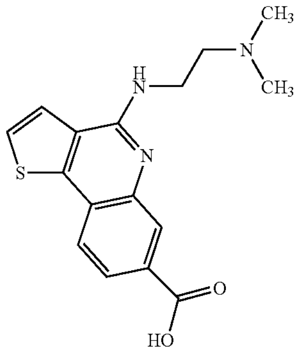 | 0.27 | | | |
| 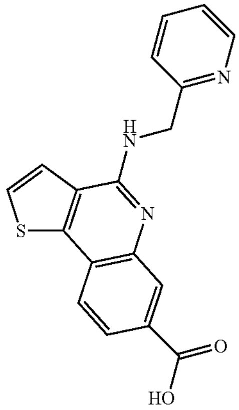 | 0.95 | | | |
| 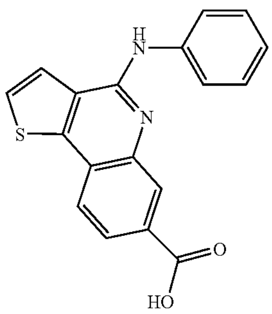 | 0.32 | | | |

TABLE 14B-continued
| Structure | CK2 IC50 (uM) | CK2 % inhibition 5 uM | 2.5 uM | 1.0 uM |
|---|---|---|---|---|
| 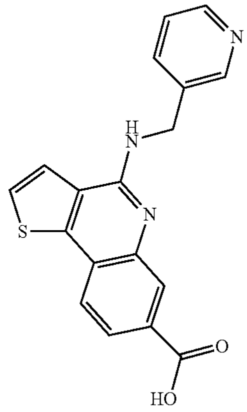 | 0.9 | | | |
| 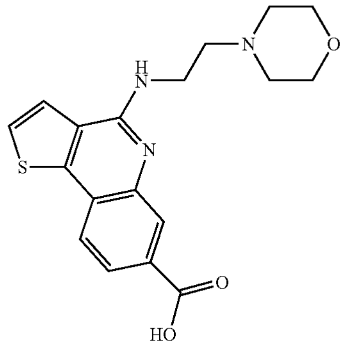 | 1.22 | | | |
| 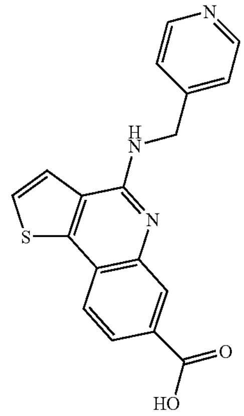 | 0.43 | | | |
| 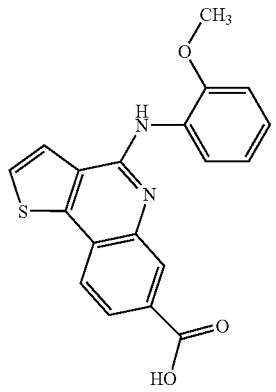 | 0.55 | | | |

TABLE 14B-continued
| Structure | CK2 IC50 (uM) | CK2 % inhibition 5 uM | 2.5 uM | 1.0 uM |
|---|---|---|---|---|
| 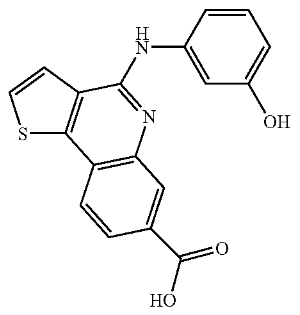 | 0.35 | | | |
| 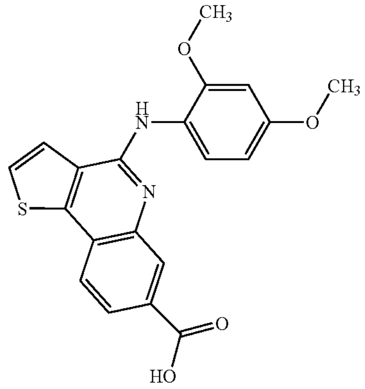 | 2 | | | |
| 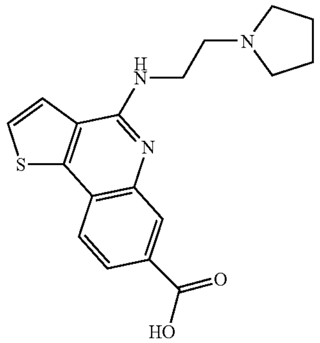 | | 84% | | |
| 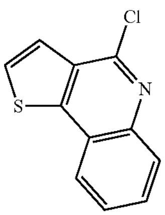 | >5 | | | |
| 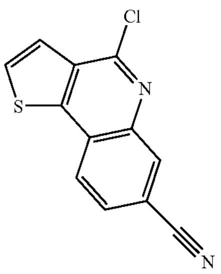 | | 63% | | |

TABLE 14B-continued
| Structure | CK2 IC50 (uM) | CK2 % inhibition 5 uM | 2.5 uM | 1.0 uM |
|---|---|---|---|---|
| 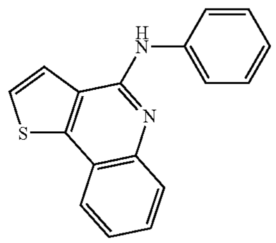 | | 0% | | |
| 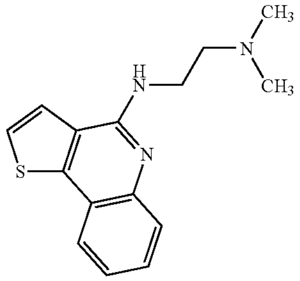 | | 0% | | |
| 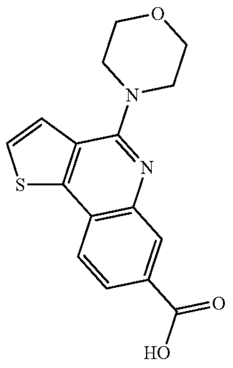 | | 28% | | |
| 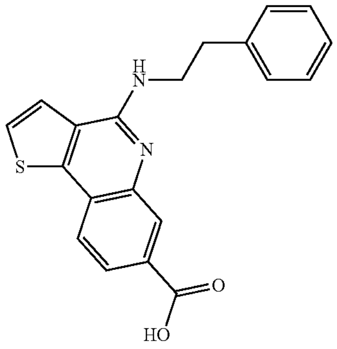 | | 78% | | |

TABLE 14B-continued
| Structure | CK2 IC50 (uM) | CK2 % inhibition 5 uM | 2.5 uM | 1.0 uM |
|---|---|---|---|---|
| 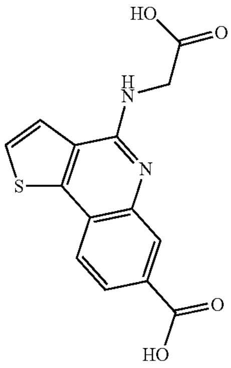 | | | 0% | |
| 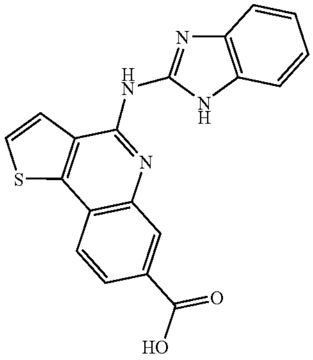 | | | 0% | |
| 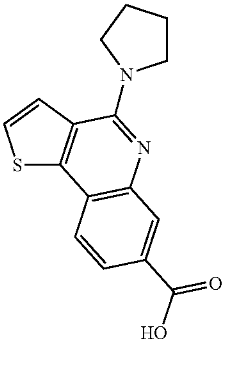 | | | 29% | |
| 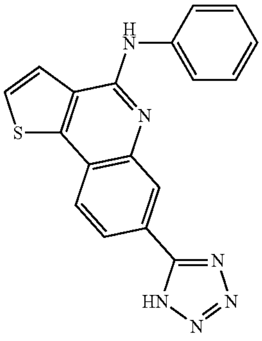 | 0.19 | | | |

TABLE 14B-continued
| Structure | CK2 IC50 (uM) | CK2 % inhibition 5 uM | 2.5 uM | 1.0 uM |
|---|---|---|---|---|
| 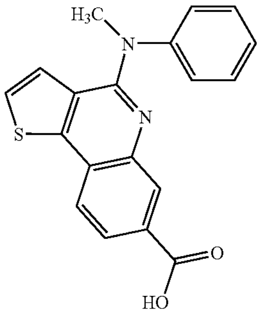 | 1.5 | | | |
| 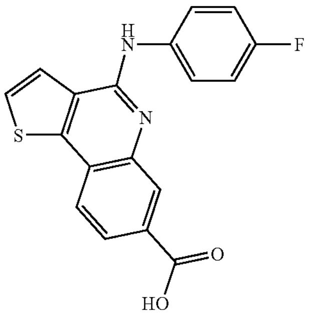 | 0.31 | | | |
| 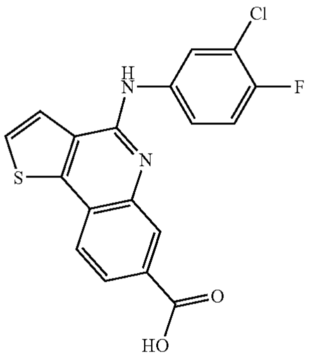 | 0.15 | | | |
| 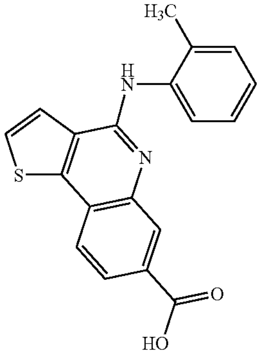 | 1.1 | | | |

TABLE 14B-continued
| Structure | CK2 IC50 (uM) | CK2 % inhibition 5 uM | 2.5 uM | 1.0 uM |
|---|---|---|---|---|
| 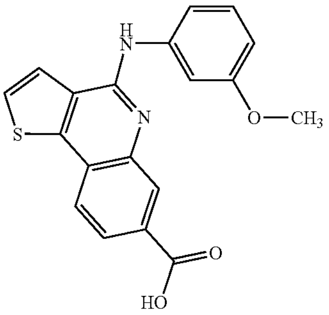 | 0.12 | | | |
| 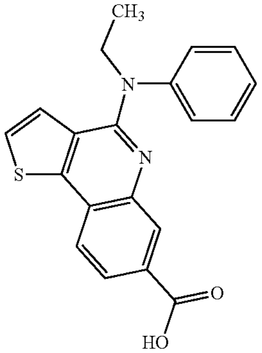 | | | 18% | |
| 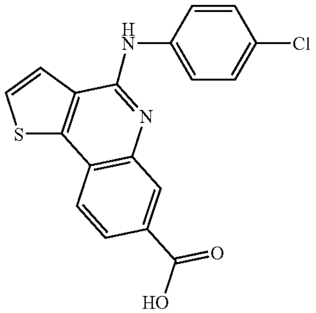 | 0.21 | | | |
| 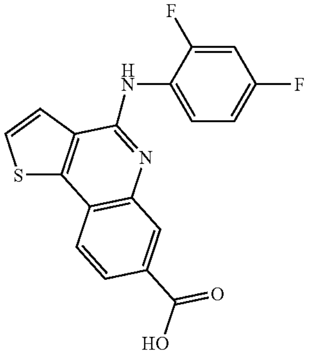 | 0.67 | | | |

TABLE 14B-continued
| Structure | CK2 IC50 (uM) | CK2 % inhibition 5 uM | 2.5 uM | 1.0 uM |
|---|---|---|---|---|
| 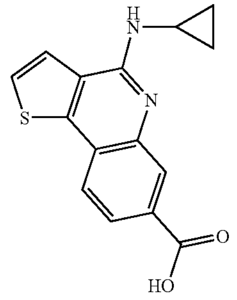 | 0.97 | | | |
| 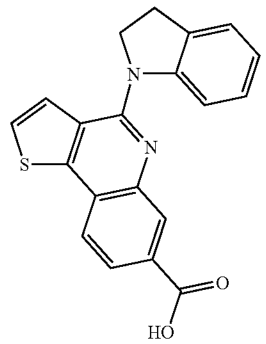 | 0.58 | | | |
| 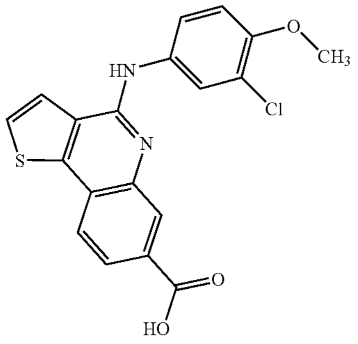 | 0.43 | | | |
| 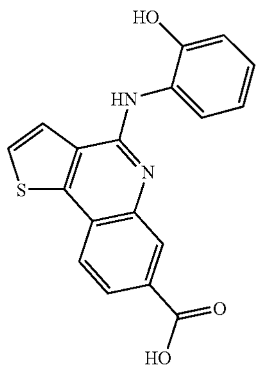 | 0.82 | | | |

TABLE 14B-continued
| Structure | CK2 IC50 (uM) | CK2 % inhibition 5 uM | 2.5 uM | 1.0 uM |
|---|---|---|---|---|
| 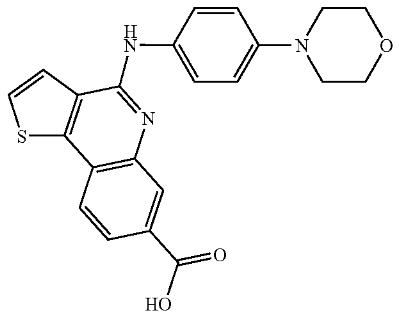 | 1.17 | | | |
| 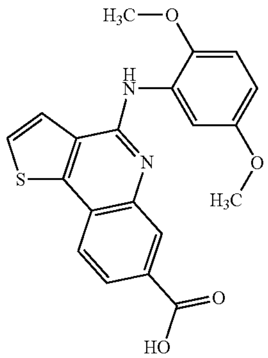 | 0.43 | | | |
| 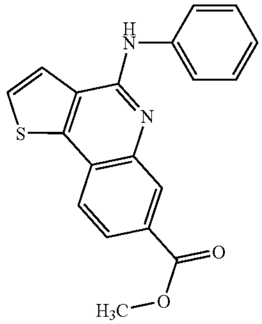 | | | 5% | |
| 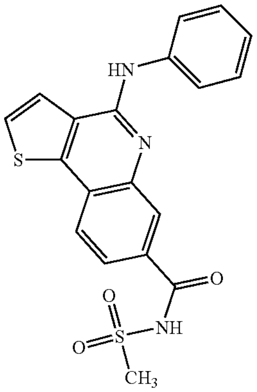 | | | 0% | |

TABLE 14B-continued
| Structure | CK2 IC50 (uM) | CK2 % inhibition 5 uM | 2.5 uM | 1.0 uM |
|---|---|---|---|---|
| 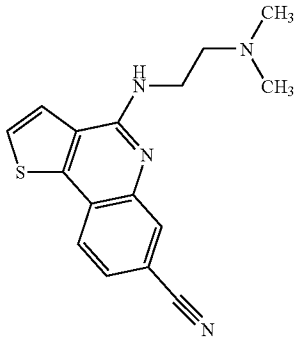 | | | | 0% |
| 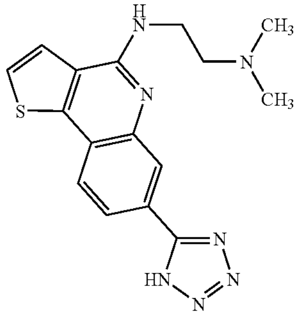 | | | | 70% |
| 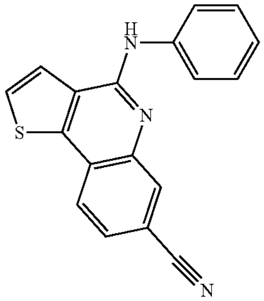 | | | | 0% |
| 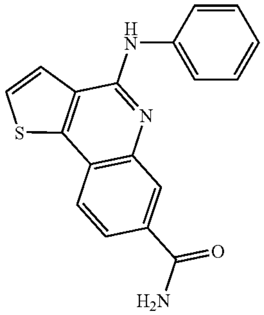 | | | | 0% |

TABLE 14B-continued
| Structure | CK2 IC50 (uM) | CK2 % inhibition 5 uM | 2.5 uM | 1.0 uM |
|---|---|---|---|---|
| 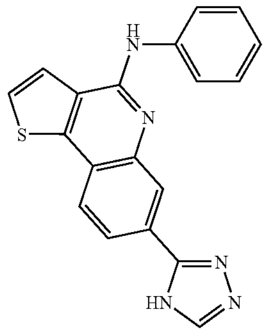 | | | | 0% |
| 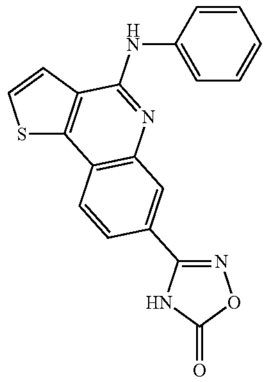 | | | | 0% |
| 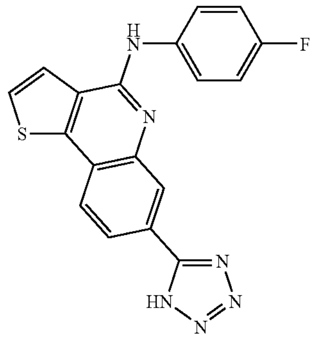 | | | | 71% |
| 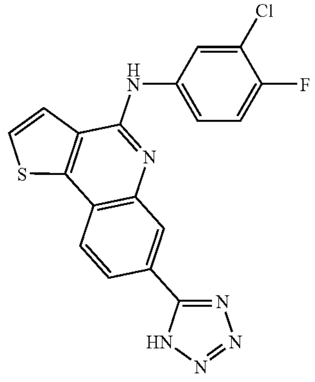 | | | | 84% |

TABLE 14B-continued
| Structure | CK2 IC50 (uM) | CK2 % inhibition 5 uM | 2.5 uM | 1.0 uM |
|---|---|---|---|---|
| 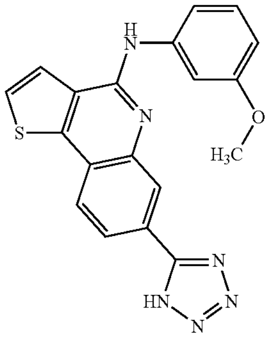 | | | | 80% |
| 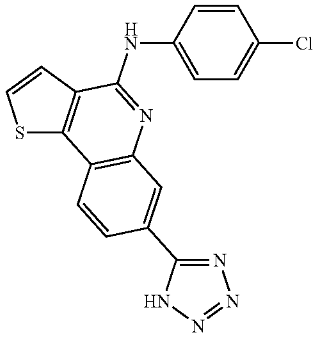 | | | | 77% |
| 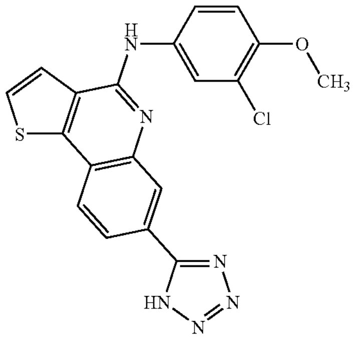 | | | | 75% |
| 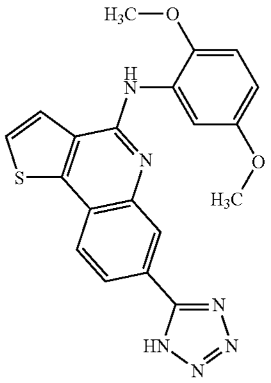 | | | | 61% |

TABLE 14B-continued
| Structure | CK2 IC50 (uM) | CK2 % inhibition 5 uM | 2.5 uM | 1.0 uM |
|---|---|---|---|---|
| 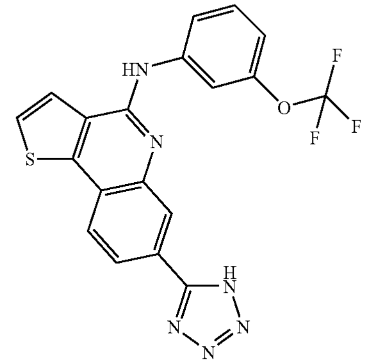 | | | | 65% |
| 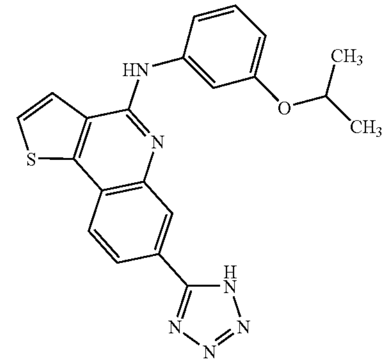 | | | | 68% |
| 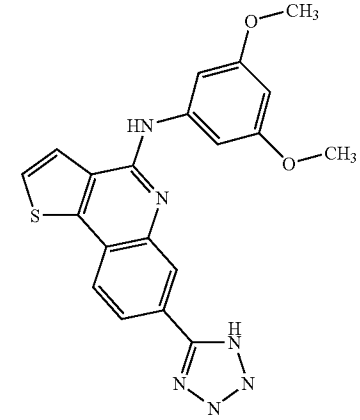 | | | | 77% |
| 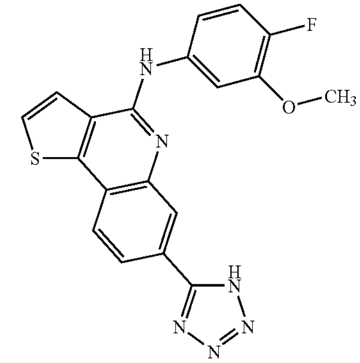 | | | | 60% |

TABLE 14B-continued
| Structure | CK2 IC50 (uM) | CK2 % inhibition 5 uM | 2.5 uM | 1.0 uM |
|---|---|---|---|---|
| 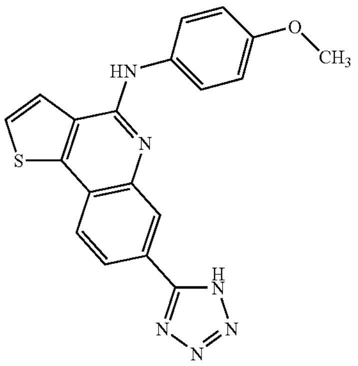 | | | | |
| 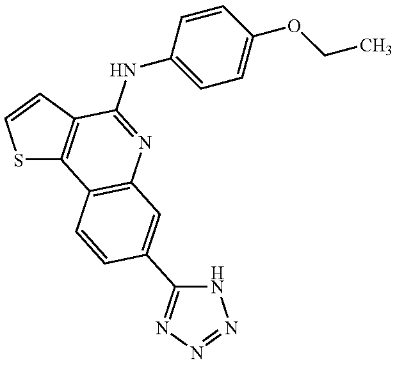 | | | | |
| 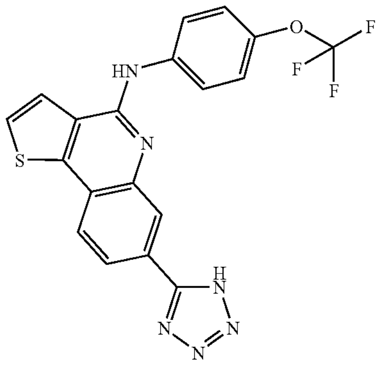 | | | | |
| 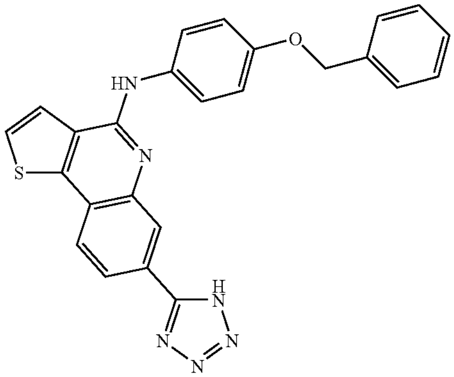 | | | | |

TABLE 14B-continued
| Structure | CK2 IC50 (uM) | CK2 % inhibition 5 uM | 2.5 uM | 1.0 uM |
|---|---|---|---|---|
| 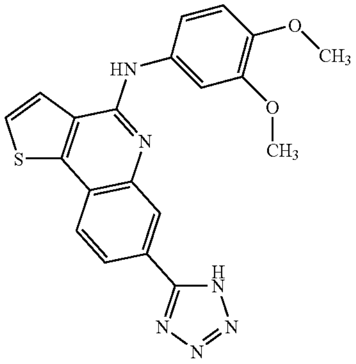 | | | | |
| 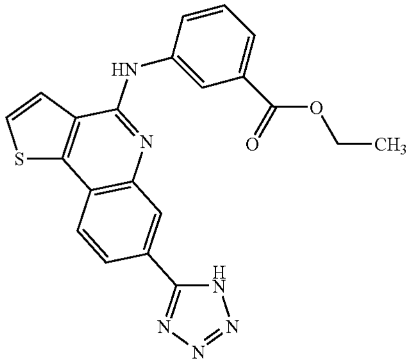 | | | | |
| 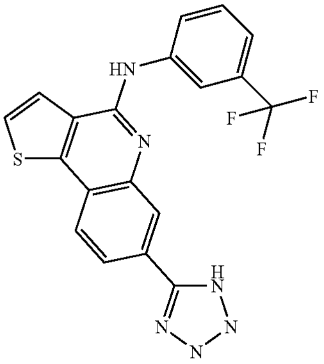 | | | | |
| 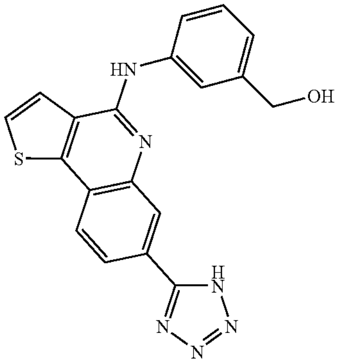 | | | | |

TABLE 14B-continued
| Structure | CK2 IC50 (uM) | CK2 % inhibition 5 uM | 2.5 uM | 1.0 uM |
|---|---|---|---|---|
| 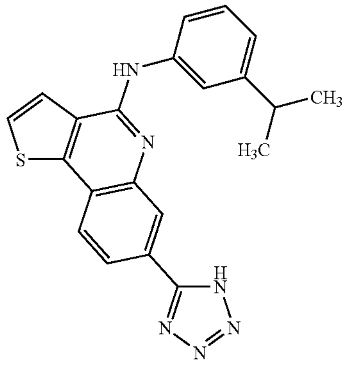 | | | | |
| 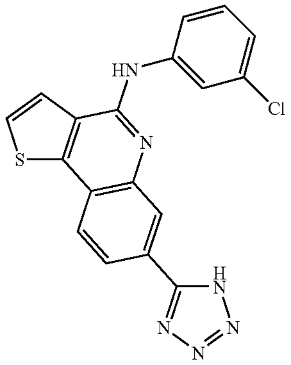 | | | | |
| 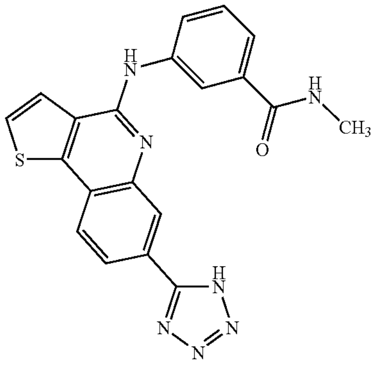 | | | | |
| 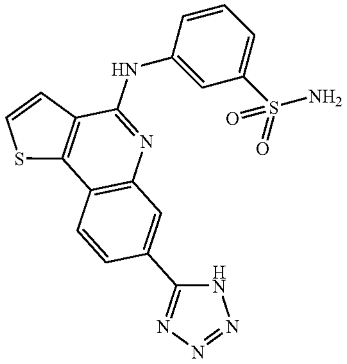 | | | | |

TABLE 14B-continued
| Structure | CK2 IC50 (uM) | CK2 % inhibition 5 uM | 2.5 uM | 1.0 uM |
|---|---|---|---|---|
| 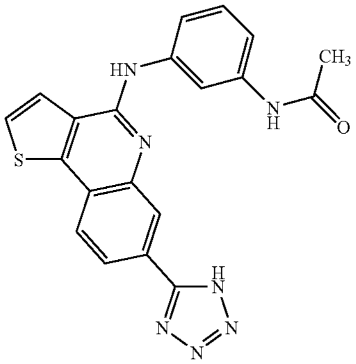 | | | | |
| 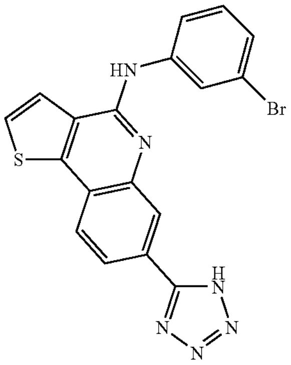 | | | | |
| 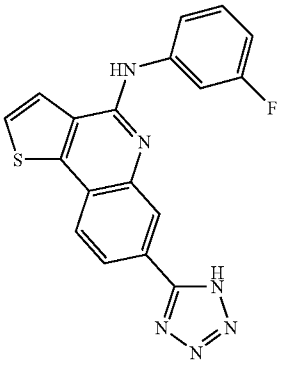 | | | | |
| 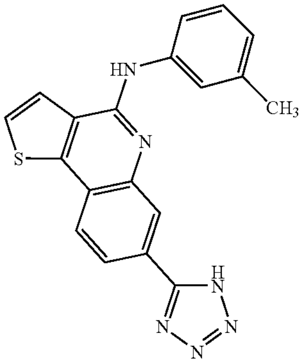 | | | | |

TABLE 14B-continued
| Structure | CK2 IC50 (uM) | CK2 % inhibition | | |
|---|---|---|---|---|
| | | 5 uM | 2.5 uM | 1.0 uM |
| 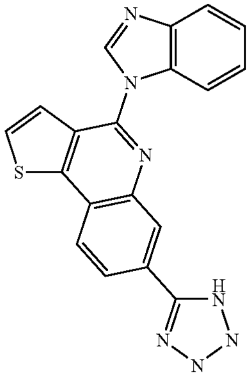 | | | | |
Table 15 shows modulatory effects of compounds on PARP and CK2.
TABLE 15
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 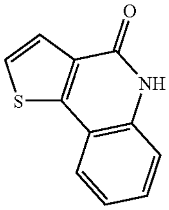 | 0 | • | • | 0 | • |
| 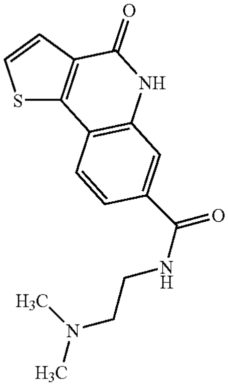 | 85 | • | • | • | • |
| 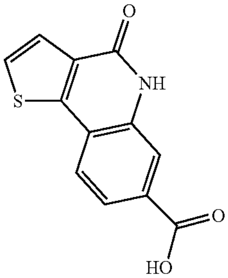 | 90 | 58 | 1 | 77 | 4 |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 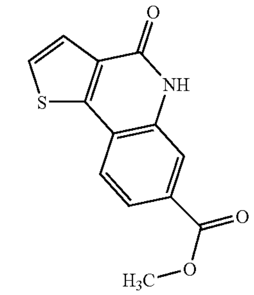 | 84 | 27 | • | 17 | |
| 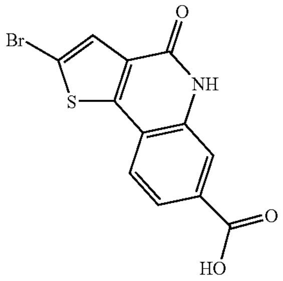 | 84 | 39 | • | 5 | |
| 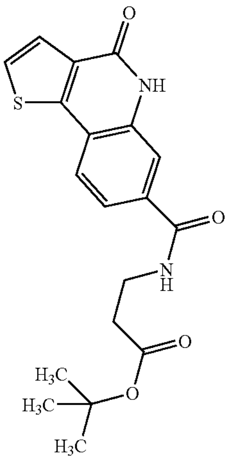 | 82 | 40 | • | 8 | • |
| 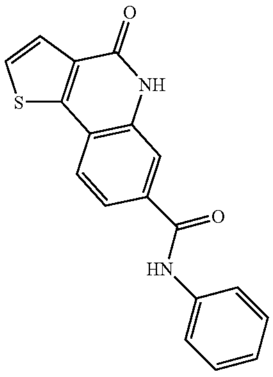 | 22 | 0 | • | 22 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 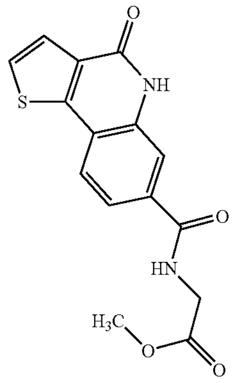 | 93 | 47 | • | 10 | • |
| 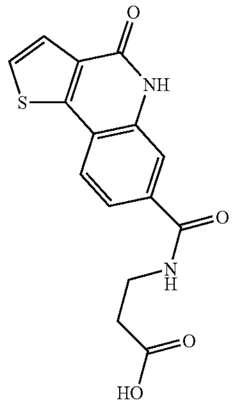 | 95 | 35 | • | 16 | |
| 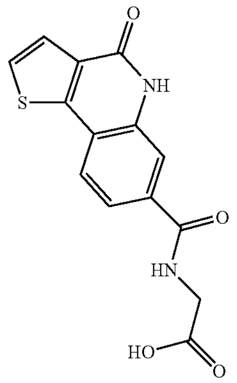 | 97 | 31 | • | 12 | |
| 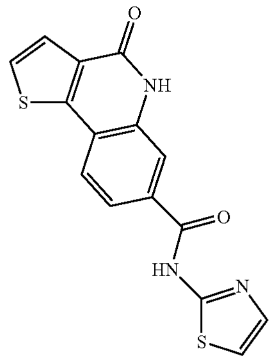 | 52 | 0 | • | 10 | |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 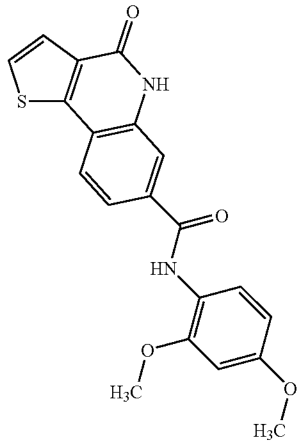 | 32 | 0 | • | 3 | |
| 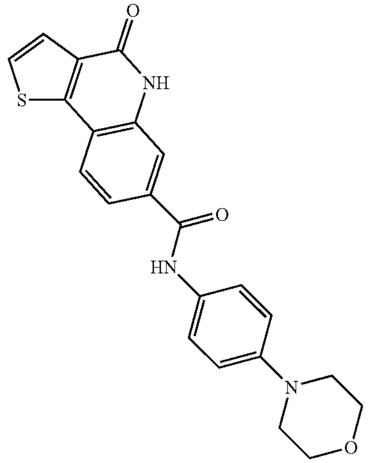 | 37 | 0 | • | −3 | |
| 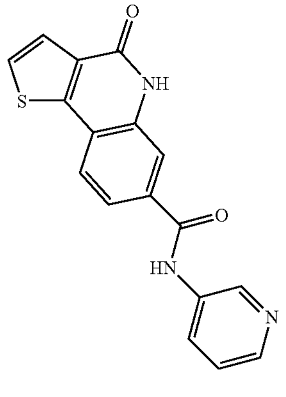 | 62 | 0 | • | −9 | |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 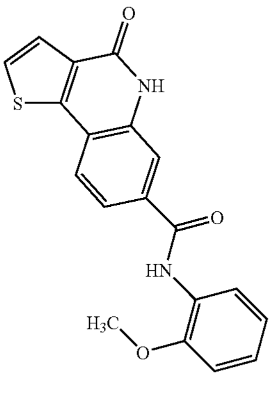 | 24 | 0 | • | −7 | |
| 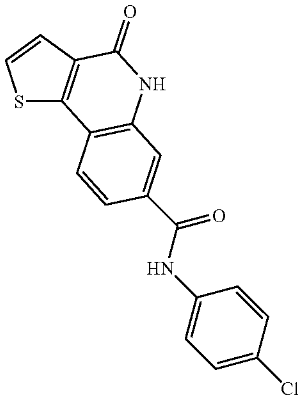 | 55 | 0 | • | −10 | |
| 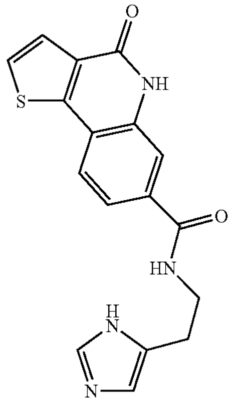 | 97 | 83 | 0.2 | 7 | |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 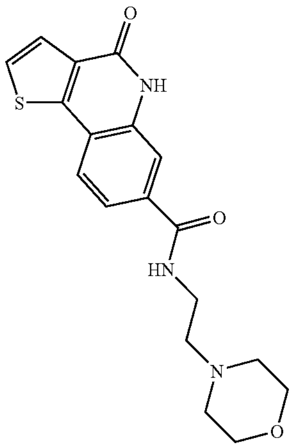 | 96 | 77 | 0.5 | −9 | |
| 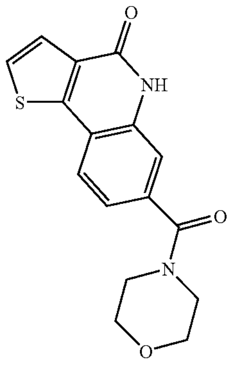 | 95 | 82 | 0.4 | 2 | |
| 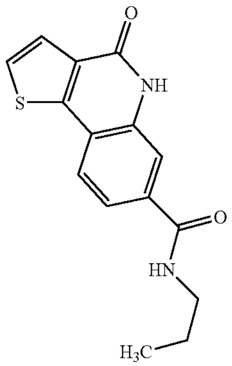 | 88 | 65 | 1 | −34 | |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 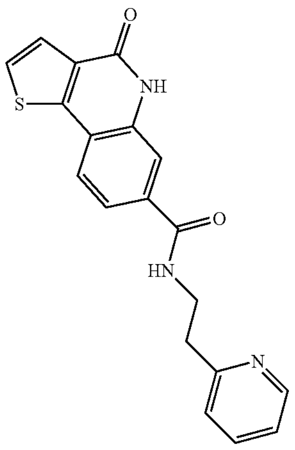 | 83 | 55 | 1 | −24 | |
| 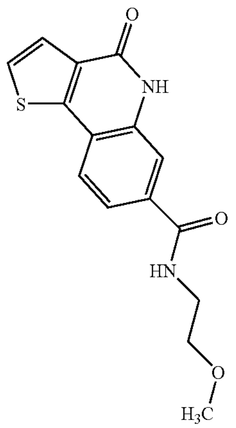 | 93 | 65 | 0.4 | −19 | |
| 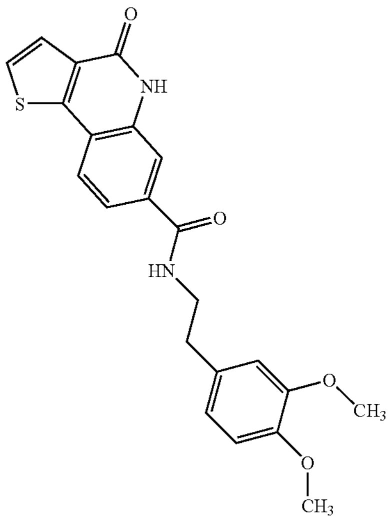 | 67 | 15 | • | −22 | |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 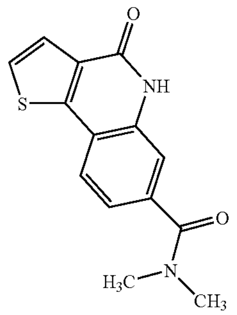 | 97 | 89 | 0.2 | 3 | |
| 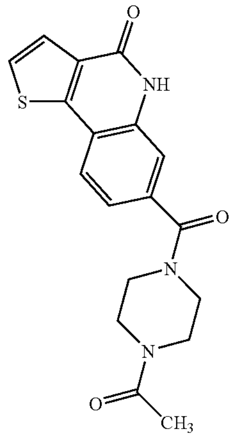 | 94 | 71 | 0.3 | 7 | • |
| 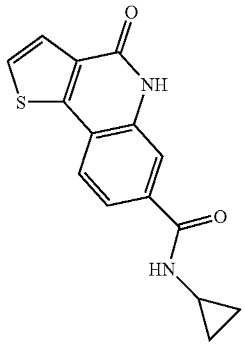 | 90 | 69 | 0.5 | 0 | • |
| 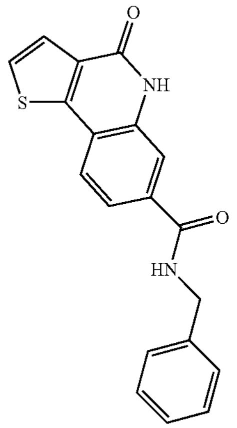 | • | 36 | • | 14 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 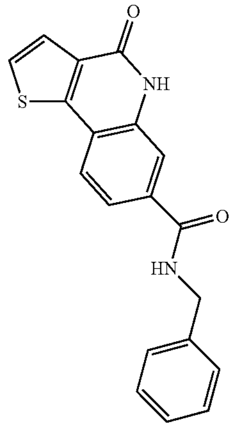 | • | • | • | −1 | • |
| 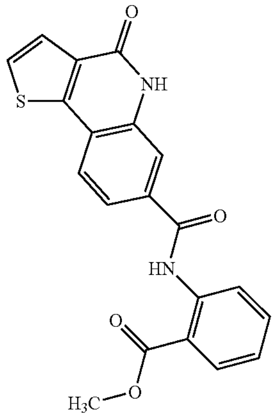 | • | 24 | • | 5 | • |
| 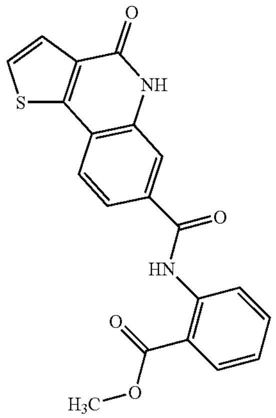 | • | • | • | −16 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 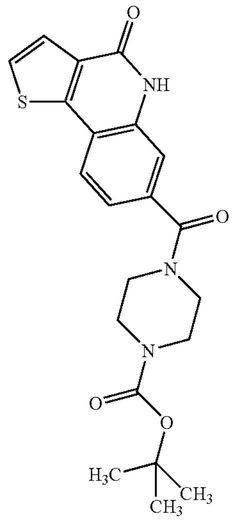 | • | 72 | 0.3 | −25 | • |
| 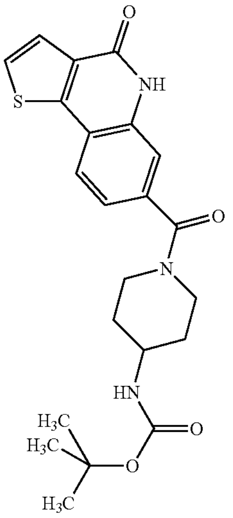 | • | 49 | • | 10 | • |
| 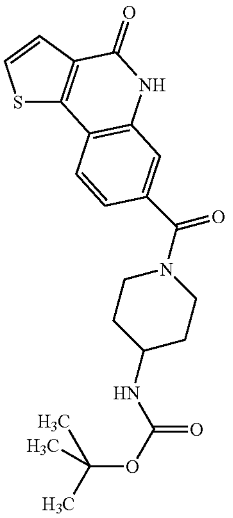 | • | • | • | 1 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 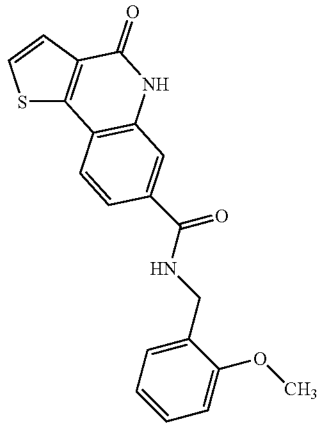 | • | 27 | • | 8 | • |
| 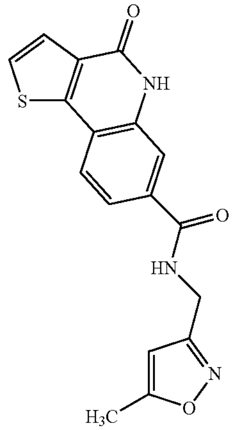 | • | 67 | 0.5 | −13 | • |
| 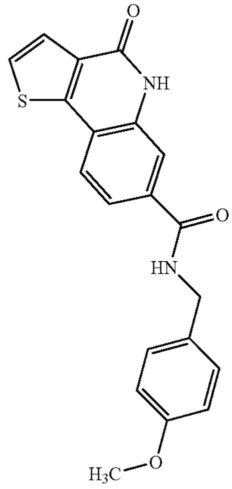 | • | 45 | • | 1 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 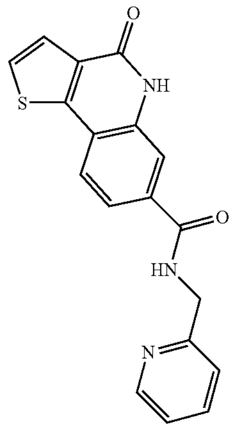 | • | 71 | 1 | 3 | • |
| 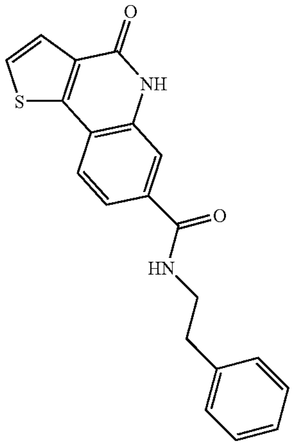 | • | 64 | 0.5 | 1 | • |
| 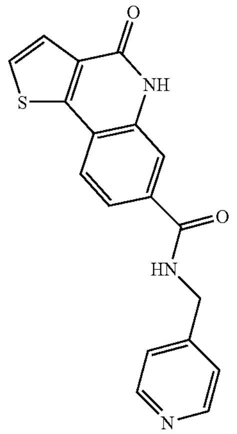 | • | 75 | 1 | −13 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 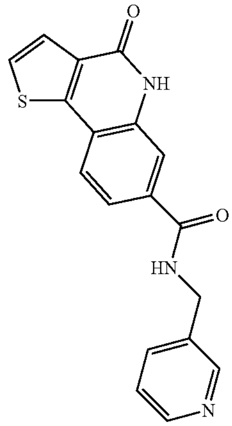 | • | 71 | • | −24 | • |
| 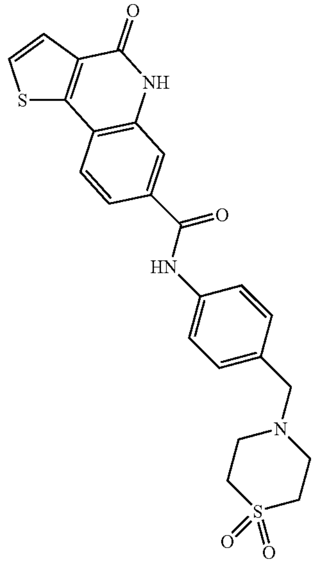 | • | 29 | • | −1 | • |
| 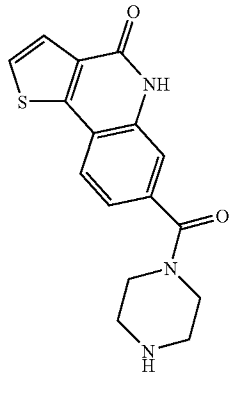 | • | 96 | 0.03 | −27 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 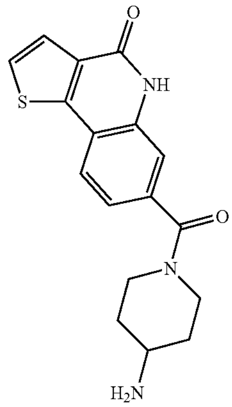 | • | 96 | 0.02 | −3 | • |
| 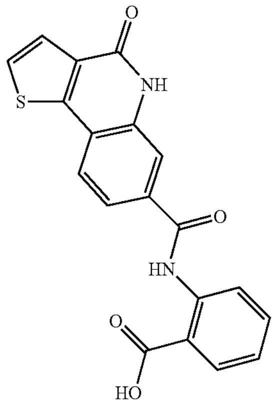 | • | 12 | • | 41 | • |
| 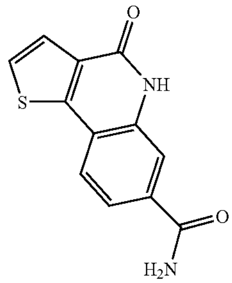 | • | 79 | 0.06 | −14 | • |
| 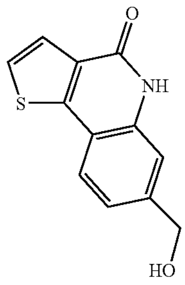 | • | 74 | 0.4 | 3 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 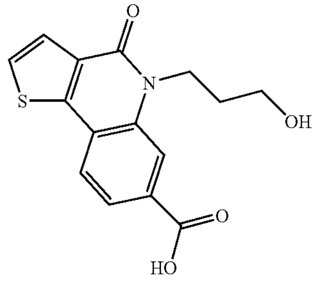 | • | 21 | • | 48 | 2.8 |
| 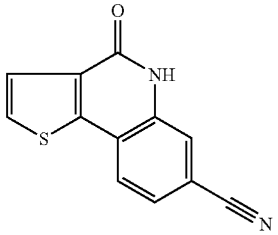 | • | 51 | 0.5 | −5 | • |
| 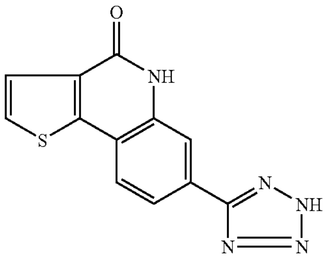 | • | 39 | • | 86 | 0.9 |
| 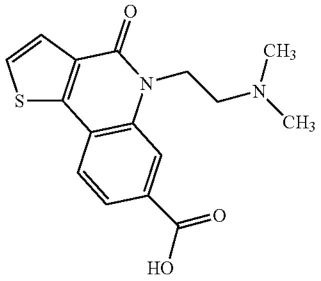 | • | 5 | • | 44 | 12.5 |
| 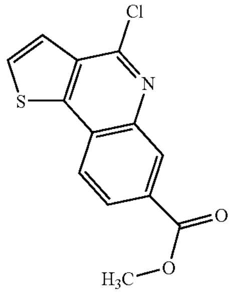 | • | 18 | • | 18 | • |

TABLE 15-continued
| Structure | PARP % inhib @ 20 uM | PARP % inhib @ 1 uM | PARP IC50 (uM) | CK2 % inhib @ 10 uM | CK2 IC50 (uM) |
|---|---|---|---|---|---|
| 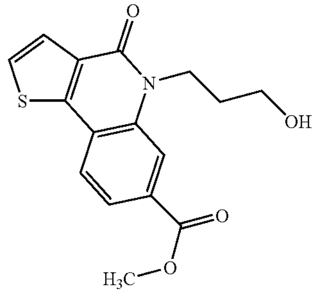 | • | 40 | • | | |
TABLE 16
| Structure | CK2: IC50 (uM) (15 uM ATP) | CK2: IC50 (uM) (20 um ATP) |
|---|---|---|
| 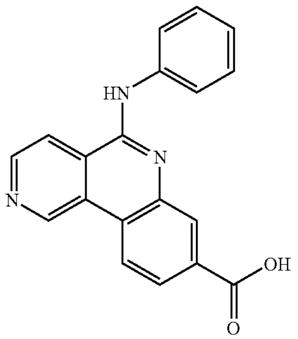 | 0.006 | 0.01 |
| 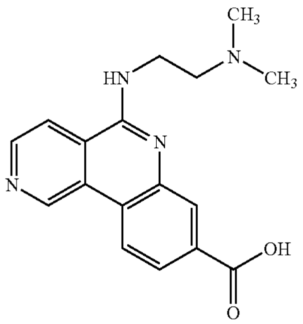 | 0.025 | 0.019 |
| 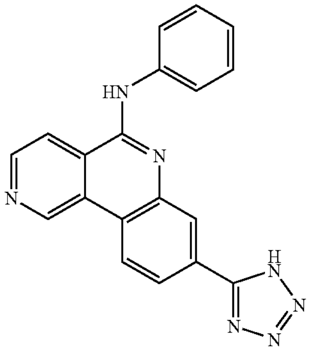 | 0.07 | 0.06 |

TABLE 16-continued
| Structure | CK2: IC50 (uM) (15 uM ATP) | CK2: IC50 (uM) (20 um ATP) |
|---|---|---|
| 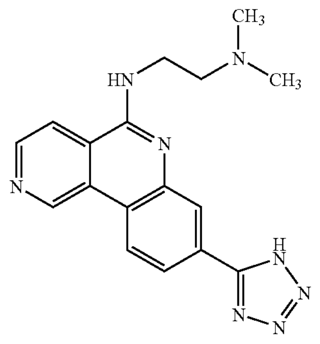 | 0.311 | 0.13 |
| 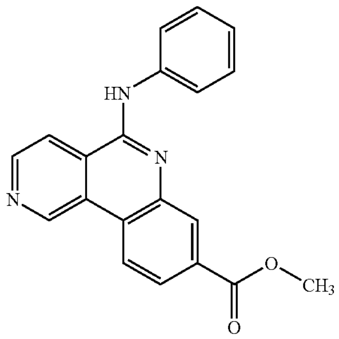 | 0.113 | 0.2 |
| 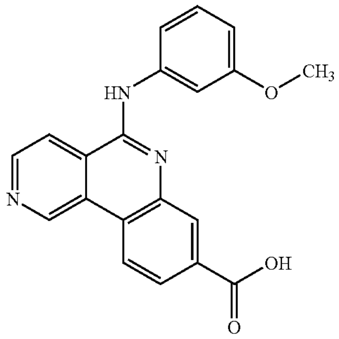 | 0.004 | 0.007 |
| 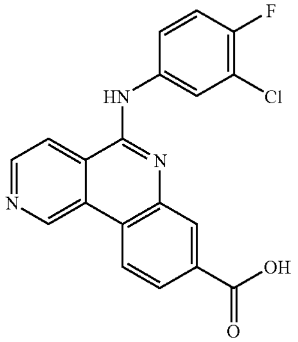 | 0.004 | 0.006 |

TABLE 16-continued
| Structure | CK2: IC50 (uM) (15 uM ATP) | CK2: IC50 (uM) (20 um ATP) |
|---|---|---|
| 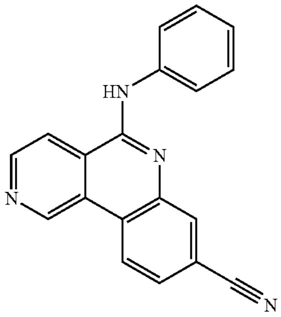 | | |
| 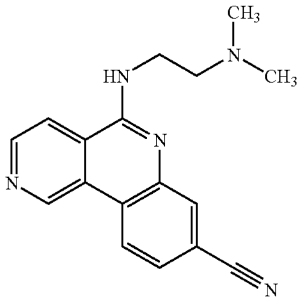 | | |
| 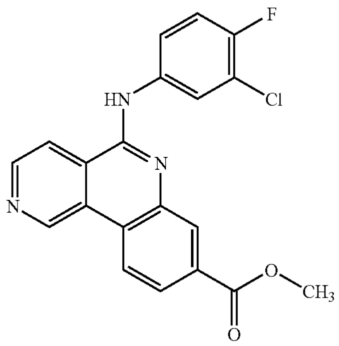 | 1.469 | 1.661 |
| 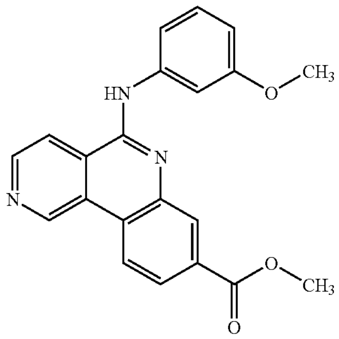 | 25 | |

TABLE 16-continued
| Structure | CK2: IC50 (uM) (15 uM ATP) | CK2: IC50 (uM) (20 um ATP) |
|---|---|---|
| 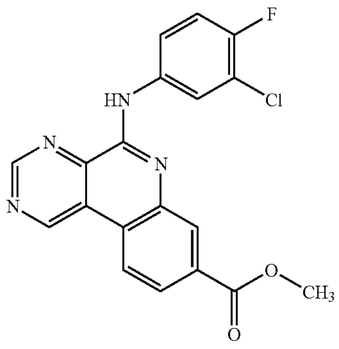 | | |
| 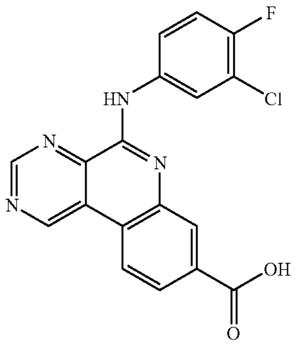 | 0.01 | |
| 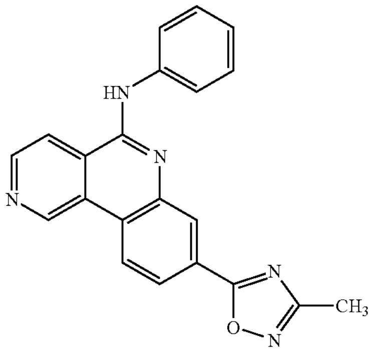 | | |
| 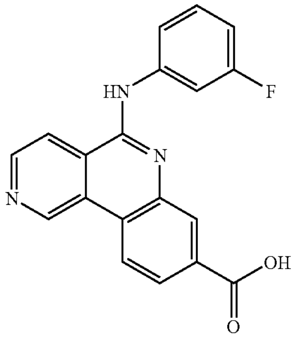 | 0.005 | |

TABLE 16-continued
| Structure | CK2: IC50 (uM) (15 uM ATP) | CK2: IC50 (uM) (20 um ATP) |
|---|---|---|
| 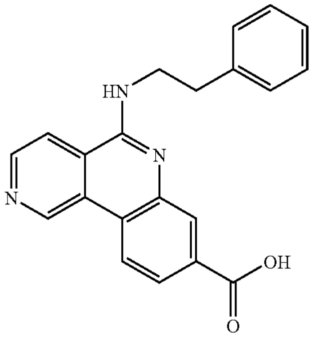 | 0.003 | |
| 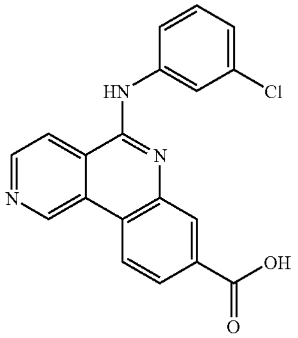 | 0.002 | |
| 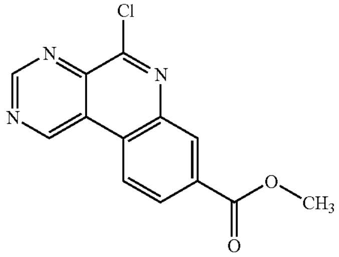 | 0.651 | |
| 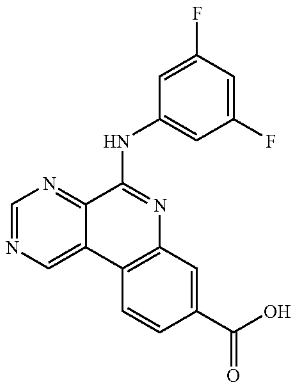 | 0.006 | |

TABLE 16-continued
| Structure | CK2: IC50 (uM) (15 uM ATP) | CK2: IC50 (uM) (20 um ATP) |
|---|---|---|
| 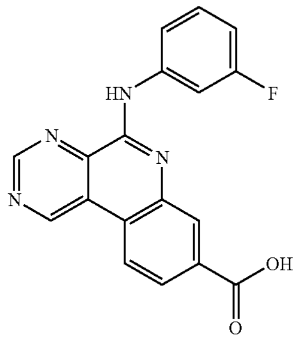 | 0.006 | |
| 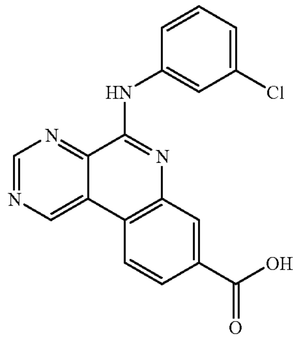 | 0.007 | |
| 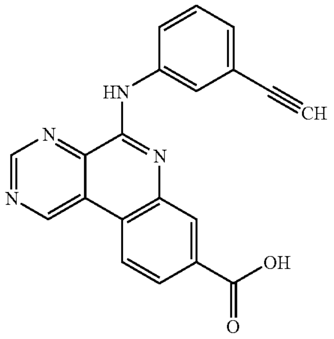 | 0.006 | |
| 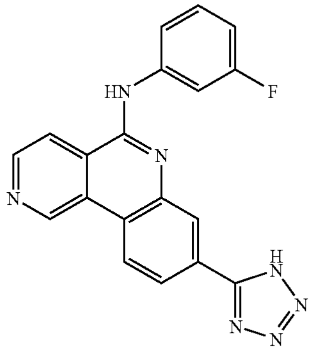 | 0.047 | |

TABLE 16-continued
| Structure | CK2: IC50 (uM) (15 uM ATP) | CK2: IC50 (uM) (20 um ATP) |
|---|---|---|
| 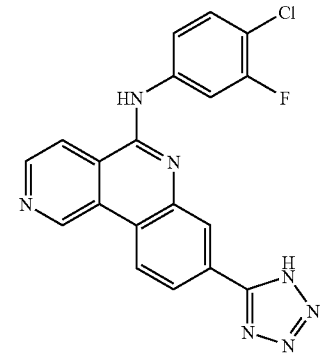 | 0.052 | |
| 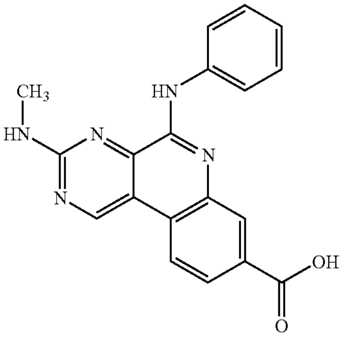 | 0.019 | |
| 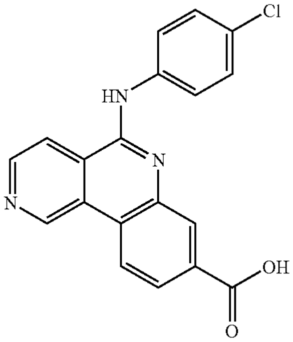 | 0.007 | |
| 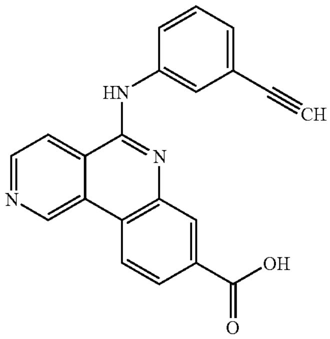 | 0.003 | |

TABLE 16-continued
| Structure | CK2: IC50 (uM) (15 uM ATP) | CK2: IC50 (uM) (20 um ATP) |
| --- | --- | --- |
| 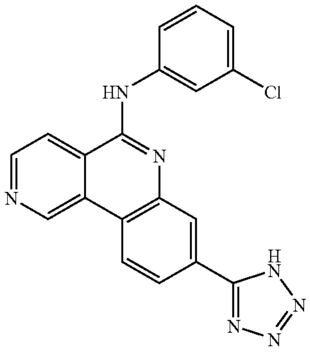 | 0.045 | |
| 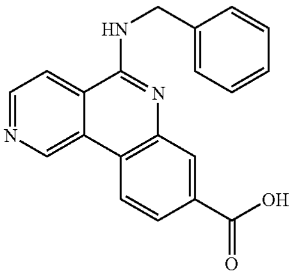 | 0.009 | |
| 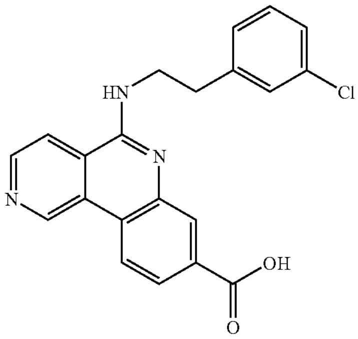 | 0.005 | |
| 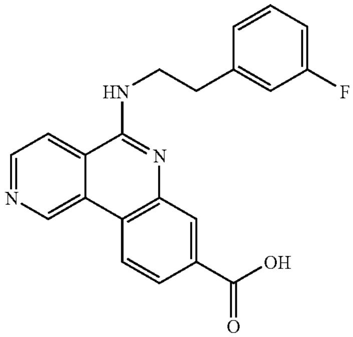 | 0.007 | |

TABLE 16-continued
| Structure | CK2: IC50 (uM) (15 uM ATP) | CK2: IC50 (uM) (20 um ATP) |
|---|---|---|
| 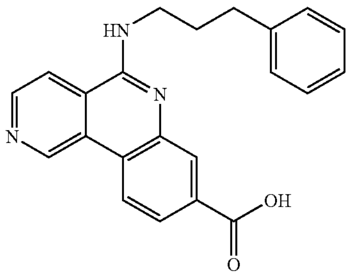 | 0.016 | |
| 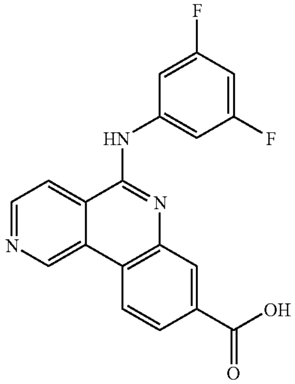 | 0.005 | |
| 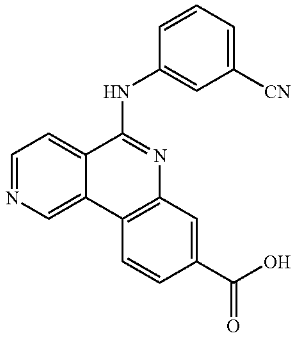 | 0.004 | |
| 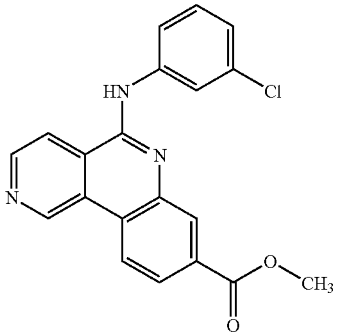 | >0.5 | |

TABLE 16-continued
| Structure | CK2: IC50 (uM) (15 uM ATP) | CK2: IC50 (uM) (20 um ATP) |
|---|---|---|
| 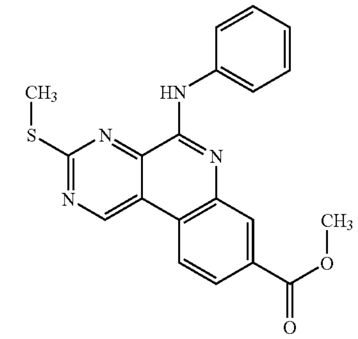 | >0.5 | |
| 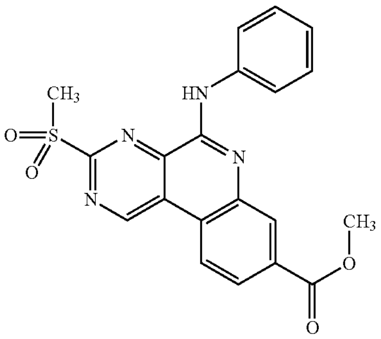 | >0.5 | |
| 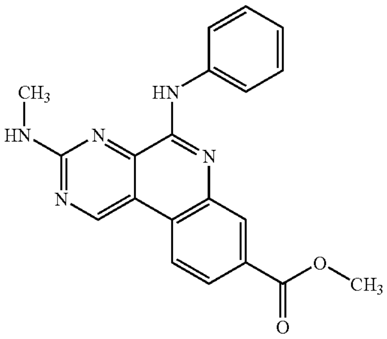 | >0.5 | |
| 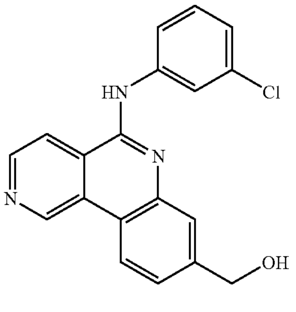 | 0.711 | |

TABLE 16-continued
| Structure | CK2: IC50 (uM) (15 uM ATP) | CK2: IC50 (uM) (20 um ATP) |
|---|---|---|
| 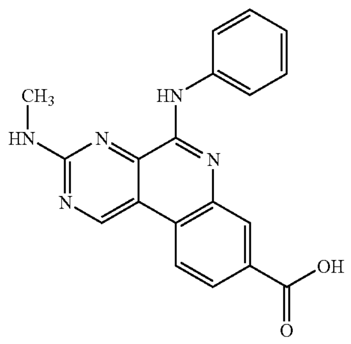 | 0.018 | |
| 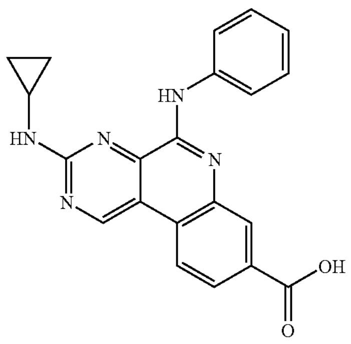 | 0.027 | |
| 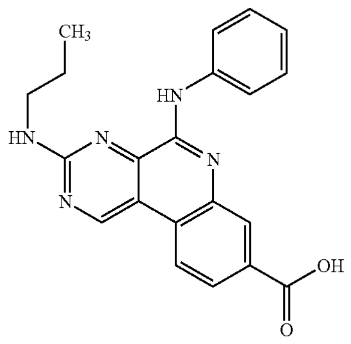 | 0.051 | |
| 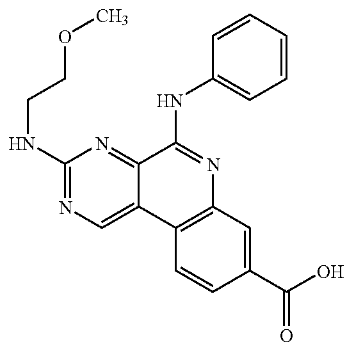 | 0.069 | |

TABLE 16-continued
| Structure | CK2: IC50 (uM) (15 uM ATP) | CK2: IC50 (uM) (20 um ATP) |
|---|---|---|
| 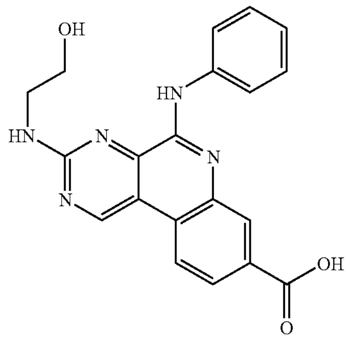 | 0.02 | |
| 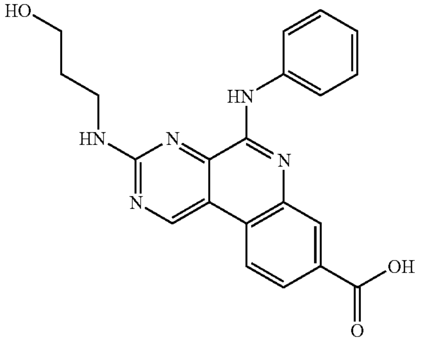 | 0.026 | |
| 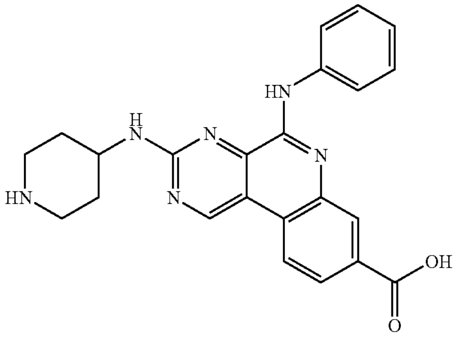 | 0.056 | |
| 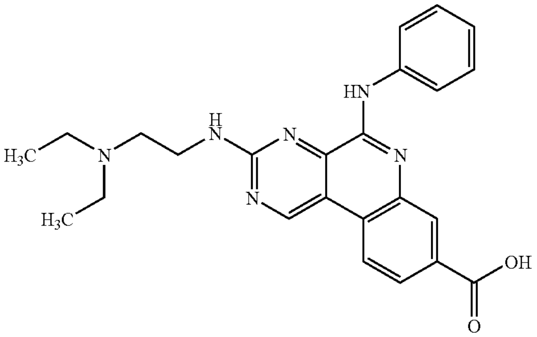 | 0.163 | |

TABLE 16-continued
| Structure | CK2: IC50 (uM) (15 uM ATP) | CK2: IC50 (uM) (20 um ATP) |
|---|---|---|
| 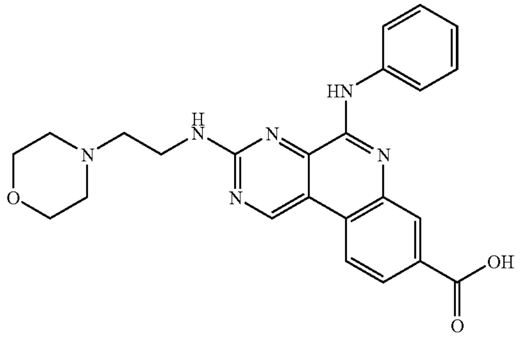 | 0.107 | |
| 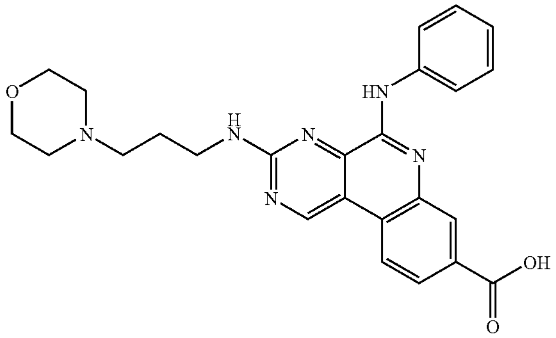 | 0.089 | |
| 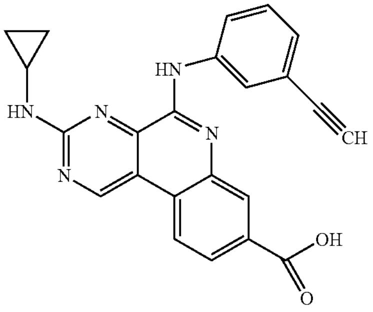 | 0.046 | |
| 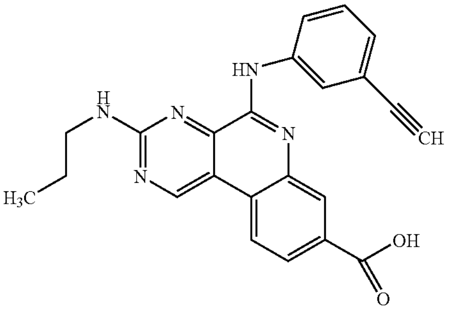 | 0.06 | |

TABLE 16-continued
| Structure | CK2: IC50 (uM) (15 uM ATP) | CK2: IC50 (uM) (20 um ATP) |
|---|---|---|
| 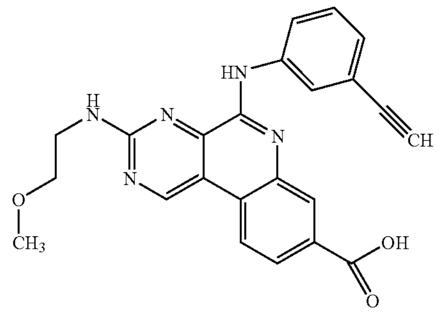 | 0.04 | |
| 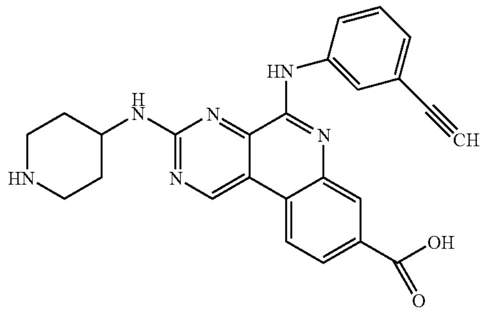 | 0.144 | |
| 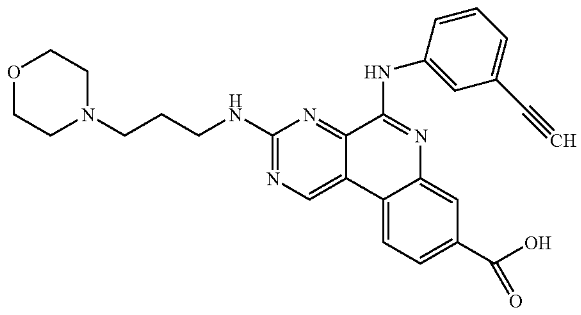 | 0.25 | |
| 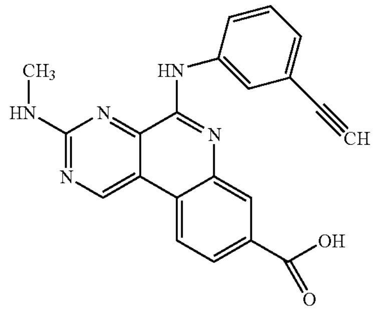 | 0.009 | |

TABLE 16-continued
| Structure | CK2: IC50 (uM) (15 uM ATP) | CK2: IC50 (uM) (20 um ATP) |
|---|---|---|
| 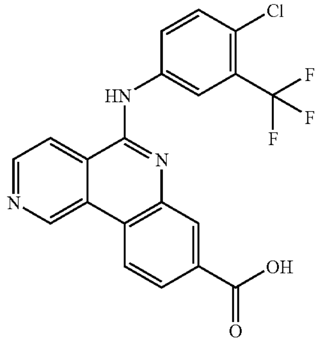 | 0.018 | |
| 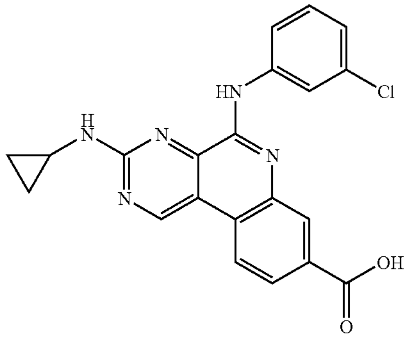 | 0.013 | |
| 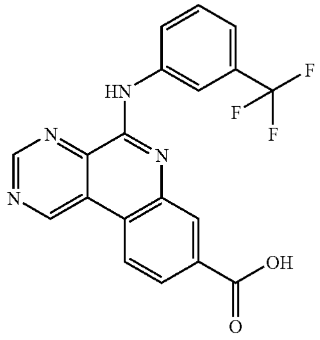 | 0.011 | |
| 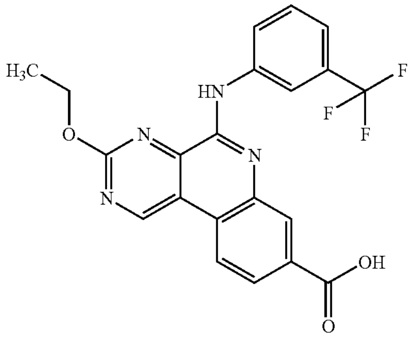 | >0.75 | |

TABLE 16-continued
| Structure | CK2: IC50 (uM) (15 uM ATP) | CK2: IC50 (uM) (20 um ATP) |
|---|---|---|
| 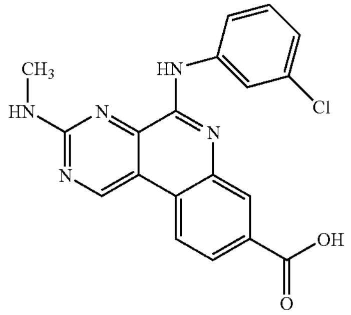 | 0.018 | |
| 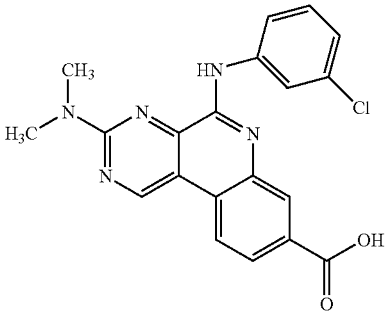 | >0.75 | |
| 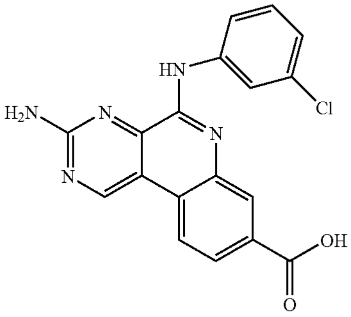 | 0.004 | |
| 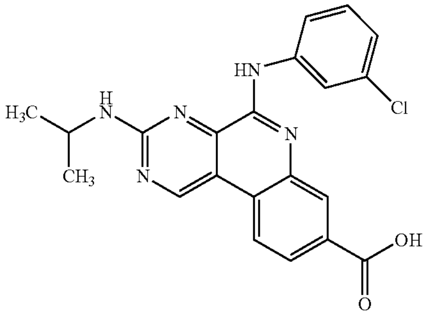 | 0.134 | |

TABLE 16-continued
| Structure | CK2: IC50 (uM) (15 uM ATP) | CK2: IC50 (uM) (20 um ATP) |
|---|---|---|
| 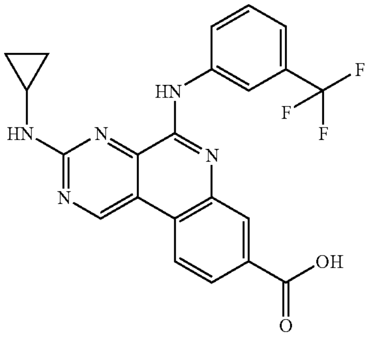 | 0.009 | |
| 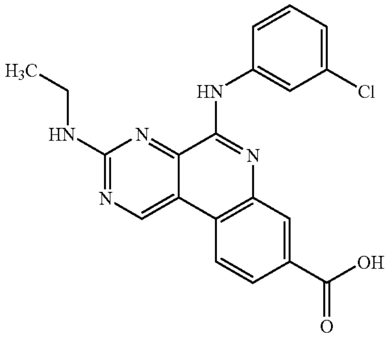 | 0.03 | |
| 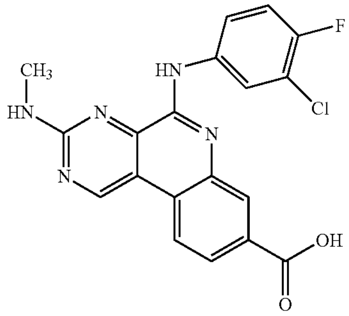 | 0.02 | |
| 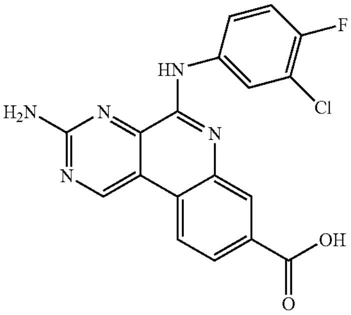 | 0.007 | |

TABLE 16-continued
| Structure | CK2: IC50 (uM) (15 uM ATP) | CK2: IC50 (uM) (20 um ATP) |
|---|---|---|
| 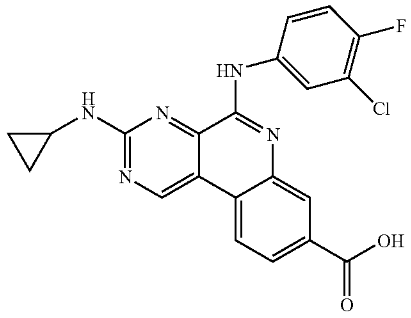 | 0.083 | |
| 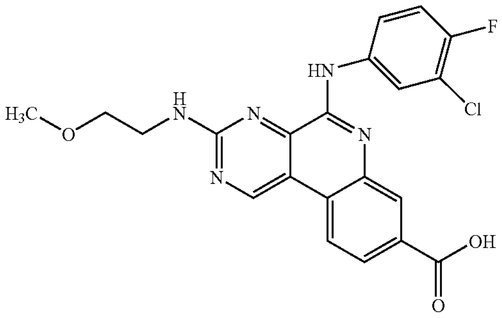 | 0.052 | |
| 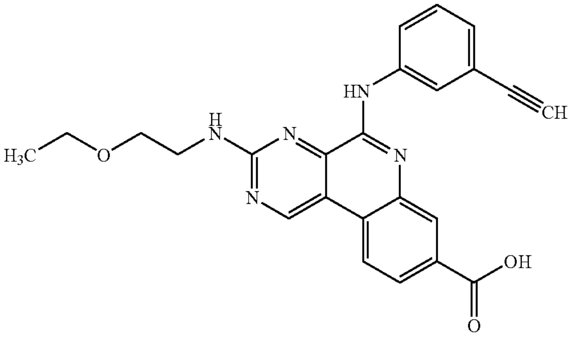 | 0.171 | |
| 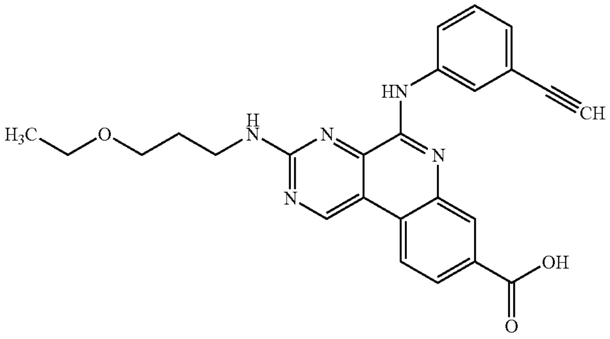 | 0.107 | |

TABLE 16-continued
| Structure | CK2: IC50 (uM) (15 uM ATP) | CK2: IC50 (uM) (20 um ATP) |
|---|---|---|
| 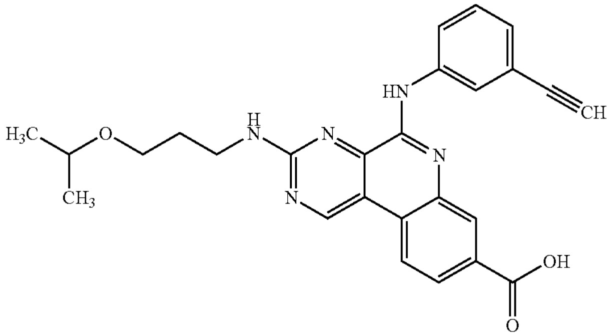 | 0.349 | |
| 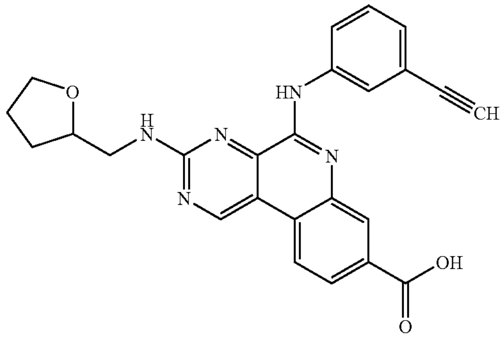 | 0.114 | |
| 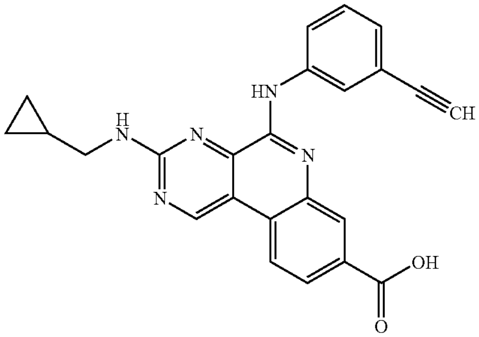 | 0.05 | |
| 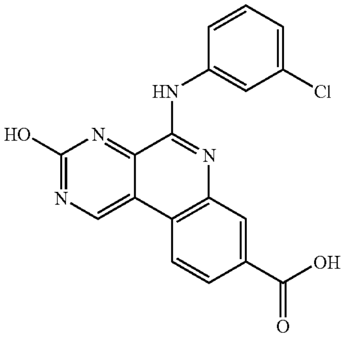 | 0.214 | |

TABLE 16-continued
| Structure | CK2: IC50 (uM) (15 uM ATP) | CK2: IC50 (uM) (20 um ATP) |
|---|---|---|
| 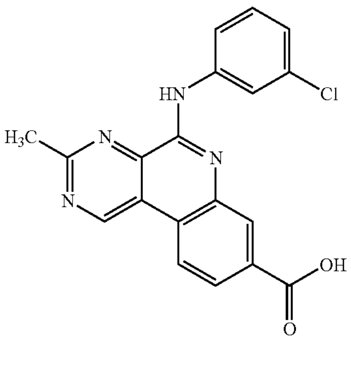 | 0.172 | |
| 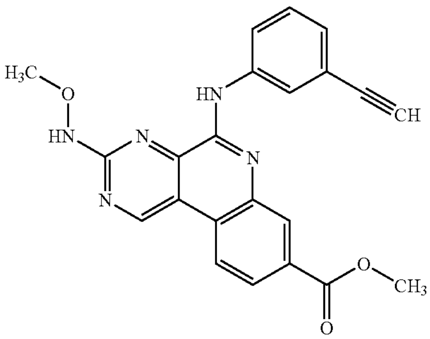 | >0.75 | |
| 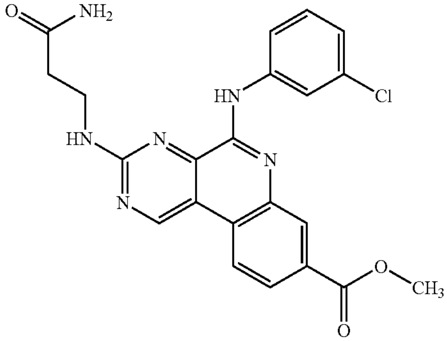 | >0.75 | |
| 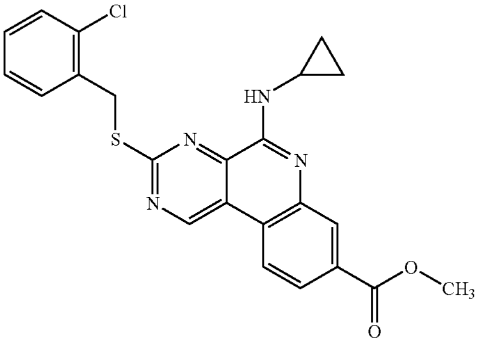 | >0.75 | |

TABLE 16-continued
| Structure | CK2: IC50 (uM) (15 uM ATP) | CK2: IC50 (uM) (20 um ATP) |
|---|---|---|
| 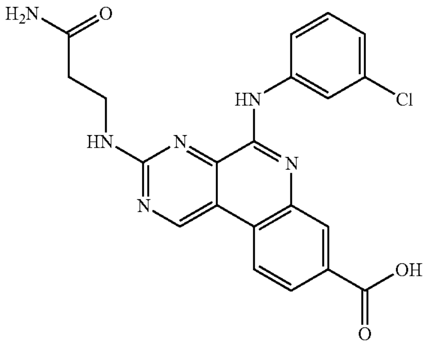 | 0.028 | |
| 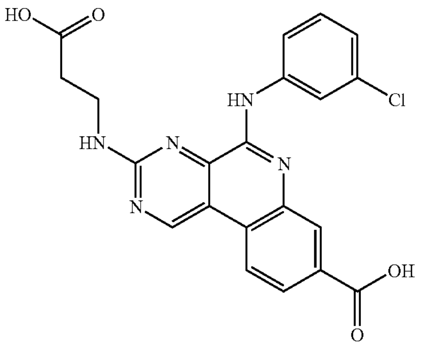 | 0.021 | |
| 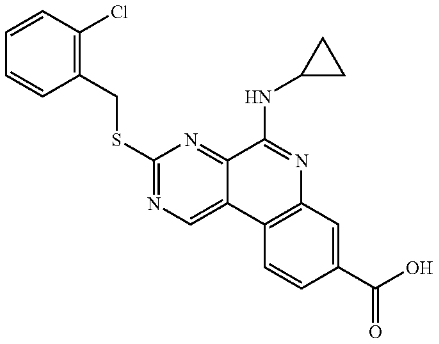 | >0.75 | |
| 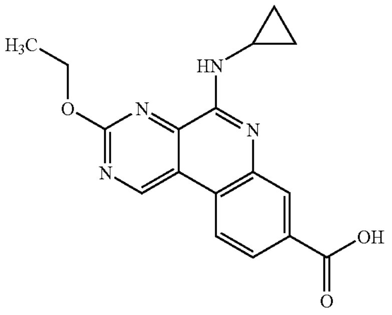 | 0.493 | |

TABLE 16-continued
| Structure | CK2: IC50 (uM) (15 uM ATP) | CK2: IC50 (uM) (20 um ATP) |
|---|---|---|
| 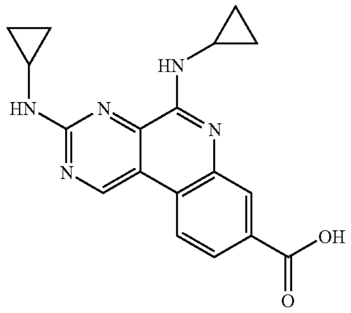 | 0.006 | |
| 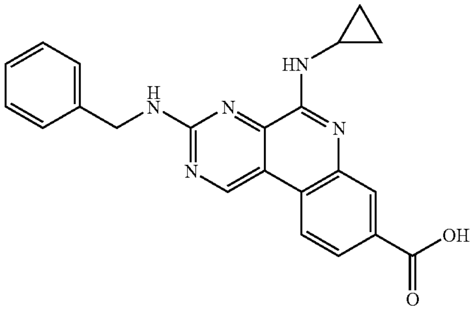 | 0.059 | |
| 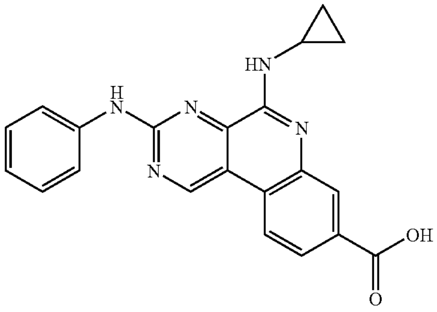 | 0.026 | |
| 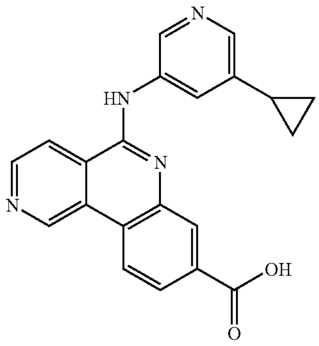 | >0.75 | |

TABLE 16-continued
| Structure | CK2: IC50 (uM) (15 uM ATP) | CK2: IC50 (uM) (20 um ATP) |
| --- | --- | --- |
| 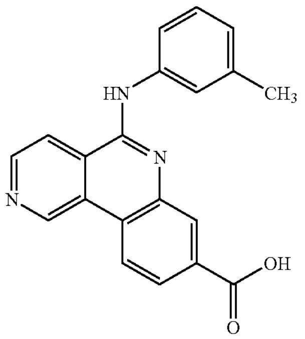 | 0.006 | |
| 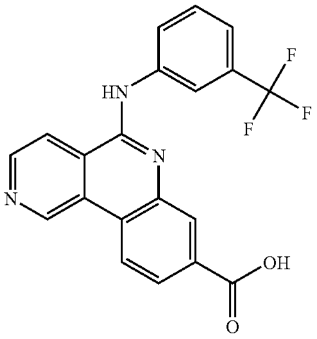 | 0.011 | |
| 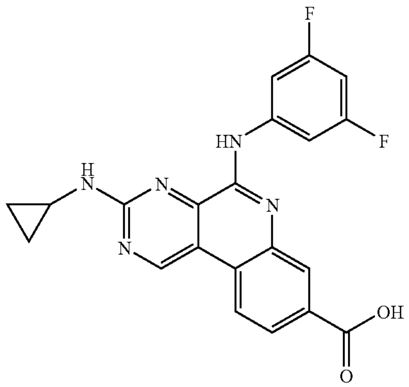 | 0.102 | |
| 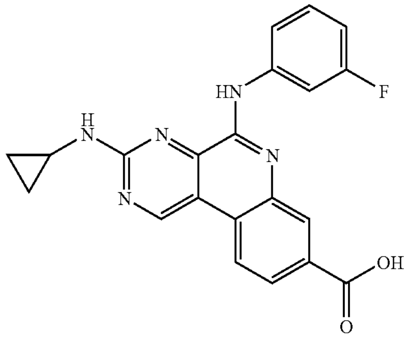 | 0.086 | |

TABLE 16-continued
| Structure | CK2: IC50 (uM) (15 uM ATP) | CK2: IC50 (uM) (20 um ATP) |
|---|---|---|
| 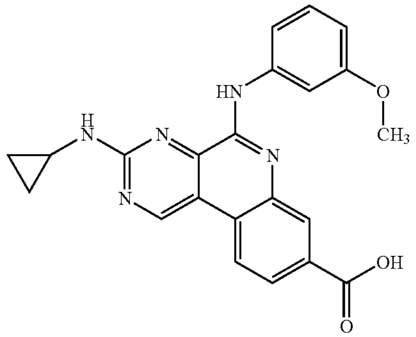 | 0.134 | |
| 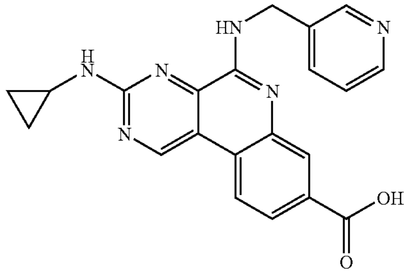 | 0.018 | |
| 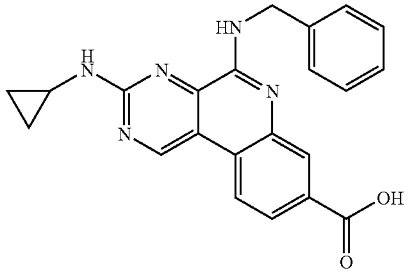 | 0.035 | |
| 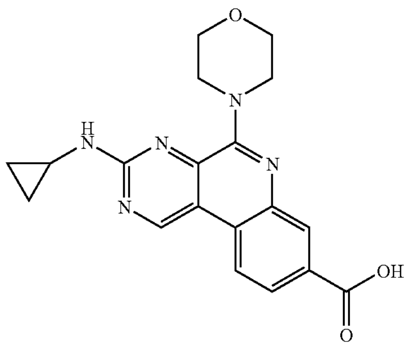 | >0.75 | |

TABLE 16-continued
| Structure | CK2: IC50 (uM) (15 uM ATP) | CK2: IC50 (uM) (20 um ATP) |
|---|---|---|
| 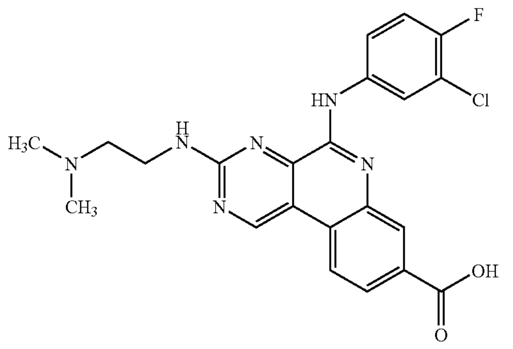 | 0.168 | |
| 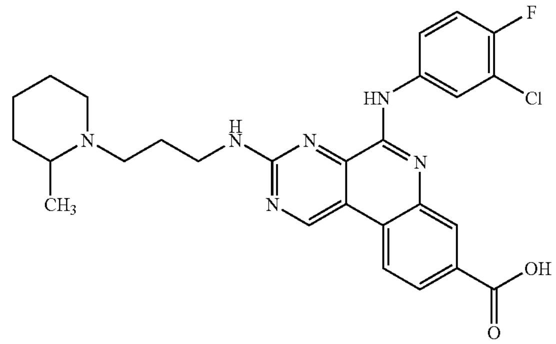 | 0.686 | |
| 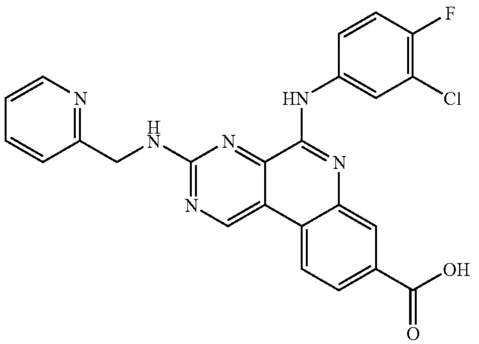 | 0.356 | |
| 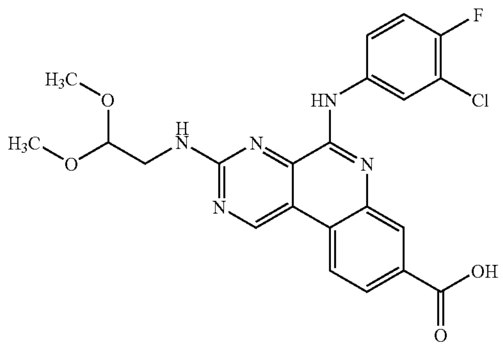 | 0.103 | |

TABLE 16-continued
| Structure | CK2: IC50 (uM) (15 uM ATP) | CK2: IC50 (uM) (20 um ATP) |
|---|---|---|
| 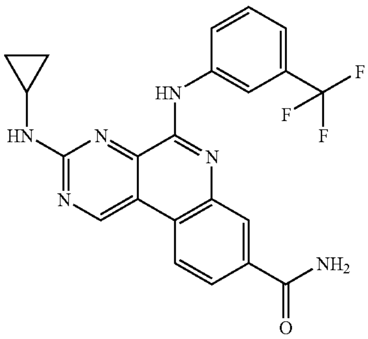 | >0.75 | |
| 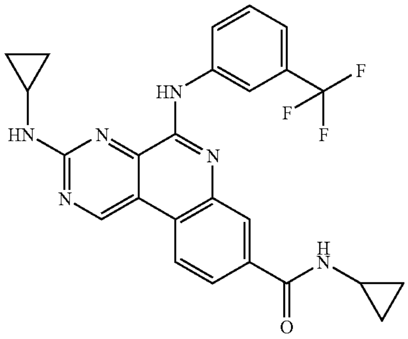 | >0.75 | |
| 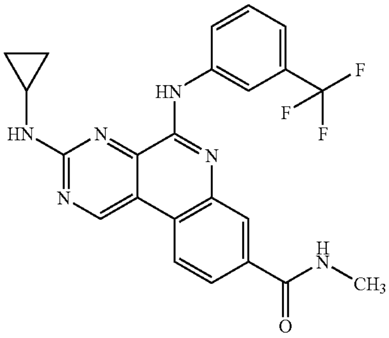 | >0.75 | |
| 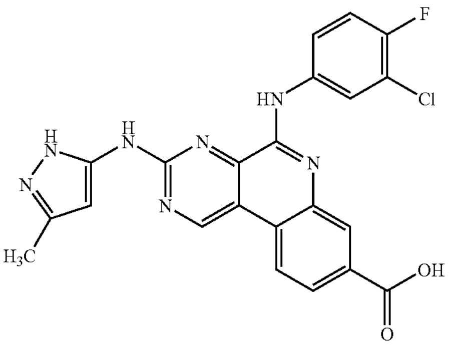 | 0.513 | |

TABLE 16-continued
| Structure | CK2: IC50 (uM) (15 uM ATP) | CK2: IC50 (uM) (20 um ATP) |
|---|---|---|
| 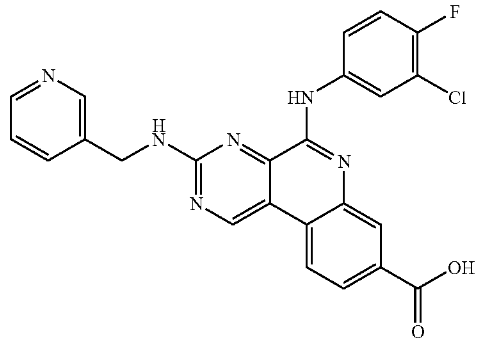 | 0.027 | |
| 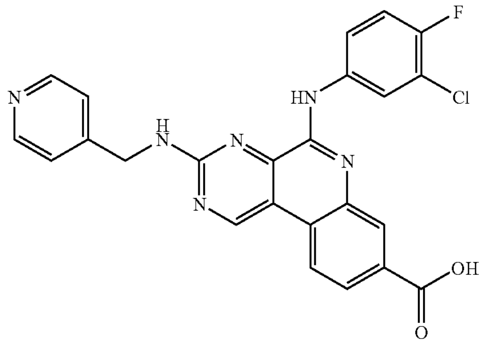 | | |
| 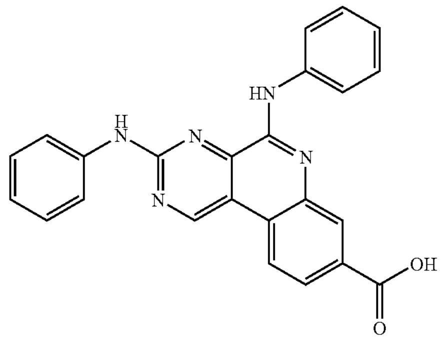 | 0.185 | |
| 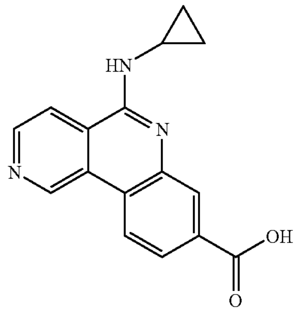 | 0.016 | |

TABLE 16-continued
| Structure | CK2: IC50 (uM) (15 uM ATP) | CK2: IC50 (uM) (20 um ATP) |
|---|---|---|
| 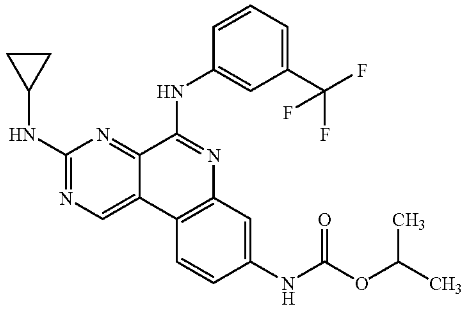 | >0.75 | |
| 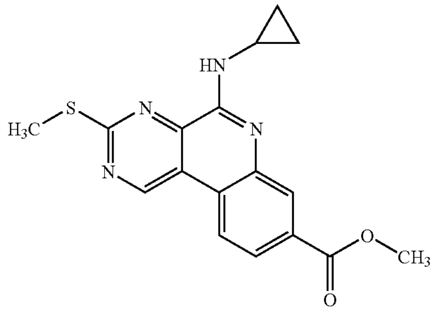 | >0.75 | |
| 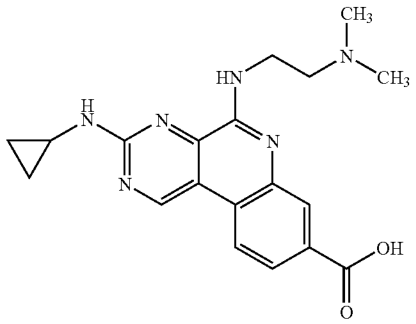 | >0.75 | |
| 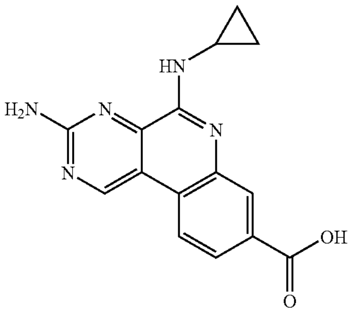 | 0.023 | |

TABLE 16-continued
| Structure | CK2: IC50 (uM) (15 uM ATP) | CK2: IC50 (uM) (20 um ATP) |
|---|---|---|
| 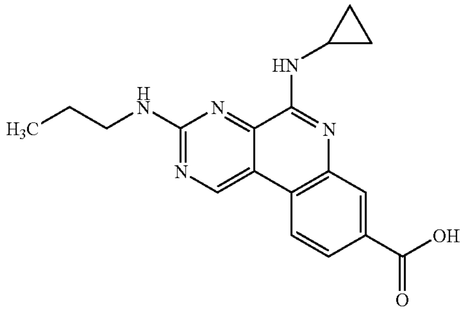 | 0.015 | |
| 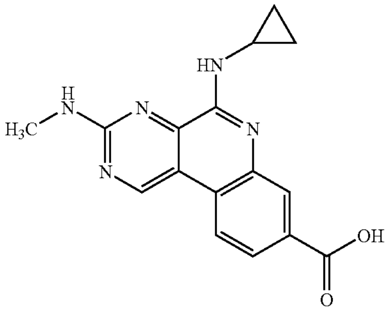 | 0.014 | |
| 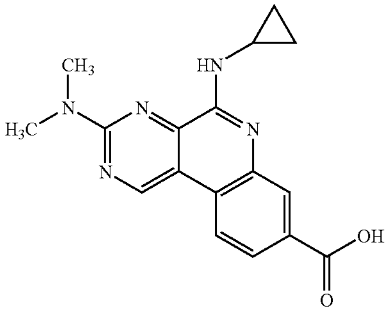 | >0.75 | |
| 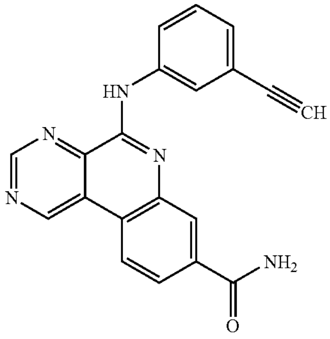 | 0.087 | |

TABLE 16-continued
| Structure | CK2: IC50 (uM) (15 uM ATP) | CK2: IC50 (uM) (20 um ATP) |
|---|---|---|
| 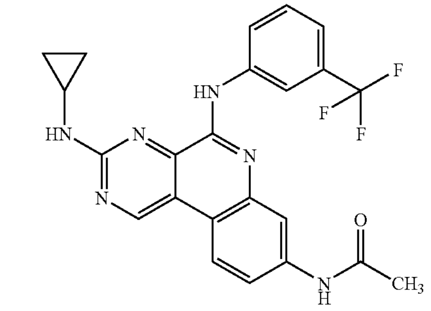 | >0.75 | |
| 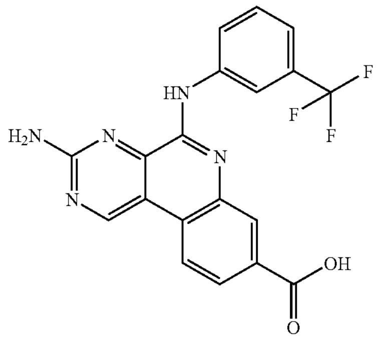 | 0.014 | |
| 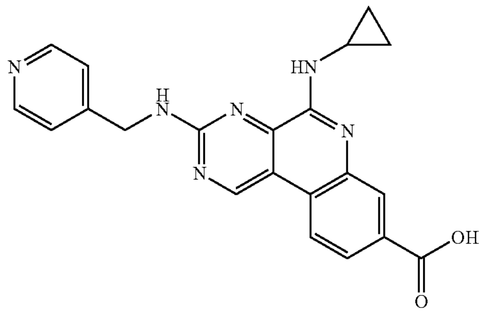 | 0.093 | |
| 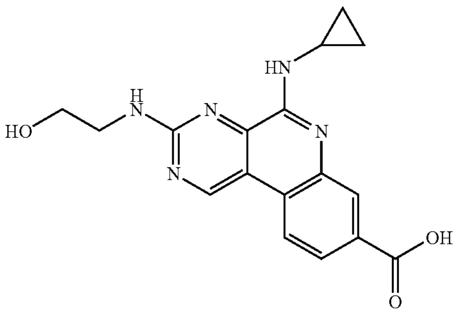 | 0.01 | |

TABLE 16-continued
| Structure | CK2: IC50 (uM) (15 uM ATP) | CK2: IC50 (uM) (20 um ATP) |
|---|---|---|
| 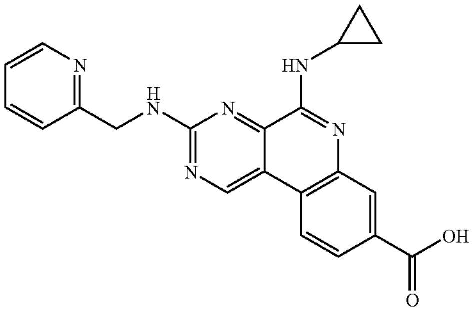 | 0.035 | |
| 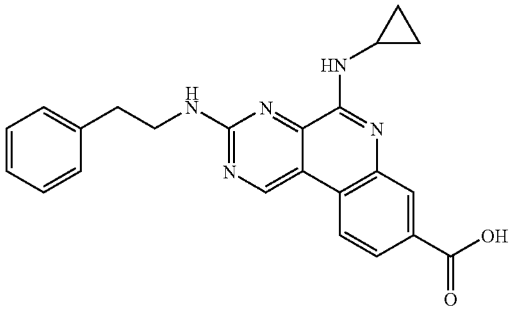 | 0.033 | |
| 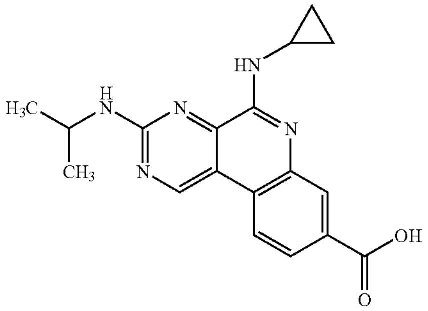 | 0.02 | |
| 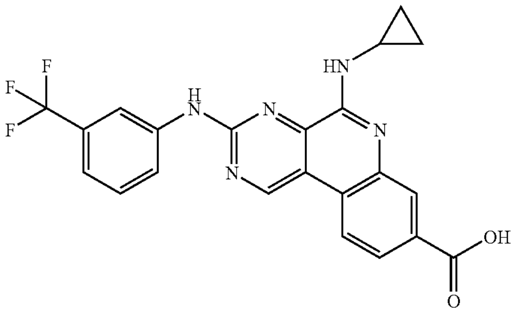 | 0.198 | |

TABLE 16-continued
| Structure | CK2: IC50 (uM) (15 uM ATP) | CK2: IC50 (uM) (20 um ATP) |
| --- | --- | --- |
| 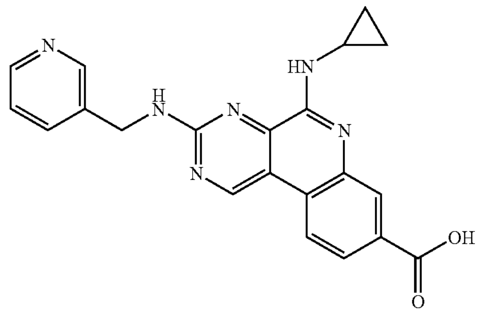 | | |
| 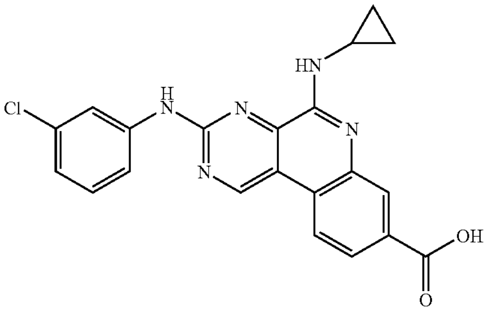 | | |
| 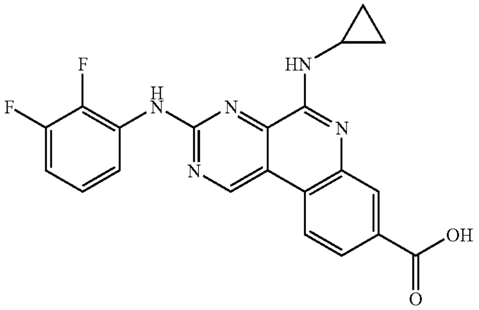 | | |
| 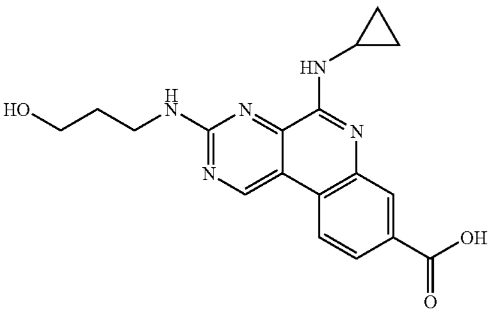 | | |

TABLE 16-continued
| Structure | CK2: IC50 (uM) (15 uM ATP) | CK2: IC50 (uM) (20 um ATP) |
|---|---|---|
| 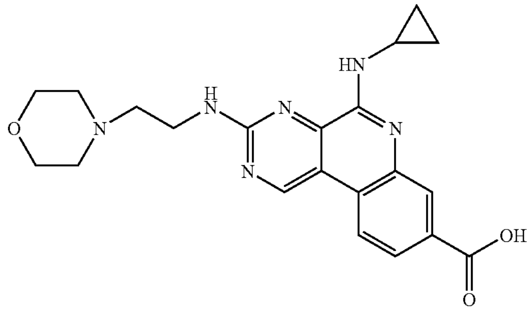 | | |
| 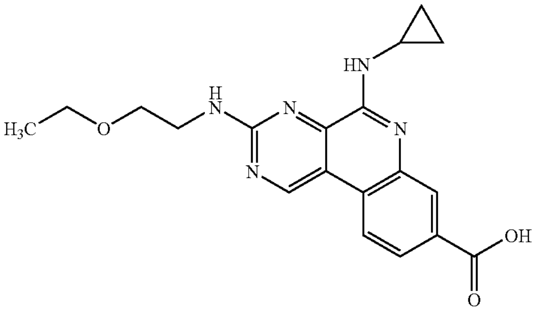 | | |
| 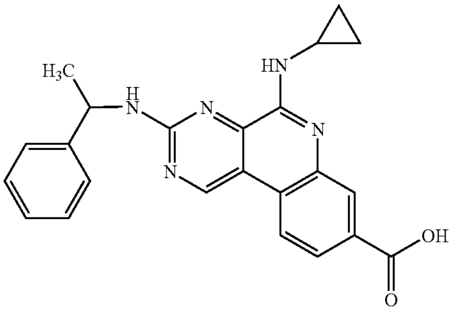 | | |
| 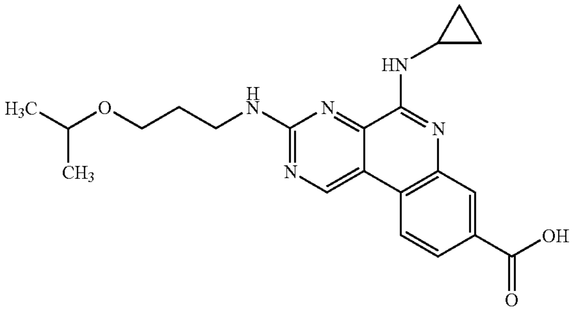 | | |

TABLE 16-continued
| Structure | CK2: IC50 (uM) (15 uM ATP) | CK2: IC50 (uM) (20 um ATP) |
|---|---|---|
| 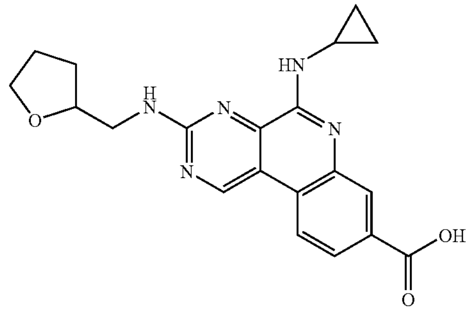 | | |
| 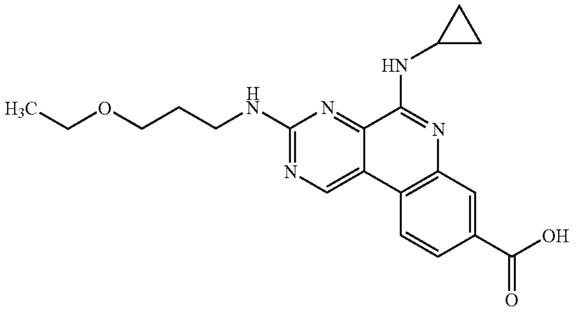 | | |
TABLE 17
| Structure | CK2: IC50 (uM) (15uMATP) | CK2: IC50(uM) (20uM ATP) |
|---|---|---|
| 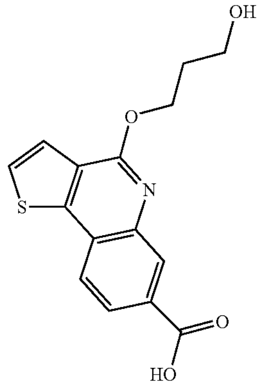 | 0.995 | 1.2 |
| 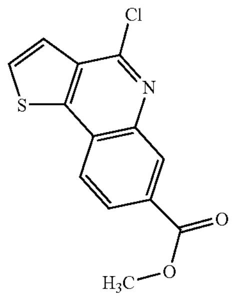 | | |

TABLE 17-continued
| Structure | CK2: IC50 (uM) (15uMATP) | CK2: IC50(uM) (20uM ATP) |
|---|---|---|
| 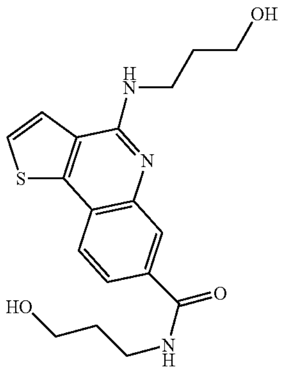 | | |
| 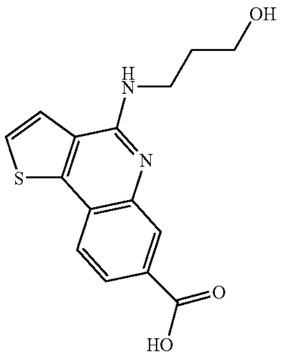 | 0.748 | 0.67 |
| 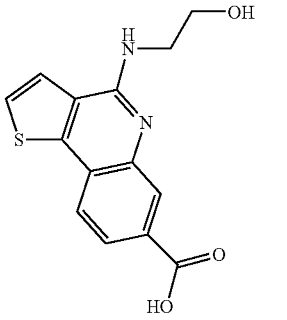 | 1.258 | 1.1 |
| 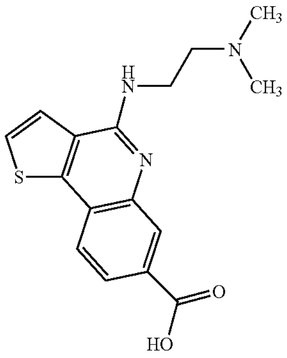 | 0.102 | 0.277 |

TABLE 17-continued
| Structure | CK2: IC50 (uM) (15uMATP) | CK2: IC50(uM) (20uM ATP) |
|---|---|---|
| 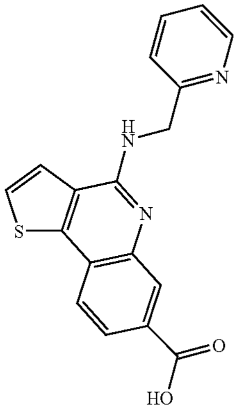 | 0.622 | 0.872 |
| 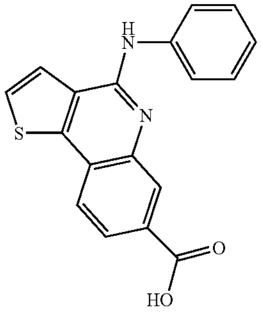 | 0.092 | 0.31 |
| 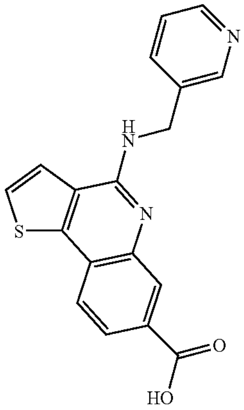 | 0.367 | 0.9 |
| 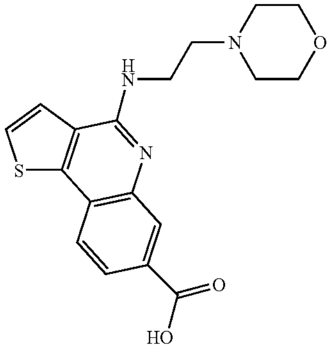 | 0.922 | 1.22 |

TABLE 17-continued
| Structure | CK2: IC50 (uM) (15uMATP) | CK2: IC50(uM) (20uM ATP) |
|---|---|---|
| 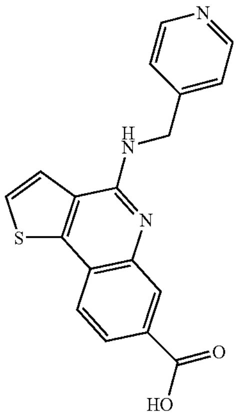 | 0.168 | 0.518 |
| 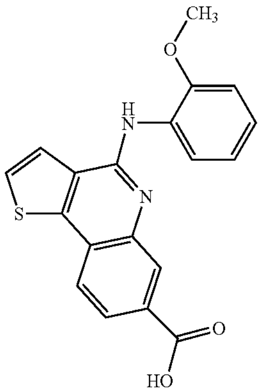 | 0.171 | 0.55 |
| 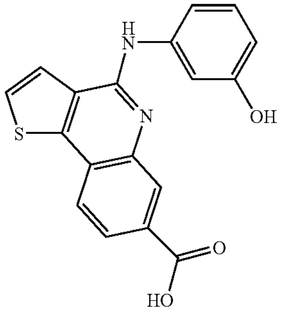 | 0.507 | 0.369 |
| 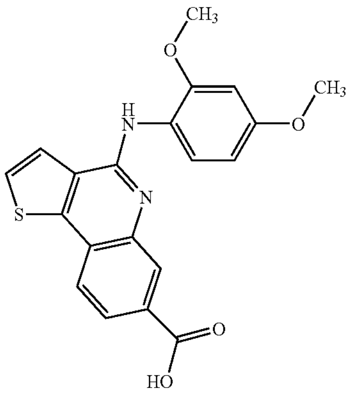 | 0.771 | 2 |

TABLE 17-continued
| Structure | CK2: IC50 (uM) (15uMATP) | CK2: IC50(uM) (20uM ATP) |
|---|---|---|
| 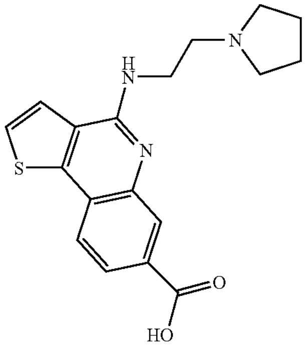 | 0.231 | 0.28 |
| 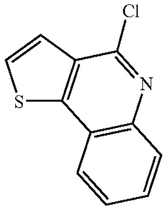 | | |
| 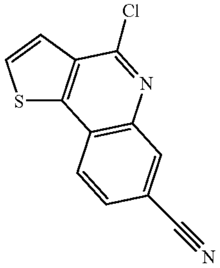 | | |
| 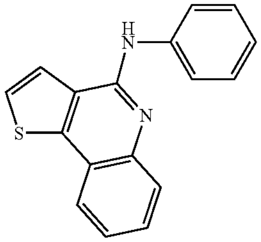 | | |
| 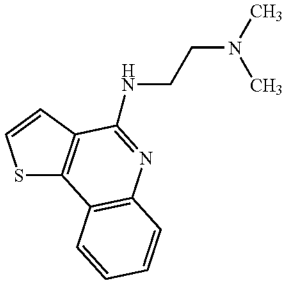 | | |

TABLE 17-continued
| Structure | CK2: IC50 (uM) (15uMATP) | CK2: IC50(uM) (20uM ATP) |
|---|---|---|
| 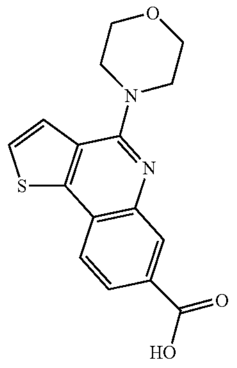 | | |
| 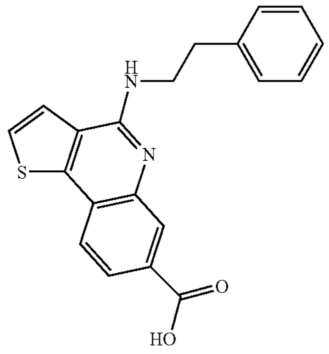 | | |
| 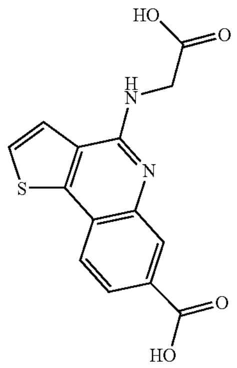 | | |
| 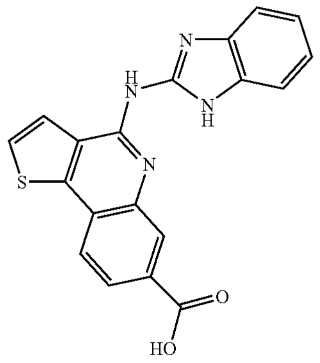 | | |

TABLE 17-continued
| Structure | CK2: IC50 (uM) (15uMATP) | CK2: IC50(uM) (20uM ATP) |
|---|---|---|
| 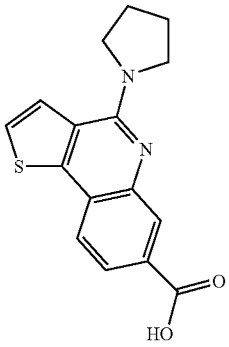 | | |
| 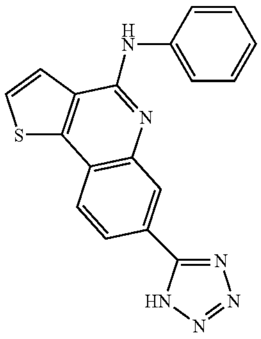 | 0.096 | 0.189 |
| 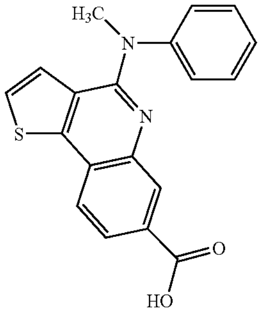 | | 1.5 |
| 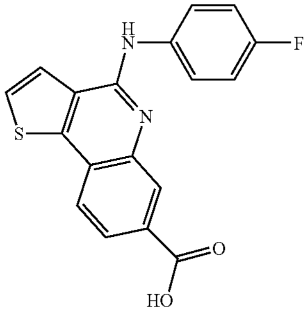 | 0.219 | 0.31 |

TABLE 17-continued
| Structure | CK2: IC50 (uM) (15uMATP) | CK2: IC50(uM) (20uM ATP) |
|---|---|---|
| 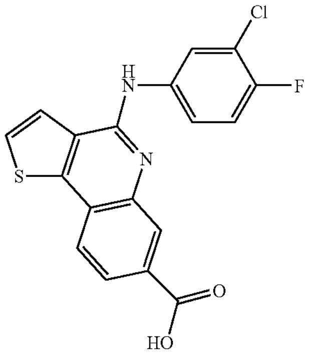 | | 0.15 |
| 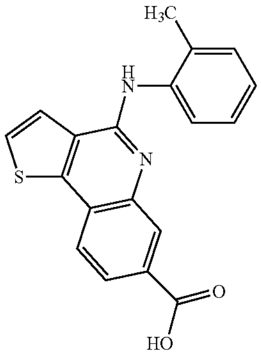 | | 1.1 |
| 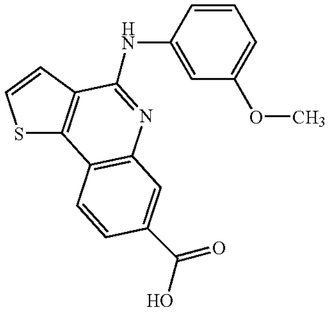 | | 0.12 |
| 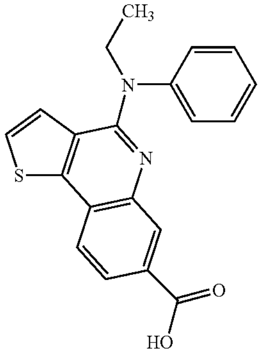 | | |

TABLE 17-continued
| Structure | CK2: IC50 (uM) (15uMATP) | CK2: IC50(uM) (20uM ATP) |
|---|---|---|
| 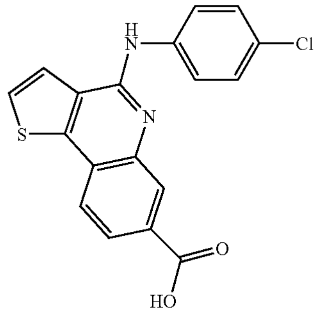 | | 0.21 |
| 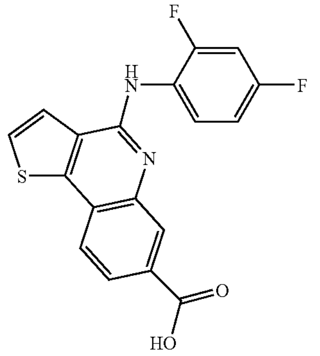 | | 0.67 |
| 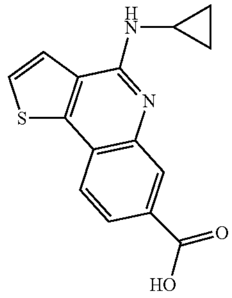 | | 0.97 |
| 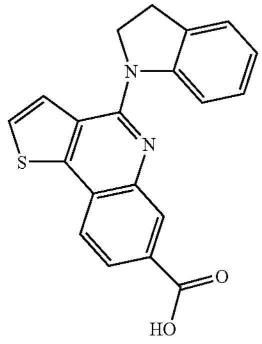 | 0.32 | 0.58 |

TABLE 17-continued
| Structure | CK2: IC50 (uM) (15uMATP) | CK2: IC50(uM) (20uM ATP) |
|---|---|---|
| 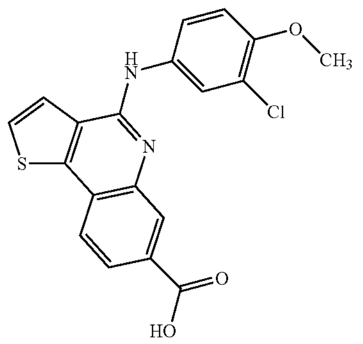 | 0.131 | 0.43 |
| 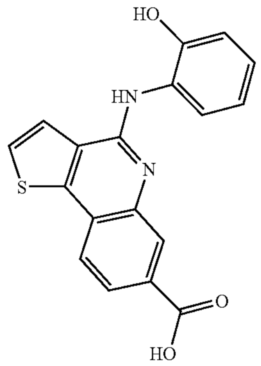 | 0.257 | 0.82 |
| 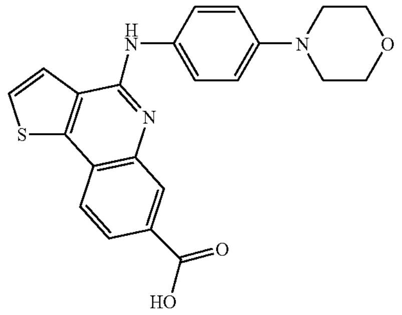 | 0.666 | 1.17 |
| 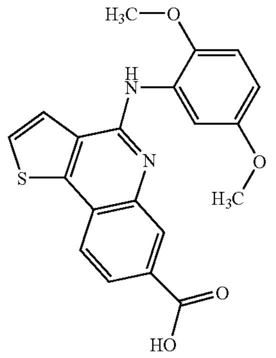 | 0.238 | 0.431 |

TABLE 17-continued
| Structure | CK2: IC50 (uM) (15uMATP) | CK2: IC50(uM) (20uM ATP) |
|---|---|---|
| 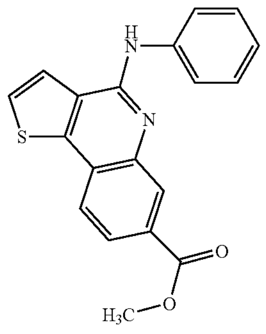 | | |
| 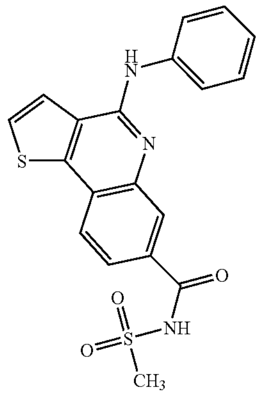 | | |
| 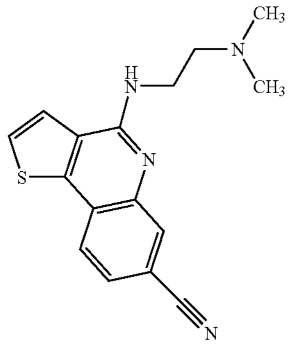 | | |
| 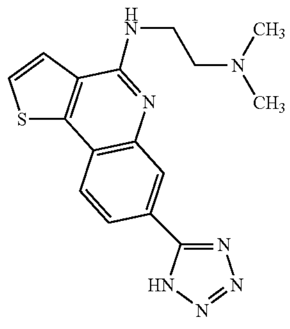 | 0.252 | 0.31 |

TABLE 17-continued
| Structure | CK2: IC50 (uM) (15uMATP) | CK2: IC50(uM) (20uM ATP) |
|---|---|---|
| 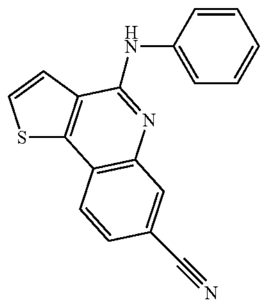 | | |
| 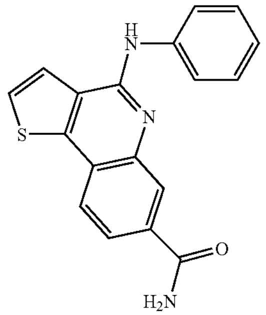 | | |
| 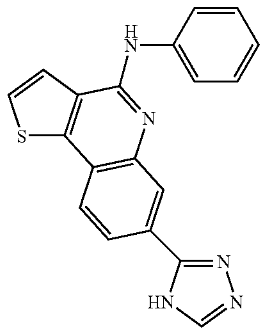 | | |
| 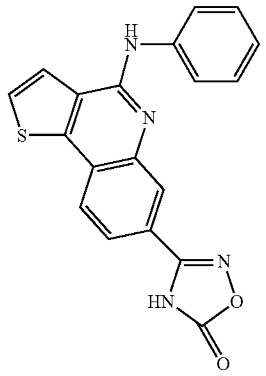 | | |

TABLE 17-continued
| Structure | CK2: IC50 (uM) (15uMATP) | CK2: IC50(uM) (20uM ATP) |
|---|---|---|
| 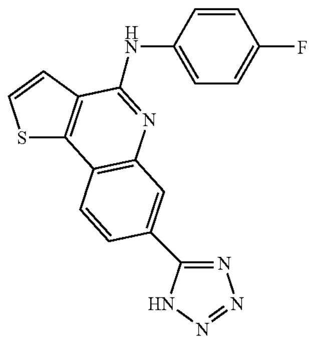 | 0.371 | 0.372 |
| 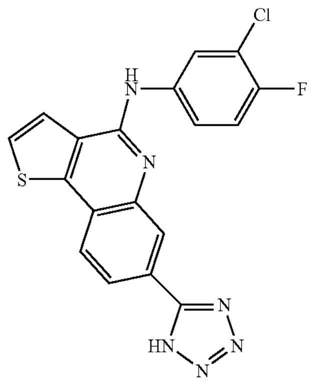 | 0.194 | 0.382 |
| 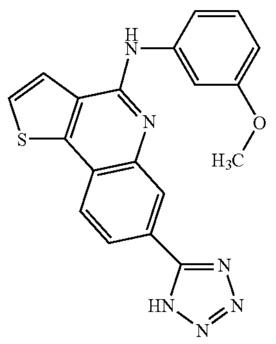 | 0.172 | 0.3 |
| 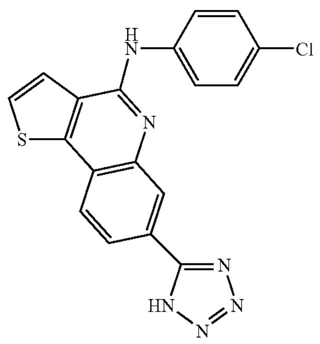 | 0.233 | 0.407 |

TABLE 17-continued
| Structure | CK2: IC50 (uM) (15uMATP) | CK2: IC50(uM) (20uM ATP) |
|---|---|---|
| 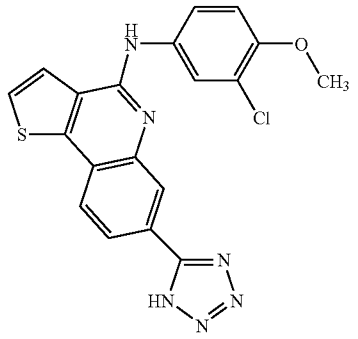 | 0.256 | 0.462 |
| 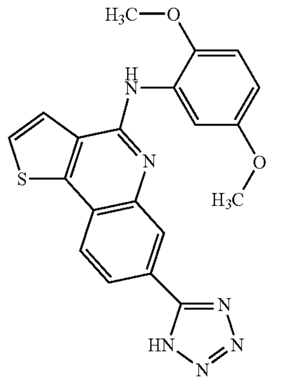 | 0.358 | 10 |
| 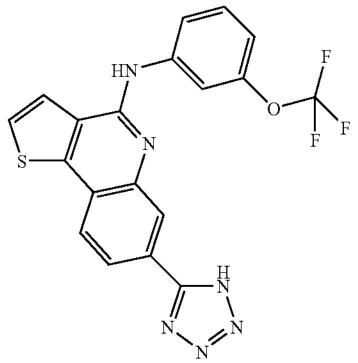 | 0.611 | 0.392 |
| 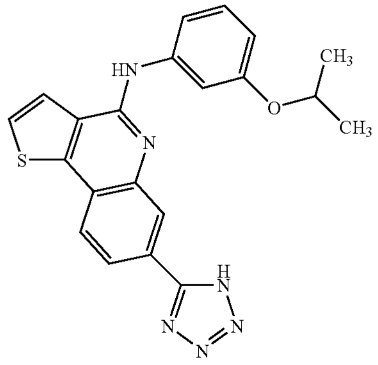 | 0.42 | 0.27 |

TABLE 17-continued
| Structure | CK2: IC50 (uM) (15uMATP) | CK2: IC50(uM) (20uM ATP) |
|---|---|---|
| 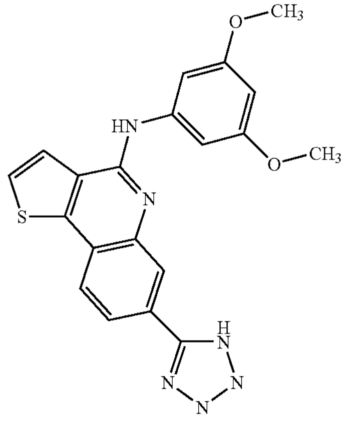 | 0.348 | 0.35 |
| 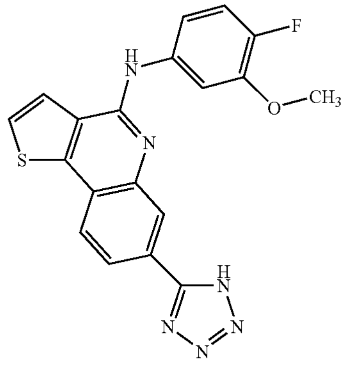 | 0.812 | 0.89 |
| 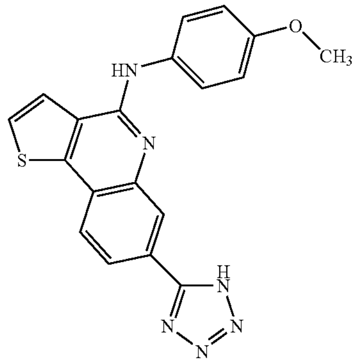 | | |
| 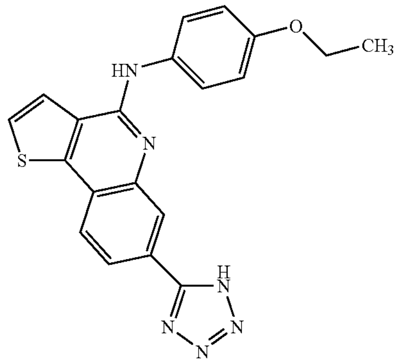 | | |

TABLE 17-continued
| Structure | CK2: IC50 (uM) (15uMATP) | CK2: IC50(uM) (20uM ATP) |
|---|---|---|
| 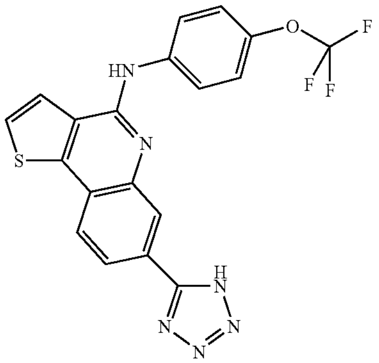 | | |
| 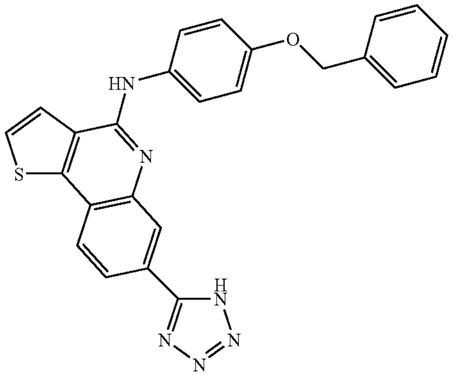 | | |
| 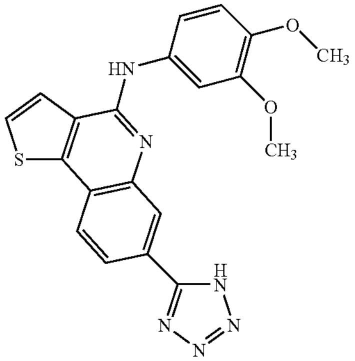 | | |
| 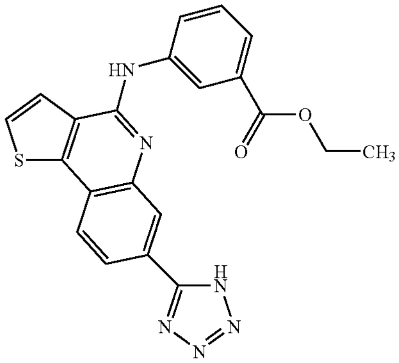 | | |

TABLE 17-continued
| Structure | CK2: IC50 (uM) (15uMATP) | CK2: IC50(uM) (20uM ATP) |
|---|---|---|
| 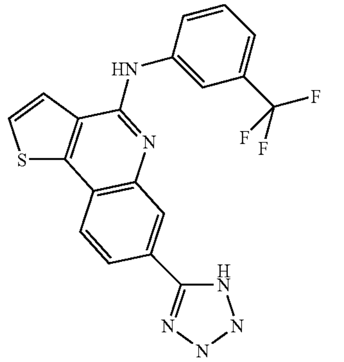 | 0.458 | 0.406 |
| 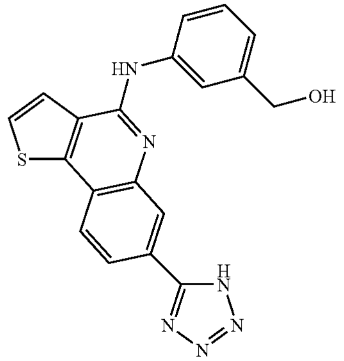 | 0.154 | 0.216 |
| 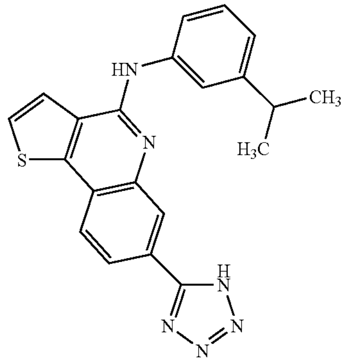 | | |
| 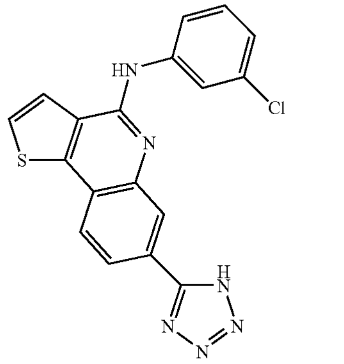 | 0.129 | 0.181 |

TABLE 17-continued
| Structure | CK2: IC50 (uM) (15uMATP) | CK2: IC50(uM) (20uM ATP) |
|---|---|---|
| 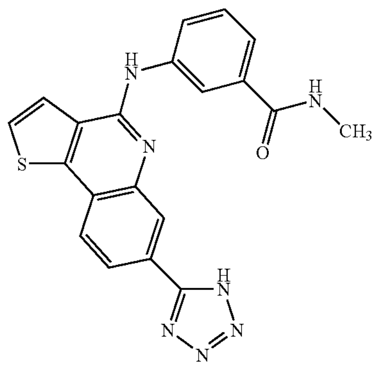 | 0.171 | 0.283 |
| 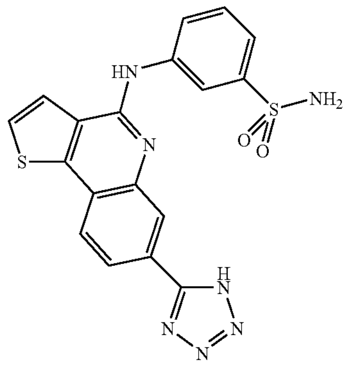 | 0.198 | 0.268 |
| 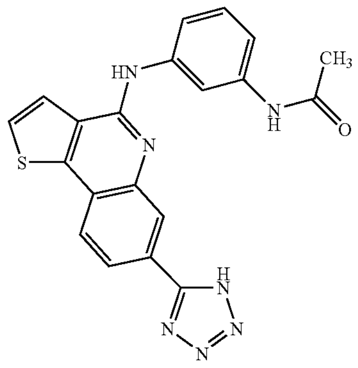 | 0.485 | 0.524 |
| 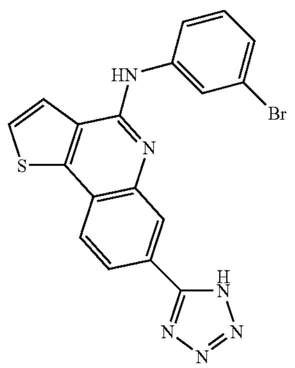 | 0.122 | 0.14 |

TABLE 17-continued
| Structure | CK2: IC50 (uM) (15uMATP) | CK2: IC50(uM) (20uM ATP) |
|---|---|---|
| 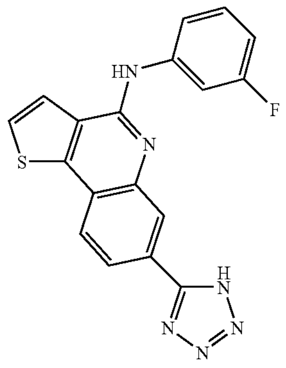 | 0.075 | 0.096 |
| 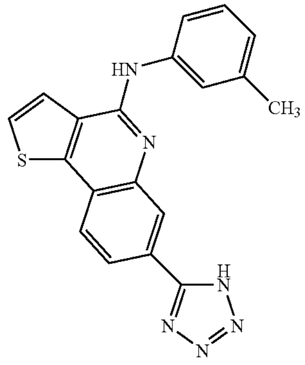 | 0.235 | 0.375 |
| 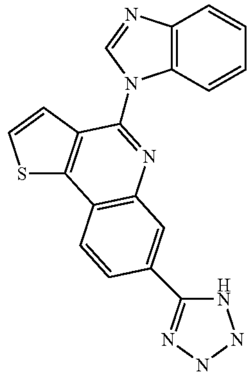 | | |
| 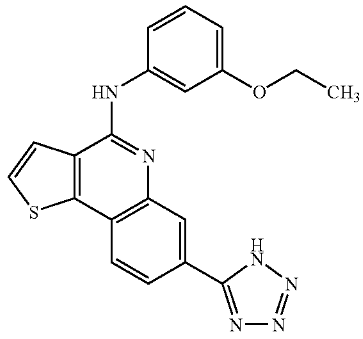 | 0.346 | 0.423 |

TABLE 17-continued
| Structure | CK2: IC50 (uM) (15uMATP) | CK2: IC50(uM) (20uM ATP) |
|---|---|---|
| 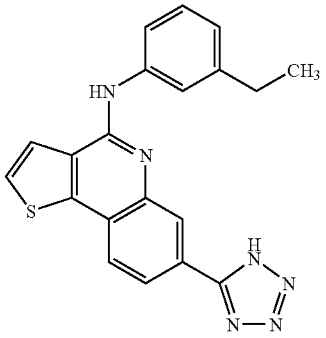 | 0.358 | 0.509 |
| 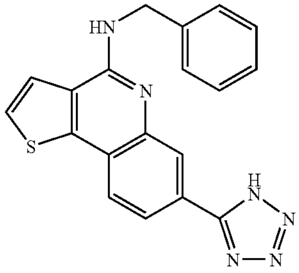 | | |
| 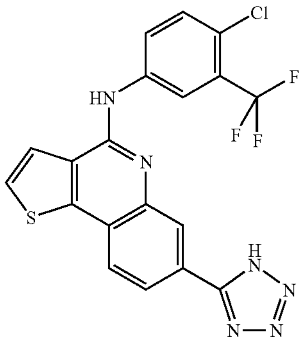 | | |
| 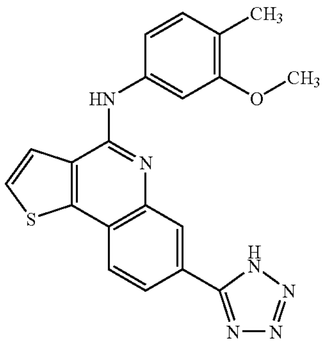 | | |

TABLE 17-continued
| Structure | CK2: IC50 (uM) (15uMATP) | CK2: IC50(uM) (20uM ATP) |
|---|---|---|
| 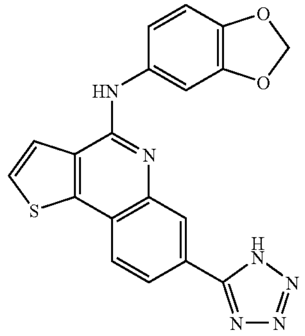 | | |
| 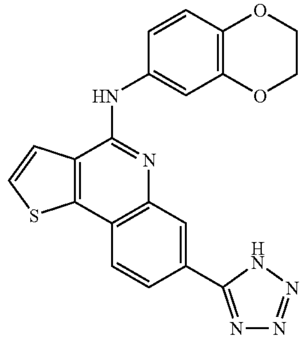 | 0.29 | 0.63 |
| 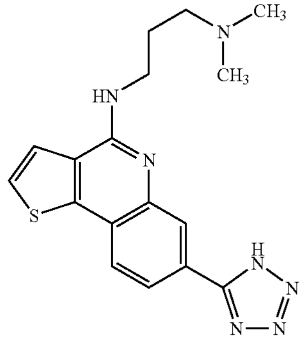 | | |
| 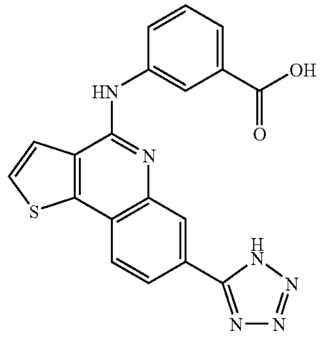 | 0.135 | |

TABLE 17-continued
| Structure | CK2: IC50 (uM) (15uMATP) | CK2: IC50(uM) (20uM ATP) |
| --- | --- | --- |
| 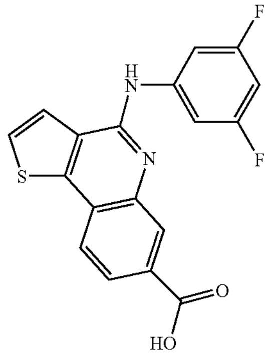 | 0.07 | |
| 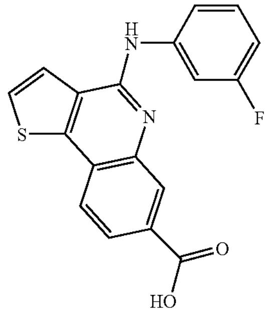 | 0.068 | |
| 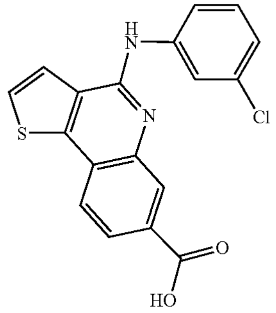 | 0.032 | |
| 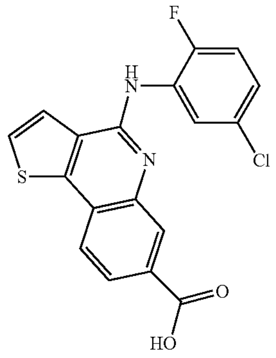 | 0.07 | |

TABLE 17-continued
| Structure | CK2: IC50 (uM) (15uMATP) | CK2: IC50(uM) (20uM ATP) |
|---|---|---|
| 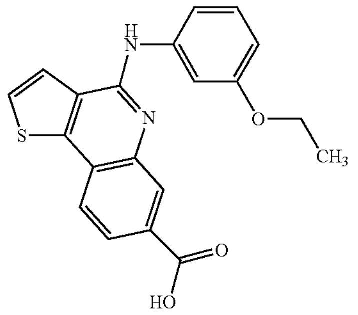 | 0.126 | |
| 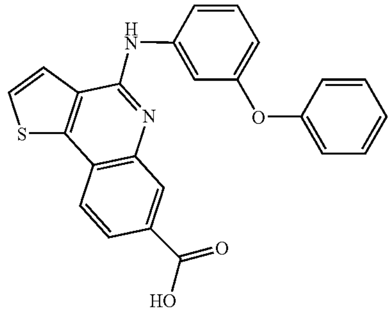 | 0.395 | |
| 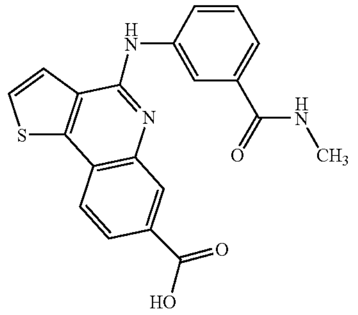 | 0.129 | |
| 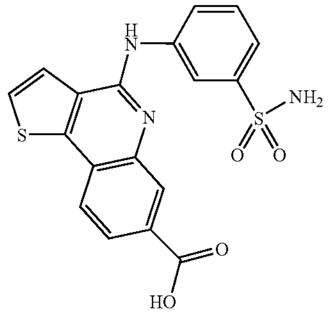 | 0.103 | |

TABLE 17-continued
| Structure | CK2: IC50 (uM) (15uMATP) | CK2: IC50(uM) (20uM ATP) |
|---|---|---|
| 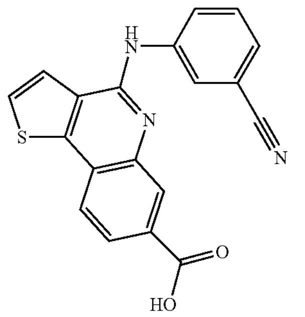 | 0.081 | |
| 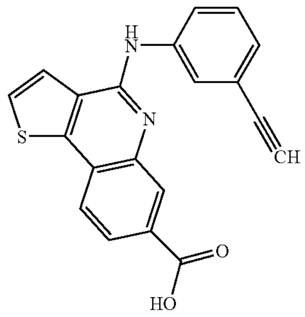 | 0.028 | |
| 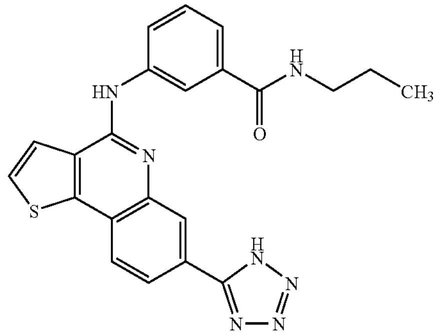 | 0.38 | |
| 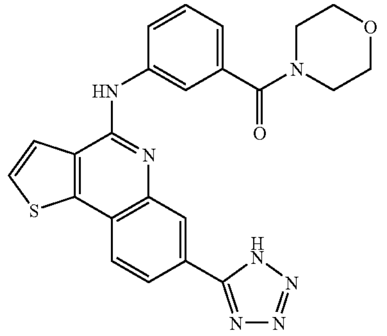 | 0.502 | |

TABLE 17-continued
| Structure | CK2: IC50 (uM) (15uMATP) | CK2: IC50(uM) (20uM ATP) |
|---|---|---|
| 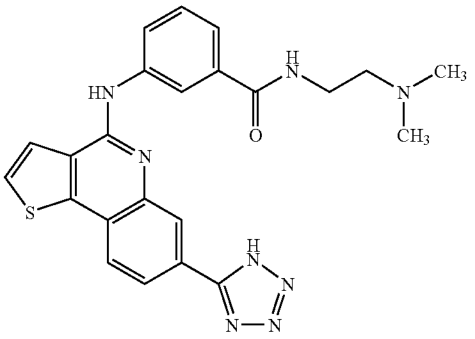 | 0.549 | |
| 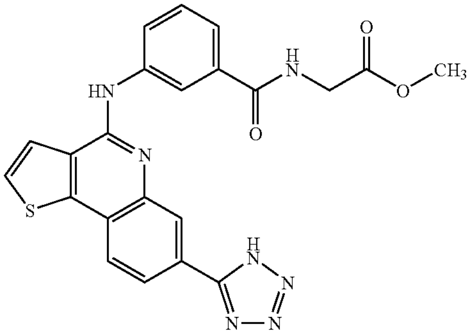 | 0.24 | |
| 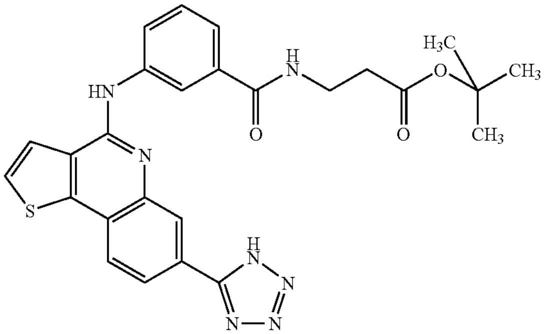 | | |
| 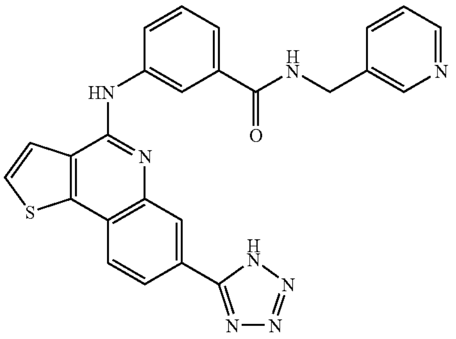 | 0.363 | |

TABLE 17-continued
| Structure | CK2: IC50 (uM) (15uMATP) | CK2: IC50(uM) (20uM ATP) |
| --- | --- | --- |
| 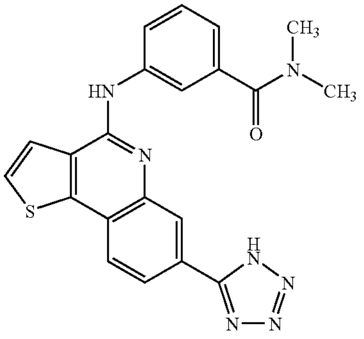 | 0.318 | |
| 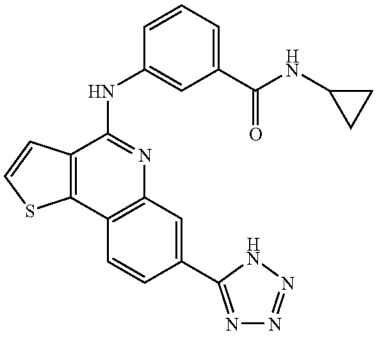 | 0.237 | |
| 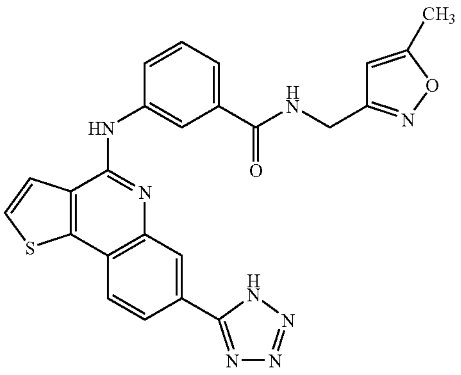 | 0.288 | |
| 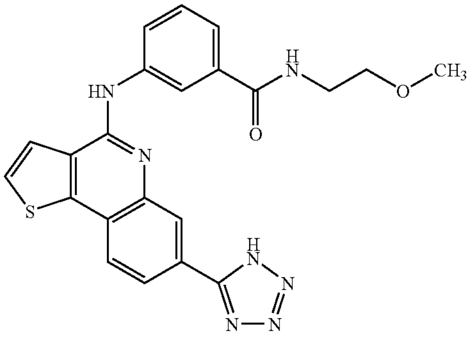 | 0.251 | |

TABLE 17-continued
| Structure | CK2: IC50 (uM) (15uMATP) | CK2: IC50(uM) (20uM ATP) |
|---|---|---|
| 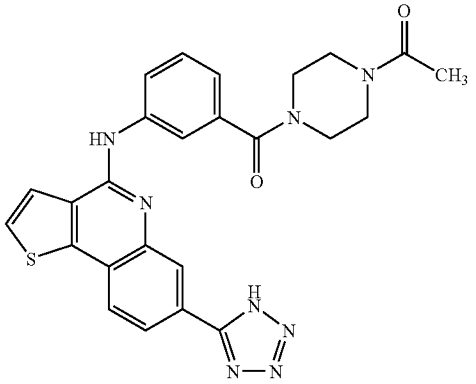 | 0.303 | |
| 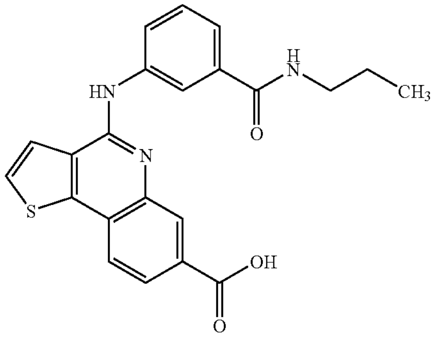 | 0.224 | |
| 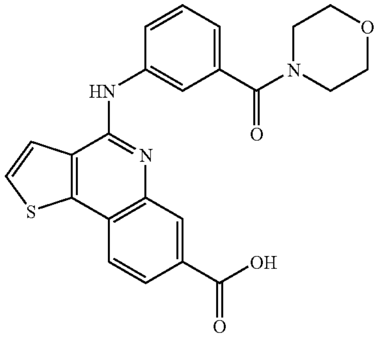 | 0.307 | |
| 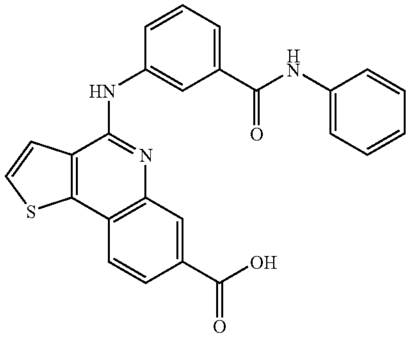 | | |

TABLE 17-continued
| Structure | CK2: IC50 (uM) (15uMATP) | CK2: IC50(uM) (20uM ATP) |
|---|---|---|
| 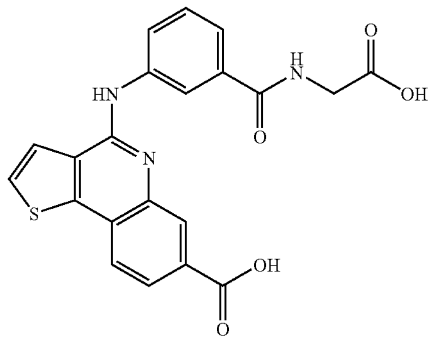 | 0.192 | |
| 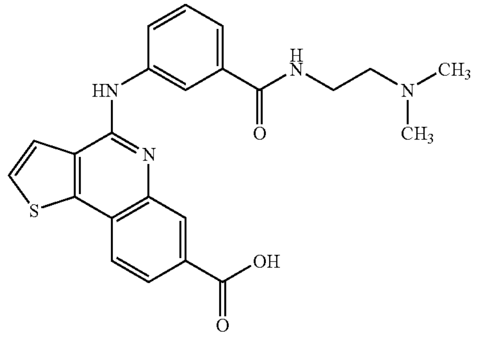 | 0.366 | |
| 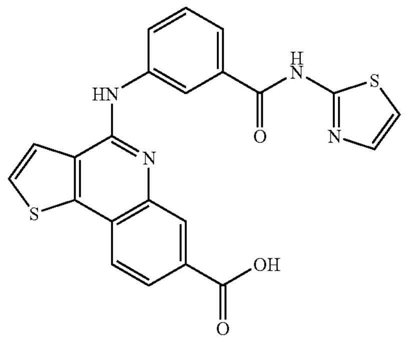 | | |
| 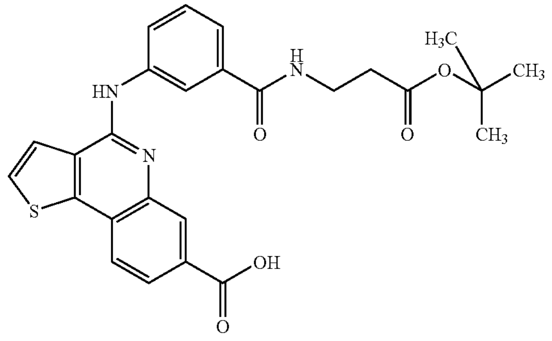 | | |

TABLE 17-continued
| Structure | CK2: IC50 (uM) (15uMATP) | CK2: IC50(uM) (20uM ATP) |
|---|---|---|
| 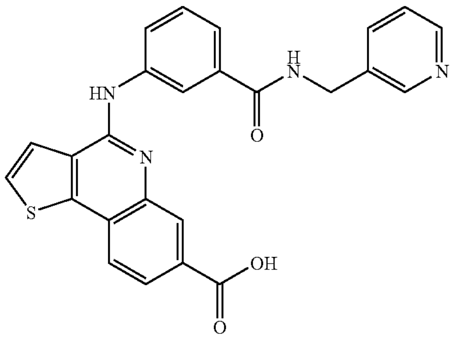 | | |
| 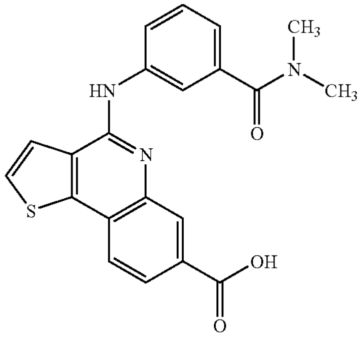 | | |
| 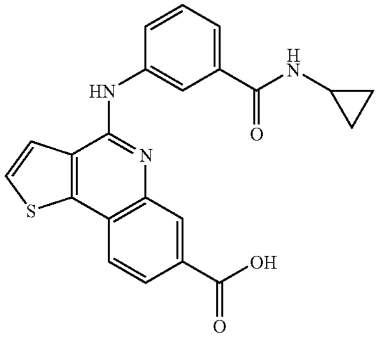 | 0.221 | |
| 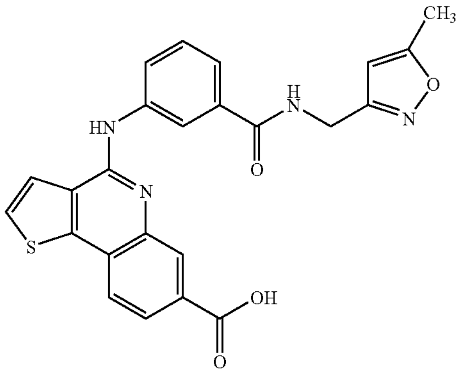 | | |

TABLE 17-continued
| Structure | CK2: IC50 (uM) (15uMATP) | CK2: IC50(uM) (20uM ATP) |
|---|---|---|
| 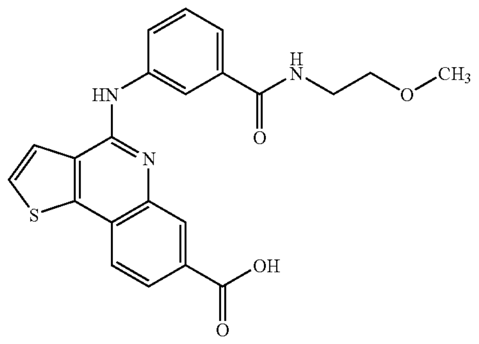 | | |
| 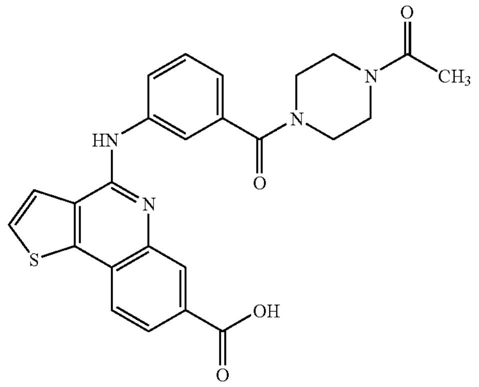 | | |
| 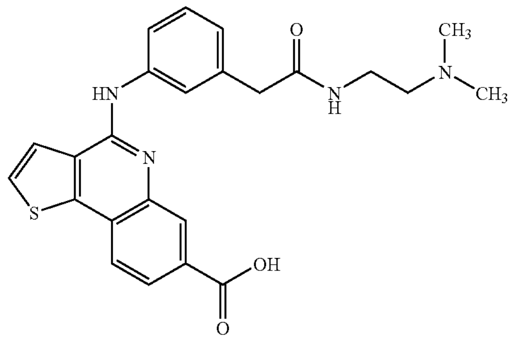 | | |
| 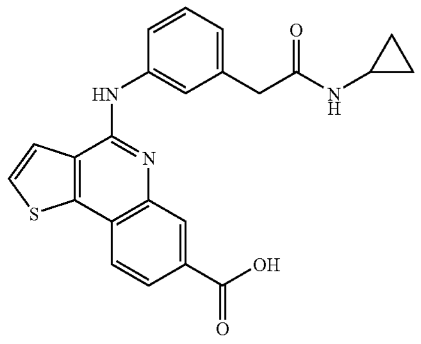 | | |

TABLE 17-continued
| Structure | CK2: IC50 (uM) (15uMATP) | CK2: IC50(uM) (20uM ATP) |
|---|---|---|
| 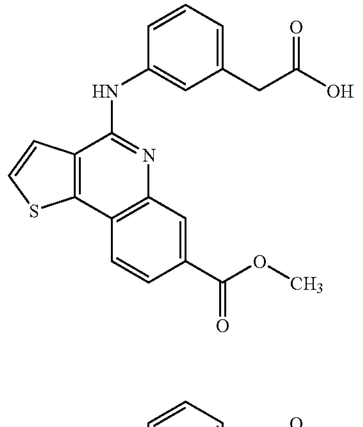 | | |
| 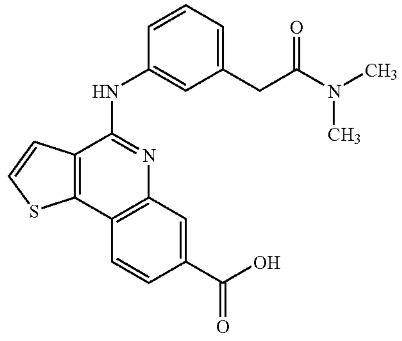 | | |
| 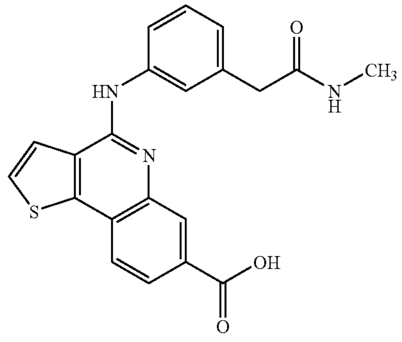 | 0.137 | |
| 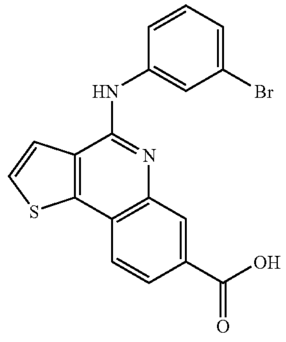 | 0.187 | |

TABLE 17-continued
| Structure | CK2: IC50 (uM) (15uMATP) | CK2: IC50(uM) (20uM ATP) |
|---|---|---|
| 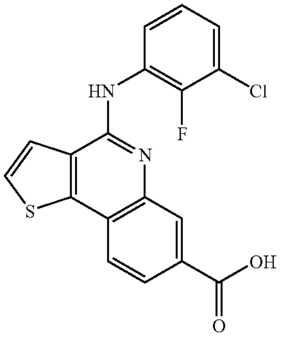 | 0.335 | |
| 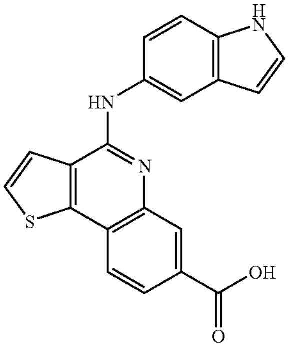 | 0.156 | |
| 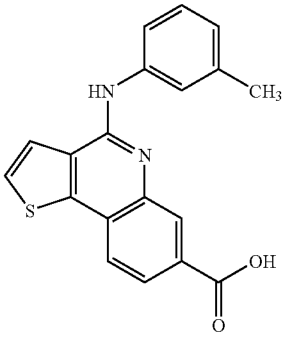 | 0.09 | |
| 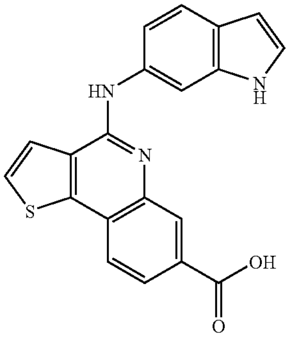 | 0.121 | |

TABLE 17-continued
| Structure | CK2: IC50 (uM) (15uMATP) | CK2: IC50(uM) (20uM ATP) |
|---|---|---|
| 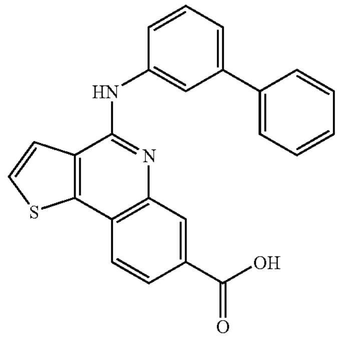 | | |
| 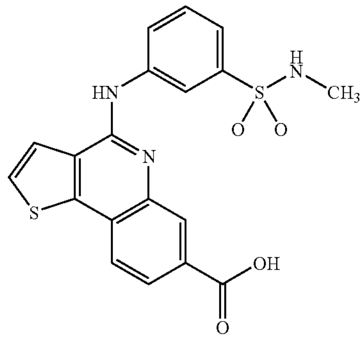 | 0.281 | |
| 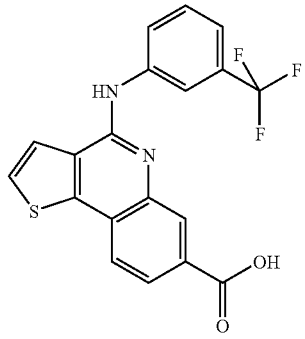 | 0.061 | |
| 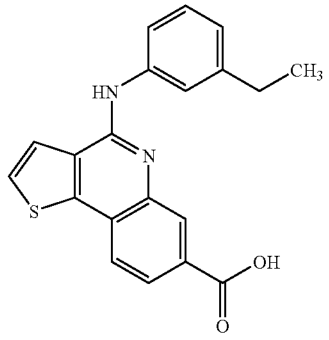 | 0.242 | |

TABLE 17-continued
| Structure | CK2: IC50 (uM) (15uMATP) | CK2: IC50(uM) (20uM ATP) |
|---|---|---|
| 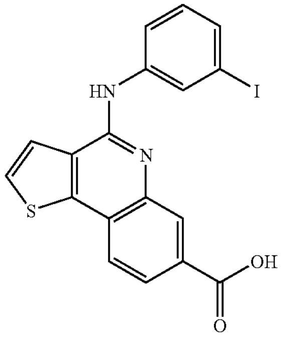 | 0.091 | |
| 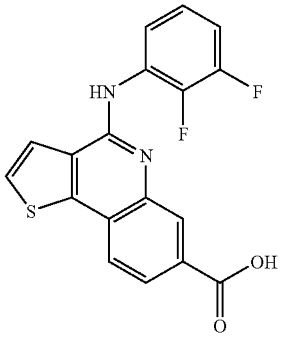 | 0.256 | |
| 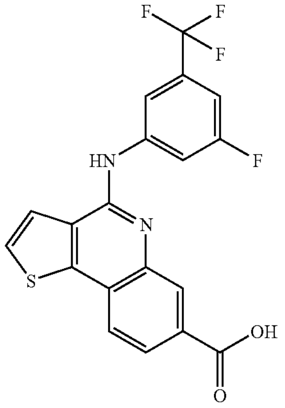 | 0.156 | |
| 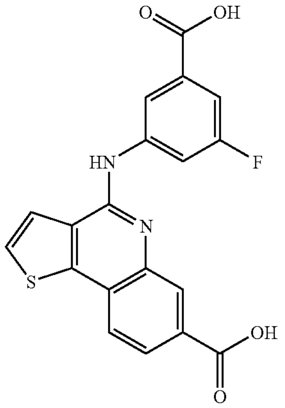 | 0.127 | |

TABLE 17-continued
| Structure | CK2: IC50 (uM) (15uMATP) | CK2: IC50(uM) (20uM ATP) |
|---|---|---|
| 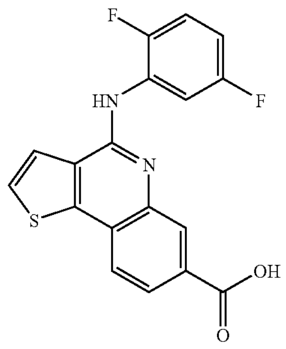 | 0.138 | |
| 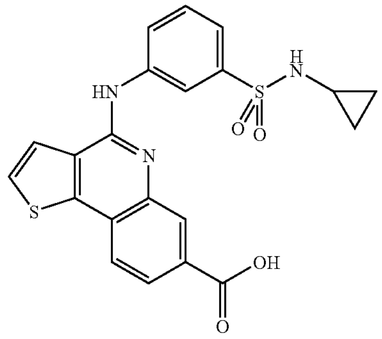 | 0.116 | |
| 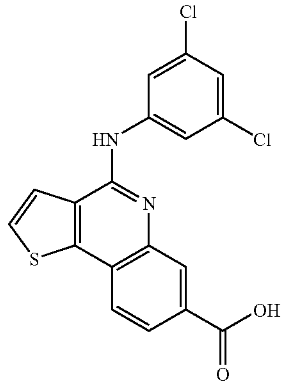 | 0.035 | |
| 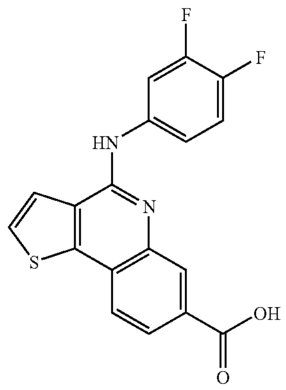 | 0.127 | |

TABLE 17-continued
| Structure | CK2: IC50 (uM) (15uMATP) | CK2: IC50(uM) (20uM ATP) |
|---|---|---|
| 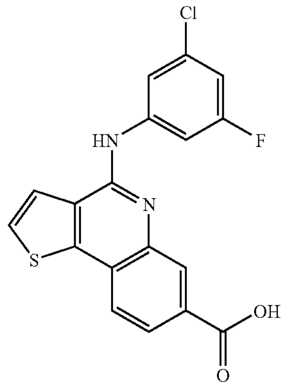 | 0.076 | |
| 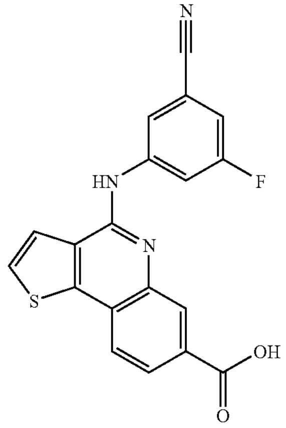 | 0.131 | |
| 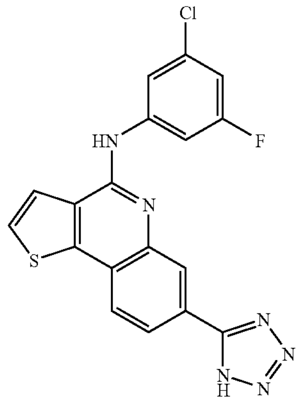 | 0.289 | |

TABLE 17-continued
| Structure | CK2: IC50 (uM) (15uMATP) | CK2: IC50(uM) (20uM ATP) |
|---|---|---|
| 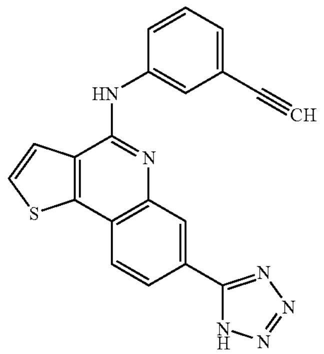 | 0.141 | |
| 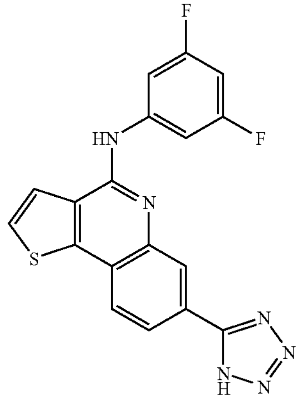 | 0.204 | |
TABLE 18
| Structure | CK2: IC50 (uM) (15 uM ATP) | CK2: IC50 (uM) (20 um ATP) |
|---|---|---|
| 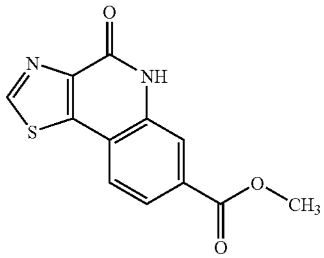 | | |
| 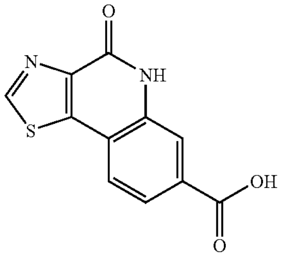 | | 4.7 |

TABLE 18-continued
| Structure | CK2: IC50 (uM) (15 uM ATP) | CK2: IC50 (uM) (20 um ATP) |
|---|---|---|
| 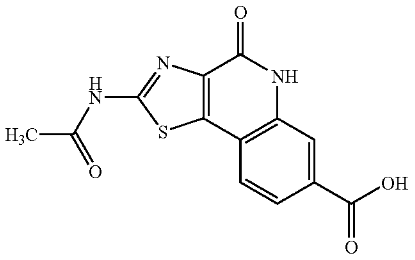 | | |
| 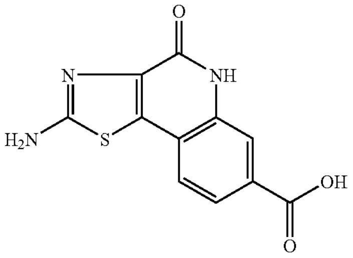 | | 3.4 |
| 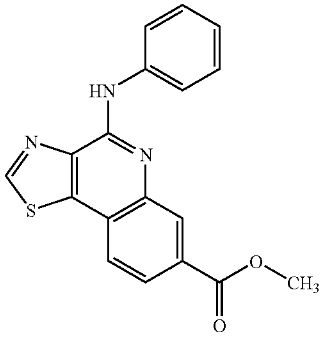 | | |
| 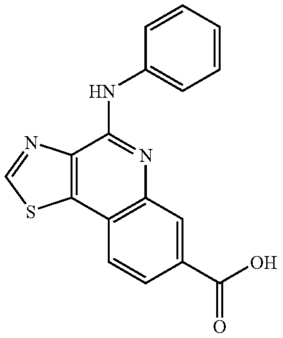 | 0.169 | 0.219 |
| 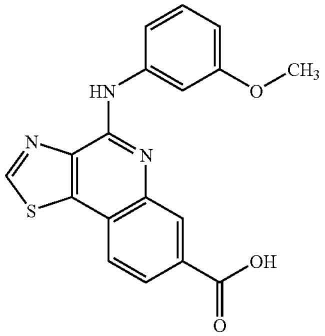 | 0.037 | |

TABLE 18-continued

| Structure | CK2: IC50 (uM) (15 uM ATP) | CK2: IC50 (uM) (20 um ATP) |
|---|---|---|
| 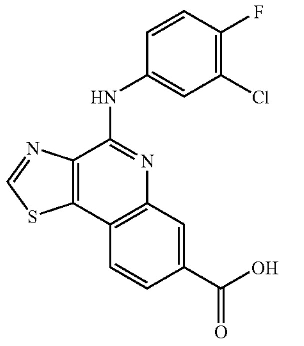 | 0.12 | |
| 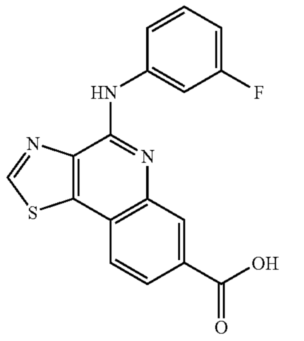 | 0.146 | |
| 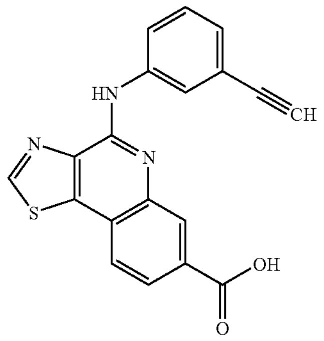 | 0.044 | |

Example 5

Cell Proliferation Modulatory Activity

A representative cell-proliferation assay protocol using Alamar Blue dye (stored at 4° C., use 20 ul per well) is described hereafter.

96-Well Plate Setup and Compound Treatment a. Split and trypsinize cells.

b. Count cells using hemocytometer.

c. Plate 4,000-5,000 cells per well in 100 μl of medium and seed into a 96-well plate according to the following plate layout. Add cell culture medium only to wells B10 to B12. Wells B1 to B9 have cells but no compound added.

| | 1 2 3 | 4 5 6 | 7 8 9 | 10 11 12 | |
|---|---|---|---|---|---|
| A | | EMPTY | | | |
| B | | NO COMPOUND ADDED | | Medium Only | |
| C | 10 nM | 100 nM | 1 uM | 10 uM | Control |
| D | 10 nM | 100 nM | 1 uM | 10 uM | Comp1 |
| E | 10 nM | 100 nM | 1 uM | 10 uM | Comp2 |
| F | 10 nM | 100 nM | 1 uM | 10 uM | Comp3 |
| G | 10 nM | 100 nM | 1 uM | 10 uM | Comp4 |
| H | | EMPTY | | | |

d. Add 100 μl of 2× drug dilution to each well in a concentration shown in the plate layout above. At the same time, add 100 μl of media into the control wells (wells B10 to B12). Total volume is 200 μl/well.

e. Incubate four (4) days at 37° C., 5% CO2 in a humidified incubator.
f. Add 20 µl Alamar Blue reagent to each well.
g. Incubate for four (4) hours at 37° C., 5% CO2 in a humidified incubator.
h. Record fluorescence at an excitation wavelength of 544 nm and emission wavelength of 590 nm using a microplate reader.

In the assays, cells are cultured with a test compound for approximately four days, the dye then is added to the cells and fluorescence of non-reduced dye is detected after approximately four hours. Different types of cells can be utilized in the assays (e.g., HCT-116 human colorectal carcinoma cells, PC-3 human prostatic cancer cells and MiaPaca human pancreatic carcinoma cells). Anti-proliferative effects of representative compounds are provided hereafter

TABLE 19A

| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 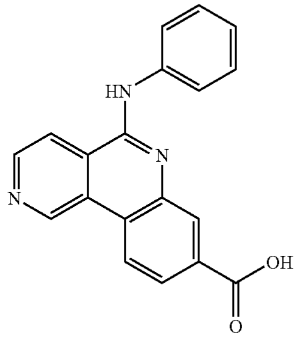 | 4.16 | 10.79 | 8.18 | 2.66 | 13.70 | 4.86 | 4.01 |
| 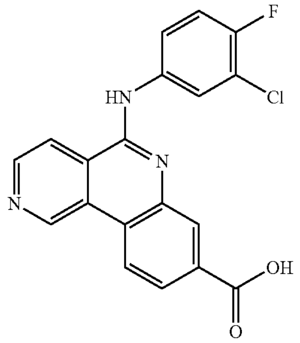 | 6.83 | 8.24 | 4.57 | 6.13 | 4.51 | 1.92 | 4.95 |
| 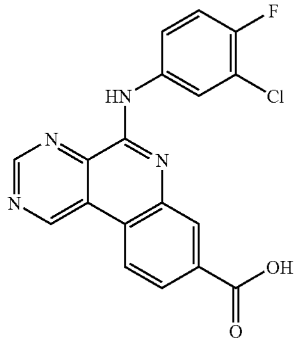 | | | | 1.11 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 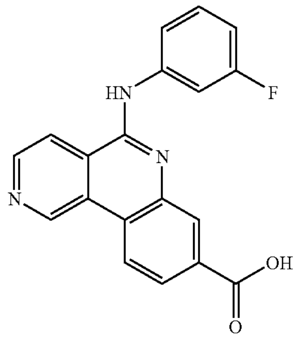 | 16.65 | | | | | | |
| 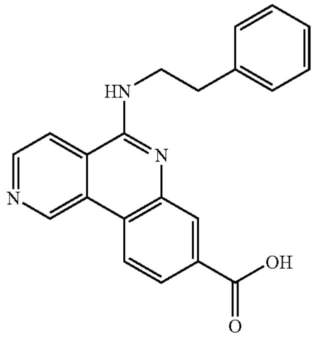 | 47.04 | 14.71 | 8.60 | | | | |
| 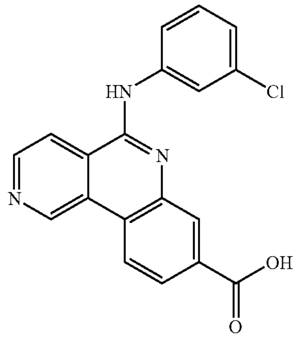 | 6.59 | 17.68 | 4.89 | 6.66 | 3.32 | 2.64 | 2.99 |
| 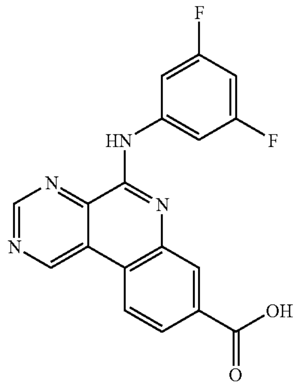 | 24.58 | 2.02 | 1.83 | 3.10 | 8.47 | 1.85 | 2.41 |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 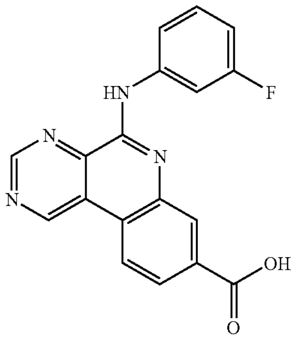 | 14.10 | 1.06 | 1.36 | 0.84 | 4.51 | 9.68 | 1.77 |
| 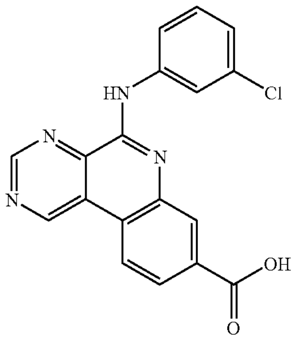 | 28.46 | 1.79 | 1.56 | 1.18 | | 7.35 | 1.13 |
| 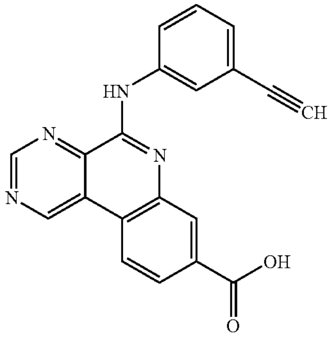 | 21.21 | 1.27 | 1.40 | 4.25 | 3.38 | 4.49 | 1.20 |
| 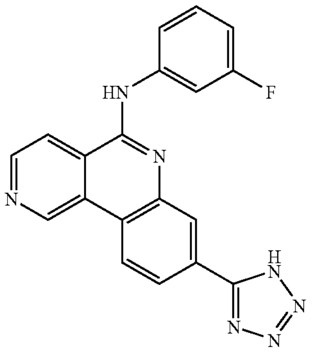 | >50 | >50 | <0.2 | >50 | | | 40.62 |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 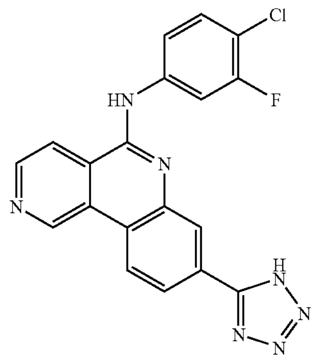 | >50 | 5.94 | 48.24 | >50 | | | >50 |
| 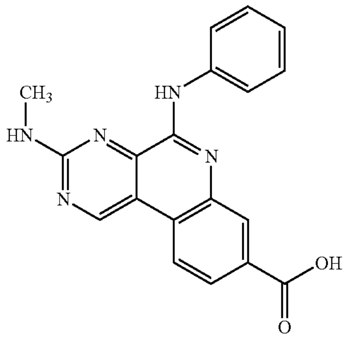 | 13.86 | 3.40 | 1.44 | 2.38 | 4.97 | 0.73 | 1.68 |
| 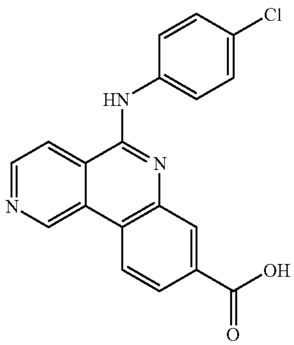 | 9.74 | 0.76 | 7.39 | 3.79 | 5.46 | 3.74 | 8.65 |
| 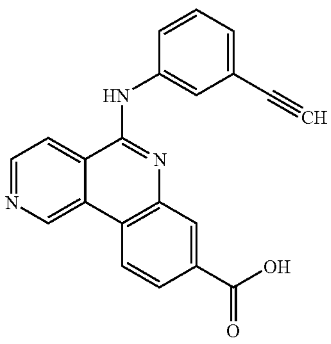 | 30.24 | 1.43 | 17.08 | 11.80 | 4.28 | 5.59 | 3.33 |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 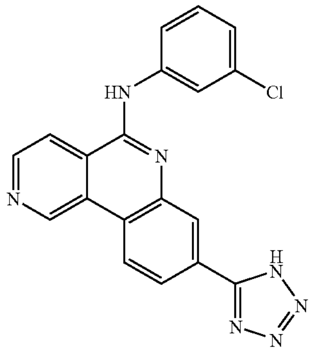 | >50 | >50 | 37.38 | >50 | | | 31.21 |
| 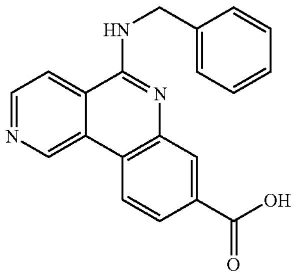 | | | | 37.98 | | | |
| 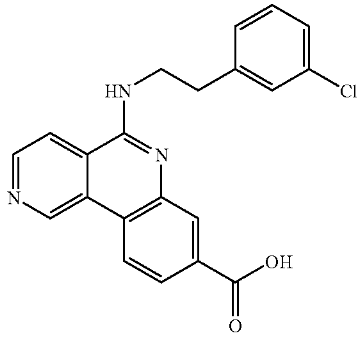 | 32.50 | 47.63 | 13.91 | 14.22 | | | 9.18 |
| 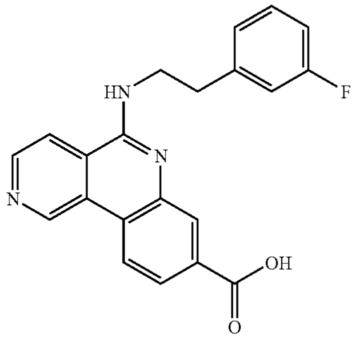 | 47.17 | >50 | 10.30 | 5.83 | | | 8.11 |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 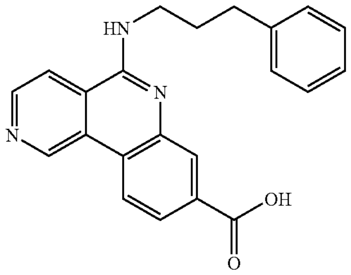 | >50 | >50 | 10.43 | 7.66 | | | 7.17 |
| 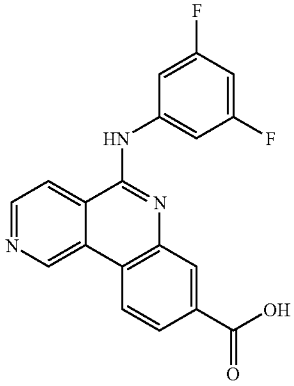 | 27.37 | 1.89 | 10.76 | 11.04 | 6.35 | 4.81 | 3.26 |
| 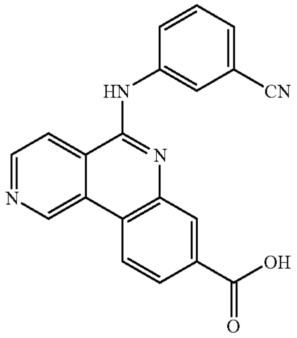 | >50 | 40.95 | 15.51 | 28.65 | | | 9.15 |
| 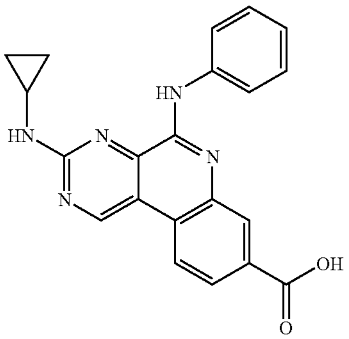 | | | | 0.73 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 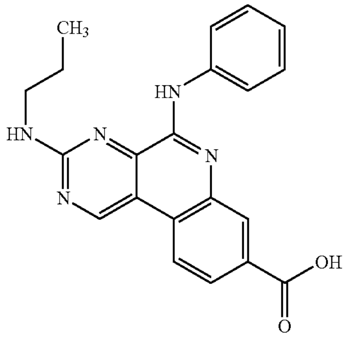 | | | | 18.16 | | | |
| 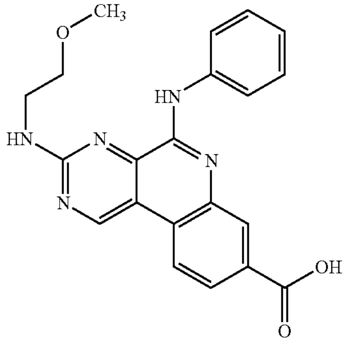 | | | | 24.45 | | | |
| 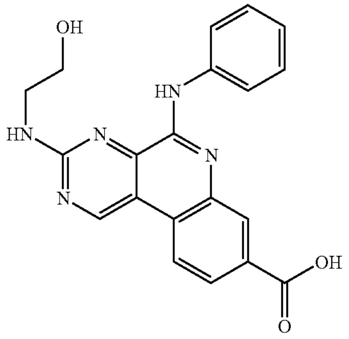 | | | | >50 | | | |
| 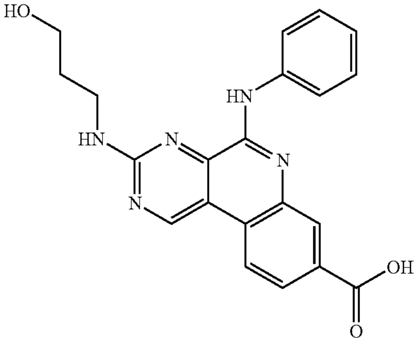 | | | | 48.21 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 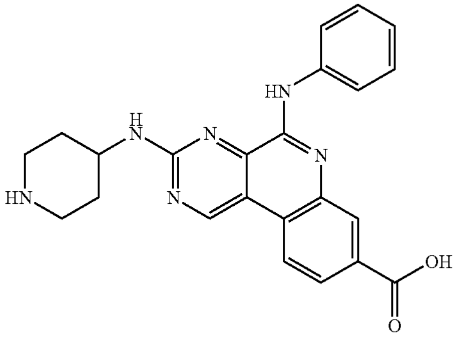 | | | | >50 | | | |
| 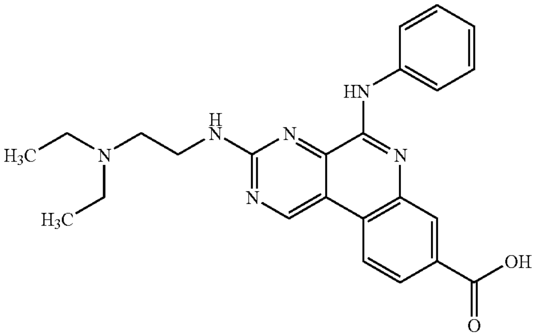 | | | | 10.51 | | | |
| 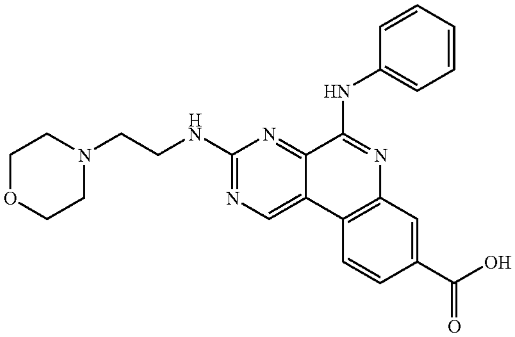 | | | | 2.44 | | | |
| 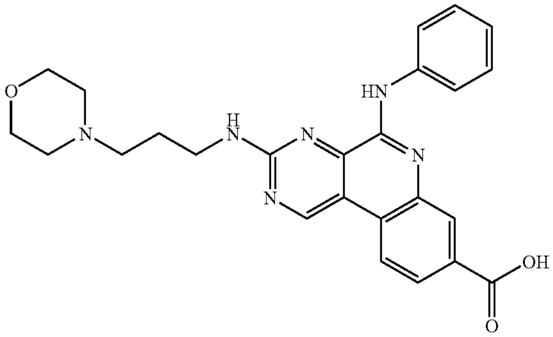 | | | | >50 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 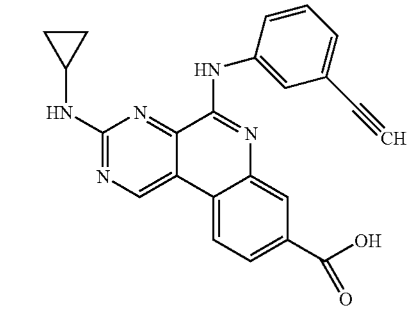 | | | | 4.90 | | | |
| 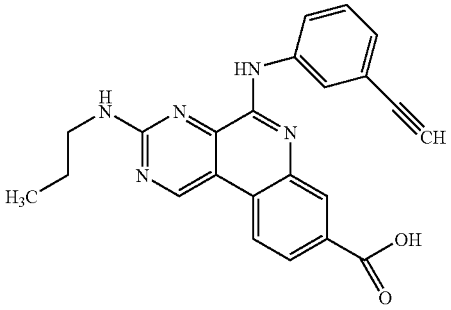 | | | | 10.44 | | | |
| 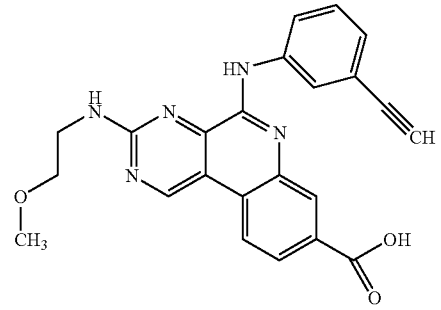 | | | | 4.74 | | | |
| 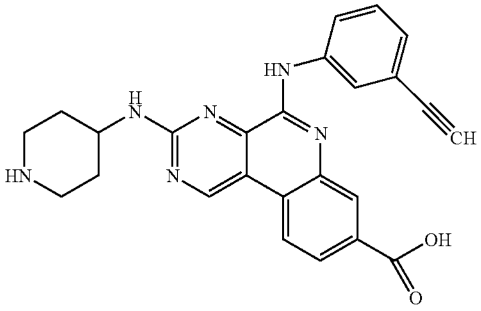 | | | | >50 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 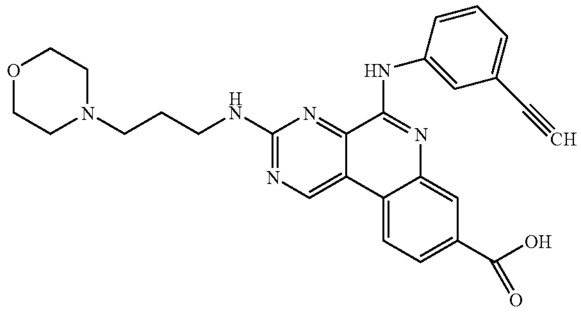 | | | | 12.45 | | | |
| 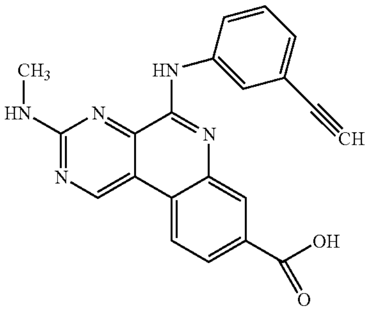 | | | | 5.21 | | | |
| 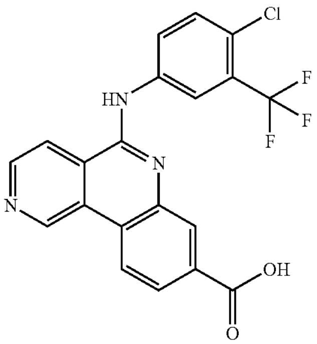 | | | | 4.43 | | | |
| 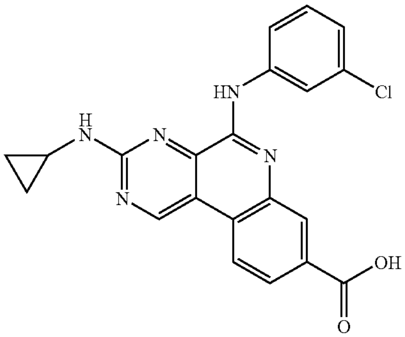 | | | | 3.93 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 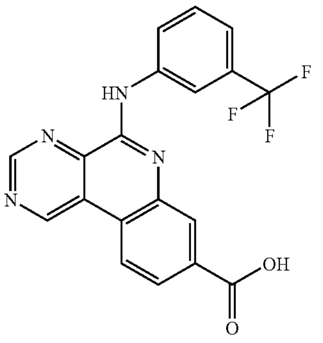 | | | | 2.93 | | | |
| 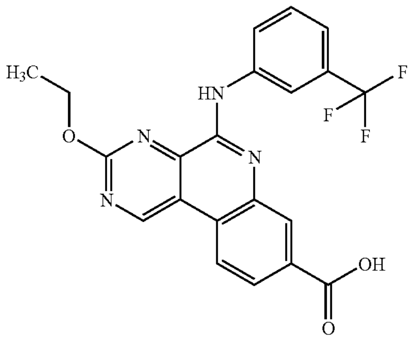 | | | | 26.52 | | | |
| 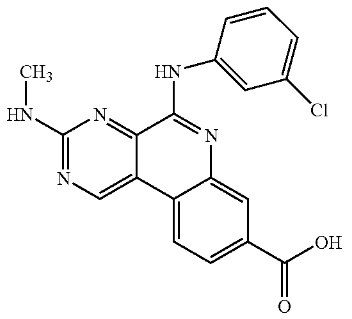 | | | | 8.28 | | | |
| 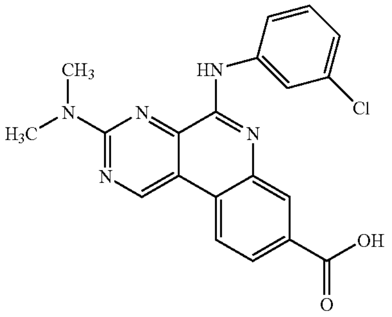 | | | | 9.82 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 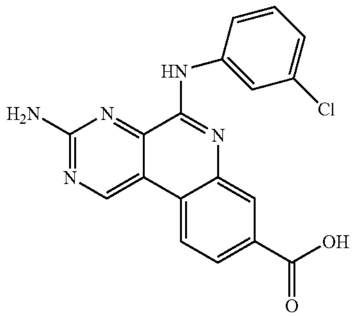 | | | | 4.12 | | | |
| 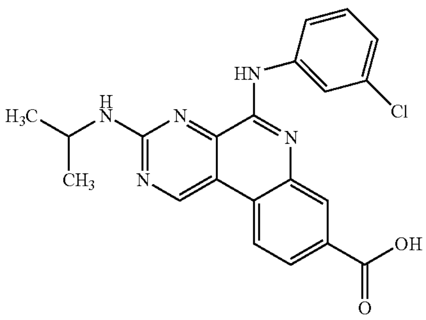 | | | | 20.77 | | | |
| 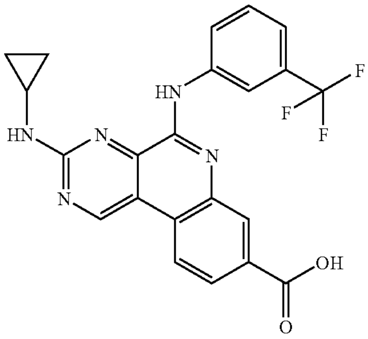 | | | | 9.19 | | | |
| 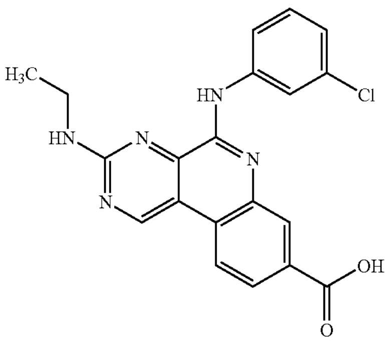 | | | | 6.87 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 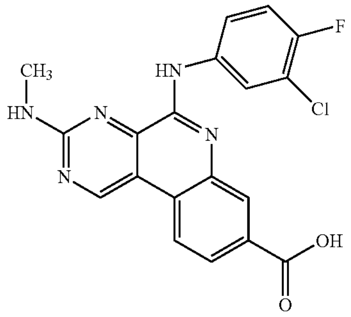 | | | | 15.77 | | | |
| 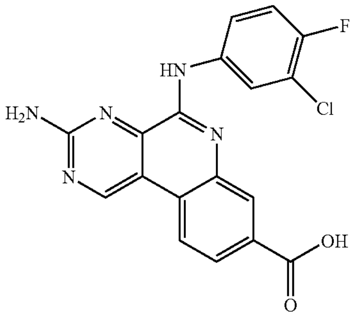 | | | | 6.53 | | | |
| 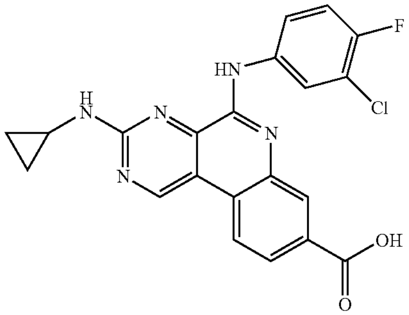 | | | | 7.12 | | | |
| 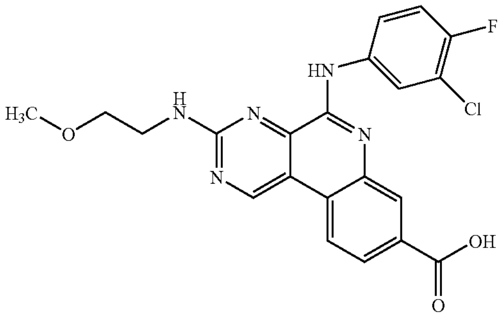 | | | | 12.63 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 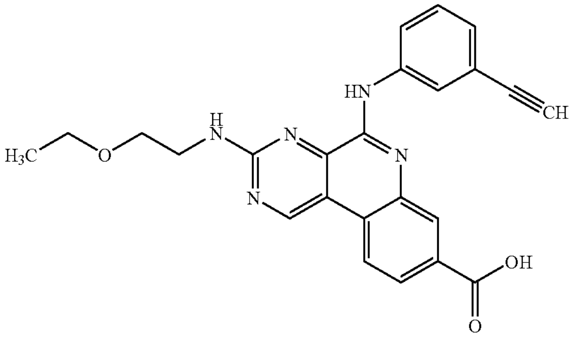 | | | | 31.58 | | | |
| 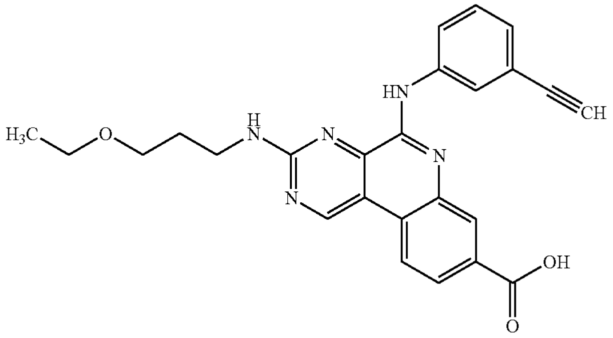 | | | | 5.22 | | | |
| 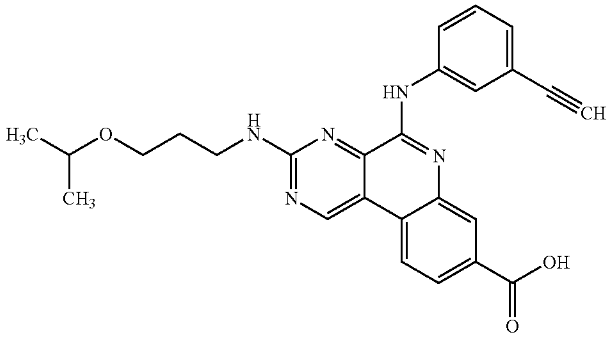 | | | | 7.05 | | | |
| 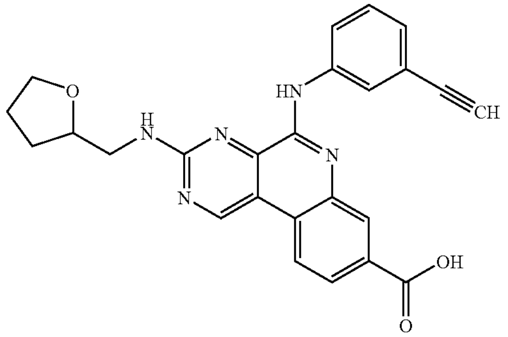 | | | | 8.38 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 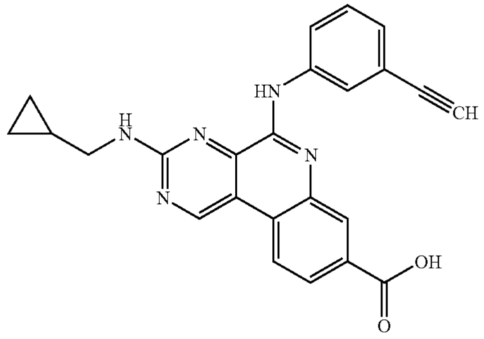 | | | | 2.63 | | | |
| 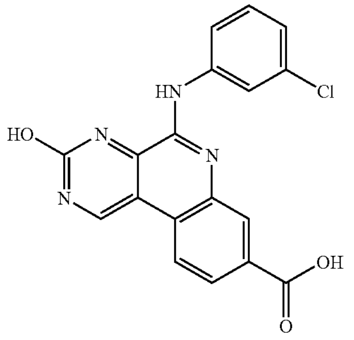 | | | | >50 | | | |
| 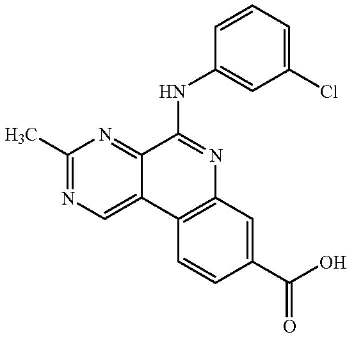 | | | | 5.48 | | | |
| 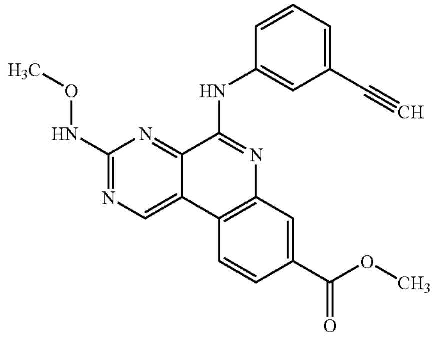 | | | | >50 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 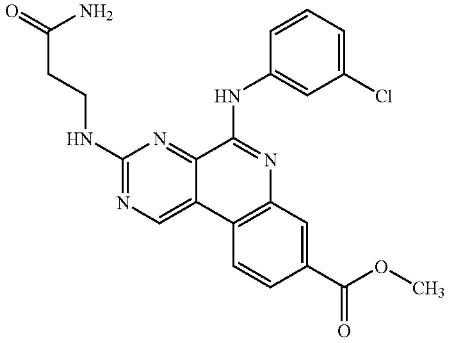 | | | | 27.18 | | | |
| 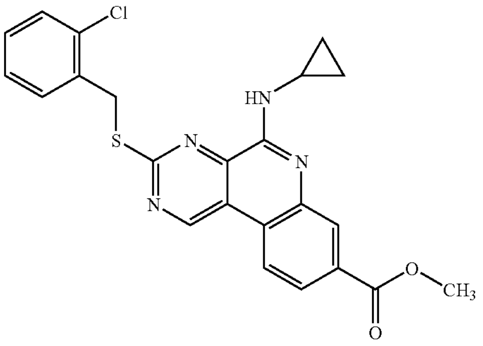 | | | | 7.23 | | | |
| 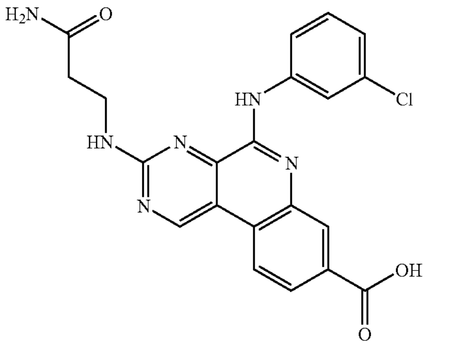 | | | | >50 | | | |
| 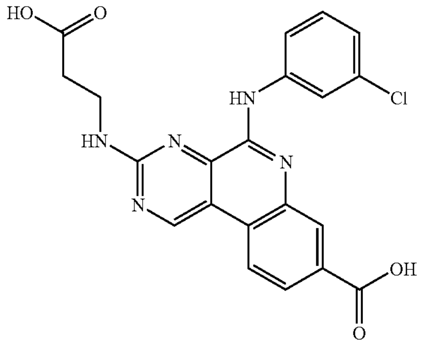 | | | | >50 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 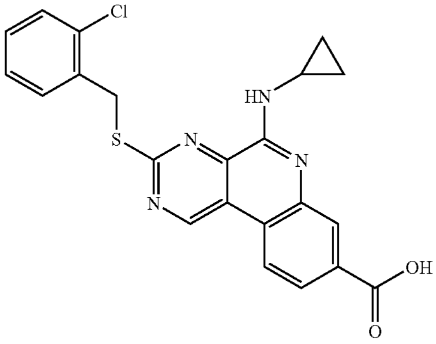 | | | | >50 | | | |
| 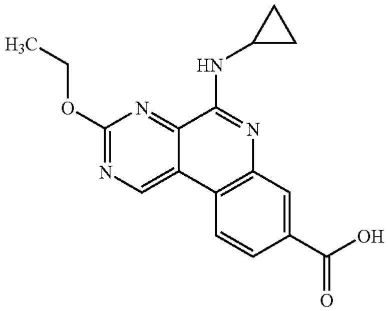 | | | | >50 | | | |
| 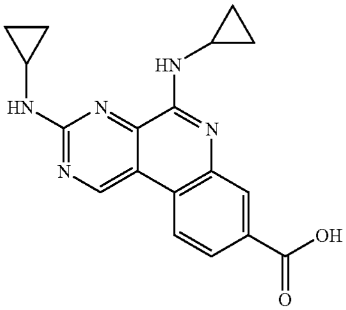 | | | | 7.22 | | | |
| 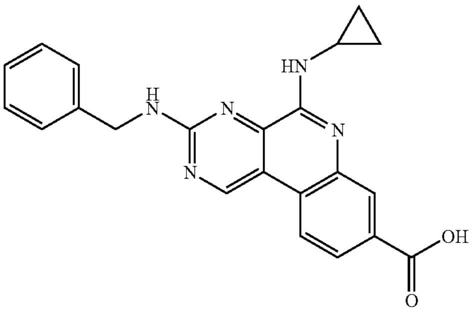 | | | | 23.54 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 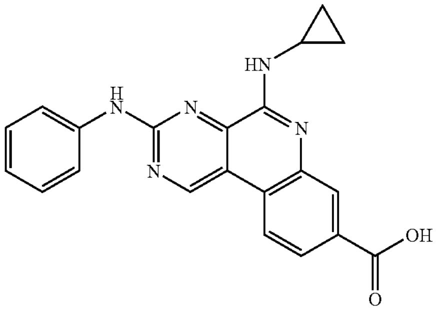 | | | | 6.88 | | | |
| 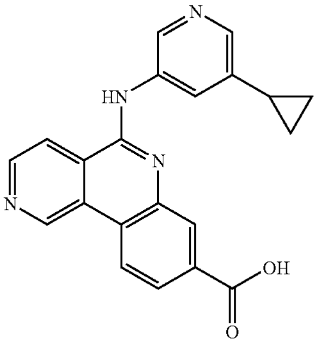 | | | | >50 | | | |
| 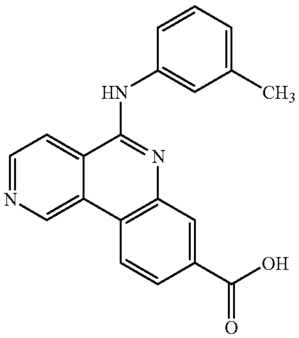 | | | | 17.50 | | | |
| 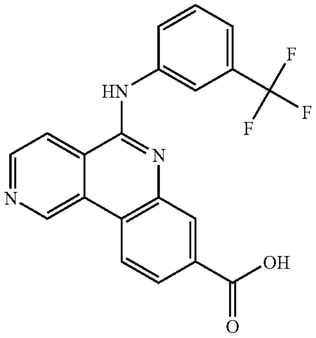 | | | | 13.02 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 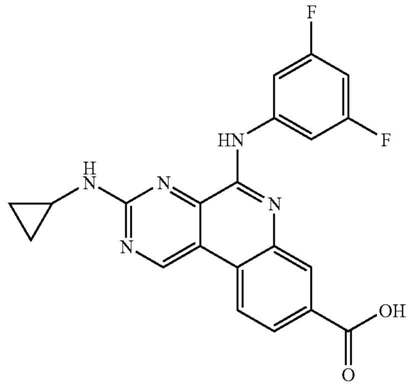 | | | | 23.04 | | | |
| 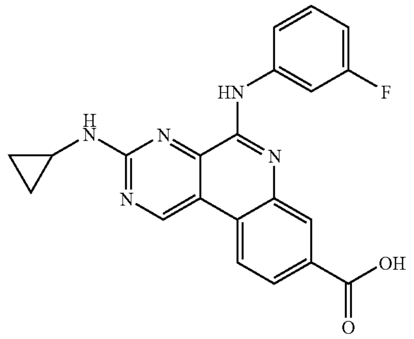 | | | | 12.77 | | | |
| 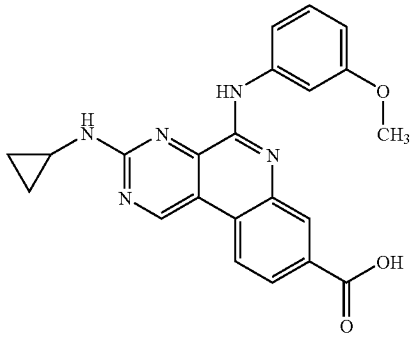 | | | | 20.11 | | | |
| 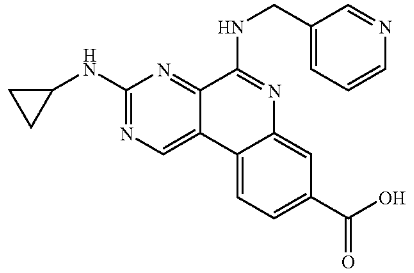 | | | | >50 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 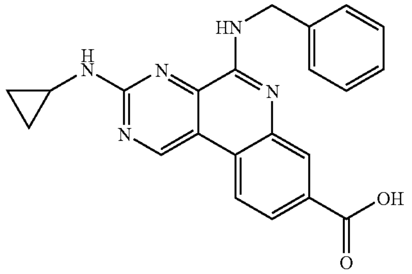 | | | | >50 | | | |
| 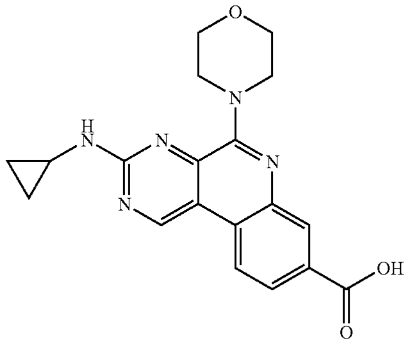 | | | | >50 | | | |
| 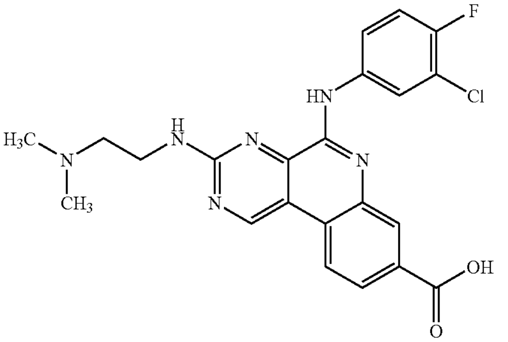 | | | | >50 | | | |
| 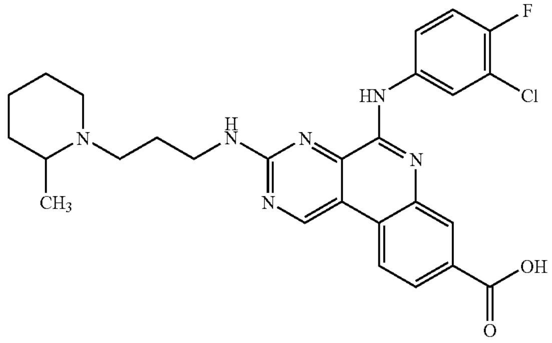 | | | | 9.66 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 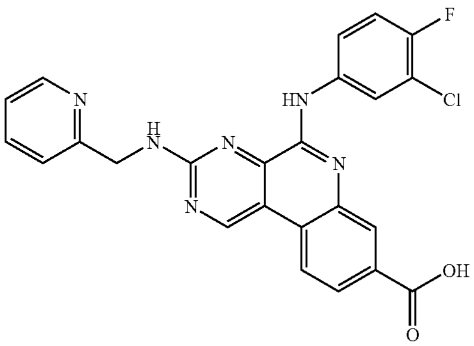 | | | | 33.72 | | | |
| 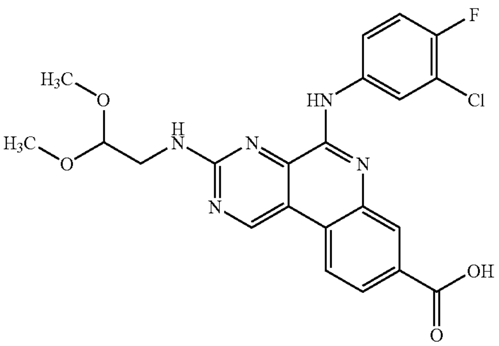 | | | | 25.43 | | | |
| 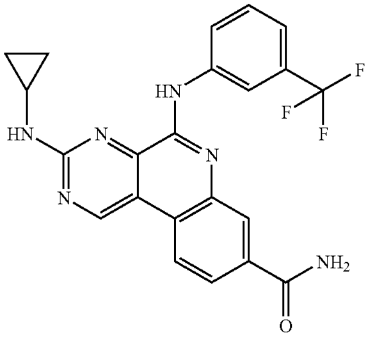 | | | | >50 | | | |
| 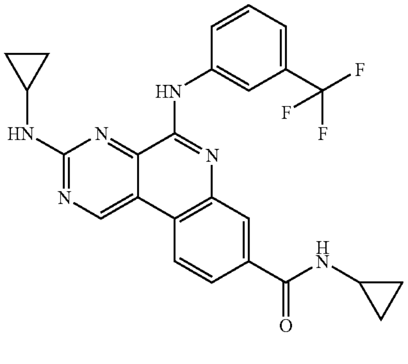 | | | | 39.84 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 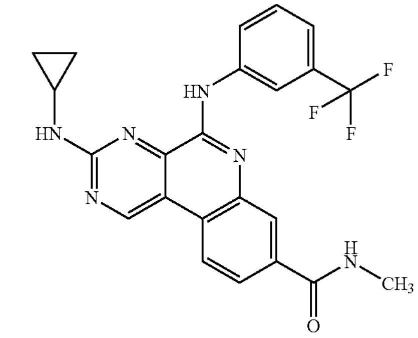 | | | | 10.47 | | | |
| 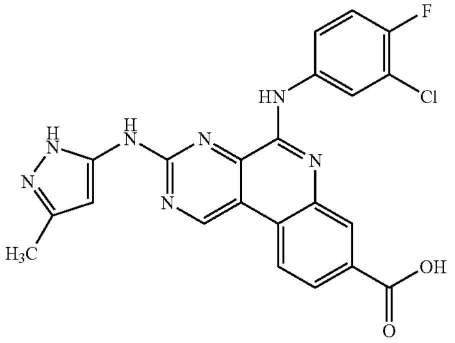 | | | | >50 | | | |
| 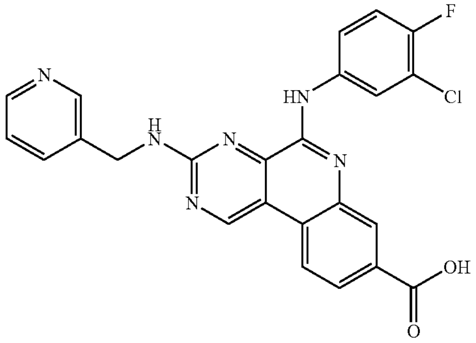 | | | | 5.48 | | | |
| 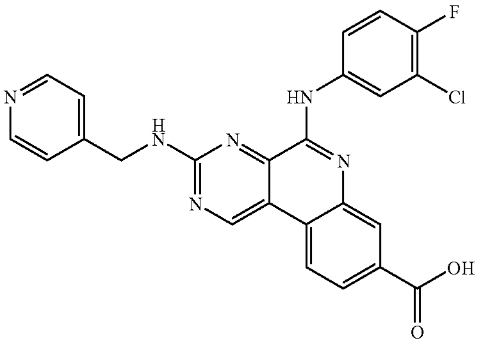 | | | | 12.11 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 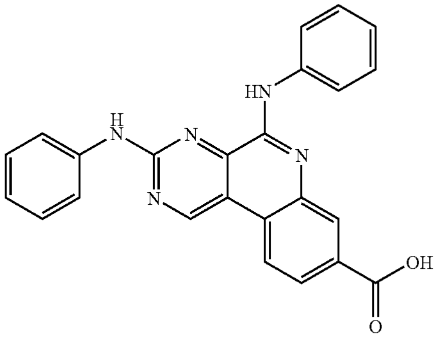 | | | | 19.23 | | | |
| 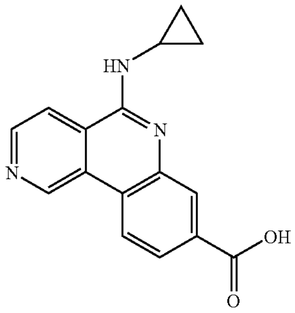 | | | | >50 | | | |
| 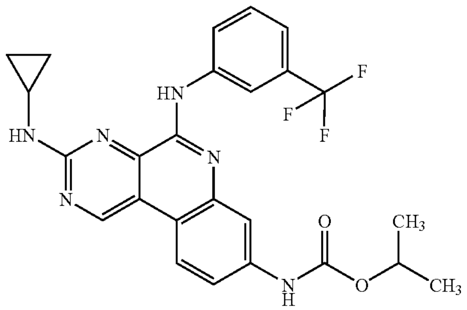 | | | | 4.27 | | | |
| 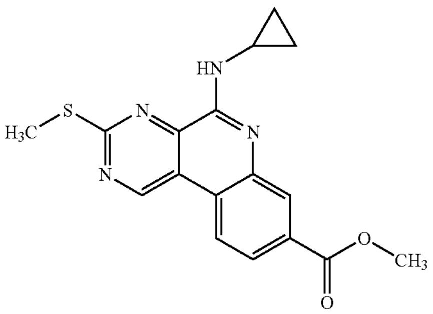 | | | | 34.23 | | | |

TABLE 19A-continued
| Structure | IC50 (uM) A549 | IC50 (uM) MCF-7 | IC50 (uM) LNCaP | IC50 (uM) MDAMB231 | IC50 (uM) Raji | IC50 (uM) HL-60 | IC50 (uM) K-562 |
|---|---|---|---|---|---|---|---|
| 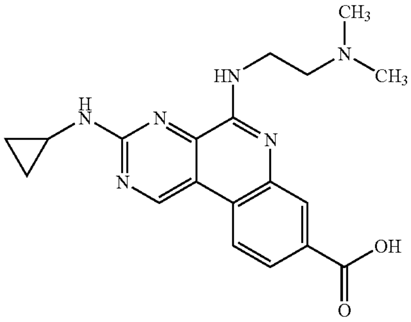 | | | | >50 | | | |
| 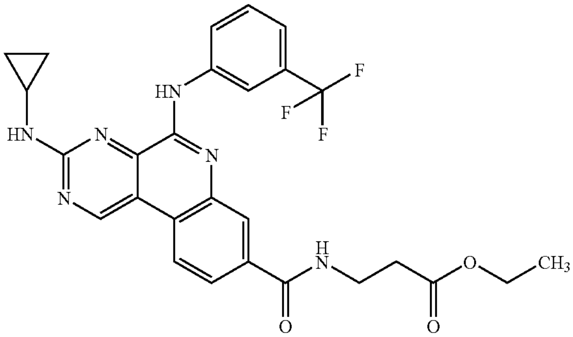 | | | | 2.52 | | | |
| 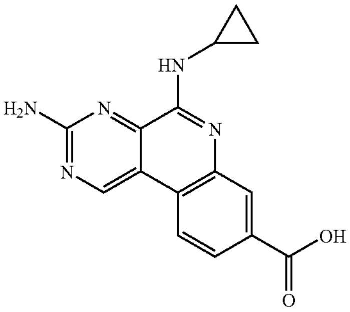 | | | | >50 | | | |
| 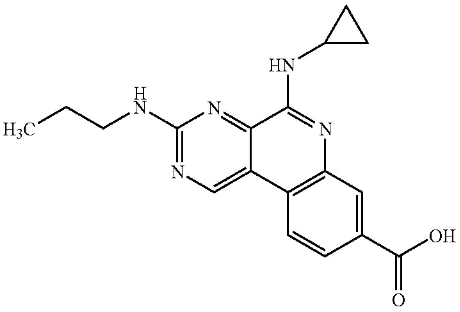 | | | | 4.36 | | | |

Example 6

Modulation of Endogenous CK2 Activity

The human leukemia Jurkat T-cell line was maintained in RPMI 1640 (Cambrex) supplemented with 10% fetal calf serum and 50 ng/ml Geutamycin. Before treatment cells were washed, resuspended at a density of about $10^6$ cells/milliliter in medium containing 1% fetal calf serum and incubated in the presence of indicated mounts of drug for two hours. Cells were recovered by centrifugation, lysed using a hypotonic buffer (20 mM Tris/HCl pH 7.4; 2 mM EDTA; 5 mM EGTA; 10 mM mercaptoethanol; 10 mM NaF; 1 uM Okadaic acid; 10% v/v glycerol; 0.05% NP-40; 1% Protease Inhibitor Cocktail) and protein from the cleared lysate was diluted to 1 microgram per microliter in Assay Dilution Buffer (ADB; 20 mM MOPS, pH 7.2, 25 mM β-glycerolphosphate, 5 mM EGTA, 1 mM sodium orthovanadate and 1 mM dithiothreitol). To 20 microliters of diluted protein was added 10 microliters of substrate peptide (RRRDDDSDDD (SEQ ID NO:4), dissolved in ADB at a concentration of 1 mM) and 10 microliters of PKA Inhibitor cocktail (Upstate). Reactions were initiated by the addition of 10 microliters of ATP Solution (90% 75 mM $MgCl_2$, 100 uM ATP dissolved in ADB; 10% [gamma-$^{33}$P]ATP (stock 1 mCi/100 microliters; 3000 Ci/mmol (Perkin Elmer)) and maintained for 15 min at 32 degrees C. The reactions were quenched with 100 microliters of 0.75% phosphoric acid, then transferred to and filtered through a phosphocellulose filter plate (Millipore). After washing each well 5 times with 0.75% phosphoric acid, the residual radioactivity was measured using a Wallac luminescence counter.

Modulatory activities of two compounds assessed by the assay are shown in FIG. 1. Structures of the compounds are provided below:

Compound 1

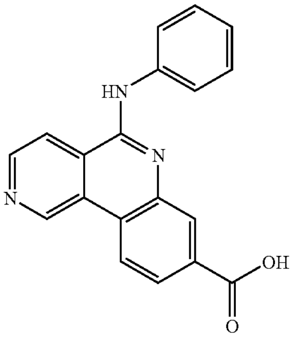

Compound 2

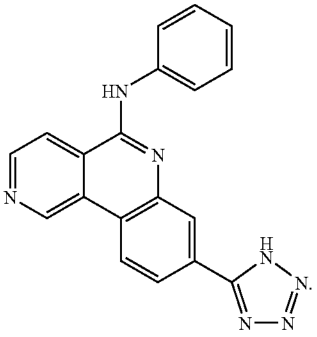

As shown in FIG. 1, each of the two compounds significantly inhibited endogenous CK2 activity as compared to the untreated control. Each of the two compounds also more potently inhibited endogenous CK2 activity as compared to reference compound 4,5,6,7-tetrabromobenzotriazole (TBB), a known CK2 inhibitor (Ruzzene et al., *Biochem J.* 15: 364(Pt 1):41-7 (2002)).

TABLE 20

| Modulation of endogenous CK2 activity | |
|---|---|
| Structure | Modulation of endogenous CK2 activity $IC_{50}$ (uM) |
| 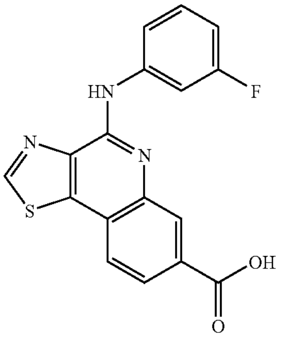 | 25.8 |
| 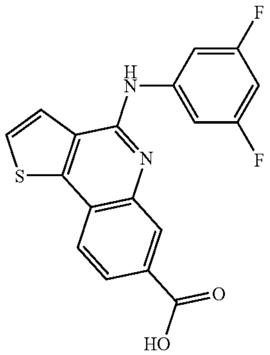 | 4.338 |
| 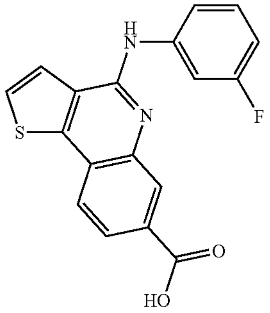 | 3.564 |
| 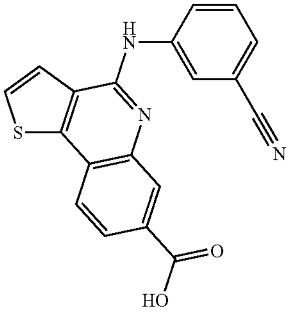 | 10.66 |

TABLE 20-continued
| Modulation of endogenous CK2 activity | |
|---|---|
| Structure | Modulation of endogenous CK2 activity $IC_{50}$ (uM) |
| 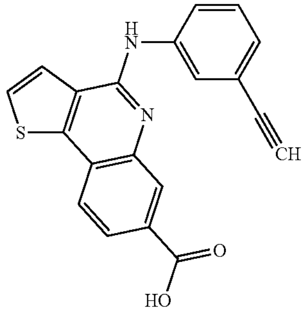 | 8.36 |
| 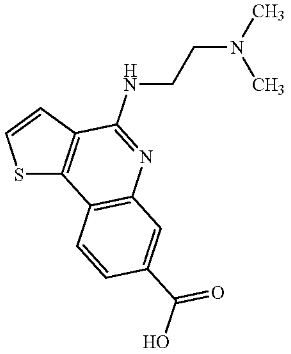 | 50 |
| 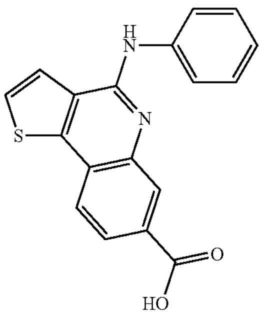 | 15.7 |
| 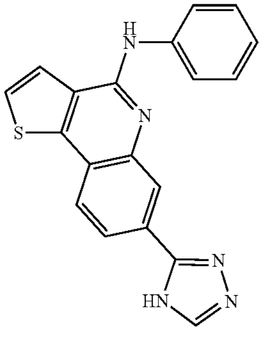 | 50 |
TABLE 20-continued
| Modulation of endogenous CK2 activity | |
|---|---|
| Structure | Modulation of endogenous CK2 activity $IC_{50}$ (uM) |
| 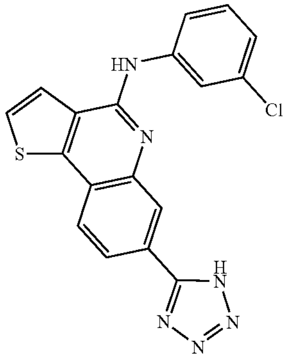 | 9.59 |
| 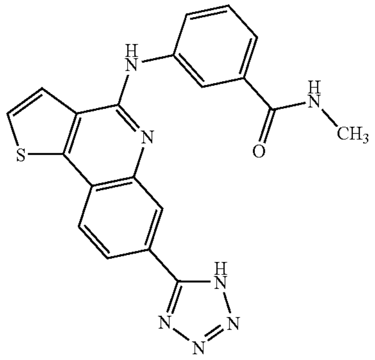 | 37.89 |
| 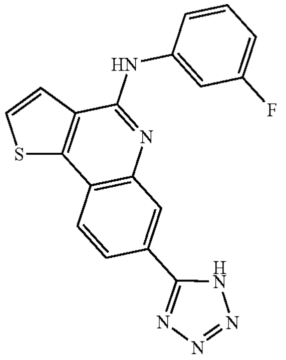 | 4.426 |
| 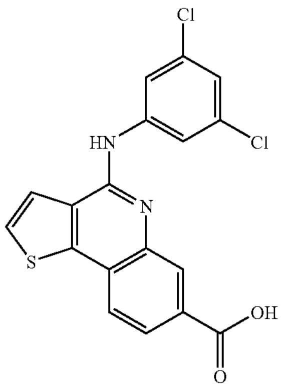 | 0.58 |

TABLE 21
| Modulation of endogenous CK2 activity | |
|---|---|
| Structure | Modulation of endogenous CK2 activity $IC_{50}$ (uM |
| 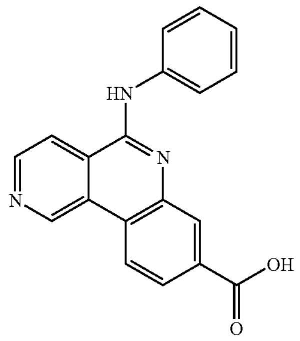 | 7.4 |
| 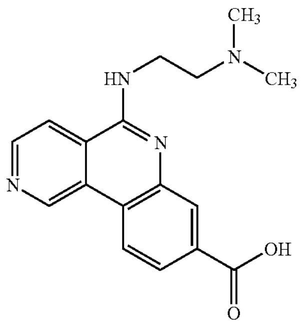 | >50 |
| 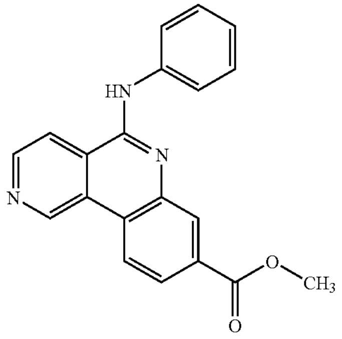 | 19.87 |
| 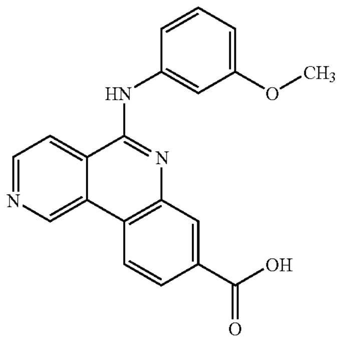 | 2.325 |

TABLE 21-continued
| Structure | Modulation of endogenous CK2 activity $IC_{50}$ (uM |
|---|---|
| 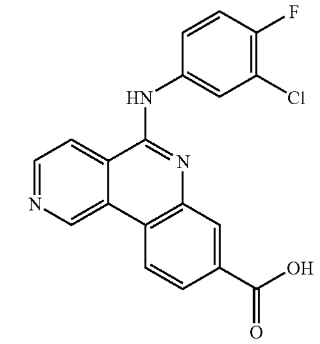 | 0.464 |
| 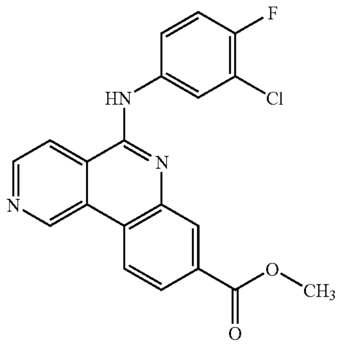 | 7.066 |
| 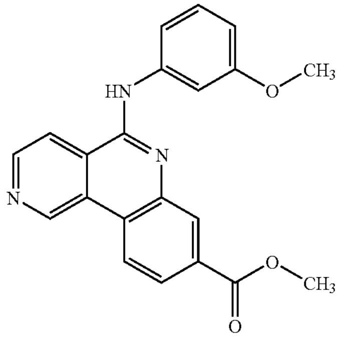 | >50 |
| 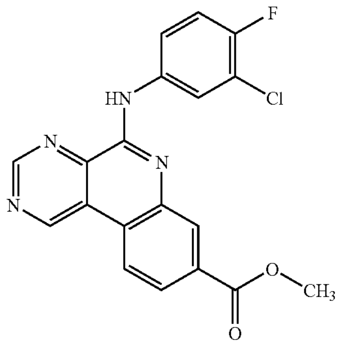 | >50 |

TABLE 21-continued
| Modulation of endogenous CK2 activity | |
|---|---|
| Structure | Modulation of endogenous CK2 activity $IC_{50}$ (uM |
| 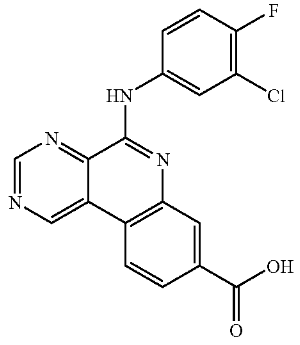 | 1.056 |
| 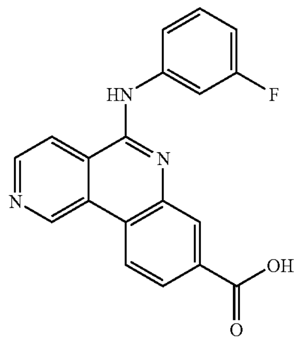 | 2.933 |
| 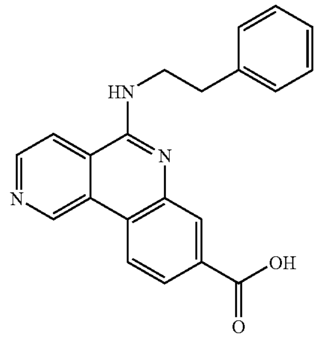 | 0.688 |
| 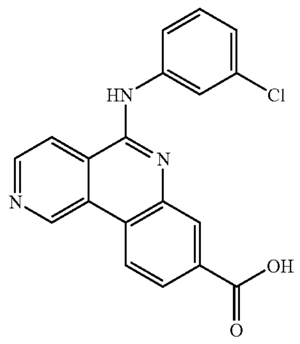 | 0.1 |

TABLE 21-continued
| Modulation of endogenous CK2 activity | |
|---|---|
| Structure | Modulation of endogenous CK2 activity $IC_{50}$ (uM |
| 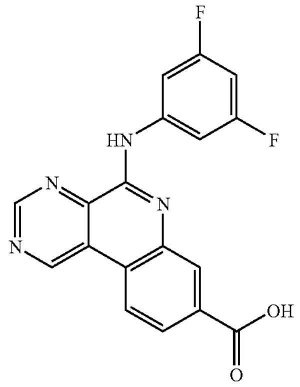 | 0.269 |
| 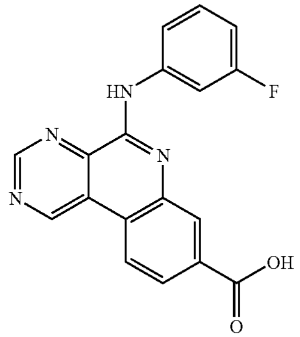 | 0.026 |
| 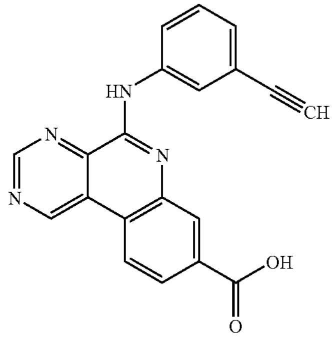 | 0.098 |
| 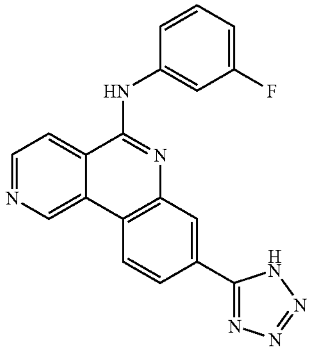 | 0.63 |

TABLE 21-continued
| Modulation of endogenous CK2 activity | |
|---|---|
| Structure | Modulation of endogenous CK2 activity IC$_{50}$ (uM |
| 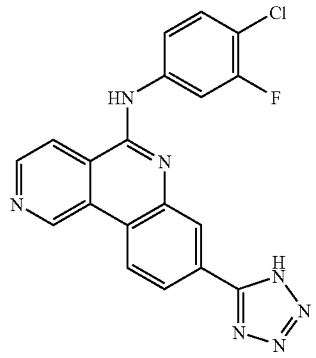 | 0.22 |
| 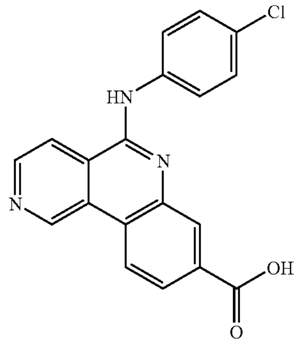 | 0.017 |
| 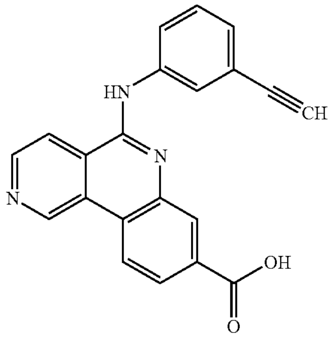 | 0.07 |
| 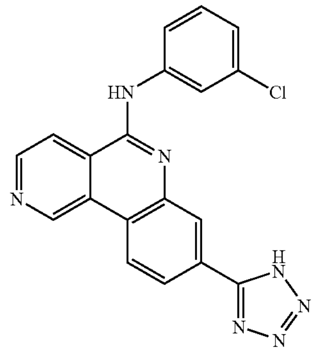 | 1.016 |

TABLE 21-continued
| Modulation of endogenous CK2 activity | |
|---|---|
| Structure | Modulation of endogenous CK2 activity IC$_{50}$ (uM |
| 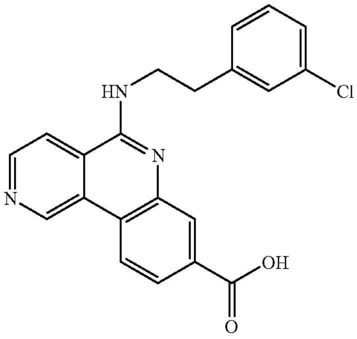 | 0.64 |
| 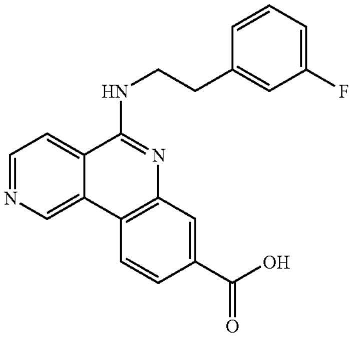 | 3.6 |
| 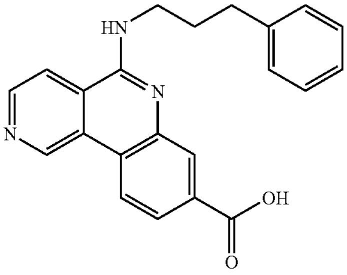 | 2.5 |
| 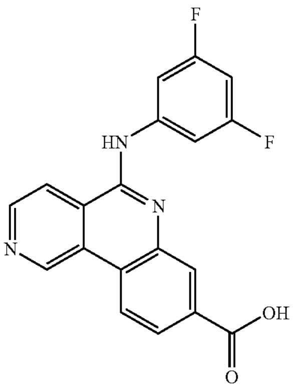 | 1.351 |

TABLE 21-continued
| Modulation of endogenous CK2 activity | |
|---|---|
| Structure | Modulation of endogenous CK2 activity $IC_{50}$ (uM |
| 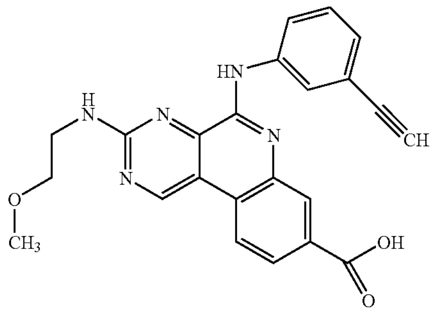 | 0.01 |
| 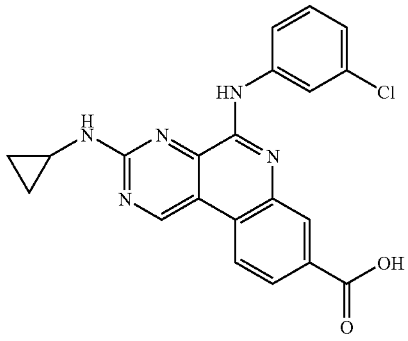 | 0.01 |
| 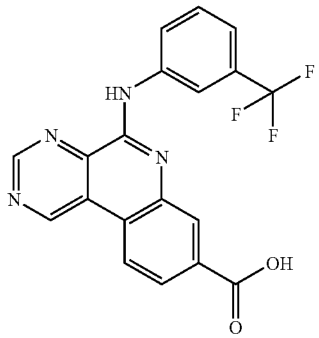 | 0.098 |
| 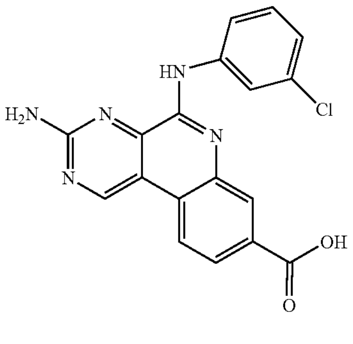 | 0.044 |

TABLE 21-continued
| Modulation of endogenous CK2 activity | |
|---|---|
| Structure | Modulation of endogenous CK2 activity $IC_{50}$ (uM |
| 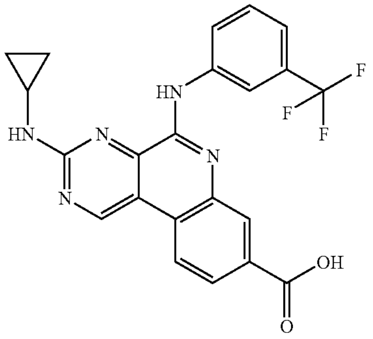 | 0.01 |
| 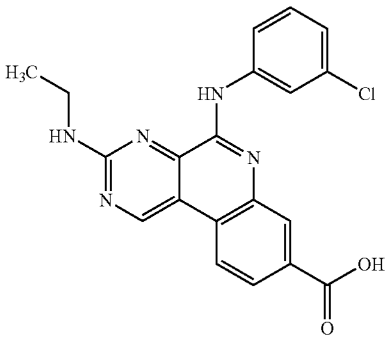 | 0.01 |
| 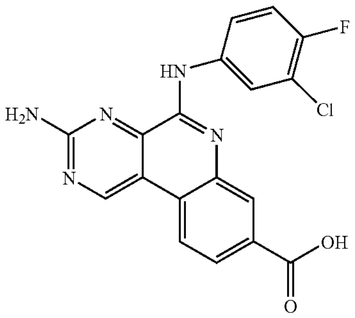 | 0.044 |
| 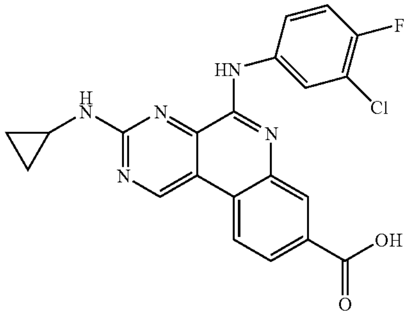 | 0.03 |

TABLE 21-continued
| Modulation of endogenous CK2 activity | |
|---|---|
| Structure | Modulation of endogenous CK2 activity $IC_{50}$ (uM |
| 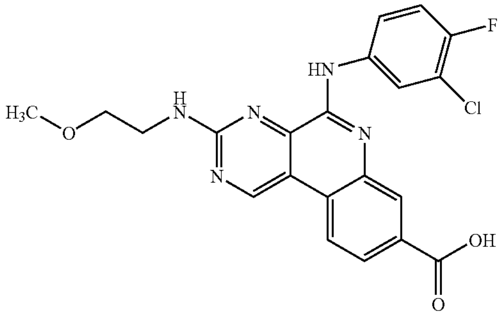 | 0.047 |
| 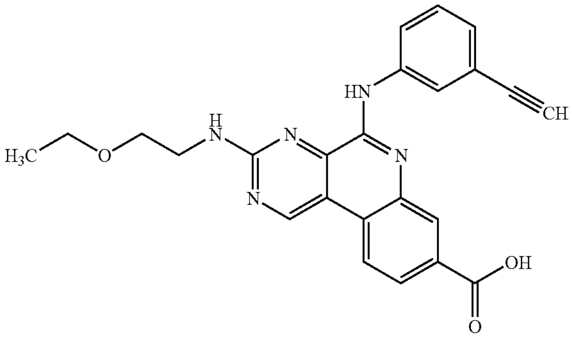 | 0.172 |
| 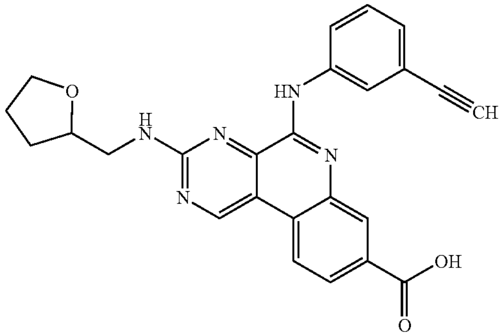 | 0.011 |
| 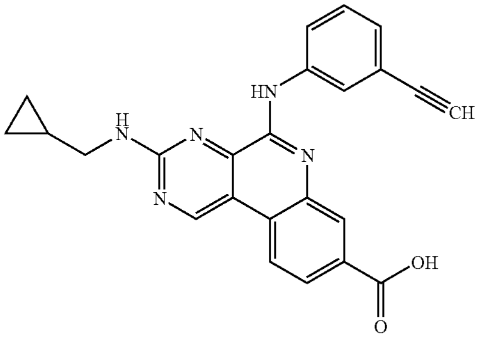 | 0.027 |

Example 7

Evaluation of Pharmacokinetic Properties

The pharmacokinetics properties of drugs were investigated in ICR mice following an intravenous (IV) bolus and oral (PO) doses of drug at 5 mg/kg and 25 mg/kg respectively. Blood samples were collected at predetermined times and the plasma separated. Plasma was separated from the blood samples collected at 5, 15 and 30 minutes and 1, 2, 4, 8 and 24 hours post-dose.

The pharmacokinetics properties of drugs were also investigated in SD rats and beagle dogs following an intravenous (IV) bolus and oral (PO) doses of drug using similar methods. Blood samples were collected at predetermined times and the plasma separated.

Drug levels were quantified by the LC/MS/MS method described below. Noncompartmental pharmacokinetic analysis was applied for intravenous administration. A linear trapezoidal rule was used to compute AUC(0-24). The terminal $t_{1/2}$ and $C_0$ were calculated using the last three and the first three data points, respectively Bioanalysis was performed using a Quattro Micro LC/MS/MS instrument in the MRM detection mode, with an internal standard (IS). Briefly, 15 □L plasma samples were prepared for analysis using protein precipitation with 120 μL of acetonitrile. The supernatants were transferred into a 96 well plate and subjected to LC-MS/MS analysis using a Phenomenex Polar-RP HPLC column. The mobile phases were 10 mM $NH_4HCO_3$ in water (Solution-A) and 10 mM $NH_4HCO_3$ in methanol (Solution-B). The column was initially equilibrated with 25% Solution-B and followed with 100% Solution B over 5 minutes. The method had a dynamic range from 1 to 10,000 ng/mL. Quantitation of the analytes was performed in the batch mode with two bracketing calibration curves according to the bioanalytical sample list.

Figure 2A:
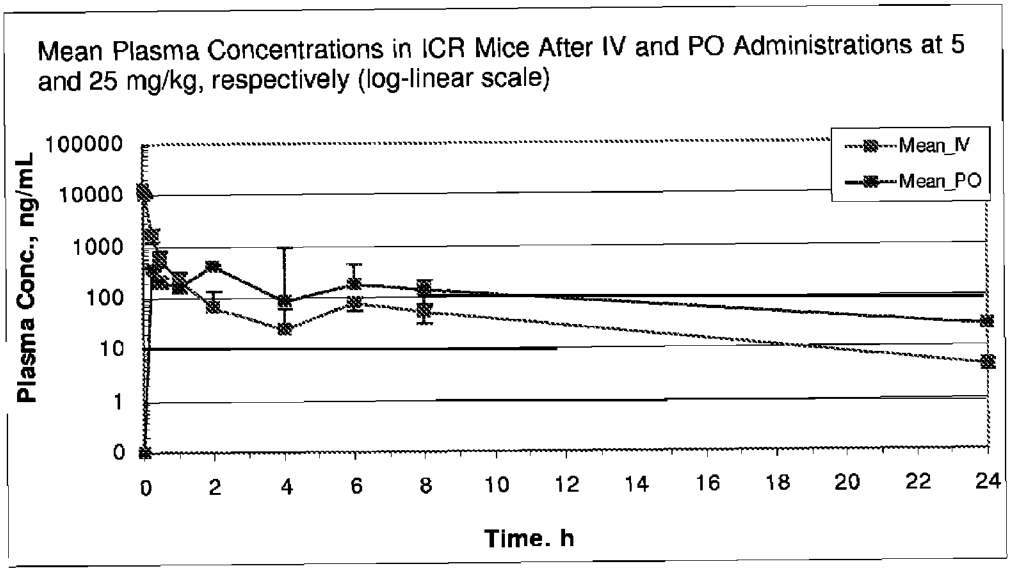
FIGS. 2A and 2B show mean plasma concentrations of compounds described herein over time after intravenous and oral administration to ICR mice.

Pharmacokinetic profiles and estimated pharmacokinetic parameters of compound A1 below are shown in FIG. 2A and in Table 22.

A1

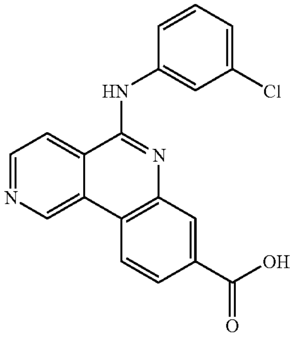

TABLE 22

Estimated pharmacokinetic parameters after intravenous and oral dosing at 5 and 25 mg/kg, respectively in ICR mice.

| PK Parameter | IV | PO | Units |
|---|---|---|---|
| Dose | 5 | 25 | mg/kg |
| $AUC_{(0\text{-}8\ h)}$ | 2910 | 1580 | |
| $AUC_{(0\text{-}24\ h)}$ | 3337 | 2915 | $ng \cdot h \cdot ml^{-1}$ |
| $AUC_{(0\text{-}Inf)}$ | 3364 | 3149 | $ng \cdot h \cdot ml^{-1}$ |
| Cmax-obs | N/A | 343 | ng/mL |
| Cp0-exp | 13201 | N/A | ng/mL |
| Tmax | N/A | 0.25 | hr |
| Kel | 0.1586 | 0.1076 | $hr^{-1}$ |
| $t_{1/2}$ | 4.4 | 6.4 | hr |
| Vd | 9.4 | N/A | L/kg |
| $CL_s$ | 1.5 | N/A | L/kg/hr |
| F(0-8 h) | N/A | 10.9 | % |
| F(0-inf h) | N/A | 18.7 | % |

Figure 2B:
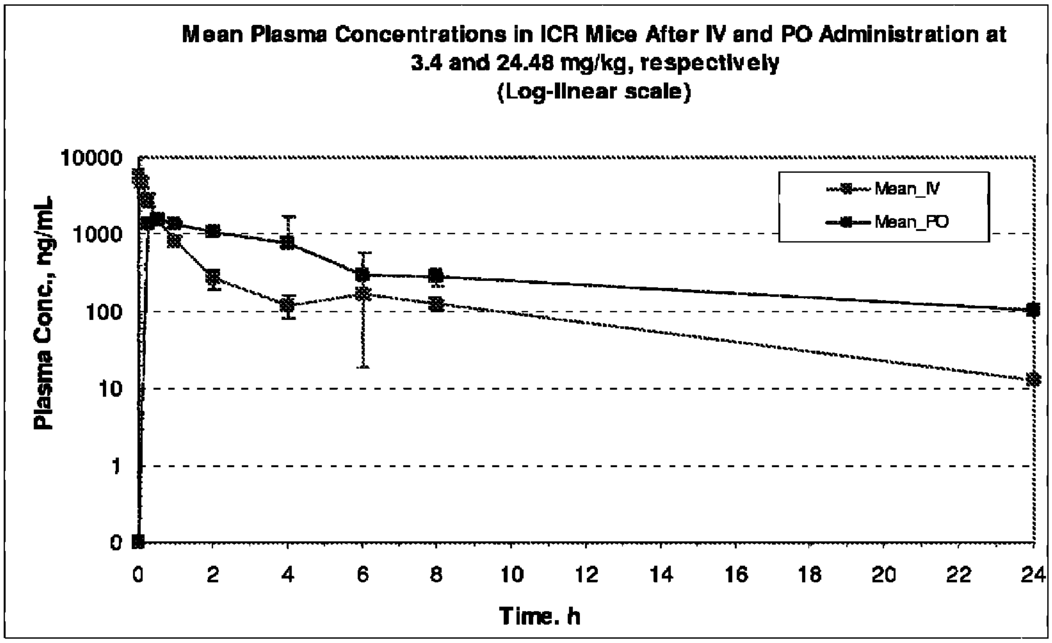

Pharmacokinetic profiles and estimated pharmacokinetic parameters of the test compound below are shown in FIG. 2B and Table 23.

A2

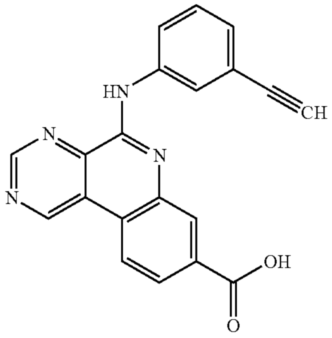

TABLE 23

Estimated pharmacokinetic parameters after IV and PO dose in ICR mice.

| PK Parameter | IV | PO | Unit |
|---|---|---|---|
| Dose | 3.4 | 24.5 | mg/kg |
| $AUC_{(0\text{-}8\ h)}$ | 3716 | 6005 | |
| $AUC_{(0\text{-}24\ h)}$ | 4806 | 9120 | $ng \cdot h \cdot ml^{-1}$ |
| $AUC_{(0\text{-}Inf)}$ | 4898 | 10895 | $ng \cdot h \cdot ml^{-1}$ |
| Cmax-obs | 4744 | 1600.5 | ng/mL |
| Cp0-exp | 5631 | N/A | ng/mL |
| Tmax | N/A | 0.5 | hr |
| Kel | 0.1418 | 0.0594 | $hr^{-1}$ |
| $t_{1/2}$ | 4.9 | 11.7 | hr |
| Vd | 4.9 | N/A | L/kg |
| $CL_s$ | 0.7 | N/A | L/kg/hr |
| $F_{(0\text{-}24\ h)}$ | N/A | 26.5 | % |
| $F_{(0\text{-}Inf)}$ | N/A | 31.1 | % |

Pharmacokinetic profiles and estimated pharmacokinetic parameters of the test compound A1 in dogs are shown in Table 24. Pharmacokinetic profiles and estimated pharmacokinetic parameters of the test compound A1 in rats are shown in Table 25.

TABLE 24

Estimated pharmacokinetic parameters of test compound A1 after IV and PO dose in Beagle dogs.

| PK Parameters | IV | PO | IV MC | PO MC | Unit |
|---|---|---|---|---|---|
| Dose | 0.80 | 3.80 | 0.80 | 3.80 | mg/kg |
| $AUC_{(0-8\ h)}$ | 345 | 1024 | 633 | 1775 | |
| $AUC_{(0-12\ h)}$ | 349 | 1064 | N/A | N/A | $ng \cdot h \cdot ml^{-1}$ |
| $AUC_{(0-Inf)}$ | 352 | 1073 | 633 | 1804 | $ng \cdot h \cdot ml^{-1}$ |
| Cmax-obs | 1043 | 494.7 | 1979 | 908 | ng/mL |
| Cp0-exp | 1406 | N/A | 2723 | N/A | ng/mL |
| Tmax | N/A | 0.5 | N/A | 0.25 | hr |
| Kel | 0.5546 | 0.5546 | N/D | 0.4318 | $hr^{-1}$ |
| $t_{1/2}$ | 1.2 | 1.2 | N/D | N/D | hr |
| Vd | 4.1 | N/A | N/D | N/D | L/kg |
| $CL_s$ | 2.3 | N/A | N/D | N/D | L/kg/hr |
| $F_{(0-8\ h)}$ | N/A | 62.5 | N/A | 59.0 | % |
| $F_{(0-12\ h)}$ | N/A | 64.2 | N/A | N/A | % |
| $F_{(0-Inf)}$ | N/A | 64.1 | N/A | N/A | % |

TABLE 25

Estimated pharmacokinetic parameters of test compound A1 after IV and PO dose in SD rats.

| PK Parameter | IV | PO | Unit |
|---|---|---|---|
| Dose | 2.50 | 12.50 | mg/kg |
| $AUC_{(0-12\ h)}$ | 13119 | 19025 | $ng \cdot h \cdot ml^{-1}$ |
| $AUC_{(0-24\ h)}$ | 14352 | 25858 | $ng \cdot h \cdot ml^{-1}$ |
| $AUC_{(0-Inf)}$ | 13997 | 26587 | $ng \cdot h \cdot ml^{-1}$ |
| Cmax-obs | 21339 | 4207.4 | ng/mL |
| Cp0-exp | 27117 | N/A | mg/mL |
| Tmax | N/A | 1.0 | hr |
| Kel | 0.0707 | 0.1529 | $hr^{-1}$ |
| $t_{1/2}$ | 9.8 | 4.5 | hr |
| Vd | 2.5 | N/A | L/kg |
| $CL_s$ | 0.2 | N/A | L/kg/hr |
| $F_{(0-12\ h)}$ | N/A | 29.0 | % |
| $F_{(0-24\ h)}$ | N/A | 36.0 | % |
| $F_{(0-Inf)}$ | N/A | 38.0 | % |

Pharmacokinetic profiles and estimated pharmacokinetic parameters of the test compound A2 in beagle dogs and SD rats are shown in Table 26.

TABLE 26

Estimated pharmacokinetic parameters of test compound A2 after IV and PO dose.

| PK Parameter | IV SD Rats | PO SD-Rats | IV Dog | PO Dog | Unit |
|---|---|---|---|---|---|
| Dose | 1.56 | 8.06 | 2.00 | 7.50 | mg/kg |
| $AUC_{(0-8\ h)}$ | 35755 | 55808 | 1394 | 2253 | |
| $AUC_{(0-12\ h)}$ | 39194 | 73945 | 1414 | 2315 | $ng \cdot h \cdot ml^{-1}$ |
| $AUC_{(0-Inf)}$ | 36659 | 80286 | 1437 | 2355 | $ng \cdot h \cdot ml^{-1}$ |
| Cmax-obs | 34264.8 | 6668.3 | 3070.8 | 1212.8 | ng/mL |
| Cp0-exp | 47935 | N/A | 3847 | N/A | ng/mL |
| Tmax | N/A | 2.0 | N/A | 1.0 | hr |
| Kel | 0.1215 | 0.1077 | 0.1360 | 0.2092 | $hr^{-1}$ |
| $t_{1/2}$ | 5.7 | 6.4 | 5.1 | 3.3 | hr |
| Vd | 0.6 | N/A | 10.2 | N/A | L/kg |
| $CL_s$ | 0.1 | N/A | 1.4 | N/A | L/kg/hr |
| $F_{(0-8\ h)}$ | N/A | 31.2 | N/A | 43.1 | % |
| $F_{(0-12\ h)}$ | N/A | 37.7 | N/A | 43.7 | % |
| $F_{(0-Inf)}$ | N/A | 43.8 | N/A | 43.7 | % |

Example 8

Evaluation of Compound Efficacy in Tumor Suppression

The in vivo activity of compound A1 and compound A2 (shown previously) was assessed by intravenous and oral administration to tumor-bearing xenograft mice. The in vivo experiments followed protocols approved by the Animal Use and Care Committee. Female NCr nu/nu mice were purchased from Taconic Farms and group housed in a ventilated rack system on a 12/12 light cycle. All housing materials and water were autoclaved prior to use. The mice were fed ad libitum with gamma irradiated laboratory chow and acidified water. Animals were handled under laminar-flow hoods.

Tumor size ($mm^3$) was calculated using the formula $(l \times w^2)/2$, where w=width and l=length in mm of the tumor. Tumor weight was estimated with the assumption that 1 mg is equivalent to 1 $mm^3$ of tumor volume.

For intravenous administration of compound A1, animals were inoculated subcutaneously in the right flank with $5 \times 10^6$ MiaPaca cells. Tumors were monitored twice weekly and then daily as they approached the appropriate size for study. On Day 1 of the study, the animals were randomized into n=5 treatment groups with group mean tumor sizes of 160 $mm^3$.

| | | | |
|---|---|---|---|
| Grp 1 | Mean | 160.966 | UTC |
| Grp 2 | Mean | 161.816 | Gemzar |
| Grp 3 | Mean | 161.807 | 30 mg/kg CK2 Compound |
| Grp 4 | Mean | 159.621 | 60 mg/kg CK2 Compound |

% Dif. 1.363
SD 1.034.

Figure 3A:
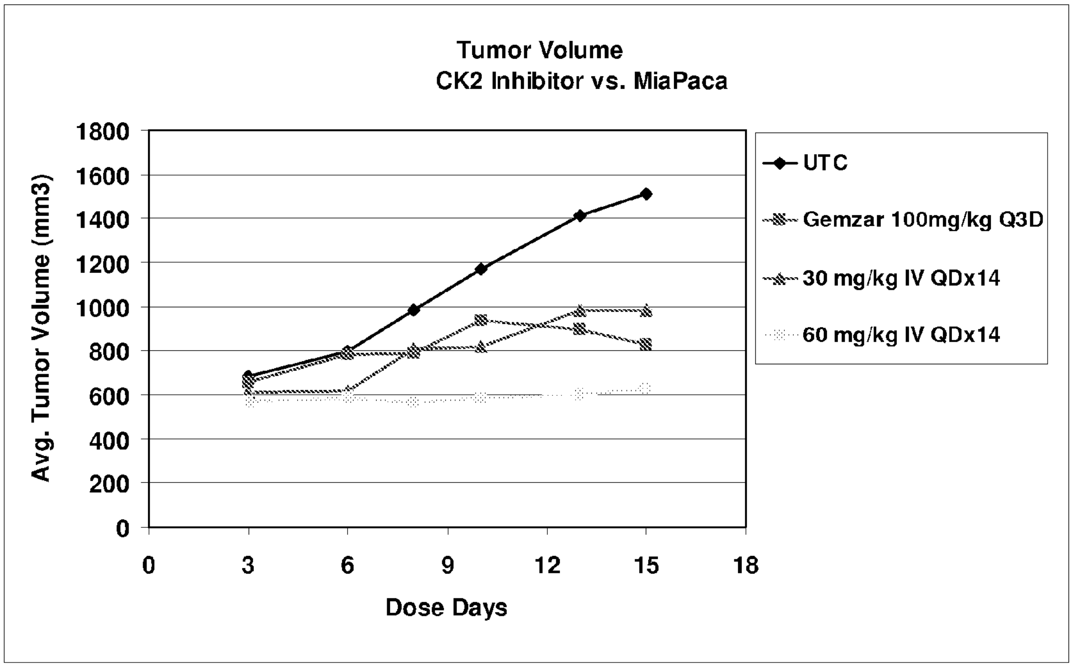
FIGS. 3A and 3B show tumor volume over time and body weight over time, respectively, in tumor-bearing xenograft animals administered a compound described herein.
Figure 3B:
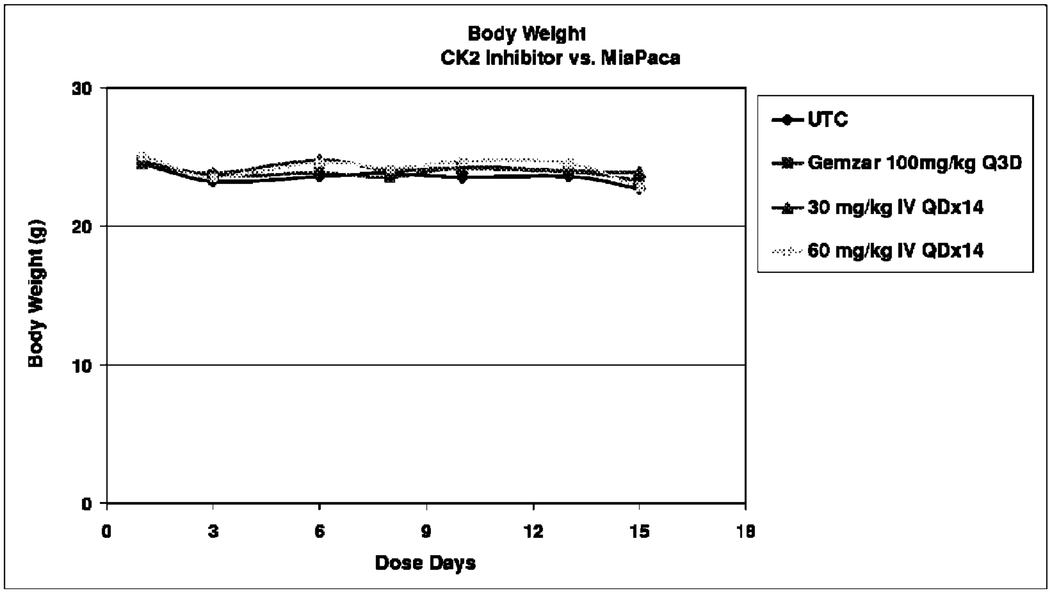
Figure 3C:
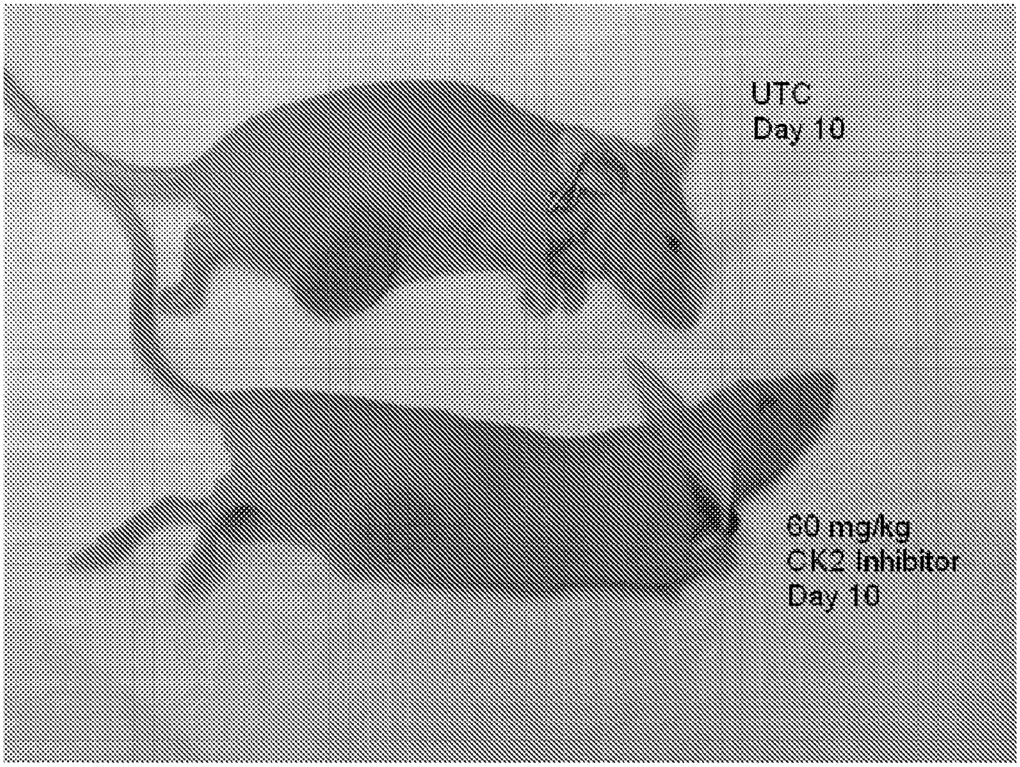
FIGS. 3C and 3D illustrate effects of the compound on tumors in individual animals.
Figure 3D:
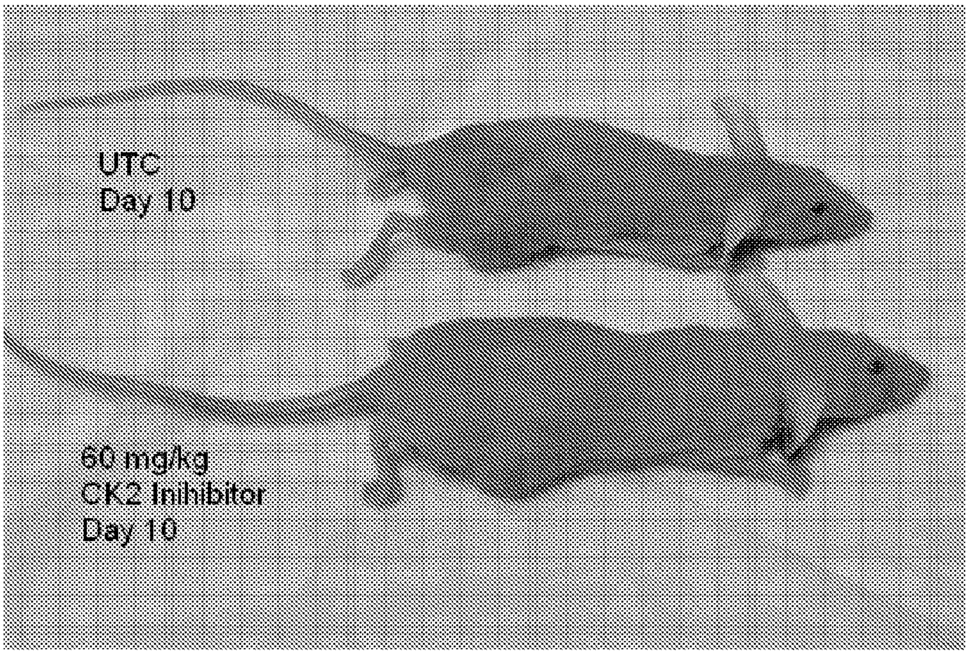

Animals received 14 doses of Vehicle, Gemzar at 100 mg/kg Q3D or compound A1 at either 30 mg/kg or 60 mg/kg by QD intravenous administration. Tumor volume measurements (FIG. 3A) and body weight (FIG. 3B) were recorded on days 3, 6, 8, 10, 13 and 15. Photographs of specific untreated control animals and animals administered 60 mg/kg compound A1 are shown in FIGS. 3C and 3D. Compound A1 is referred to as "CK2 inhibitor" in FIGS. 3A, 3B, 3C and 3D.

Compound A1 also was administered orally to MiaPaca xenograft animals and inhibited tumor growth. Compound A1 was formulated as a sodium salt at 10 mg/mL with 2% PEG 300 and buffered to pH 8.4 using sodium phosphate buffer. Compound A1 when administered orally to the animals at a dose of 100 mg/kg QD×8 and then 200 mg/kg QD×5 significantly inhibited tumor growth relative to an untreated control group. Gemzar™ administered at a dose of 80 mg/kg IP Q3D was used as a positive control. Compound A1 also was delivered by oral administration at 100 mg/kg to animals bearing MCF-7 xenografts and at 150 mg/kg to animals bearing PC-3 xenografts, and in both sets of studies, significantly inhibited tumor growth.

It also was determined that compound A1 reduced CK2 activity in tumors. Assessment of CK2 activity in tumors revealed that tumors from animals treated with compound A1 had about 40% of the CK2 activity of tumors from animals not treated with compound A1 or treated with Gemzar™.

The distribution of compound A1 in the plasma and tumors of animals was assessed. In animals administered 30 mg/kg compound A1 IV, 60 mg/kg compound A1 IV and 200 mg/kg compound A1 orally, about 6.8, 2.2 and 9.5 micromolar compound A1, respectively, was identified in plasma, and about 42.9, 7.0 and 6.4 micromolar compound A1, respectively, was identified in tumors.

Caspase staining also was assessed as a biomarker for compound A1 treatment of tumors. In animals treated with 60 mg/kg of compound A1 by IV administration, caspase-3 cell staining levels were four-fold greater than in untreated control cells. These results suggest caspase-3 staining can be a useful biomarker for monitoring inhibition of cell proliferation and tumor inhibition.

It was also determined that compound A1 significantly inhibited tumor growth in A549 (human lung cancer cells) and BX-PC3 (human pancreatic cancer cells) xenograft mice. The compound was delivered by oral administration for such determinations.

For assessment of compound A2, the compound was delivered by intravenous and intraperitoneal administration to tumor-bearing xenograft mice. Animals were inoculated subcutaneously in the right flank with $5\times10^6$ BC-PC3 cells. Tumors were monitored twice weekly and then daily as they approached the appropriate size for study. On Day 1 of the study, the animals were randomized into n=8 treatment groups (n=5 for positive and negative control groups) with group mean tumor sizes of 97 mm3.

| | | | |
|---|---|---|---|
| Grp 1 | Mean | 97.80 | UTC |
| Grp 2 | Mean | 96.95 | Gemzar Q3D |
| Grp 3 | Mean | 96.68 | 50 mg/kg CX-5011 IV BID × 10days |
| Grp 4 | Mean | 98.95 | 60 mg/kg CX-5011 IV QD × 17days |
| Grp 5 | Mean | 96.51 | 100 mg/kg CX-5011 IP BID × 17days |

% Dif 2.50
SD 1.01

Figure 4A:
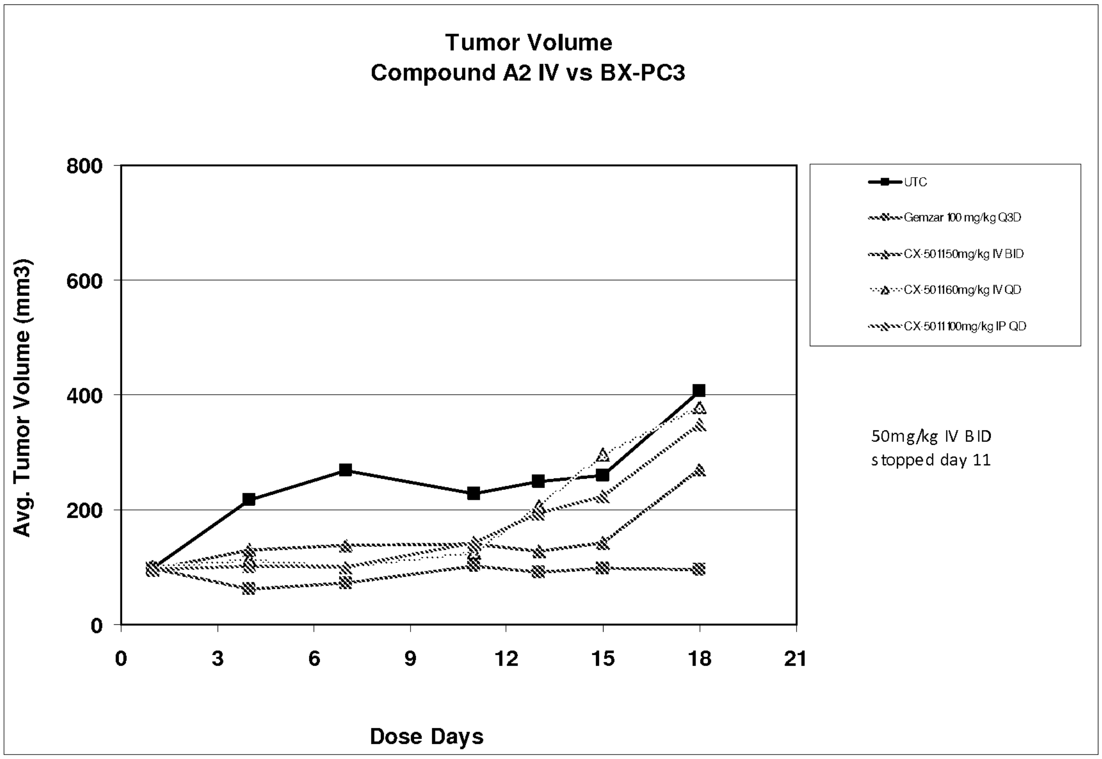
FIGS. 4A and 4B show tumor volume over time and body weight over time, respectively, in tumor-bearing xenograft animals administered a compound described herein.
Figure 4B:
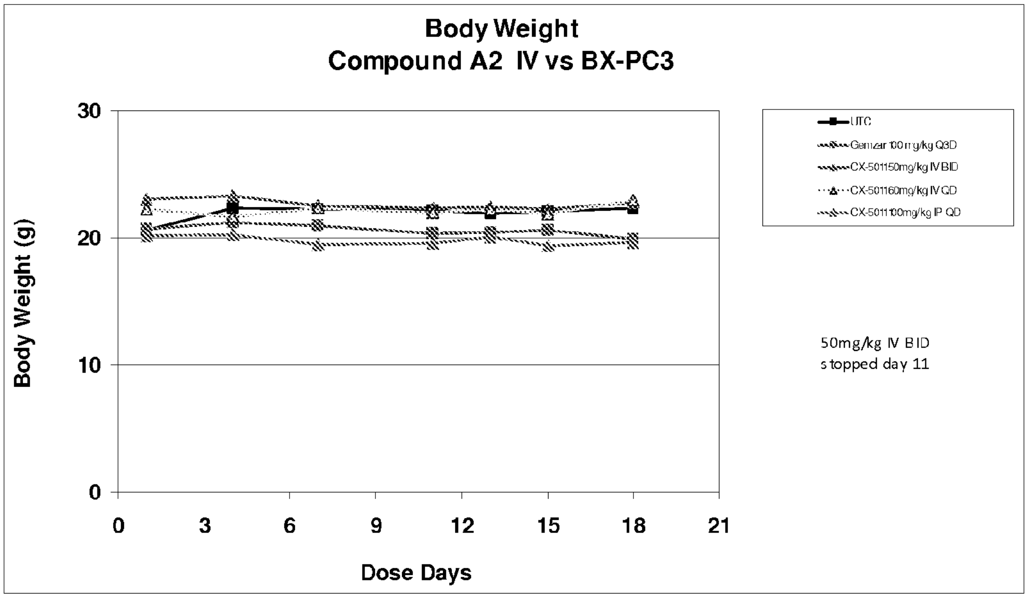

Animals received 17 doses of Vehicle, Gemzar at 100 mg/kg Q3D or compound at either 60 mg/kg QD intravenous administration or 100 mg/kg BID intraperitoneal administration. One group (#3) received 10 doses of compound at 50 mg/kg BID intravenous administration. Tumor volume measurements and body weight were recorded on days 1, 4, 7, 11, 13, 15, and 18, and data showed compound A2 significantly inhibited tumor progression (FIG. 4A) while not significantly altering body weight (FIG. 4B). Delivery of compound A2 to animals bearing MiaPaca xenografts by IV administration at 50 and 60 mg/kg and by IP administration at 100 mg/kg significantly inhibited tumor progression. Also, delivery of compound A2 to animals bearing MDA-MB-231 xenografts by IV administration at 30 and 60 mg/kg and by oral administration at 200 mg/kg significantly inhibited tumor progression. Delivery of compound A2 to animals bearing MiaPaca xenografts by oral administration at 100 mg/kg QD×8 and 200 mg/kg QD×6 significantly inhibited tumor progression. A meglumine salt of compound A2 at pH 10.0 and at 10 mg/mL was utilized as an oral formulation for the studies.

Tumor pharmacokinetic studies of compound A2 were carried out in which 30 mg/kg of the compound was dosed IV QD×6. Plasma, blood and tumor samples were taken on day 1, 4 and 6 and three animals sacrificed for each time point. Steady state was reached after about three days, the terminal slope decreases, the half life about doubles, the minimum concentration was 4-5 times higher after six days and there were no significant differences between day 4 and 6.

Delivery of compound A3 to animals bearing MiaPaca xenografts by IV administration also significantly inhibited tumor progression.

Compound A3

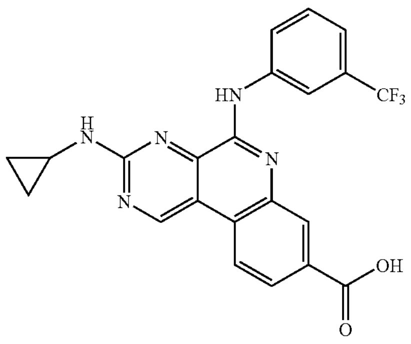

Example 9

Modulation of Non-CK2 Protein Kinase Activity

Compounds described herein are profiled for in vitro modulatory activity against protein kinases other than CK2. The in vitro analysis is conducted using known protocols (e.g., assay protocols described at world-wide web address upstate.com/img/pdf/KP_Assay Protocol_Booklet_v3.pdf). Compounds described herein are screened in the assays and prioritized based upon modulatory activity against protein kinases other than CK2 and specificity for CK2 or PARP.

Example 10

Evaluation of Angiogenesis Inhibition by Endothelial Tube Formation Assay

A human endothelial tube formation assay was performed using the 96-well BD BioCoat™ Angiogenesis System from BD Biosciences, using the manufacturer's recommended protocol.

Briefly, HUVEC cells (from ATCC) were suspended in 150 ul of media containing 10% FBS at $4\times10^5$ cells/ml in each of the 96-wells of the matrigel coated plate in the presence or absence of various concentrations of compound A2. The plate was incubated for 18 hrs at 37° C. The cells were stained with calcein AM and the results visualized by fluorescent microscopy or by phase contrast. It was observed that compound A2 inhibited tube formation in the assay described above over a concentration range of 1 to 5 μM.

Example 11

Modulation of Protein Kinase Activity in Cell-Free In Vitro Assay

The biological activity of several compounds were tested in various protein kinase assays.

Modulation of PIM-1 Kinase Activity in Cell-Free In Vitro Assay

Test compounds (10 ml) dissolved in 95% 20 mM MOPS pH7.2, 5% DMSO were added to a reaction mixture comprising 10 ul of 5× Reaction Buffer (40 mM MOPS pH 7.0, 5 mM EDTA), 10 ul of substrate peptide (KKRNRTLTV (SEQ ID NO:5), dissolved in water at a concentration of 1 mM), 10 ml of recombinant human PIM1, 4 ng dissolved in PIM1 dilution buffer (20 mM MOPS pH 7.0; EDTA 1 mM; 5% Glycerol; 0.01% Brij 35; 0.1%; 0.1% 2-mercaptoethanol; 1 mg/ml BSA). Reactions were initiated by the addition of 10 ul of ATP Solution (49% (15 mM $MgCl_2$; 75 uM ATP) 1% ([γ-33P] ATP: Stock 1 mCi/100 μl; 3000 Ci/mmol (Perkin Elmer)) and maintained for 10 min at 30° C. The reactions were quenched with 100 ul of 0.75% Phosphoric acid, then transferred to and filtrered through a Phosphocellulose filter plate (Millipore). After washing each well 4 times with 0.75% Phosphoric acid, the residual radioactivity was measured using a Wallac luminescence counter.

Modulation of FLT-3 Kinase Activity in Cell Free In Vitro Assay

FLT-3 Inhibition was determined by measuring the inhibition of recombinant human FLT-3 phosphorylation of the peptide EAIYAAPFAKKK (SEQ ID NO:6) using 10 uM ATP in a reaction mixture containing 20 mM Hepes pH 7.5, 10 mM $MgCl_2$, 1 mM EGTA, 0.02% Brij35, 0.02 mg/ml BSA, 0.1 mM $Na_3VO_4$, 2 mM DTT, and 1% DMSO.

Modulation of Protein Kinase Activity in Standardized Radiometric Kinase Assays

Compounds were tested further for activity against other protein kinases. Protein kinase inhibition $IC_{50}$ data were determined using standardized radiometric kinase assays for each individual kinase, which entail filter binding of $^{33}P$ labeled substrate proteins by the kinase of interest. Each $IC_{50}$ value was determined over a range of 10 drug concentrations. Reaction conditions are available from the World Wide Web URL upstate.com/discovery/services/ic50_profiler.q.

| KINASE | 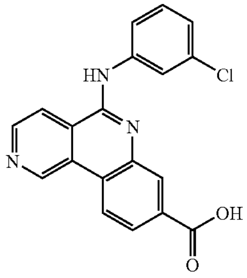 | 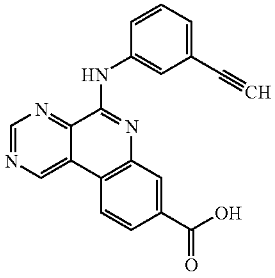 | 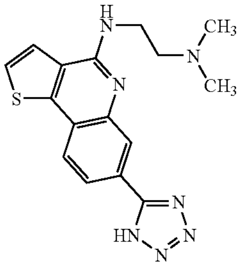 | 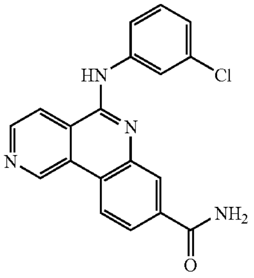 |
|---|---|---|---|---|
| PIM1 | 46.35 | 108 | 40 | |
| PIM2 | 599 | >1,000 | 66 | |
| PIM3 | 204 | >1,000 | 58 | |
| CK2 alpha 1 | 3 | | 96 | 102 |
| CK2 alpha 2 | 1 | 1 | 78 | 39 |
| DYRK2 | 91 | 354 | | 138 |
| FLT3(D835Y) | | | | 1 |
| FLT3 | 35 | 721 | | 9 |
| HIPK2 | | | | 86 |
| LCK | | | | 240 |
| MELK | | | | 184 |
| CDK1/cyclinB | 56 | 226 | | |
| RAF1 | 238 | | | |
| FLT4 | 316 | 815 | | |
| GSK3B | 512 | | | |
| HIPK3 | 45 | 56 | | |
| RPS6KA1 | 390 | | | |
| DAPK3 | 17 | | | |

The following kinase inhibition data were determined using standardized radiometric kinase assays for each individual kinase, which entail filter binding of $^{33}P$ labeled substrate proteins by the kinase of interest. Each percentage of activity was determined at 0.5 μM concentration of the drug. Reaction conditions are available at the World Wide Web URL upstate.com/discovery/services/ic50_profiler.q.

| KINASE | 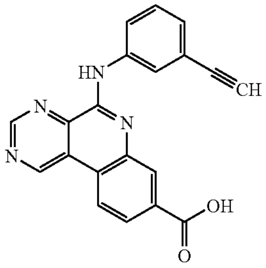 | 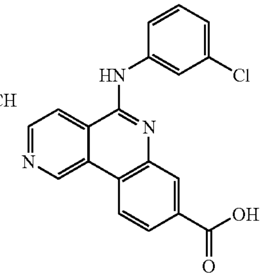 | 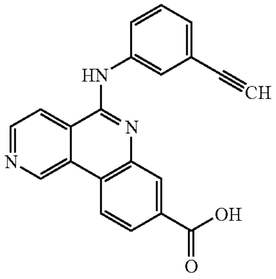 | 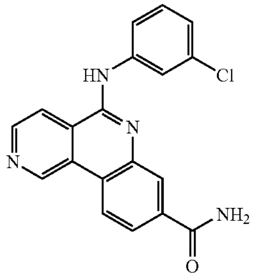 |
|---|---|---|---|---|
| ABL1 | 9 | 7 | 20 | 14 |
| ALK | −12 | −4 | −20 | −2 |
| ARK5 | −8 | −18 | 14 | 5 |
| ASK | −16 | −18 | −1 | 2 |
| AURKA | 6 | −3 | 3 | 11 |
| Blk(m) | 0 | 14 | 33 | |
| BMX | −18 | −4 | 8 | |
| BRK | −10 | 10 | 18 | |
| CAMK1 | −4 | −2 | 1 | 4 |
| CDK1/cyclinB | 48 | 86 | 84 | 63 |
| CDK2/cyclin A | 37 | 60 | 53 | 53 |
| CDK6/ cyclinD3 | −8 | 3 | 12 | 6 |
| CDK7/cyclinH/ MAT1 | 23 | 42 | 36 | 57 |
| CDK9/cyclin T1 | 0 | 24 | 27 | 45 |
| CHK1 | 1 | 12 | 13 | −1 |
| CK1 gamma 1 | −5 | 8 | 10 | 7 |
| CK1 gamma 2 | −7 | 19 | 35 | −5 |
| CK1 gamma 3 | 0 | 24 | 32 | −5 |
| CK2 alpha 1 | 102 | 112 | 97 | 84 |
| CK2 alpha 2 | 107 | 103 | 100 | 96 |
| cKit(h) | −14 | 2 | 15 | −10 |
| cKit(D816H) | −1 | 40 | 87 | 63 |
| cKit(V560G) | −11 | 19 | 69 | 75 |
| RAF1 | 31 | 72 | 62 | 62 |
| CSK | −46 | −32 | −9 | 14 |
| DDR2 | −9 | −4 | 12 | 5 |
| DRAK1 | 38 | 73 | 65 | −5 |
| DYRK2 | 50 | 95 | 55 | 82 |
| eEF-2K(h) | −6 | 3 | −8 | −3 |
| EGFR | −23 | −2 | 24 | 15 |
| EGFR(L858R) | 11 | 56 | 24 | 63 |
| EGFR(L861Q) | 21 | 56 | 59 | 70 |
| EGFR(T790M) | 8 | 15 | 16 | 43 |
| EGFR(T790M, L858R) | −21 | 5 | 26 | 48 |
| EPHA5 | −25 | −35 | 12 | 8 |
| EPHA7 | 1 | 2 | 5 | 0 |
| EPHB4 | −44 | −31 | −8 | −16 |
| ERBB4 | −26 | −1 | 17 | 33 |
| FAK | 3 | −13 | −2 | 4 |
| FER | −3 | −17 | 6 | 8 |
| FES | −39 | −33 | 1 | −2 |
| FGFR1 | −3 | 16 | 23 | 17 |
| FGFR2 | −7 | 0 | 11 | 9 |
| FLT1 | 5 | 28 | 75 | 19 |
| FLT3(D835Y) | 83 | 91 | 97 | 99 |
| FLT3 | 58 | 82 | 90 | 100 |
| FLT4 | 101 | 81 | 101 | 40 |
| CSF1R | −74 | −3 | −12 | 52 |
| FYN | −14 | 18 | 18 | 32 |
| GSK3B | 44 | 55 | 28 | 26 |
| HCK | −11 | 25 | 26 | 28 |
| HIPK2 | 89 | 85 | 96 | 89 |
| HIPK3 | 90 | 93 | 91 | 57 |
| IGF1R | 27 | 21 | −9 | −23 |
| IKK alpha | −1 | −2 | 3 | −13 |
| INSR | −5 | −6 | −7 | 0 |
| IRAK4 | −19 | −14 | 4 | 12 |
| JAK2 | 1 | 2 | 38 | −4 |
| VEGFR2 | 33 | 61 | 55 | 15 |
| LCK | 37 | 58 | 33 | 79 |
| LOK | 16 | 78 | 72 | 56 |
| LYN | 8; −9 | 21; 13 | 20 | 16 |

-continued

| KINASE | 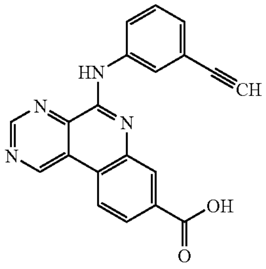 | 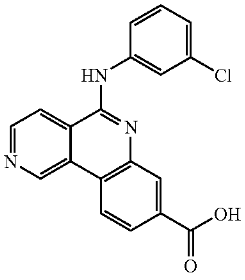 | 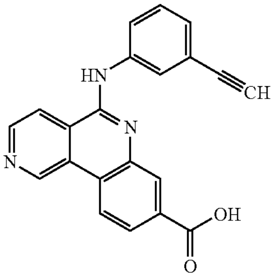 | 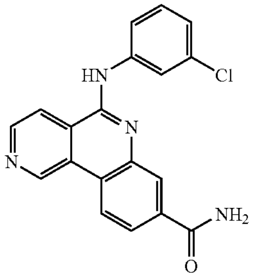 |
|---|---|---|---|---|
| ERK2 | 5 | 6 | 21 | 15 |
| MAPKAPK2 | −7 | 3 | −12 | −2 |
| MEK1 | −36 | 7 | 4 | 8 |
| MELK | 51 | 71 | 77 | 73 |
| MER | 54 | 82 | 86 | 62 |
| MET | −22 | −21 | −16 | −6 |
| MAP2K7 beta | −33 | −32 | 7 | 12 |
| MLK1 | 20 | 43 | 21 | 49 |
| Mnk2 | 37 | 79 | −2 | 32 |
| MSK2 | 44 | 34 | 41 | 9 |
| MST1 | 4 | 20 | −3 | 15 |
| NEK2 | 23 | 66 | 73 | 13 |
| p70S6K | 20 | 32 | 36 | 8 |
| PAK2 | −12 | −12 | 1 | 4 |
| PDGFRA | −9 | −6 | −2 | 5 |
| PDGFRA (D842V) | −9 | 17 | 78 | 64 |
| PDGFRB | −10 | −2 | −2 | 3 |
| PDK1 | −10 | −9 | 8 | 7 |
| PIM1 | 73 | 94 | 75 | 18 |
| PKA | −6; 10 | 2; 22 | −9 | −1 |
| AKT1 | −4 | 1 | 7 | 7 |
| PRKCA | 1 | 0 | 9 | 1 |
| PRKCT | −11 | −3 | 10 | 1 |
| PRKd_nM2 | −7 | −4 | 0 | 25 |
| PRKG1 | −5 | 1 | −4 | 4 |
| PLK3 | −6 | 3 | −1 | 0 |
| MAPKAPK5 | 7 | 1 | 22 | 22 |
| ROCK-I | 3 | 4 | 12 | 11 |
| RON | −6 | −6 | 9 | −3 |
| ROS | −10 | −8 | 5 | −3 |
| TYRO3 | −9 | 14 | 22 | 2 |
| RPS6KA1 | 22 | 60 | 54 | 55 |
| PLK2 | −17 | 12 | 30 | 9 |
| Src(1-530) | −1 | 16 | 11 | |
| SRPK1 | 34 | 31 | 63 | 7 |
| TAK1 | −1 | 4 | 6 | 12 |
| TIE2 | 1 | 2 | −12 | 45 |
| TRKA | 10 | 76 | 56 | 62 |
| YES | −9 | 18 | 34 | 30 |
| ZAP70 | −18 | −8 | 2 | −2 |
| DAPK3 | 88 | 93 | 87 | 34 |
| ABL1(T3151) | −7 | 0 | | |
| ALK4 | −15 | −27 | | |
| ABL2 | 2 | 7 | | |
| AXL | 16 | 59 | | |
| BRSK1 | −1 | −3 | | |
| BRSK2 | 7 | 15 | | |
| BTK | −5 | −8 | | |
| CAMK2B | 11 | 14 | | |
| CAMK2G | 36 | 40 | | |
| CAMK2D | 41;6 | 40; 22 | | |
| CAMK4 | 2 | 3 | | |
| CDK2/cyclinE | −13 | 0 | | |
| CDK3/cyclinE | −19 | −3 | | |
| CDK5/p25 | 4 | 34 | | |
| CDK5/p35 | −7 | 26 | | |
| CHK2 | 5 | 20 | | |
| CHK2(1157T) (h) | 3 | 15 | | |
| CHK2(R145W) (h) | 0 | 6 | | |
| CK1 delta | −4 | 5 | | |
| cKit(D816V) | 2 | 17 | | |
| cKit(V654A) | 8 | 9 | | |
| CLK3 | 83 | 103 | | |

-continued

| KINASE | 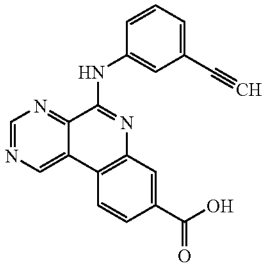 | 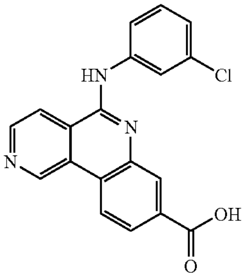 | 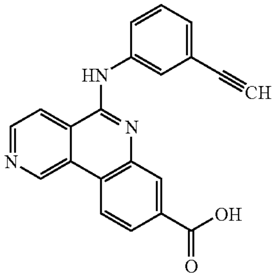 | 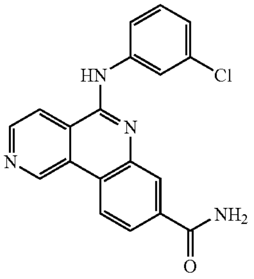 |
|---|---|---|---|---|
| SRC | −2 | 1 | 22 | |
| DAPK1 | 58 | 77 | | |
| DAPK2 | 91 | 94 | | |
| DCAMKL2 | −3 | 2 | | |
| DMPK | 4 | 3 | | |
| EPHA1 | −6 | 7 | | |
| EPHA2 | 2 | 16 | | |
| EPHA3 | −6 | 2 | | |
| EPHA4 | −3 | 10 | | |
| EPHA8 | −15 | −10 | | |
| EPHB1 | 1 | 21 | | |
| EPHB2 | 13 | 29 | | |
| EPHB3 | −36 | −24 | | |
| FGFR1 (V561M) | 12 | 16 | | |
| FGFR2 (N549H) | 4 | 18 | | |
| FGFR3 | −2 | 3 | | |
| FGFR4 | 14 | 14 | | |
| FGR | 39 | 38 | | |
| GCK | 1 | 26 | | |
| GRK5 | 11 | 74 | | |
| GRK6 | −2 | 44 | | |
| GSK3A | 51 | 56 | | |
| GSG2 | 4 | 45 | | |
| HIPK1 | 90 | 89 | | |
| IKK beta | 5 | 13 | | |
| IRAK1 | 4 | 32 | | |
| INSRR | −21 | −18 | | |
| ITK;Itk(h) | 0 | 4 | | |
| JAK3 | 8 | 37 | | |
| JNK1A1 | −9 | −7 | | |
| JNK2A2 | −7 | −12 | | |
| JNK3 | −3 | 4 | | |
| LIMK1 | 3 | 4 | | |
| LKB1 | −2 | 19 | | |
| MAPK2 | −4 | −1 | | |
| MAPK2(m) | −6 | −7 | | |
| MAPKAPK3 | −8 | 5 | | |
| MARK1 | 0 | 6 | | |
| MINK | −13 | −7 | | |
| MKK4(m) | −2 | −17 | | |
| MEK6 | 6 | 11 | | |
| MLCK | −3 | −4 | | |
| MRCKA | −10 | −19 | | |
| MRCKB | 0 | −4 | | |
| MSK1 | 19 | 16 | | |
| MSSK1 | −3 | 11 | | |
| MST2 | −6 | −8 | | |
| MST3 | 0 | 17 | | |
| MUSK | −6 | 3 | | |
| NEK11 | −2 | 0 | | |
| NEK3 | −12 | −9 | | |
| NEK6 | −3 | −1 | | |
| NEK7 | −14 | −20 | | |
| NLK | 3 | 24 | | |
| PAK3 | 21 | 16 | | |
| PAK4 | −12 | −12 | | |
| PAK5 | −8 | −10 | | |
| PAK6 | −14 | −1 | | |
| PAR-1B alpha | 7 | 8 | | |
| PASK | 87 | 85 | | |
| PDGFRB (V561D) | −4 | 13 | | |
| PIM2 | 25 | 39 | 6 | |
| PIM3 | 13 | 55 | −2 | |

-continued
| KINASE | 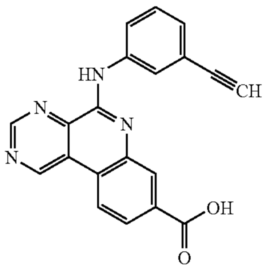 | 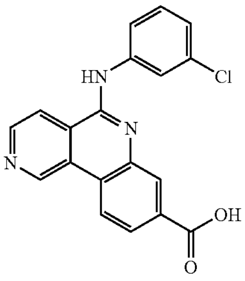 | 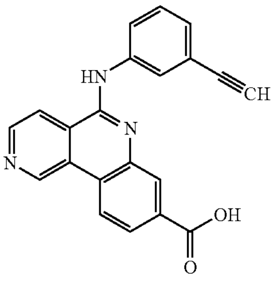 | 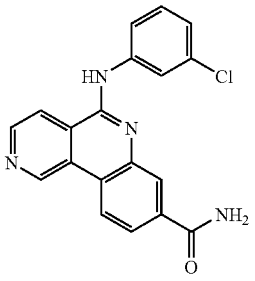 |
|---|---|---|---|---|
| AKT2 | −10 | −11 | | |
| AKT3 | 0 | −5 | | |
| PRKCB1 | 0 | 2 | | |
| PRKCB2 | 1 | 8 | | |
| PRKCG | 0 | 6 | | |
| PRKCD | 7 | 0 | | |
| PRKCE | 0 | −9 | | |
| PRKCZ | −9 | −12 | | |
| PRKCN | 2 | −3 | | |
| PRKCI | −5 | −4 | | |
| PRKCM | −4 | −5 | | |
| PRKG2 | 2 | −10 | | |
| PRK2 | 3 | 8 | | |
| PRKX | 3 | −2 | | |
| FRK | 3 | 5 | | |
| Pyk2 | −3 | −1 | | |
| RET | 14 | 38 | 35 | |
| RIPK2 | 2 | 26 | | |
| ROCK-II | −4 | 1 | | |
| RPS6KA3 | 34 | 67 | 53 | |
| RPS6KA2 | 37 | 65 | 59 | |
| RPS6KA6 | 22 | 80 | 65 | |
| p38-alpha | 1 | 33 | | |
| p38-alpha (T106M) | −8 | −3 | | |
| p38-beta | 5 | −1 | | |
| p38-gamma | 12 | 21 | | |
| p38-delta | −1 | 7 | | |
| SGK | −1 | 9 | | |
| SGK2 | 2 | 4 | | |
| SGK3 | 2 | −4 | | |
| SLK | −15 | −10 | | |
| SRPK2 | 36 | 34 | | |
| STK33 | 0 | 67 | | |
| SYK | −9 | 10 | | |
| TAO2 | 3 | 14 | | |
| TAO3 | 22 | 57 | | |
| TBK1 | 70 | 97 | | |
| TLK2 | 8 | 35 | | |
| TRKB | 10 | 24 | | |
| TSSK1 | −18 | −12 | | |
| TSSK2 | −9 | −11 | | |
| VRK2 | −3 | −3 | | |
| WNK2 | 11 | 4 | | |
| WNK3 | −17 | 15 | | |
| mTOR | 15 | | | |
| PLK1 | | | | |

Example 12

Synthetic Processes

Process 1

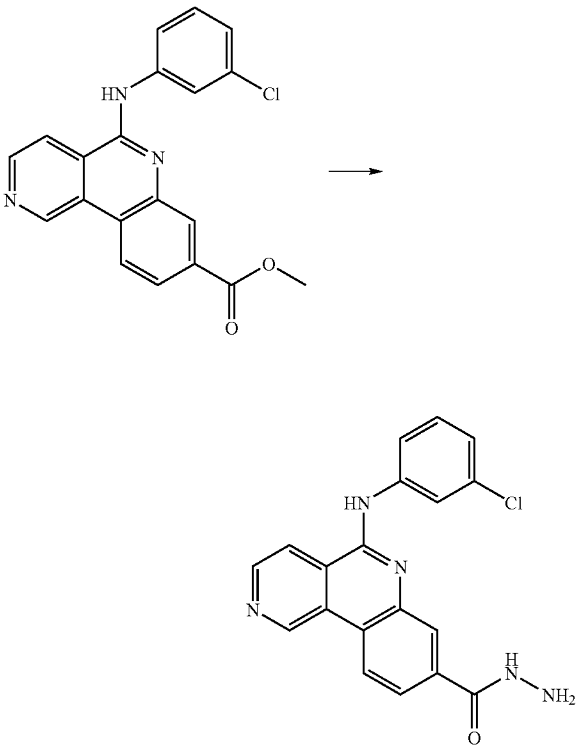

Methyl 5-(3-chlorophenylamino)benzo[c][2,6]naphthyridine-8-carboxylate (47 mg, 0129 mmol) was suspended in a mixture of methanol (1 ml) and hydrazine hydrate (1 ml). 3 drops of DMF were added and the mixture stirred at 60-70° C. for 2 hours. The volatiles were removed in vacuo. The resulting material was suspended in AcOEt/Hexanes, filtered and dried to afford 5-(3-chlorophenylamino)benzo[c][2,6]naphthyridine-8-carbohydrazide as solid (47 mg, 100% yield). LCMS (ES): 95% pure, m/z 364 $[M+1]^+$.

Process 2

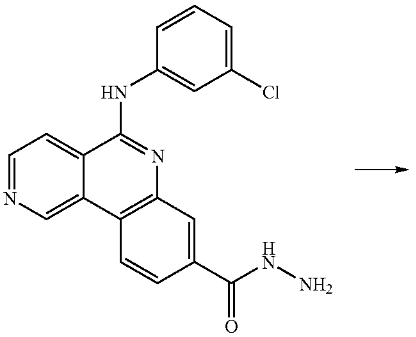

-continued

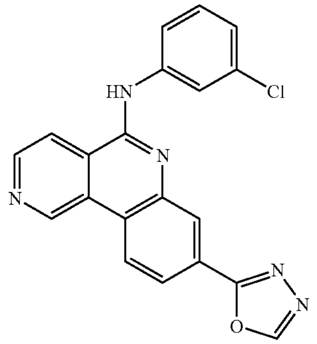

5-(3-chlorophenylamino)benzo[c][2,6]naphthyridine-8-carbohydrazide (1.0 eq, 21 mg, 0.057 mmol) was suspended in triethyl orthoformate (0.5 ml) and the mixture reacted in a microwave reactor at 120° C. for 80 minutes. The precipitate that formed upon cooling was filtered and dried to afford N-(3-chlorophenyl)-8-(1,3,4-oxadiazol-2-yl)benzo[c][2,6]naphthyridin-5-amine as a solid (12 mg, 56% yield). LCMS (ES): 95% pure, m/z 374 $[M+1]^+$.

Process 3

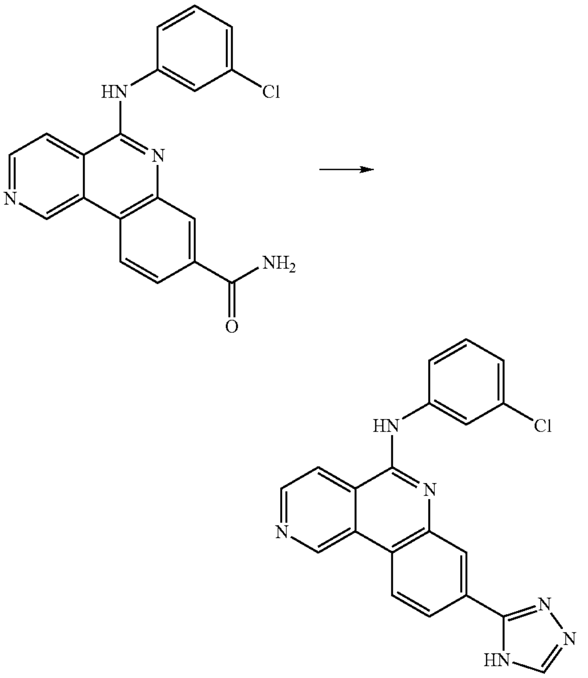

5-(3-chlorophenylamino)benzo[c][2,6]naphthyridine-8-carboxamide (1.0 eq, 36 mg) was stirred in N,N-dimethylformamide dimethyl acetal (2 ml) at 80° C. for 4 hours. The volatiles were removed in vacuo. Acetic acid was added (0.5 ml) and hydrazine hydrate (0.1 ml). The mixture was stirred at 80° C. for 1 hour. Water was added and the solid filtered and tried. After trituration in a mixture of $CH_2Cl_2$ and hexanes, N-(3-chlorophenyl)-8-(4H-1,2,4-triazol-3-yl)benzo[c][2,6]naphthyridin-5-amine was isolated as a solid (22 mg, 67% yield). LCMS (ES): 95% pure, m/z 373 $[M+1]^+$.

Process 4

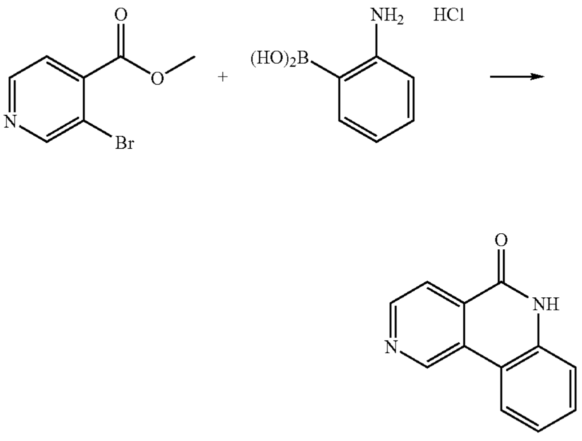

Methyl 3-bromoisonicotinate (1.0 eq, 1.76 g, 7.65 mmol), 2-aminophenylboronic acid hydrochloride (1.0 eq, 1.33 g, 7.67 mmol) and cesium carbonate (2.0 eq, 4.99 g, 15.31 mmol) were suspended in dioxane (15 ml). The mixture was degassed by bubbling nitrogen for 10 minutes. $PdCl_2$(dppf) (0.05 eq, 280 mg, 0.383 mmol) was added and the mixture was stirred at reflux for 2 hours. The resulting solid was filtered, washed with methanol, water and methanol and dried. Benzo[c][2,6]naphthyridin-5(6H)-one was isolated as an off-white solid (823 mg, 55% yield). LCMS (ES): 95% pure, m/z 197 $[M+1]^+$.

Process 5

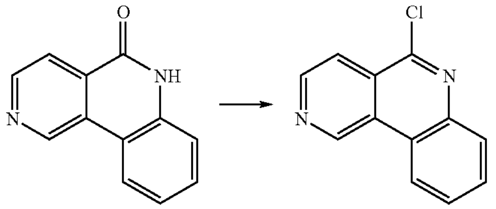

Benzo[c][2,6]naphthyridin-5(6H)-one (1.0 eq, 813 mg, 4.15 mmol) was stirred in phosphorus oxychloride (5.0 eq, 2 ml, 21.84 mmol) and acetonitrile (10 ml). The mixture was stirred at reflux for 5 hours. The mixture was poured on ice, and the resulting solid filtered and dried. 5-chlorobenzo[c][2,6]naphthyridine was isolated as a grey solid (459 mg, 52% yield). LCMS (ES): 95% pure, m/z 215 $[M+1]^+$.

Process 6

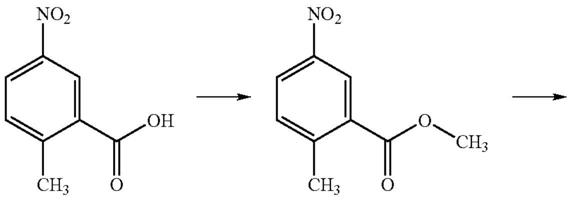

-continued

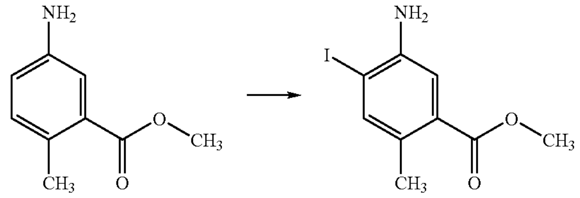

2-methyl-5-nitrobenzoic acid (24 g) was dissolved in methanol (240 ml) and concentrated sulfuric acid (8 ml). The mixture was stirred at reflux overnight. Upon cooling the ester crystallized out. The material was isolated by filtration to afford methyl 2-methyl-5-nitrobenzoate as a white solid (19.0 g, 74% yield). A second crop of material (4.92 g, 19% yield) was isolated upon concentration and addition of water to the mother liquor.

Methyl 2-methyl-5-nitrobenzoate (5.06 g) was suspended in methanol (100 ml). The mixture was degassed by bubbling nitrogen for 15 minutes. Pd/C 10% wet Degussa type E101 NE/WW (260 mg) was added and the mixture stirred under hydrogen atmosphere (balloon) overnight. The suspension was filtered and the solvents evaporated to afford methyl 5-amino-2-methylbenzoate as an orange oil (4.18 g, 97% yield).

Methyl 5-amino-2-methylbenzoate (1.0 eq, 3.75 g) was dissolved in acetic acid (70 ml). N-Iodosuccinimide (1.0 eq, 5.27 g) was added portionwise over 60 minutes. The mixture was stirred at room temperature for 30 minutes. Acetic acid was evaporated. The residue was diluted with ethyl acetate (80 ml) and neutralized with saturated sodium carbonate (80 ml). The organic layer was washed with 1M sodium thiosulfate (2×40 ml), then water (2×40 ml) and brine (2×40 ml). The material was purified by flash chromatography on silica gel (gradient 10% to 30% ethyl acetate in hexanes) to provide methyl 5-amino-4-iodo-2-methylbenzoate as a yellow-orange solid (3.19 g, 49% yield). GCMS>95% pure, m/z 291. $^1$H NMR (400 MHz, DMSO, $d_6$) δ 2.30 (s, 3H), 3.78 (s, 3H), 5.27 (br s, 2H), 7.24 (s, 1H), 7.54 (s, 1H).

Process 7

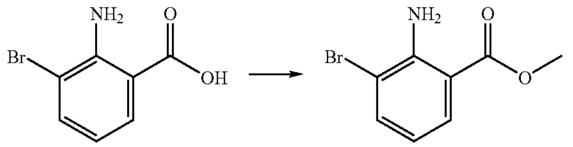

2-amino-3-bromobenzoic acid (1.00 g) was mixed with methanol (10 ml) and concentrated sulfuric acid (1 ml). The mixture was stirred at reflux for 31 hours. The solvent were evaporated, and saturated aqueous sodium bicarbonate was carefully added. The solid was extracted with $CH_2Cl_2$ (3×). The combined extracts were dried over $Na_2SO_4$ and the solvents removed in vacuo to afford methyl 2-amino-3-bromobenzoate as a semi-crystalline solid (976 mg, 91% yield). LCMS (ES): >85% pure, m/z 230 $[M+1]^+$.

Process 8

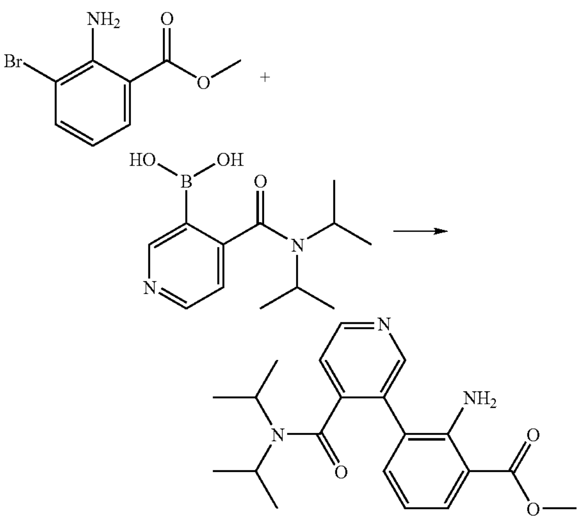

Methyl 2-amino-3-bromobenzoate (1.0 eq, 652 mg, 2.61 mmol) and 4-(diisopropylcarbamoyl)pyridin-3-ylboronic acid (prepared according to the procedure described in PCT patent application WO2005/105814), 1.0 eq, 600 mg, 2.61 mmol) were combined with cesium carbonate (2.0 eq, 1.699 g, 5.21 mmol) in dioxane containing 5% of water (6 ml). The mixture was degassed by bubbling nitrogen for 10 minutes. $PdCl_2$(dppf) (0.05 eq, 95 mg) was added and the reaction stirred at reflux for 2 hours. Dioxane was evaporated, water was added and the material extracted with $CH_2Cl_2$ (3×). The combined extracts were dried over $Na_2SO_4$ and the solvents removed in vacuo. The material was purified by flash chromatography on silica gel (eluant 0.5% MeOH in $CH_2Cl_2$) to afford methyl 2-amino-3-(4-(diisopropylcarbamoyl)pyridin-3-yl)benzoate as a greenish foam (244 mg, 31% yield). LCMS (ES): >95% pure, m/z 356 $[M+1]^+$.

Process 9

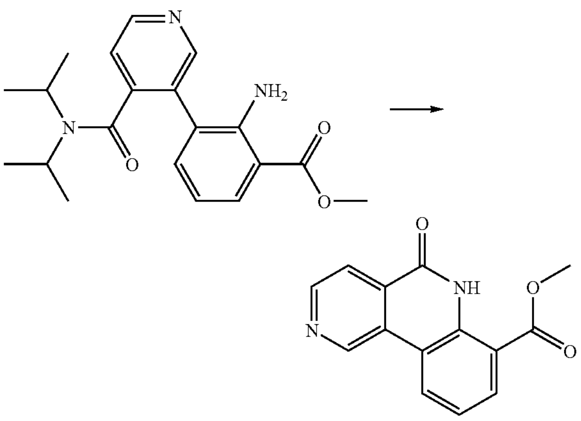

Methyl 2-amino-3-(4-(diisopropylcarbamoyl)pyridin-3-yl)benzoate (1.0 eq, 244 mg, 0.686 mmol) was dissolved under nitrogen atmosphere in anhydrous THF (1.5 ml). A NaHMDS solution (1.0 M in THF, 2.0 eq, 1.4 ml, 1.4 mmol) was added dropwise through syringe. The resulting suspension was stirred at room temperature for 1 hour. The reaction was quenched by addition of a saturated aqueous solution of ammonium chloride. The solid that formed was filtered and dried. After trituration in methanol and filtration, methyl 5-oxo-5,6-dihydrobenzo[c][2,6]naphthyridine-7-carboxylate was isolated as a grey fluffy solid (93 mg, 53% yield). LCMS (ES): >95% pure, m/z 255 $[M+1]^+$.

The molecules in the following table were prepared using a similar two step procedure from 4-(diisopropylcarbamoyl)pyridin-3-ylboronic acid and suitable 2-iodo or 2-bromo amines:

TABLE 27

| Structure | MW | LCMS(ES) m/z, [M + 1]+ |
|---|---|---|
| 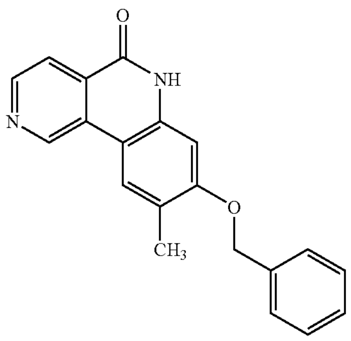 | 316.35 | 317 |
| 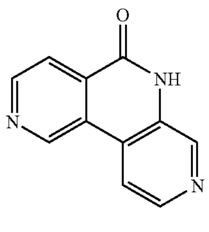 | 197.19 | 198 |
| 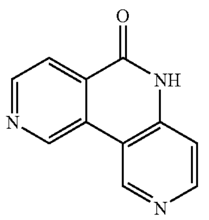 | 197.19 | 198 |
| 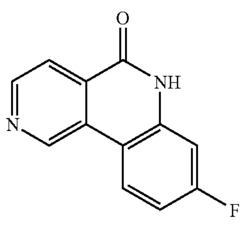 | 214.20 | 215 |

TABLE 27-continued

| Structure | MW | LCMS(ES) m/z, [M + 1]+ |
|---|---|---|
| 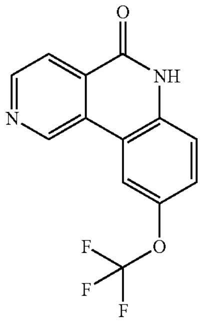 | 280.20 | 281 |
| 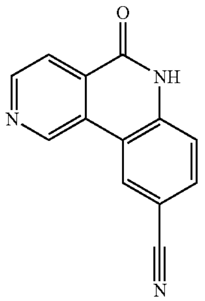 | 221.21 | 222 |
| 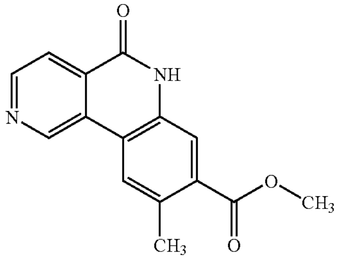 | 268.27 | 269 |
| 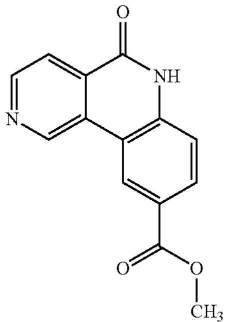 | 254 | 255 |

Process 10

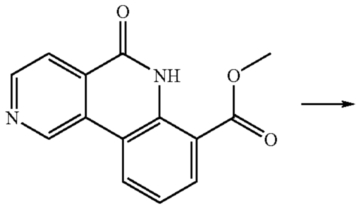

-continued

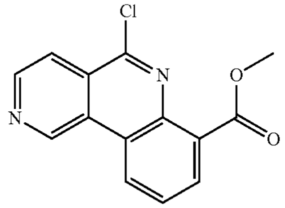

Methyl 5-oxo-5,6-dihydrobenzo[c][2,6]naphthyridine-7-carboxylate (1.0 eq, 85 mg, 0.334 mmol) was stirred in phosphorus oxychloride (2 ml) at 120° C. for 2 hours. The solvent was removed in vacuo. Ice and water were added. The resulting solid was filtered and dried to afford methyl 5-chlorobenzo[c][2,6]naphthyridine-7-carboxylate as a solid (84 mg, 92% yield). LCMS (ES): >95% pure, m/z 273 [M+1]$^+$.

The molecules in the following table were prepared using a similar procedure:

TABLE 28

| Structure | MW | LCMS(ES) m/z, [M + 1]+ |
|---|---|---|
| 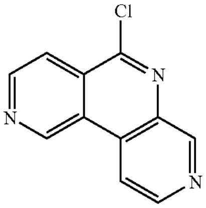 | 215.64 | 216 |
| 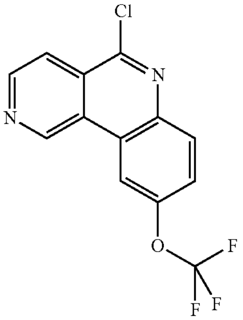 | 298.65 | 299 |
| 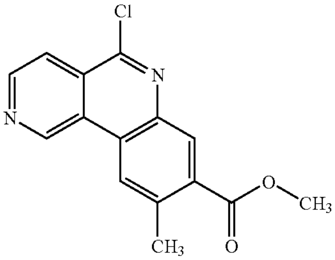 | 286.71 | 287 |

TABLE 28-continued

| Structure | MW | LCMS(ES) m/z, [M + 1]+ |
|---|---|---|
| 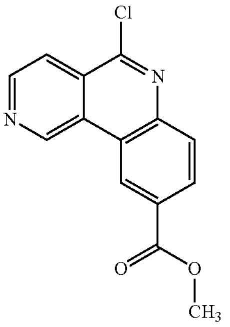 | 272.69 | 273 |

Process 11

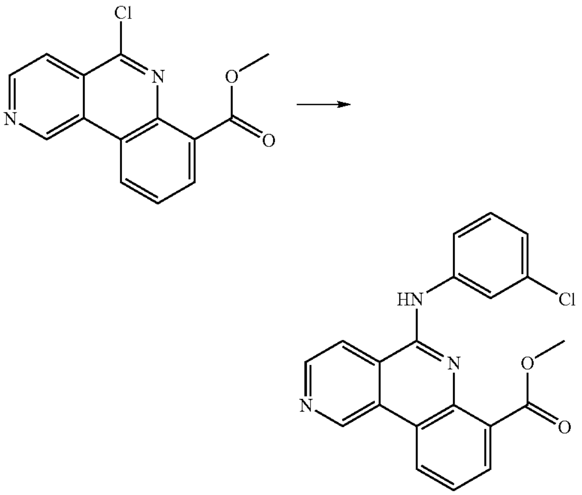

Methyl 5-chlorobenzo[c][2,6]naphthyridine-7-carboxylate (1.0 eq, 48 mg, 0.176 mmol) and 3-chloroaniline (3.0 eq, 60 ul, 0.56 mmol) were stirred under microwave heating at 120° C. in NMP (0.3 ml) for 10 minutes. Water was added and the solid isolated by filtration. Trituration in methanol and filtration afforded methyl 5-(3-chlorophenylamino)benzo[c][2,6]naphthyridine-7-carboxylate as a solid (29 mg, 45% yield). LCMS (ES): >85% pure, m/z 364 [M+1]$^+$.

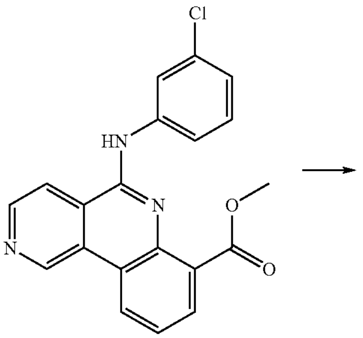

-continued

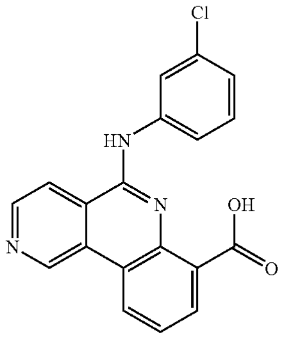

5-(3-chlorophenylamino)benzo[c][2,6]naphthyridine-7-carboxylate (29 mg) was stirred in ethanol (2 ml) and 6N aqueous NaOH (1 ml) at 60° C. for 30 minutes. Water and HCl were added to reach pH=1. The resulting precipitate was filtered, washed with water and dried to afford. LCMS (ES): >95% pure, m/z 350 [M+1]$^+$.

The molecules in the following table were prepared using a similar procedure.

TABLE 29

| Structure | MW | LCMS(ES) m/z [M + 1]+ |
|---|---|---|
| 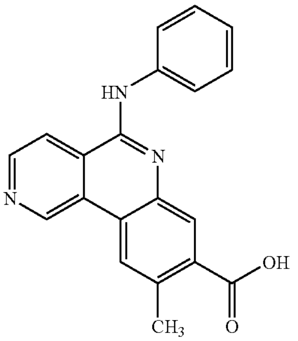 | 329.35 | 330 |
| 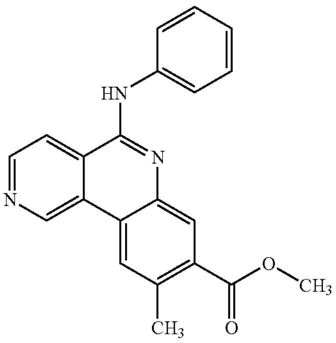 | 343.38 | 344 |

TABLE 29-continued
| Structure | MW | LCMS(ES) m/z [M + 1]+ |
|---|---|---|
| 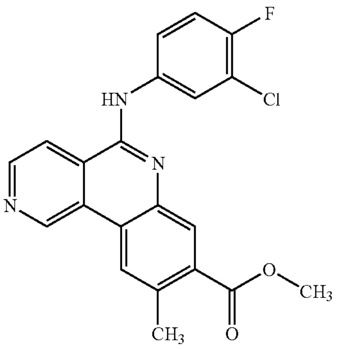 | 395.81 | 396 |
| 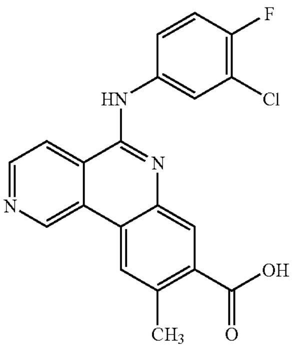 | 381.79 | 382 |
| 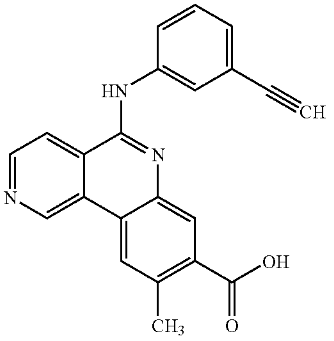 | 353.37 | 354 |
| 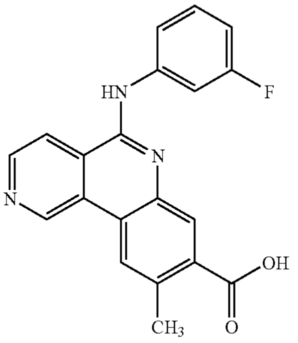 | 347.34 | 348 |
TABLE 29-continued
| Structure | MW | LCMS(ES) m/z [M + 1]+ |
|---|---|---|
| 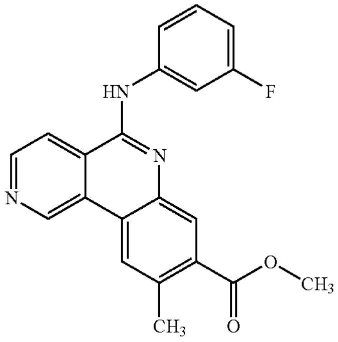 | 361.37 | 362 |
| 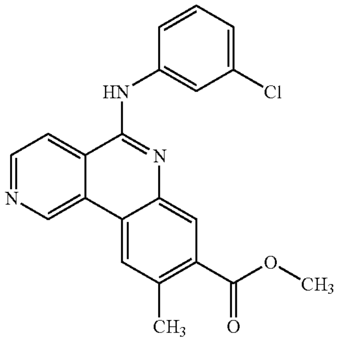 | 377.82 | 378 |
| 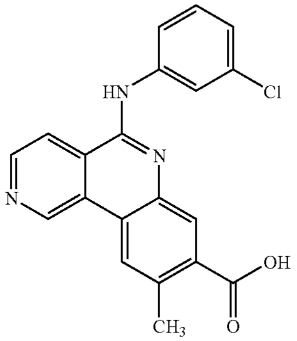 | 363.80 | 364 |
| 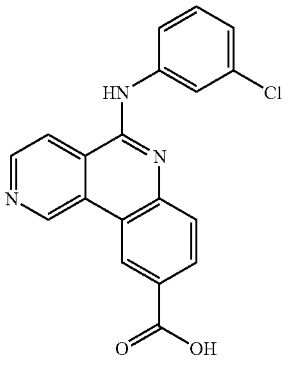 | 349.77 | 350 |

TABLE 29-continued

| Structure | MW | LCMS(ES) m/z [M + 1]+ |
|---|---|---|
| 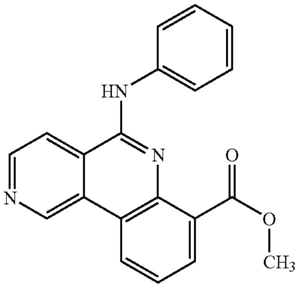 | 329.35 | 330 |
| 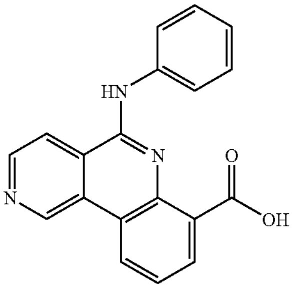 | 315.33 | 316 |

Process 12

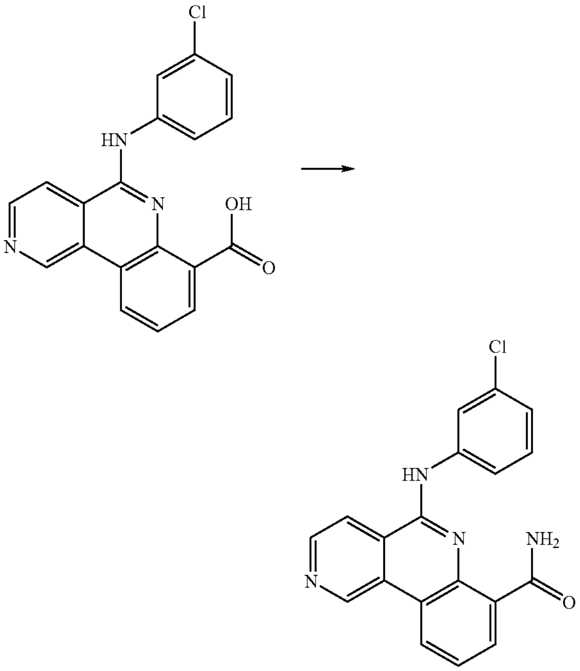

5-(3-chlorophenylamino)benzo[c][2,6]naphthyridine-7-carboxylic acid (20 mg) was reacted in NMP (0.4 ml) with HOBt.$H_2O$ (40 mg), ammonium chloride (40 mg), DIEA (100 ul) and EDCI (50 mg) at 70° C. for 1 hour. Water was added and the precipitate filtered and dried. After trituration in methanol and filtration, 5-(3-chlorophenylamino)benzo[c][2,6]naphthyridine-7-carboxamide was isolated as a solid (8 mg). LCMS (ES): >95% pure, m/z 349 $[M+1]^+$.

Process 13

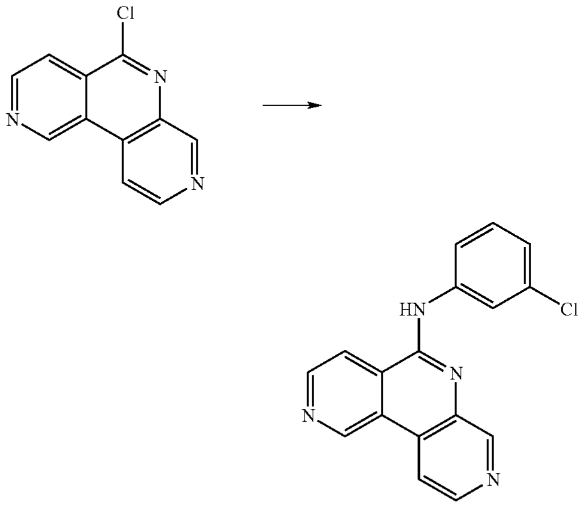

5-chloropyrido[4,3-c][1,7]naphthyridine (10 mg) was mixed in NMP (0.3 ml) with 3-chloroaniline (60 ul) and the mixture was heated at 120° C. for 10 min. Water was added and the resulting solid was filtered and dried. N-(3-chlorophenyl)pyrido[4,3-c][1,7]naphthyridin-5-amine was isolated as a solid (5 mg). LCMS (ES)>95% pure, m/z 307 $[M+1]^+$.

The molecules in the following table were prepared using a similar procedure.

TABLE 30

| Structure | MW | LCMS (ES) m/z [M + 1]+ |
|---|---|---|
| 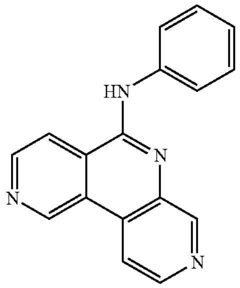 | 272.30 | 273 |
| 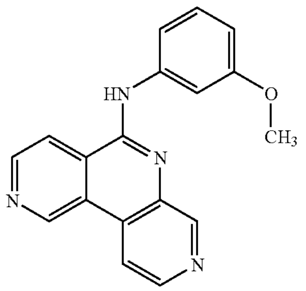 | 302.33 | 303 |

TABLE 30-continued
| Structure | MW | LCMS (ES) m/z [M + 1]+ |
|---|---|---|
| 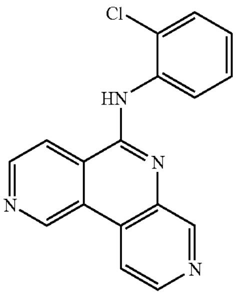 | 306.75 | 307 |
| 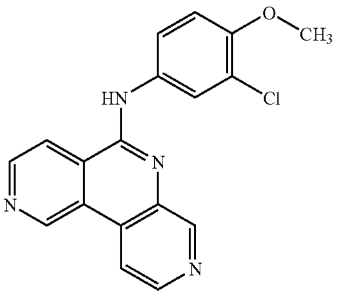 | 336.78 | 337 |
| 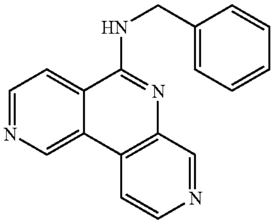 | 286.33 | 287 |
| 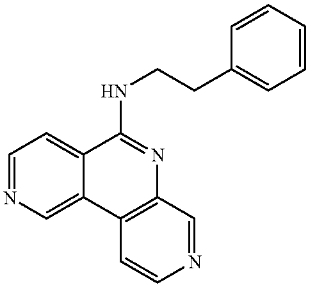 | 300.36 | 301 |
| 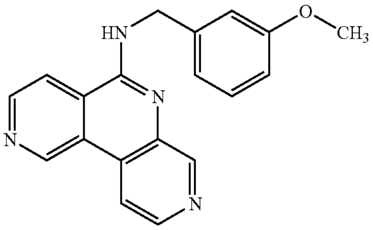 | 316.36 | 317 |
TABLE 30-continued
| Structure | MW | LCMS (ES) m/z [M + 1]+ |
|---|---|---|
| 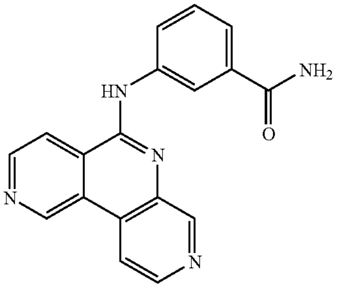 | 315.33 | 316 |
| 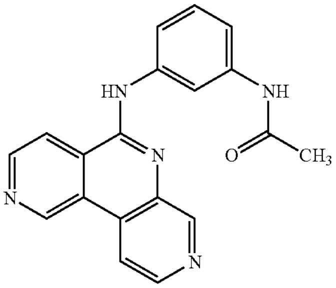 | 329.36 | 330 |
| 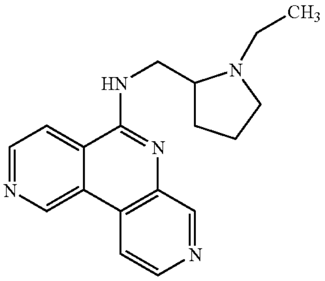 | 307.39 | 308 |
| 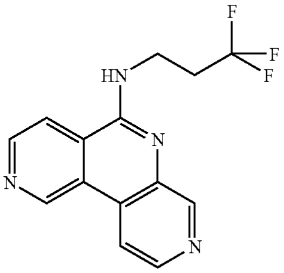 | 292.26 | 293 |
Process 14
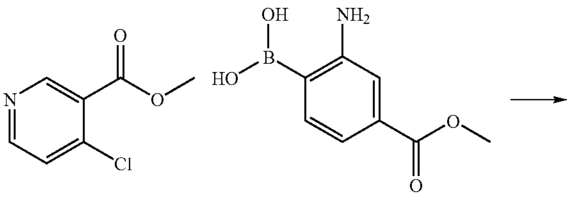

-continued

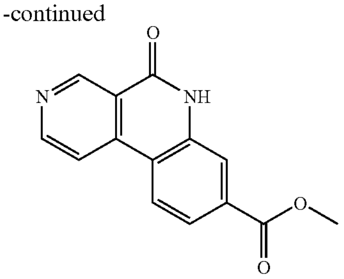

A solution of methyl 4-chloronicotinate (1.68 g, 6.05 mmol), 2-amino-4-(methoxycarbonyl)phenylboronic acid hydrochloride (3.17 g, 13.70 mmol), $Cs_2CO_3$ (8.90 g, 27.32 mmol), and $PdCl_2$(dppf) (335 mg, 0.46 mmol) in dioxane (5% $H_2O$, 60 mL) was heated at reflux for 40 min. The reaction was cooled to rt, the precipitate was collected by filtration, and washed (dioxane, $H_2O$, then with MeOH) to yield the desired lactam (2.07 g, 90%). LCMS (ES): >95% pure, m/z 255 $[M+1]^+$.

Process 15

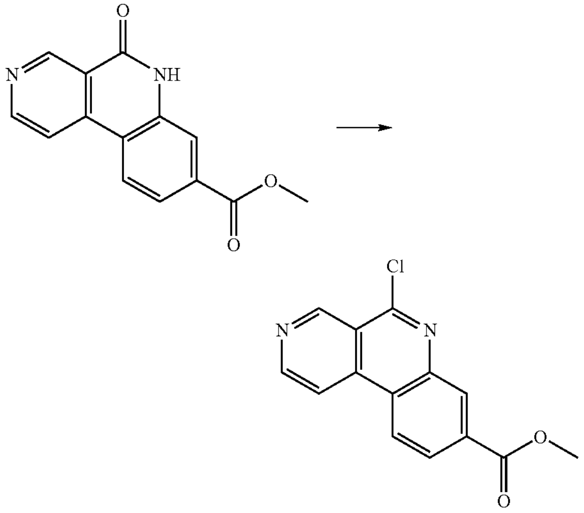

A solution methyl 5-oxo-5,6-dihydrobenzo[c][2,7]naphthyridine-8-carboxylate (650 mg, 2.56 mmol) in $POCl_3$ (4.0 mL) was heated at 12° C. for 2.5 h. The reaction was concentrated under reduced pressure and diluted with ACN (20 mL) and $H_2O$ (40 mL). The solution was neutralized with NaOH (3N) and the resulting precipitate was collected by filtration to give the desired chloride (600 mg, 86%). LCMS (ES): >95% pure, m/z 273 $[M+1]^+$.

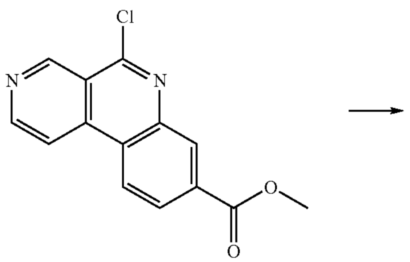

-continued

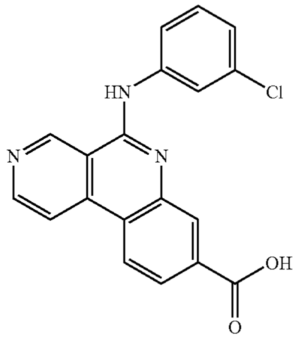

A solution methyl 5-chlorobenzo[c][2,7]naphthyridine-8-carboxylate (60 mg, 0.22 mmol) and 3-chloroaniline (50 uL) in NMP (1.0 mL) was heated at 80 C for 1 h. Aqueous NaOH (3N, 0.3 mL) was added and continued heating for additional 30 min. The reaction was cooled to rt and added HCl (1N) until precipitate formed. The solid was collected by filtration and washed with ACN to yield desired product (50 mg, 77%). LCMS (ES): >95% pure, m/z 350 $[M+1]^+$.

The molecules in the following table were prepared using a similar procedure.

TABLE 31

| Structure | MW | LCMS(ES) m/z, [M + 1]+ |
|---|---|---|
| 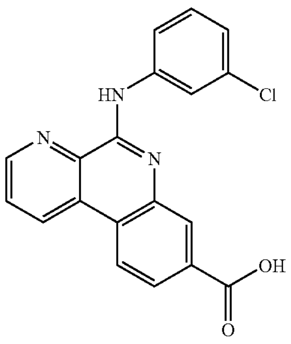 | 349.77 | 350 |
| 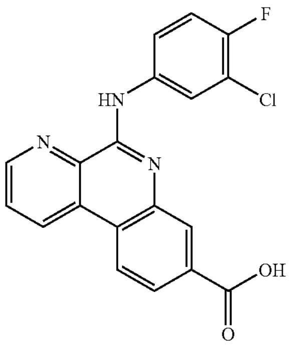 | 367.76 | 368 |

TABLE 31-continued
| Structure | MW | LCMS(ES) m/z, [M + 1]+ |
|---|---|---|
| 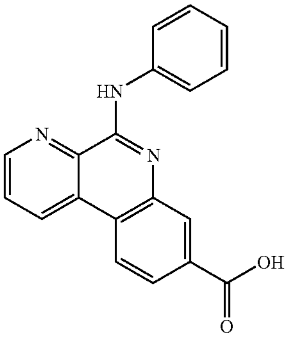 | 315.33 | 316 |
| 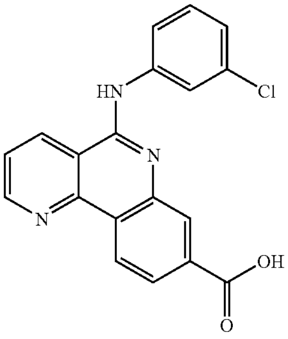 | 349.77 | 350 |
| 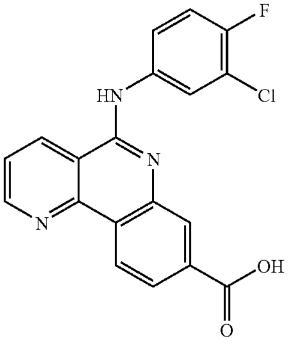 | 367.76 | 368 |
| 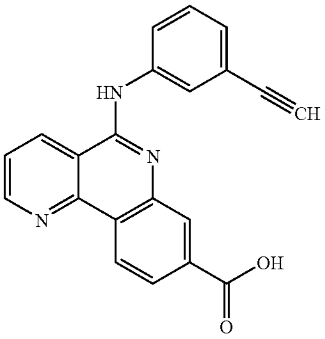 | 339.35 | 340 |
TABLE 31-continued
| Structure | MW | LCMS(ES) m/z, [M + 1]+ |
|---|---|---|
| 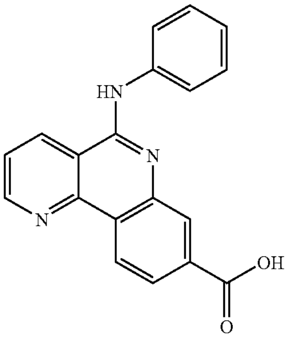 | 315.33 | 316 |
| 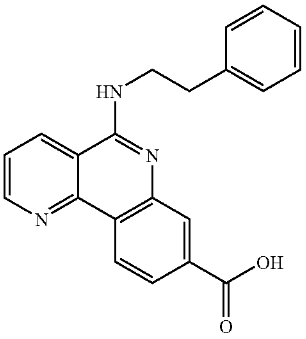 | 343.38 | 344 |
| 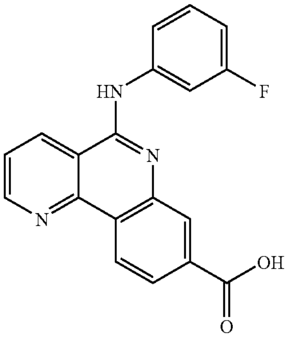 | 333.32 | 334 |
| 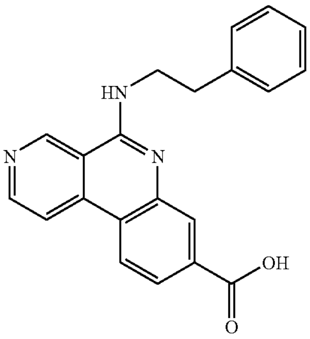 | 343.38 | 344 |

TABLE 31-continued
| Structure | MW | LCMS(ES) m/z, [M + 1]+ |
|---|---|---|
| 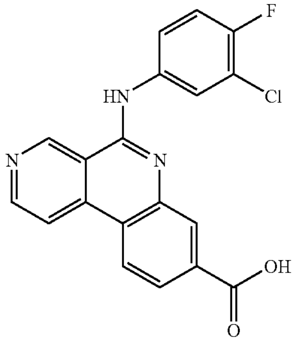 | 367.76 | 368 |
| 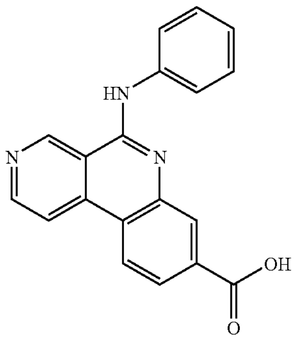 | 315.33 | 316 |
| 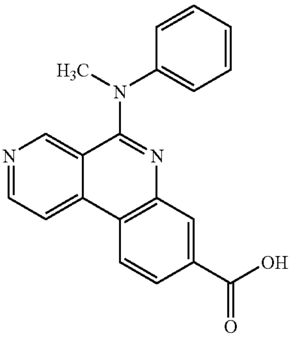 | 329.35 | 330 |
| 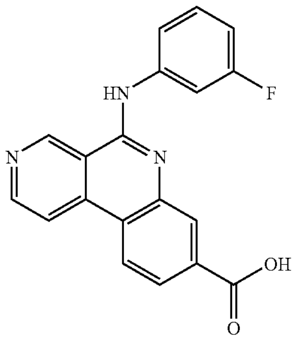 | 333.32 | 334 |
TABLE 31-continued
| Structure | MW | LCMS(ES) m/z, [M + 1]+ |
|---|---|---|
| 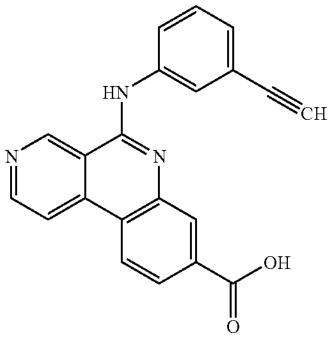 | 339.35 | 340 |
| 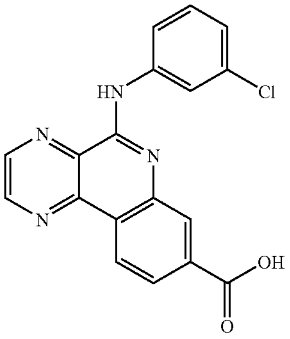 | 350.76 | 351 |
| 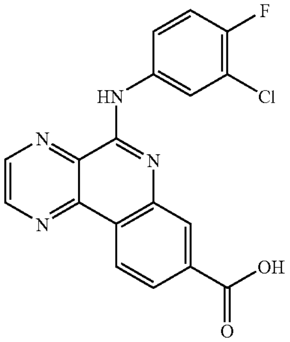 | 368.75 | 369 |
| 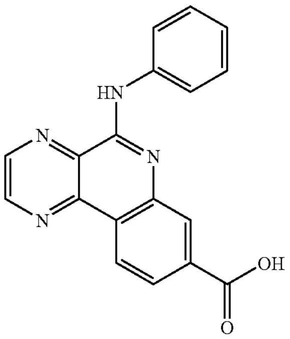 | 316.31 | 317 |

TABLE 31-continued

| Structure | MW | LCMS(ES) m/z, [M + 1]+ |
|---|---|---|
| 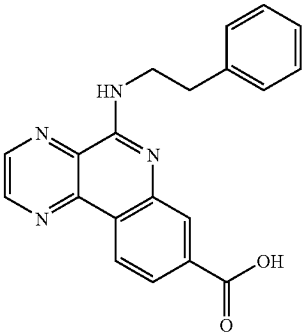 | 344.37 | 345 |
| 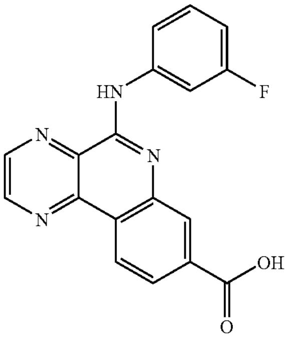 | 334.30 | 335 |
| 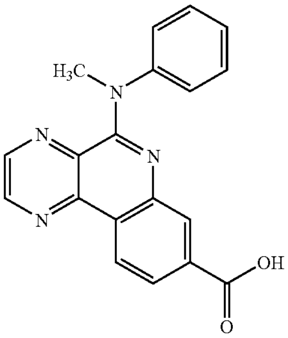 | 330.34 | 331 |
| 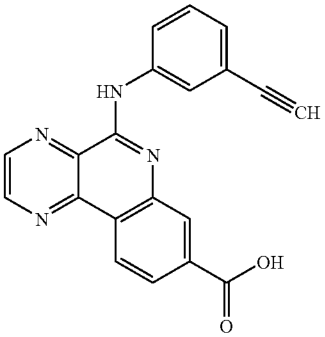 | 340.33 | 341 |

Process 16

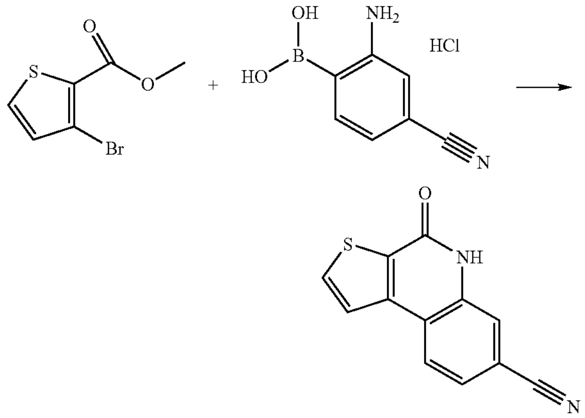

Methyl-3-bromothiophene carboxylate (1.0 eq, 2.42 g, 10.95 mmol), 2-amino-4-cyanophenylboronic acid hydrochloride (1.05 eq, 2.28 g, 11.49 mmol) and cesium carbonate (2.0 eq, 7.13 g, 21.9 mmol) were suspended in dioxane (25 ml) containing 5% water. The mixture was degassed by bubbling nitrogen for 10 minutes. $PdCl_2$(dppf) (0.05 eq, 400 mg, 0.55 mmol) was added and the mixture was stirred at reflux for 1.5 hours. The mixture was cooled down, the solid filtered, washed with dioxane, water and methanol. After drying in vacuo, 4-oxo-4,5-dihydrothieno[2,3-c]quinoline-7-carbonitrile was isolated as a solid (1.81 g, 73% yield). LCMS (ES) m/z 227 $[M+1]^+$.

The molecules in the following table were prepared using a similar procedure:

TABLE 32

| Structure | MW | LCMS (ES) m/z [M + 1]+ |
|---|---|---|
| 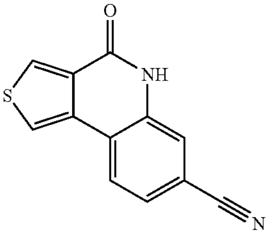 | 226.3 | 227 |
| 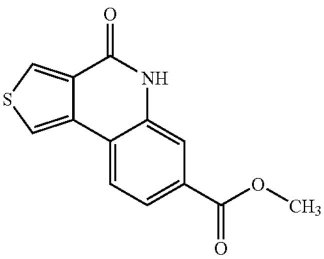 | 259.0 | 260 |

Process 17

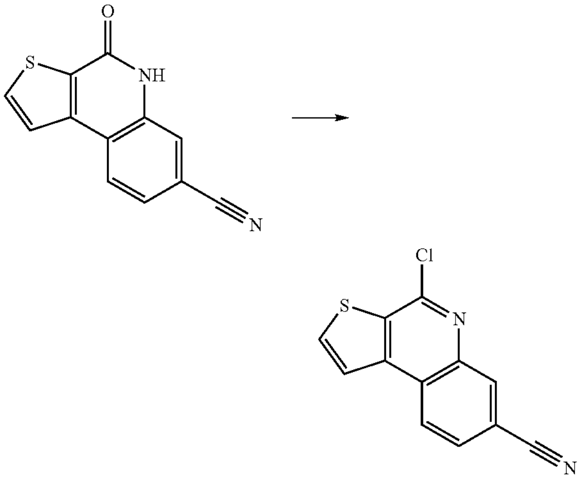

4-oxo-4,5-dihydrothieno[2,3-c]quinoline-7-carbonitrile (1.0 eq, 1.22 g, 5.40 mmol) was stirred under reflux in acetonitrile (12 ml) and phosphorus oxychloride (5.0 eq, 2.5 ml, 26.8 mmol) for 6 hours. The volatiles were removed in vacuo, water and ice were added. The resulting solid was filtered, washed with water and dried to afford 4-chlorothieno[2,3-c] quinoline-7-carbonitrile as a light brown solid (1.18 g, 90% yield). LCMS (ES)>95% pure, m/z 245 $[M+1]^+$.

The molecules in the following table were prepared using a similar procedure:

TABLE 33

| Structure | MW | LCMS (ES) m/z [M + 1]+ |
|---|---|---|
| 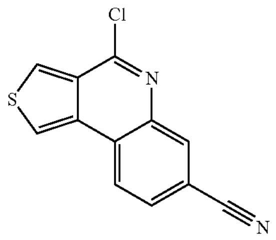 | 244 | 245 |
| 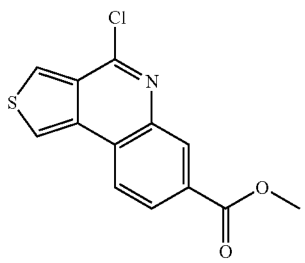 | 277 | 278 |

Process 18

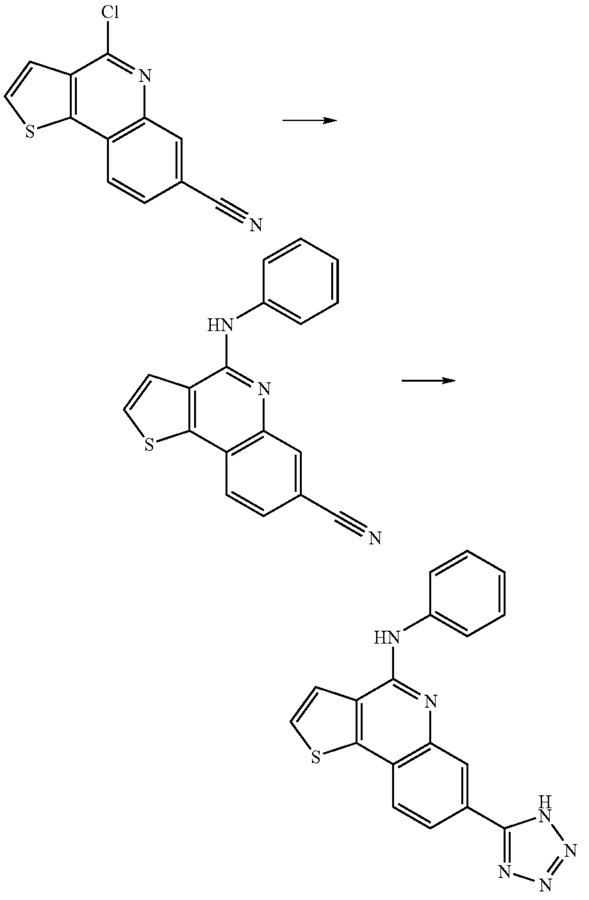

4-chlorothieno[3,2-c]quinoline-7-carbonitrile (1.0 eq, 23 mg, 0.094 mmol), aniline (0.1 ml) and NMP (0.1 ml) were mixed in a vial. The mixture was heated in a microwave oven at 120° C. for 10 nm. Water was added and the resulting solid 4-(phenylamino)thieno[3,2-c]quinoline-7-carbonitrile was filtered and dried. LCMS (ES): 95% pure, m/z 302 $[M+1]^+$. This material was mixed in a vial with DMF (0.5 ml), $NH_4Cl$ (50 mg) and $NaN_3$ (50 mg). The mixture was stirred at 120° C. for 3 hours. After addition of water and filtration, N-phenyl-7-(1H-tetrazol-5-yl)thieno[3,2-c]quinolin-4-amine was isolated as a beige solid (13 mg, 41% yield). LCMS (ES): 95% pure, m/z 345 $[M+1]^+$, 317 $[M+1-N_2]^+$. $^1$H NMR (DMSO-$d_6$, 400 MHz) δ 7.07 (t, J=7.2, 1H), 7.40 (t, J=7.6, 2H), 8.00 (dd, J=1.6, J=8.4, 1H), 8.04 (d, J=5.2, 1H), 8.10 (dd, J=1.2, J=8.8, 2H), 8.19 (d, J=8.0, 1H), 8.25 (d, J=5.6, 1H), 8.43 (d, J=1.6, 1H), 9.34 (s, 1H) ppm.

Process 19

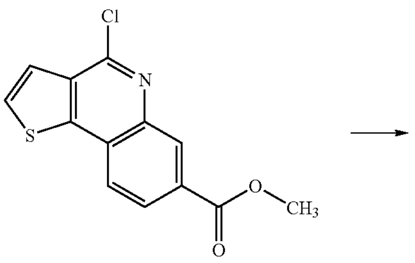

-continued

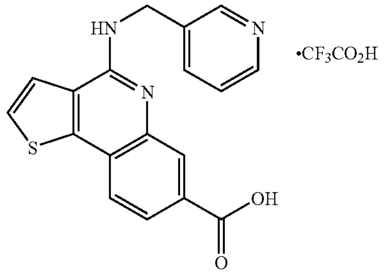

4-chlorothieno[3,2-c]quinoline-7-carboxylate (10 mg, 0.036 mmol) was suspended in NMP (0.1 ml) and 3-aminomethylpyridine (0.1 ml). The mixture was heated in a microwave oven at 120° C. for 10 nm. The reaction mixture was dissolved in a mixture of NMP and MeOH and the ester intermediate purified by preparative HPLC. After genevac evaporation of the solvents, the resulting solid was dissolved in a 1:1 mixture of THF and MeOH (0.6 ml). 5N aqueous LiOH (0.2 ml) was added and the mixture stirred at room temperature for 17 hrs. Water and aqueous HCl were added and the solution of 4-(pyridin-3-ylmethylamino)thieno[3,2-c]quinoline-7-carboxylic acid was purified by preparative HPLC. Removal of the solvents by genevac evaporation provided compound 4-(pyridin-3-ylmethylamino)thieno[3,2-c]quinoline-7-carboxylic acid as a white solid (10 mg, 62% yield). LCMS (ES): 95% pure, m/z 336 $[M+1]^+$. $^1H$ NMR ($CDCl_3$, 400 MHz) δ 5.23 (s, 2H), 7.71-7.78 (m, 4H), 8.11 (d, J=5.6, 1H), 8.47 (d, J=8.0, 1H), 8.49 (d, J=0.8, 1H), 8.62 (d, J=5.2, 1H), 8.97 (s, 1H) ppm.

The molecules in the following table were prepared using a procedure similar to processes 18 and 19, using the appropriate starting materials.

TABLE 34

| Structure | MW | LCMS (ES) m/z, [M + 1]+ |
|---|---|---|
| 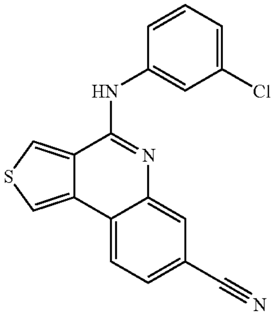 | 335.81 | 336 |

TABLE 34-continued

| Structure | MW | LCMS (ES) m/z, [M + 1]+ |
|---|---|---|
| 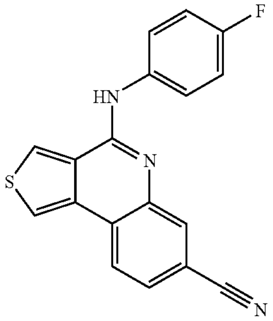 | 319.36 | 320 |
| 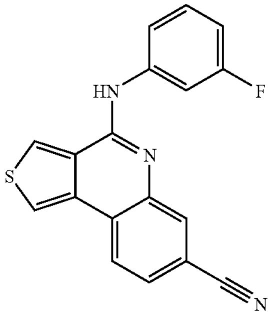 | 319.36 | 320 |
| 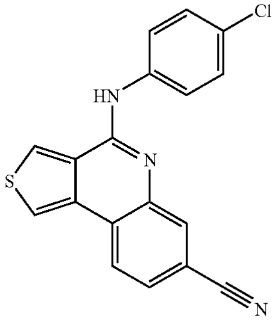 | 335.81 | 336 |
| 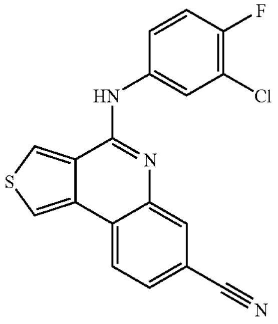 | 353.80 | 354 |

TABLE 34-continued
| Structure | MW | LCMS (ES) m/z, [M + 1]+ |
|---|---|---|
| 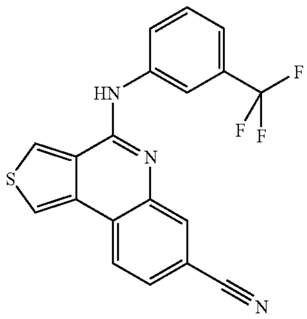 | 369.36 | 370 |
| 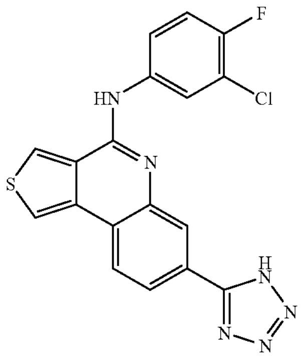 | 396.83 | 397 |
| 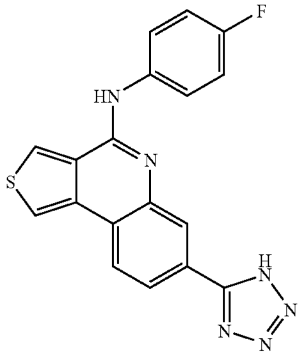 | 362.38 | 363 |
| 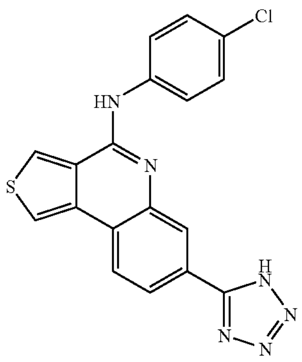 | 378.84 | 379 |
TABLE 34-continued
| Structure | MW | LCMS (ES) m/z, [M + 1]+ |
|---|---|---|
| 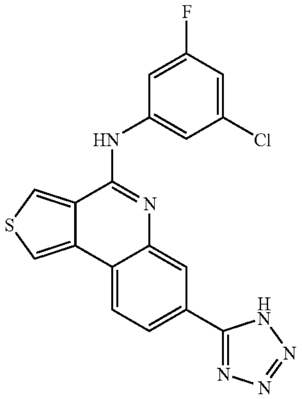 | 396.83 | 397 |
| 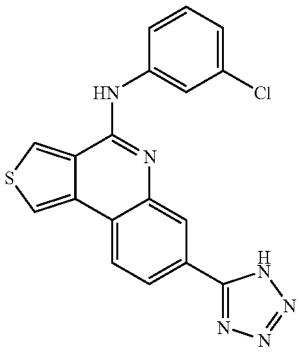 | 378.84 | 379 |
| 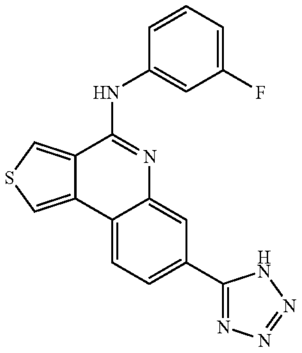 | 362.38 | 363 |
| 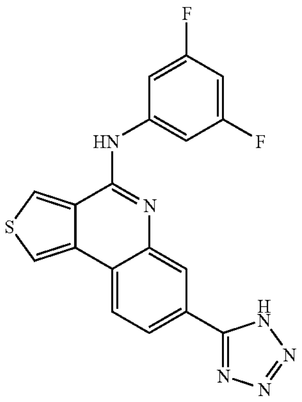 | 380.37 | 381 |

TABLE 34-continued
| Structure | MW | LCMS (ES) m/z, [M + 1]+ |
|---|---|---|
| 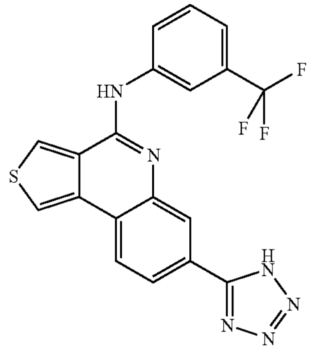 | 412.39 | 413 |
| 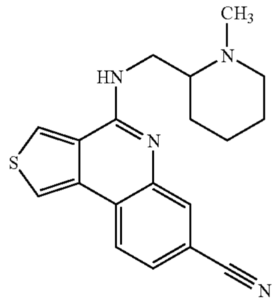 | 336.45 | 337 |
| 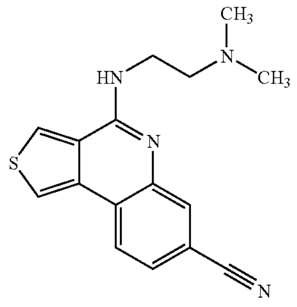 | 296.39 | 297 |
| 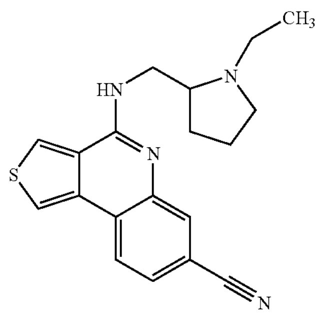 | 336.45 | 337 |
TABLE 34-continued
| Structure | MW | LCMS (ES) m/z, [M + 1]+ |
|---|---|---|
| 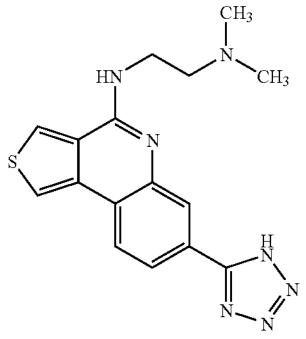 | 339.42 | 340 |
| 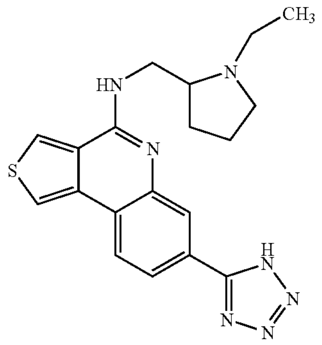 | 379.48 | 380 |
| 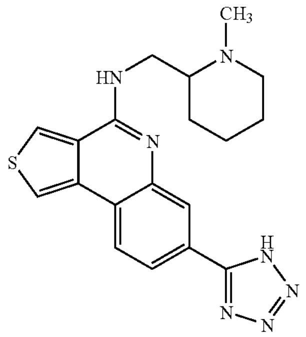 | 379.48 | 380 |
| 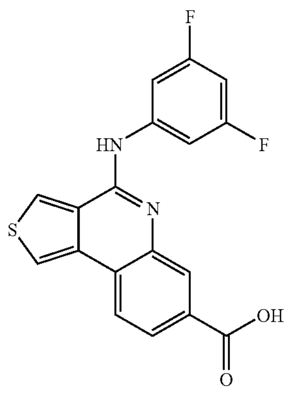 | 356.35 | 357 |

TABLE 34-continued
| Structure | MW | LCMS (ES) m/z, [M + 1]+ |
|---|---|---|
| 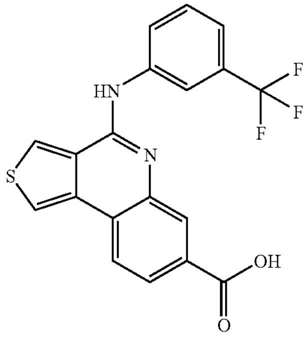 | 388.36 | 389 |
| 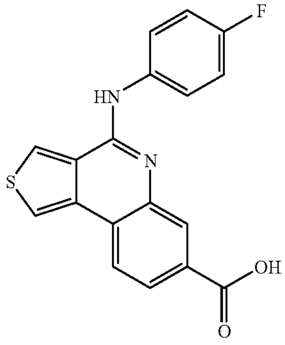 | 338.36 | 339 |
| 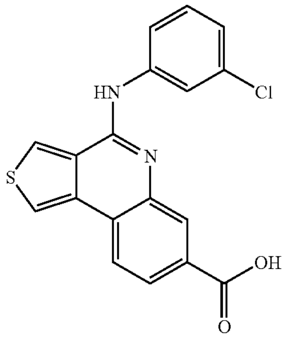 | 354.81 | 355 |
| 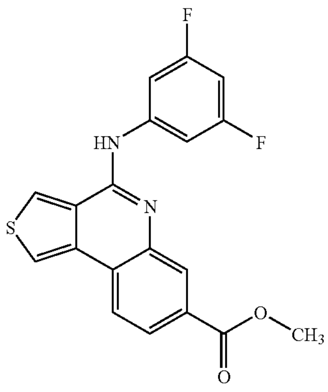 | 370.37 | 371 |
| 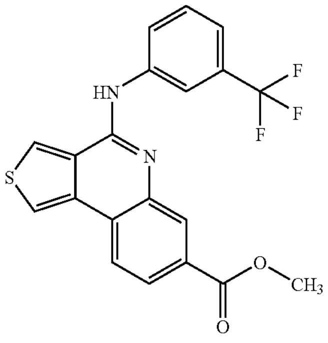 | 402.39 | 403 |
| 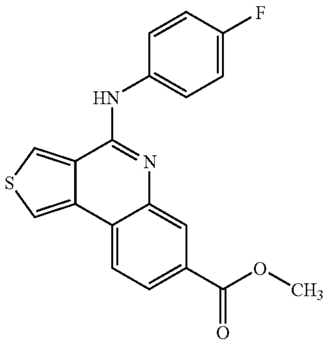 | 352.38 | 353 |
| 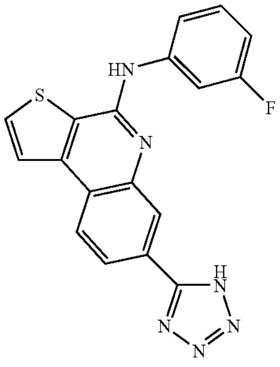 | 362.38 | 363 |
| 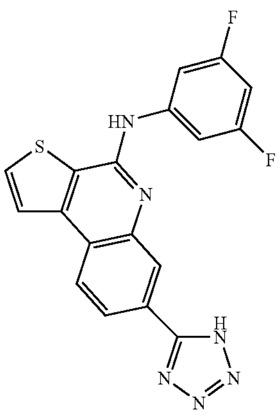 | 380.37 | 381 |

TABLE 34-continued
| Structure | MW | LCMS (ES) m/z, [M + 1]+ |
|---|---|---|
| 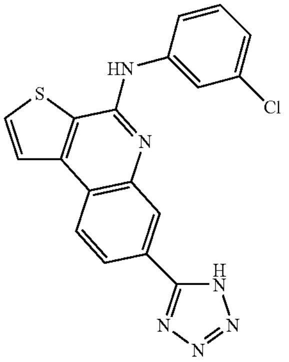 | 378.84 | 379 |
| 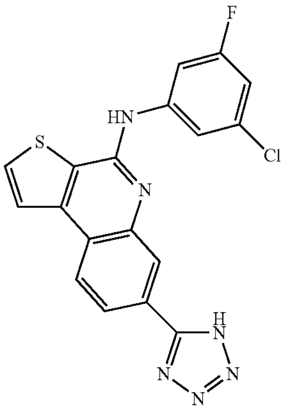 | 396.83 | 397 |
| 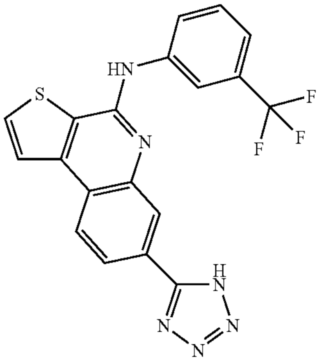 | 412.39 | 413 |
| 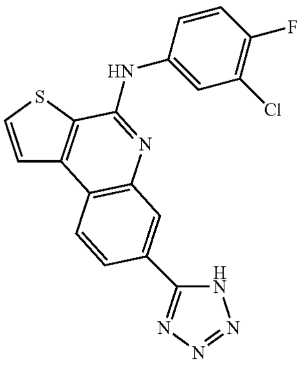 | 396.83 | 397 |
TABLE 34-continued
| Structure | MW | LCMS (ES) m/z, [M + 1]+ |
|---|---|---|
| 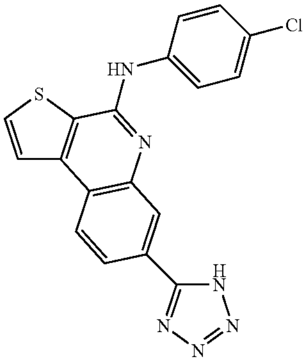 | 378.84 | 379 |
| 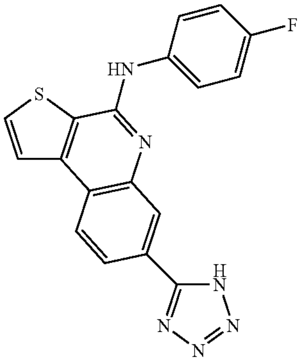 | 362.38 | 363 |
| 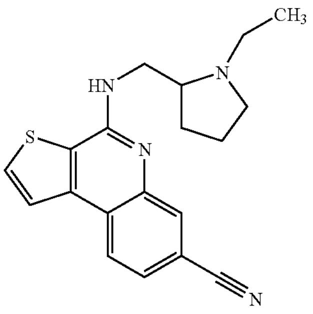 | 336.45 | 337 |
| 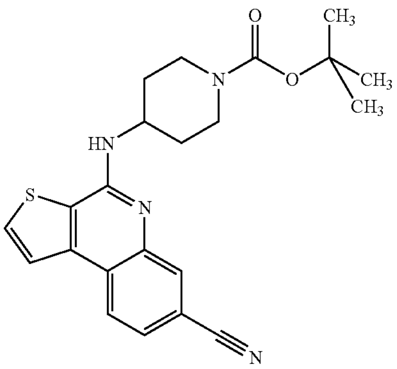 | 408.52 | 409 |

TABLE 34-continued

| Structure | MW | LCMS (ES) m/z, [M + 1]+ |
|---|---|---|
| 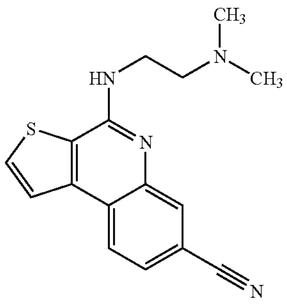 | 296.39 | 297 |
| 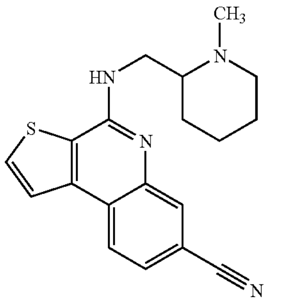 | 336.45 | 337 |
| 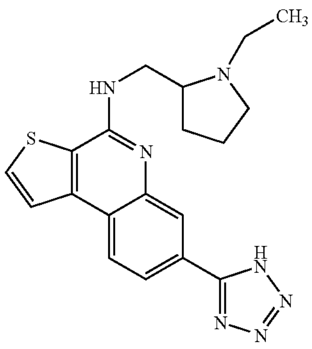 | 379.48 | 380 |
| 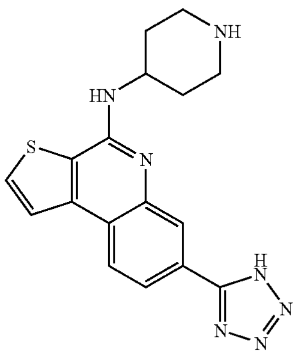 | 351.43 | 352 |
| 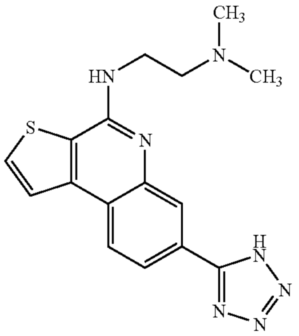 | 339.42 | 340 |
| 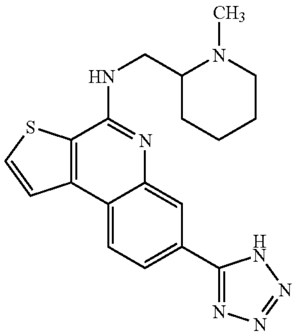 | 379.48 | 380 |

Process 20

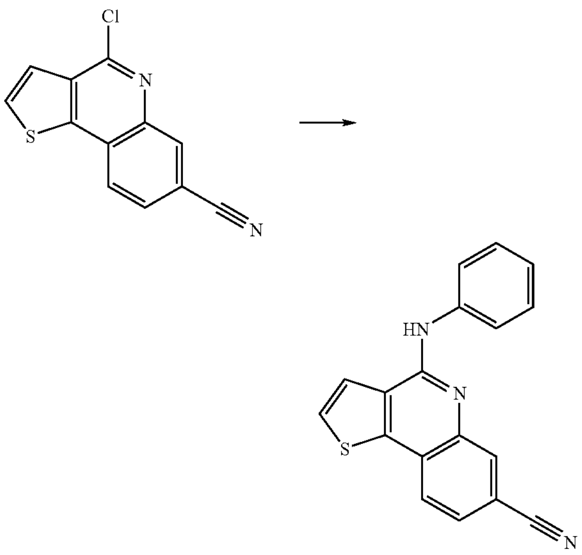

4-chlorothieno[3,2-c]quinoline-7-carbonitrile (1.0 eq, 23 mg, 0.094 mmol), aniline (0.1 ml) and NMP (0.1 ml) were mixed in a vial. The mixture was heated in a microwave oven at 120° C. for 10 nm. Water was added and the resulting solid 4-(phenylamino)thieno[3,2-c]quinoline-7-carbonitrile was filtered and dried. LCMS (ES): 95% pure, m/z 302 $[M+1]^+$ The molecules in the following table were prepared using a similar procedure.

TABLE 35
| Structure | MW | LCMS (ES) m/z, [M + 1]+ |
| --- | --- | --- |
| 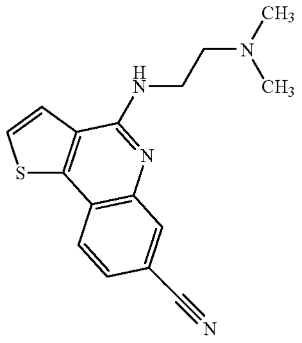 | 296.39 | 297 |
| 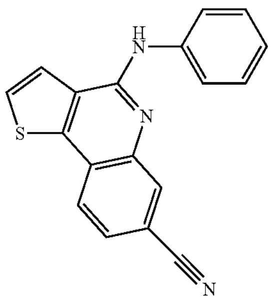 | 301.37 | 302 |
| 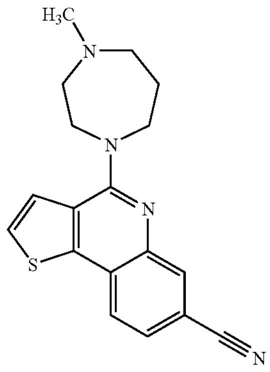 | 322.43 | 323 |
| 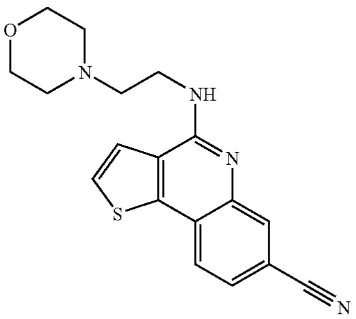 | 338.43 | 339 |
TABLE 35-continued
| Structure | MW | LCMS (ES) m/z, [M + 1]+ |
| --- | --- | --- |
| 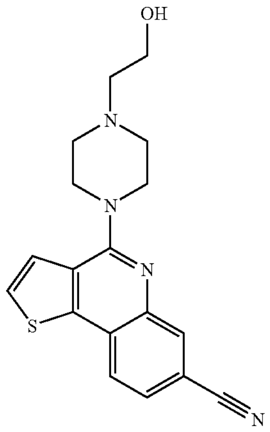 | 338.43 | 339 |
| 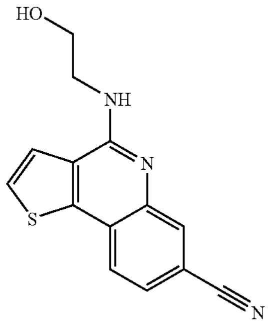 | 269.32 | 270 |
| 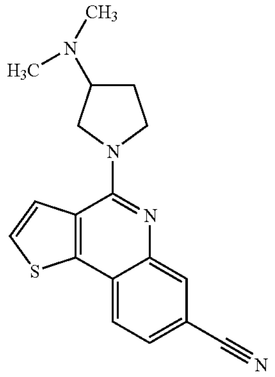 | 322.43 | 323 |
| 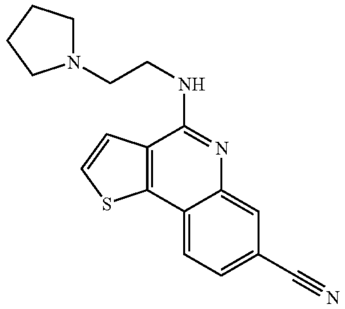 | 322.43 | 323 |

TABLE 35-continued
| Structure | MW | LCMS (ES) m/z, [M + 1]+ |
|---|---|---|
| 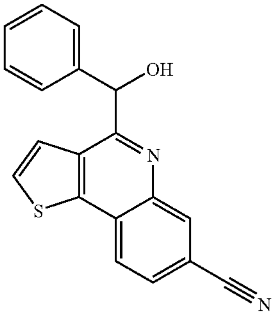 | 345.42 | 346 |
| 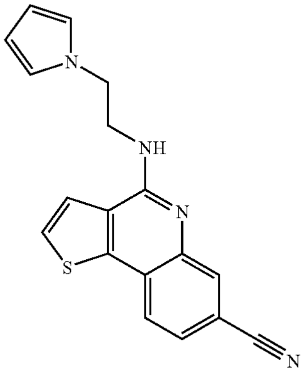 | 318.40 | 319 |
| 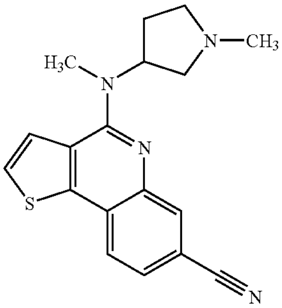 | 322.43 | 323 |
| 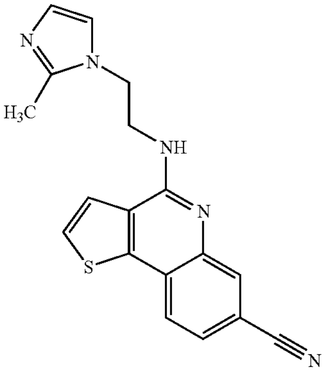 | 333.41 | 334 |
| 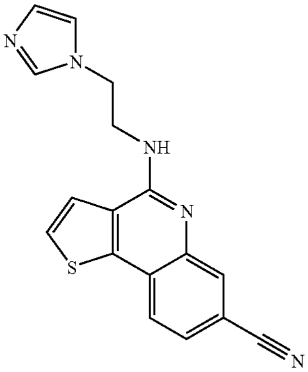 | 319.38 | 320 |
| 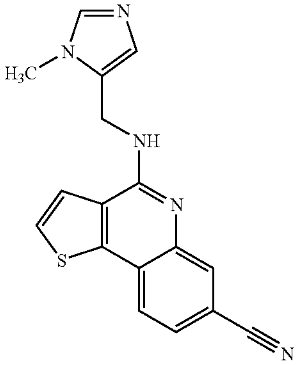 | 319.38 | 320 |
| 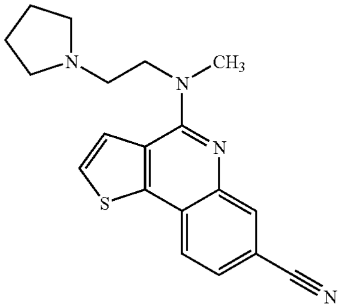 | 336.45 | 337 |
| 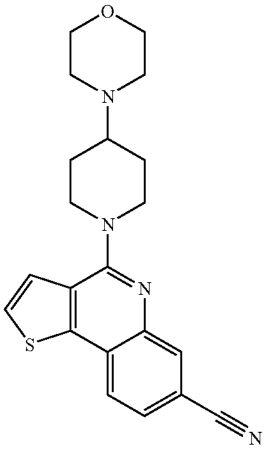 | 378.49 | 379 |

TABLE 35-continued
| Structure | MW | LCMS (ES) m/z, [M + 1]+ |
|---|---|---|
| 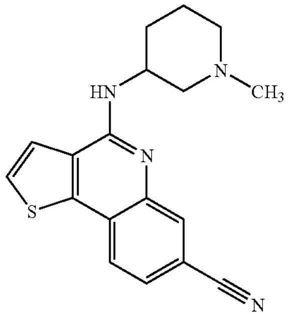 | 322.43 | 323 |
| 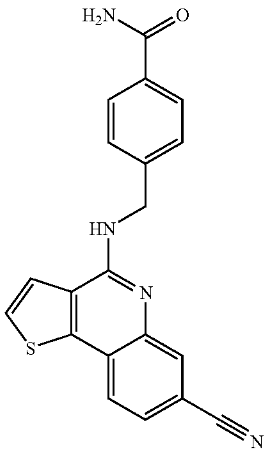 | 358.42 | 359 |
| 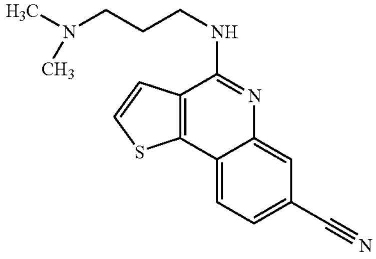 | 310.42 | 311 |
| 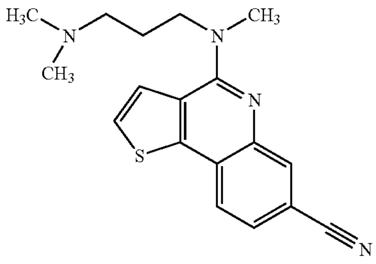 | 324.44 | 325 |
TABLE 35-continued
| Structure | MW | LCMS (ES) m/z, [M + 1]+ |
|---|---|---|
| 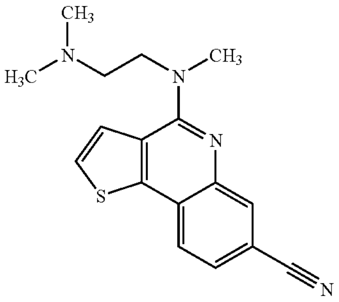 | 310.42 | 311 |
| 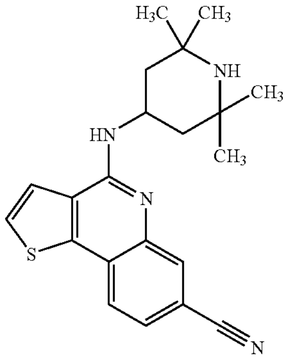 | 364.51 | 365 |
| 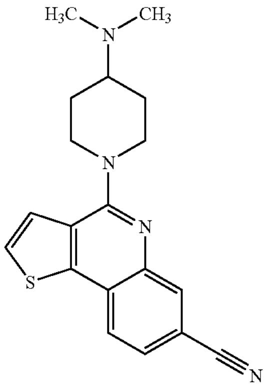 | 336.45 | 337 |
| 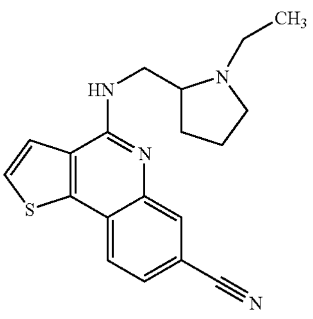 | 336.45 | 337 |

TABLE 35-continued
| Structure | MW | LCMS (ES) m/z, [M + 1]+ |
|---|---|---|
| 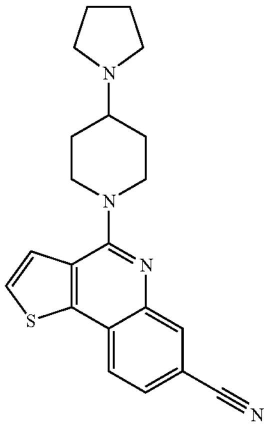 | 362.49 | 363 |
| 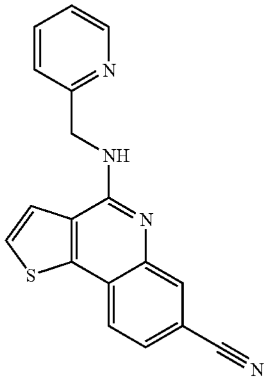 | 316.38 | 317 |
| 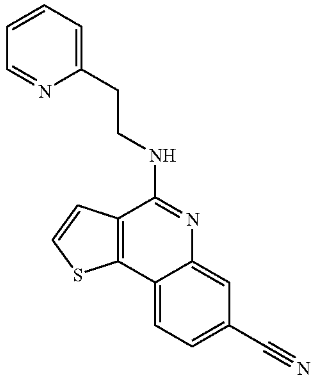 | 330.41 | 331 |
| 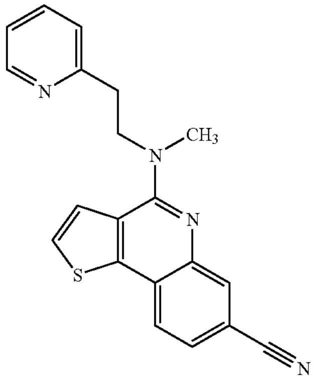 | 344.43 | 345 |
TABLE 35-continued
| Structure | MW | LCMS (ES) m/z, [M + 1]+ |
|---|---|---|
| 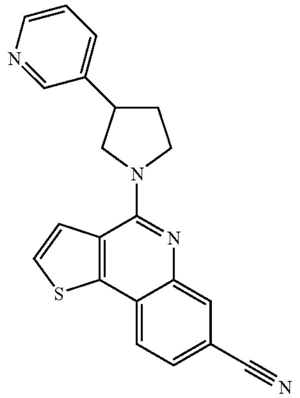 | 356.44 | 357 |
| 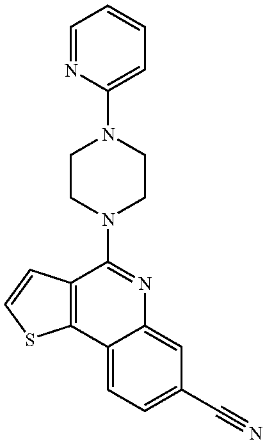 | 371.46 | 372 |
| 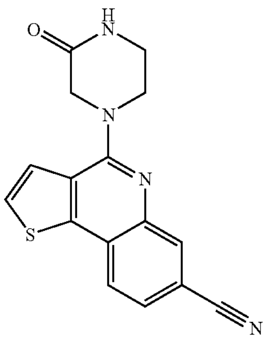 | 308.36 | 309 |

TABLE 35-continued
| Structure | MW | LCMS (ES) m/z, [M + 1]+ |
|---|---|---|
| 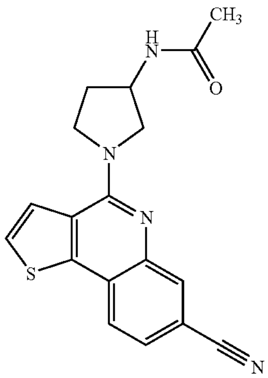 | 336.41 | 337 |
| 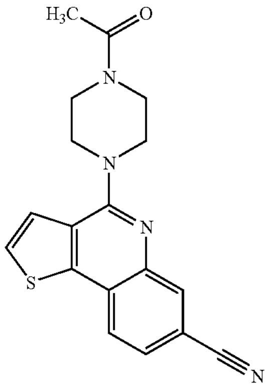 | 336.41 | 337 |
| 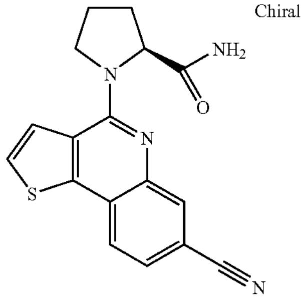 Chiral | 322.38 | 323 |
| 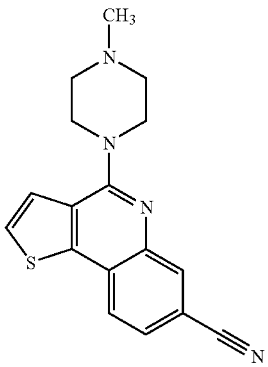 | 308.40 | 309 |
TABLE 35-continued
| Structure | MW | LCMS (ES) m/z, [M + 1]+ |
|---|---|---|
| 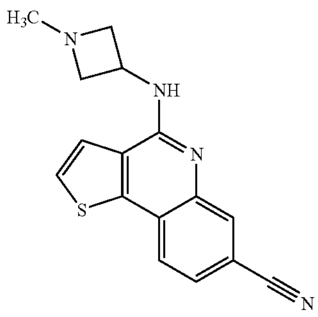 | 294.37 | 295 |
| 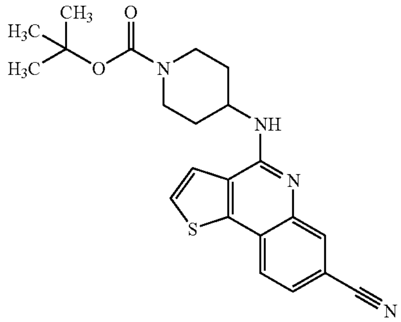 | 408.52 | 409 |
| 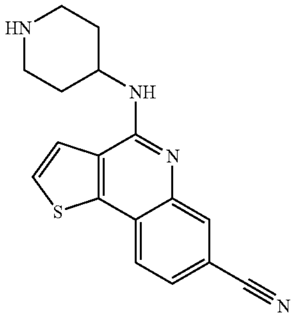 | 308.40 | 309 |
| 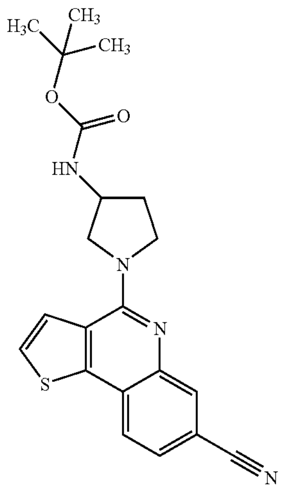 | 394.49 | 395 |

TABLE 35-continued
| Structure | MW | LCMS (ES) m/z, [M + 1]+ |
|---|---|---|
| 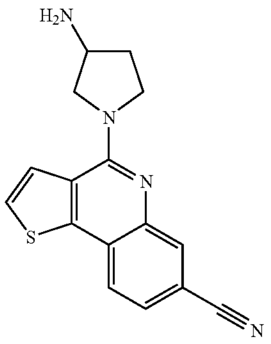 | 294.37 | 295 |
| 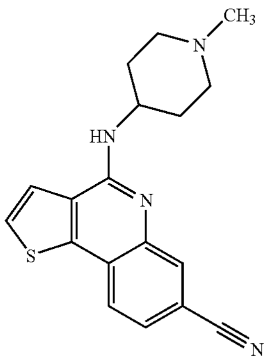 | 322.43 | 323 |
| 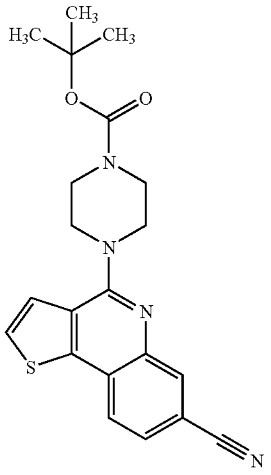 | 394.49 | 395 |
| 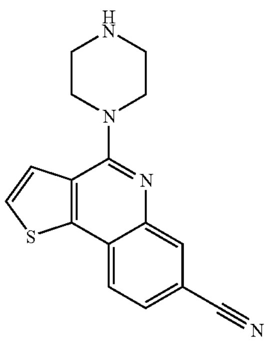 | 294.37 | 295 |
TABLE 35-continued
| Structure | MW | LCMS (ES) m/z, [M + 1]+ |
|---|---|---|
| 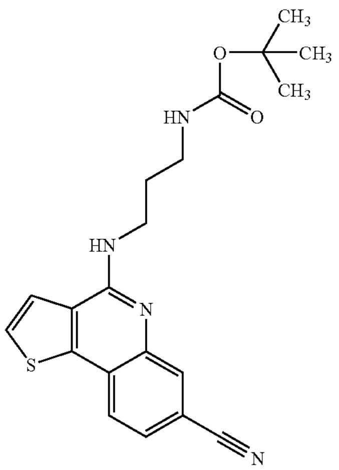 | 382.48 | 383 |
| 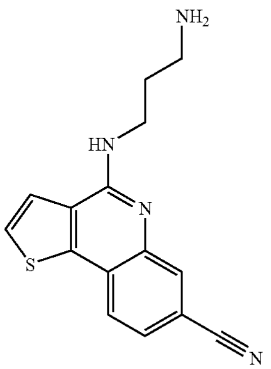 | 282.36 | 283 |
| 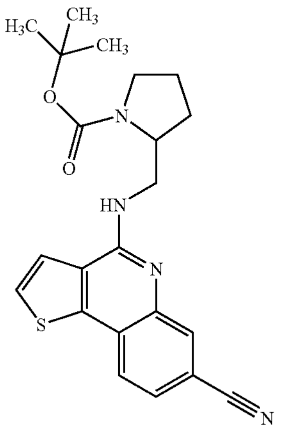 | 408.52 | 409 |

TABLE 35-continued
| Structure | MW | LCMS (ES) m/z, [M + 1]+ |
|---|---|---|
| 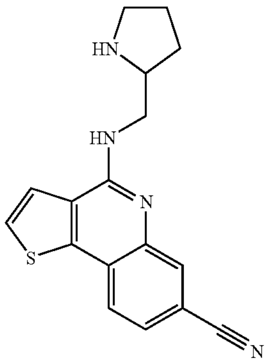 | 308.40 | 309 |
| 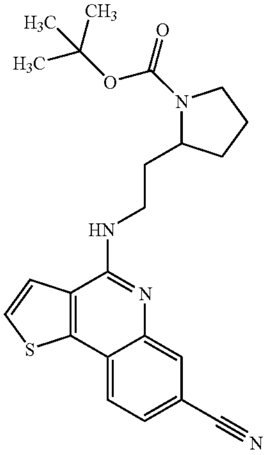 | 422.54 | 423 |
| 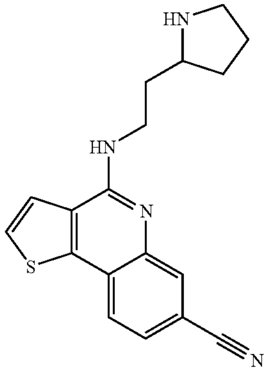 | 322.43 | 323 |
| 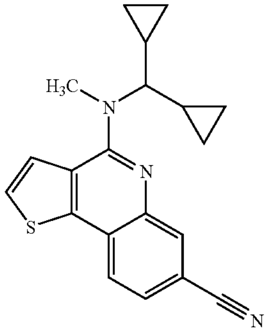 | 333.45 | 334 |
TABLE 35-continued
| Structure | MW | LCMS (ES) m/z, [M + 1]+ |
|---|---|---|
| 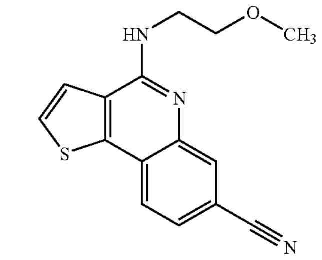 | 283.35 | 284 |
| 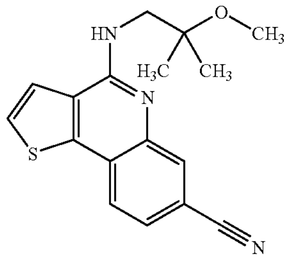 | 311.40 | 312 |
| 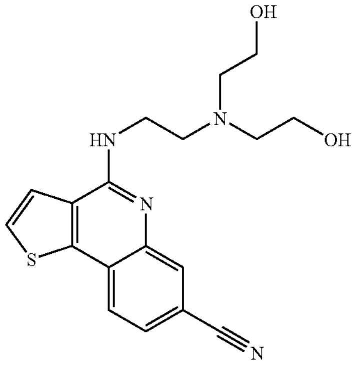 | 356.44 | 357 |
| 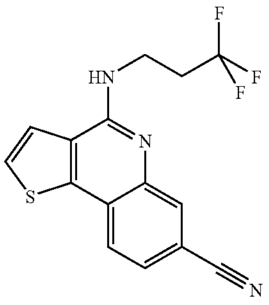 | 321.32 | 322 |
| 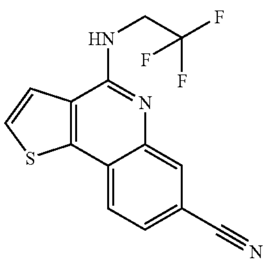 | 307.29 | 308 |

TABLE 35-continued

| Structure | MW | LCMS (ES) m/z, [M + 1]+ |
|---|---|---|
| 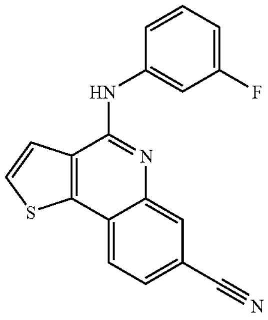 | 319.36 | 320 |

Process 21

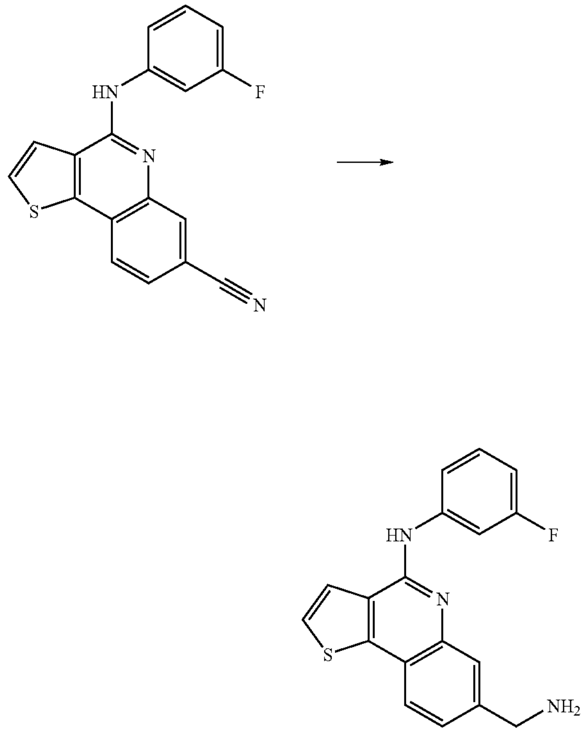

To a solution of potassium t-butoxide (59 mg, 0.53 mmol) and EtOH washed Raney-Nickel in EtOH (50 mL) was added 4-(3-fluorophenylamino)thieno-[3,2-c]quinoline-7-carbonitrile (560 mg, 1.75 mmol) in EtOH (5 mL). The reaction mixture was charged with $H_2$ and stirred at rt for 3 h. Raney-Nickel was removed by filtration through Celite and the solvent was removed under reduced pressure. Trituration in $Et_2O$ gave the desired amine (300 mg, 53%) as a white solid. LCMS (ES): >95% pure, m/z 324 $[M+1]^+$.

Process 22

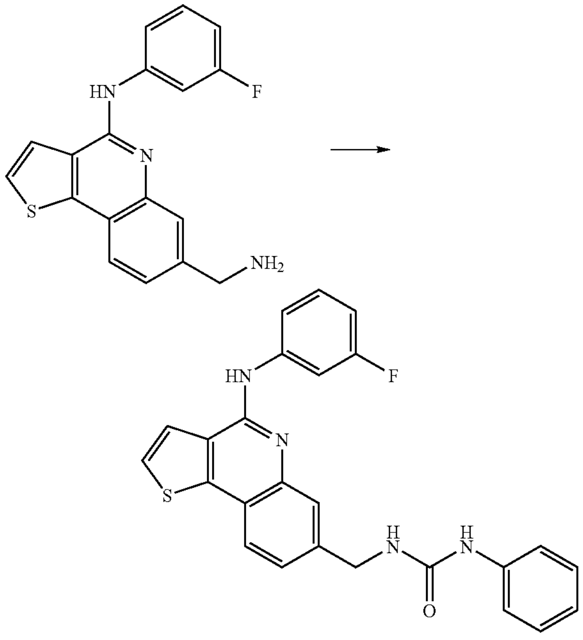

To a solution of 7-(aminomethyl)-N-(3-fluorophenyl)thieno[3,2-c]quinolin-4-amine (30 mg, 0.09 mmol) in DCM (2 mL) was added phenyl isocyanate (10 uL, 0.09 mmol). The precipitate immediately appeared and it was collected by filtration to give the desired urea as a white solid. LCMS (ES): >95% pure, m/z 443 $[M+1]^+$.

The molecules in the following table were prepared using a similar procedure from corresponding amine and either isocyanate or chloride.

TABLE 36

| Structure | MW | LCMS (ES) m/z, [M + 1]+ |
|---|---|---|
| 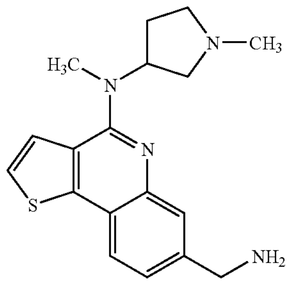 | 326.46 | 327 |
| 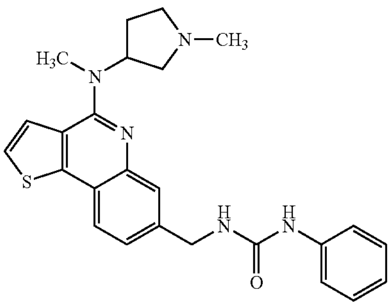 | 445.58 | 446 |

TABLE 36-continued
| Structure | MW | LCMS (ES) m/z, [M + 1]+ |
|---|---|---|
| 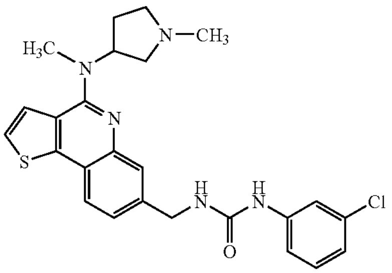 | 480.02 | 480 |
| 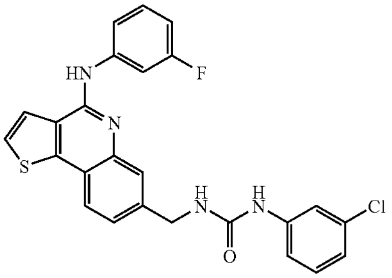 | 476.95 | 477 |
| 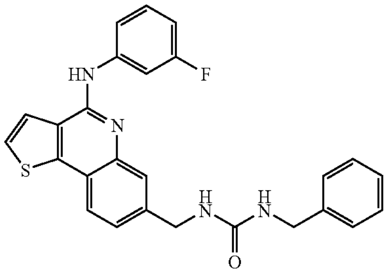 | 456.53 | 457 |
| 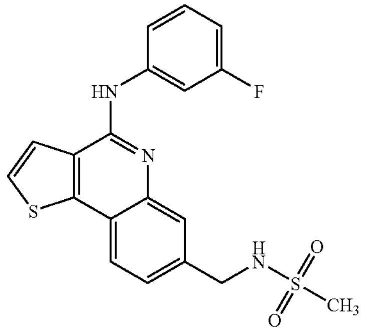 | 401.48 | 402 |
| 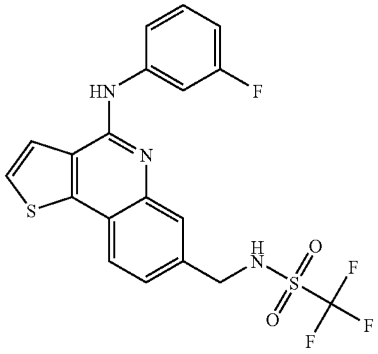 | 455.45 | 456 |
| 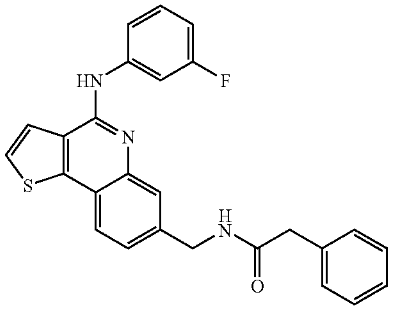 | 441.52 | 442 |
| 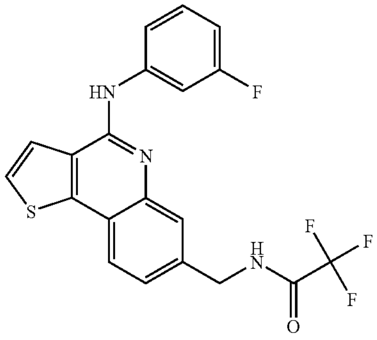 | 419.40 | 420 |
| 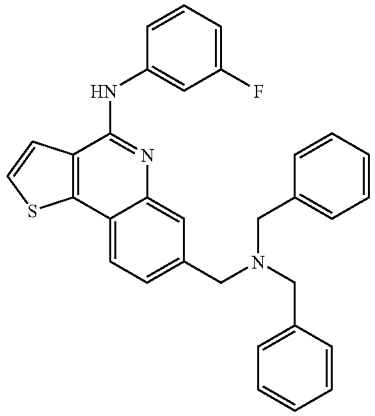 | 503.63 | 504 |
| 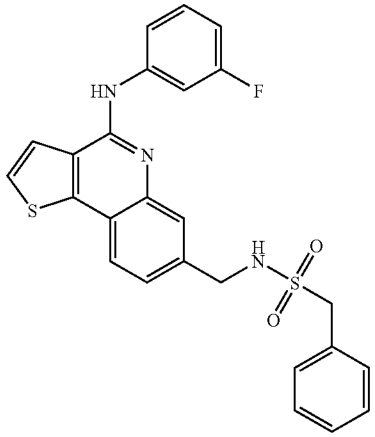 | 477.57 | 478 |

TABLE 36-continued

| Structure | MW | LCMS (ES) m/z, [M + 1]+ |
|---|---|---|
| 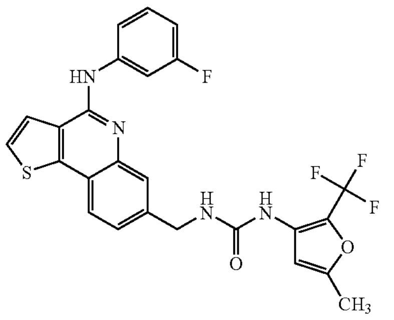 | 514.49 | 515 |
| 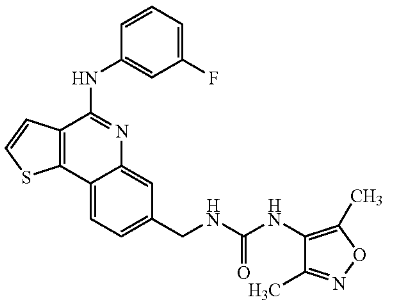 | 461.51 | 462 |
| 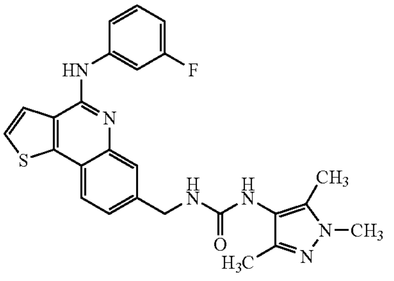 | 474.55 | 475 |

Process 23

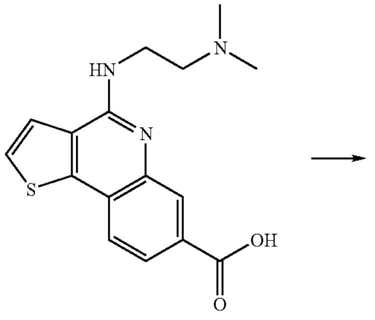

-continued

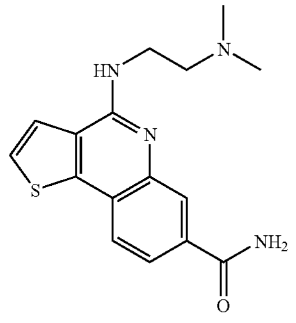

4-(2-(dimethylamino)ethylamino)thieno[3,2-c]quinoline-7-carboxylic acid (1.0 eq, 100 mg) was mixed with ammonium chloride (2.0 eq, 34 mg), DIEA (114 ul), HOBt.$H_2O$ (2.0 eq, 86 mg), EDCI (2.0 eq, 122 mg) in NMP (3 ml). The mixture was stirred at 70° C. until LCMS monitoring indicated a complete reaction. Water was added, the pH was adjusted to 10 and the material was extracted with $CH_2Cl_2$. After evaporation of the solvents, the material was purified by preparative HPLC. Genevac evaporation afforded the TFA salt of 4-(2-(dimethylamino)ethylamino)thieno[3,2-c]quinoline-7-carboxamide as yellow solid (92 mg, 69% yield). LCMS (ES)>95% pure, m/z 315 $[M+1]^+$.

The molecules in the following table were prepared using a similar procedure.

TABLE 37

| Structure | MW | LCMS (ES) m/z [M + 1]+ |
|---|---|---|
| 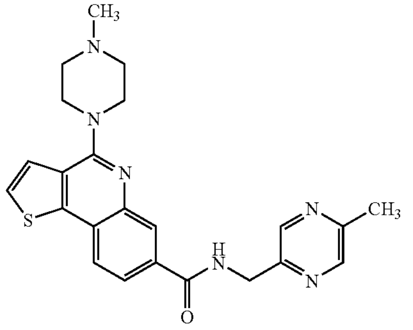 | 432.54 | 433 |
| 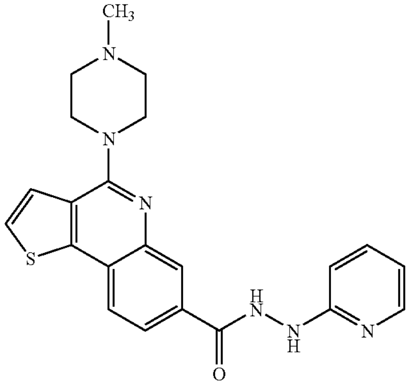 | 418.51 | 419 |

TABLE 37-continued
| Structure | MW | LCMS (ES) m/z [M + 1]+ |
| --- | --- | --- |
| 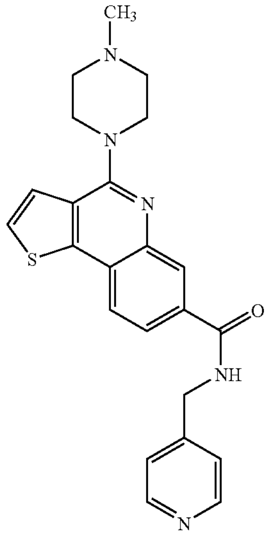 | 417.53 | 418 |
| 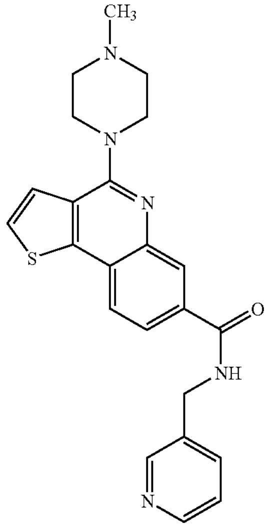 | 417.53 | 418 |
| 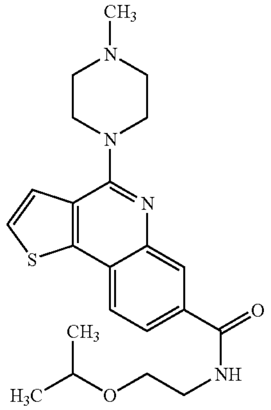 | 412.55 | 413 |
TABLE 37-continued
| Structure | MW | LCMS (ES) m/z [M + 1]+ |
| --- | --- | --- |
| 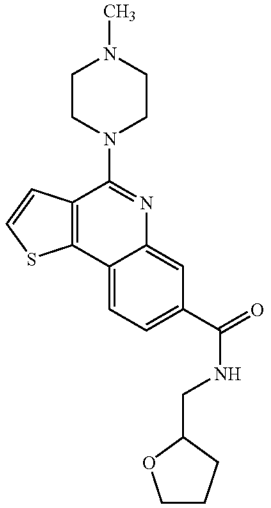 | 410.53 | 411 |
| 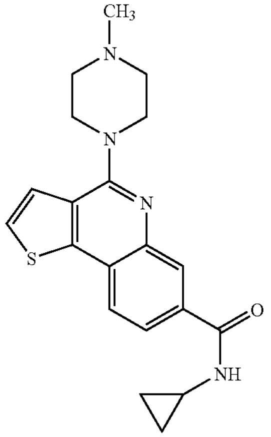 | 366.48 | 367 |
| 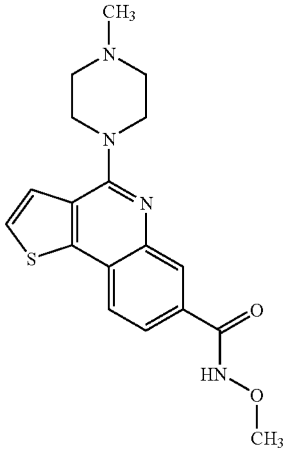 | 356.44 | 357 |

TABLE 37-continued
| Structure | MW | LCMS (ES) m/z [M + 1]+ |
| --- | --- | --- |
| 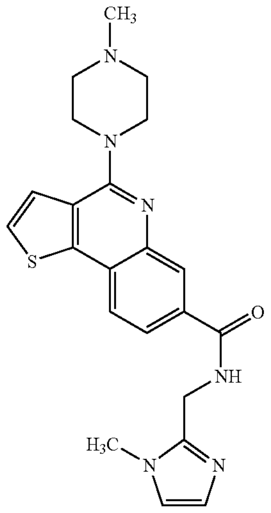 | 420.53 | 421 |
| 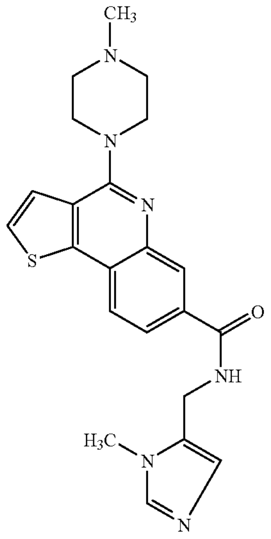 | 420.53 | 421 |
| 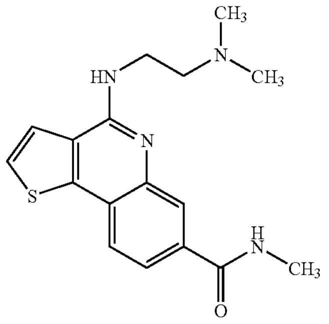 | 328.43 | 329 |
TABLE 37-continued
| Structure | MW | LCMS (ES) m/z [M + 1]+ |
| --- | --- | --- |
| 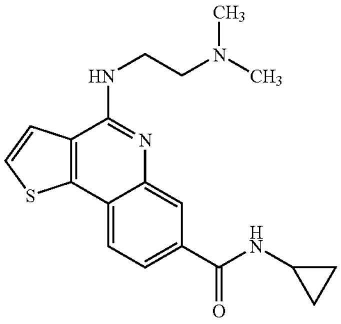 | 354.47 | 355 |
| 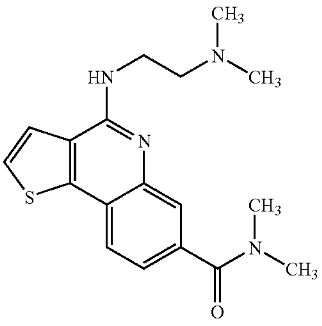 | 342.46 | 343 |
| 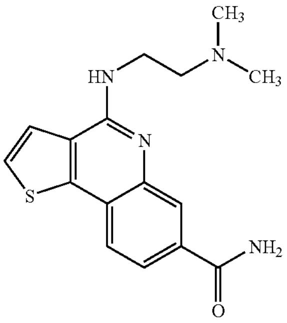 | 314.41 | 315 |
| 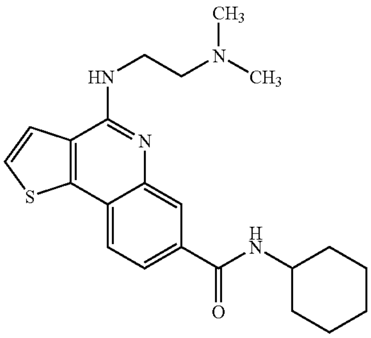 | 396.55 | 397 |

TABLE 37-continued

| Structure | MW | LCMS (ES) m/z [M + 1]+ |
|---|---|---|
| 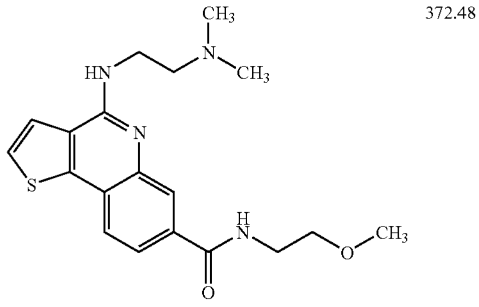 | 372.48 | 373 |

Process 24

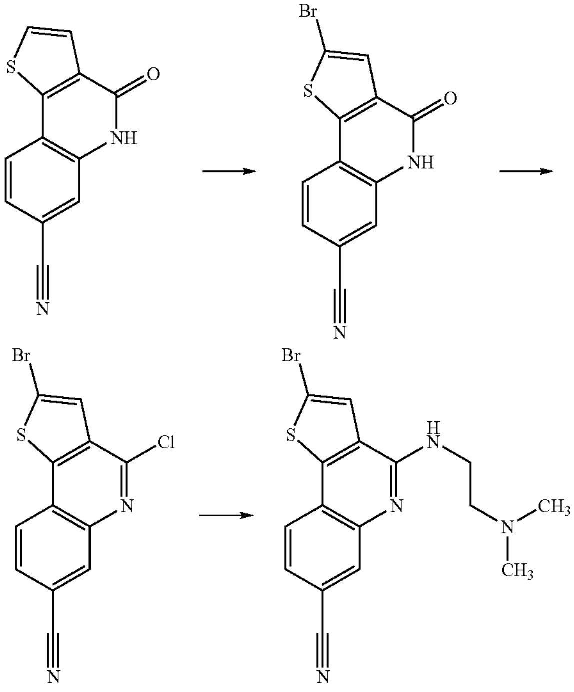

4-oxo-4,5-dihydrothieno[3,2-c]quinoline-7-carbonitrile (1.0 eq, 350 mg, 1.55 mmol) was mixed with N-bromosuccinimide (1.1 eq, 303 mg, 1.70 mmol) in acetic acid (4 ml). The mixture was stirred at 100° C. for 4 hours. The mixture was cooled down to 80° C., more NBS (303 mg) was added and the mixture stirred overnight. Water was added and the material filtered and dried. Trituration in methanol and filtration afforded 2-bromo-4-oxo-4,5-dihydrothieno[3,2-c]quinoline-7-carbonitrile as a grey solid (396 mg, 84% yield). LCMS (ES)>80% pure, m/z 305 [M]$^+$, 307 [M+2]$^+$.

This crude material was treated with phosphorus oxychloride (5.0 eq, 0.6 ml, 6.33 mmol) in acetonitrile (4 ml) at reflux for 4 hours. More $POCl_3$ (2 ml) was added and the mixture heated at 110° C. for 7 hours. The volatiles were removed, Ice was added and the solid filtered. After trituration in ethyl acetate/hexanes and filtration, 2-bromo-4-chlorothieno[3,2- c]quinoline-7-carbonitrile was isolated as a solid (324 mg, 78% yield). LCMS (ES)>80% pure, m/z 323 [M]$^+$, 325 [M+2]$^+$.

2-bromo-4-chlorothieno[3,2-c]quinoline-7-carbonitrile (1.0 eq, 309 mg, 0.955 mmol) and N,N-dimethylene diamine (3.0 eq, 312 ul, 2.85 mmol) were mixed in NMP (1 ml). The mixture was heated under microwave at 100° C. for 10 min. Water was added and the solid filtered. The material was purified by trituration in hot ethyl acetate. 2-bromo-4-(2-(dimethylamino)ethylamino)thieno[3,2-c]quinoline-7-carbonitrile was isolate as a solid (252 mg, 70% yield). LCMS (ES)>95% pure, m/z 375 [M]$^+$, 377 [M+2]$^+$.

Process 25

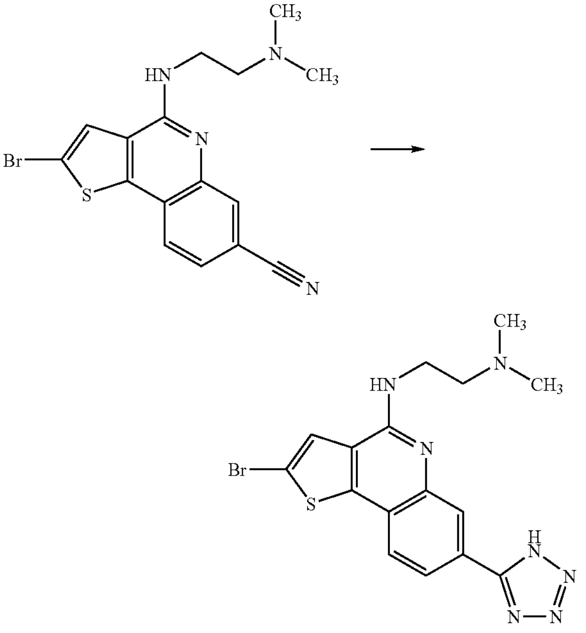

2-bromo-4-(2-(dimethylamino)ethylamino)thieno[3,2-c]quinoline-7-carbonitrile (20 mg) was mixed with sodium azide (50 mg) and ammonium chloride (50 mg) in DMF. The mixture was stirred at 120° C. for 3 hours. Water was added and the solid isolated by filtration. (6 mg). LCMS (ES)>95% pure, m/z 418[M]$^+$, 420 [M+2]$^+$.

Process 26

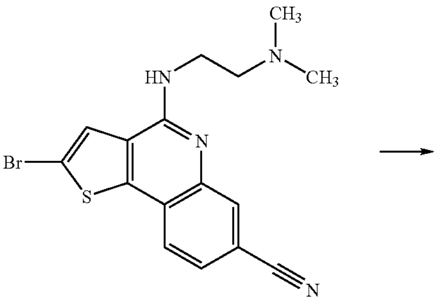

-continued

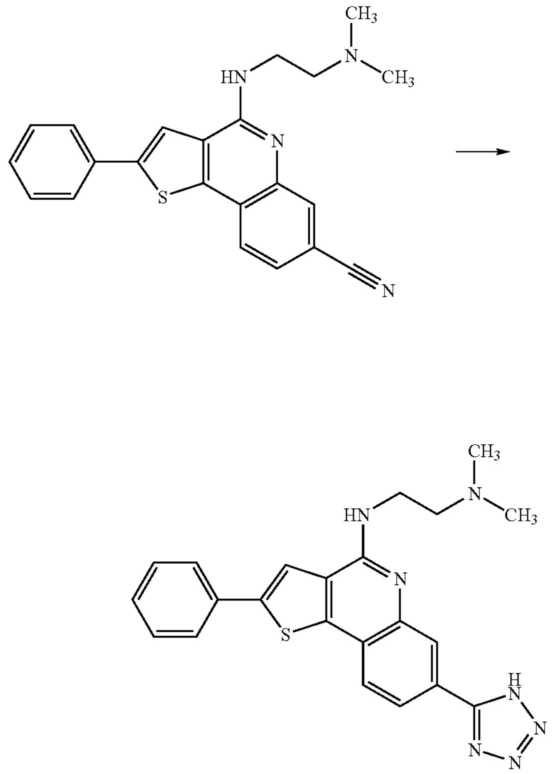

2-bromo-4-(2-(dimethylamino)ethylamino)thieno[3,2-c]quinoline-7-carbonitrile (1.0 eq, 55 mg, 0.146 mmol), benzene boronic acid (2.0 eq, 36 mg, 0.295 mmol), cesium carbonate (2.0 eq, 95 mg, 0.292 mmol) and $PdCl_2$(dppf) (0.05 eq, 5 mg, 0.068 mmol) were mixed in dioxane (0.5 ml) containing 5% of water. The mixture was heated under microwave for 10 min at 120° C. After addition of water and filtration, 4-(2-(dimethylamino)ethylamino)-2-phenylthieno[3,2-c]quinoline-7-carbonitrile was isolated as a solid. LCMS (ES) m/z 373 $[M+1]^+$.

This solid was dissolved in DMF (0.5 ml) and treated with sodium azide (100 mg) and ammonium chloride (100 mg) at 120° C. for 1.5 hours. Water was added and filtration of the solid provided N1,N1-dimethyl-N2-(2-phenyl-7-(1H-tetrazol-5-yl)thieno[3,2-c]quinolin-4-yl)ethane-1,2-diamine. (35 mg). LCMS (ES)>85% pure, m/z 416 $[M+1]^+$.

Process 27

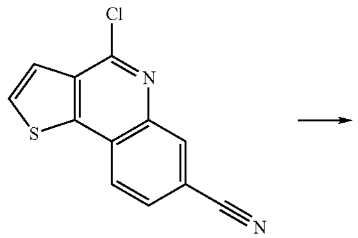

-continued

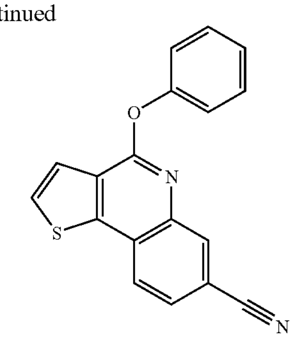

Phenol (2.0 eq, 85 mg) was dissolved in anhydrous DMF. 60% sodium hydride (2.0 eq, 36 mg) was added and the reaction mixture stirred for a few minutes. 4-chlorothieno[3,2-c]quinoline-7-carbonitrile (1.0 eq, 110 mg) was added to the mixture and the whole reaction was stirred at 100° C. for two days. Water was added and the solid was filtered and dried. 4-phenoxythieno[3,2-c]quinoline-7-carbonitrile was isolated as a solid (114 mg). LCMS (ES)>95% pure, m/z 303 $[M+1]^+$.

Process 28

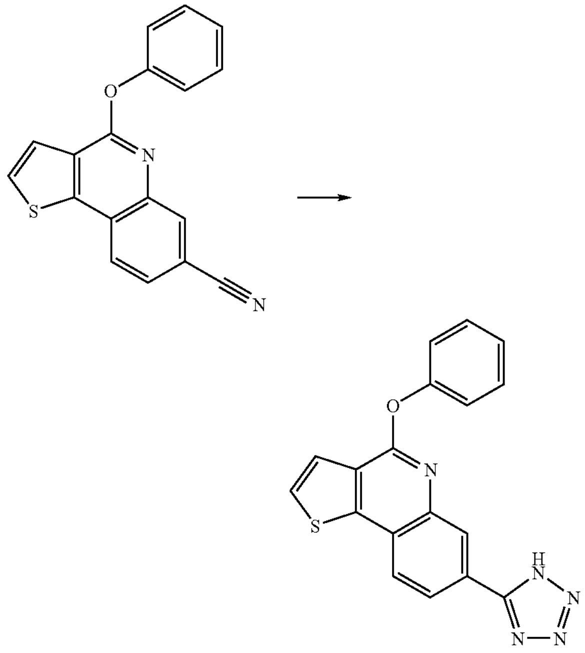

In an oven dried flask, under nitrogen atmosphere, was charged sodium azide (1.4 eq, 84 mg). $Et_2AlCl$ (1.4 eq, 1.08 ml of 1.8 M solution in toluene) was added through syringe. The mixture was stirred at room temperature for 4 hours. 4-phenoxythieno[3,2-c]quinoline-7-carbonitrile (1.0 eq, 20 mg) was charged in a vial. $Et_2AlN_3$ solution (0.15 ml) was added and the resulting mixture stirred at 80° C. for 5 days. The mixture was treated by a solution of NaOH and some sodium nitrite was added (pH=13-14). The pH was adjusted to 1.5 with HCl 6N. The material was extracted with ethyl acetate. The material was extracted from the organic phase using a saturated aqueous solution of $K_2CO_3$. The pH was adjusted to 2.5 with HCl 6N and the material was extracted with ethyl acetate. The solvent were evaporated to afford 4-phenoxy-7-(1H-tetrazol-5-yl)thieno[3,2-c]quinoline. LCMS (ES)>95% pure, m/z 303 [M+1]$^+$.
The molecules in the following table were prepared using a procedure similar to process 27 and process 28.
TABLE 38
| Structure | MW | LCMS (ES) m/z [M + 1]+ |
|---|---|---|
| 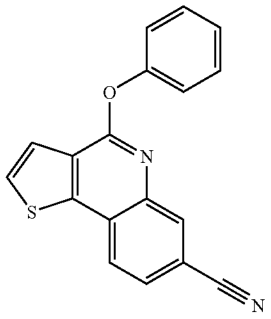 | 302.35 | 303 |
| 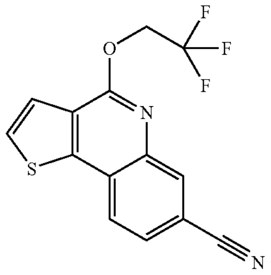 | 308.28 | 309 |
| 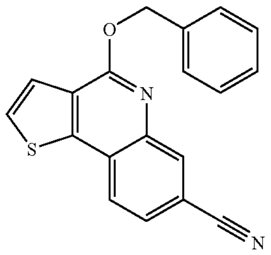 | 316.38 | 317 |
| 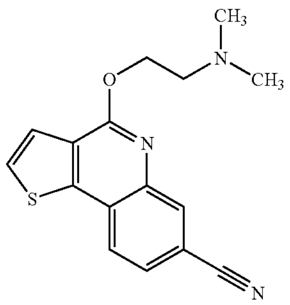 | 297.37 | 298 |
TABLE 38-continued
| Structure | MW | LCMS (ES) m/z [M + 1]+ |
|---|---|---|
| 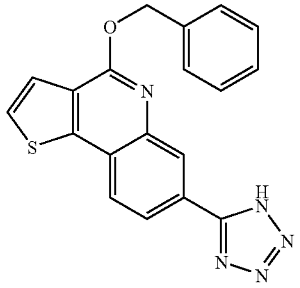 | 359.40 | 360 |
| 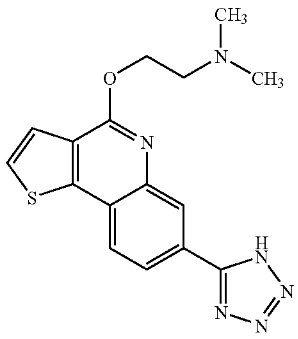 | 340.40 | 341 |
| 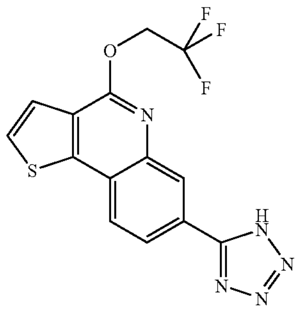 | 351.31 | 352 |
| 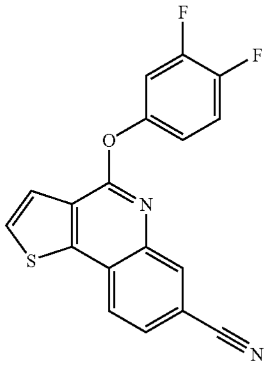 | 338.33 | 339 |

TABLE 38-continued
| Structure | MW | LCMS (ES) m/z [M + 1]+ |
|---|---|---|
| 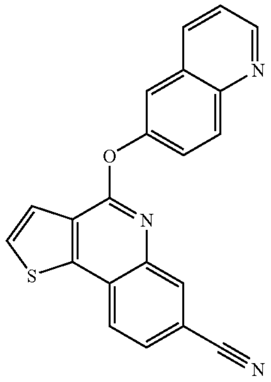 | 353.40 | 354 |
| 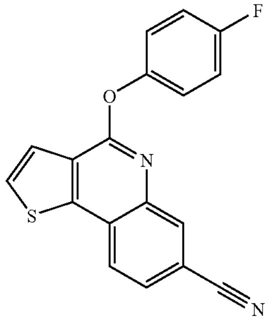 | 320.34 | 321 |
| 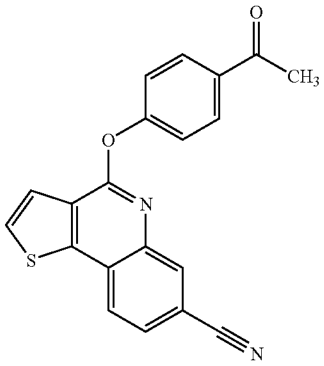 | 344.39 | 345 |
| 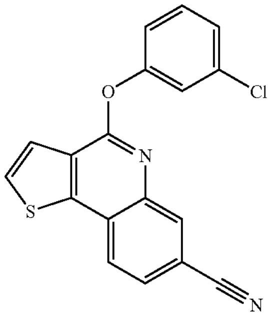 | 336.79 | 337 |
TABLE 38-continued
| Structure | MW | LCMS (ES) m/z [M + 1]+ |
|---|---|---|
| 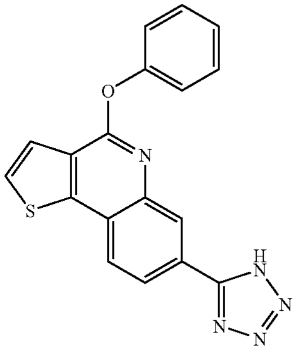 | 345.38 | 346 |
| 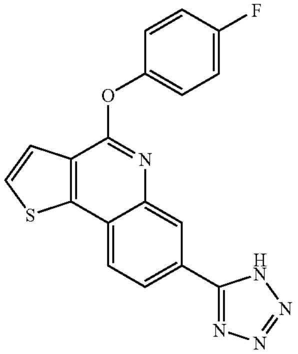 | 363.37 | 364 |
| 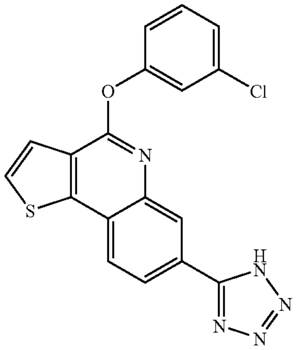 | 379.82 | 380 |
Biological activities for various compounds are summarized in the following table.

TABLE 39
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 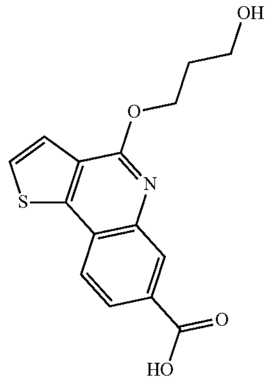 | −34.721 | | 1.2 | 0.995 | | | 10 | | | | |
| 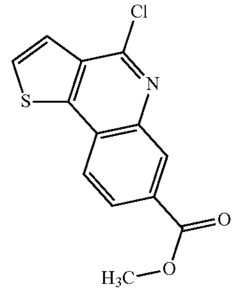 | −30.004 | | | | | | 10 | | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 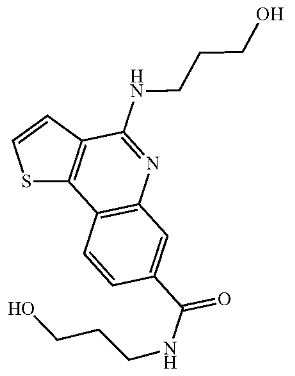 | −24.665 | | | | | | 10 | | | | |
| 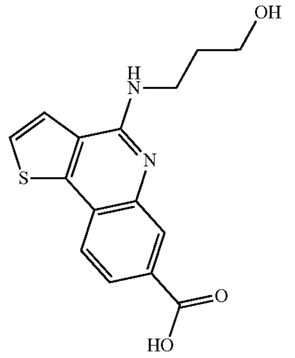 | −0.688 | | 0.67 | 0.748 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 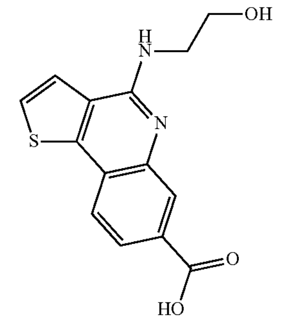 | −49.418 | | 1.1 | 1.258 | | | 10 | | | | |
| 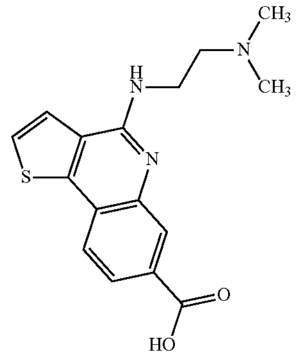 | 83.428 | 0.103 | 0.278 | 0.102 | | | 10 | | 26.018 | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 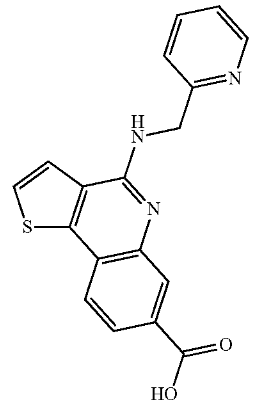 | −36.568 | | 0.875 | 0.622 | | | 10 | | | | |
| 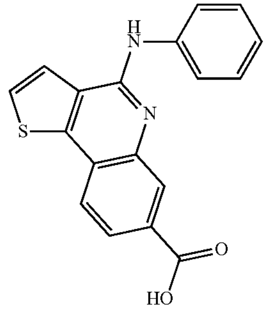 | 15.679 | 0.454 | 0.32 | 0.092 | | | 10 | >10 | 6.116 | >10 | 8.326 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 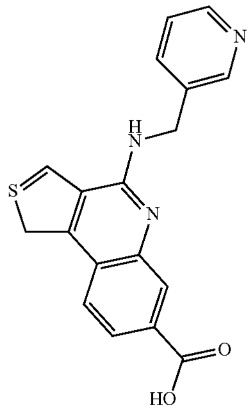 | 59.969 | | 0.9 | 0.367 | | | 10 | | | | |
| 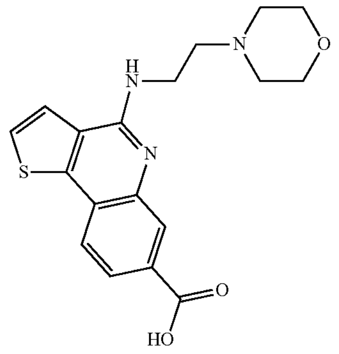 | −10.031 | | 1.22 | 0.922 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 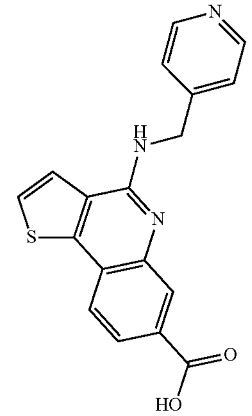 | 71.259 | | 0.527 | 0.168 | | | 10 | | | | |
| 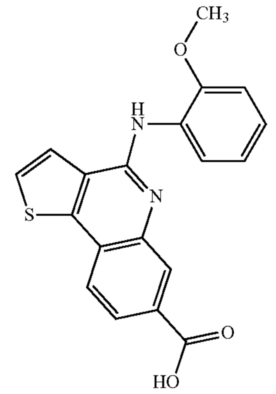 | 0.445 | | 0.55 | 0.171 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 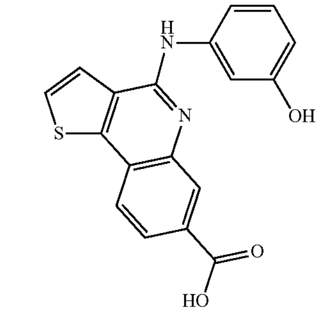 | 6.497 | | 0.37 | 0.507 | | | 10 | | | | |
| 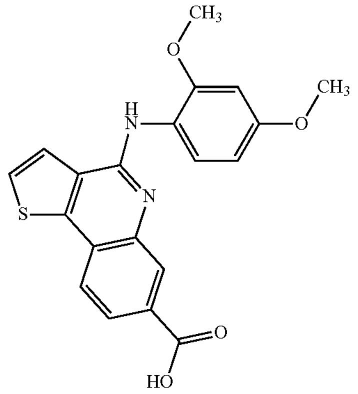 | 3.875 | | 2 | 0.771 | | | 10 | | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 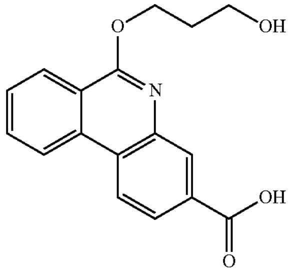 | 1.05 | | | | | | 10 | | | | |
| 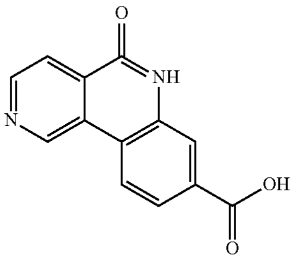 | 1.035 | | 0.18 | 0.084 | | | 10 | | | | |
| 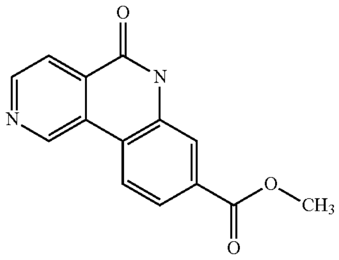 | 0.802 | | 2.5 | 1.027 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 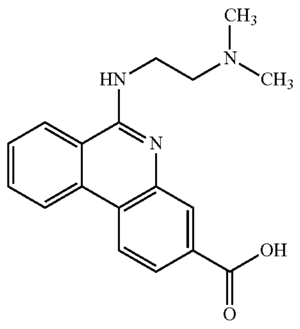 | 34.995 | | 1 | 0.569 | | | 10 | | | | |
| 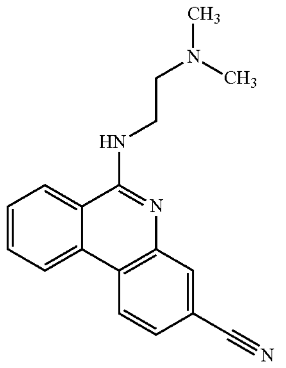 | −63.591 | | | | | | 0.5 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 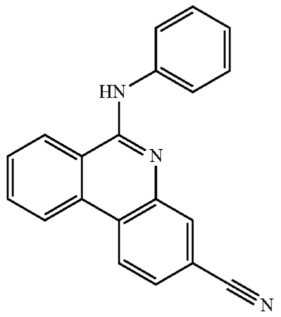 | −65.42 | | | | | | 10 | | | | |
| 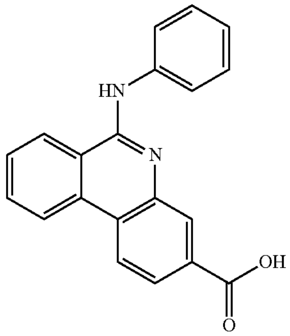 | 28.133 | | 1.6 | >2.5 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 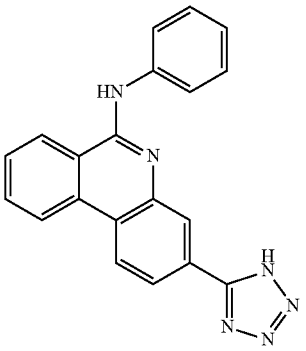 | 15.754 | | | | | | 10 | | | | |
| 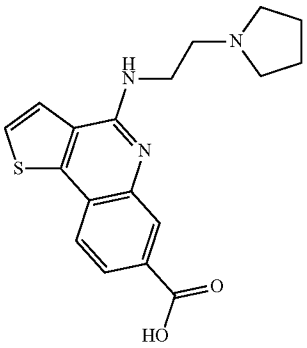 | 67.244 | 0.244 | 0.28 | 0.231 | | | 10 | | | >10 | >10 |
| 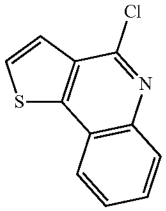 | −22.124 | | | | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 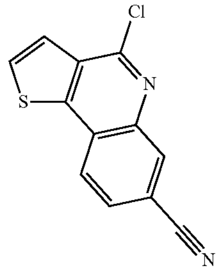 | −20.218 | | | | | | 10 | | | | |
| 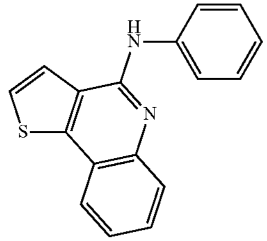 | −22.009 | | | | | | 10 | | | | |
| 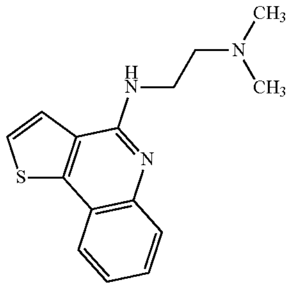 | −24.185 | | | | | | 2.3 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 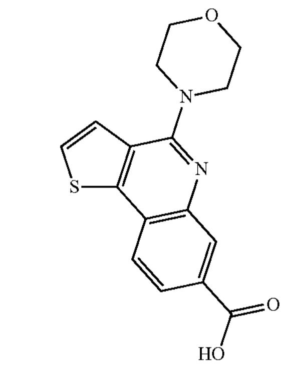 | 35.744 | | | | | | 10 | | | | |
| 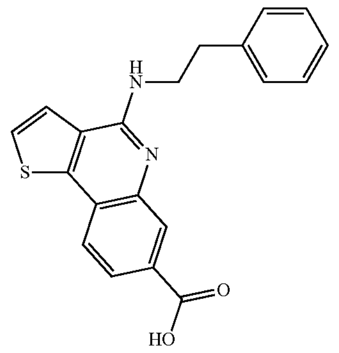 | 19.939 | | 1.006 | 0.516 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 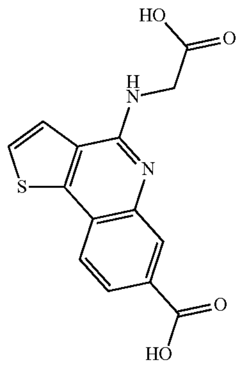 | −26.078 | | | | | | 10 | | | | |
| 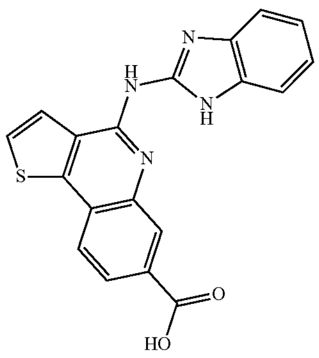 | −40.065 | | | | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 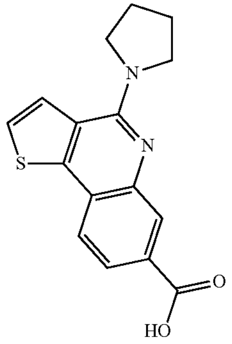 | −16 | | | | | | 10 | | | | |
| 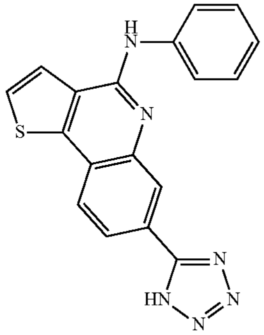 | 70.879 | 0.262 | 0.19 | 0.096 | | | 10 | | 16.326 | >10 | 1.086 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 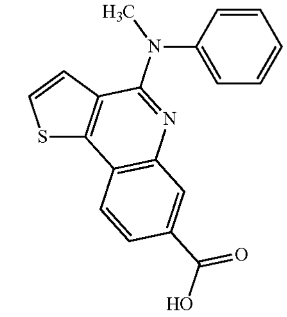 | 61.399 | 0.404 | 1.5 | | | | 10 | | | >10 | >10 |
| 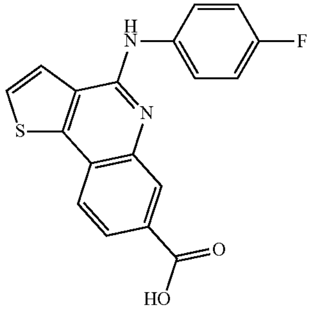 | 66.705 | 0.32 | 0.31 | 0.219 | | | 10 | | | | |
| 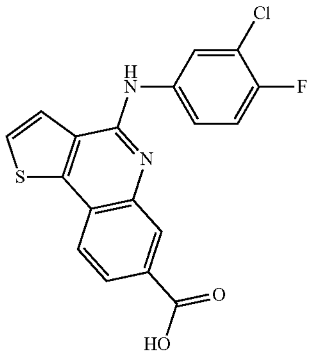 | 80.781 | 0.257 | 0.15 | 0.096 | | | 10 | | | >10 | 0.455 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 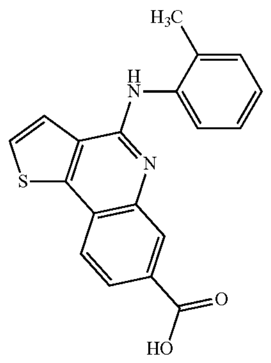 | −15.51 | | 1.1 | 0.97 | | | 10 | | | | |
| 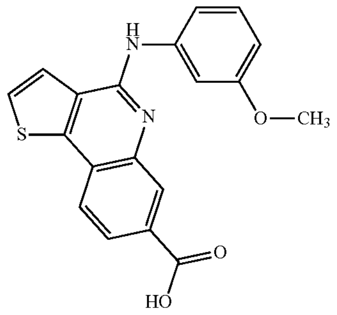 | 23.408 | | 0.12 | 0.077 | | | 10 | | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 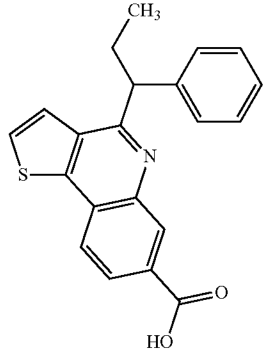 | 35.414 | | | | | | 10 | | | | |
| 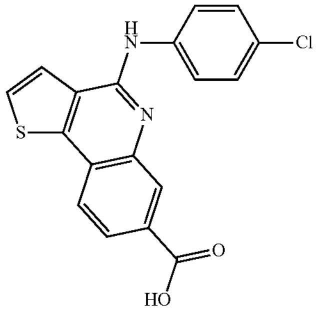 | 69.128 | 0.289 | 0.21 | 0.178 | | | 10 | | | >10 | 0.258 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 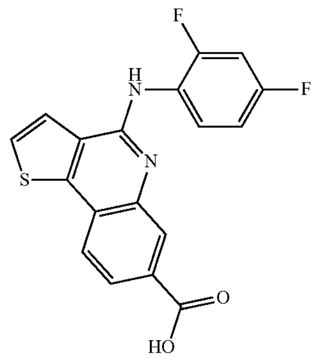 | 67.178 | 0.362 | 0.67 | 0.823 | | | 10 | | | | |
| 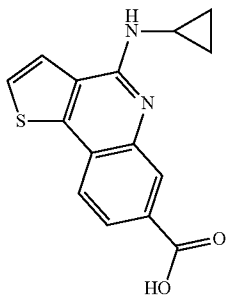 | 37.385 | | 0.97 | 0.807 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 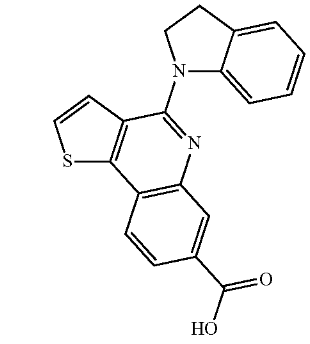 | −9.953 | | 0.58 | 0.32 | | | 10 | | | | |
| 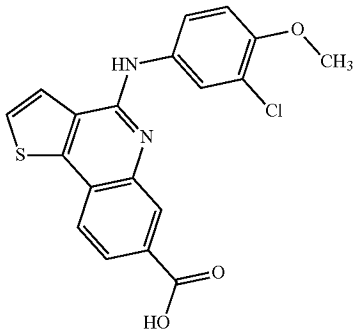 | −2.651 | | 0.43 | 0.131 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 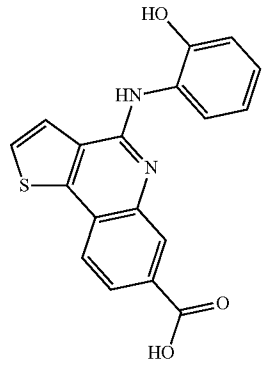 | −3.124 | | 0.82 | 0.257 | | | 10 | | | | |
| 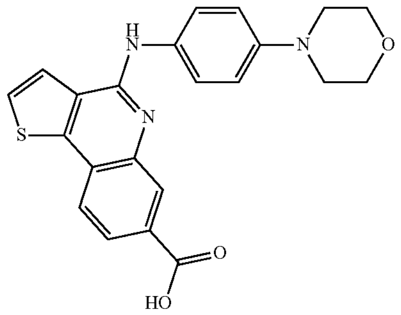 | 1.171 | | 1.17 | 0.666 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 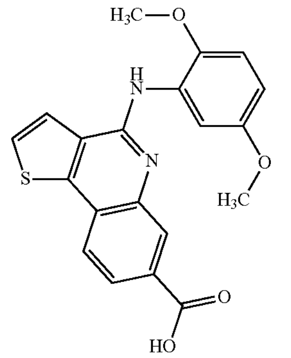 | −3.223 | | 0.431 | 0.238 | | | 10 | | | | |
| 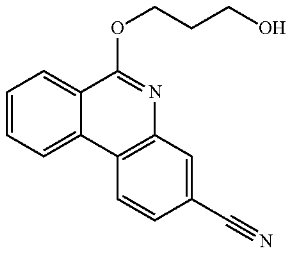 | 3.044 | | | | | | 10 | | | | |
| 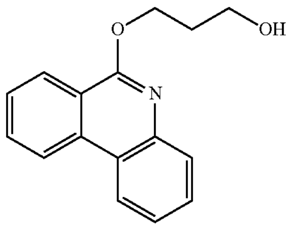 | 7.284 | | | | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 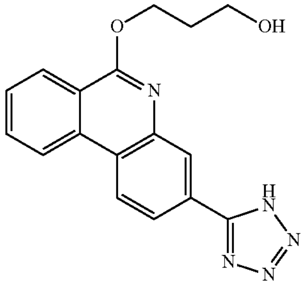 | 40.811 | | | | | | 10 | | | | |
| 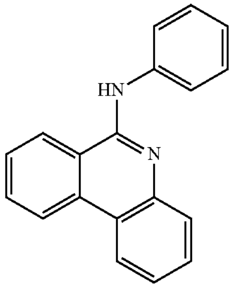 | −23.853 | | | | | | 10 | | | | |
| 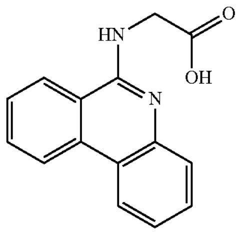 | −17.542 | | | | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 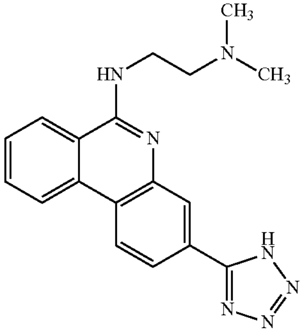 | 56.924 | | | | | | 10 | | | | |
| 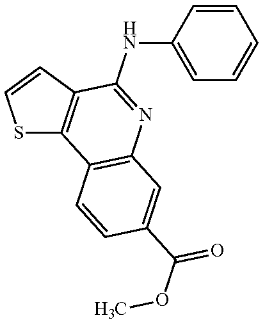 | 2.592 | | | | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 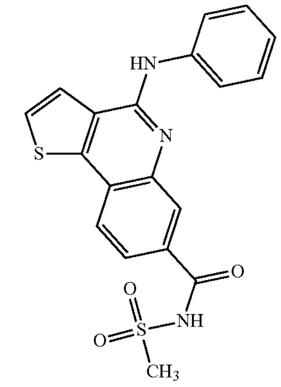 | −15.713 | | | | | | 10 | | | | |
| 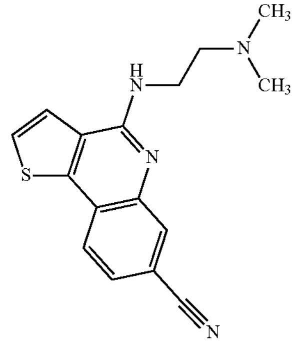 | −3.839 | | | | | | 0.4 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 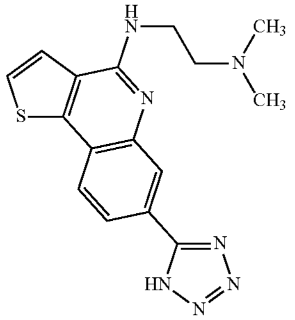 | 92.87 | 0.047 | 0.31 | 0.252 | −2.848 | | 10 | >10 | | >10 | >10 |
| 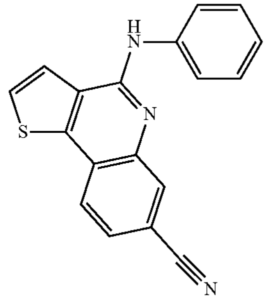 | −22.328 | | | | | | 10 | | | | |
| 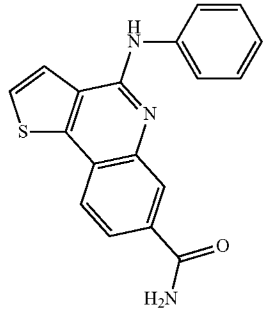 | −38.122 | | | | | | | 8.7 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 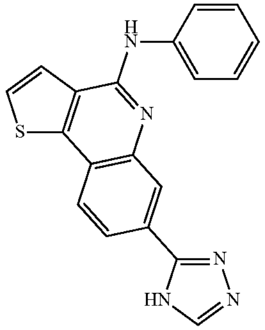 | −3.302 | | | | | | | 4.9 | 7.597 | 6.257 | |
| 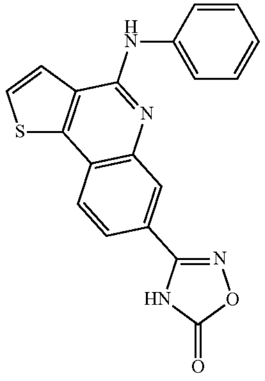 | 5.779 | | | | | | | 10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 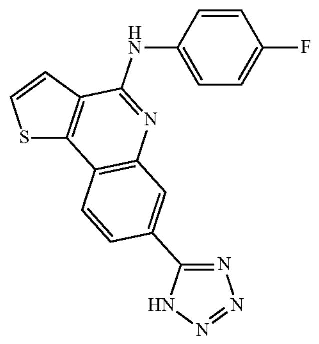 | 74.316 | 0.174 | 0.372 | 0.371 | | | 10 | | | >10 | 4.528 |
| 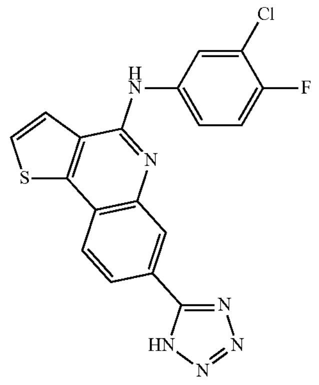 | 67.411 | 0.702 | 0.382 | 0.194 | | | 10 | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 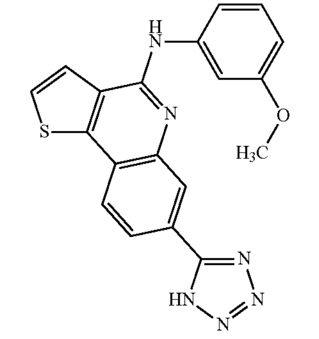 | 55.664 | 0.352 | 0.3 | 0.172 | | | 10 | | | | |
| 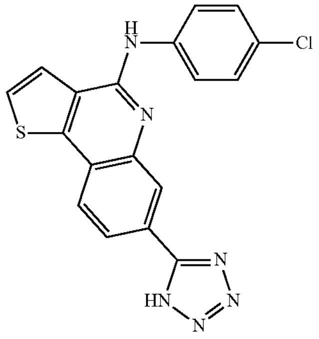 | 66.357 | 0.501 | 0.407 | 0.233 | | | 10 | | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 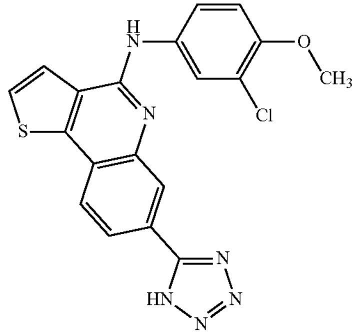 | 25.563 | | 0.462 | 0.256 | | | 10 | | | | |
| 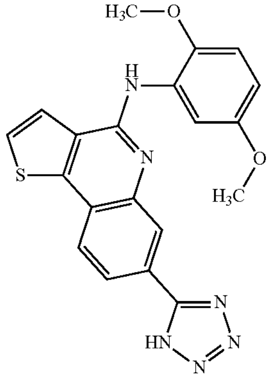 | 21.756 | | 10 | 0.358 | | | 10 | | | | |
| 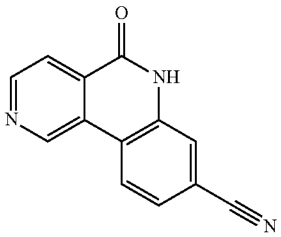 | −16.047 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 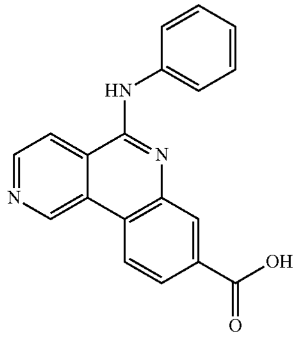 | 21.873 | 1.02 | 0.01 | 0.006 | 100.145 | | | 13.289 | 23.672 | 4.014 | 6.447 |
| 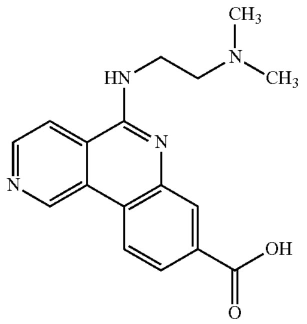 | 63.579 | 0.242 | 0.019 | 0.025 | | | | >10 | 23.792 | >10 | >10 |
| 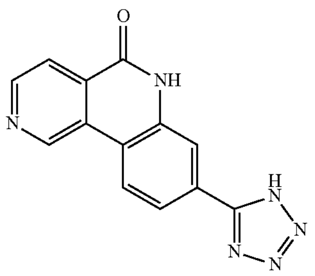 | 3.296 | | | | | | | 15 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 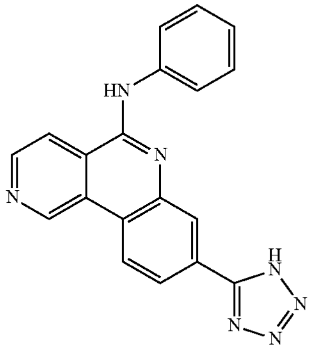 | 33.144 | | 0.06 | 0.07 | | | | >10 | | | |
| 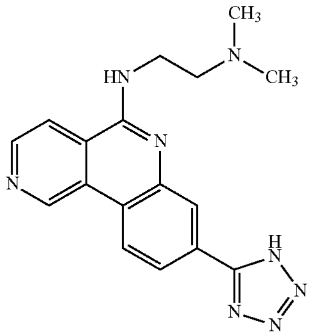 | 38.052 | | 0.13 | 0.311 | | | | | | | |
| 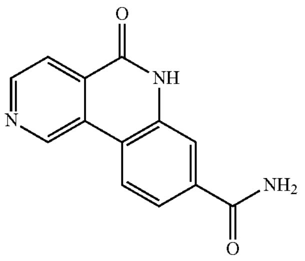 | 4.178 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 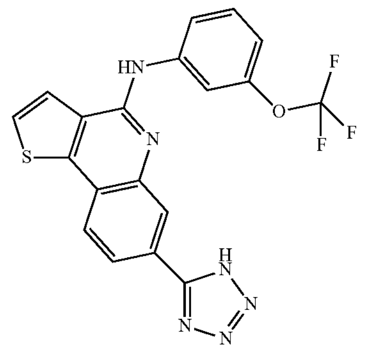 | 30.731 | | 0.42 | 0.611 | | | | 15 | | | |
| 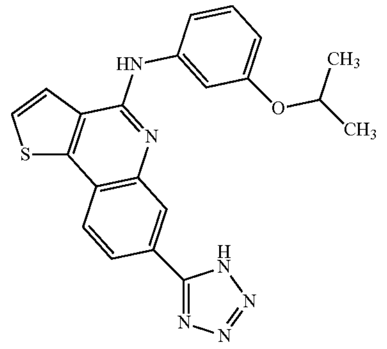 | 31.92 | | 0.27 | 0.42 | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 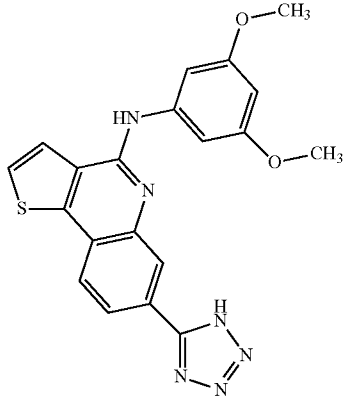 | 55.827 | 0.465 | 0.35 | 0.348 | | | | 15 | | | |
| 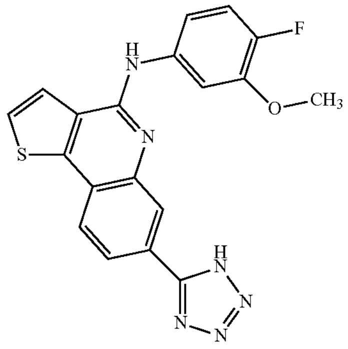 | 34.951 | | 0.89 | 0.812 | | | | >10 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 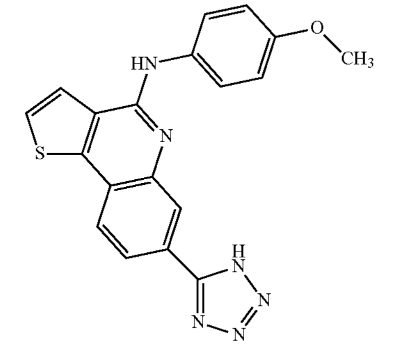 | 62.952 | >1.1 | | | | | | >10 | | | |
| 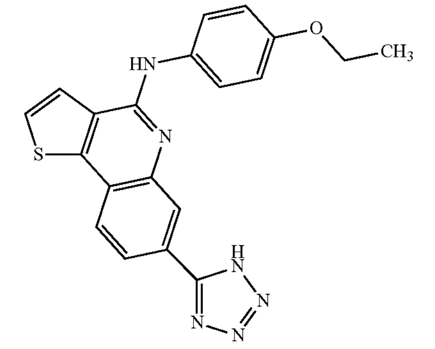 | 46.132 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 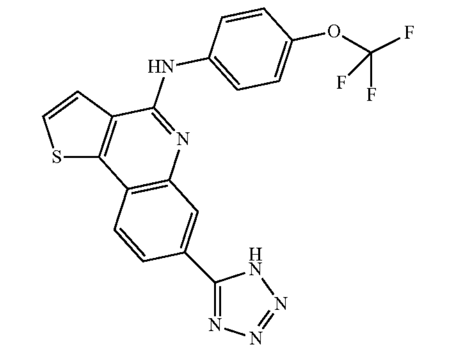 | 32.467 | | | | | | | >10 | | | |
| 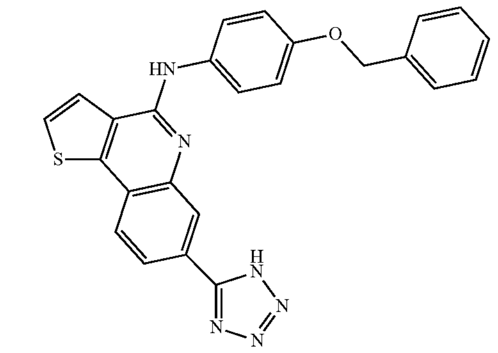 | 9.03 | | | | | | | 15 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 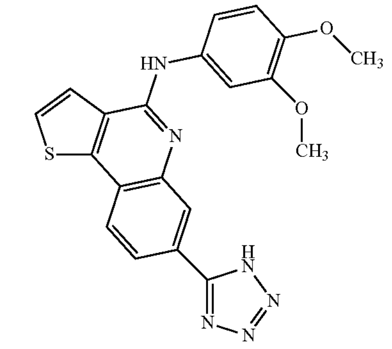 | 55.549 | 0.809 | | | | | | >10 | | | |
| 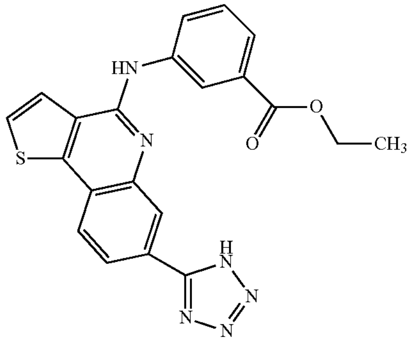 | 34.021 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 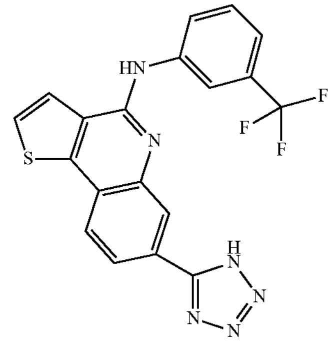 | 59.03 | 0.205 | 0.406 | 0.458 | | >0.4 | | >10 | | >10 | 0.093 |
| 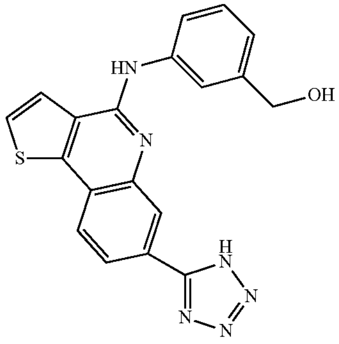 | 87.626 | 0.162 | 0.216 | 0.154 | | | | 15 | | >10 | 0.609 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 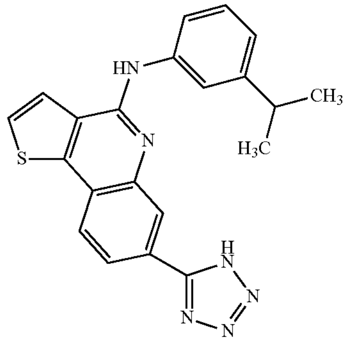 | 35.938 | | | | | | | >10 | | | |
| 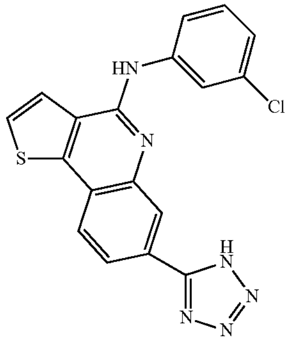 | 83.349 | 0.345 | 0.181 | 0.129 | | | | 15 | 8.888 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 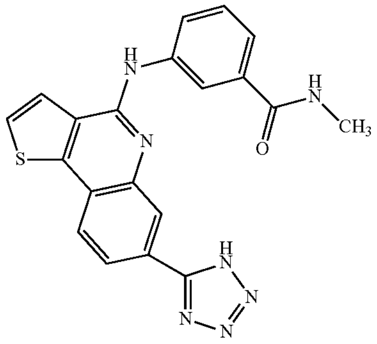 | 81.719 | 0.329 | 0.283 | 0.171 | | | | >10 | 4.222 | | |
| 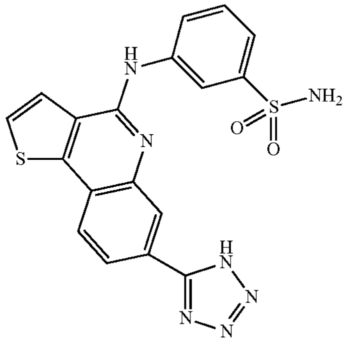 | 83.858 | 0.088 | 0.268 | 0.198 | | | | 10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 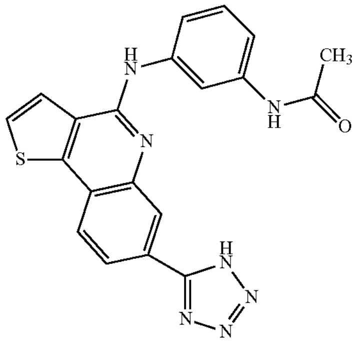 | 27.077 | | 0.524 | 0.485 | | | | 15 | | | |
| 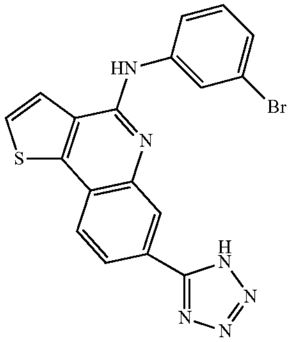 | 65.881 | 0.22 | 0.14 | 0.122 | | | | >10 | | >10 | 0.549 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 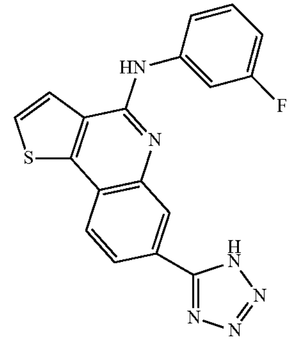 | 76.628 | 0.138 | 0.096 | 0.075 | 87.59 | >0.4 | | 15 | 5.11 | >10 | 0.525 |
| 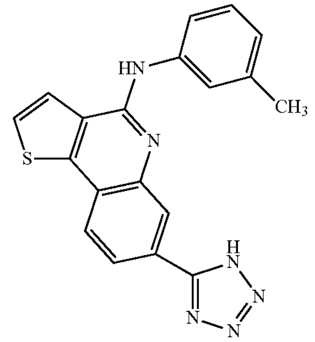 | 58.044 | 0.386 | 0.375 | 0.235 | | | | 15 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 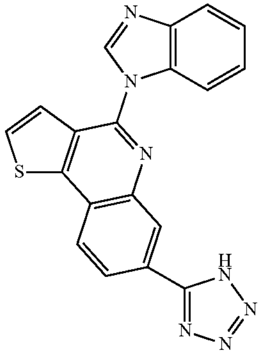 | 71.589 | >1.1 | | | | | | 15 | | | |
| 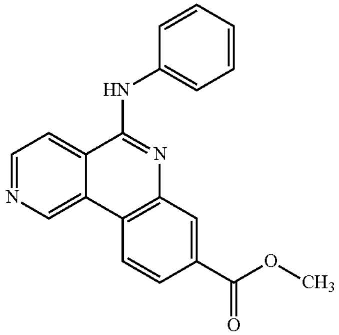 | −3.017 | | 0.2 | 0.113 | | | | 15 | 0.6831 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 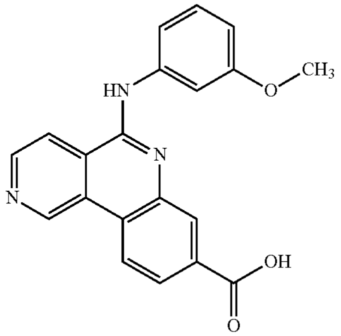 | 75.919 | 0.088 | 0.007 | 0.004 | | 0.009 | | >10 | 6.517 | 5.856 | 1.119 |
| 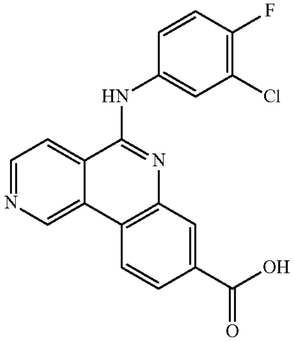 | 82.028 | 0.115 | 0.006 | 0.004 | | 0.041 | | 4.336 | 2.683 | 7.444 | 1.7 |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 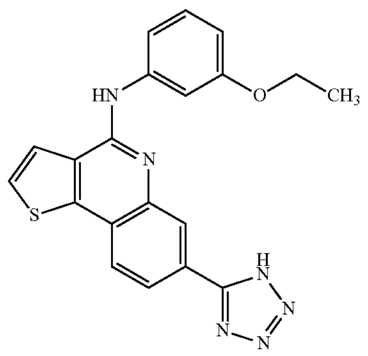 | 57.652 | 0.384 | 0.423 | 0.346 | | | | >10 | | | |
| 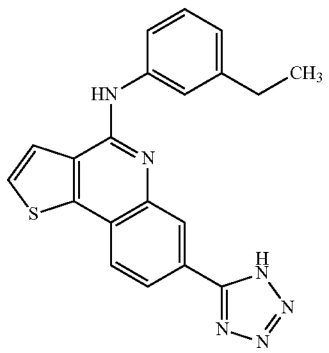 | 61.042 | >1.1 | 0.509 | 0.358 | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 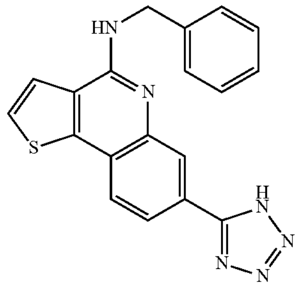 | −21.224 | | | | | | | >10 | | | |
| 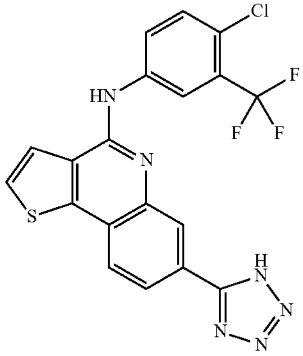 | −46.388 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 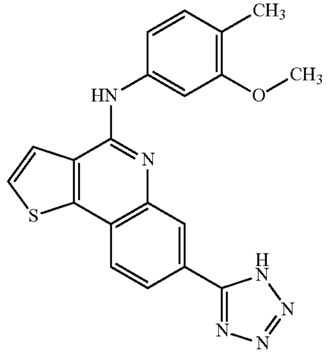 | 34.124 | | | | | | | >10 | | | |
| 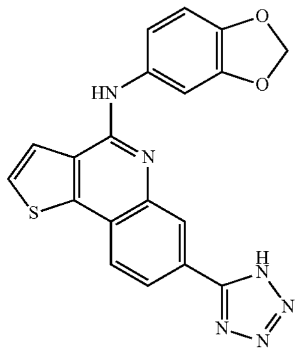 | 17.972 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 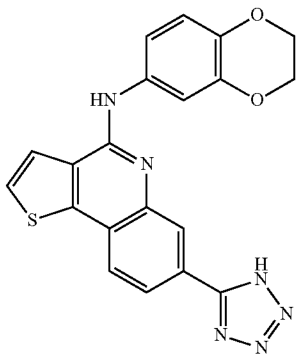 | 26.725 | | 0.63 | 0.29 | | | | >10 | | | |
| 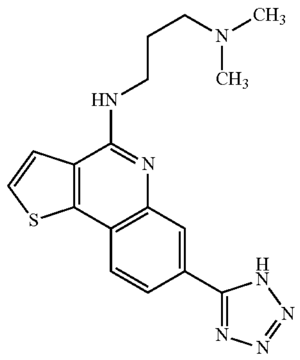 | 58.153 | 0.511 | | | | | | 15 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 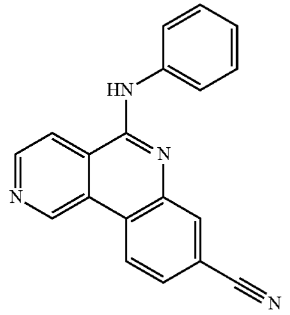 | 2.124 | | | | | | | 6.896 | | | |
| 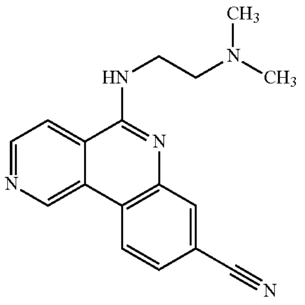 | −11.505 | | | | | | | 1.604 | | | |
| 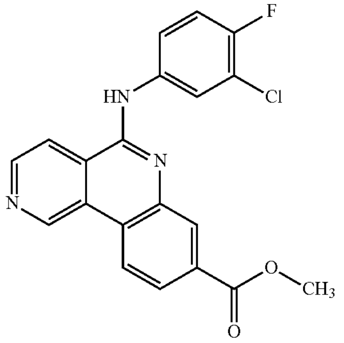 | 10.23 | | 1.661 | 1.469 | | | | 3.939 | 4.249 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 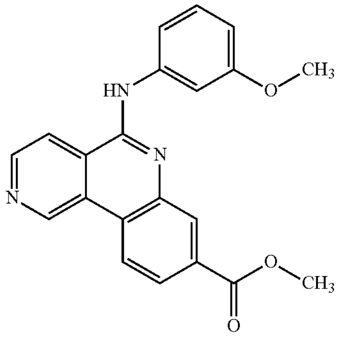 | 19.442 | | | >2.5 | | | | 15 | 3.402 | | |
| 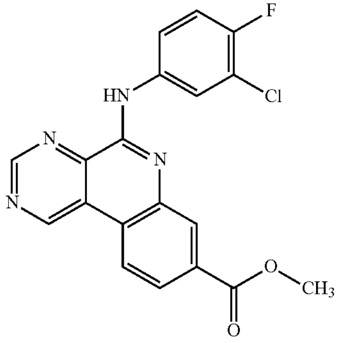 | −17.88 | | | | 6.259 | | | >10 | 20.261 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 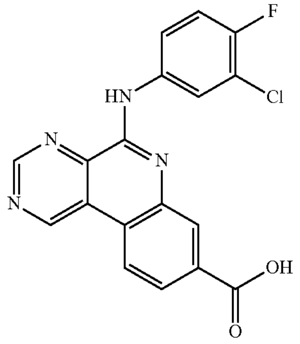 | 54.779 | 0.368 | | 0.01 | 99.163 | | | >10 | 4.286 | | |
| 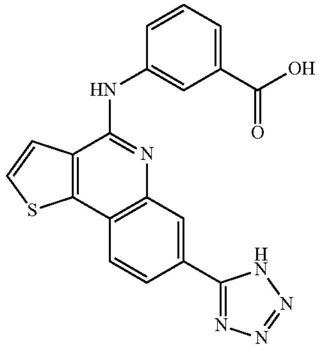 | 58.044 | 0.648 | | 0.135 | 79.122 | | | 15 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 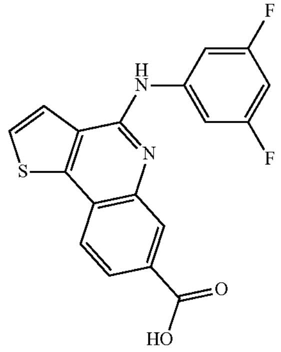 | 84.375 | 0.082 | | 0.07 | 84.652 | | | >10 | 5.855 | >10 | 0.333 |
| 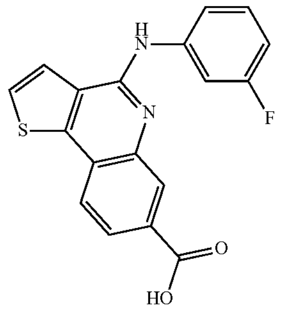 | 82.723 | 0.136 | | 0.068 | 84.968 | | | >10 | 5.925 | >10 | 0.475 |
| 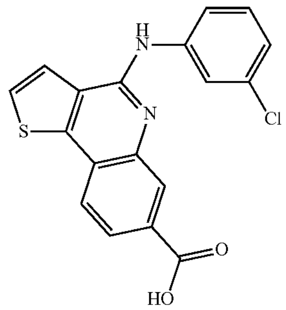 | 81.078 | 0.391 | | 0.032 | 94.192 | | | 15 | 12.363 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 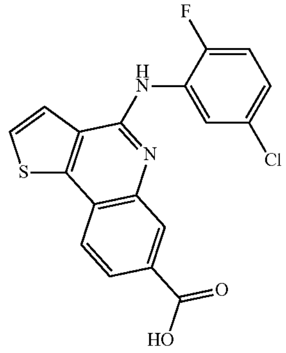 | 52.79 | 0.42 | | 0.07 | 86.553 | | | >10 | 17.642 | | |
| 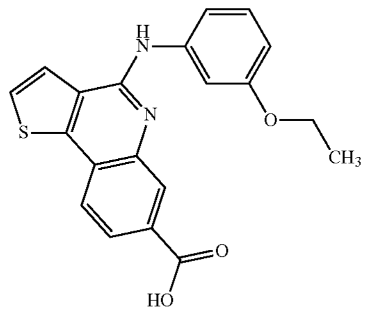 | 16.805 | | | 0.126 | 78.381 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 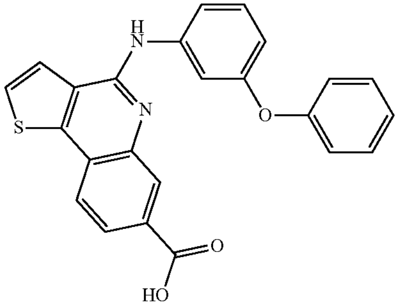 | −10.177 | | | 0.395 | 59.832 | | | >10 | | | |
| 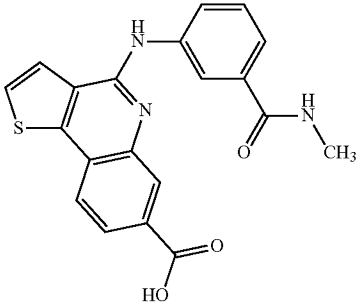 | 18.31 | | | 0.129 | 75.49 | | | >10 | 8.686 | | |
| 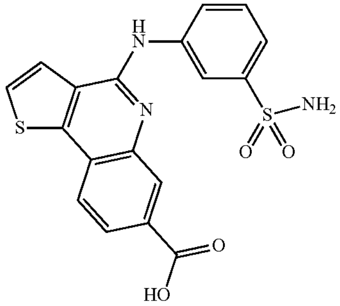 | 21.733 | | | 0.103 | 83.303 | | | >10 | 10.159 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 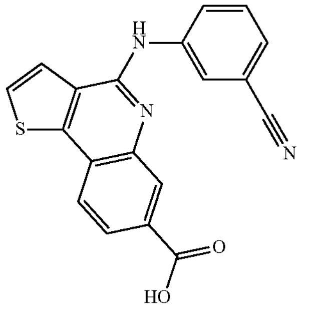 | 71.405 | 0.213 | | 0.081 | 91.712 | | | 15 | 17.611 | >10 | 0.226 |
| 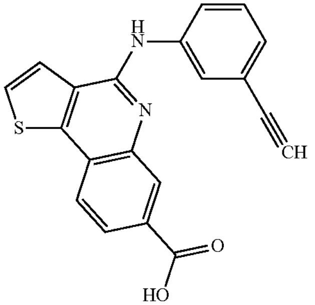 | 26.036 | | | 0.028 | 96.506 | | | 15 | 13.571 | | |
| 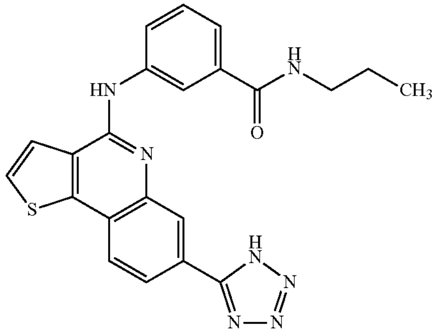 | 47.706 | | | 0.38 | 66.492 | | | 15 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 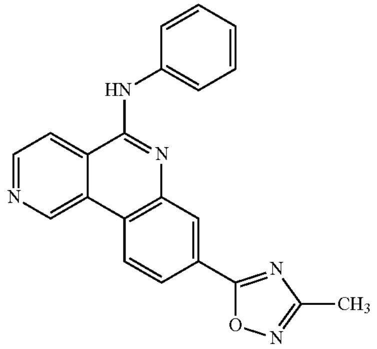 | 32.697 | >1.1 | | | 27.173 | | | >10 | | | |
| 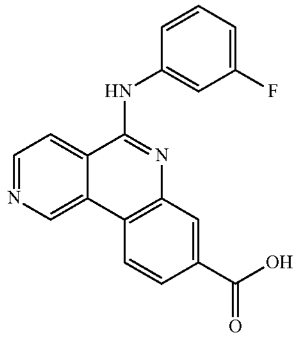 | 96.115 | 0.143 | | 0.005 | 99.605 | | | | 3.198 | >10 | 2.282 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 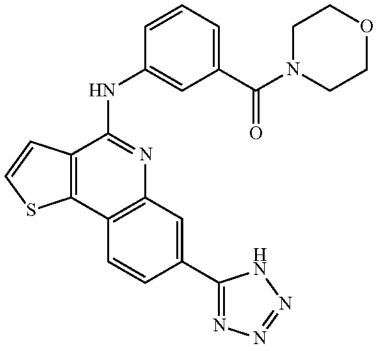 | 20.991 | | | 0.502 | 58.802 | | | >10 | | | |
| 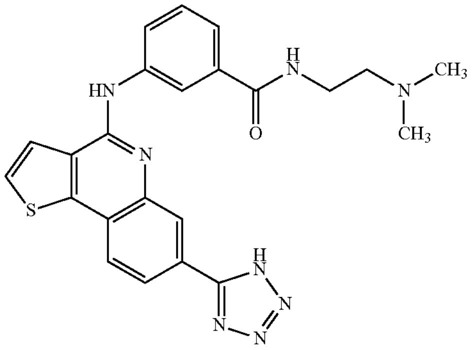 | 71.063 | 0.38 | | 0.549 | 63.541 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 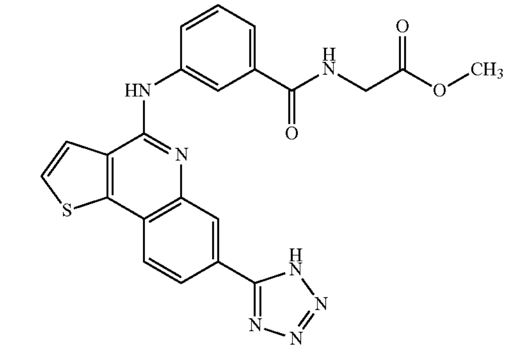 | 48.035 | | | 0.24 | 80.931 | | | >10 | | | |
| 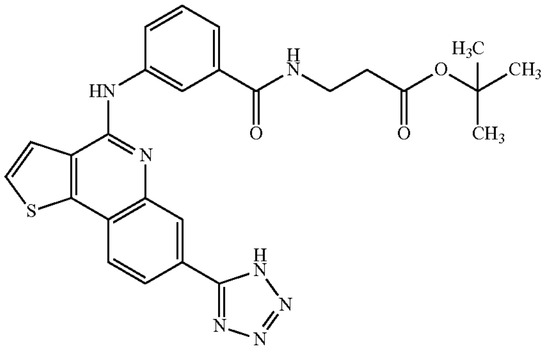 | −11.727 | | | | 40.455 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 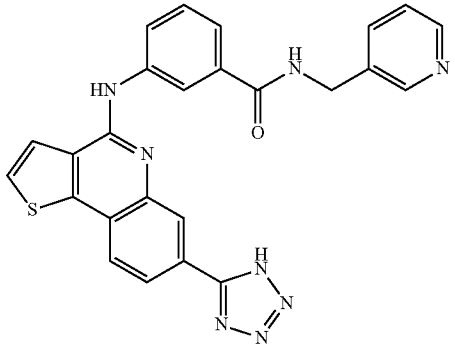 | 29.587 | | | 0.363 | 64.678 | | | >10 | | | |
| 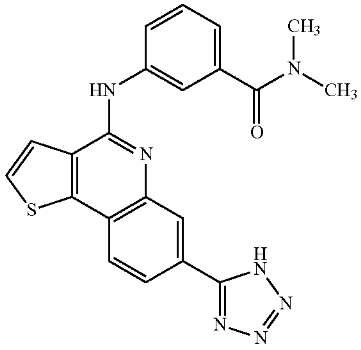 | 49.094 | | | 0.318 | 71.772 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 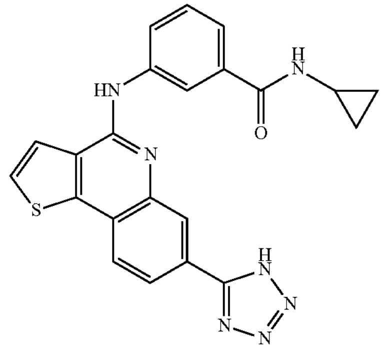 | 46.755 | | | 0.237 | 79.18 | | | >10 | 6.973 | | |
| 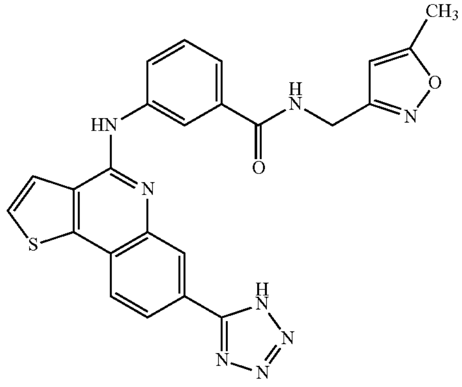 | 37.569 | | | 0.288 | 68.853 | | | >10 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 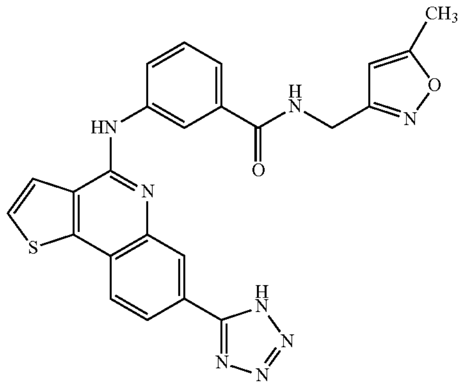 | 55.402 | 0.581 | | 0.251 | 72.159 | | | >10 | | | |
| 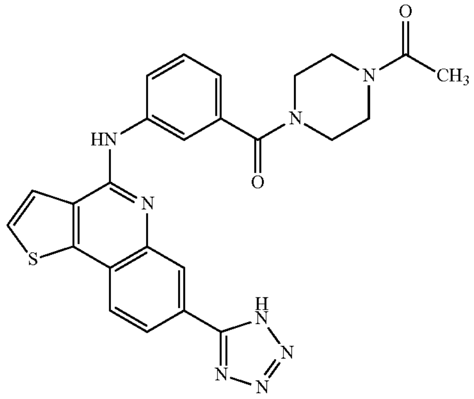 | 48.436 | | | 0.303 | 70.649 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 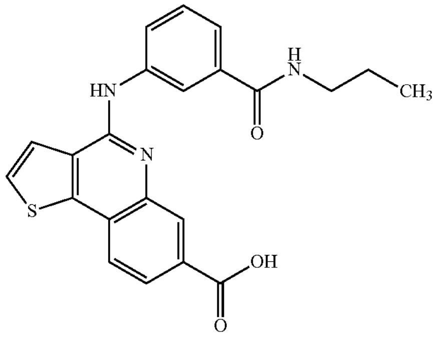 | 13.29 | | | 0.224 | 77.094 | | | >10 | | | |
| 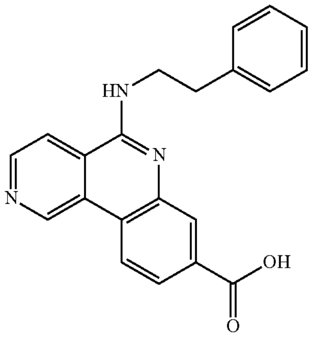 | 80.935 | 0.536 | | 0.003 | 100.142 | | | >10 | 11.106 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 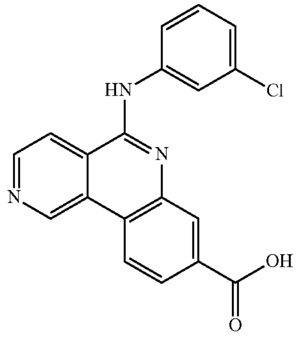 | 89.956 | 0.075 | | 0.002 | 101.868 | 0.016 | | 5.092 | 3.417 | 4.388 | 1.676 |
| 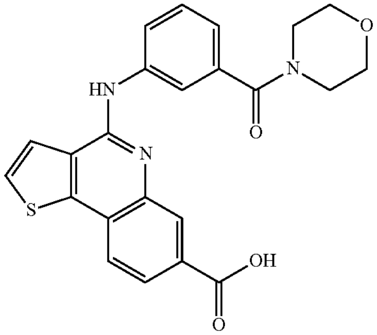 | 46.375 | | | 0.307 | 70.294 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 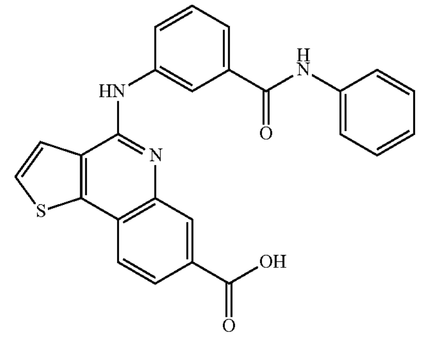 | −20.874 | | | | 37.732 | | | >10 | | | |
| 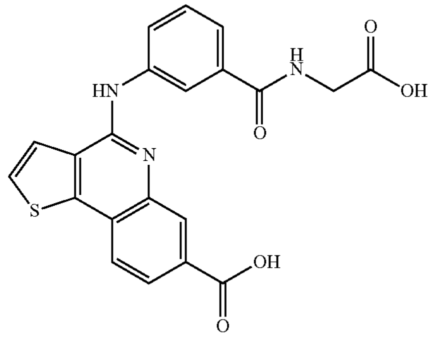 | 24.017 | | | 0.192 | 75.224 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 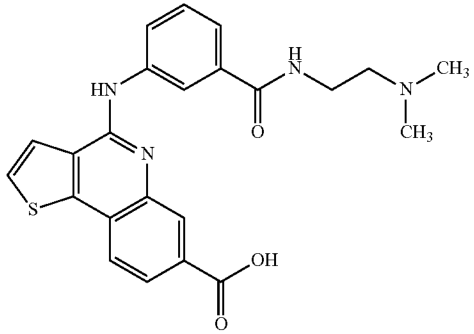 | 74.734 | 0.436 | | 0.366 | 74.521 | | | >10 | | | |
| 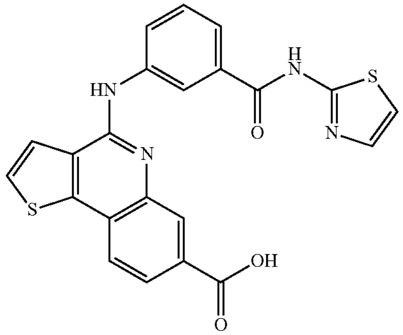 | 5.991 | | | | 52.922 | | | >10 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 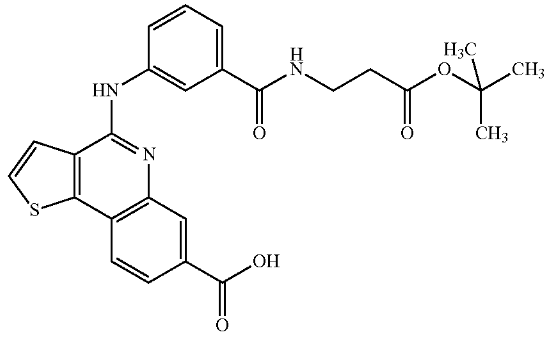 | 22.361 | | | | 65.495 | | | >10 | | | |
| 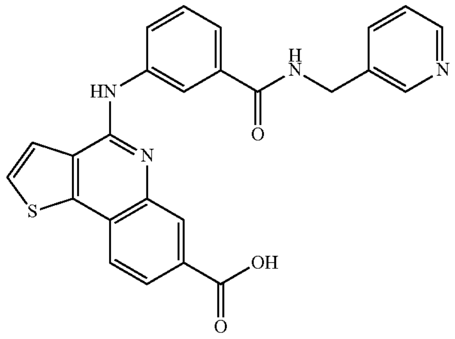 | 25.758 | | | | 62.212 | | | >10 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 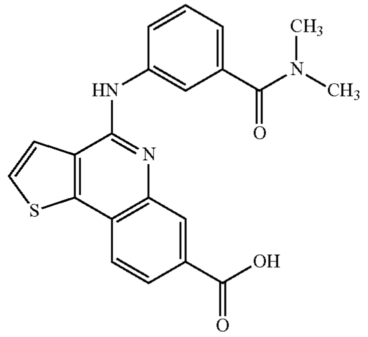 | −12.166 | | | | 21.344 | | | >10 | | | |
| 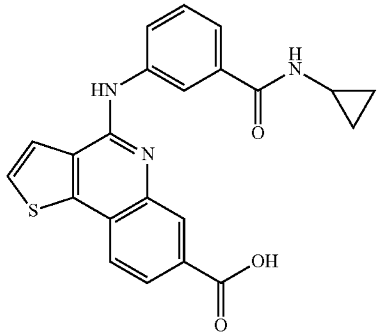 | 37.539 | | | 0.221 | 70.228 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 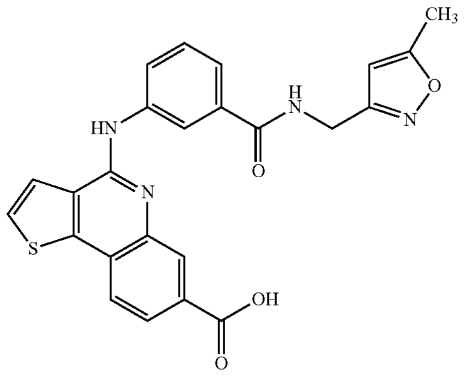 | 10.606 | | | | 62.693 | | | >10 | | | |
| 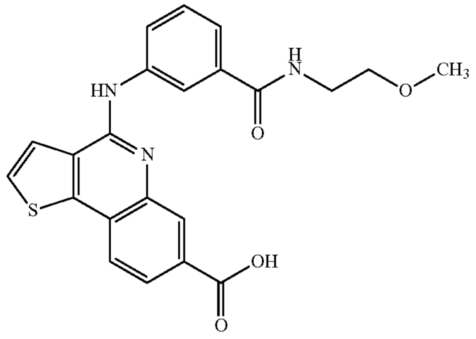 | 11.997 | | | | 65.154 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 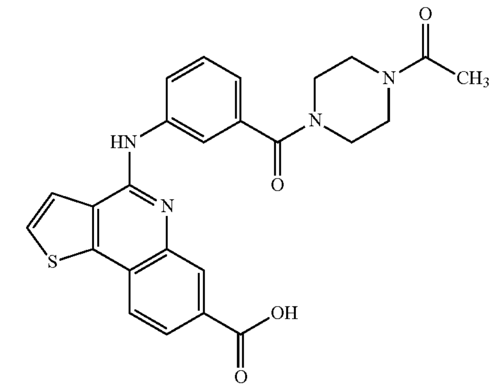 | 20.824 | | | | 36.458 | | | >10 | | | |
| 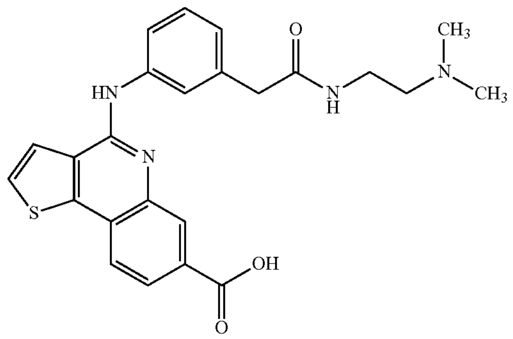 | 69.236 | 0.283 | | | 53.346 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 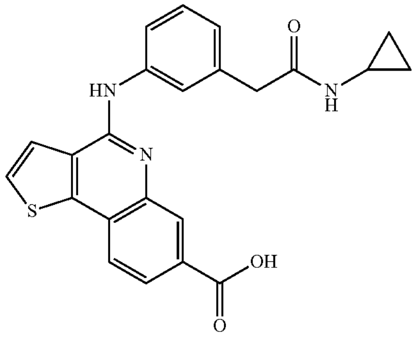 | 19.057 | | | | 51.176 | | | >10 | | | |
| 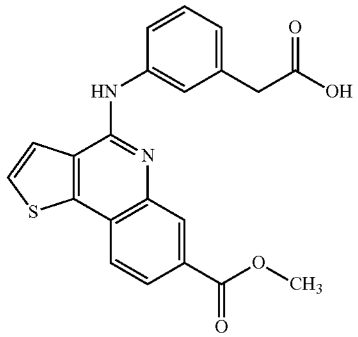 | 8.937 | | | | −6.267 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 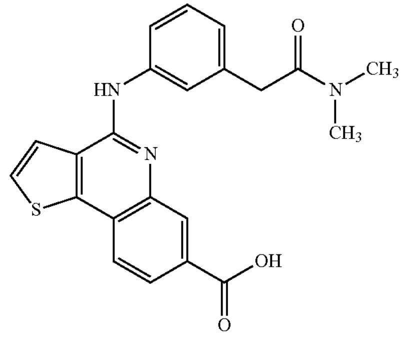 | 42.542 | | | | 55.423 | | | >10 | | | |
| 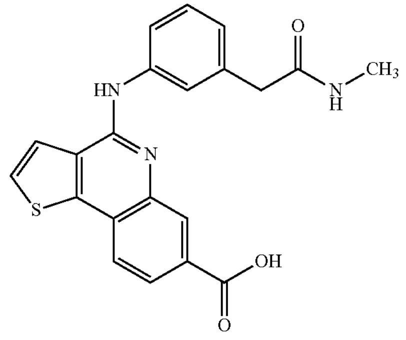 | 37.992 | | | 0.137 | 78.051 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 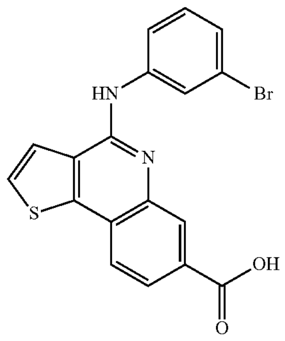 | 57.899 | 0.553 | | 0.187 | 94.151 | | | >10 | | | |
| 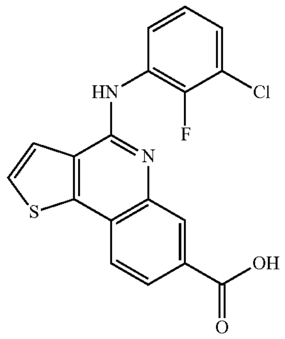 | 27.607 | | | 0.335 | 66.452 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 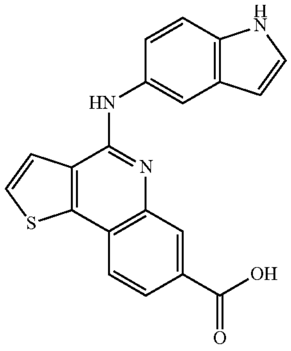 | 51.924 | 0.679 | | 0.156 | 76.964 | | | >10 | | | |
| 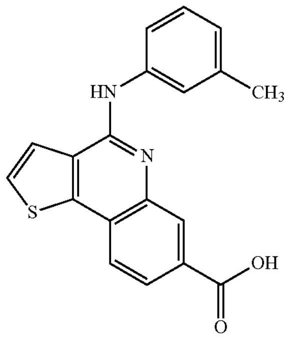 | 59.09 | 0.53 | | 0.09 | 86.542 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 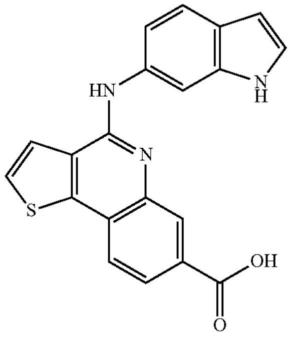 | 47.173 | | | 0.121 | 88.594 | | | >10 | | | |
| 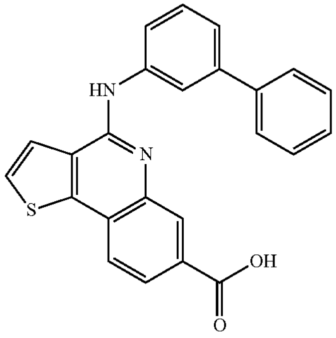 | 4.583 | | | | 65.753 | | | >10 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 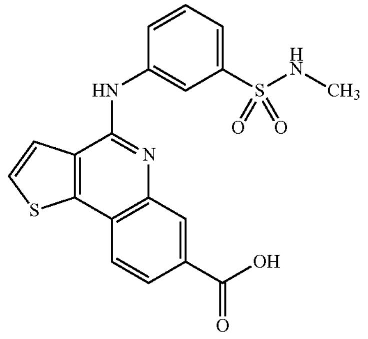 | 82.844 | 0.159 | | 0.281 | 85.186 | | | >10 | | >10 | >10 |
| 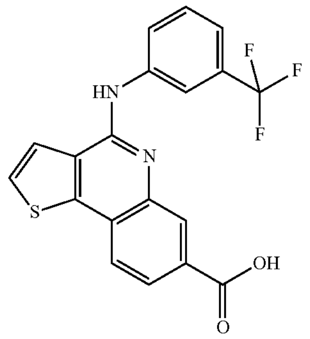 | 74.738 | 0.197 | | 0.061 | 82.187 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 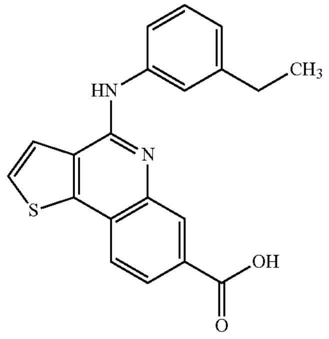 | 51.599 | 0.814 | | 0.242 | 83.847 | | | >10 | | | |
| 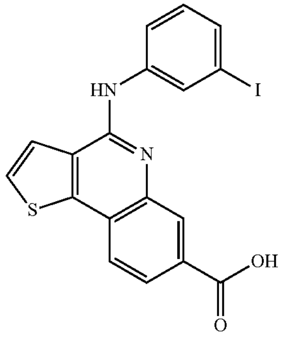 | 40.548 | | | 0.091 | 94.496 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 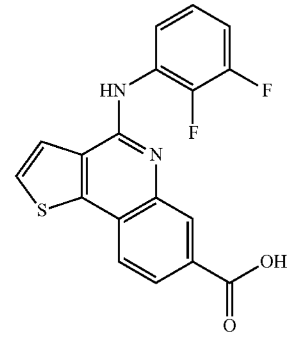 | 72.851 | 0.855 | | 0.256 | 48.438 | | | >10 | | | |
| 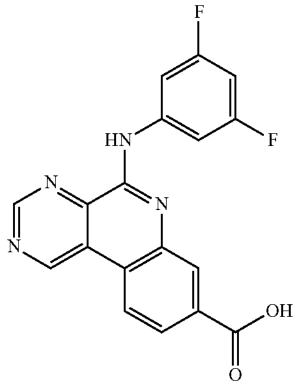 | 79.98 | >1.1 | | 0.009 | 97.434 | | | 4.055 | 2.591 | 2.407 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 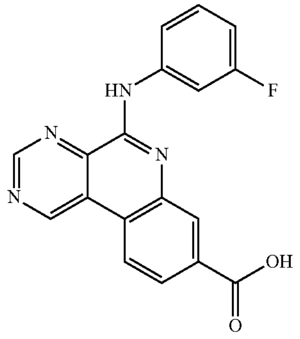 | 77.768 | 0.367 | | 0.005 | 94.26 | | | 7.102 | 1.89 | 1.768 | |
| 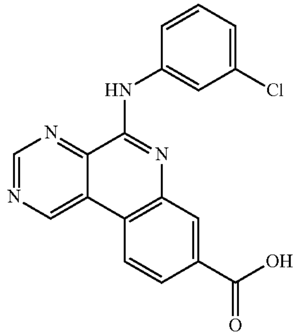 | 68.18 | 0.37 | | 0.007 | 97.005 | | | 7.194 | 0.882 | 1.129 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 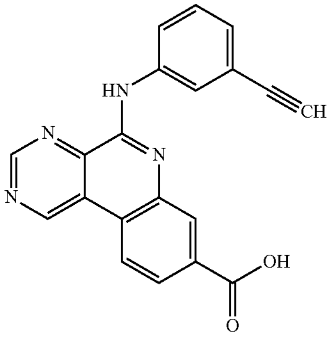 | 65.855 | 0.306 | | 0.004 | 98.351 | | | 5.863 | 3.341 | 2.485 | 0.464 |
| 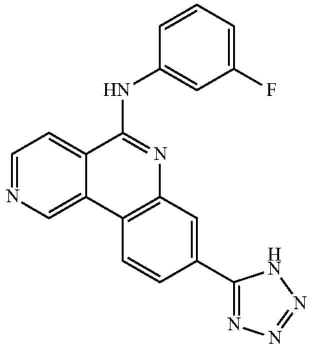 | 45.018 | | | 0.045 | 96.964 | | | >10 | 9.434 | 40.616 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 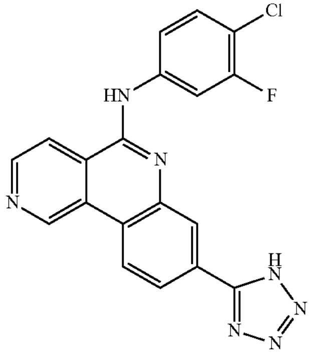 | 9.304 | | | 0.049 | 94.381 | | | >10 | 18.757 | >50 | |
| 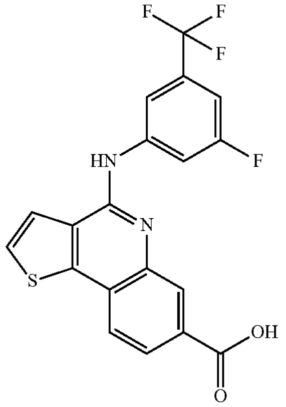 | 82.573 | 0.336 | | 0.156 | 80.942 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 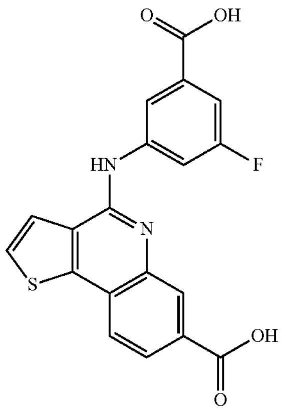 | 50.956 | 0.521 | | 0.127 | 79.922 | | | >10 | | | |
| 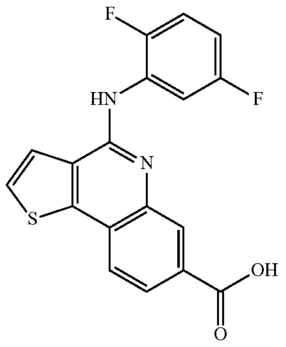 | 67.062 | 0.308 | | 0.138 | 76.36 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 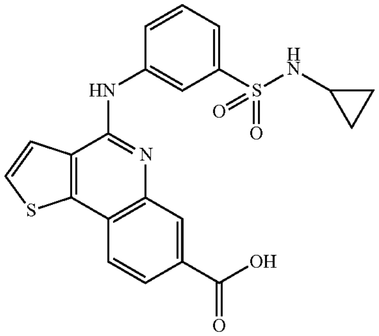 | 75.362 | 0.568 | | 0.116 | 81.193 | | | >10 | | | |
| 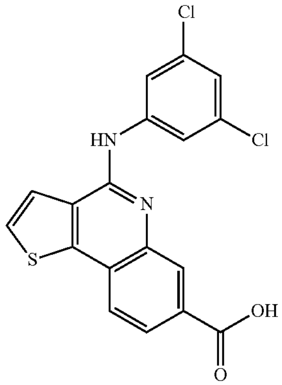 | 67.148 | | | 0.035 | 93.175 | | | 8.758 | 4.309 | 11.026 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 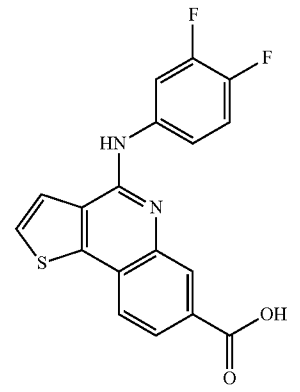 | 85.716 | 0.239 | | 0.127 | 75.678 | | | 0.832 | | >10 | 0.658 |
| 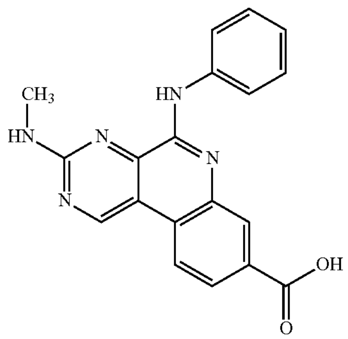 | 20.832 | | | 0.018 | 97.556 | | | 2.989 | 0.728 | 1.68 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 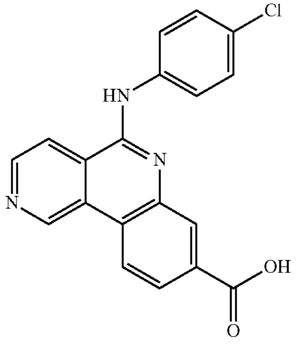 | 82.988 | 0.284 | | 0.007 | 98.442 | | | 6.724 | 2.525 | 8.652 | 1.56 |
| 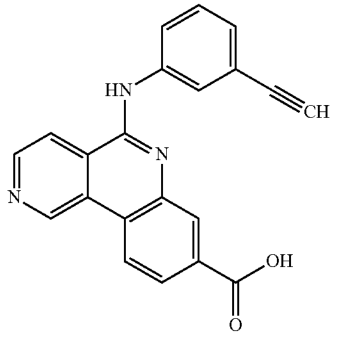 | 84.075 | 0.296 | | 0.003 | 99.706 | | | 10.796 | 2.778 | 3.333 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 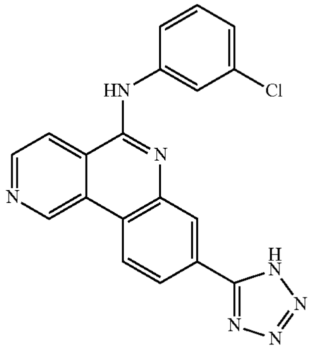 | 48.622 | 0.863 | | 0.045 | 95.316 | 0.305 | | >10 | 14.25 | 8.204 | 0.032 |
| 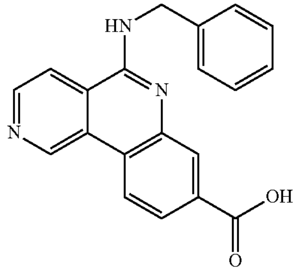 | 44.441 | 0.675 | | 0.009 | 98.918 | | | >10 | 17.697 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 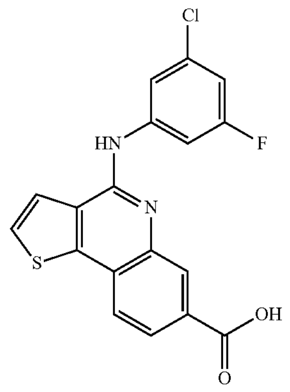 | 89.997 | 0.299 | | 0.076 | 89.803 | | | >10 | | >10 | 0.745 |
| 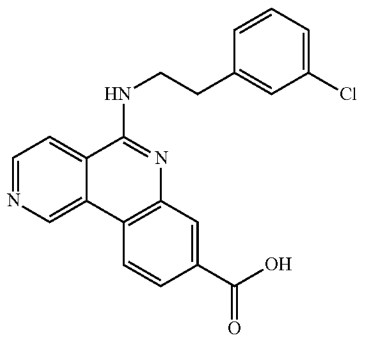 | 43.108 | 1.059 | | 0.005 | 99.218 | | | >10 | 18.881 | 9.181 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 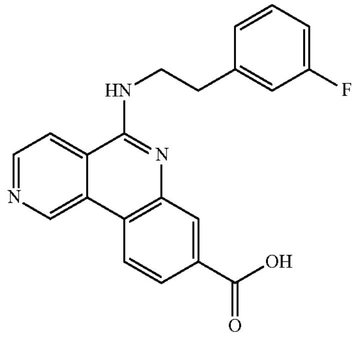 | 73.95 | 0.351 | | 0.007 | 99.713 | | | >10 | 12.222 | 8.11 | >10 |
| 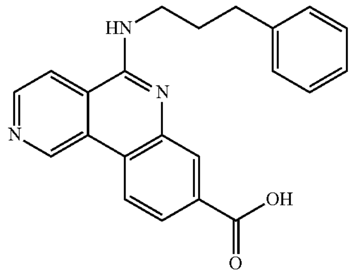 | 69.65 | 0.441 | | 0.016 | 98.386 | | | >10 | 13.227 | 7.171 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 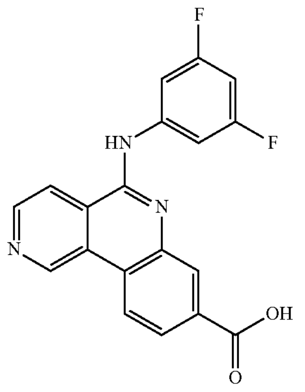 | 92.423 | 0.111 | | 0.005 | 99.511 | | | 4.326 | 2.41 | 3.264 | >10 |
| 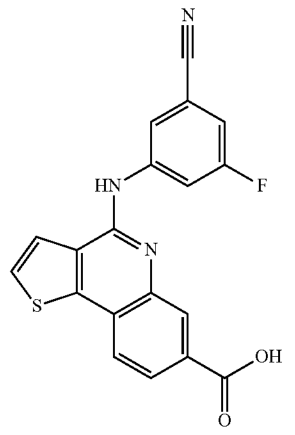 | 86.97 | 0.252 | | 0.131 | 86.23 | | | >10 | | >10 | 1.455 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 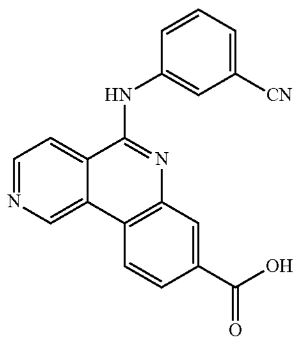 | 92.38 | 0.058 | | 0.004 | 99.643 | 0.012 | | >10 | 21.997 | 9.153 | >10 |
| 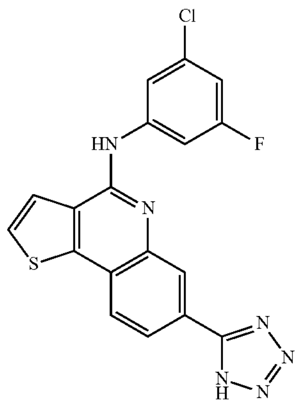 | 81.956 | 0.562 | | 0.289 | 83.744 | | | >10 | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 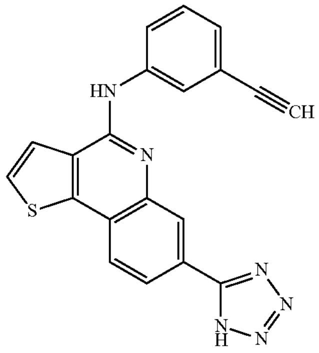 | 64.561 | 0.716 | | 0.141 | 91.808 | | | >10 | | | |
| 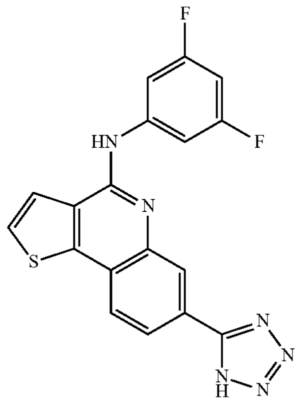 | 86.909 | 0.414 | | 0.204 | 83.045 | | | >10 | | >10 | 2.198 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 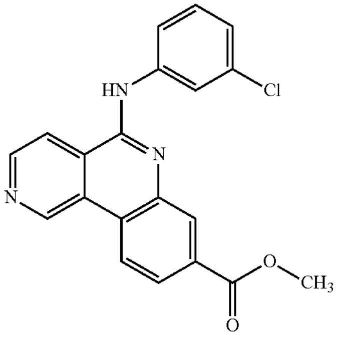 | 7.825 | | | >0.75 | 13.355 | >0.4 | | >10 | | 0.217 | 0.161 |
| 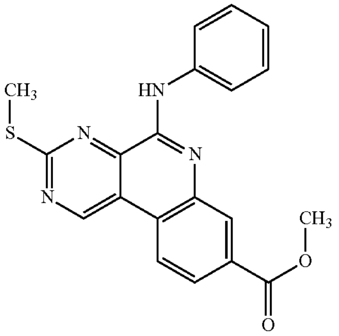 | −26.653 | | | >0.75 | 6.431 | | | 9.564 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 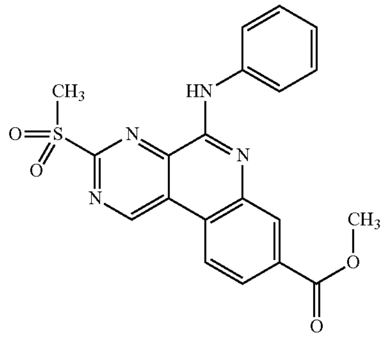 | −27.759 | | | >0.75 | −44.24 | | | 0.967 | | | |
| 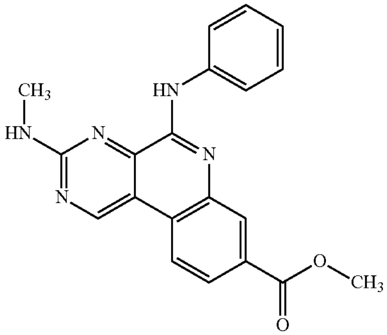 | −9.762 | | | >0.75 | −12.109 | | | 4.06 | | | |
| 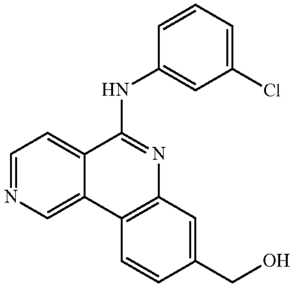 | 4.222 | | | 0.711 | 26.885 | 0.013 | | 4.284 | | 5.522 | 0.529 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 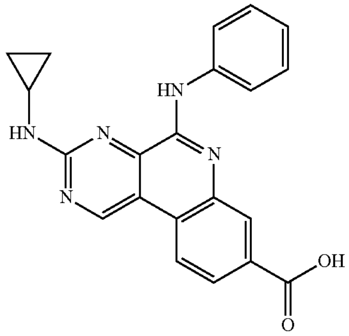 | 18.359 | | | 0.027 | 101.583 | | | 1.943 | 2.416 | 0.494 | 0.195 |
| 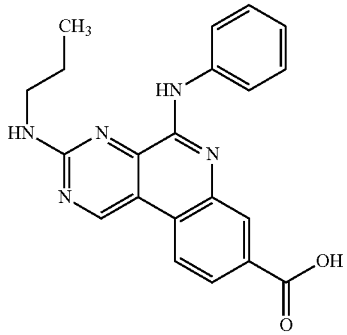 | 29.916 | | | 0.051 | 100.779 | | | >10 | 4.533 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 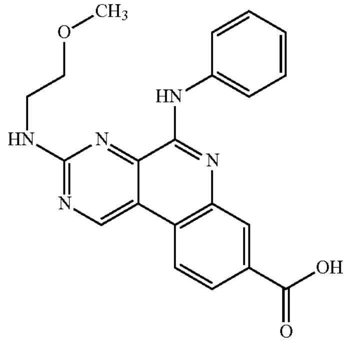 | 19.752 | | | 0.069 | 98.141 | | | >10 | 5.803 | | |
| 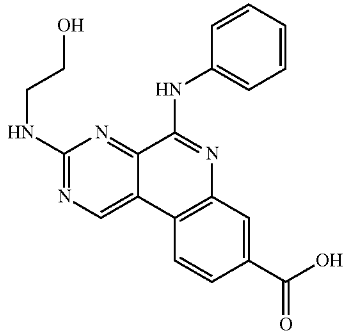 | 45.65 | | | 0.02 | 99.594 | | | >10 | 26.127 | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 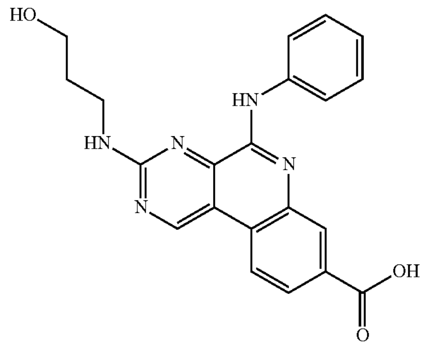 | 49.341 | | | 0.026 | 98.566 | | | >10 | 7.896 | | |
| 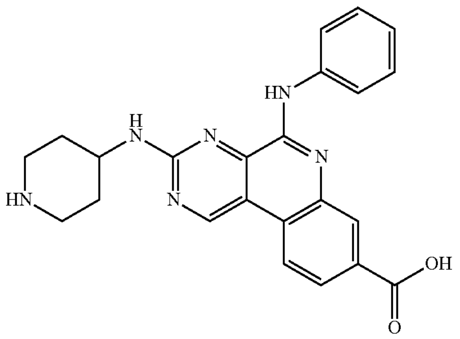 | −2.53 | | | 0.056 | 99.806 | | | >10 | 18.909 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 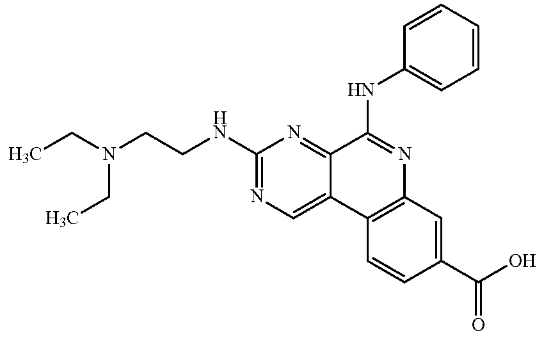 | 4.268 | | | 0.163 | 93.689 | | | >10 | 13.068 | | |
| 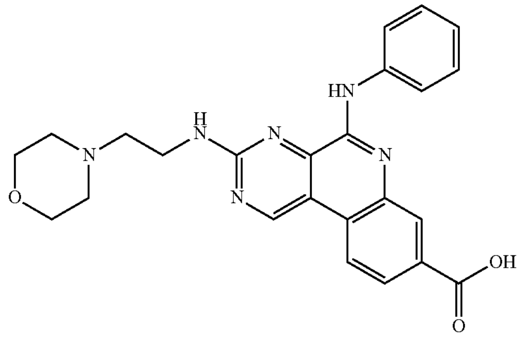 | 30.573 | | | 0.107 | 90.209 | | | >10 | 5.701 | 1.155 | 0.358 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 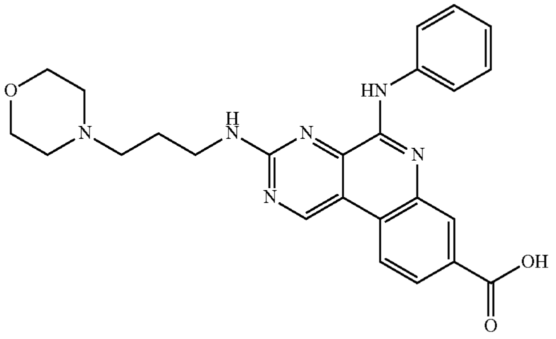 | 33.671 | | | 0.089 | 93.141 | | | >10 | 2.176 | | |
| 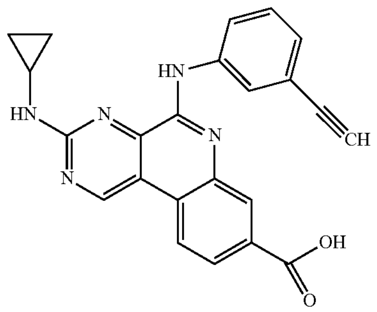 | −38.646 | | | 0.046 | 99.762 | | | 7.303 | 1.272 | | |
| 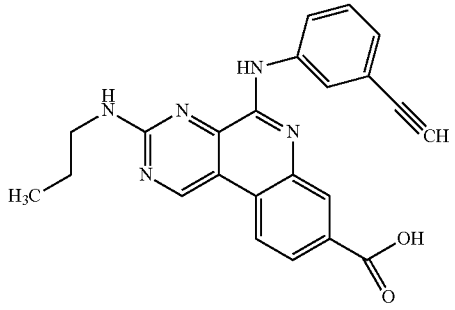 | 45.618 | | | 0.06 | 98.155 | | | >10 | 2.673 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 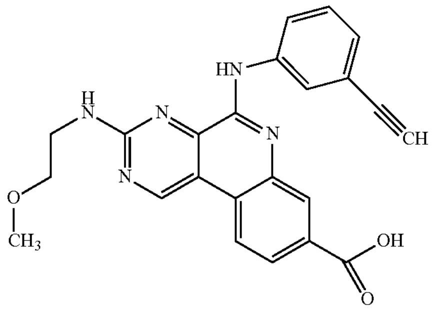 | 55.5 | >1.1 | | 0.04 | 98.926 | | | 8.054 | 0.94 | | |
| 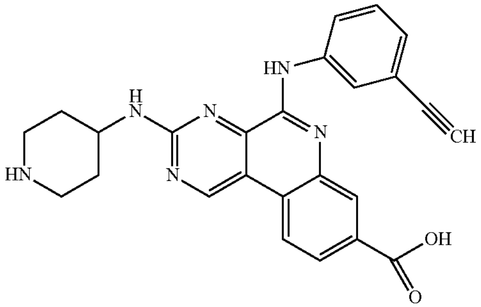 | 28.955 | | | 0.144 | 91.618 | | | >10 | 9.55 | >10 | 0.237 |
| 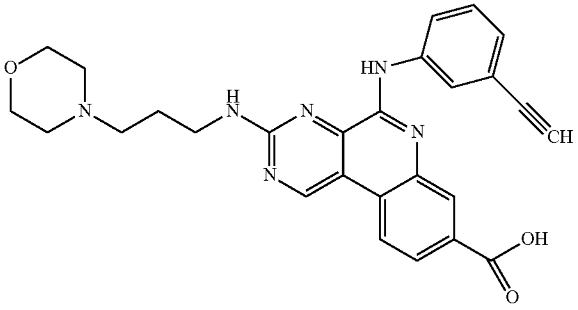 | 41.564 | | | 0.25 | 84.584 | | | >10 | 3.688 | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 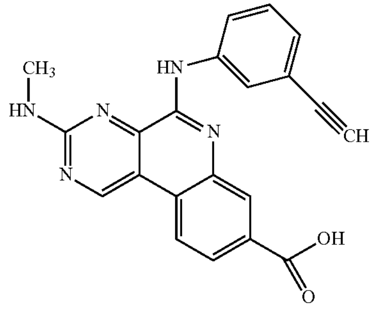 | 68.181 | 0.661 | | 0.009 | 99.937 | | | 4.694 | 1.288 | | |
| 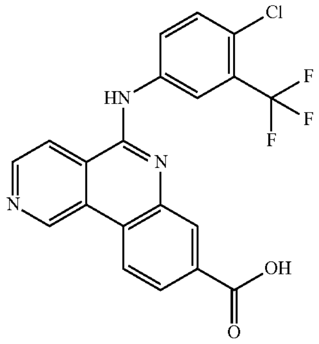 | 73.593 | 0.408 | | 0.018 | 95.155 | | | 3.989 | 3.046 | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 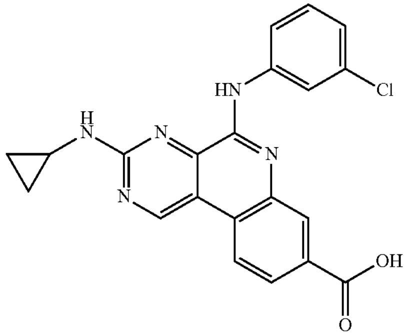 | | | | 0.013 | 98.928 | | | 7.818 | 1.289 | 0.158 | 0.257 |
| 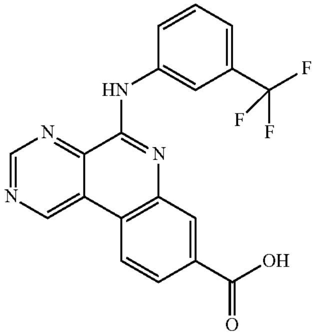 | | | | 0.011 | 97.839 | | | >10 | 2.529 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 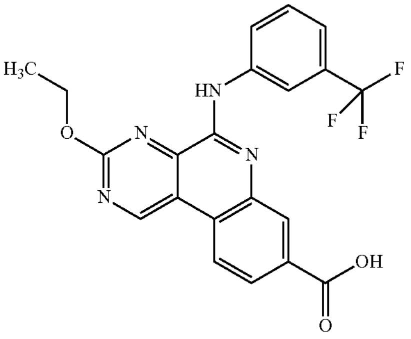 | −5.004 | | | >0.75 | | | | >10 | 35.933 | | |
| 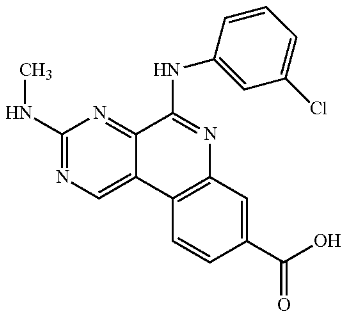 | 51.49 | | | 0.018 | | | | >10 | 1.093 | | |
| 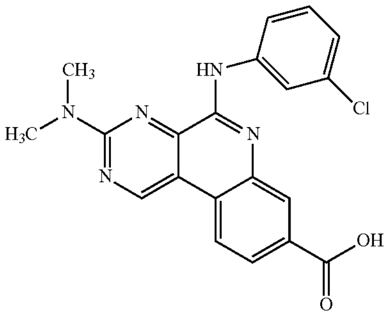 | | | | >0.75 | | | | >10 | 5.83 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 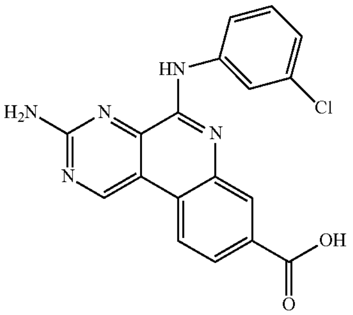 | 85.705 | | | 0.004 | | | | >10 | 1.144 | | |
| 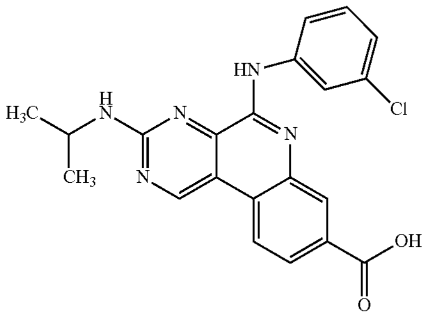 | −0.505 | | | 0.134 | | | | >10 | 18.418 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 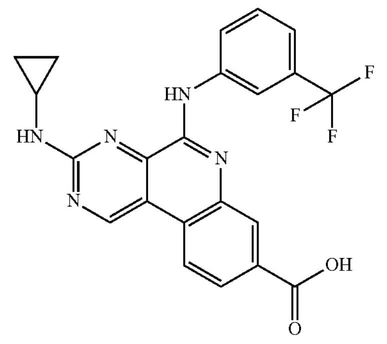 | −17.317 | | | 0.009 | | >0.4 | | >10 | 3.134 | >10 | >10 |
| 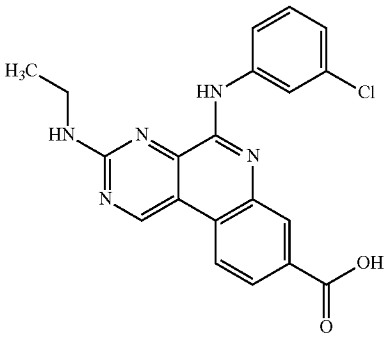 | | | | 0.03 | | | | >10 | 3.056 | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 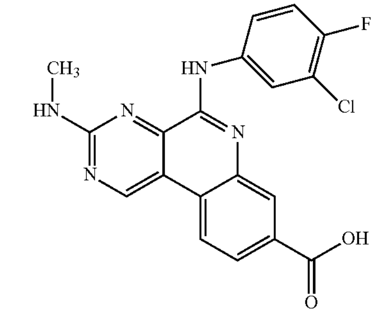 | 18.631 | | | 0.02 | | | | >10 | 1.238 | >10 | 0.655 |
| 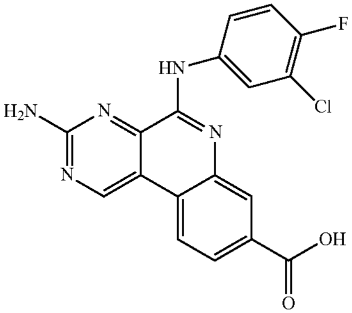 | 38.832 | | | 0.007 | 103.334 | | | 11.25 | 4.338 | | |
| 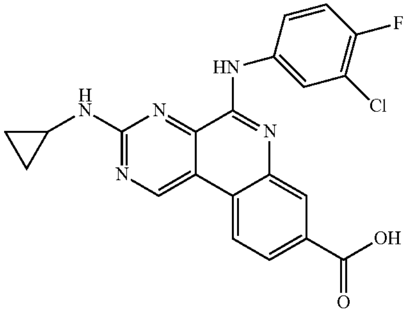 | 6.633 | | | 0.083 | 97.894 | | | >10 | 1.538 | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 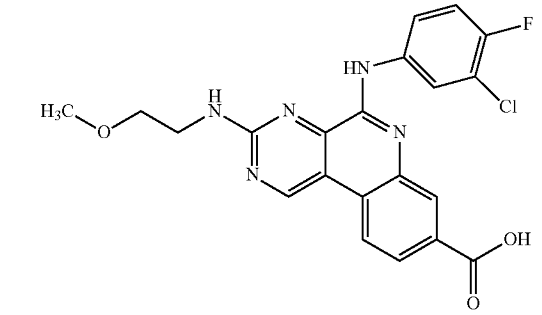 | 22.914 | | | 0.052 | 99.02 | | | >10 | 0.413 | | |
| 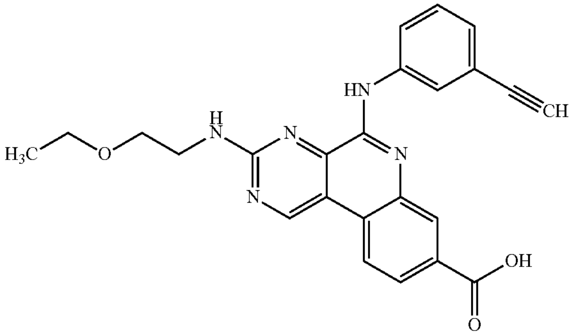 | 12.114 | | | 0.171 | 87.163 | | | >10 | 1.133 | >10 | 0.141 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 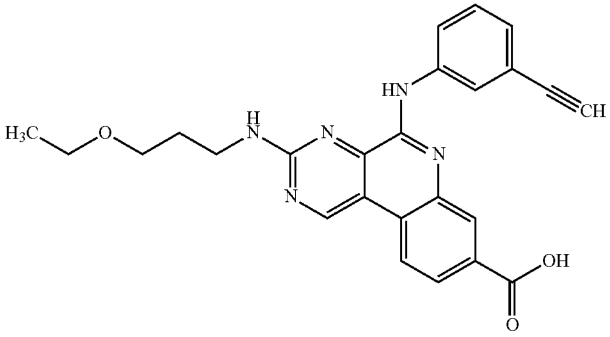 | 2.186 | | | 0.107 | 98.251 | | | >10 | 0.389 | | |
| 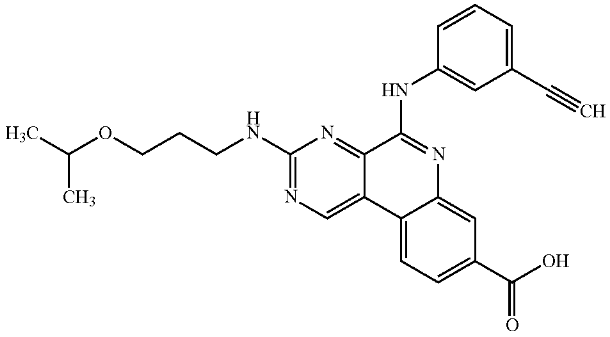 | −1.778 | | | 0.349 | 58.822 | | | >10 | 2.365 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 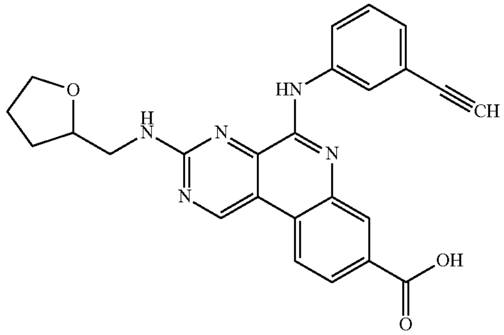 | 1.483 | | | 0.114 | 92.801 | | | >10 | 2.043 | >10 | 0.284 |
| 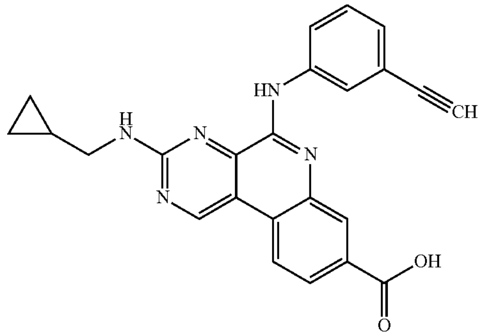 | 3.075 | | | 0.05 | 97.77 | | | >10 | 0.424 | 0.25 | 0.128 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 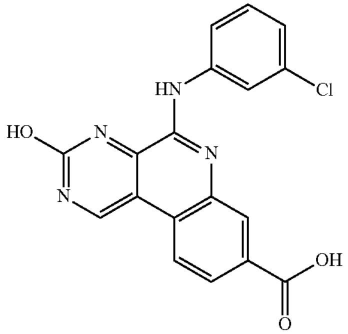 | 3.529 | | | 0.214 | 67.991 | | | >10 | >50 | | |
| 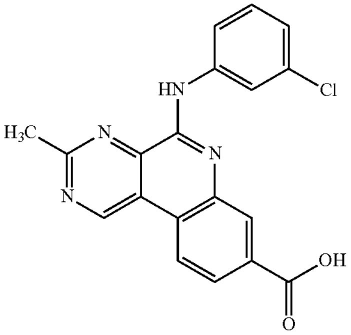 | 12.92 | | | 0.172 | 87.317 | | | >10 | 4.95 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 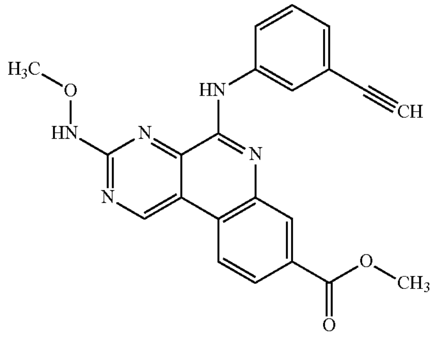 | 0.371 | | | ?0.75 | | | | >10 | 26.984 | | |
| 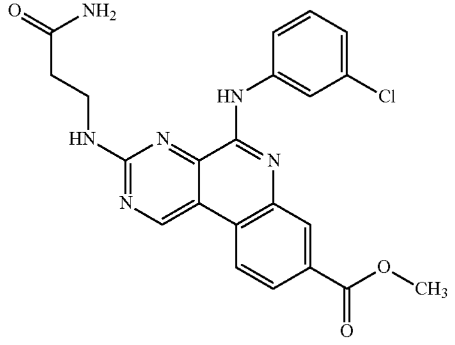 | −12.555 | | | >0.75 | | | | >10 | 4.406 | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 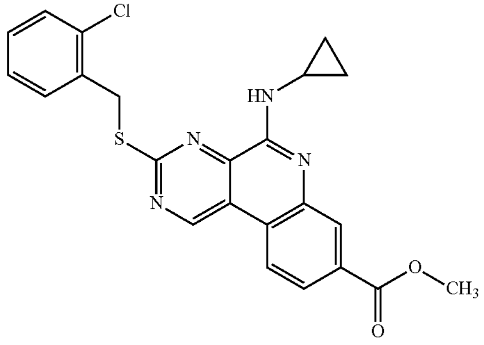 | −0.924 | | | >0.75 | | | | >10 | 4.669 | | |
| 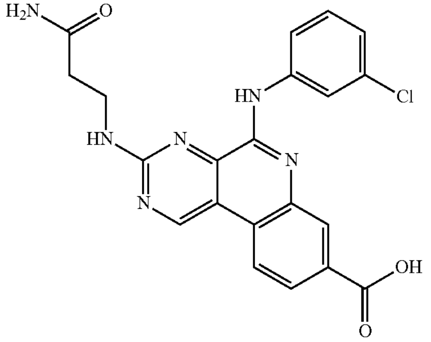 | | | | 0.028 | | | | >10 | 37.705 | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 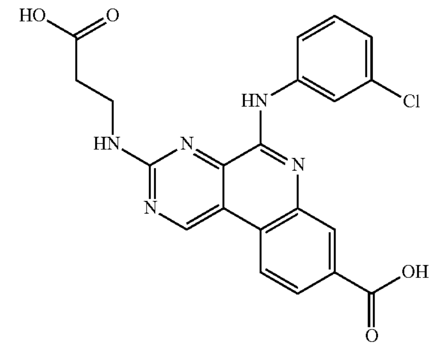 | 24.195 | | | 0.021 | | | | >10 | >50 | | |
| 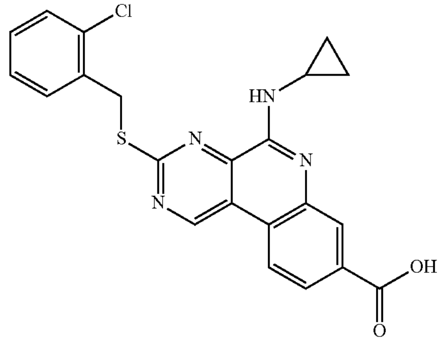 | 7.487 | | | >0.75 | | | | >10 | 29.325 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 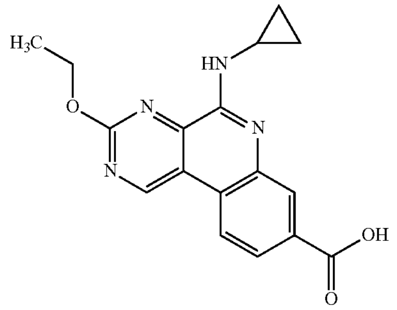 | 11.127 | | | 0.493 | | | | >10 | 18.503 | | |
| 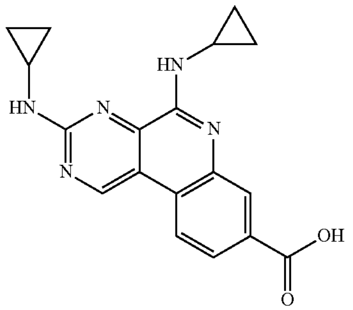 | 27.103 | | | 0.006 | | | | >10 | 3.449 | | |
| 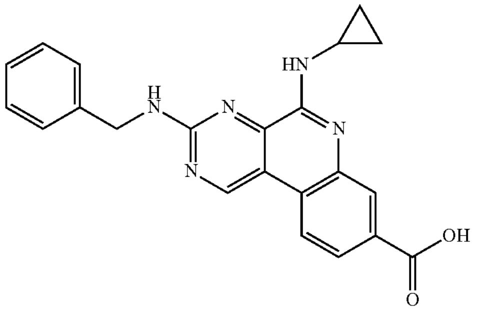 | 34.532 | | | 0.059 | | | | >10 | 8.819 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 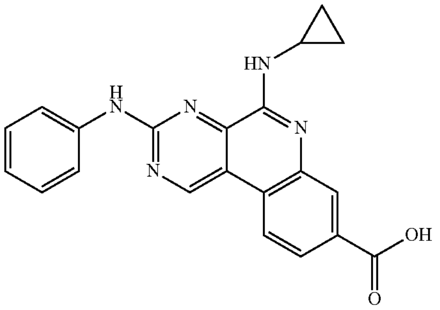 | 45.952 | | | 0.026 | | | | >10 | 4.598 | | |
| 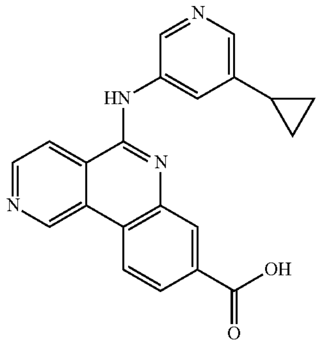 | | | | >0.75 | | | | >10 | >50 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 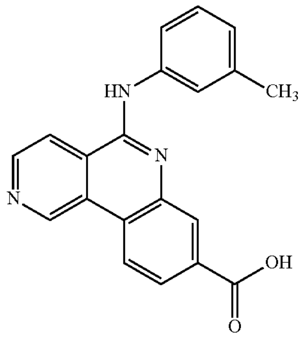 | 86.687 | 0.177 | | 0.006 | | | | >10 | 3.453 | >10 | 0.593 |
| 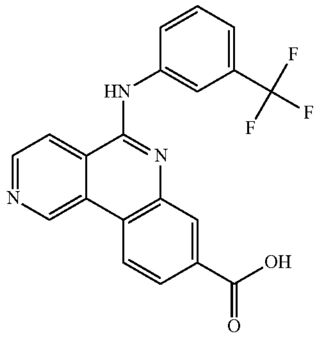 | 88.846 | 0.16 | | 0.011 | | | | 5.139 | 3.146 | >10 | 0.354 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 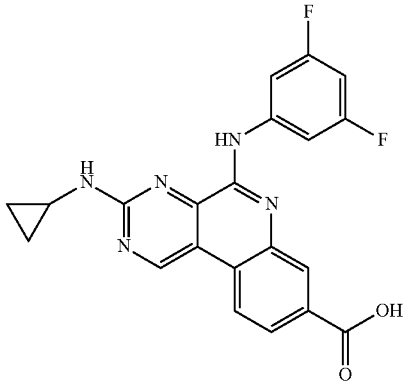 | 48.944 | | | 0.102 | | | | >10 | 6.024 | | |
| 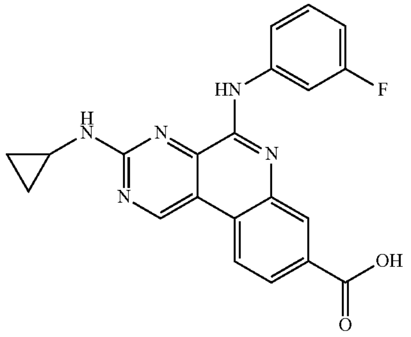 | 59.276 | | | 0.086 | | | | >10 | 3.56 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 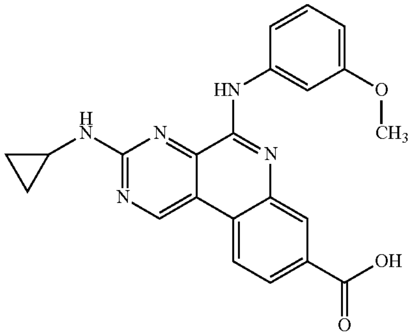 | 36.467 | | | 0.134 | | | | >10 | 3.443 | | |
| 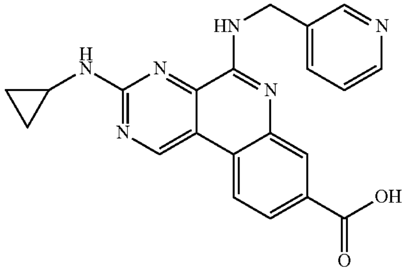 | 26.902 | | | 0.018 | | | | >10 | 25.751 | | |
| 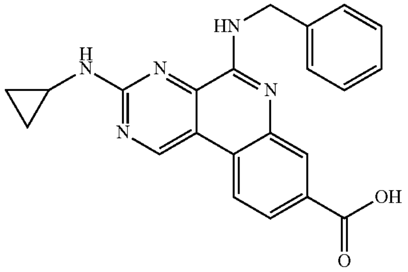 | 25.269 | | | 0.035 | | | | >10 | 16.923 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 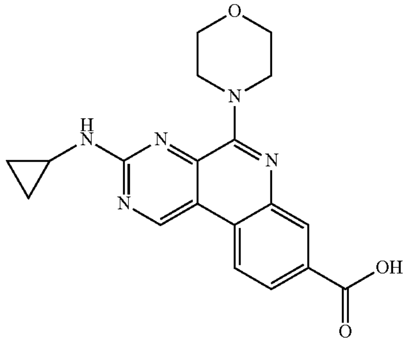 | 26.017 | | | >0.75 | | | | >10 | 3.667 | | |
| 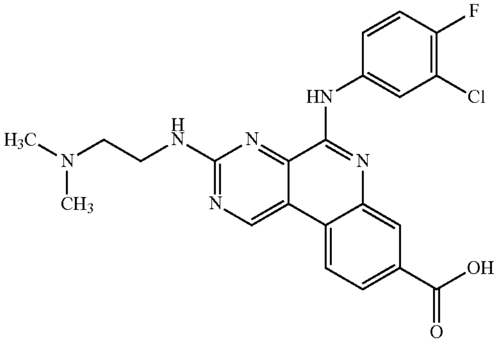 | 52.998 | | | 0.168 | | | | >10 | 1.253 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 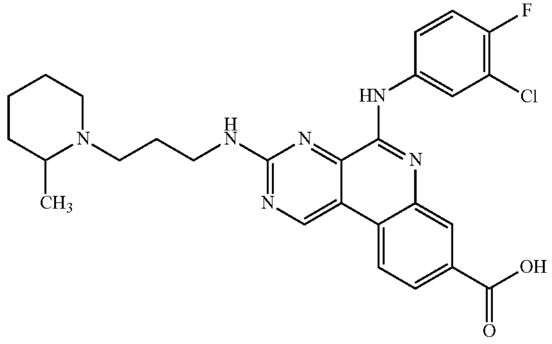 | 38.927 | | | 0.686 | | | | 9.8 | 2.864 | | |
| 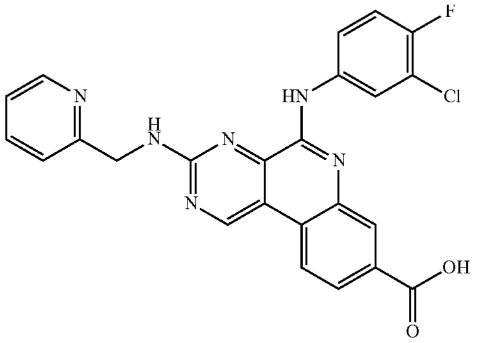 | 59.089 | | | 0.356 | | | | >10 | 2.586 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 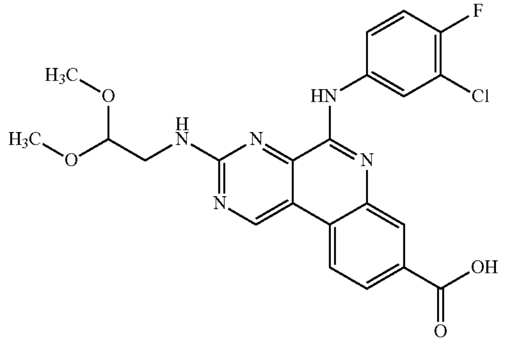 | 57.642 | | | 0.103 | | | | >10 | 1.124 | | |
| 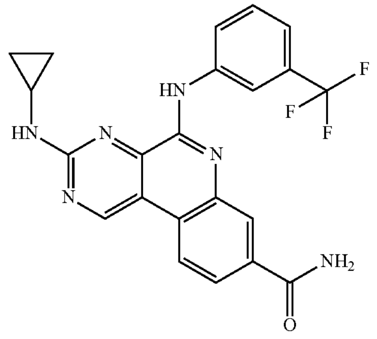 | 12.537 | | | >0.75 | | 0.343 | | >10 | 1.158 | 0.157 | 0.149 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 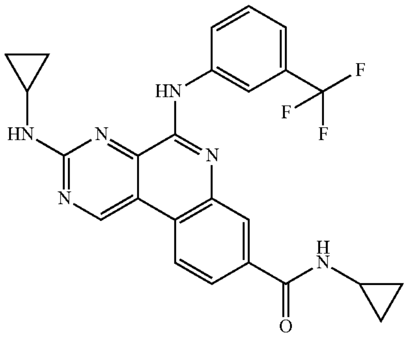 | 16.738 | | | >0.75 | | | | >10 | 3.923 | | |
| 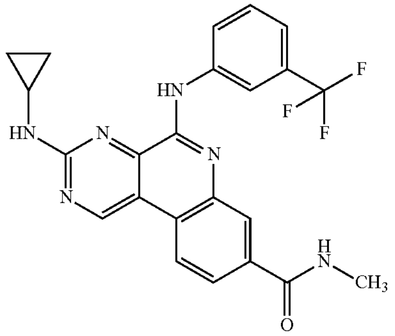 | 16.241 | | | >0.75 | | | | >10 | 3.646 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 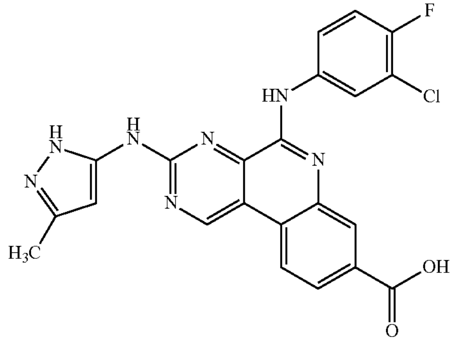 | 66.105 | | | 0.513 | | | | >10 | 1.34 | | |
| 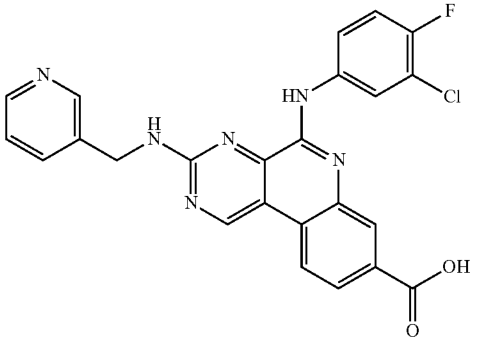 | 19.611 | | | 0.027 | | | | >10 | 1.495 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 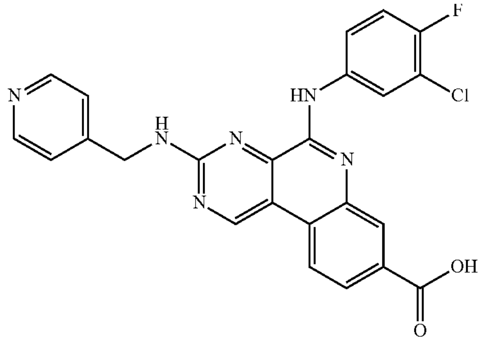 | | | | | | | | >10 | 5.11 | | |
| 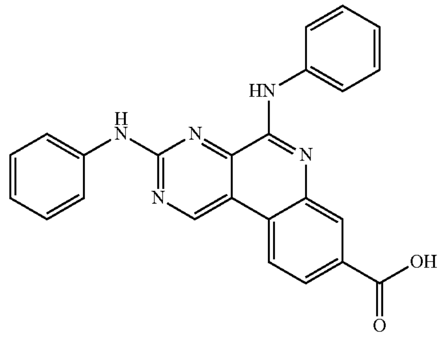 | 13.008 | | | 0.185 | | | | >10 | 8.977 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 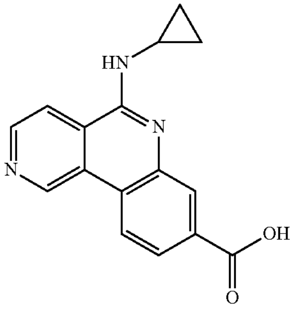 | 28.079 | | | 0.016 | | | | >10 | 37.461 | | |
| 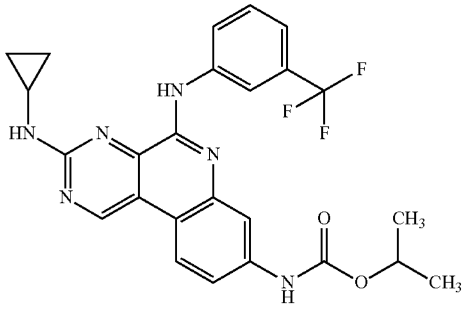 | 10.136 | | | >0.75 | | >0.4 | | >10 | 1.158 | 0.061 | 0.108 |
| 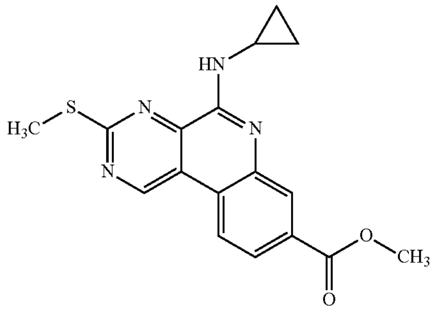 | 17.072 | | | >0.75 | | | | >10 | >50 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 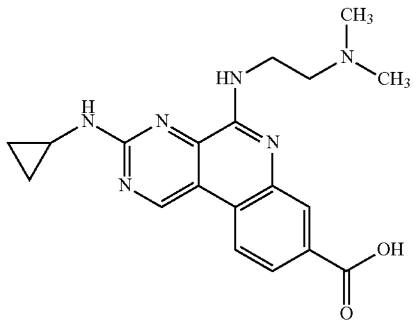 | −37.543 | | | >0.75 | | | | >10 | 33.951 | | |
| 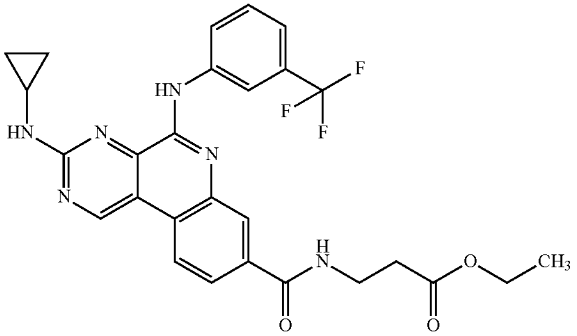 | 10.486 | | | | | | | >10 | 7.242 | | |
| 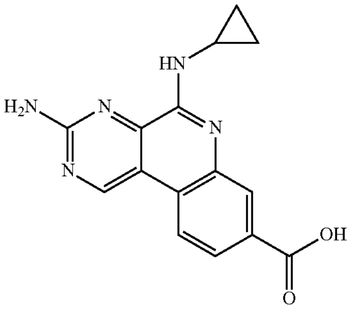 | 60.101 | 0.432 | | 0.023 | | | | >10 | 26.676 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 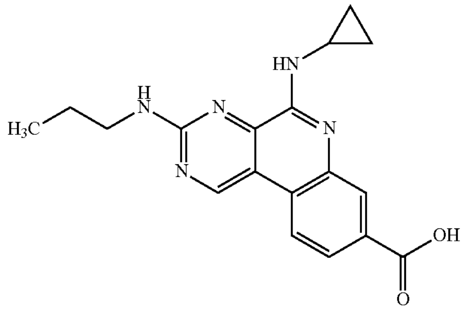 | 13.151 | | | 0.015 | | | | >10 | 9.374 | | |
| 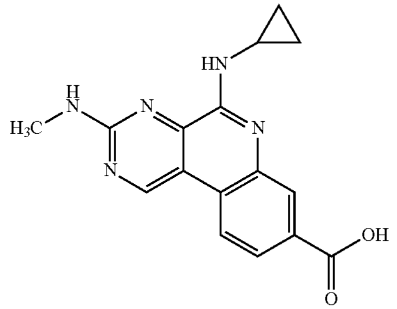 | 52.427 | 0.535 | | 0.014 | | | | >10 | 9.678 | | |
| 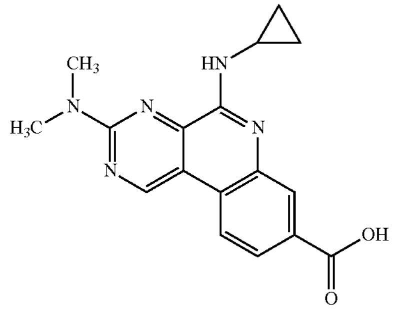 | −38.492 | | | >0.75 | | | | >10 | >50 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 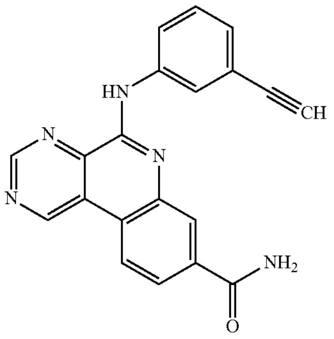 | −38.116 | | | | | | | >10 | 31.501 | | |
| 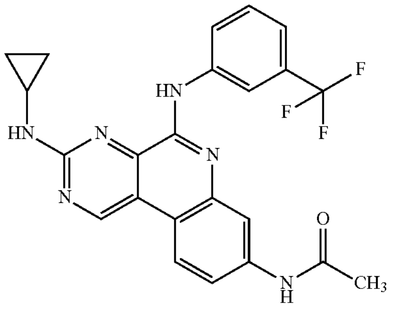 | −39.83 | | | >0.75 | | | | >10 | 1.219 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 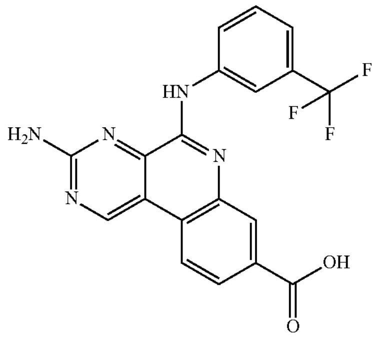 | 74.326 | 0.443 | | 0.014 | | | | >10 | 2.656 | | |
| 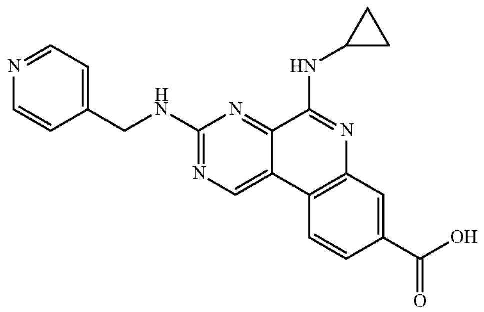 | 8.179 | | | 0.093 | | | | >10 | 35.553 | | |
| 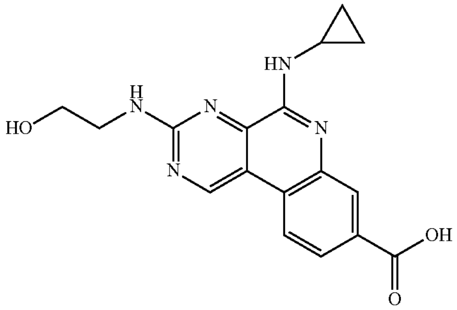 | 22.448 | | | 0.01 | | | | >10 | >50 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 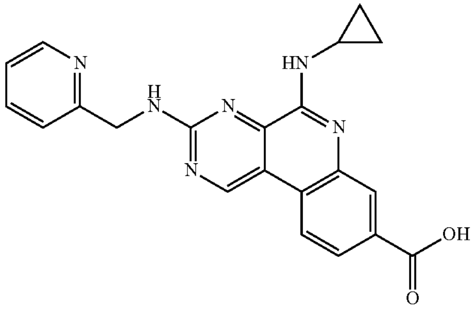 | 11.2 | | | 0.035 | | | | >10 | 23.256 | | |
| 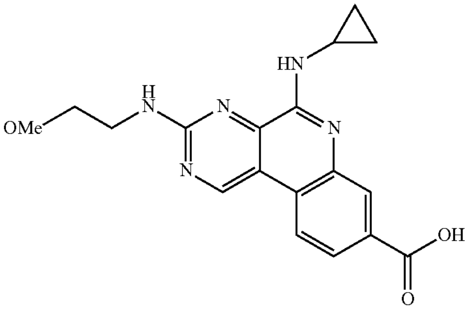 | 17.223 | | | 0.013 | | | | >10 | 13.692 | | |
| 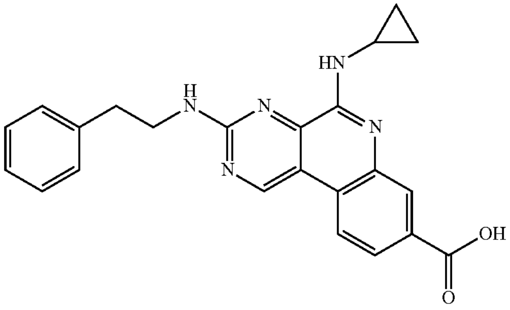 | −11.09 | | | 0.033 | | | | >10 | 0.826 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 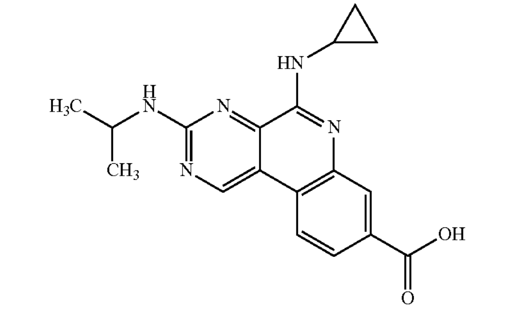 | 73.28 | >1.1 | | 0.02 | | | | >10 | 2.142 | | |
| 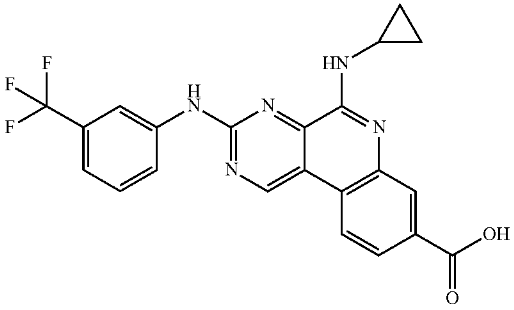 | 44.161 | | | 0.198 | | | | >10 | 2.389 | | |
| 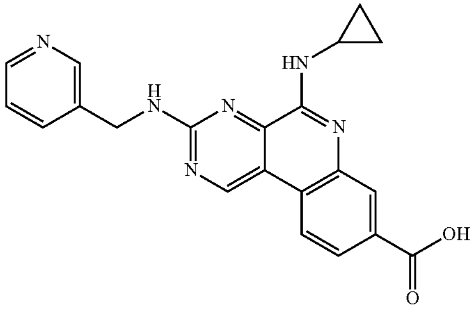 | | | | 0.023 | | | | >10 | >50 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 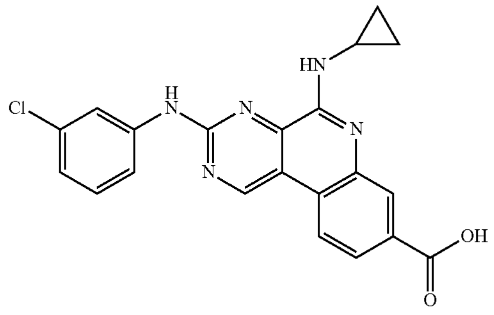 | 23.172 | | | 0.095 | | | | >10 | 2.17 | | |
| 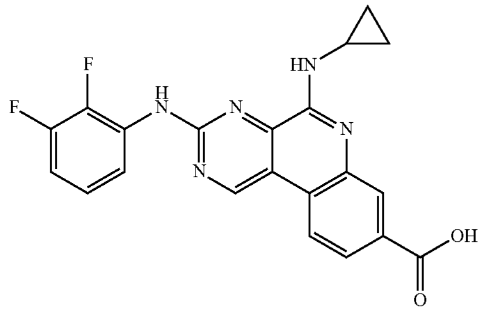 | 71.688 | | | 0.017 | | | | >10 | 2.377 | | |
| 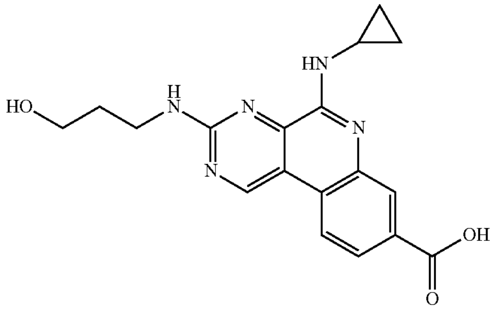 | −15.942 | | | 0.164 | | | | >10 | >50 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 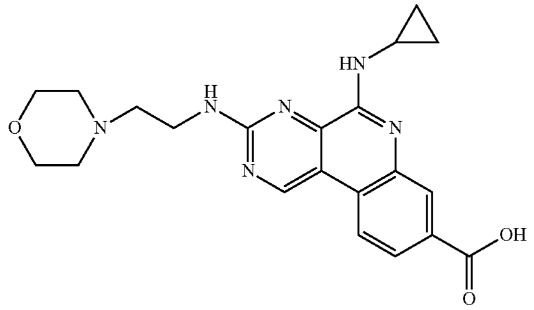 | 41.202 | | | | | | | >10 | 20.967 | | |
| 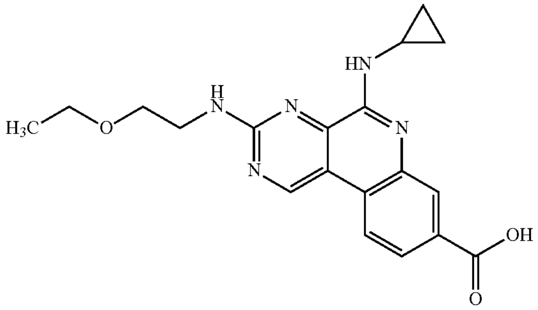 | −8.193 | | | 0.058 | | | | >10 | 18.081 | | |
| 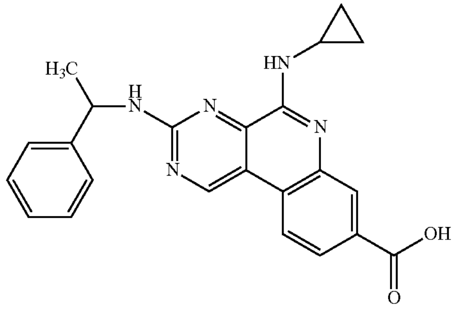 | −32.739 | | | 0.228 | | | | >10 | 28.662 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 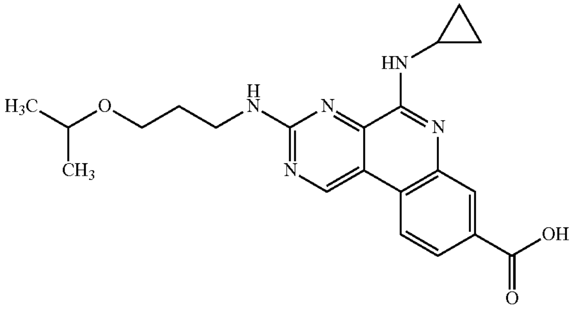 | −40.186 | | | 0.074 | | | | >10 | 16.613 | | |
| 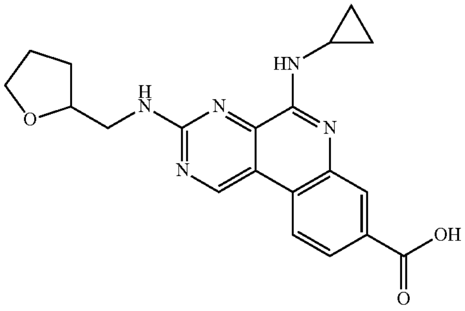 | 10.54 | | | 0.042 | | | | >10 | 21.506 | | |
| 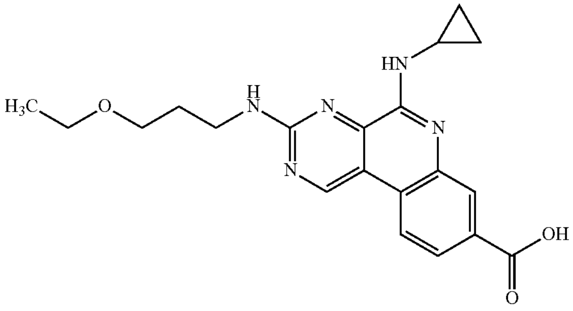 | 9.555 | | | 0.045 | | | | 3.644 | 2.021 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 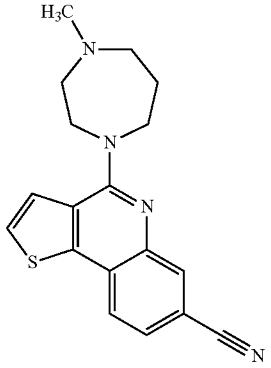 | −10.016 | | | | | | | 2.634 | | | |
| 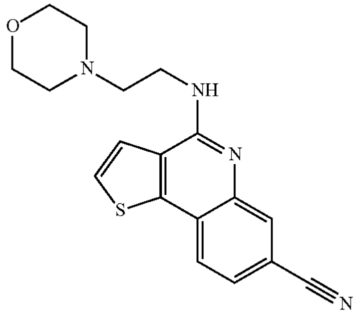 | −23.756 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 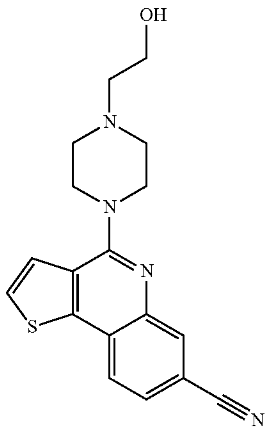 | −17.567 | | | | | | | 9.378 | | | |
| 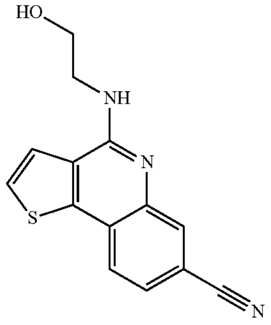 | −2.909 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 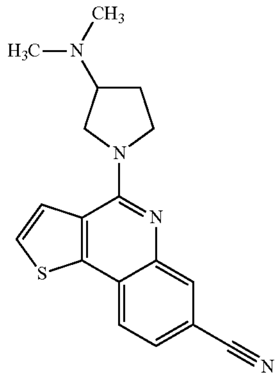 | −16.483 | | | | | | | 3.864 | | | |
| 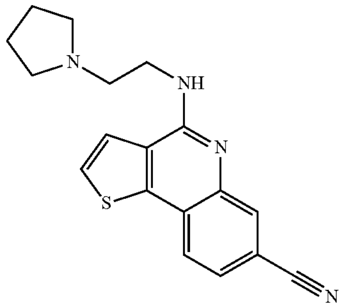 | −22.431 | | | | | | | 2.198 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 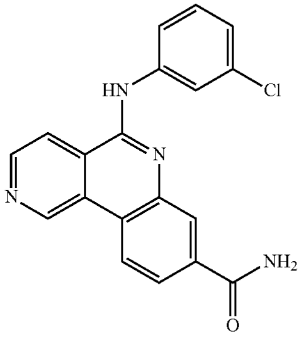 | −3.438 | | | 0.417 | 91.207 | 0.003 | | 2.133 | 0.91 | 1.226 | 0.037 |
| 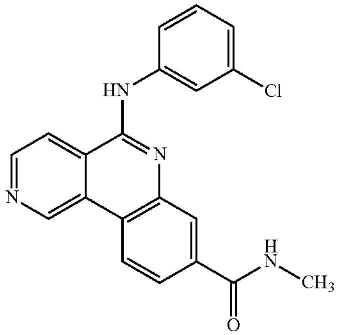 | −39.827 | | | >0.75 | | >0.4 | | >10 | 13.691 | >10 | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 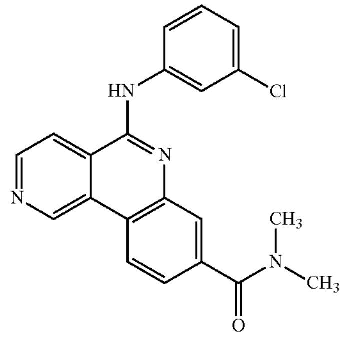 | 4.853 | | | >0.75 | | >0.4 | | 8.167 | 1.512 | >10 | >10 |
| 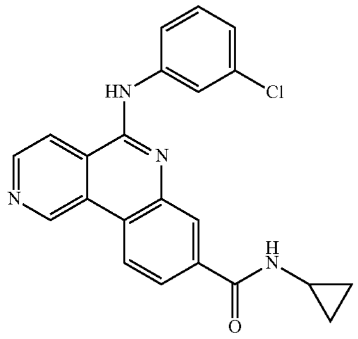 | −5.179 | | | 0.487 | | >0.4 | | >10 | 2.159 | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 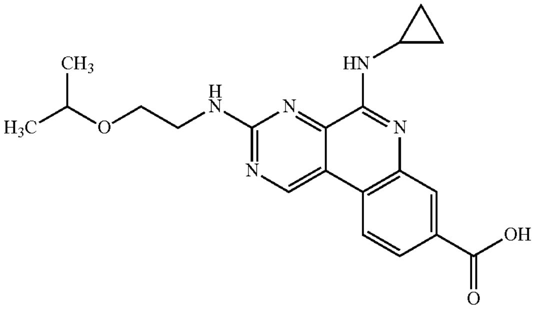 | −2.455 | >1.1 | | 0.064 | | | | >10 | 7.373 | | |
| 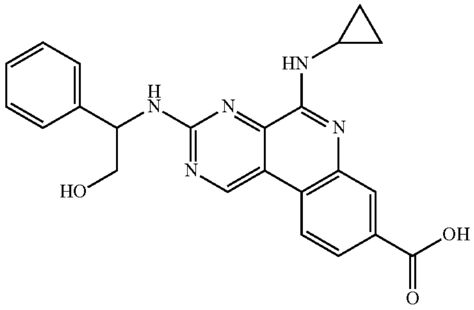 | −22.83 | | | | | | | >10 | 27.526 | | |
| 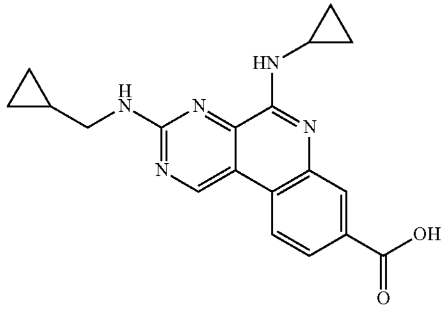 | 15.714 | | | 0.008 | | | | >10 | 4.408 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 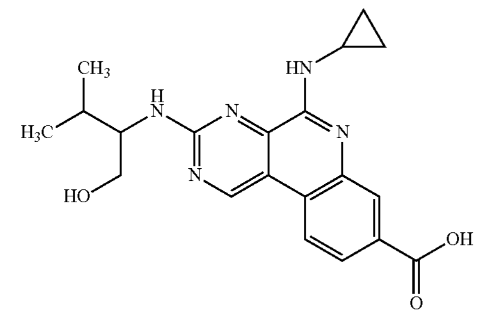 | −8.311 | | | 0.167 | | | | >10 | 44.678 | | |
| 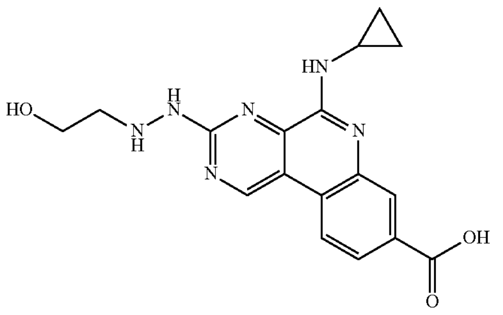 | −37.024 | | | | | | | >10 | >50 | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 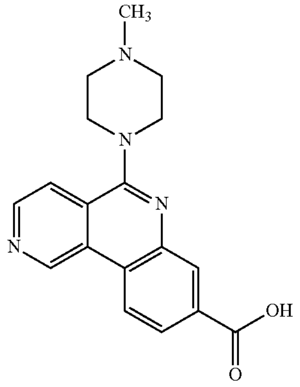 | 40.092 | | | | | | | >10 | | | |
| 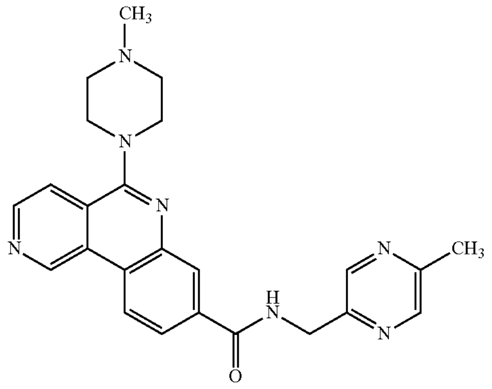 | −23.085 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 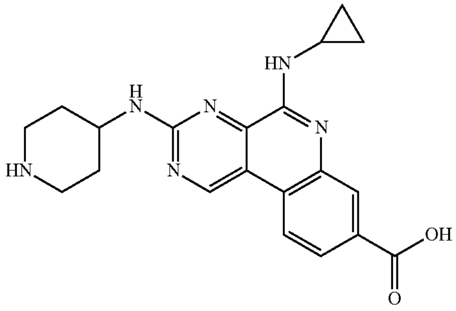 | 18.864 | | | | | | | >10 | >50 | | |
| 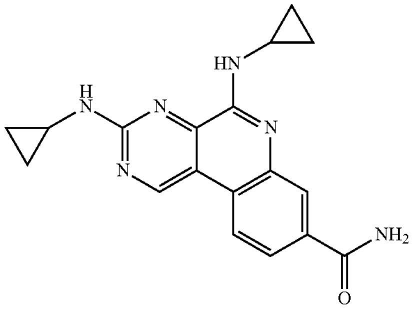 | −10.766 | | | 0.135 | | | | 1.33 | 0.504 | | |
| 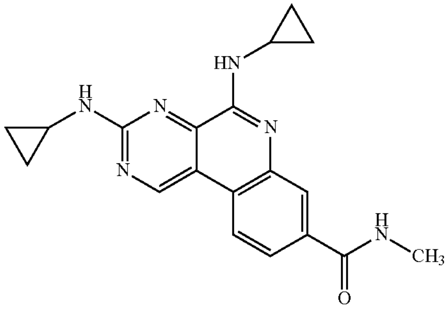 | −16.167 | | | >0.75 | | | | 1.077 | 0.618 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 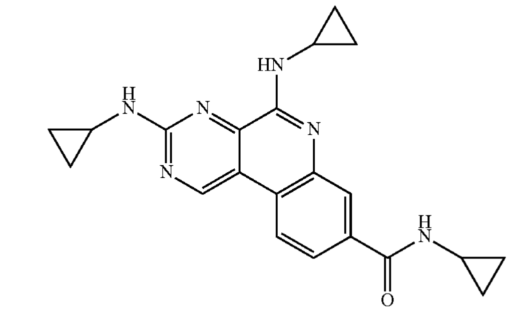 | −11.854 | | | >0.75 | | | | 0.818 | 0.436 | >10 | 0.497 |
| 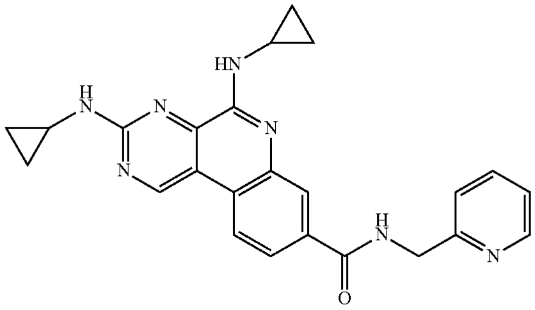 | −17.13 | | | >0.75 | | | | 3.074 | 1.949 | | |
| 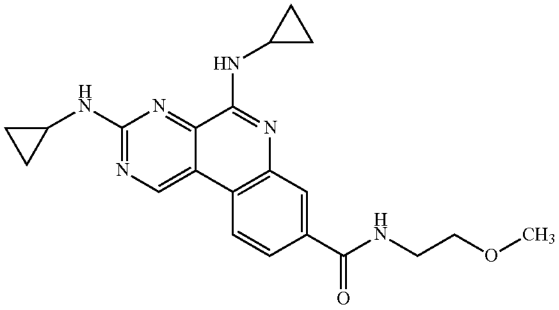 | −16.089 | | | >0.75 | | | | 3.865 | 1.635 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 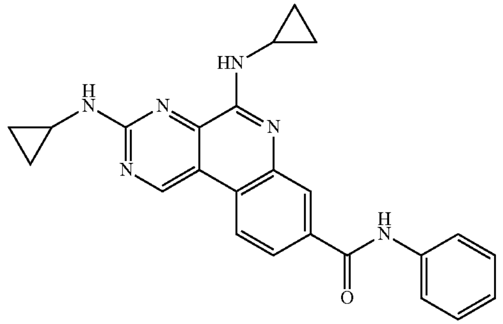 | −5.167 | | | >0.75 | | | | 3.162 | 0.989 | | |
| 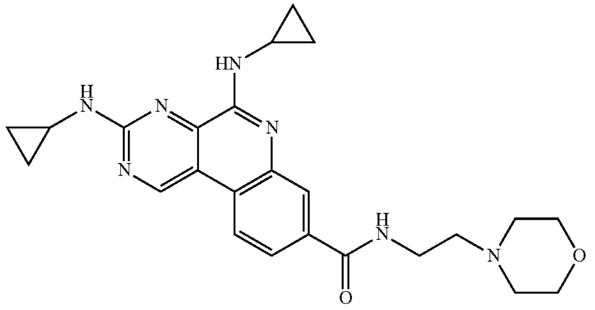 | 2.65 | | | >0.75 | | | | >10 | 1.425 | | |
| 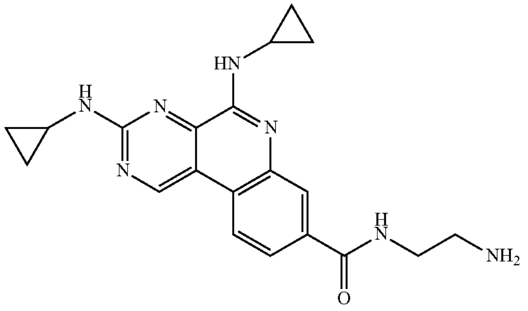 | 3.789 | | | >0.75 | | | | >10 | 2.359 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 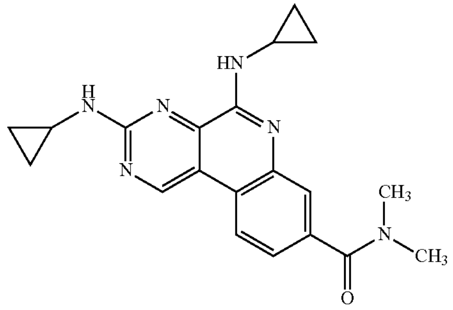 | 1.617 | | | >0.75 | | | | 1.119 | 0.583 | | |
| 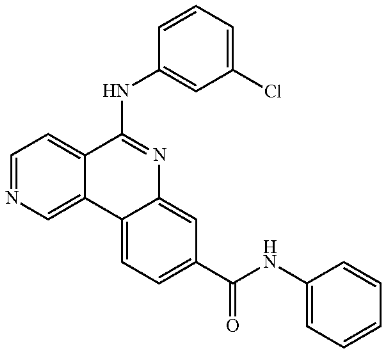 | −0.772 | | | | | >0.4 | | >10 | | >10 | 0.069 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 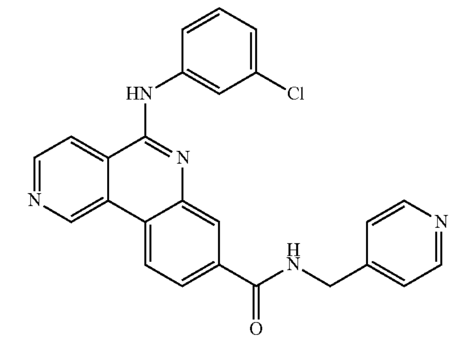 | −12.783 | | | | | >0.4 | | 2.502 | | >10 | 0.181 |
| 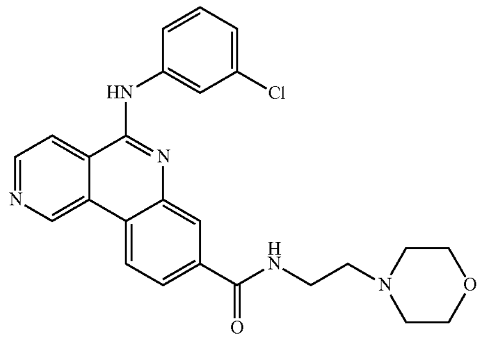 | 1.157 | | | | | >0.4 | | >10 | | >10 | 0.099 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 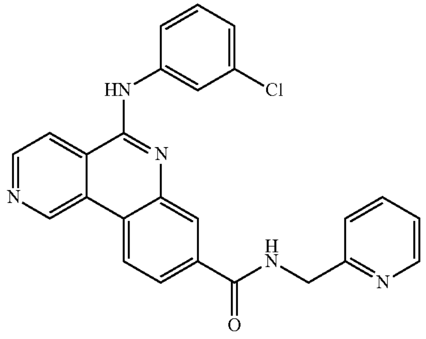 | −11.062 | | | | | 0.289 | | 9.877 | | >10 | >10 |
| 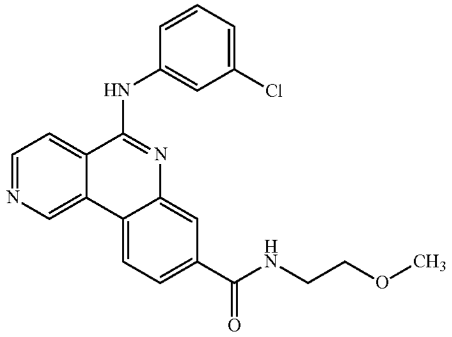 | −29.688 | | | | | >0.4 | | >10 | | >10 | 0.043 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 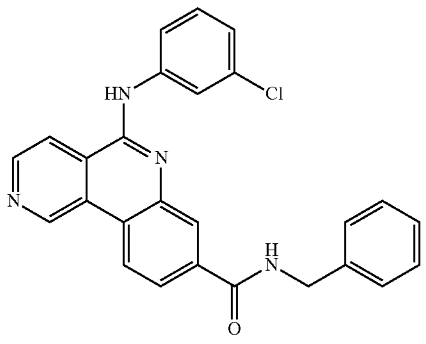 | −29.363 | | | | | 0.331 | | >10 | | >10 | 0.095 |
| 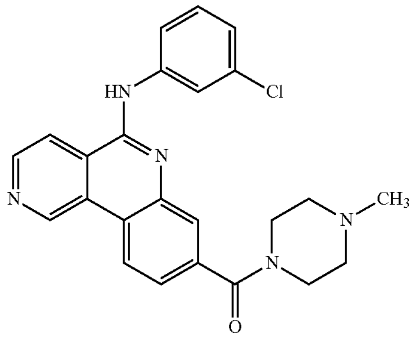 | −28.36 | | | | | >0.4 | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 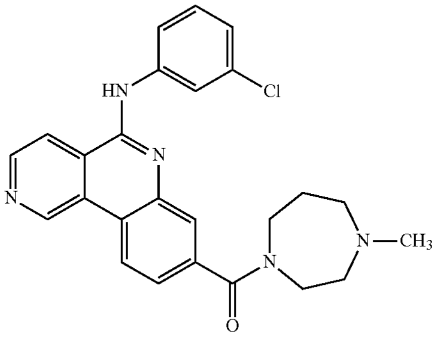 | −11.834 | | | | | >0.4 | | 2.672 | | >10 | 0.171 |
| 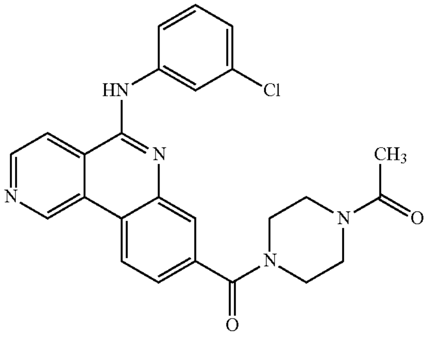 | −5.012 | | | | | >0.4 | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 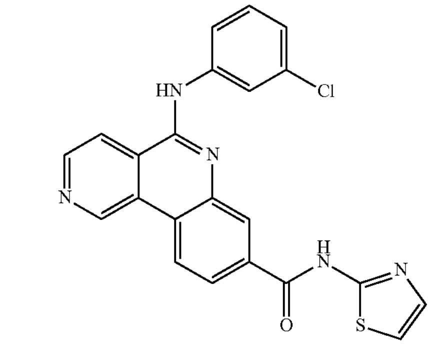 | −6.62 | | | | | >0.4 | | >10 | | >10 | >10 |
| 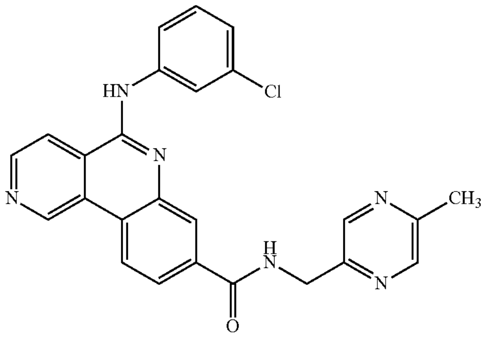 | −19.784 | | | | | 0.362 | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 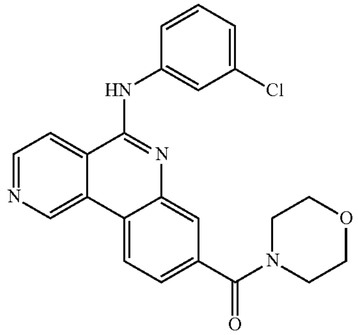 | −14.358 | | | | | >0.4 | | >10 | | >10 | >10 |
| 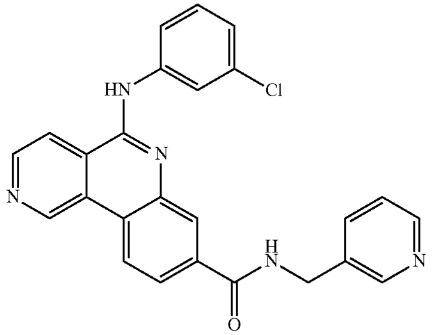 | −16.193 | | | | | >0.4 | | >10 | | >10 | 0.112 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 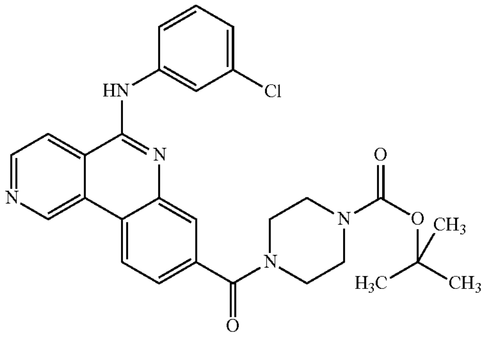 | −7.41 | | | | | >0.4 | | 5.974 | | >10 | >10 |
| 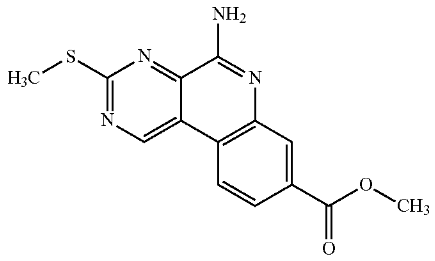 | −13.229 | | | | | | | 4.772 | 1.14 | | |
| 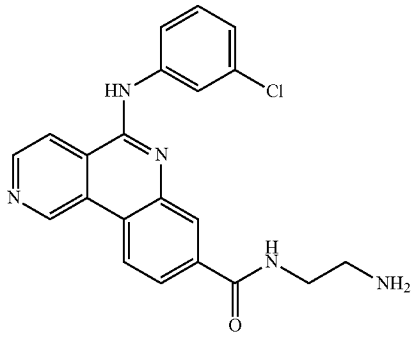 | −19.822 | | | | | >0.4 | | 7.219 | 7.675 | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 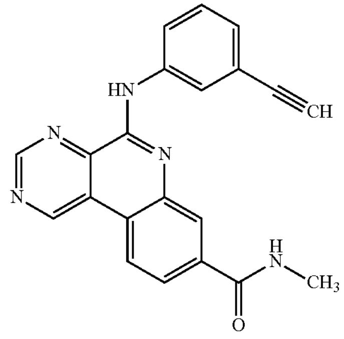 | −28.274 | | | | | | | 7.169 | 1.946 | | |
| 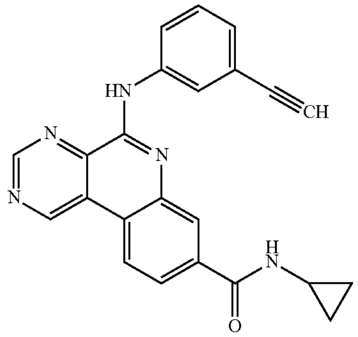 | −13.143 | | | | | | | 3.49 | 1.535 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 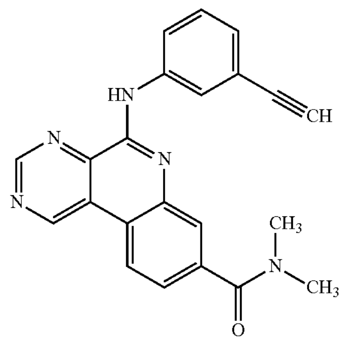 | −27.848 | | | | | | | 0.545 | 1.175 | 9.786 | 4.616 |
| 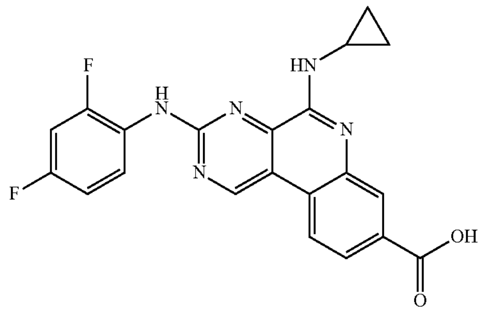 | | | | | | | | >10 | | >10 | 2.293 |
| 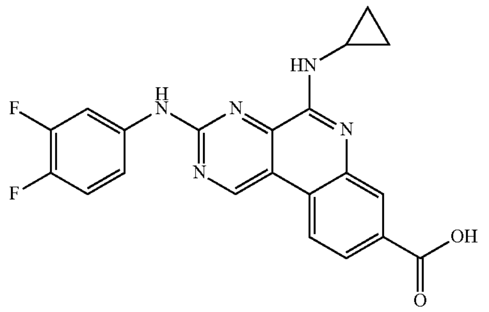 | 14.053 | | | | 96.306 | | | >10 | | >10 | 1.86 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 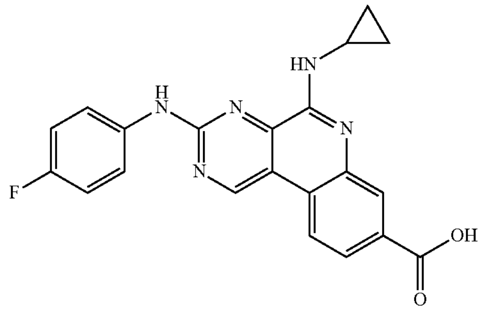 | 49.326 | 1.073 | | | | | | >10 | 5.02 | | |
| 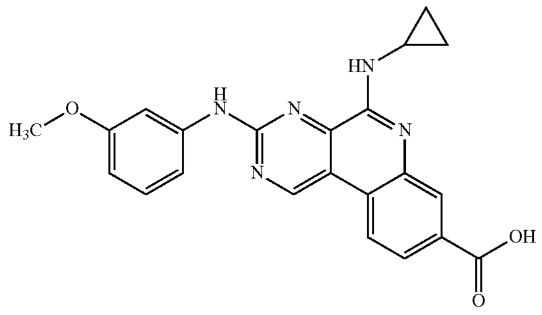 | 5.494 | | | | | | | >10 | 54.594 | | |
| 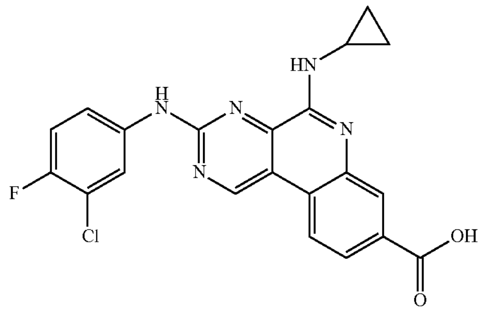 | 8.762 | | | | | | | >10 | 26.632 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 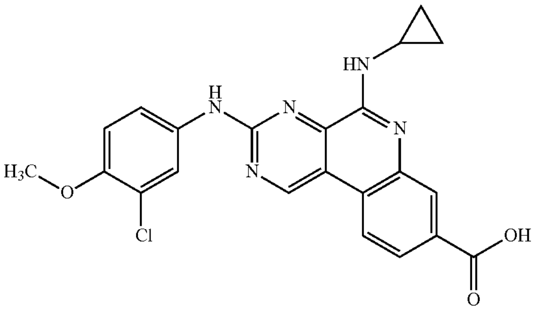 | 38.71 | | | | | | | 2.307 | 9.17 | | |
| 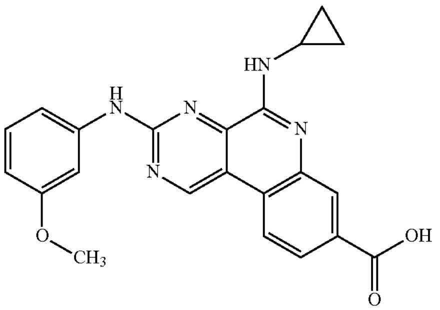 | 60.859 | 0.97 | | | | | | 1.58 | 3.147 | | |
| 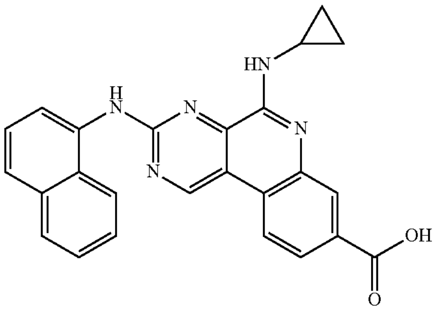 | 22.931 | | | | | | | >10 | 23.258 | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 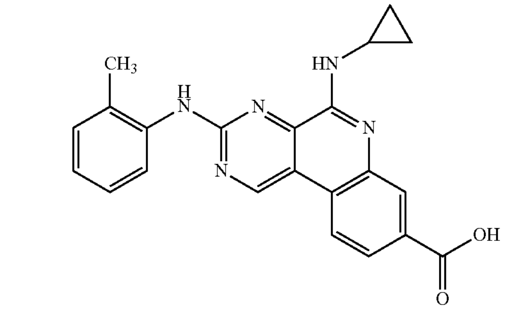 | 52.831 | 0.994 | | | | | | >10 | 18.639 | | |
| 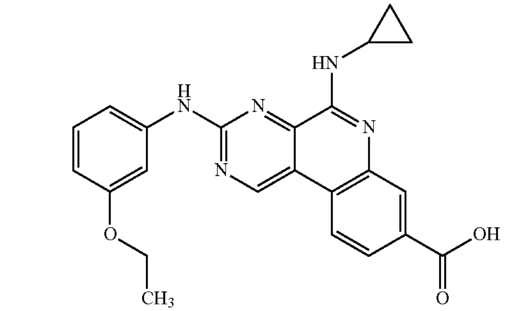 | 32.829 | | | | | | | 3.773 | 5.173 | | |
| 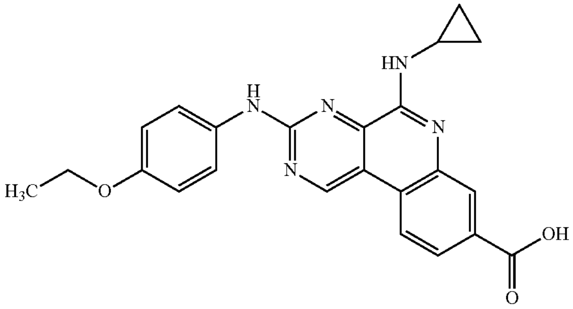 | 45.893 | | | | | | | >10 | 9.262 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 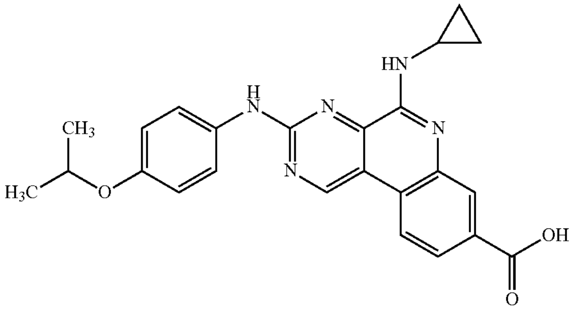 | 26.285 | | | | | | | >10 | 18.859 | | |
| 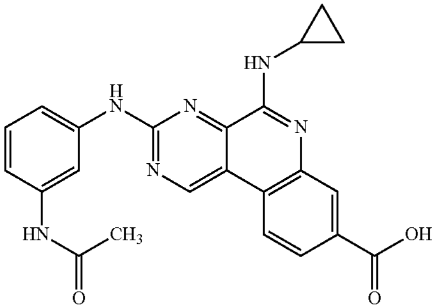 | 31.977 | | | | | | | >10 | >62.5 | | |
| 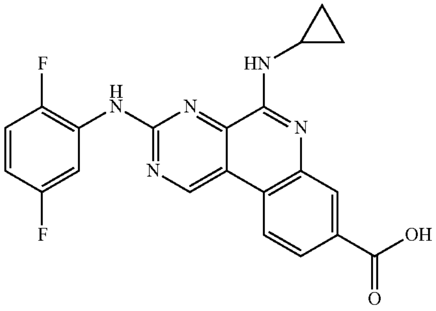 | 50.36 | >1.1 | | | | | | >10 | 15.724 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 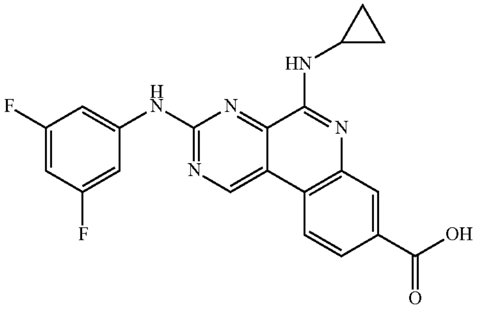 | 46.295 | | | | | | | >10 | 35.41 | | |
| 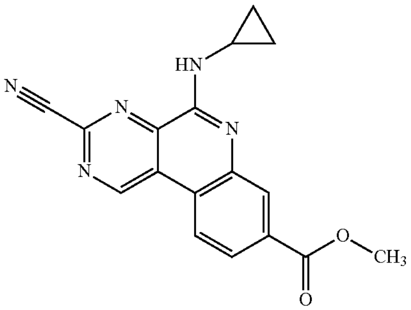 | 2.814 | | | | | | | >10 | | 1.342 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 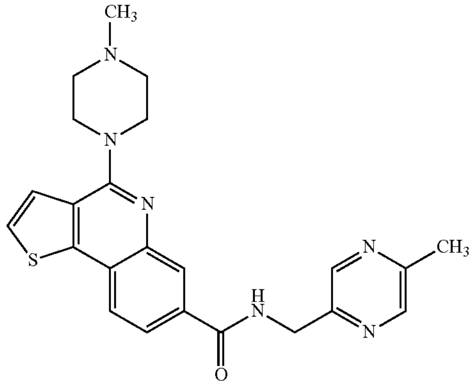 | 37.31 | | | | −15.002 | | | >10 | | >10 | >10 |
| 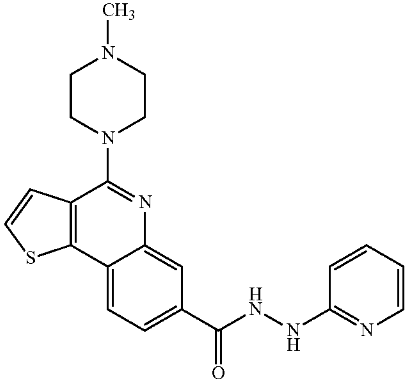 | −10.904 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 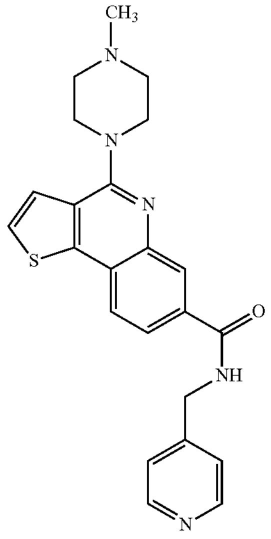 | −14.093 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 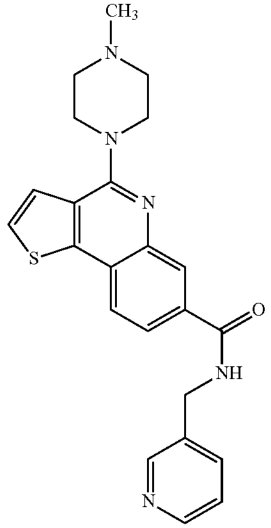 | −16.012 | | | | | | | >10 | | | |
| 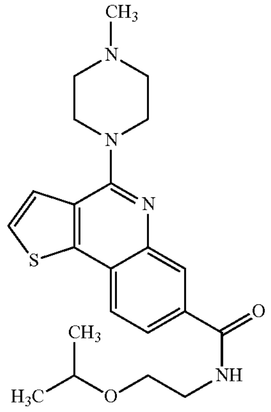 | −3.617 | | | | | | | >10 | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 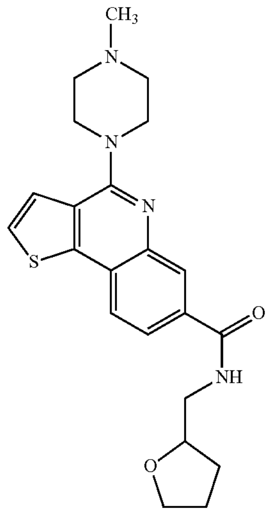 | 11.04 | | | | | | | >10 | | | |
| 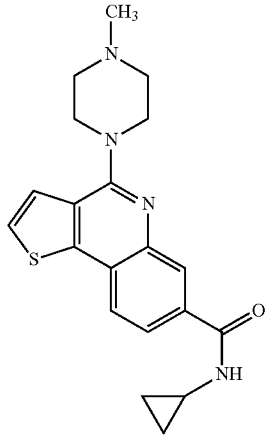 | −12.694 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 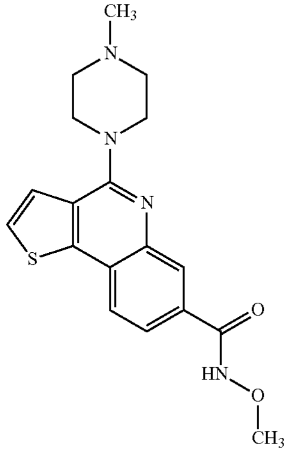 | −0.965 | | | | | | | >10 | | | |
| 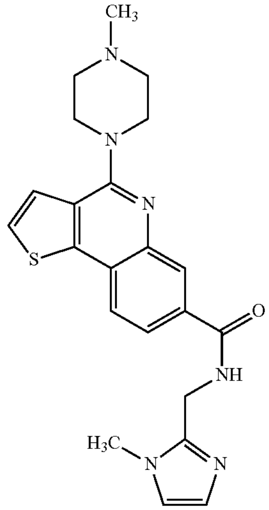 | −14.516 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 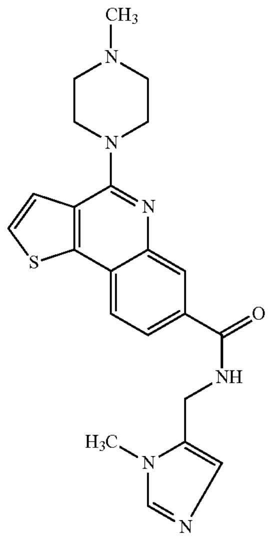 | −22.47 | | | | | | | >10 | | | |
| 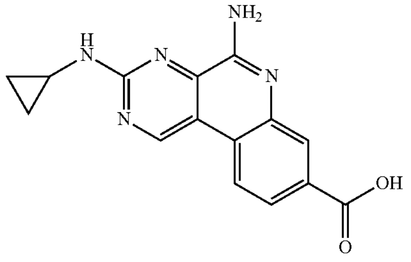 | 0.938 | | | | | | | >10 | 55.189 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 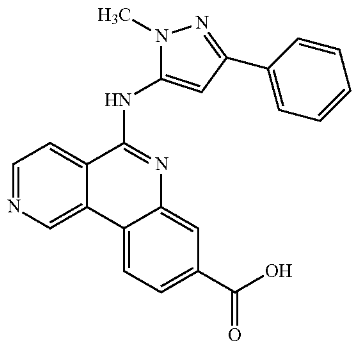 | 58.345 | 0.914 | | | | | | >10 | | | |
| 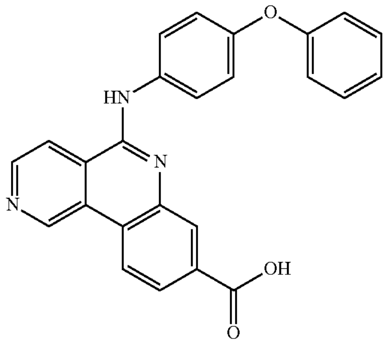 | 57.206 | >1.1 | | | | | | >10 | 22.898 | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 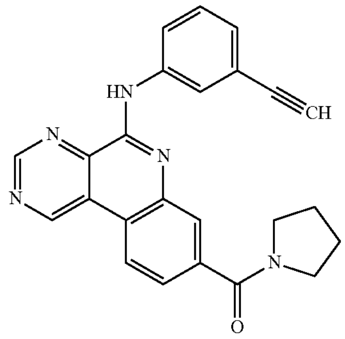 | −7.602 | | | | | | | >10 | 13.259 | | |
| 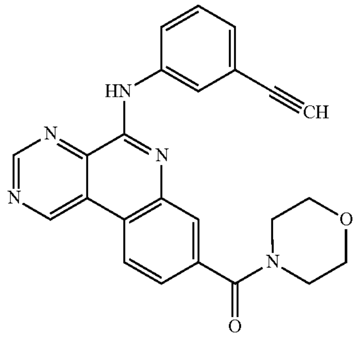 | −17.59 | | | | | | | >10 | >30 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 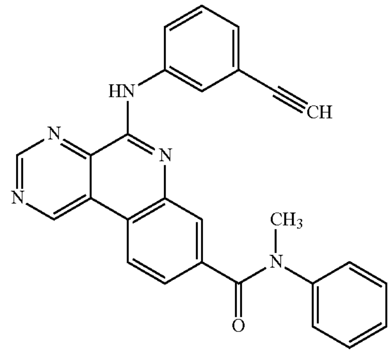 | −11.197 | | | | | | | >10 | 18.829 | | |
| 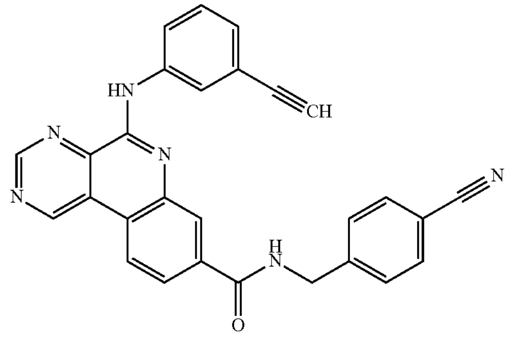 | −14.565 | | | | | | | >10 | 9.09 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 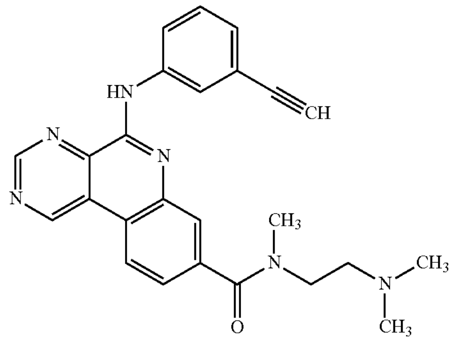 | −15.459 | | | | | | | 4.388 | 4.373 | | |
| 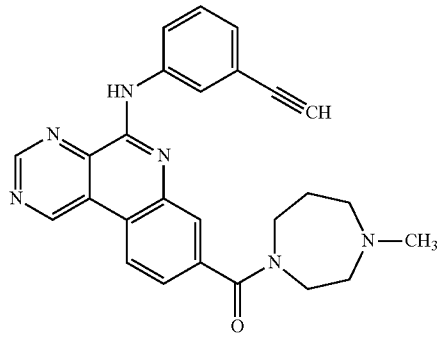 | −11.181 | | | | | | | >10 | 3.219 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 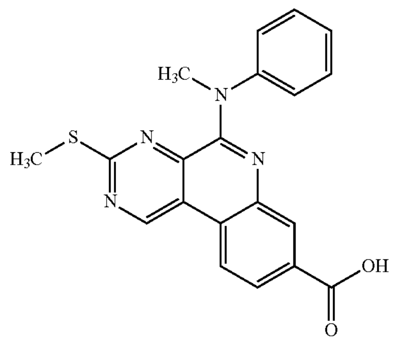 | 48.373 | 1.088 | | | | | | >10 | >30 | | |
| 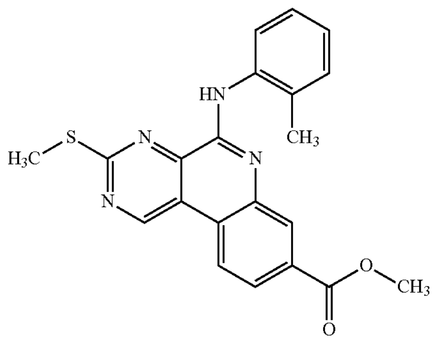 | 12.488 | | | | | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 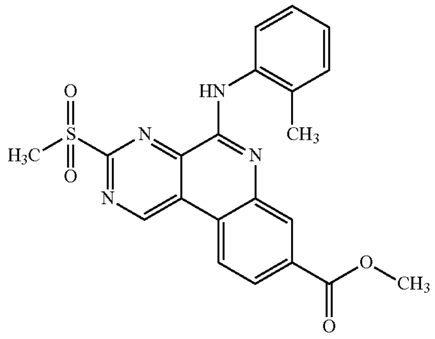 | 25.274 | | | | | | | >10 | >30 | | |
| 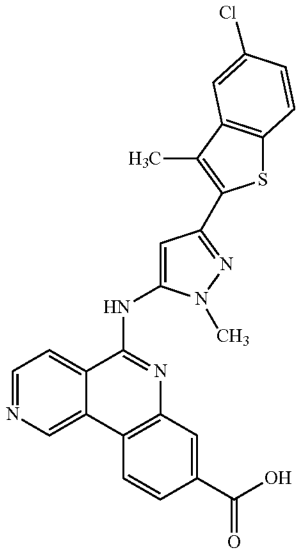 | 4.533 | | | | | | | >10 | 19.634 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 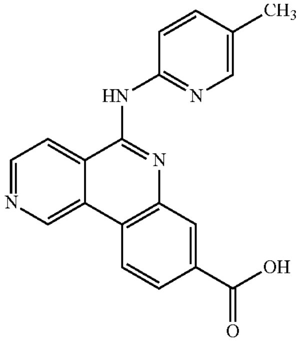 | 48.308 | >1.1 | | | | | | >10 | 1.263 | | |
| 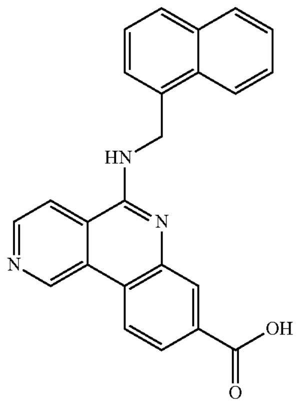 | 15.611 | | | | | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 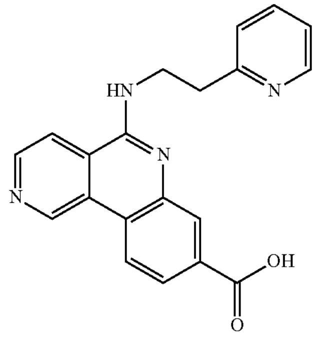 | −8.951 | | | | 96.074 | | | >10 | | >10 | >10 |
| 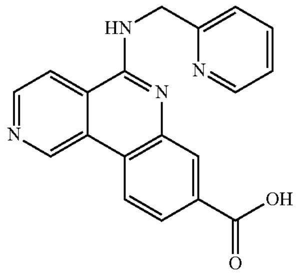 | 14.338 | | | | 96.609 | | | >10 | | >10 | >10 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 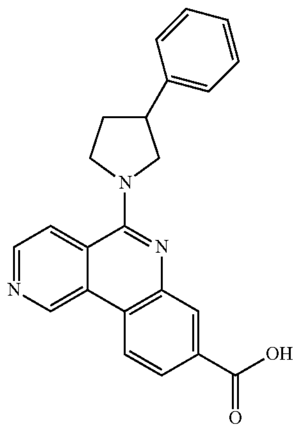 | 1.036 | | | | | | | >10 | >30 | | |
| 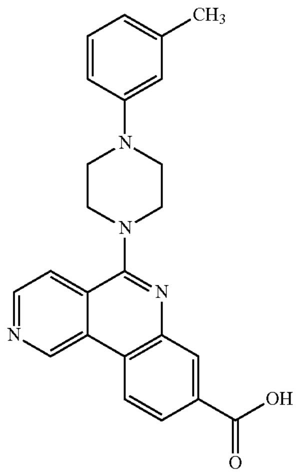 | 33.684 | | | | | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 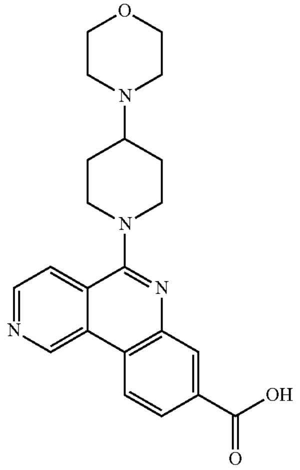 | 20.671 | 0.31 | | | 90.535 | | | >10 | | >10 | >10 |
| 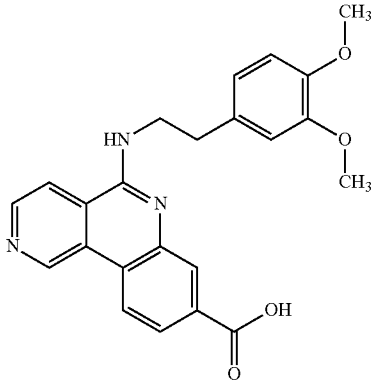 | 9.849 | | | | 99.005 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 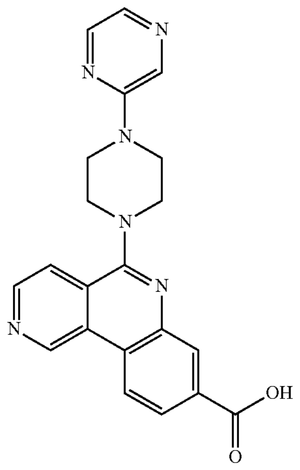 | −2.364 | | | | | | | | | | |
| 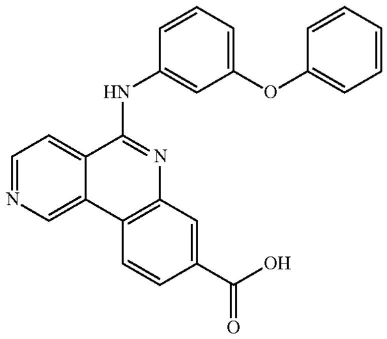 | 44.128 | | | | | | | >10 | >30 | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 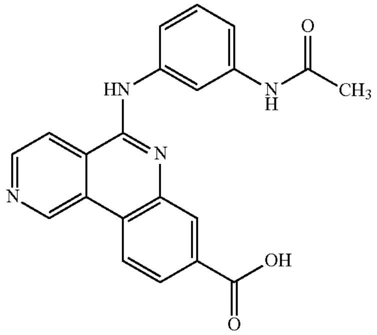 | 73.555 | 0.369 | | | | | | >10 | | | |
| 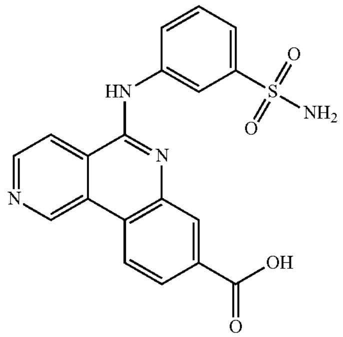 | 83.397 | 0.397 | | | | | | >10 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 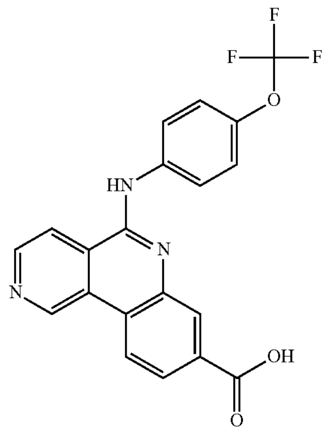 | 68.284 | 0.668 | | | | | | >10 | 4.699 | | |
| 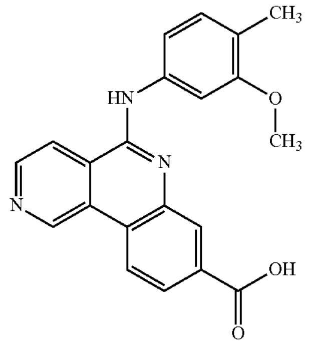 | 75.784 | 0.744 | | | | | | >10 | 10.714 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 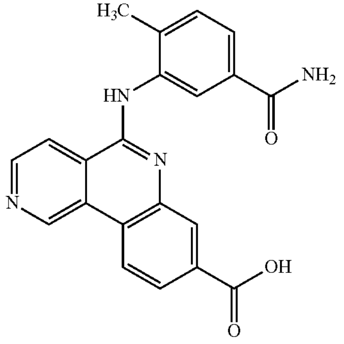 | 9.95 | | | | | | | >10 | >30 | | |
| 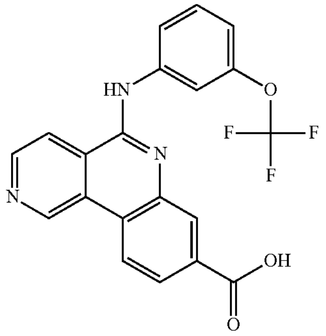 | 87.35 | 0.711 | | | | | | >10 | 7.436 | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 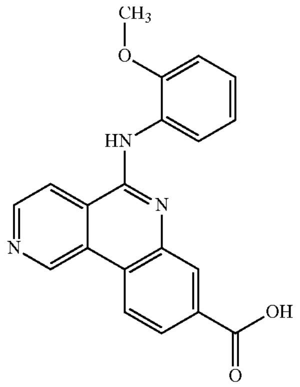 | 75.849 | 0.698 | | | | | | >10 | 10.384 | | |
| 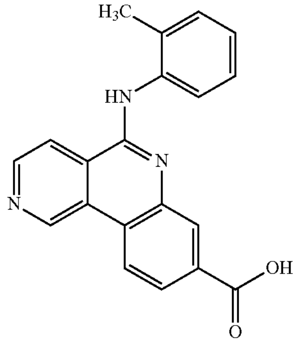 | 92.327 | 0.158 | | | | | | >10 | 15.713 | >10 | 0.985 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 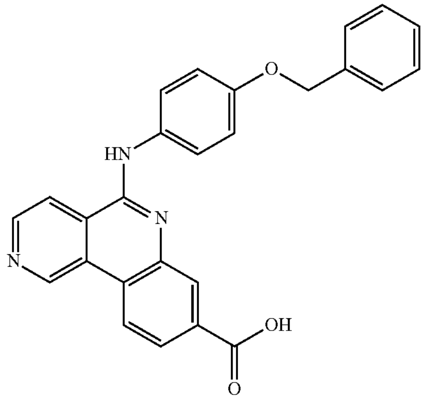 | 44.258 | | | | | | | >10 | 14.174 | | |
| 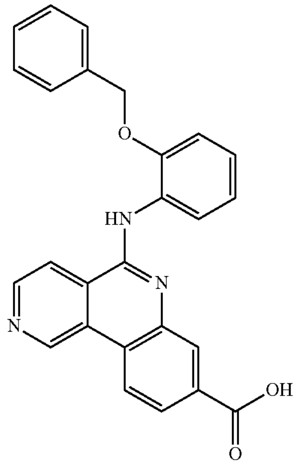 | 27.73 | | | | | | | >10 | 29.845 | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 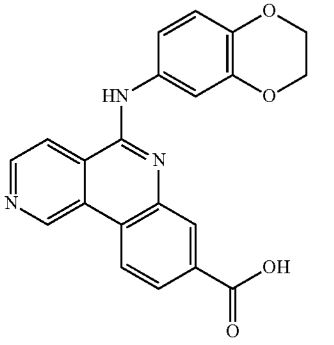 | 88.391 | 0.259 | | | | | | >10 | 29.624 | >10 | >10 |
| 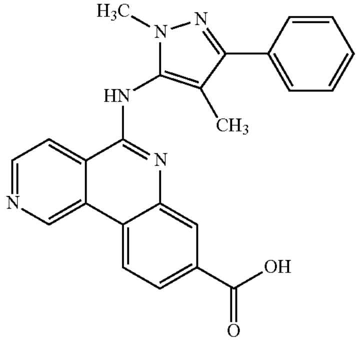 | 26.233 | | | | 76.189 | | | 2.343 | | >10 | 1.429 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 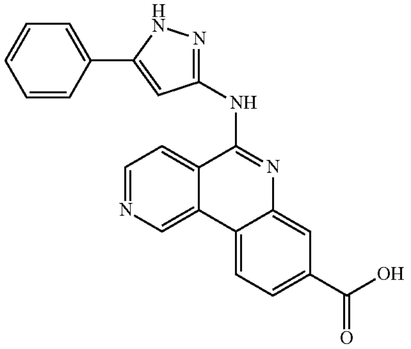 | 55.97 | >1.1 | | | | | | >10 | | | |
| 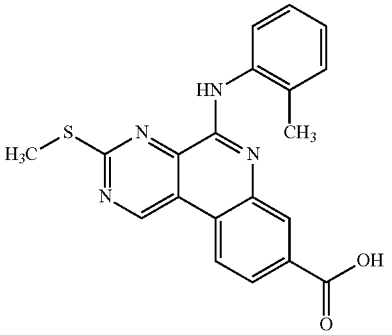 | 9.674 | | | | | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 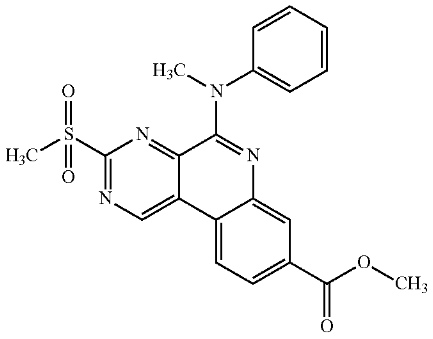 | 9.836 | | | | | | | 4.36 | | 0.334 | |
| 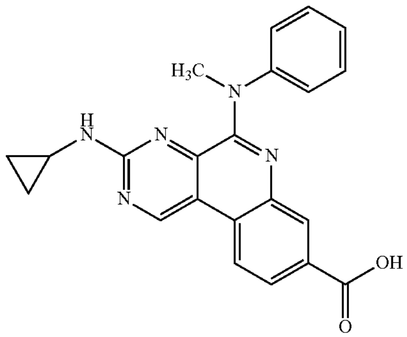 | 31.439 | | | | | | | >10 | | >10 | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 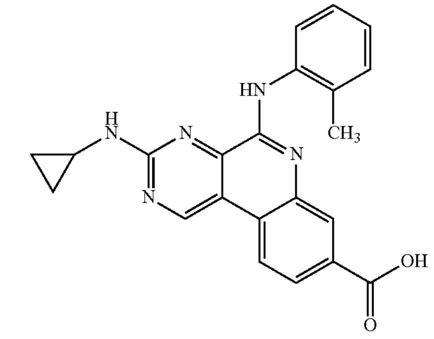 | 31.862 | | | | | | | 10 | | 0.769 | 0.165 |
| 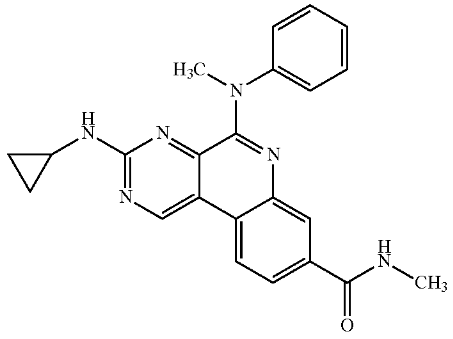 | 12.585 | | | | | | | 9.743 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 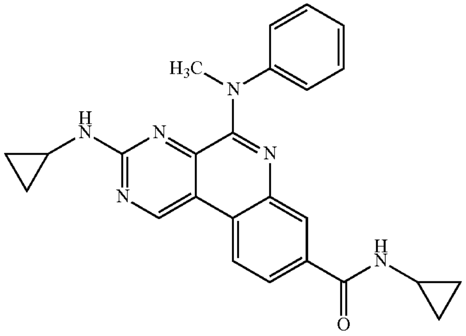 | 16.115 | | | | | | | >10 | | >10 | |
| 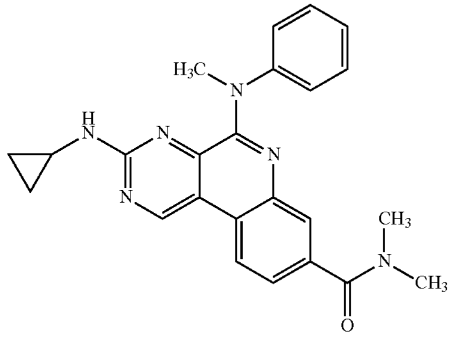 | −0.201 | | | | | | | 5.191 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 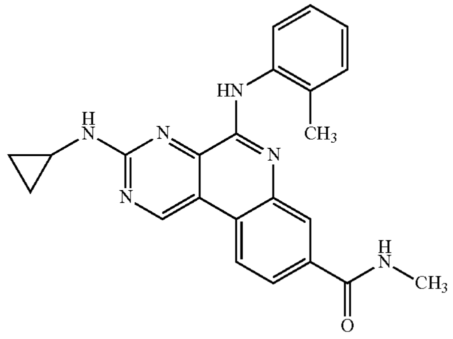 | 4.208 | | | | | | | 1.611 | | >10 | |
| 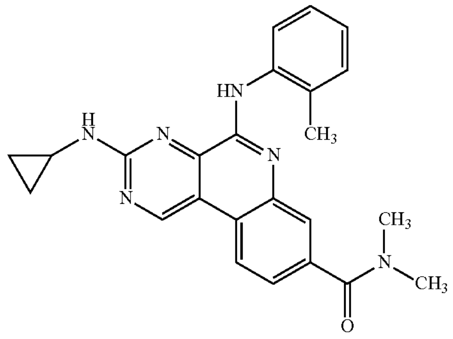 | 0.71 | | | | | | | >10 | | >10 | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 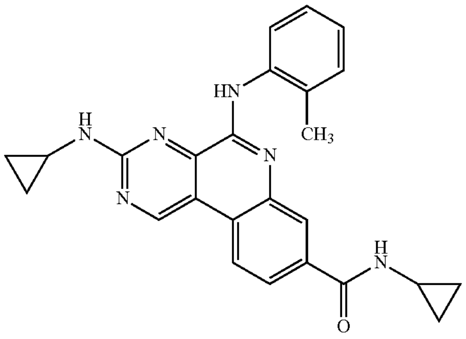 | 5.721 | | | | | | | >10 | | >10 | |
| 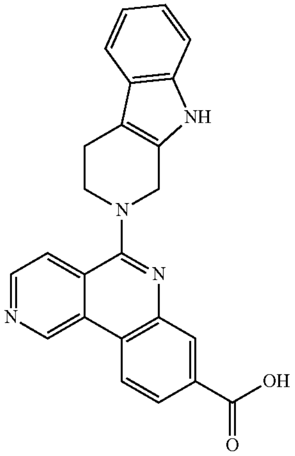 | 38.808 | | | | | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 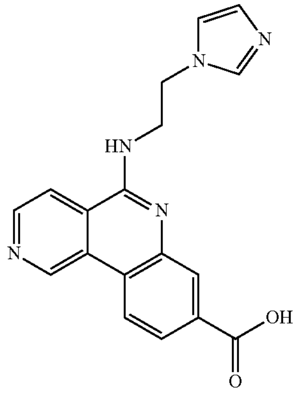 | 51.838 | >1.1 | | | | | | >10 | | >10 | |
| 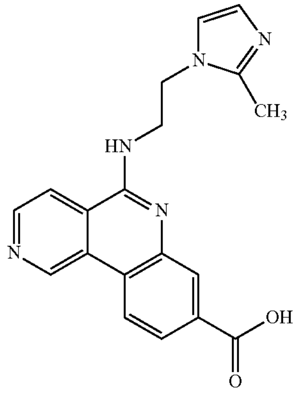 | 97.077 | 0.287 | | | | | | >10 | | >10 | >10 |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 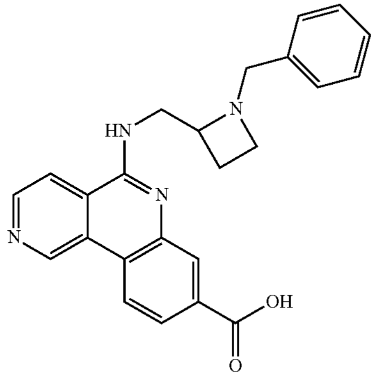 | −7.797 | | | | 55.94 | | | >10 | | >10 | |
| 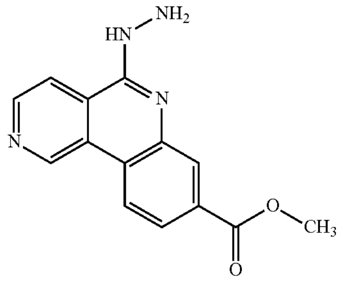 | −32.409 | | | | −8.654 | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 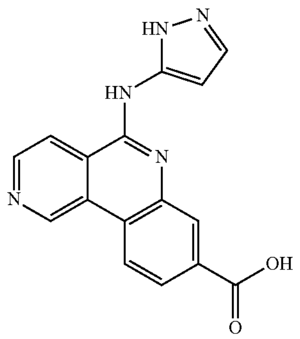 | 1.371 | | | | 94.778 | | | >10 | | >10 | |
| 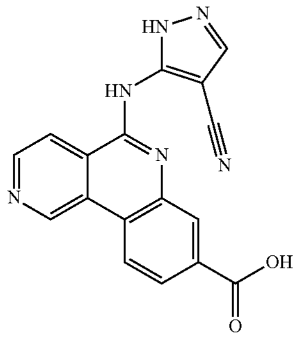 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 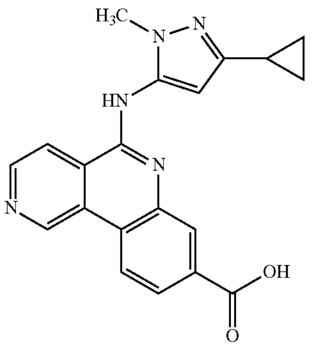 | 45.761 | | | | 96.163 | | | >10 | | >10 | |
| 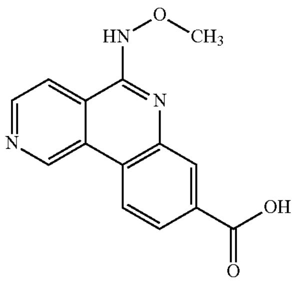 | 34.888 | | | | 94.661 | | | >10 | | >10 | |
| 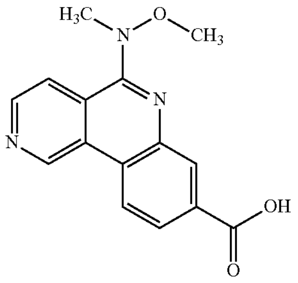 | 55.708 | 0.897 | | | 84.735 | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 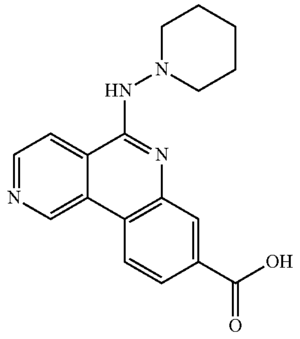 | | >1.1 | | | | | | >10 | | >10 | |
| 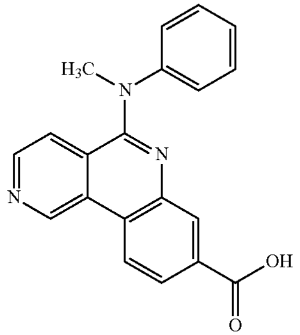 | 71.151 | 0.439 | | | 89.046 | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 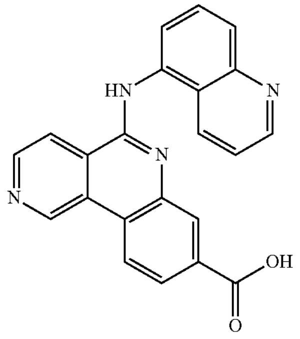 | 79.057 | 0.281 | | | 100.813 | | | >10 | | >10 | >10 |
| 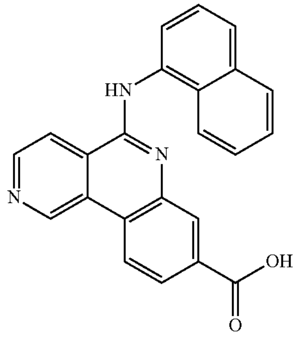 | 35.74 | | | | 93.074 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 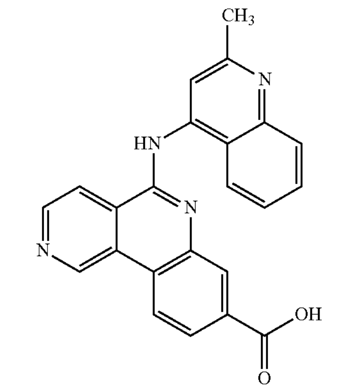 | 24.852 | | | | 96.637 | | | >10 | | >10 | |
| 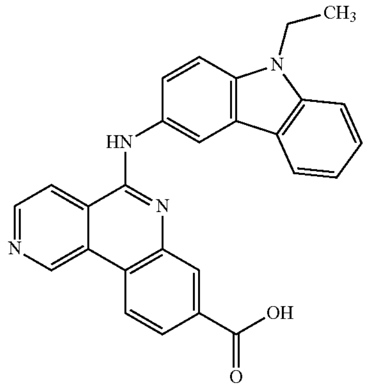 | 32.61 | | | | 98.087 | | | 9.821 | | 0.11 | 3.281 |

TABLE 39-continued
| Structure | Modulatory activity in cell-free assays IC50 (uM) PIM-1: % inh 500 nM | PIM1 | CK2 (20 um ATP) | CK2 (15 um ATP) | CK2: % inh 500 nM | FLT-3 (uM) | Cell proliferation modulatory activity HCT-116 (uM) | HCT-116 (uM) | Jurkat (uM) | K-562 (uM) | MV-4-11 (uM) |
|---|---|---|---|---|---|---|---|---|---|---|---|
| 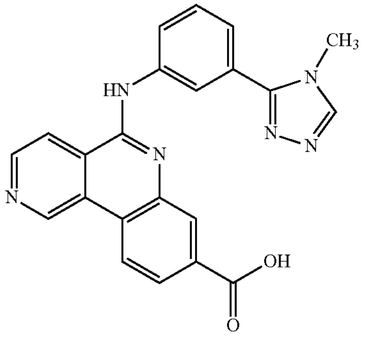 | 54.9 | 0.344 | | | 94.413 | | | >10 | | >10 | >10 |
| 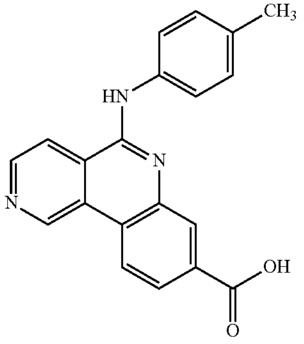 | 60.616 | 0.478 | | | 97.972 | | | >10 | | 0.132 | 9.311 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 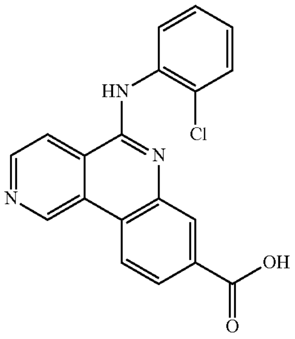 | 70.667 | 0.372 | | | 97.325 | | | >10 | | >10 | |
| 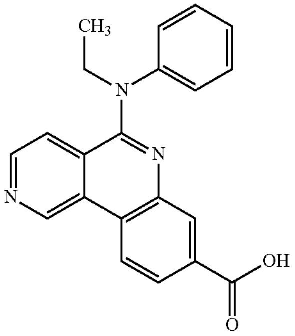 | 27.982 | | | | 91.845 | | | >10 | | 0.339 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 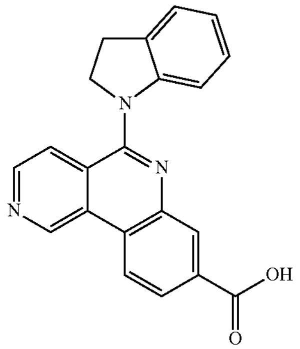 | 9.629 | | | | 90.25 | | | >10 | | >10 | |
| 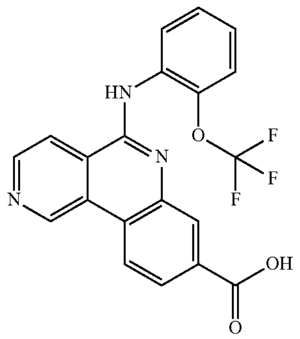 | 32.463 | | | | 91.996 | | | >10 | | >10 | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 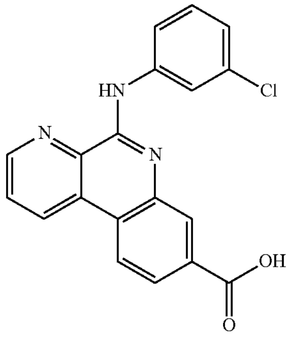 | 16.682 | | | | 40.015 | | | >10 | | >10 | |
| 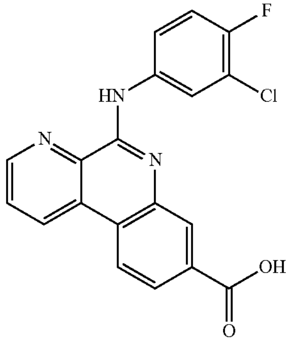 | −15.526 | | | | 12.328 | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 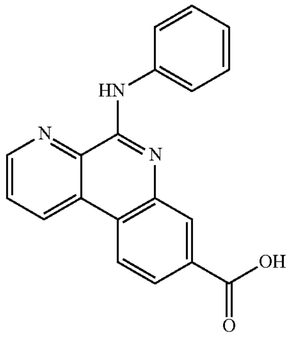 | | | | | | | | >10 | | >10 | |
| 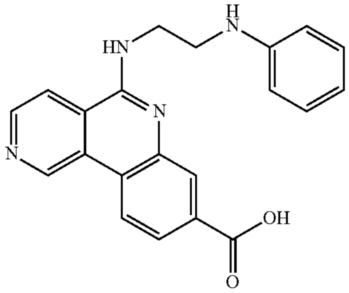 | | 0.7 | | | | | | >10 | | >10 | 0.185 |
| 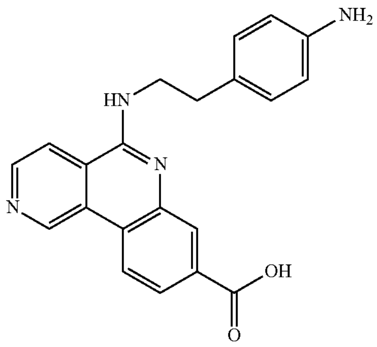 | 81.819 | 0.321 | | | 100.119 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 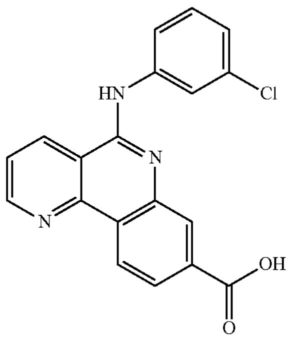 | 59.943 | 0.634 | | | 61.1 | | | >10 | | >10 | >10 |
| 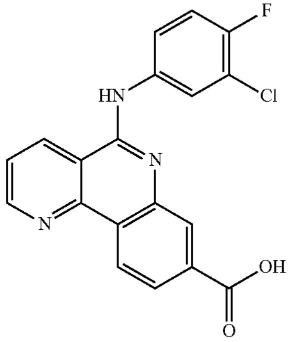 | 22.134 | | | | 19.609 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 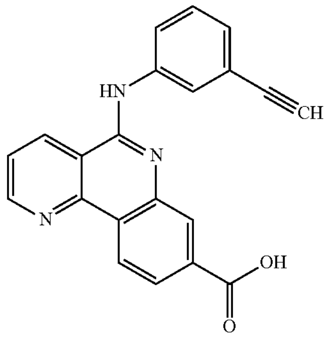 | 34.858 | | | | 77.485 | | | >10 | | >10 | >10 |
| 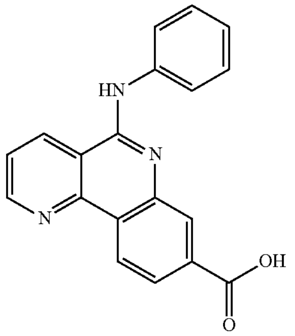 | 34.741 | | | | 25.452 | | | >10 | | >10 | >10 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 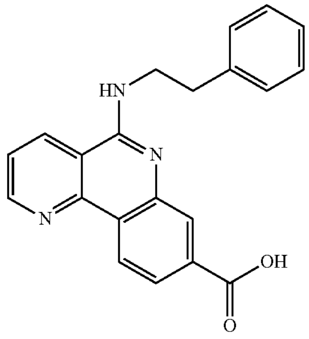 | 13.743 | | | | 5.709 | | | >10 | | >10 | >10 |
| 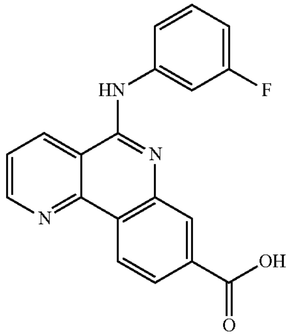 | 37.768 | | | | 35.026 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 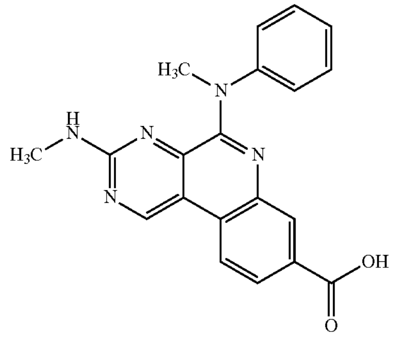 | 86.624 | 0.147 | | | 94.518 | | | >10 | | >10 | >10 |
| 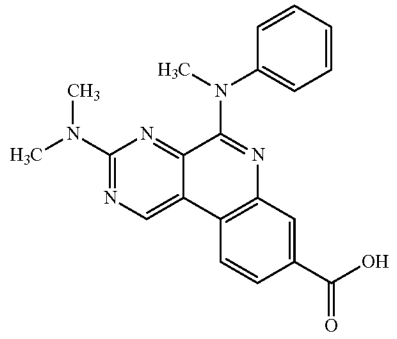 | 12.157 | | | | 13.976 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 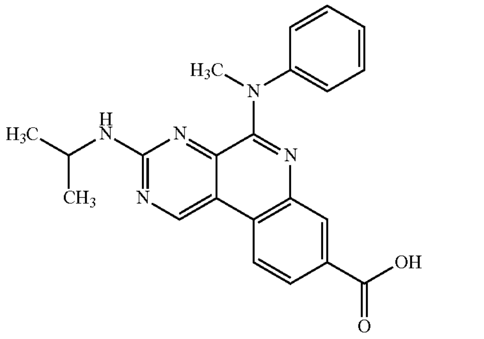 | 39.869 | | | | 91.665 | | | >10 | | >10 | >10 |
| 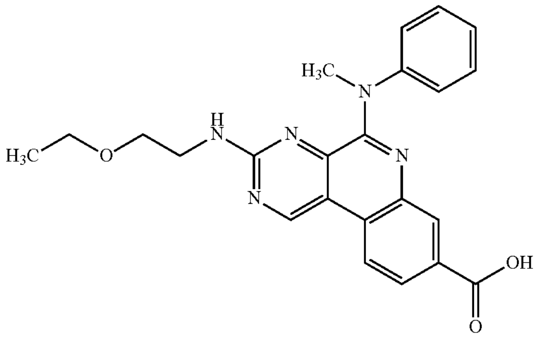 | 54.93 | 0.649 | | | 79.441 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 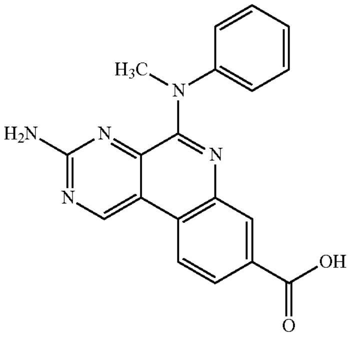 | | 0.223 | | | | | | >10 | | >10 | >10 |
| 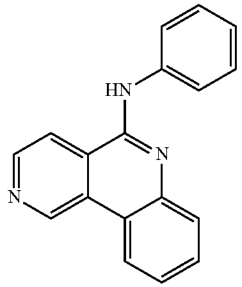 | 6.999 | | | | 0.786 | | | >10 | | >10 | 7.045 |
| 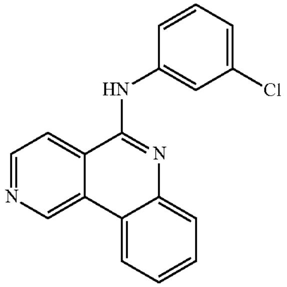 | −22.789 | | | | −42.842 | 0.344 | | >10 | | >10 | 2.816 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 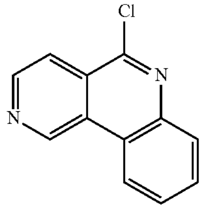 | −2.611 | | | | 9.994 | | | >10 | | >10 | >10 |
| 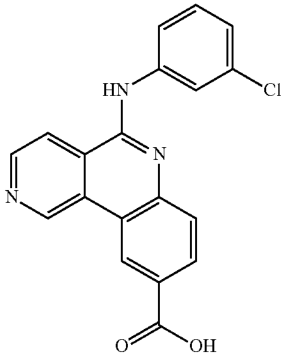 | 11.907 | | | | 67.842 | >0.4 | | >10 | | >10 | >10 |
| 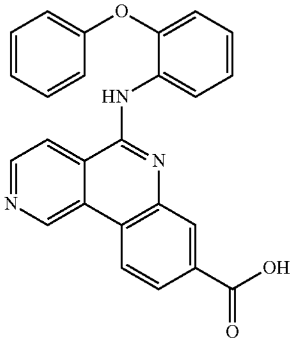 | 24.999 | | | | 96.462 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 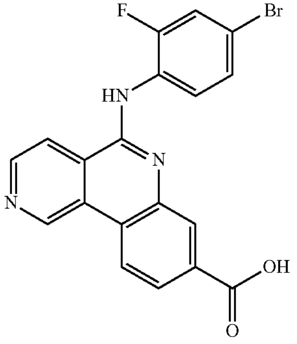 | | 0.339 | | | | 0.087 | | >10 | | >10 | 7.259 |
| 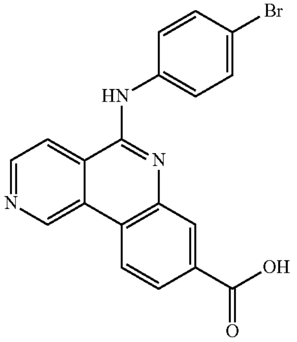 | 76.706 | 0.365 | | | 97.782 | | | >10 | | >10 | 5.898 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 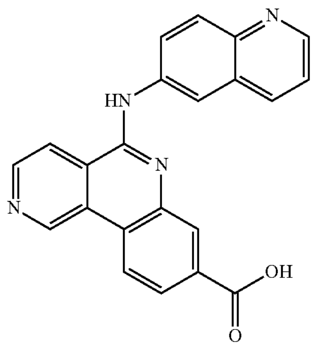 | 93.927 | 0.089 | | | 100.994 | | | >10 | | >10 | 3.201 |
| 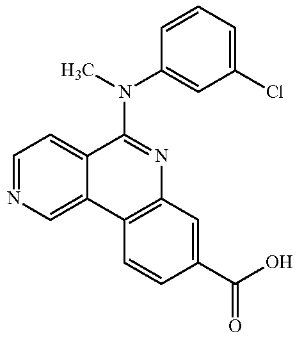 | 34.844 | | | | 89.617 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 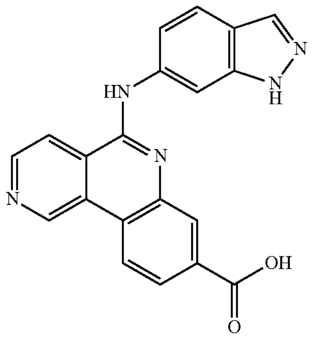 | 75.133 | 0.228 | | | 101.113 | | | >10 | | >10 | >10 |
| 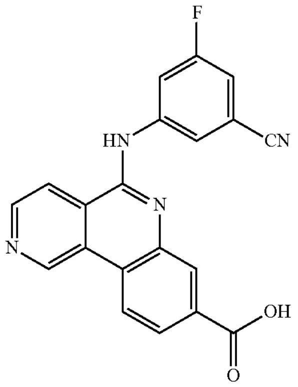 | 94.58 | 0.096 | | | 101.32 | | | >10 | | >10 | >10 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 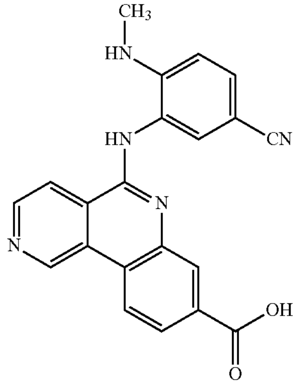 | 19.013 | | | | 64.981 | | | >10 | | >10 | 6.148 |
| 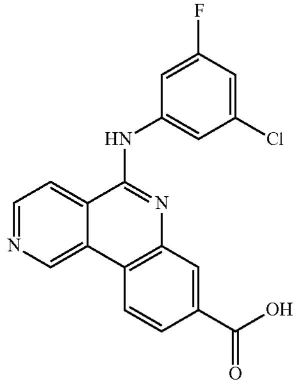 | 100.759 | 0.075 | | | 98.748 | 0.031 | | >10 | | 1.557 | 0.25 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 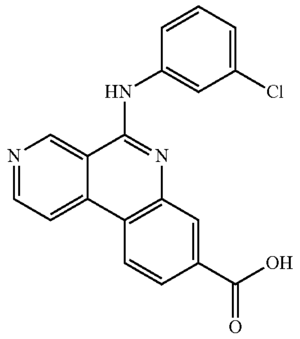 | 71.45 | 0.122 | | | −9.321 | >0.4 | | >10 | | >10 | >10 |
| 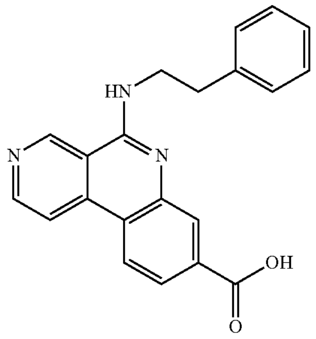 | 42.249 | | | | −0.531 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 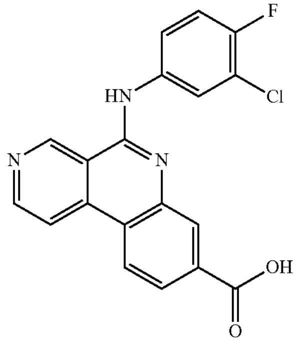 | 10.769 | | | | 1.686 | | | >10 | | >10 | >10 |
| 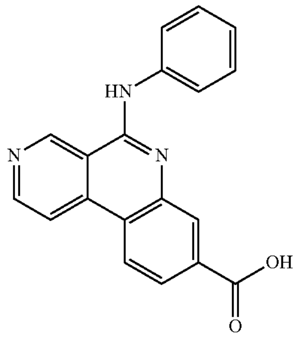 | −22.754 | | | | −40.346 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 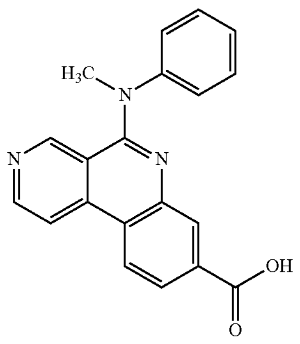 | 56.829 | 0.602 | | | 15.262 | | | >10 | | >10 | >10 |
| 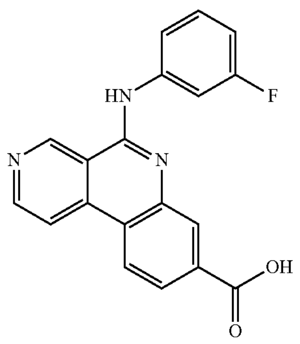 | 55.356 | 0.746 | | | 35.763 | | | >10 | | >10 | >10 |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 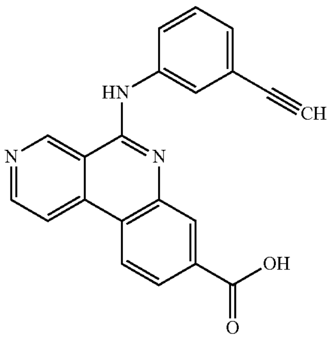 | 46.551 | | | | 72.431 | | | >10 | | >10 | >10 |
| 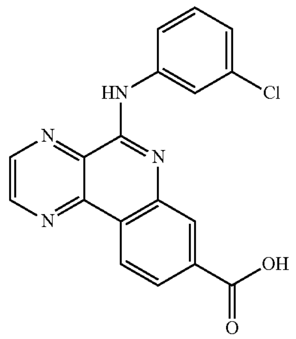 | 9.605 | | | | 69.268 | | | >10 | | >10 | 5.81 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 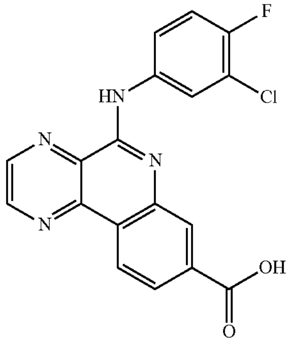 | −0.602 | | | | 36.516 | | | >10 | | >10 | >10 |
| 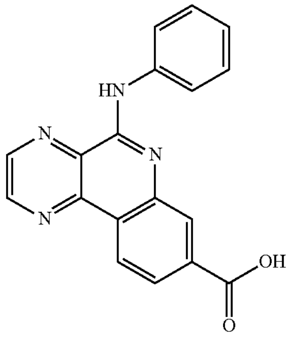 | −7.654 | | | | 41.55 | | | >10 | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 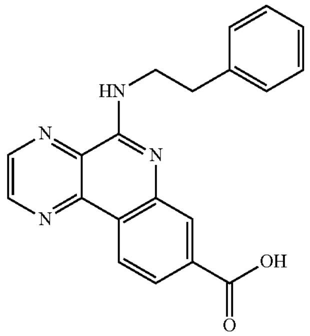 | −26.038 | | | | 5.493 | | | >10 | | | |
| 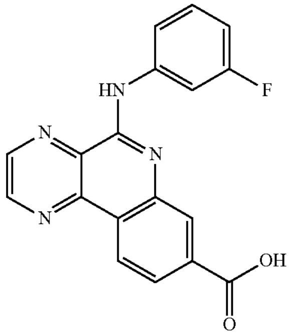 | 21.856 | | | | 88.694 | | | >10 | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 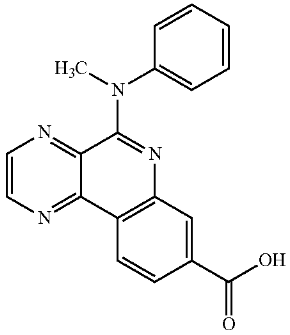 | 1.147 | | | | 19.305 | | | >10 | | | |
| 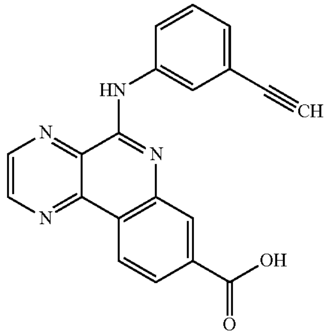 | −4.595 | | | | 85.274 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 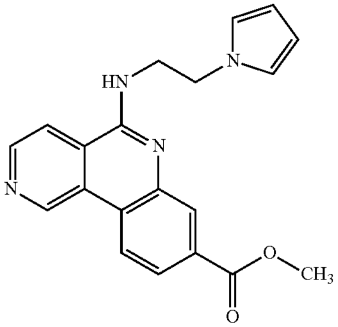 | −34.6 | | | | 9.014 | | | 9.973 | | >10 | 2.825 |
| 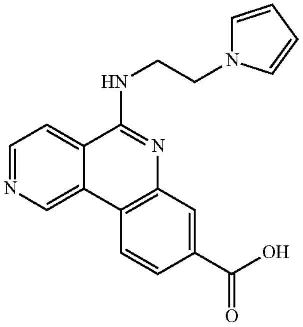 | 74.534 | 0.094 | | | 99.64 | | | >10 | | >10 | >10 |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 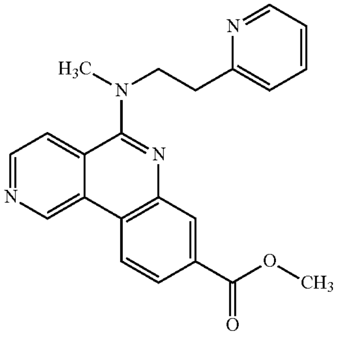 | −5.841 | | | | −3.682 | | | >10 | | >10 | >10 |
| 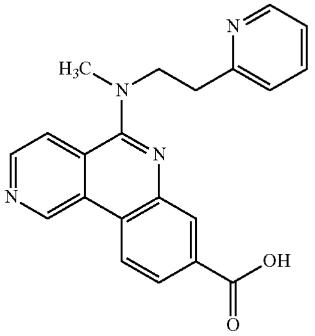 | 3.735 | | | | 90.843 | | | 0.902 | | 7.202 | 1.541 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 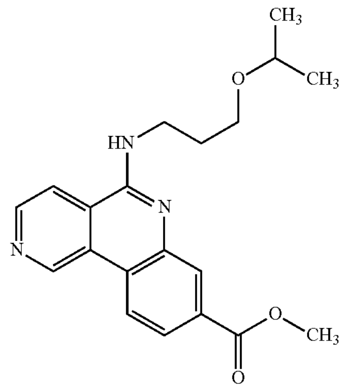 | 24.228 | | | | 90.929 | | | >10 | | >10 | 6.422 |
| 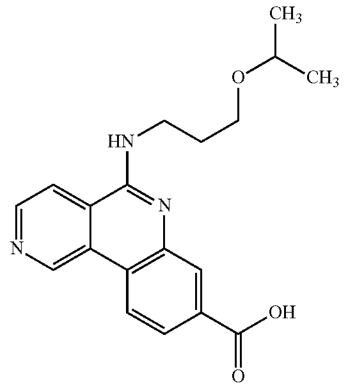 | 60.782 | 0.402 | | | 98.47 | | | >10 | | >10 | 7.01 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 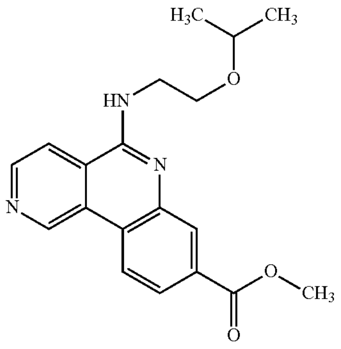 | 39.067 | | | | 15.577 | | | >10 | | >10 | 2.935 |
| 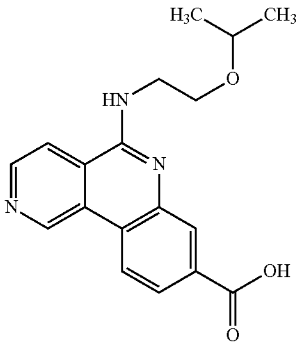 | 48.219 | | | | 92.967 | | | >10 | | >10 | 9.461 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 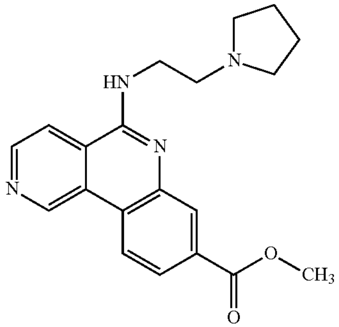 | 17.847 | | | | 8.147 | | | 0.9 | | 1.247 | 0.368 |
| 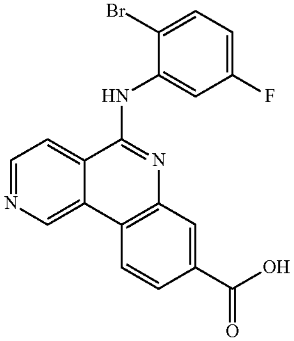 | 64.508 | 0.376 | | | 98.42 | | | >10 | | >10 | 4.126 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 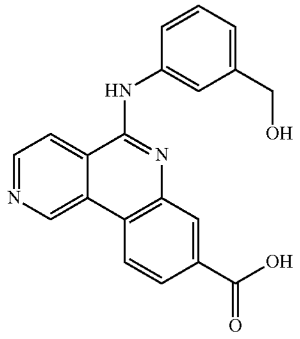 | 64.654 | 0.321 | | | 97.462 | | | >10 | | >10 | >10 |
| 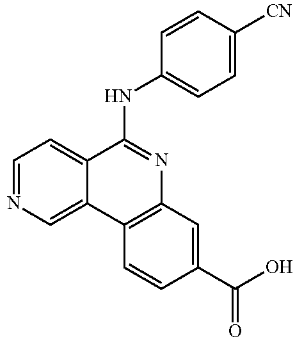 | 67.253 | 0.31 | | | 95.596 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 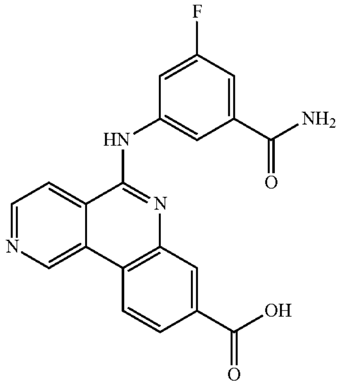 | 85.05 | 0.093 | | | 99.232 | | | >10 | | >10 | >10 |
| 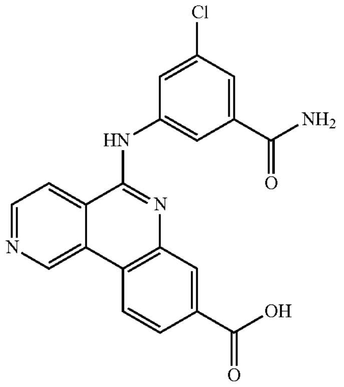 | 90.484 | 0.09 | | | 101.591 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 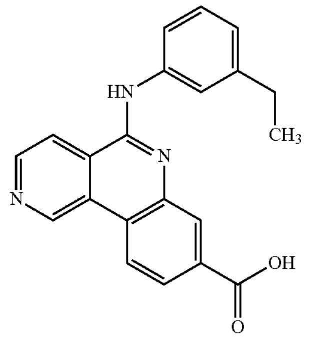 | 85.02 | 0.122 | | | 100.987 | | | >10 | | >10 | 3.638 |
| 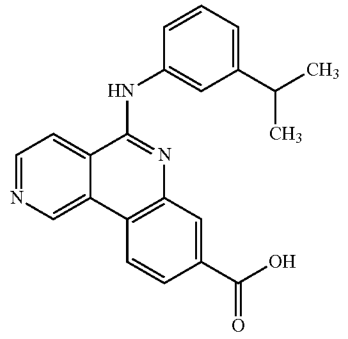 | 72.434 | 0.485 | | | 99.484 | | | >10 | | >10 | 3.159 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 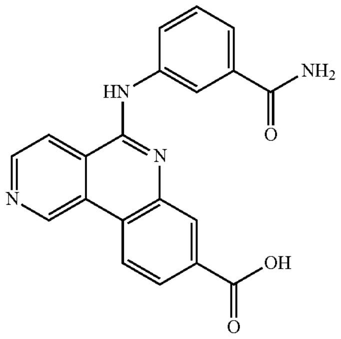 | 74.786 | 0.16 | | | 100.838 | | | >10 | | >10 | >10 |
| 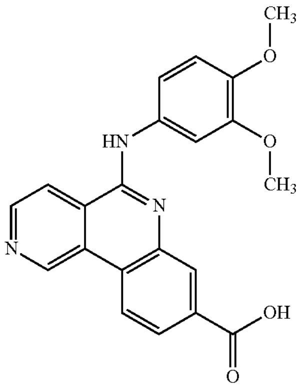 | 59.317 | 0.311 | | | 98.475 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 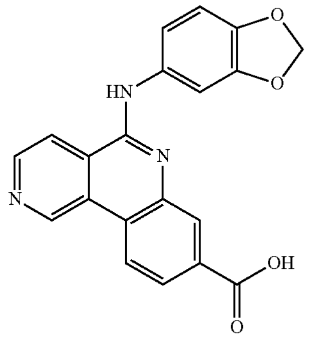 | 75.981 | 0.157 | | | 101.372 | | | >10 | | >10 | 8.868 |
| 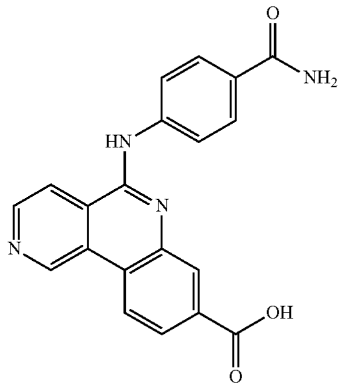 | 78.184 | 0.248 | | | −5.093 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 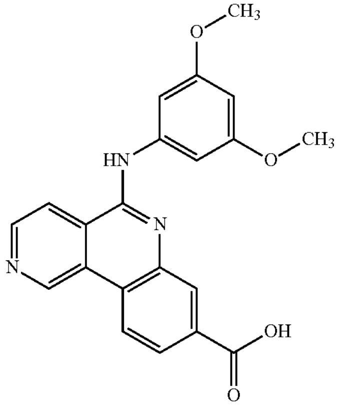 | 71.985 | 0.152 | | | 99.396 | | | >10 | | >10 | 6.943 |
| 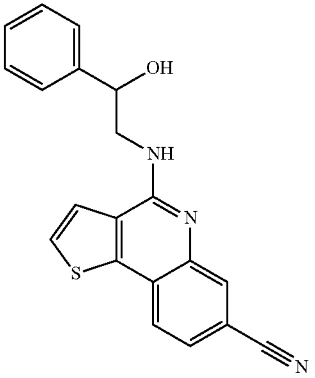 | 6.384 | | | | −9.577 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 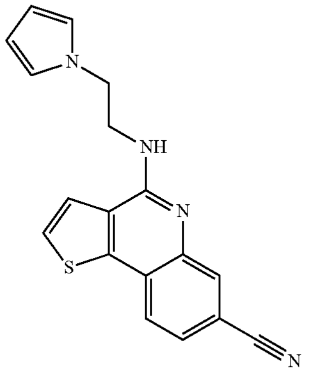 | −25.631 | | | | −22.263 | | | >10 | | 6.074 | >10 |
| 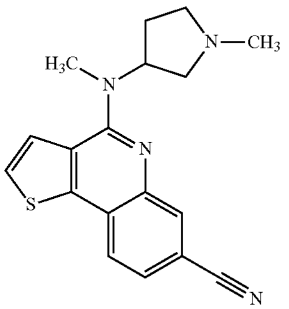 | −6.139 | | | | −14.084 | | | 4.645 | | >10 | 7.873 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 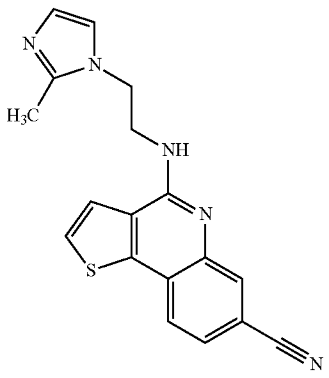 | 8.615 | | | | −15.694 | | | >10 | | >10 | >10 |
| 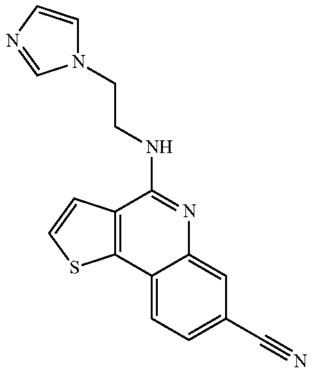 | −0.12 | | | | −14.887 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 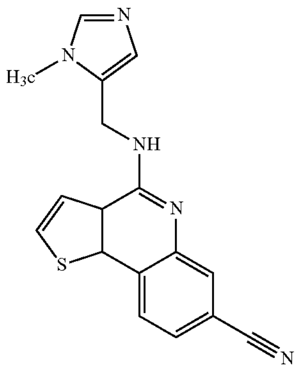 | 13.653 | | | | −1.407 | | | >10 | | >10 | >10 |
| 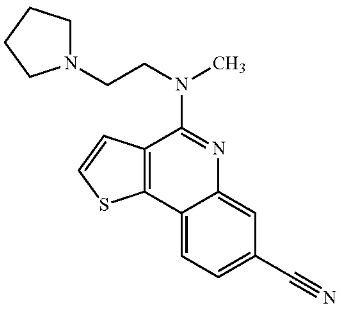 | −3.97 | | | | −20.288 | | | 1.41 | | 3.035 | 1.839 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 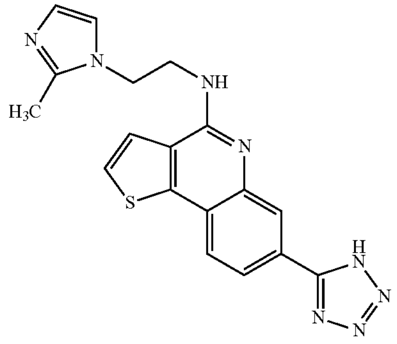 | 81.485 | 0.119 | | | 62.071 | | | >10 | | >10 | >10 |
| 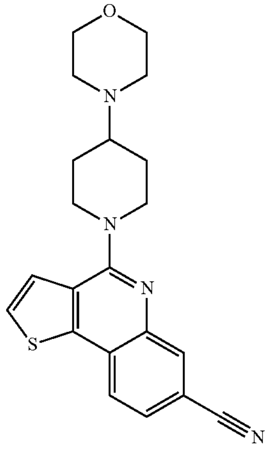 | 0.408 | | | | −34.722 | | | >10 | | >10 | >10 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 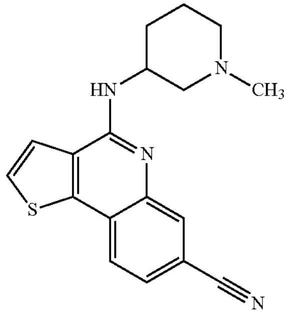 | 20.755 | | | | −17.46 | | | 1.416 | | 5.059 | 3.234 |
| 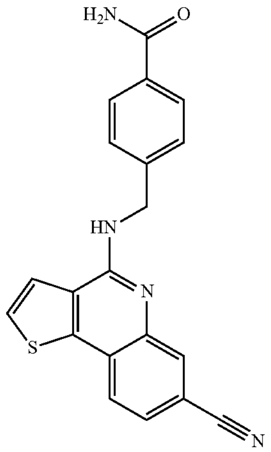 | −23.811 | | | | −4.691 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 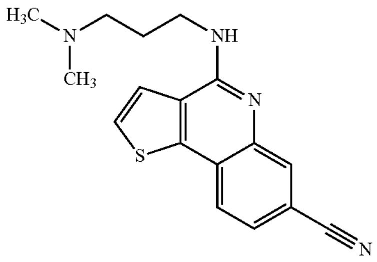 | 23.778 | | | | −30.497 | | | 3.368 | | >10 | 7.814 |
| 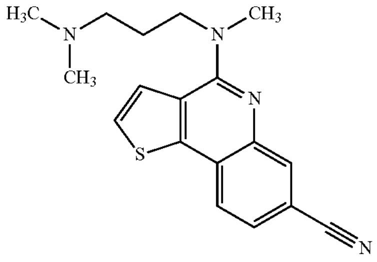 | 15.272 | | | | −4.718 | | | 3.92 | | 7.983 | 3.55 |
| 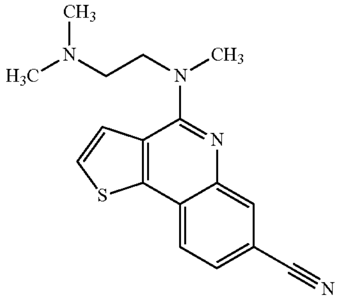 | −3.15 | | | | 64.133 | | | 0.511 | | 1.874 | 1.073 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 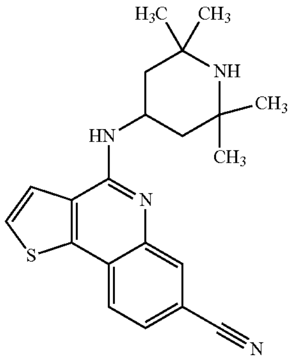 | −1.378 | | | | −3.984 | | | 6.749 | | >10 | 9.877 |
| 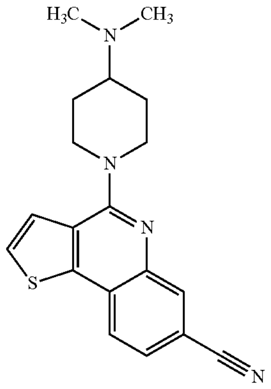 | 20.29 | | | | −0.522 | | | 6.572 | | >10 | 6.053 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 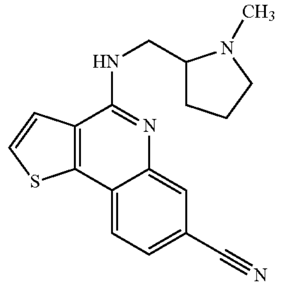 | 8.142 | | | | 0.724 | | | 4.414 | | 6.502 | 3.744 |
| 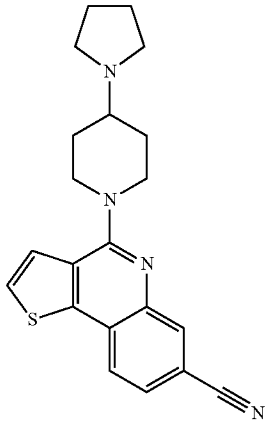 | 35.668 | | | | −6.675 | | | 5.657 | | 6.935 | 3.357 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 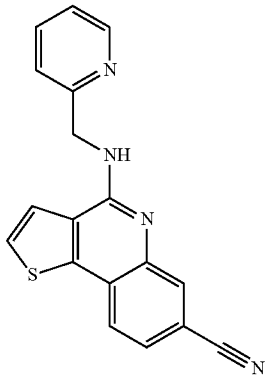 | 2.166 | | | | 100.496 | | | >10 | | >10 | >10 |
| 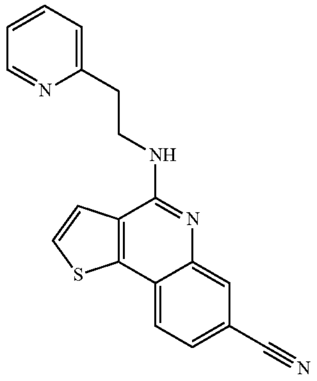 | 10.602 | | | | 5.185 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 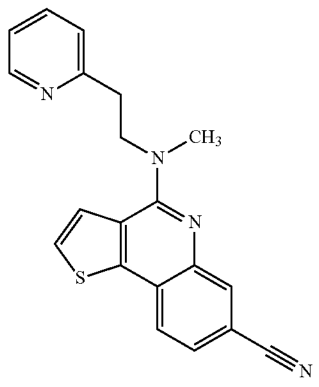 | 19.358 | | | | 44.481 | | | >10 | | >10 | >10 |
| 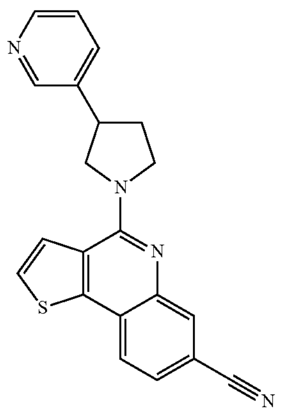 | −11.191 | | | | 0.642 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 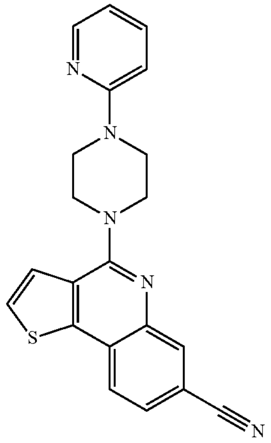 | 10.978 | | | | 7.662 | | | >10 | | >10 | >10 |
| 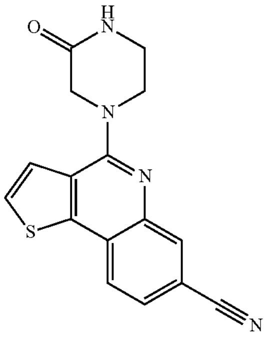 | 8.038 | | | | −4.509 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 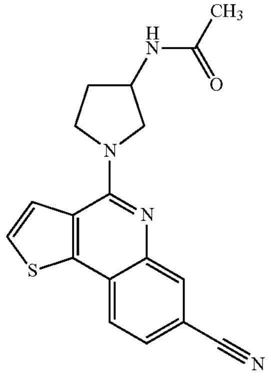 | 5.745 | | | | −8.883 | | | >10 | | >10 | >10 |
| 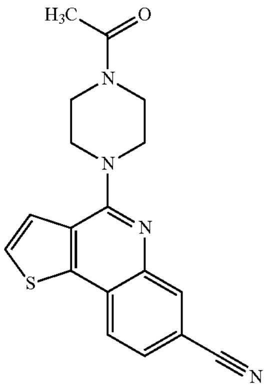 | 7.135 | | | | 3.479 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 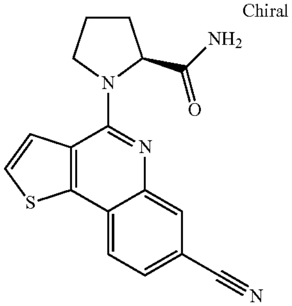 Chiral | 12.215 | | | | 4.419 | | | >10 | | >10 | >10 |
| 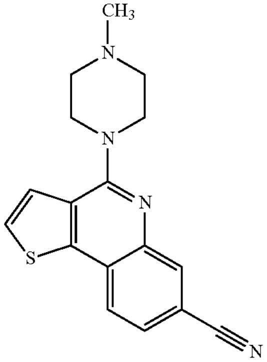 | 15.779 | | | | 24.322 | | | 8.768 | | >10 | 4.787 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 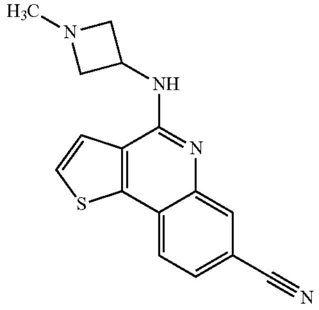 | 0.859 | | | | 20.627 | | | 0.437 | | >10 | 0.882 |
| 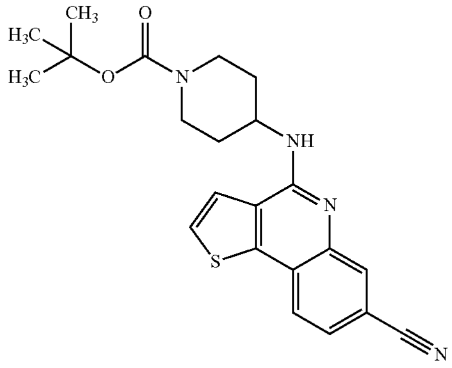 | 2.444 | | | | 1.983 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 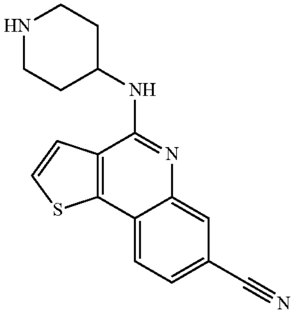 | 70.123 | 0.416 | | | 27.078 | | | 3.146 | | >10 | 1.264 |
| 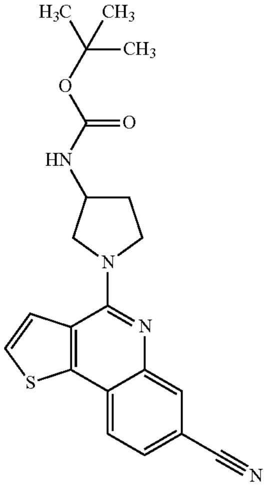 | 10.012 | | | | 10.951 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 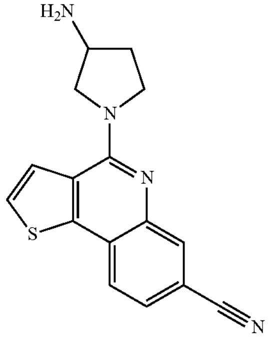 | 9.101 | | | | −2.469 | | | >10 | | >10 | >10 |
| 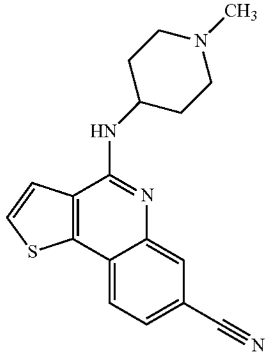 | 59.115 | 1.031 | | | −8.222 | | | 3.441 | | >10 | 7.52 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 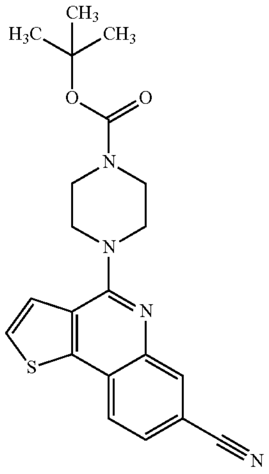 | −30.861 | | | | −34.964 | | | >10 | | >10 | >10 |
| 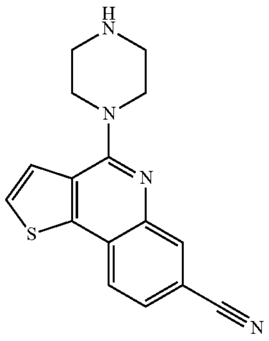 | 7.876 | | | | −27.253 | | | 4.088 | | >10 | 9.331 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 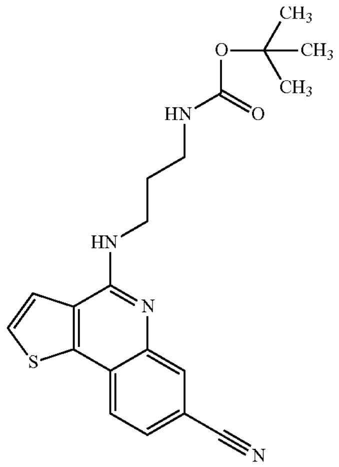 | −30.8 | | | | −11.527 | | | >10 | | >10 | >10 |
| 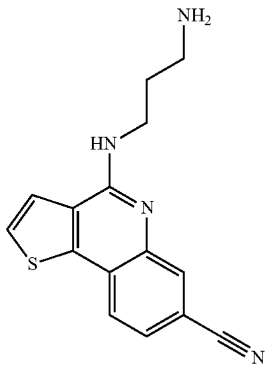 | 76.584 | 0.129 | | | 61.362 | | | 2.512 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 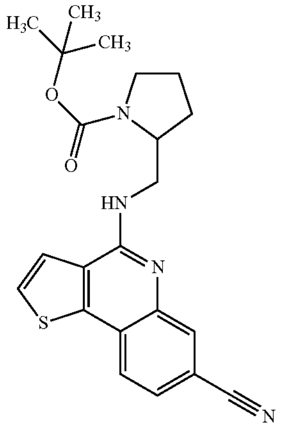 | −14.707 | | | | −35.196 | | | >10 | | >10 | >10 |
| 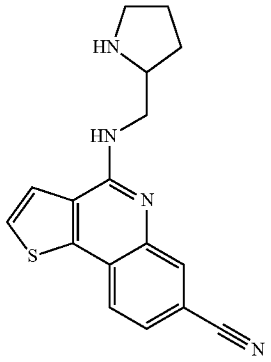 | 14.06 | | | | −23.807 | | | 2.725 | | >10 | 2.441 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 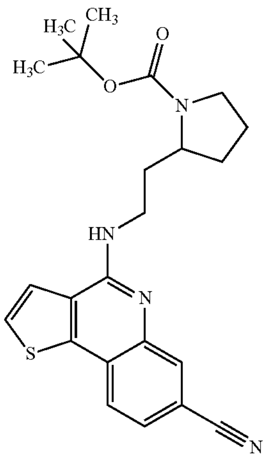 | −12.973 | | | | −22.399 | | | >10 | | >10 | >10 |
| 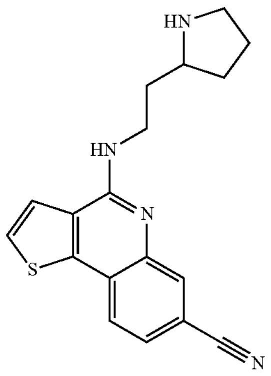 | 36.197 | | | | 37.105 | | | 1.874 | | >10 | 2.82 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 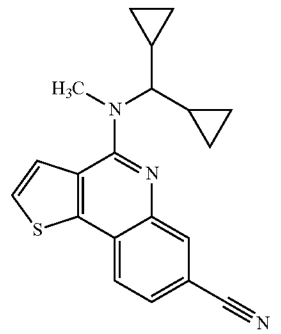 | −19.037 | | | | −17.124 | | | >10 | | >10 | >10 |
| 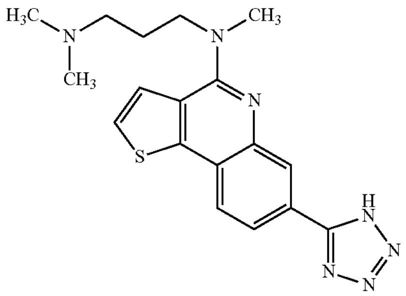 | 70.474 | 0.221 | | | 60.15 | | | >10 | | >10 | >10 |
| 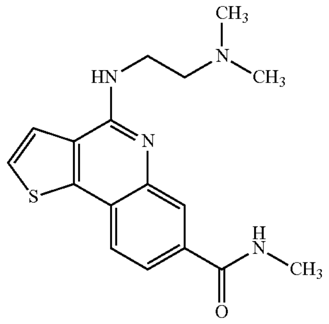 | 5.732 | | | | 8.238 | | | >10 | | >10 | 0.535 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 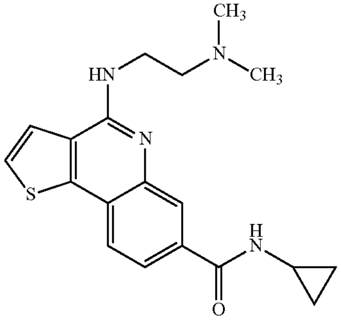 | 13.684 | | | | 1.394 | | | 2.343 | | 1.89 | >10 |
| 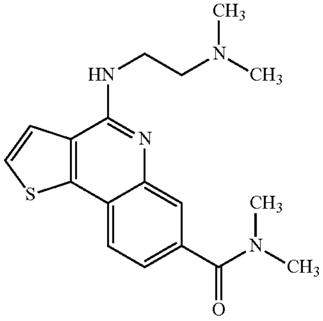 | −3.561 | | | | 11.844 | | | >10 | | >10 | 0.999 |
| 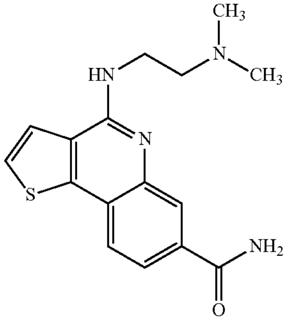 | 34.011 | | | | 15.629 | | | 4.295 | | 0.198 | 0.402 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 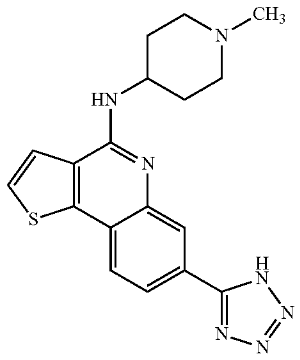 | 83.9 | 0.161 | | | 1.283 | | | >10 | | >10 | >10 |
| 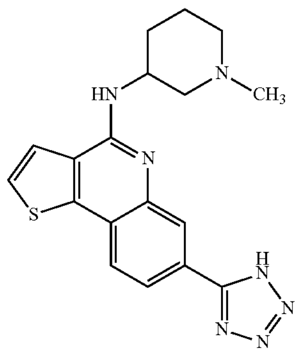 | 90.947 | 0.109 | | | 31.369 | | | >10 | | >10 | 0.658 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 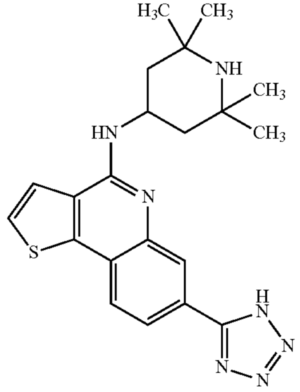 | 32.686 | | | | −5.334 | | | >10 | | >10 | >10 |
| 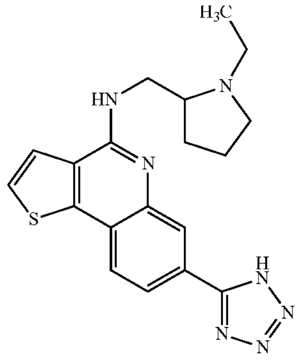 | 102.799 | 0.098 | | | 55.691 | | | 0.397 | | 0.175 | 0.174 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 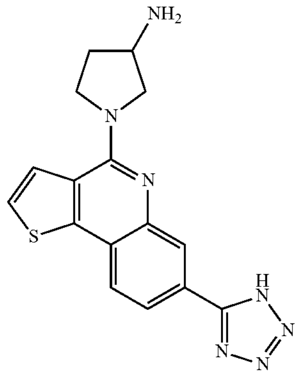 | 63.629 | 0.489 | | | 30.768 | | | >10 | | >10 | 1.146 |
| 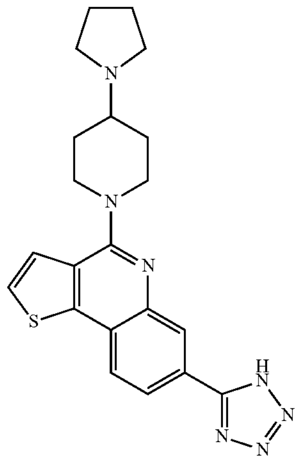 | 90.011 | 0.119 | | | 38.617 | | | >10 | | >10 | 1.067 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 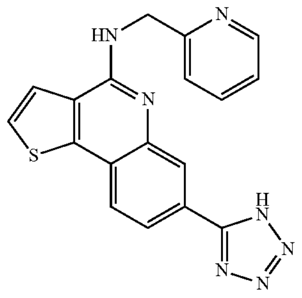 | 16.784 | | | | 27.932 | | | >10 | | >10 | 1.002 |
| 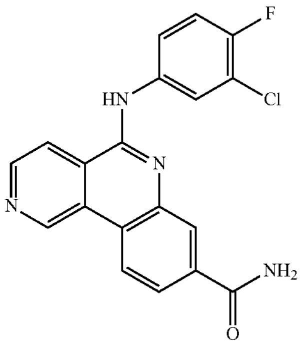 | −9.454 | | | | 66.123 | 0.167 | | >10 | | >10 | 0.373 |
| 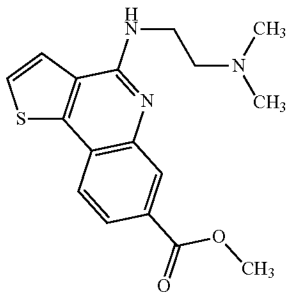 | −6.893 | | | | −0.704 | | | 1.523 | | 1.092 | 0.73 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 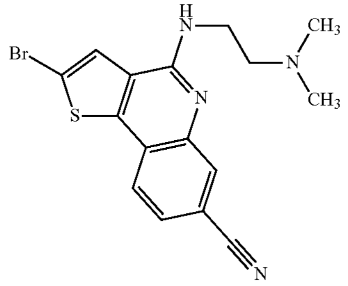 | 12.105 | | | | −7.274 | | | 0.704 | | 0.719 | 0.588 |
| 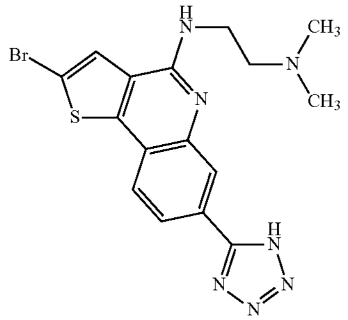 | 60.652 | 0.656 | | | 24.786 | | | >10 | | >10 | >10 |
| 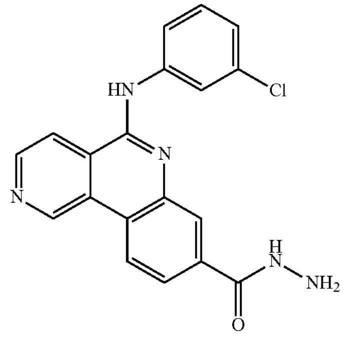 | −10.838 | | | | 34.858 | 0.075 | | >10 | | >10 | 2.144 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 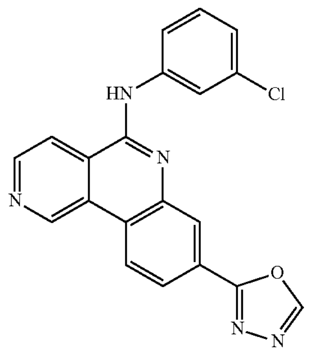 | −0.614 | | | | 29.931 | 0.236 | | 5.168 | | >10 | 0.501 |
| 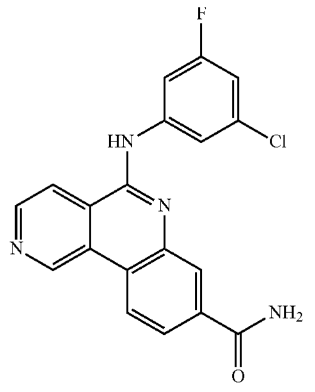 | 5.674 | | | | 55.86 | 0.012 | | | | >10 | 0.222 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 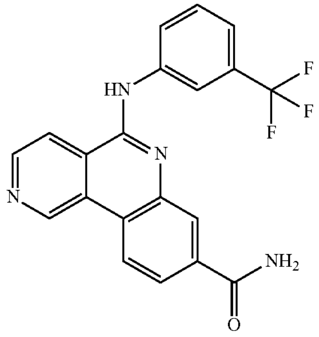 | 1.088 | | | | 34.352 | 0.006 | | 4.279 | | 2.462 | 0.12 |
| 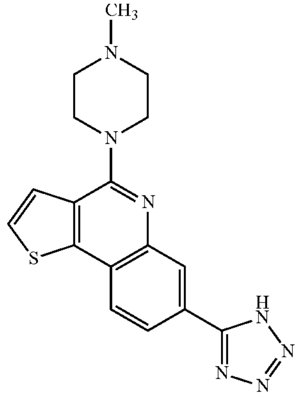 | 81.32 | 0.178 | | | 7.305 | | | >10 | | >10 | >10 |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 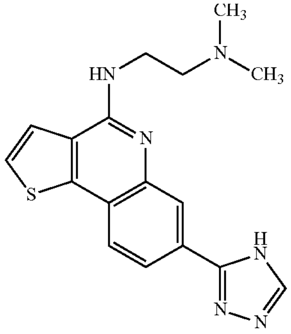 | −2.141 | | | | −76.93 | | | >10 | | >10 | 6.04 |
| 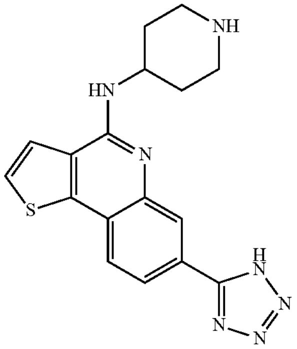 | 85.695 | 0.078 | | | −21.194 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 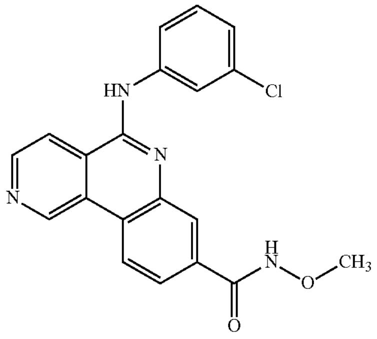 | −15.589 | | | | 14.204 | >0.4 | | 4.542 | | 2.613 | 0.691 |
| 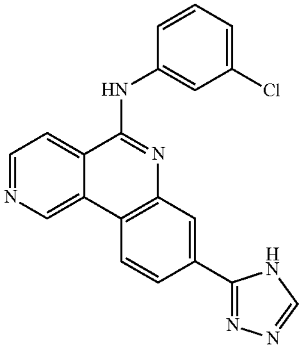 | −19.267 | | | | −2.181 | 0.09 | | >10 | | 0.546 | 1.058 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 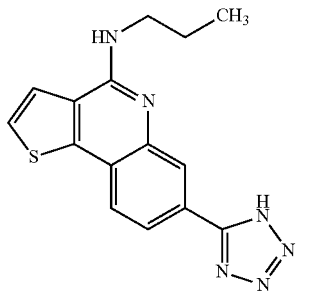 | 59.128 | >1.1 | | | 31.106 | | | >10 | | >10 | >10 |
| 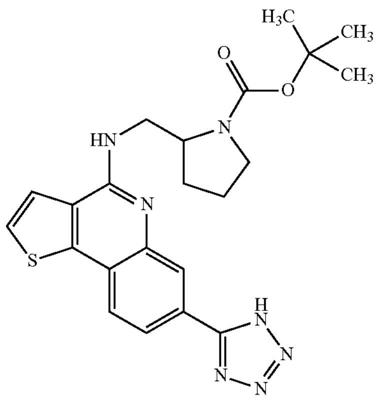 | 34.971 | | | | 26.965 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 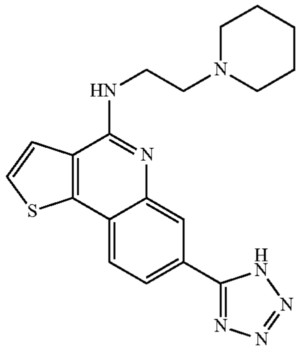 | 81.059 | 0.313 | | | 37.131 | | | >10 | | >10 | >10 |
| 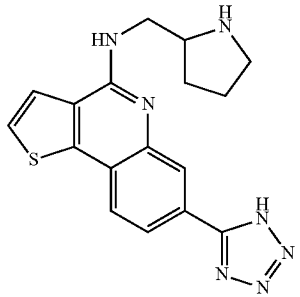 | 93.442 | 0.046 | | | 86.066 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 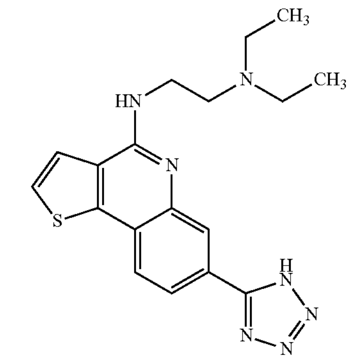 | 87.291 | 0.127 | | | 52.618 | | | >10 | | >10 | >10 |
| 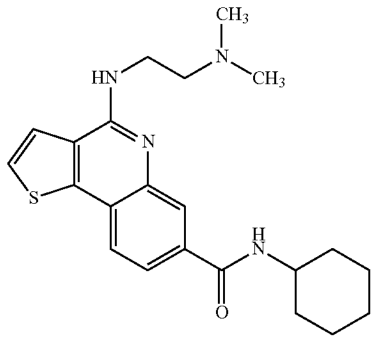 | −3.104 | | | | −10.648 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 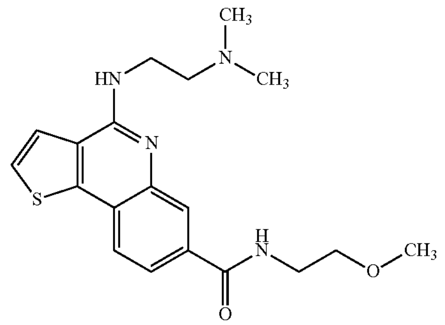 | −3.758 | | | | −12.904 | | | >10 | | >10 | >10 |
| 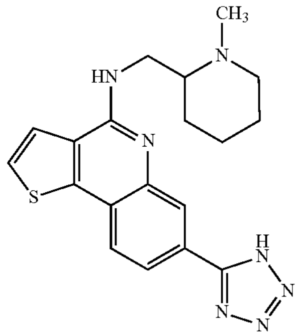 | 90.871 | 0.064 | | | 32.772 | | | >10 | | >10 | >10 |
| 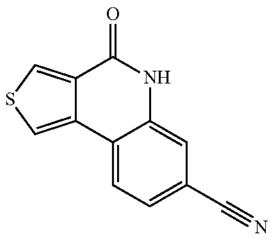 | −26.689 | | | | −0.336 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 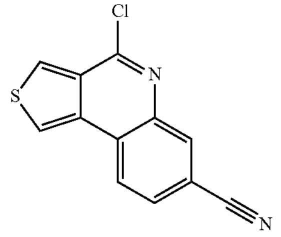 | −20.264 | | | | −6.517 | | | >10 | | >10 | 1.811 |
| 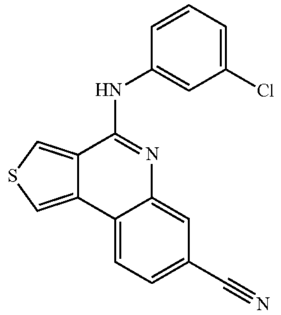 | −32.782 | | | | −9.4 | | | >10 | | >10 | >10 |
| 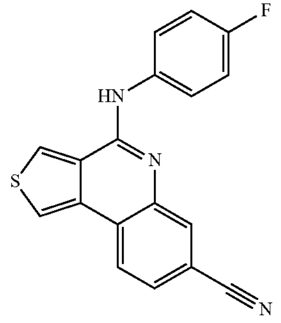 | −6.768 | | | | 9.207 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 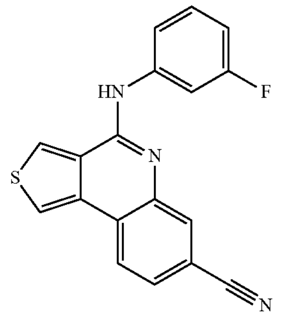 | −28.597 | | | | −20.139 | | | >10 | | 8.043 | >10 |
| 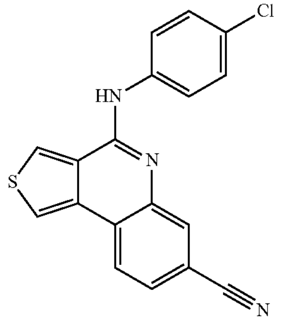 | −35.844 | | | | −2.494 | | | >10 | | >10 | >10 |
| 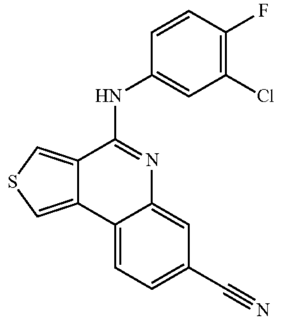 | −26.289 | | | | −8.355 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 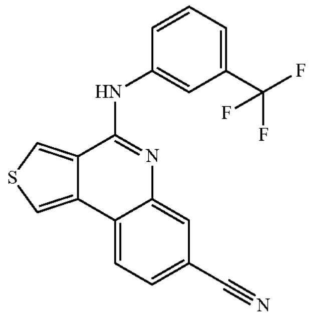 | −33.154 | | | | −2.652 | | | >10 | | >10 | >10 |
| 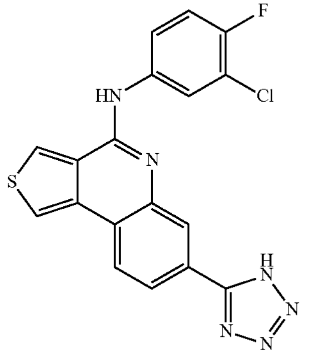 | 14.249 | | | | 51.093 | | | >10 | | >10 | 5.715 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 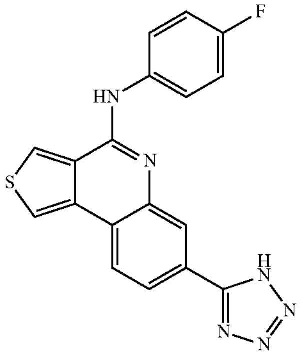 | 30.601 | | | | 37.559 | | | >10 | | >10 | 5.466 |
| 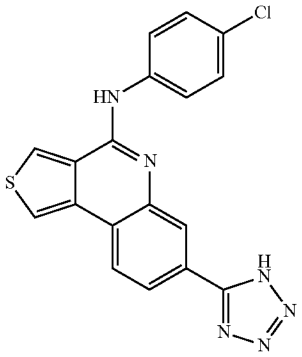 | 15.227 | | | | 39.511 | | | >10 | | >10 | 6.436 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 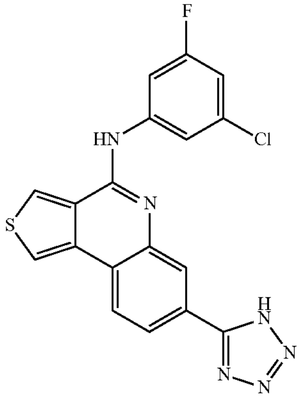 | 11.433 | | | | 57.262 | | | >10 | | >10 | >10 |
| 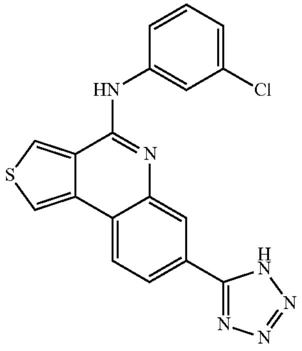 | 17.897 | | | | 63.267 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 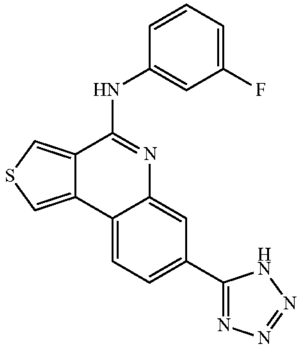 | 13.966 | | | | 52.579 | | | >10 | | >10 | >10 |
| 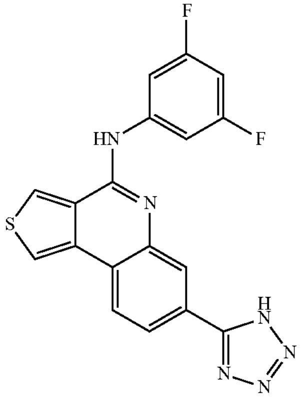 | 11.11 | | | | 52.617 | | | >10 | | >10 | >10 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 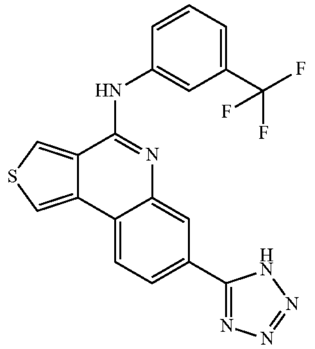 | −6.513 | | | | 23.077 | | | >10 | | >10 | >10 |
| 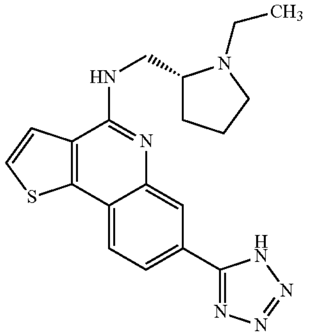 Chiral | 89.858 | 0.065 | | | 78.073 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 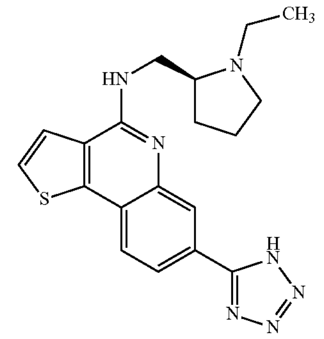 Chiral | 84.127 | 0.118 | | | 59.805 | | | >10 | | >10 | >10 |
| 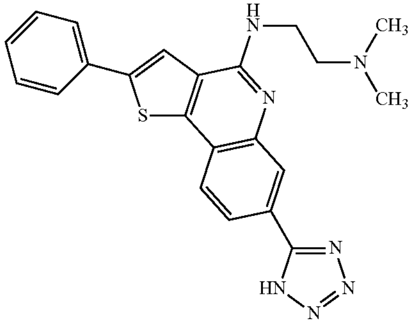 | −14.836 | | | | 0.269 | | | >10 | | >10 | >10 |
| 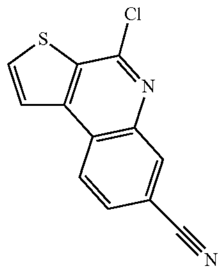 | −23.873 | | | | −11.528 | | | >10 | | >10 | >10 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 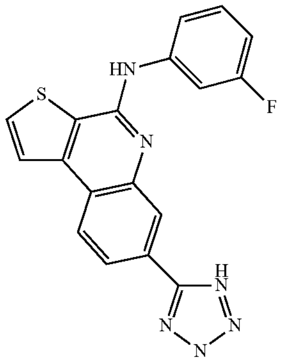 | 50.289 | 0.834 | | | 57.627 | | | >10 | | >10 | 2.192 |
| 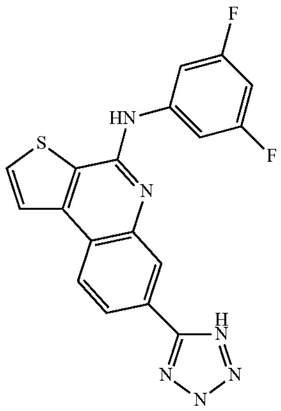 | 50.279 | 1.009 | | | 57.35 | | | >10 | | >10 | 3.658 |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 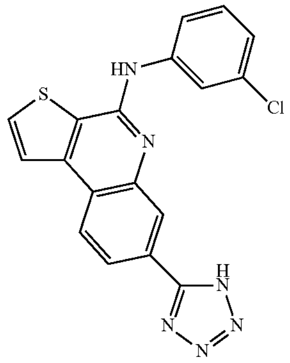 | 31.853 | | | | 56.179 | | | >10 | | >10 | 4.473 |
| 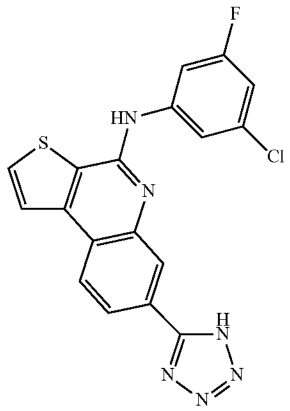 | 22.856 | | | | 45.403 | | | >10 | | >10 | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 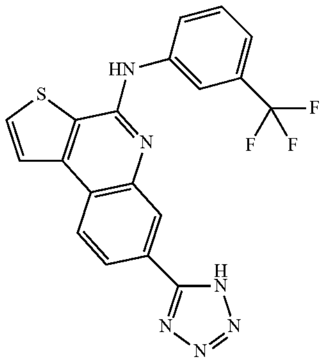 | 10.846 | | | | 17.403 | | | >10 | | >10 | 1.103 |
| 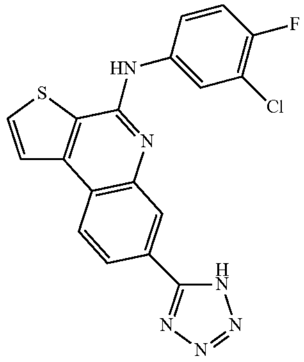 | 29.086 | | | | 37.572 | | | >10 | | >10 | 0.721 |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 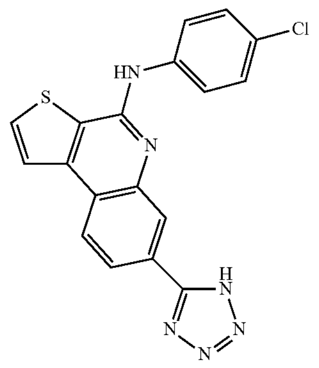 | 40.44 | | | | 23.95 | | | >10 | | >10 | >10 |
| 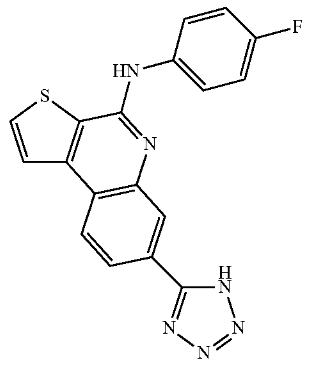 | 54.738 | 0.738 | | | 30.295 | | | >10 | | >10 | >10 |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 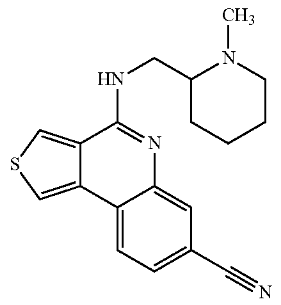 | 46.406 | | | | 24.554 | | | | | | |
| 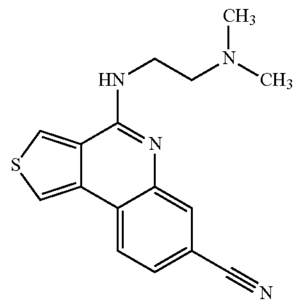 | 20.049 | | | | 23.396 | | | | | | |
| 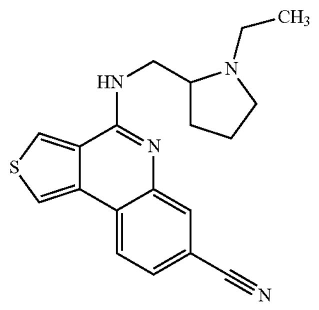 | 6.895 | | | | 20.689 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 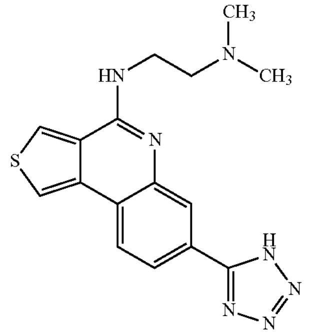 | 89.741 | 0.087 | | | 65.987 | | | | | | |
| 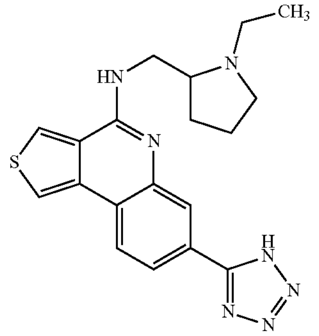 | 95.902 | 0.079 | | | 72.836 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 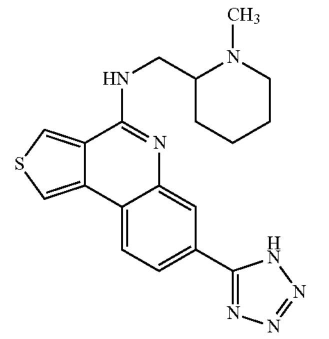 | 93.868 | 0.054 | | | 57.401 | | | | | | |
| 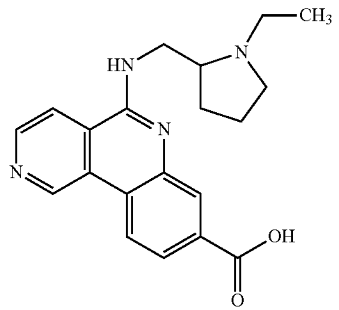 | 79.423 | 0.155 | | | 107.306 | | | | | | |
| 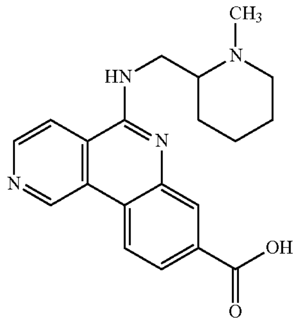 | 82.504 | 0.211 | | | 102.635 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 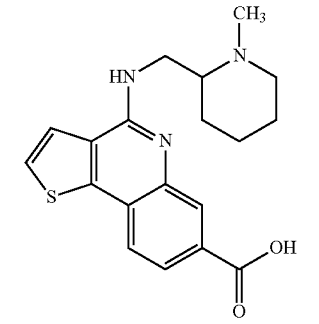 | 88.01 | 0.104 | | | 80.125 | | | | | | |
| 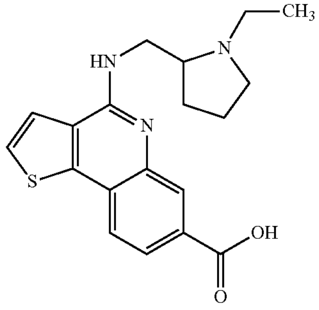 | 93.262 | 0.1 | | | 92.79 | | | | | | |
| 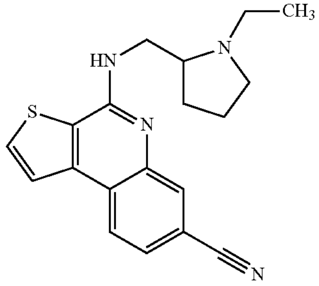 | −9.291 | | | | −29.414 | | | | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 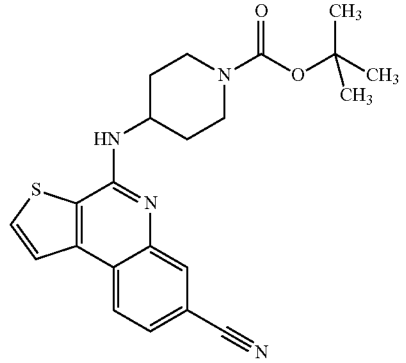 | −29.418 | | | | −16.961 | | | | | | |
| 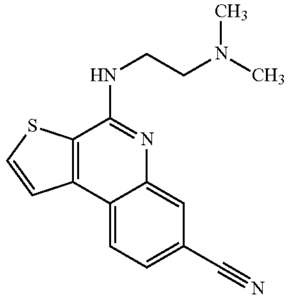 | 115.316 | | | | −16.763 | | | | | | |
| 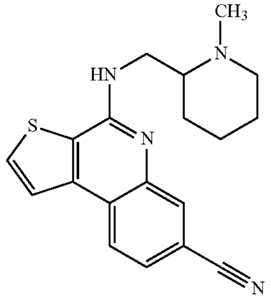 | 59.481 | | | | 5.506 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 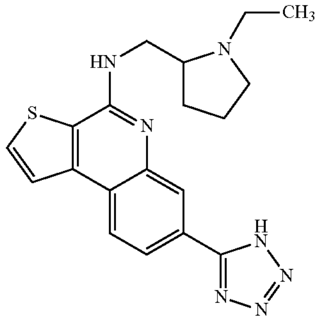 | 80.025 | | | | 1.86 | | | | | | |
| 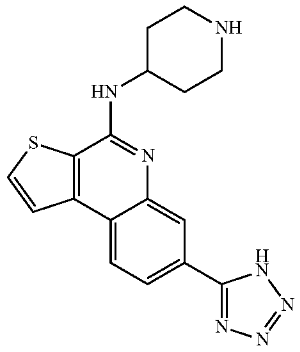 | 111.43 | 0.138 | | | 53.732 | | | | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 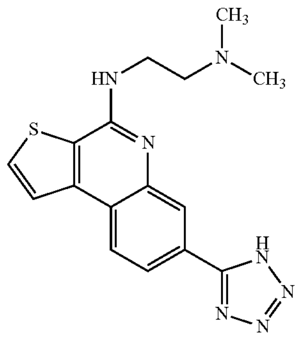 | 99.241 | 0.267 | | | 24.226 | | | | | | |
| 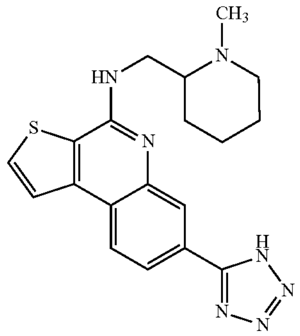 | 14.747 | | | | −29.124 | | | | | | |
| 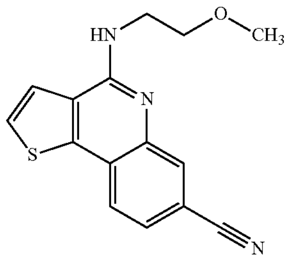 | −30.595 | | | | −18.043 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 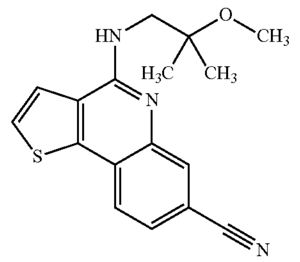 | −30.025 | | | | −17.062 | | | | | | |
| 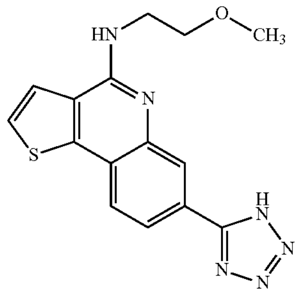 | 65.025 | | | | 47.245 | | | | | | |
| 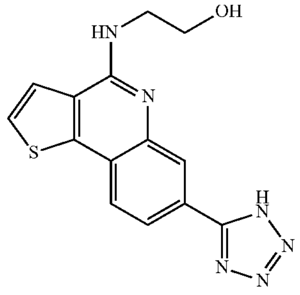 | 101.063 | 0.143 | | | 51.292 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 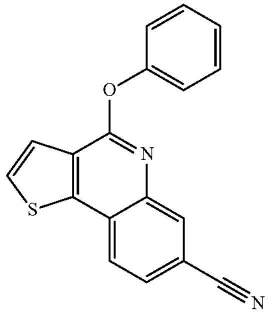 | −38.646 | | | | −54.197 | | | | | | |
| 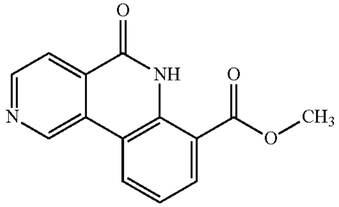 | −70.544 | | | | 16.749 | | | | | | |
| 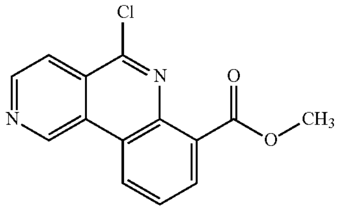 | −29.152 | | | | 10.096 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 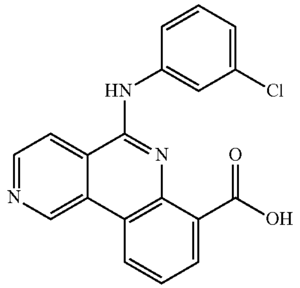 | 20.177 | | | | 15.474 | | | | | | |
| 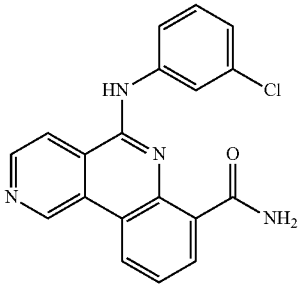 | 78.886 | | | | 36.606 | | | | | | |
| 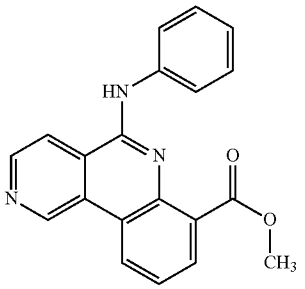 | 3.962 | | | | −7.868 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 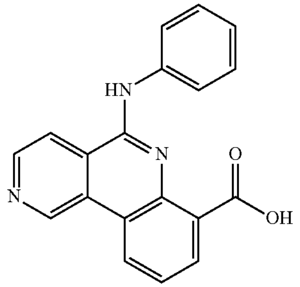 | −77.38 | | | | −13.462 | | | | | | |
| 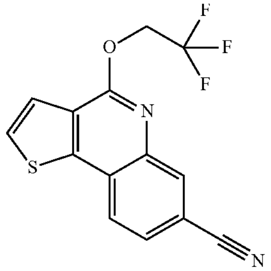 | −50.152 | | | | −9.048 | | | | | | |
| 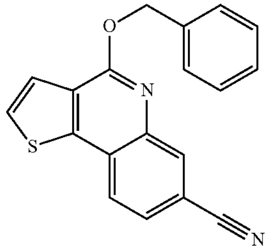 | −18.443 | | | | 1.846 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 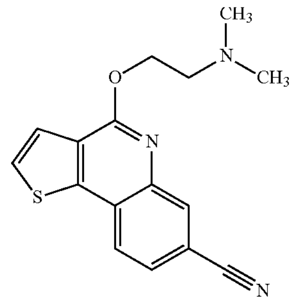 | −43.165 | | | | −17.978 | | | | | | |
| 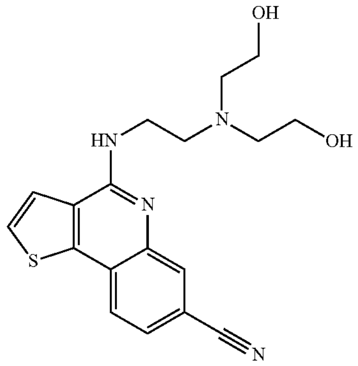 | −17.684 | | | | −9.967 | | | | | | |
| 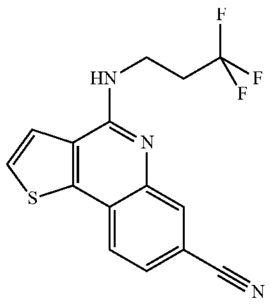 | −89.646 | | | | −7.758 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 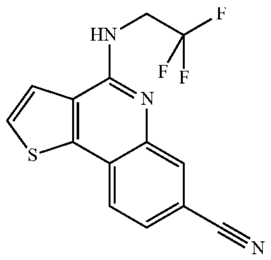 | −32 | | | | −18.374 | | | | | | |
| 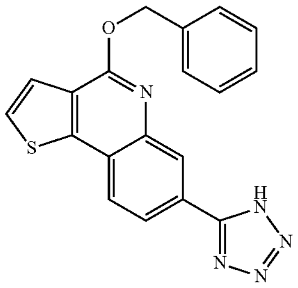 | −6.975 | | | | 5.713 | | | | | | |
| 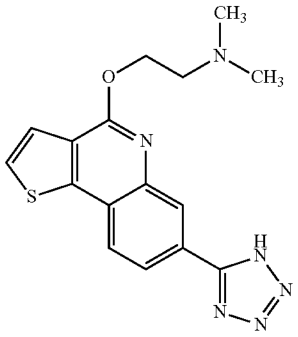 | 91.646 | | | | 31.431 | | | | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 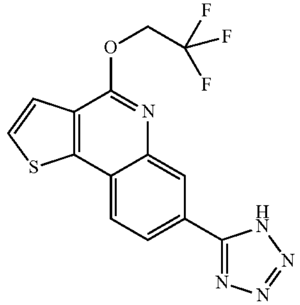 | 32.253 | | | | 32.978 | | | | | | |
| 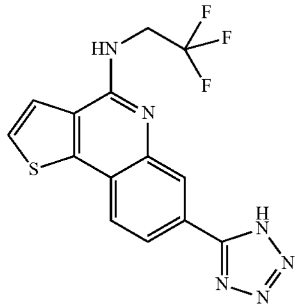 | 93.165 | | | | 49.041 | | | | | | |
| 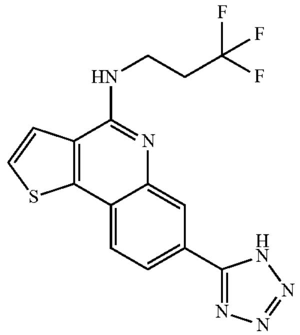 | 92.253 | | | | 58.35 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 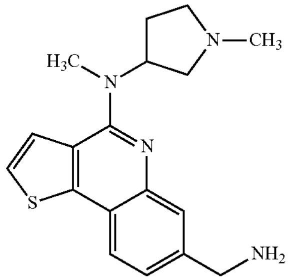 | −39.823 | | | | −35.33 | | | | | | |
| 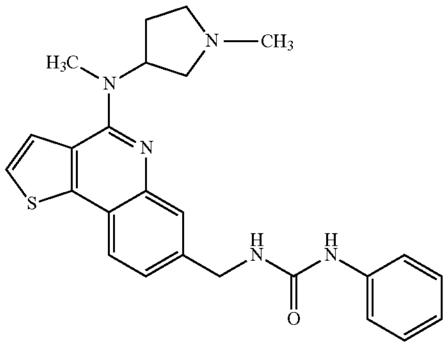 | −83.532 | | | | −44.17 | | | | | | |
| 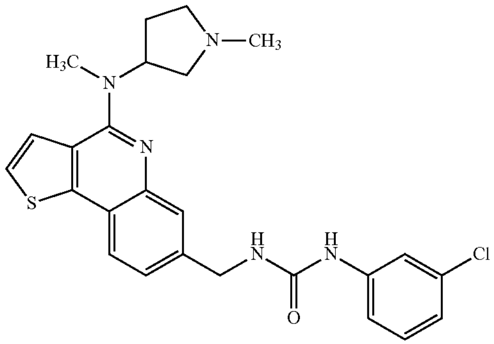 | −38.494 | | | | −50.413 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 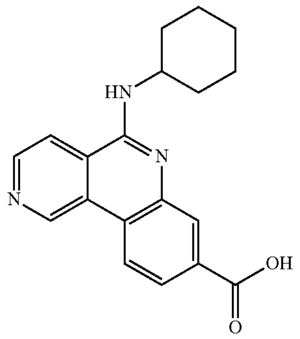 | 64.835 | | | | 95.826 | | | | | | |
| 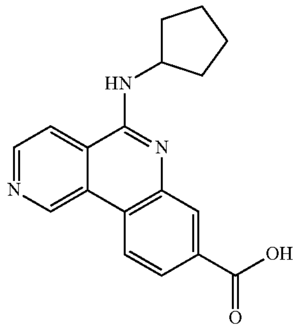 | 106.266 | 0.565 | | | 101.134 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 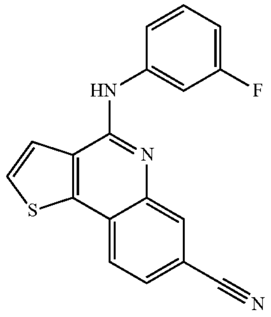 | −4.848 | | | | 3.057 | | | | | | |
| 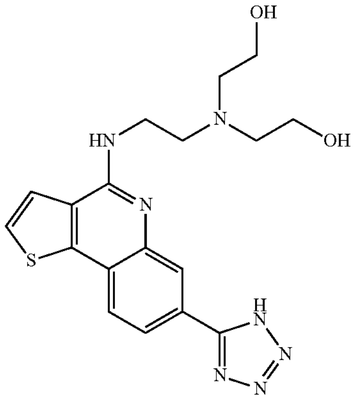 | 118.38 | 0.116 | | | 50.68 | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 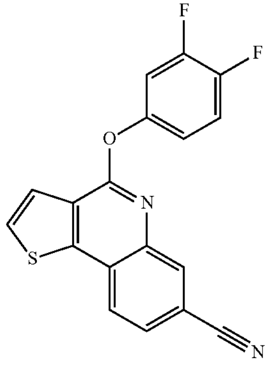 | 27.81 | | | | −9.995 | | | | | | |
| 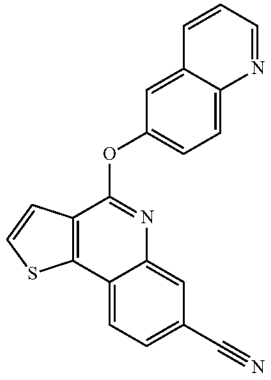 | −22.165 | | | | −7.325 | | | | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 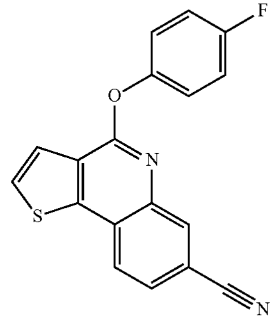 | 10.038 | | | | −3.78 | | | | | | |
| 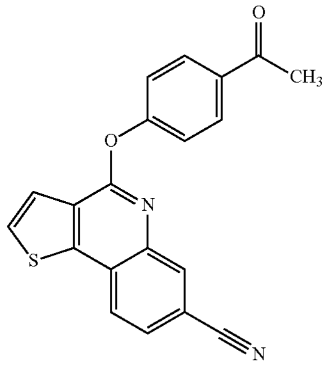 | 1.38 | | | | −17.9 | | | | | | |

TABLE 39-continued
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
|---|---|---|---|---|---|---|---|---|---|---|---|
| | Modulatory activity in cell-free assays IC50 (uM) | | | | | | Cell proliferation modulatory activity | | | | |
| 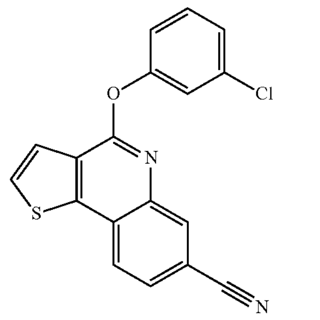 | 10.57 | | | | −10.755 | | | | | | |
| 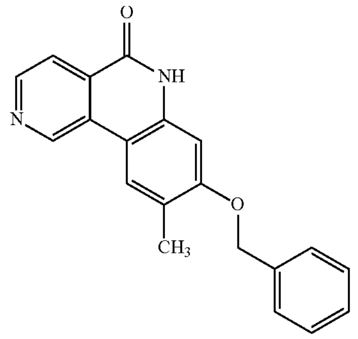 | −10.051 | | | | −7.767 | | | | | | |
| 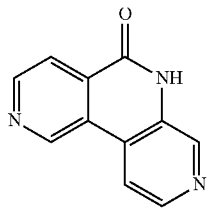 | 19.797 | | | | 7.504 | | | | | | |

TABLE 39-continued
| Structure | Modulatory activity in cell-free assays IC50 (uM) PIM-1: % inh 500 nM | PIM1 | CK2 (20 um ATP) | CK2 (15 um ATP) | CK2: % inh 500 nM | FLT-3 (uM) | Cell proliferation modulatory activity HCT-116 (uM) | HCT-116 (uM) | Jurkat (uM) | K-562 (uM) | MV-4-11 (uM) |
|---|---|---|---|---|---|---|---|---|---|---|---|
| 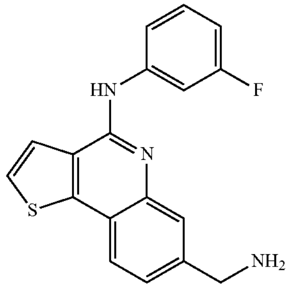 | −16.354 | | | | −8.77 | | | | | | |
| 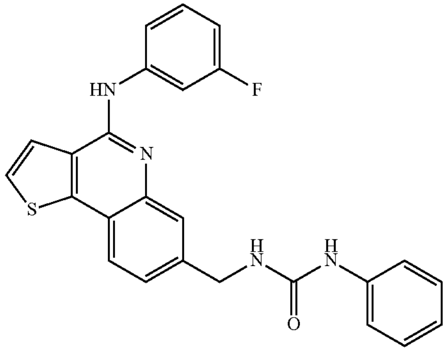 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 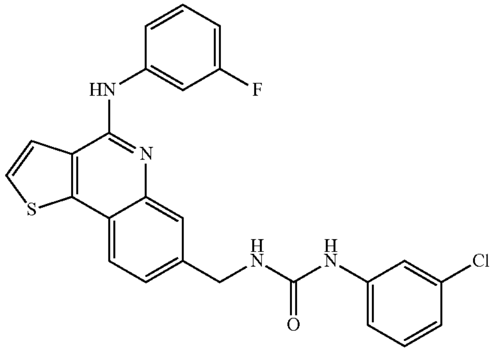 | | | | | | | | | | | |
| 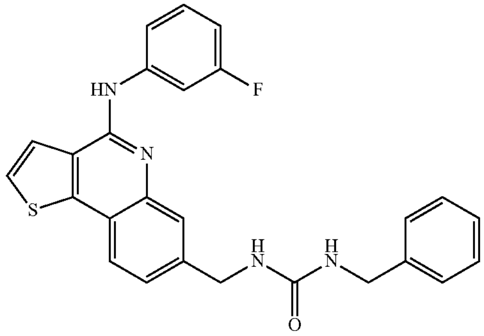 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 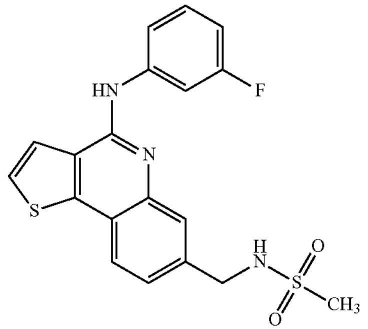 | | | | | | | | | | | |
| 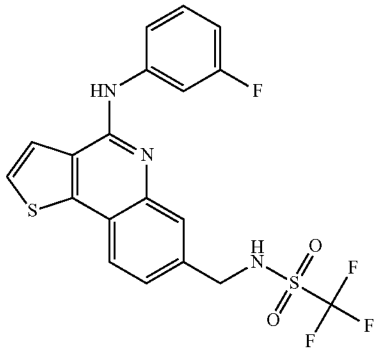 | | | | | | | | | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 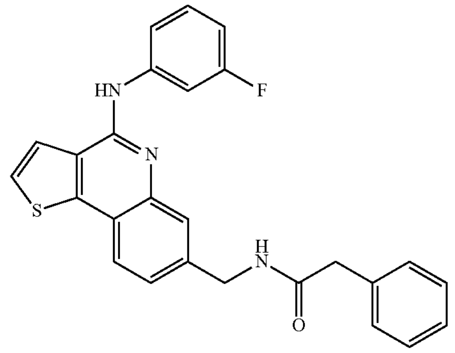 | | | | | | | | | | | |
| 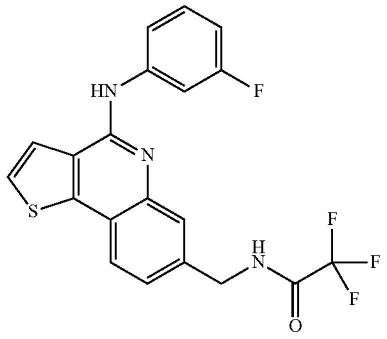 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 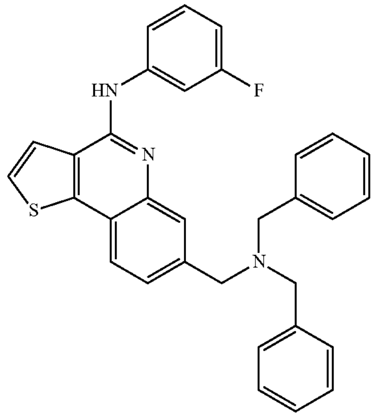 | 2.975 | | | | −2.293 | | | | | | |
| 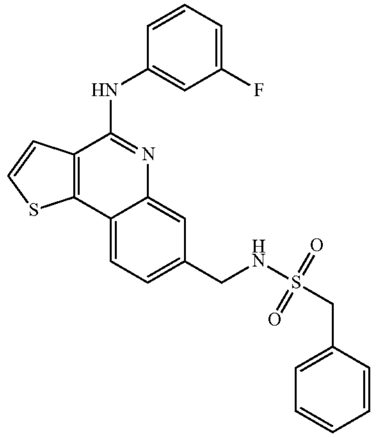 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 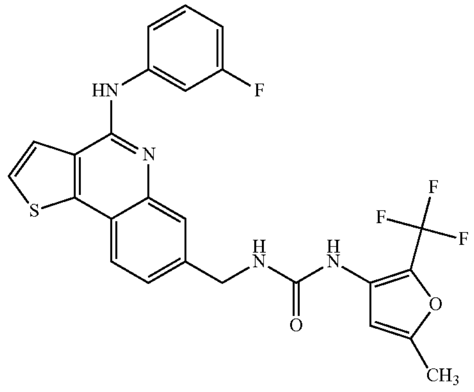 | −17.532 | | | | −9.986 | | | | | | |
| 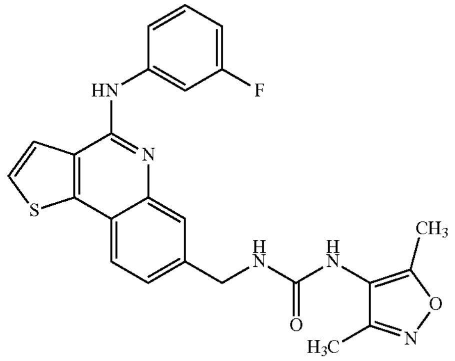 | −11.228 | | | | −4.71 | | | | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 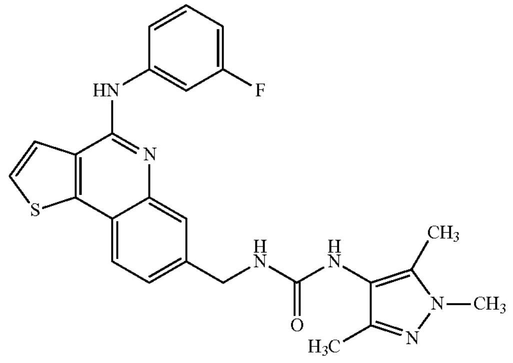 | 11.025 | | | | −5.428 | | | | | | |
| 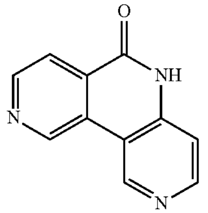 | | | | | | | | | | | |
| 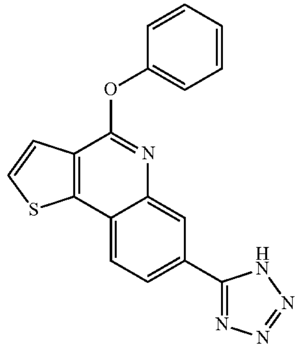 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 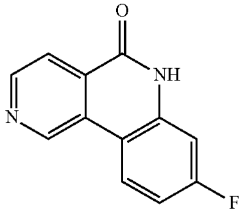 | 15.316 | | | | −1.096 | | | | | | |
| 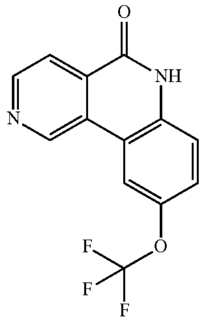 | 9.089 | | | | 1.22 | | | | | | |
| 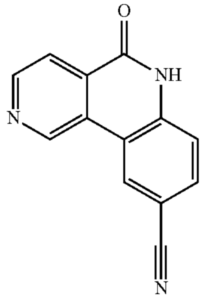 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 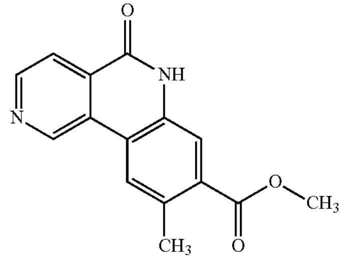 | | | | | | | | | | | |
| 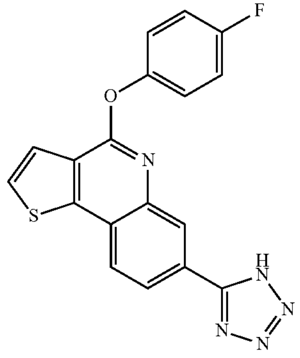 | | | | | | | | | | | |
| 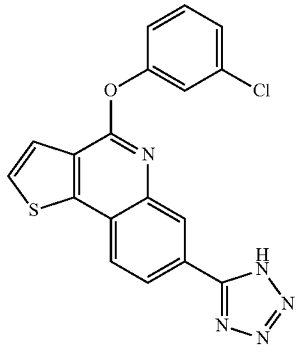 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 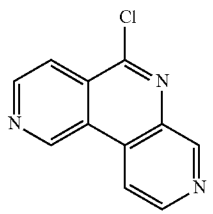 | | | | | | | | | | | |
| 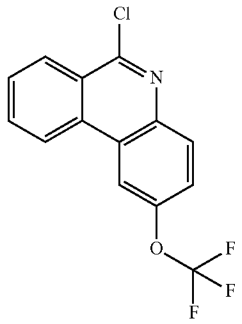 | | | | | | | | | | | |
| 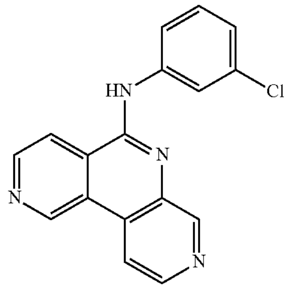 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 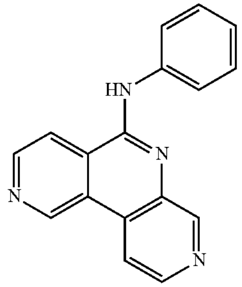 | | | | | | | | | | | |
| 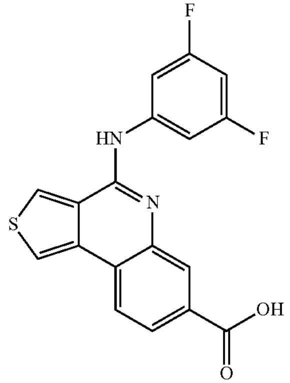 | | | | | | | | | | | |
| 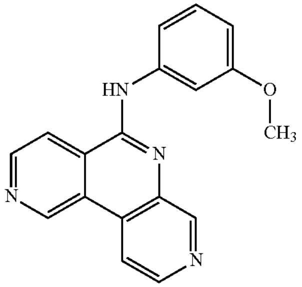 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 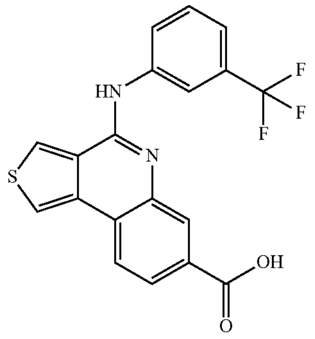 | | | | | | | | | | | |
| 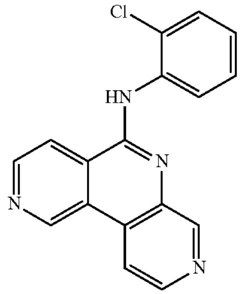 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 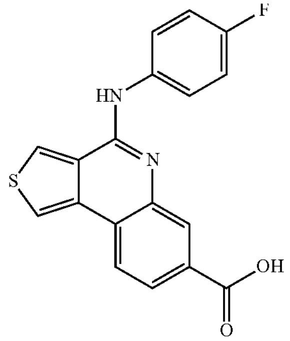 | | | | | | | | | | | |
| 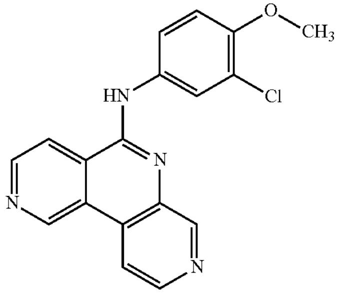 | | | | | | | | | | | |
| 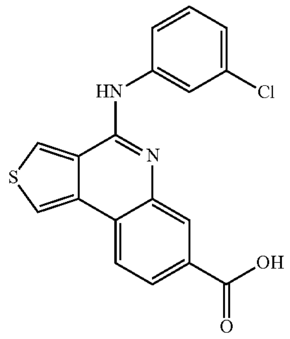 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 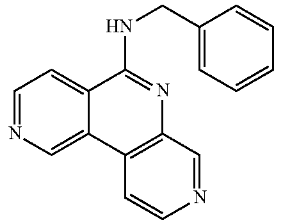 | | | | | | | | | | | |
| 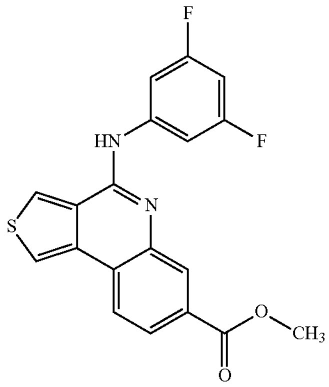 | | | | | | | | | | | |
| 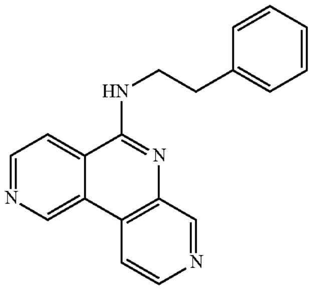 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 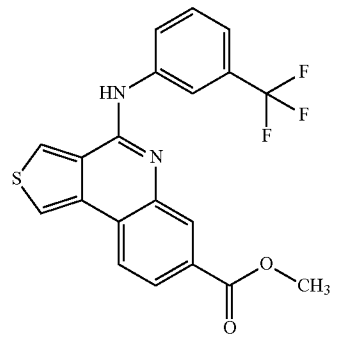 | | | | | | | | | | | |
| 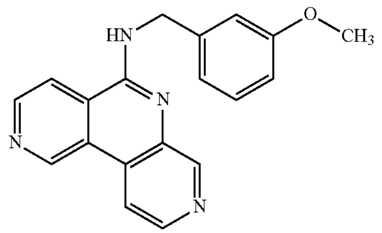 | | | | | | | | | | | |
| 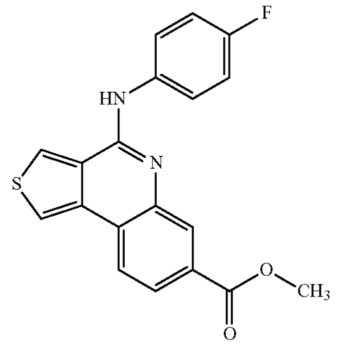 | | | | | | | | | | | |

TABLE 39-continued
| | Modulatory activity in cell-free assays IC50 (uM) | | | | | | Cell proliferation modulatory activity | | | | |
|---|---|---|---|---|---|---|---|---|---|---|---|
| Structure | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 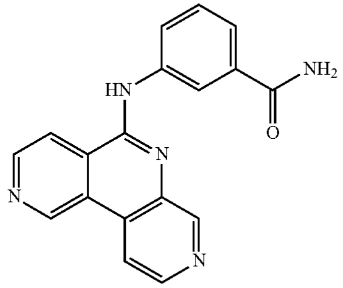 | | | | | | | | | | | |
| 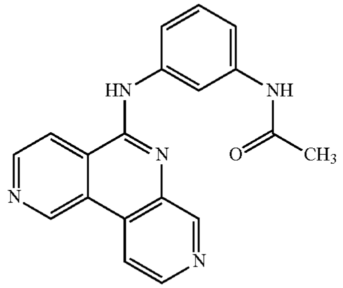 | | | | | | | | | | | |

TABLE 39-continued
| Structure | Modulatory activity in cell-free assays IC50 (uM) | | | | | | Cell proliferation modulatory activity | | | | |
|---|---|---|---|---|---|---|---|---|---|---|---|
| | PIM-1: % inh 500 nM | PIM1 | CK2 (20 um ATP) | CK2 (15 um ATP) | CK2: % inh 500 nM | FLT-3 (uM) | HCT-116 (uM) | HCT-116 (uM) | Jurkat (uM) | K-562 (uM) | MV-4-11 (uM) |
| 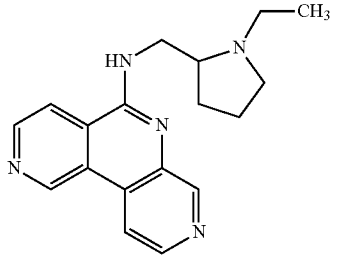 | | | | | | | | | | | |
| 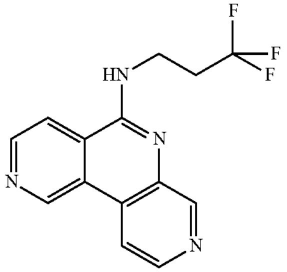 | | | | | | | | | | | |

Additional methods for preparing certain compounds of the invention, including compounds of Formula IA, IB and IC, are provided.

Process 29: Synthesis of Halogeno Aniline

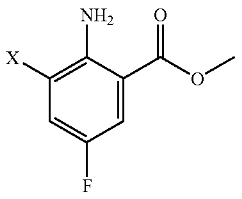

Methyl 2-amino-5-fluorobenzoate (1.0 eq, 8.47 g, 0.051 mol) was reacted with N-Iodo succinimide (1.03 eq, 11.6 g, 0.0515 mol) in acetic acid (100 ml) at room temperature for 20 minutes. The solvent was removed in vacuo. A $K_2CO_3$ aqueous solution was added and the compound extracted with ethylacetate. The organic layer was washed with 1M sodium thiosulfate, water and then brine. After drying over $Na_2SO_4$, and evaporation of the solvent, methyl 2-amino-5-fluoro-3-iodobenzoate was isolated as a purple solid (14.21 g, 96% yield). $^1H$ NMR ($CDCl_3$, 400 MHz) δ 3.8 (s, 3H), 6.3 (br s, 2H), 7.6 (m, 2H) ppm.

Process 30

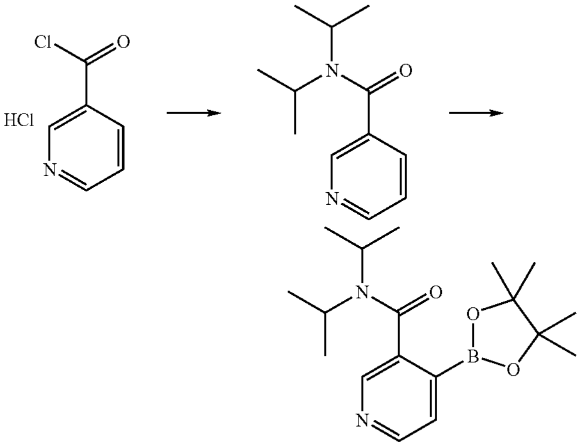

The boronic ester was prepared in two steps using the procedures described by Alessi et al., *J. Org. Chem.*, 2007, 72, 1588-1594.

Process 31

Step A

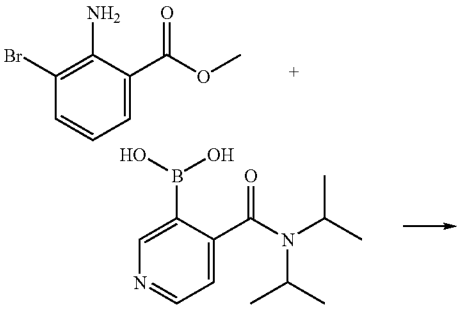

-continued

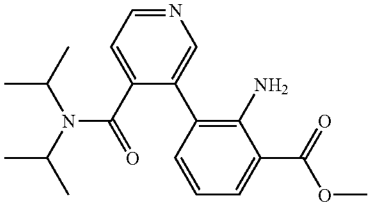

Methyl 2-amino-3-bromobenzoate (1.0 eq, 652 mg, 2.61 mmol) and 4-(diisopropylcarbamoyl)pyridin-3-ylboronic acid (prepared according to the procedure described in PCT patent application WO2005/105814, 1.0 eq, 600 mg, 2.61 mmol) were combined with cesium carbonate (2.0 eq, 1.699 g, 5.21 mmol) in dioxane containing 5% of water (6 ml). The mixture was degassed by bubbling nitrogen for 10 minutes. $PdCl_2$(dppf) (0.05 eq, 95 mg) was added and the reaction stirred at reflux for 2 hours. Dioxane was evaporated, water was added and the material extracted with $CH_2Cl_2$ (3×). The combined extracts were dried over $Na_2SO_4$ and the solvents removed in vacuo. The material was purified by flash chromatography on silica gel (eluant 0.5% MeOH in $CH_2Cl_2$) to afford methyl 2-amino-3-(4-(diisopropylcarbamoyl)pyridin-3-yl)benzoate as a greenish foam (244 mg, 31% yield). LCMS (ES): >95% pure, m/z 356 $[M+1]^+$.

Step B:

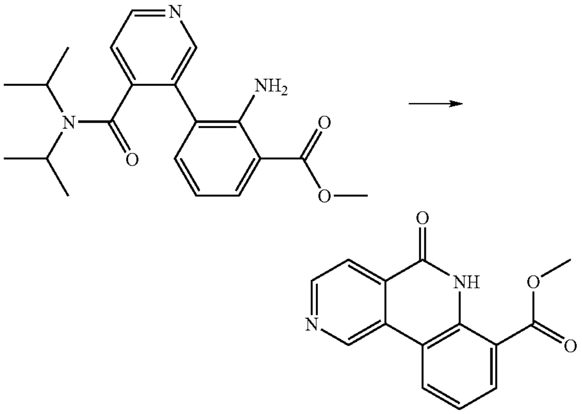

Methyl 2-amino-3-(4-(diisopropylcarbamoyl)pyridin-3-yl)benzoate (1.0 eq, 244 mg, 0.686 mmol) was dissolved under nitrogen atmosphere in anhydrous THF (1.5 ml). A NaHMDS solution (1.0 M in THF, 2.0 eq, 1.4 ml, 1.4 mmol) was added dropwise through syringe. The resulting suspension was stirred at room temperature for 1 hour. The reaction was quenched by addition of a saturated aqueous solution of ammonium chloride. The solid that formed was filtered and dried. After trituration in methanol and filtration, methyl 5-oxo-5,6-dihydrobenzo[c][2,6]naphthyridine-7-carboxylate was isolated as a grey fluffy solid (93 mg, 53% yield). LCMS (ES): >95% pure, m/z 255 $[M+1]^+$.

The following compounds were prepared using similar chemistries by reacting appropriate boronic esters and acids with appropriate 2-halogenoanilines.

TABLE 40

| Structure | M.W. | LCMS (ES) m/z |
| --- | --- | --- |
| 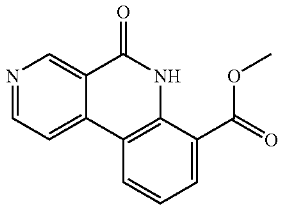 | 254.24 | 255 $[M + 1]^+$ |
| 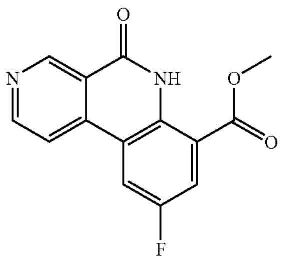 | 272.23 | 273 $[M + 1]^+$ |
| 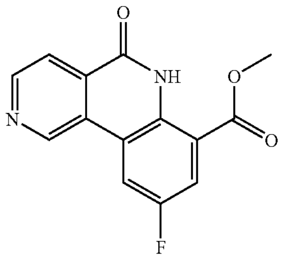 | 272.23 | 273 $[M + 1]^+$ |

Process 32

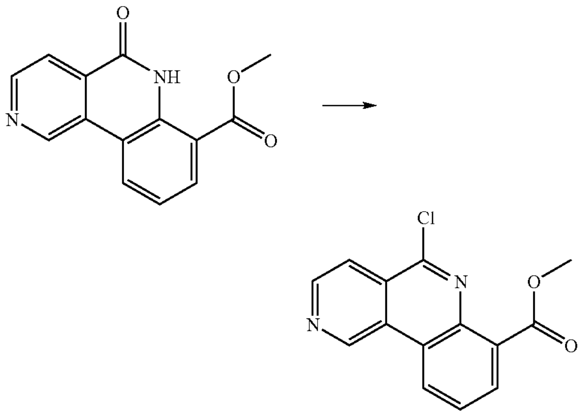

Methyl 5-oxo-5,6-dihydrobenzo[c][2,6]naphthyridine-7-carboxylate (1.0 eq, 85 mg, 0.334 mmol) was stirred in phosphorus oxychloride (2 ml) at 120° C. for 2 hours. The solvent was removed in vacuo. Ice and water were added. The resulting solid was filtered and dried to afford methyl 5-chlorobenzo[c][2,6]naphthyridine-7-carboxylate as a solid (84 mg, 92% yield). LCMS (ES): >95% pure, m/z 273 $[M+1]^+$.

The following compounds were prepared using similar chemistries on the appropriate lactams:

TABLE 41

| Structure | M.W. | LCMS (ES) m/z |
| --- | --- | --- |
| 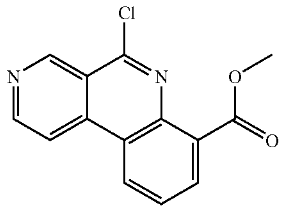 | 272.69 | 273 $[M + 1]^+$ |
| 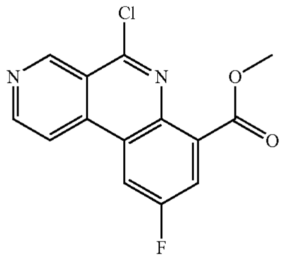 | 290.68 | 291 $[M + 1]^+$ |
| 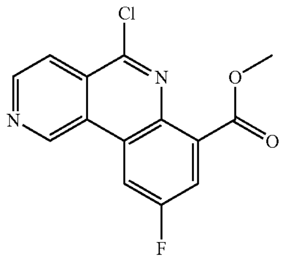 | 290.68 | 291 $[M + 1]^+$ |

Certain compounds of the present invention, including compounds of Formula IA, IB and IC, can be prepared according to the following general processes, using appropriate materials.

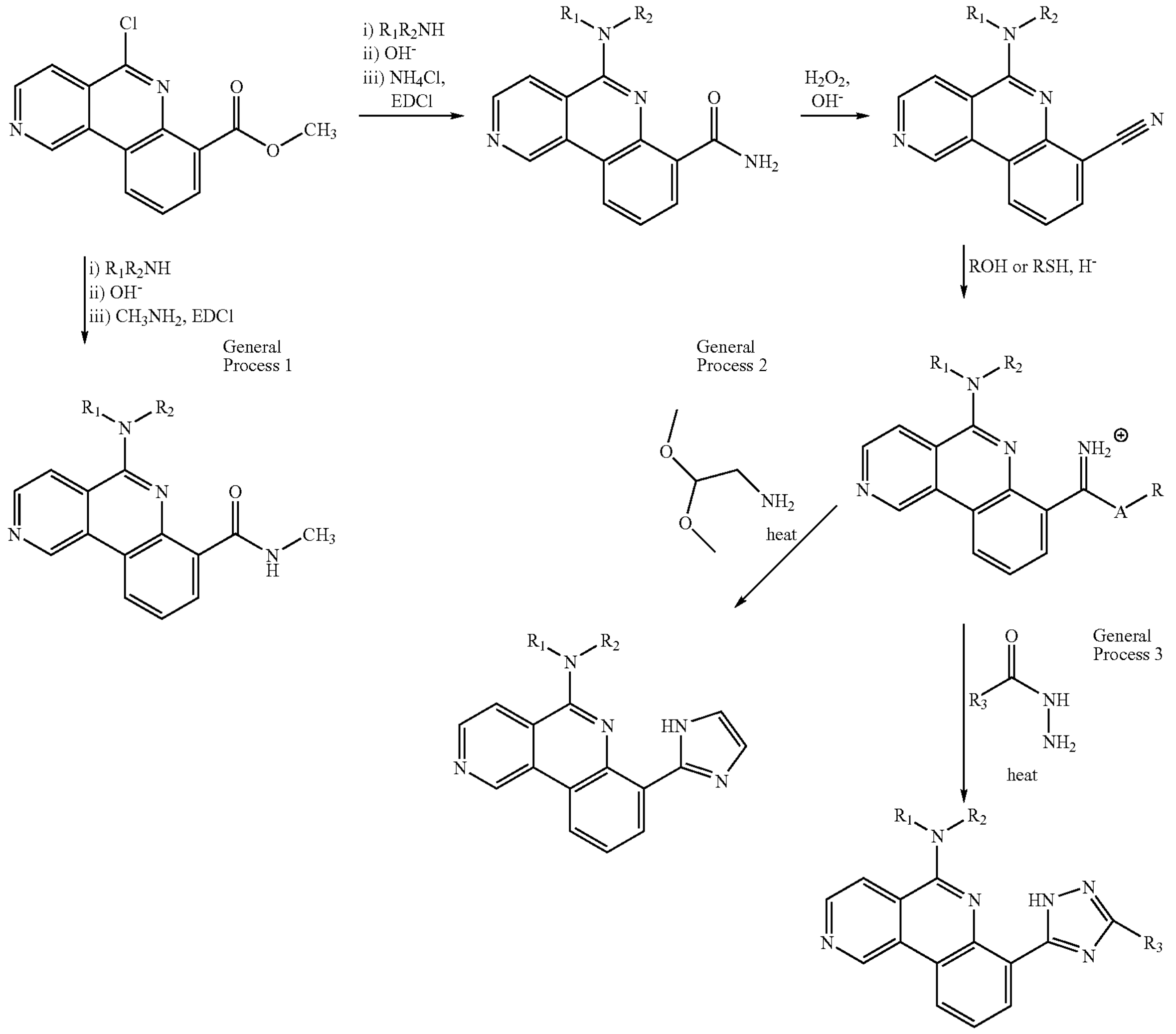
The following molecules can be prepared using the chemistry of General Process 1:
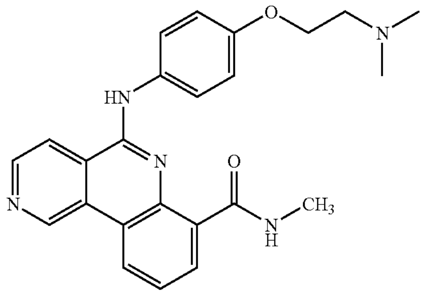
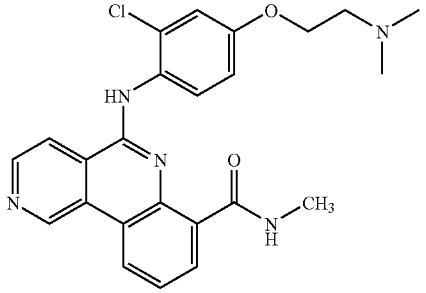
-continued
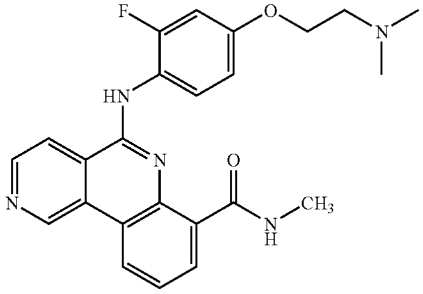
The following molecules can be prepared using chemistry of General Process 2:
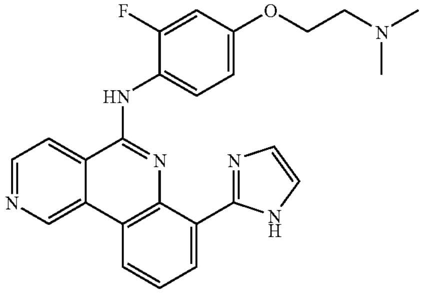

-continued
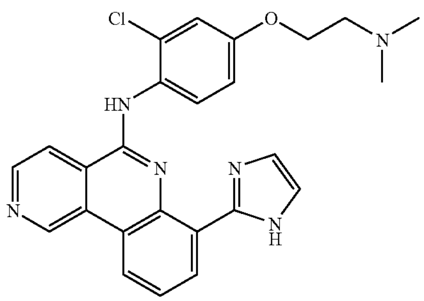
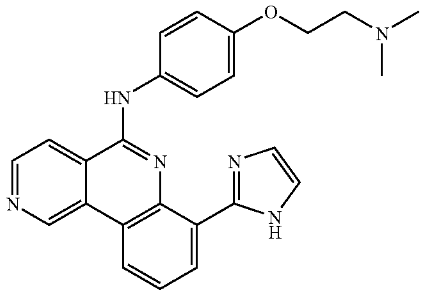
The following molecules can be prepared using chemistry of General Process 3:
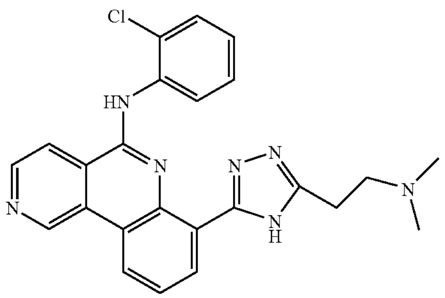
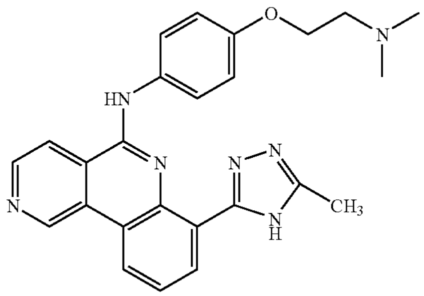
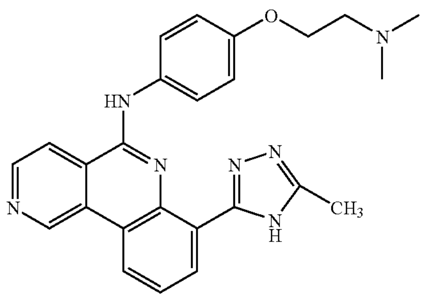
-continued
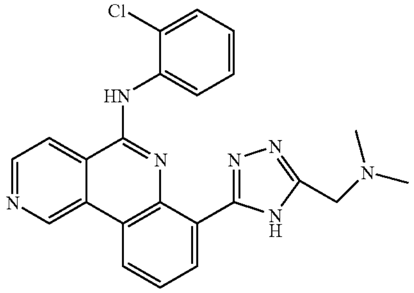
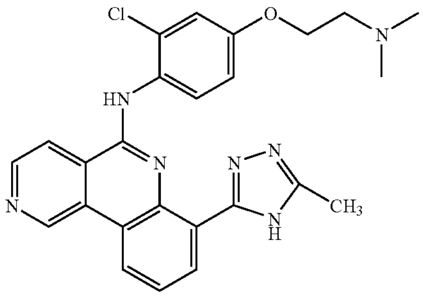
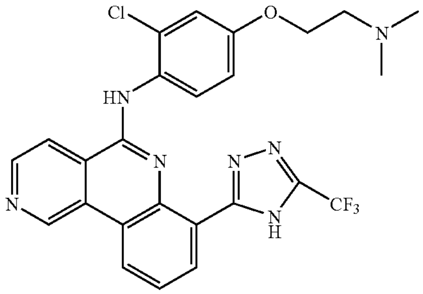
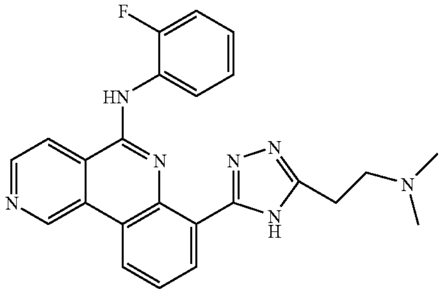
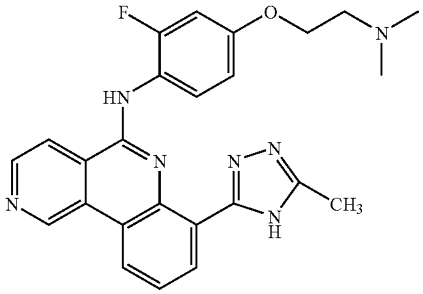

-continued

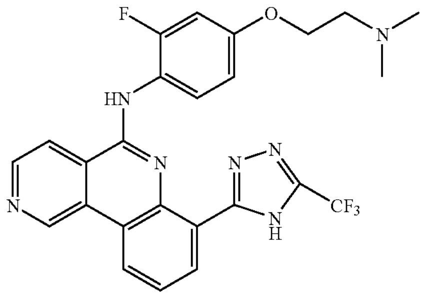

Process 33

Step A:

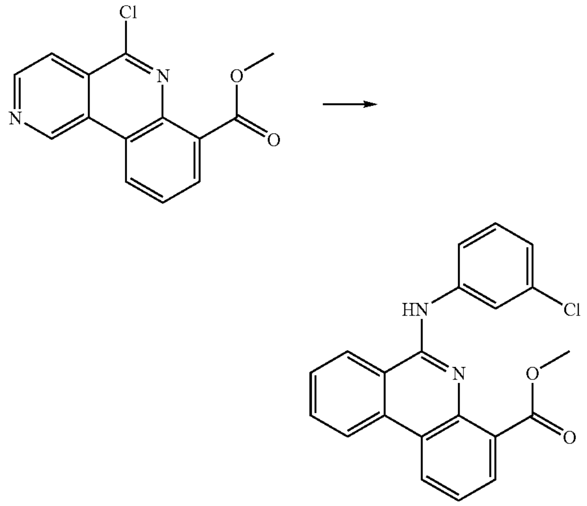

Methyl 5-chlorobenzo[c][2,6]naphthyridine-7-carboxylate (1.0 eq, 48 mg, 0.176 mmol) and 3-chloroaniline (3.0 eq, 60 ul, 0.56 mmol) were stirred under microwave heating at 120° C. in NMP (0.3 ml) for 10 minutes. Water was added and the solid isolated by filtration. Trituration in methanol and filtration afforded methyl 5-(3-chlorophenylamino)benzo[c][2,6]naphthyridine-7-carboxylate as a solid (29 mg, 45% yield). LCMS (ES): >85% pure, m/z 364 $[M+1]^+$.

Step B:

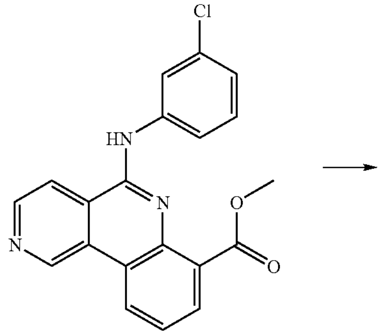

-continued

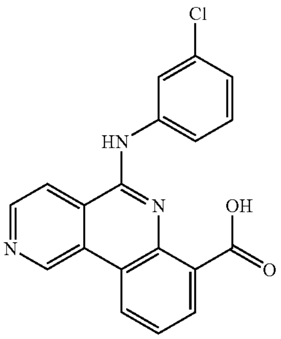

5-(3-chlorophenylamino)benzo[c][2,6]naphthyridine-7-carboxylate (29 mg) was stirred in ethanol (2 ml) and 6N aqueous NaOH (1 ml) at 60° C. for 30 minutes. Water and HCl were added to reach pH=1. The resulting precipitate was filtered, washed with water and dried to afford 5-(3-chlorophenylamino)benzo[c][2,6]naphthyridine-7-carboxylic acid as a solid. LCMS (ES): >95% pure, m/z 350 $[M+1]^+$.

The following compounds were prepared using similar chemistries

TABLE 42

| Structure | MW | LCMS (ES) m/z $[M + 1]^+$ |
|---|---|---|
| 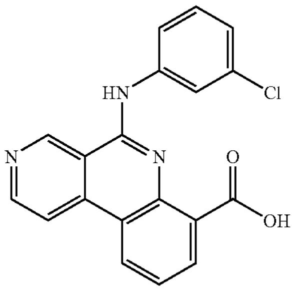 | 349.77 | 350 |
| 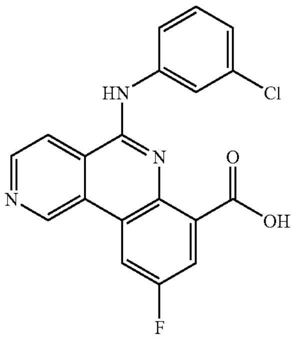 | 367.76 | 368 |

TABLE 42-continued

| Structure | MW | LCMS (ES) m/z [M + 1]$^+$ |
|---|---|---|
| 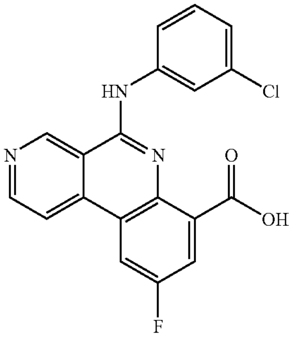 | 367.76 | 368 |
| 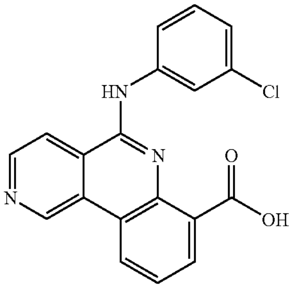 | 349.77 | 350 |
| 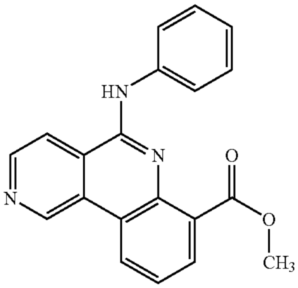 | 329.35 | 330 |
| 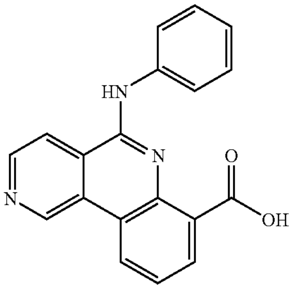 | 315.33 | 316 |
| 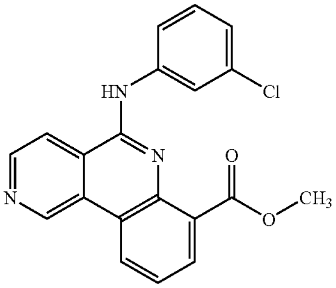 | 363.80 | 364 |

Process 34

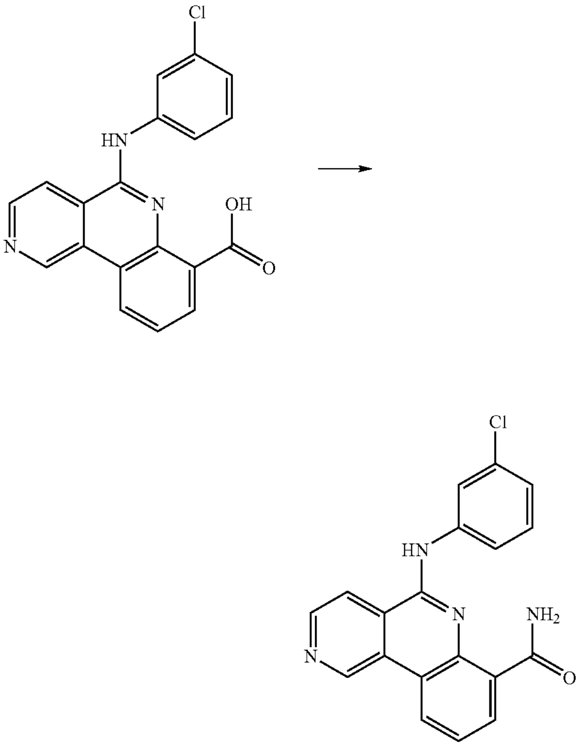

5-(3-chlorophenylamino)benzo[c][2,6]naphthyridine-7-carboxylic acid (20 mg) was reacted in NMP (0.4 ml) with HOBt.$H_2O$ (40 mg), ammonium chloride (40 mg), DIEA (100 ul) and EDCI (50 mg) at 70° C. for 1 hour. Water was added and the precipitate filtered and dried. After trituration in methanol and filtration, 5-(3-chlorophenylamino)benzo[c][2,6]naphthyridine-7-carboxamide was isolated as a solid (8 mg). LCMS (ES): >95% pure, m/z 349 [M+1]$^+$.

The following compounds were prepared using similar chemistries by reacting the appropriate carboxylic acid and the appropriate substituted or unsubstituted amines.

TABLE 43

| Structure | MW | LCMS (ES) m/z [M + 1]$^+$ |
|---|---|---|
| 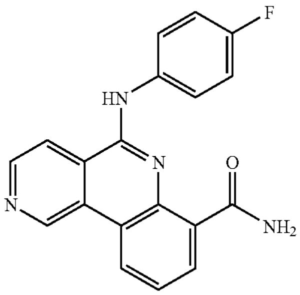 | 332.33 | 333 |

TABLE 43-continued
| | | |
|---|---|---|
| 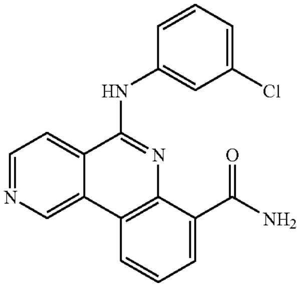 | 348.79 | 349 |
| 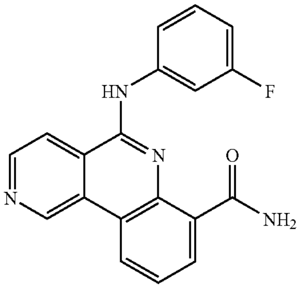 | 332.33 | 333 |
| 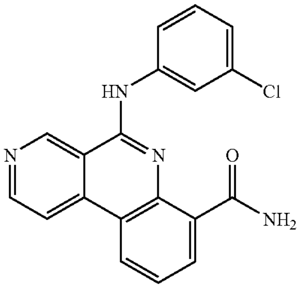 | 348.79 | 349 |
| 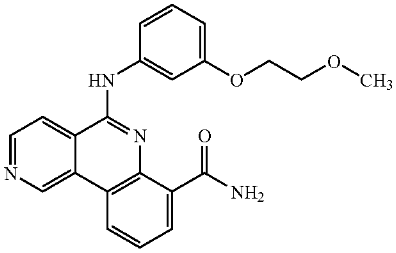 | 388.42 | 389 |
| 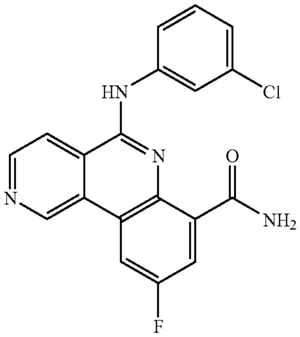 | 366.78 | 367 |
TABLE 43-continued
| | | |
|---|---|---|
| 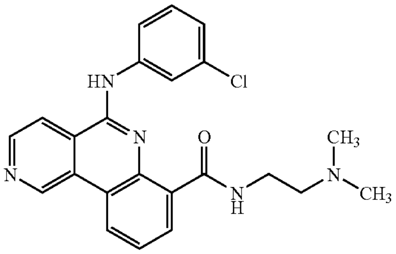 | 419.91 | 420 |
| 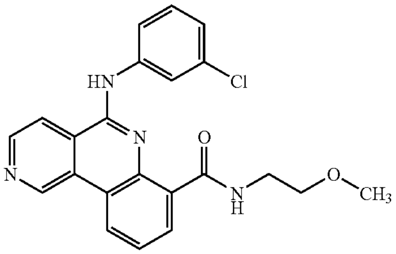 | 406.86 | 407 |
| 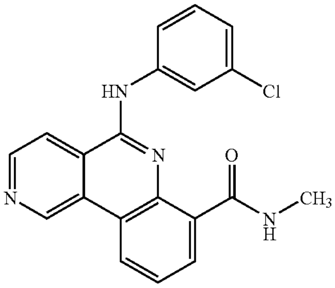 | 362.81 | 363 |
| 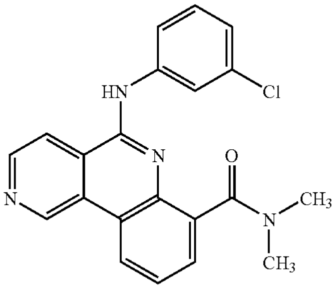 | 376.84 | 377 |
| 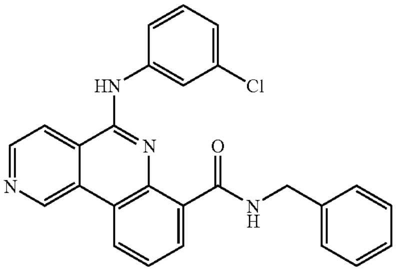 | 438.91 | 439 |

TABLE 43-continued

| | | |
|---|---|---|
| 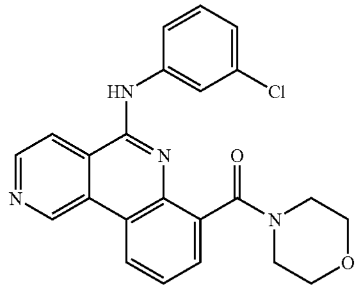 | 418.88 | 419 |
| 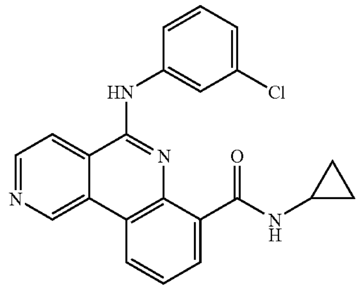 | 388.85 | 389 |
| 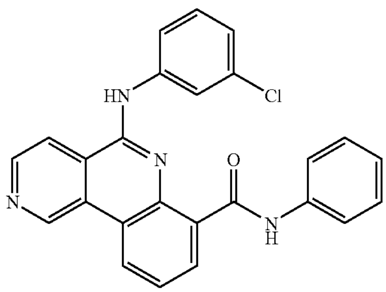 | 424.88 | 425 |
| 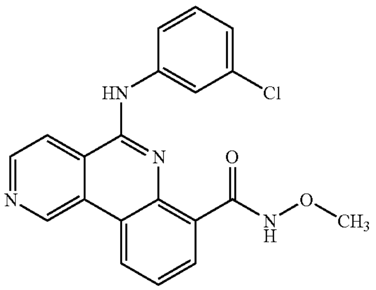 | 378.81 | 379 |

Process 35

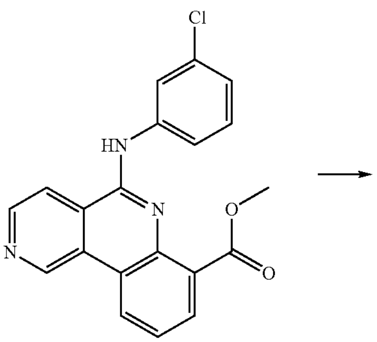

-continued

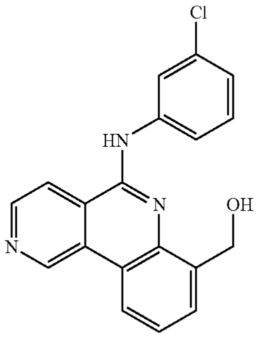

Methyl 5-(3-chlorophenylamino)benzo[c][2,6]naphthyridine-7-carboxylate (19 mg, 0.052 mmol) was suspended in anhydrous THF (0.5 ml). A 1.0 M THF solution of $LiAlH_4$ (0.2 ml, 0.2 mmol) was added and the mixture was stirred at room temperature for 3 hours. Another amount of $LiAlH_4$ solution (0.3 ml, 0.3 mmol) was added and the mixture stirred at 60° C. for 45 min. Water was added and the mixture was stirred at room temperature overnight. Methanol was added and the mixture was filtered through celite. The solvent were evaporated. The material was purified by preparative TLC on silica gel (5% MeOH in $CH_2Cl_2$) and preparative HPLC. Genevac evaporation afforded 4 mg of the TFA salt of (5-(3-chlorophenylamino)benzo[c][2,6]naphthyridin-7-yl)methanol as a solid. LCMS (ES): >90% pure, m/z 336 $[M+1]^+$.

Process 36

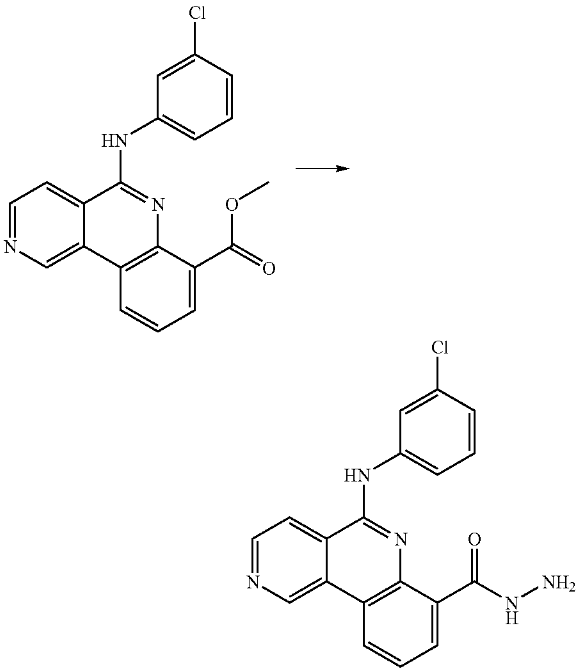

Methyl 5-(3-chlorophenylamino)benzo[c][2,6]naphthyridine-7-carboxylate (47 mg) was mixed with Methanol (1 ml) and Hydrazine hydrate (1 ml). 2-3 drops of DMF were added and the mixture was stirred at 60° C. for 2 hours. The volatiles were removed and another amount of reagent Methanol (1 ml) and Hydrazine (1 ml) were added, and the mixture was stirred at 60° C. for an extra 2 hours. The volatiles were removed in vacuo and the material was crashed out using AcOEt/hexanes. Filtration and drying afforded 5-(3-chlorophenylamino)benzo[c][2,6]naphthyridine-7-carbohydrazide as a solid (29 mg, 62% yield). LCMS (ES): >85% pure, m/z 364 $[M+1]^+$.

Process 37

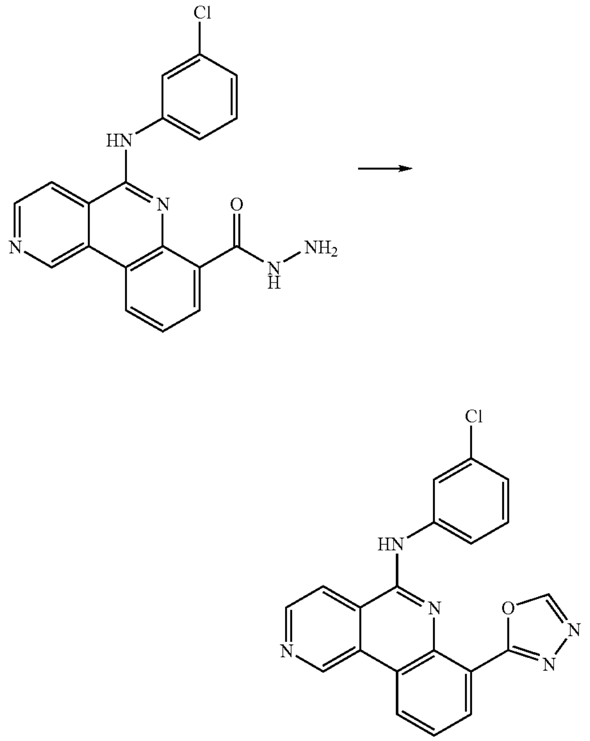

5-(3-chlorophenylamino)benzo[c][2,6]naphthyridine-7-carbohydrazide (24 mg) was stirred in triethylorthoformate (1 ml) at 120° C. for 4 hours. The solid was filtered and triturated in $CH_2Cl_2$/MeOH. Impurities (mainly starting material) were removed by filtration and the filtrate containing the expecting compound was concentrated. The material was purified by preparative TLC on silica gel (5% methanol in $CH_2Cl_2$) to afford N-(3-chlorophenyl)-7-(1,3,4-oxadiazol-2-yl)benzo[c][2,6]naphthyridin-5-amine as a solid (8 mg). LCMS (ES): >95% pure, m/z 374 $[M+1]^+$.

Process 38

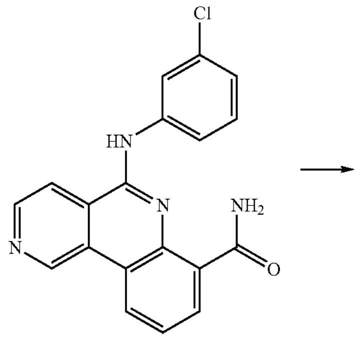

-continued

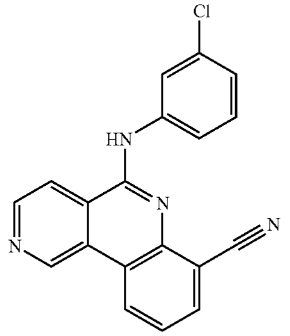

5-(3-chlorophenylamino)benzo[c][2,6]naphthyridine-7-carboxamide (12 mg, 0.034 mmol) was suspended in dichloroethane (0.2 ml). Sodium chloride (70 mg) was added followed by Phosphorus oxychloride (20 ul). The mixture was stirred at 80° C. for 1.5 hours. An extra amount of Phosphorus oxychloride (50 ul) was added and the mixture was heated at 80° C. for 8 hours. The volatiles were removed in vacuo. Water was added and the solid was filtered. The material was purified by preparative TLC on silica gel (5% MeOH in $CH_2Cl_2$) to provide 6 mg of 5-(3-chlorophenylamino)benzo[c][2,6]naphthyridine-7-carbonitrile. LCMS (ES): >95% pure, m/z 331 $[M+1]^+$.

Process 39

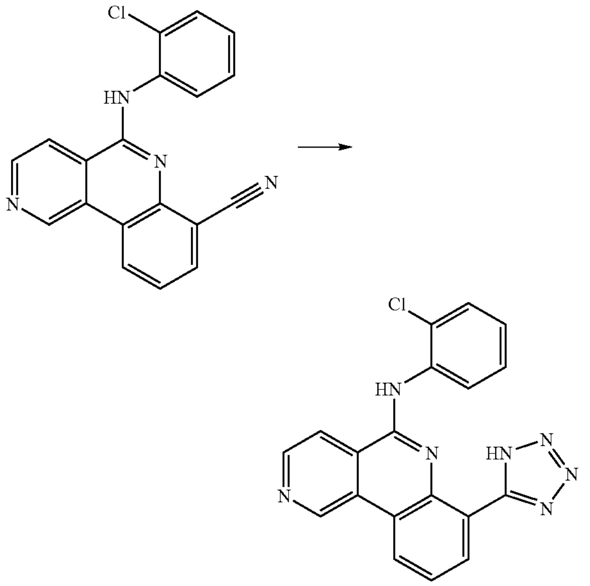

5-(2-chlorophenylamino)benzo[c][2,6]naphthyridine-7-carbonitrile (50 mg, 0.151 mmol) was stirred in a vial at 120° C. for 2 hours in the presence of DMF (0.5 ml), sodium azide (88 mg, 1.35 mmol) and ammonium chloride (72 mg, 1.35 mmol). Water was added, the pH was lowered and the resulting solid was filtered. The material was dissolved in NMP and purified by preparative HPLC. Genevac evaporation afforded the TFA salt of N-(2-chlorophenyl)-7-(1H-tetrazol-5-yl)benzo[c][2,6]naphthyridin-5-amine (8 mg). LCMS (ES): >95% pure, m/z 374 $[M+1]^+$, 346 $[M+1-N2]^+$.

Process 40

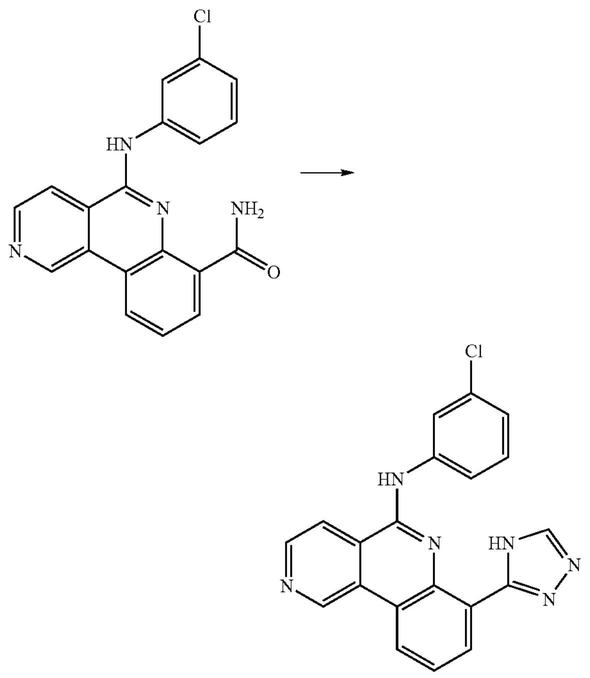

5-(3-chlorophenylamino)benzo[c][2,6]naphthyridine-7-carboxamide (18.5 mg) was stirred at 80° C. overnight in DMF-DMA (0.7 ml). The solvent was evaporated. Hydrazine hydrate (1 ml) and acetic acetic (1 ml) were added and the mixture stirred at 80° C. for one hour. Water was added and the resulting solid was filtered. The material was suspended in Methanol, filtered and dried to afford N-(3-chlorophenyl)-7-(4H-1,2,4-triazol-3-yl)benzo[c][2,6]naphthyridin-5-amine as a yellow solid (4.8 mg). LCMS (ES): >90% pure, m/z 373 $[M+1]^+$.

Process 41

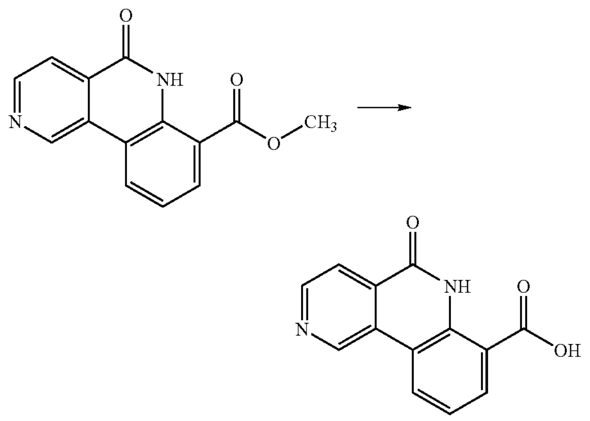

Methyl 5-oxo-5,6-dihydrobenzo[c][2,6]naphthyridine-7-carboxylate (2.17 g, 8.53 mmol) was mixed with 6N aqueous sodium hydroxide (10 ml) and Ethanol (40 ml). The mixture was stirred at reflux for 5 hours. After cooling down, water was added and the mixture was acidified by 6N HCl. After filtration and drying 5-oxo-5,6-dihydrobenzo[c][2,6]naphthyridine-7-carboxylic acid was isolated as a grey solid (1.91 g, 93% yield). LCMS (ES): m/z 241 $[M+1]^+$.

Process 42

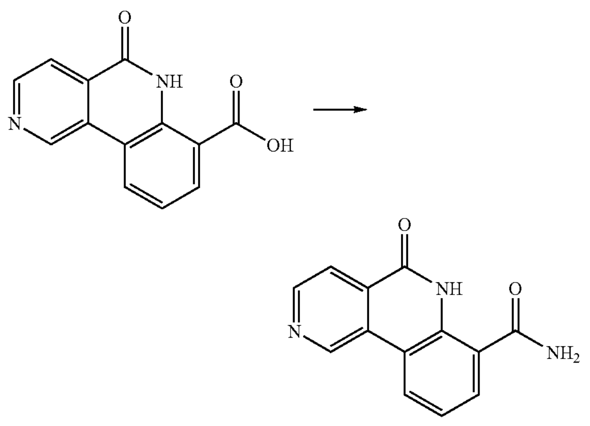

5-oxo-5,6-dihydrobenzo[c][2,6]naphthyridine-7-carboxylic acid (1.0 eq, 1.91 g, 7.96 mmol) was mixed with $HOBt.H_2O$ (2.0 eq, 2.15 g, 15.91 mmol) and $NH_4Cl$ (8.0 eq, 3.41 g, 63.6 mmol) in NMP (30 ml). DIEA (4.0 eq, 5.5 ml, 31.57 mmol) and EDCI (2.0 eq, 3.05 g, 15.91 mmol) was added and the mixture was stirred in a closed vessel at 80° C. for 2.5 hours. Water and brine were added. The solid was filtered, washed with water, washed with methanol and dried in a vacuum oven. 5-oxo-5,6-dihydrobenzo[c][2,6]naphthyridine-7-carboxamide was isolated as an off-white solid (1.81 g, 96% yield). LCMS (ES): m/z 240 $[M+1]^+$.

Process 43

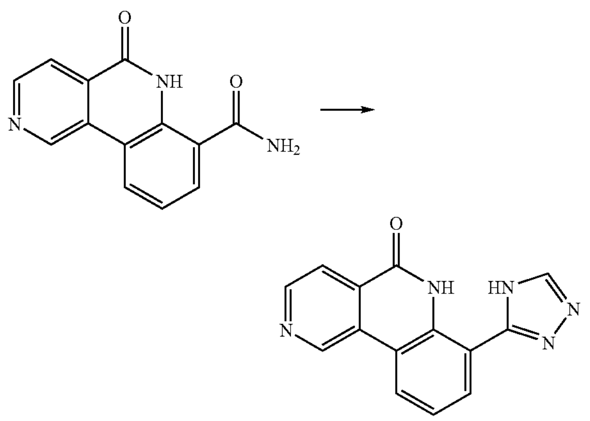

5-oxo-5,6-dihydrobenzo[c][2,6]naphthyridine-7-carboxamide (1.81 g, 7.59 mmol) was stirred in DMF-DMA (20 ml) at 80° C. for 1.5 hours. The volatiles were removed in vacuo. This operation was repeated several times until the amount of starting material detected by LCMS remained constant. After evaporation of the volatiles, the crude intermediate was suspended in acetic acid (40 ml). Hydrazine hydrate (4 ml) was added dropwise and the reaction mixture was stirred without external temperature control for about 10 minutes. The reaction was then stirred at 80° C. for 45 minutes upon which the mixture turned into a thick mass. Water was added and the solid filtered. After washing with water and drying, 7-(4H-1,2,4-triazol-3-yl)benzo[c][2,6]naphthyridin-5(6H)-one was isolated as a pale grey solid (1.84 g, 92% yield). LCMS (ES): m/z 264 $[M+1]^+$.

Process 44

Step A:

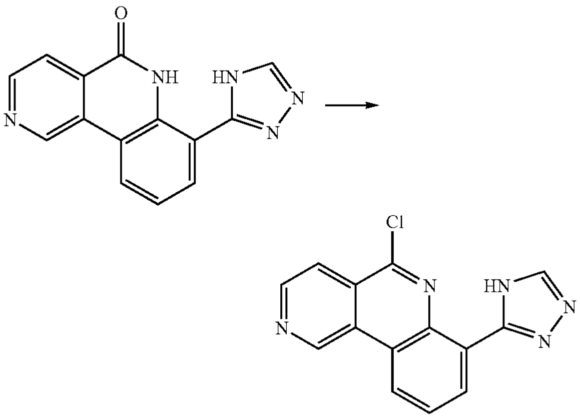

Under nitrogen atmosphere, 7-(4H-1,2,4-triazol-3-yl)benzo[c][2,6]naphthyridin-5(6H)-one (1.8 g, 6.84 mmol) was mixed with Phosphorus oxychloride (3.2 ml) in acetonitrile (20 ml). The mixture was stirred overnight at 100° C. The volatiles were removed in vacuo. The resulting solid was suspended in $CH_2Cl_2$ and a little bit of MeOH. After filtration and drying, crude 5-chloro-7-(4H-1,2,4-triazol-3-yl)benzo[c][2,6]naphthyridine (2.04 g) was isolated as a greenish solid. LCMS (ES) m/z 282 $[M+1]^+$.

Step B:

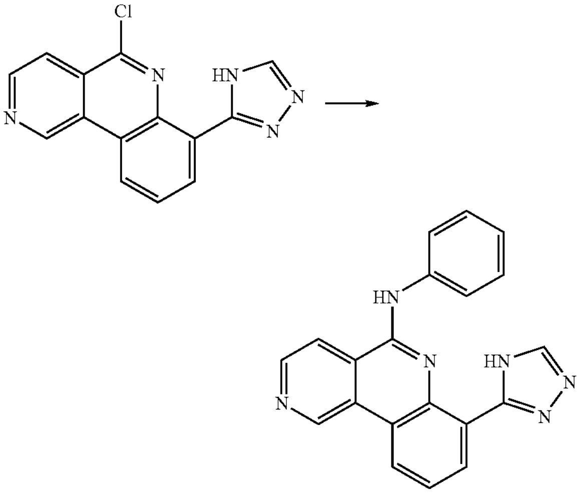

The product of step A (57 mg) was mixed with aniline (100 ul) in NMP (0.5 ml) and the mixture heated in a microwave oven at 120° C. for 10 minutes. An additional NMP (1.5 ml) was added and the solution filtered. Purification by preparative HPLC and Genevac evaporation provided a solid that was further purified by trituration in AcOEt/hexanes. The TFA salt of N-phenyl-7-(4H-1,2,4-triazol-3-yl)benzo[c][2,6]naphthyridin-5-amine was isolated as a solid (34 mg). LCMS (ES): >95% pure, m/z 339 $[M+1]^+$.

The molecules depicted in the following table were prepared using chemistries similar to the one described in Processes 40 and 44:

TABLE 44

| Structure | MW | LCMS (ES) m/z $[M + 1]^+$ |
|---|---|---|
| 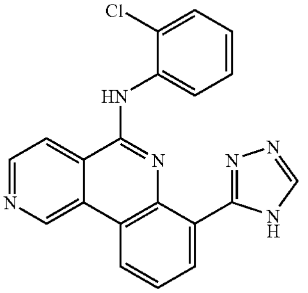 | 372.81 | 373 |
| 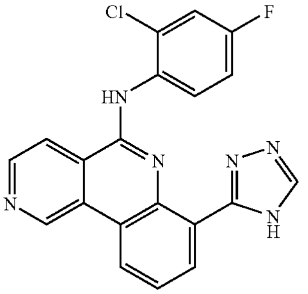 | 390.80 | 391 |
| 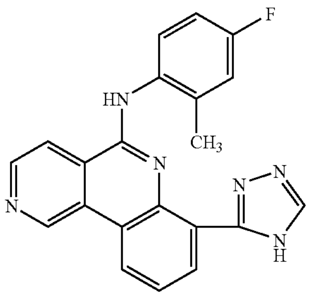 | 370.38 | 371 |
| 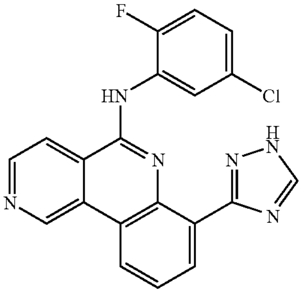 | 390.80 | 391 |
| 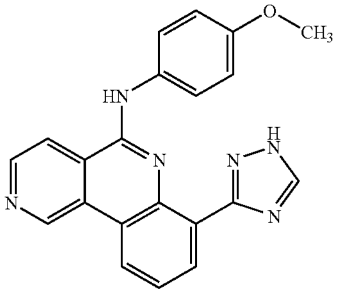 | 368.39 | 369 |

TABLE 44-continued
| Structure | MW | LCMS (ES) m/z [M + 1]+ |
|---|---|---|
| 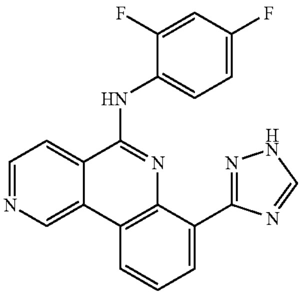 | 374.35 | 375 |
| 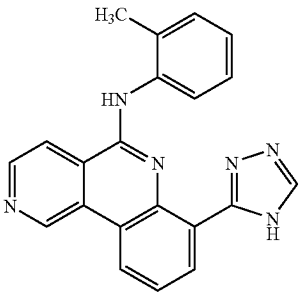 | 352.39 | 353 |
| 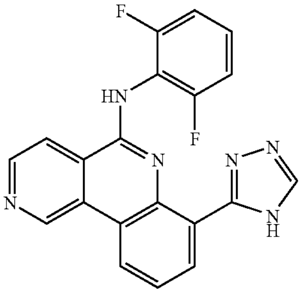 | 374.35 | 375 |
| 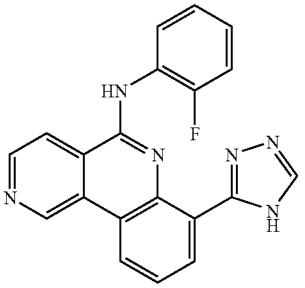 | 356.36 | 357 |
| 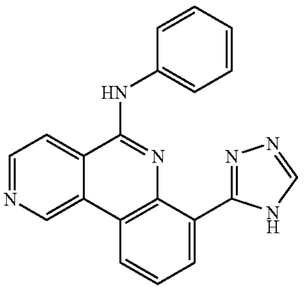 | 338.37 | 339 |
TABLE 44-continued
| Structure | MW | LCMS (ES) m/z [M + 1]+ |
|---|---|---|
| 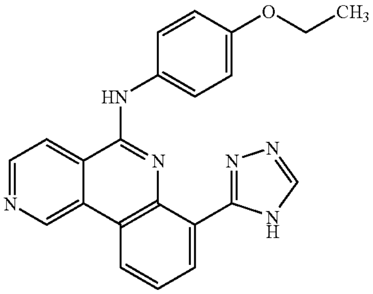 | 382.42 | 383 |
| 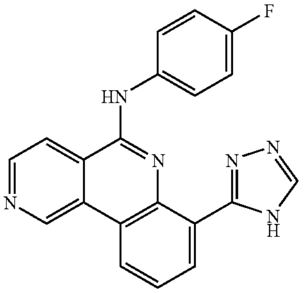 | 356.36 | 357 |
| 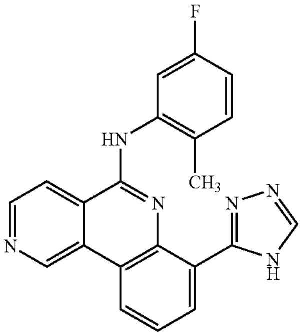 | 370.38 | 371 |
| 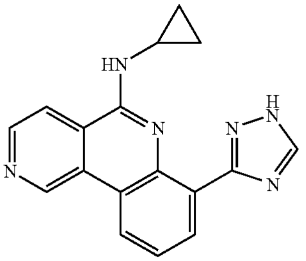 | 302.33 | 303 |
| 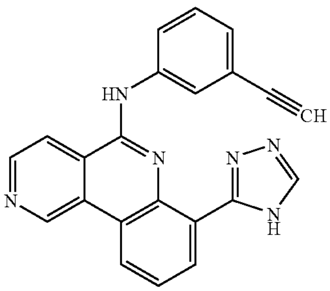 | 362.39 | 363 |

TABLE 44-continued
| Structure | MW | LCMS (ES) m/z [M + 1]$^+$ |
|---|---|---|
| 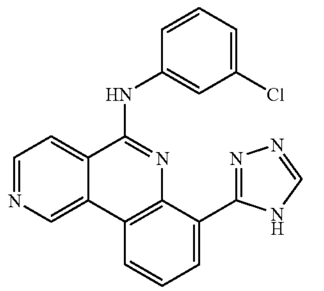 | 372.81 | 373 |
| 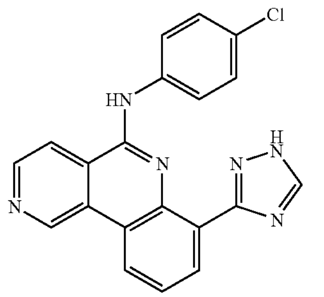 | 372.81 | 373 |
| 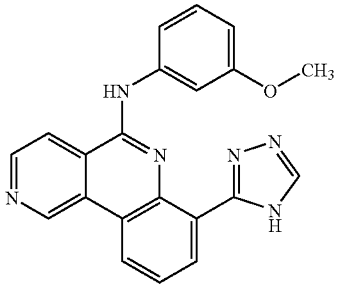 | 368.39 | 369 |
| 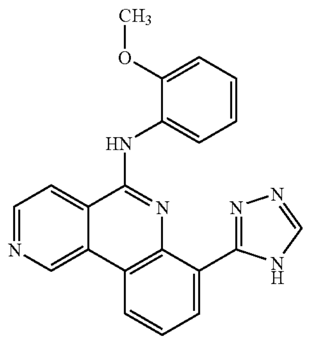 | 368.39 | 369 |
TABLE 44-continued
| Structure | MW | LCMS (ES) m/z [M + 1]$^+$ |
|---|---|---|
| 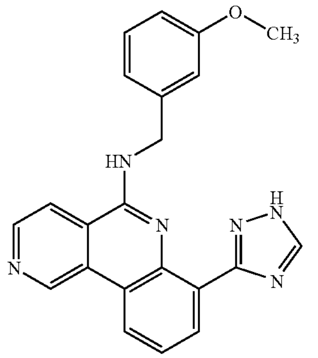 | 382.42 | 383 |
| 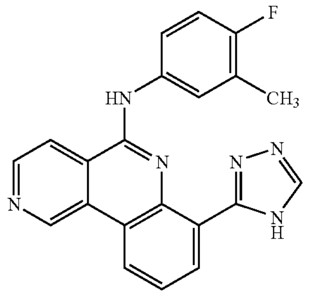 | 370.38 | 371 |
| 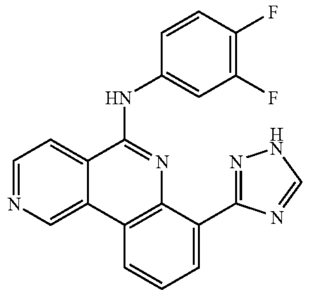 | 374.35 | 375 |
| 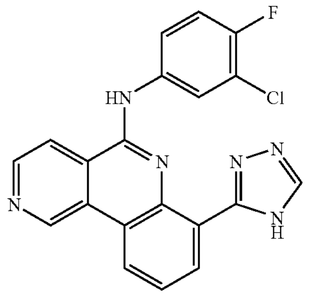 | 390.80 | 391 |
| 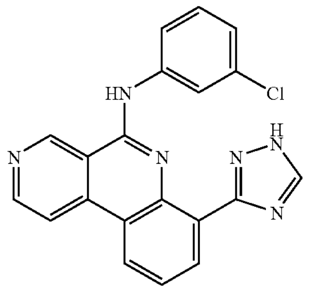 | 372.81 | 373 |

TABLE 44-continued
| Structure | MW | LCMS (ES) m/z $[M+1]^+$ |
|---|---|---|
| 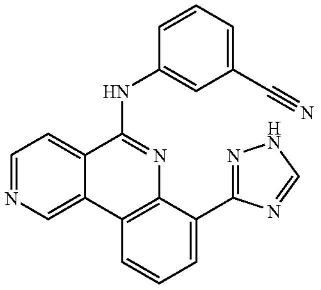 | 363.37 | 364 |
| 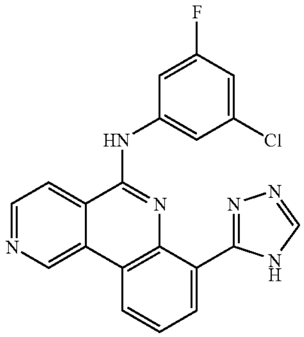 | 390.80 | 391 |
| 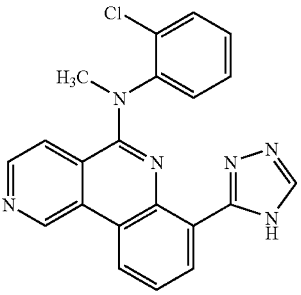 | 386.84 | 387 |
| 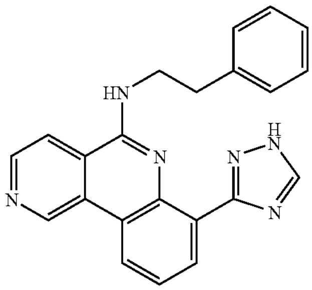 | 366.42 | 367 |
| 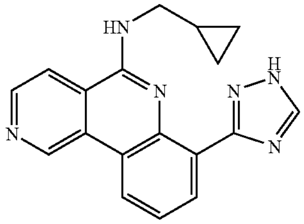 | 316.36 | 317 |
TABLE 44-continued
| Structure | MW | LCMS (ES) m/z $[M+1]^+$ |
|---|---|---|
| 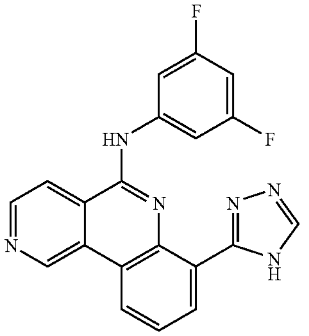 | 374.35 | 375 |
| 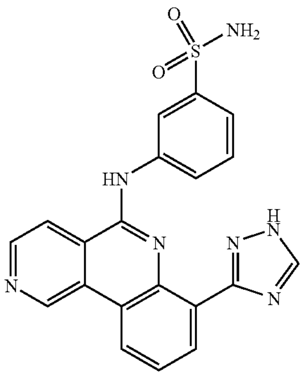 | 417.44 | 418 |
| 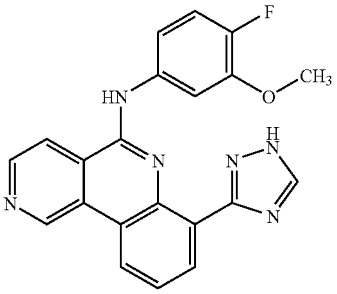 | 386.38 | 387 |
| 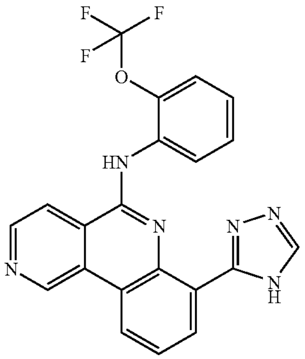 | 422.36 | 423 |

TABLE 44-continued
| Structure | MW | LCMS (ES) m/z [M + 1]+ |
|---|---|---|
| 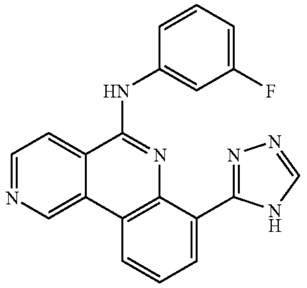 | 356.36 | 357 |
| 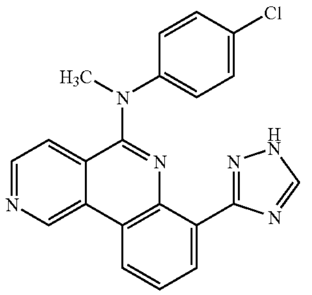 | 386.84 | 387 |
| 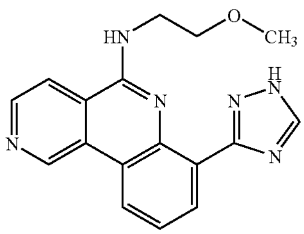 | 320.35 | 321 |
| 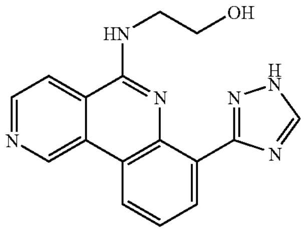 | 306.32 | 307 |
| 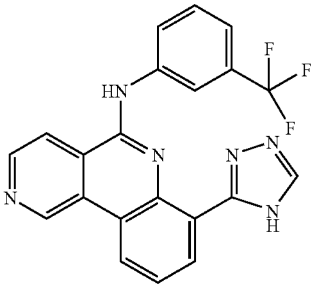 | 406.36 | 407 |
TABLE 44-continued
| Structure | MW | LCMS (ES) m/z [M + 1]+ |
|---|---|---|
| 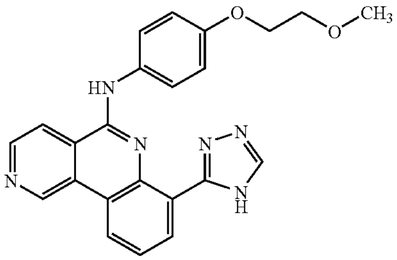 | 412.44 | 413 |
| 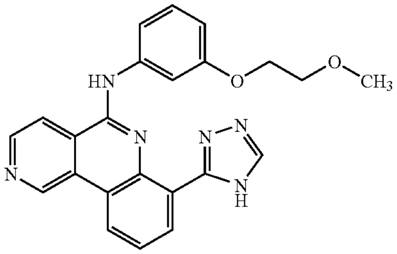 | 412.44 | 413 |
| 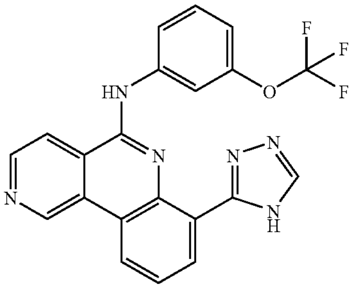 | 422.36 | 423 |
| 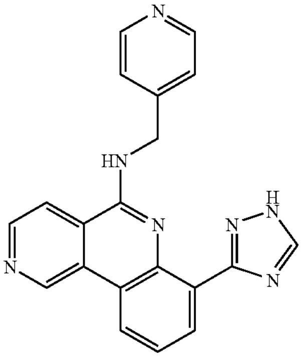 | 353.38 | 354 |
| 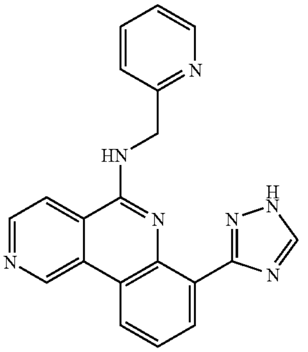 | 353.38 | 354 |

TABLE 44-continued
| Structure | MW | LCMS (ES) m/z [M + 1]+ |
|---|---|---|
| 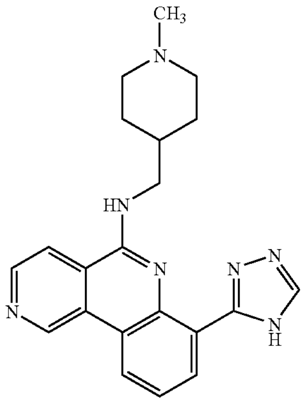 | 373.45 | 374 |
| 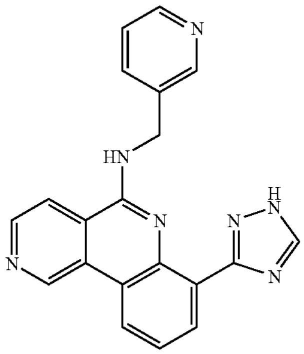 | 353.38 | 354 |
| 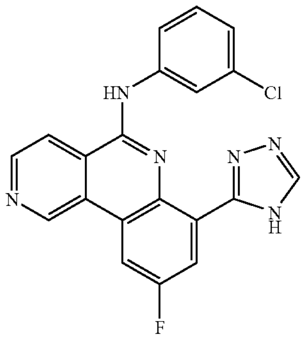 | 390.80 | 391 |
| 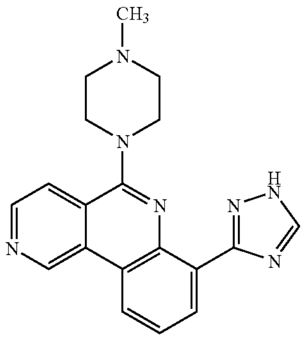 | 345.40 | 346 |
TABLE 44-continued
| Structure | MW | LCMS (ES) m/z [M + 1]+ |
|---|---|---|
| 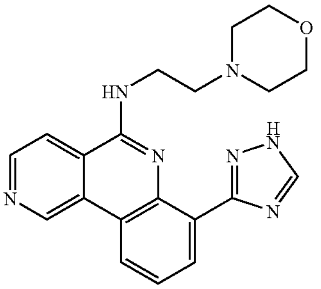 | 375.43 | 376 |
| 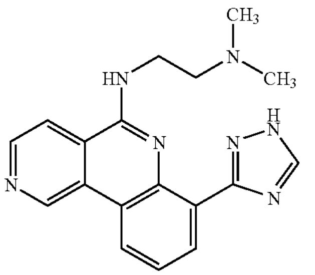 | 333.39 | 334 |
| 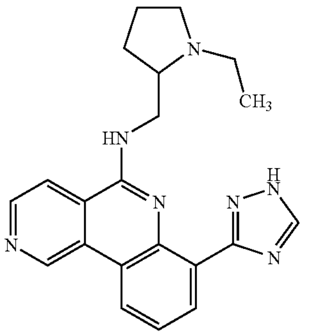 | 373.45 | 374 |
| 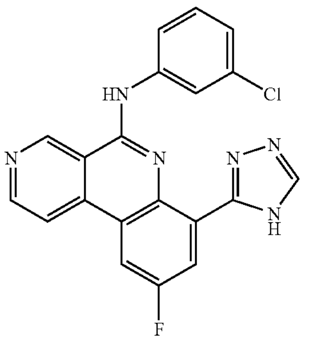 | 390.80 | 391 |
| 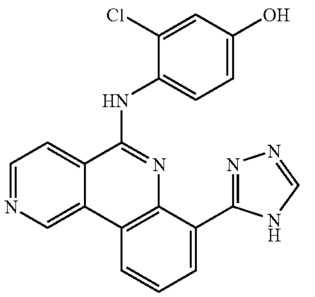 | 388.81 | 389 |

TABLE 44-continued
| Structure | MW | LCMS (ES) m/z [M + 1]+ |
|---|---|---|
| 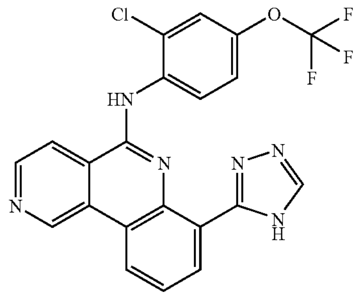 | 456.81 | 457 |
| 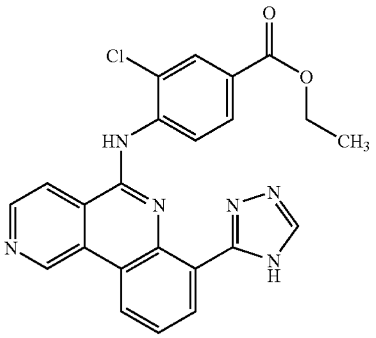 | 444.87 | 445 |
| 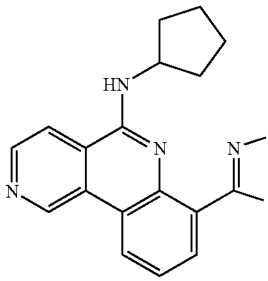 | 330.39 | 331 |
| 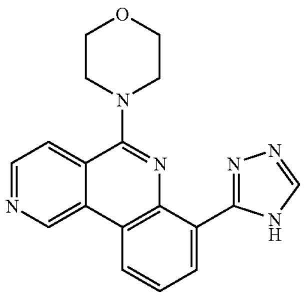 | 332.36 | 333 |
| 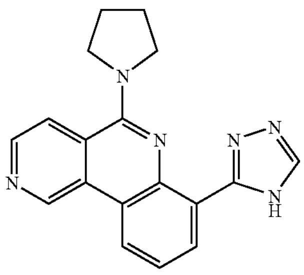 | 316.36 | 317 |
TABLE 44-continued
| Structure | MW | LCMS (ES) m/z [M + 1]+ |
|---|---|---|
| 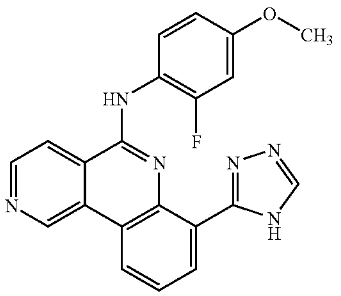 | 386.38 | 387 |
| 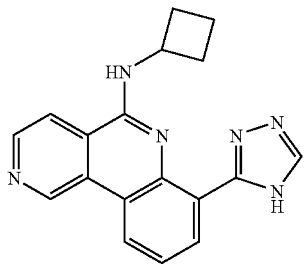 | 316.36 | 317 |
| 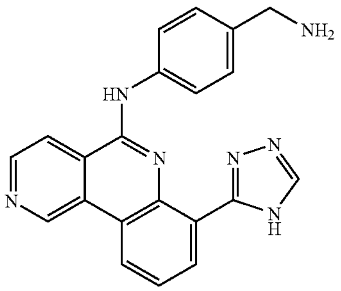 | 367.41 | 368 |
| 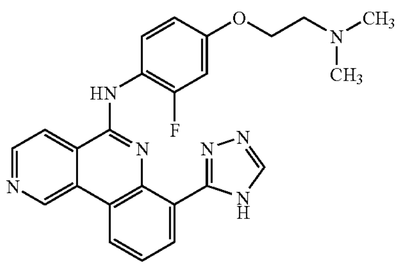 | 443.48 | 444 |
| 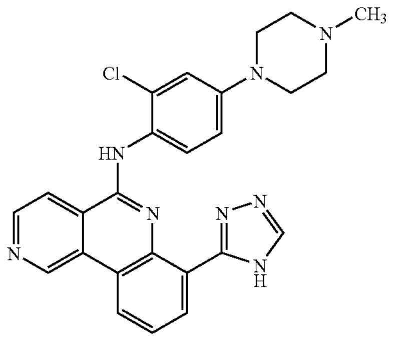 | 470.96 | 471 |

TABLE 44-continued
| Structure | MW | LCMS (ES) m/z [M + 1]+ |
|---|---|---|
| 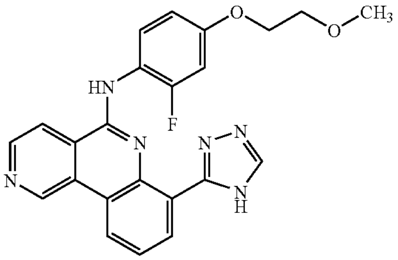 | 430.43 | 431 |
| 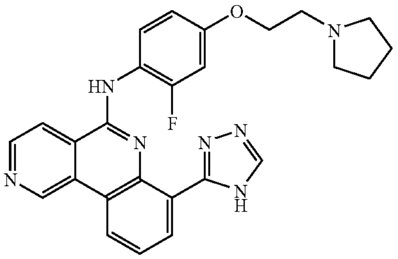 | 469.51 | 470 |
| 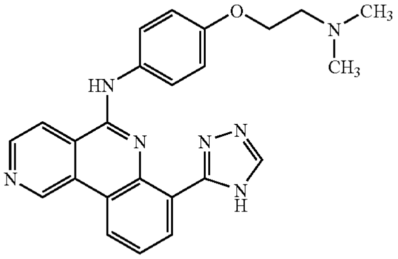 | 425.49 | 426 |
| 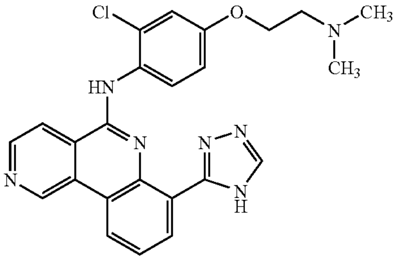 | 459.93 | 460 |
| 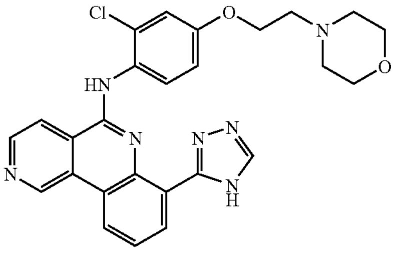 | 501.97 | 502 |
TABLE 44-continued
| Structure | MW | LCMS (ES) m/z [M + 1]+ |
|---|---|---|
| 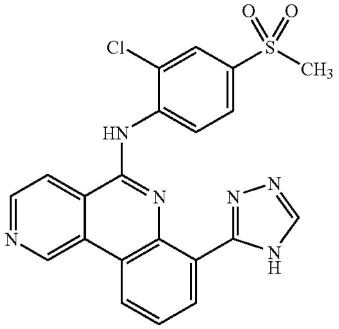 | 450.90 | 451 |
| 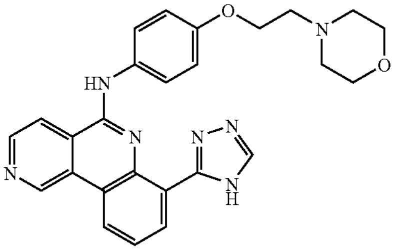 | 467.52 | 468 |
| 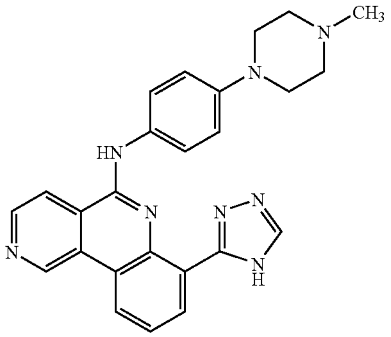 | 436.51 | 437 |
The following molecules can be prepared using similar chemistry:
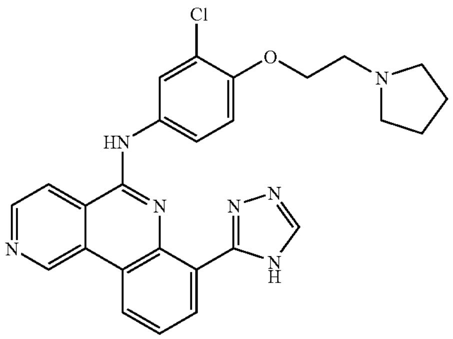

-continued

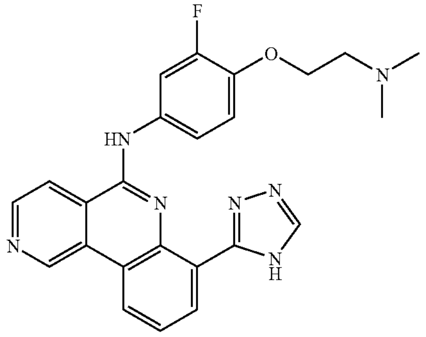

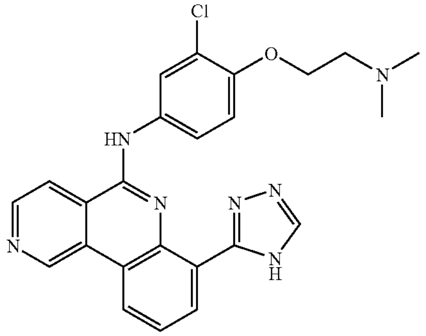

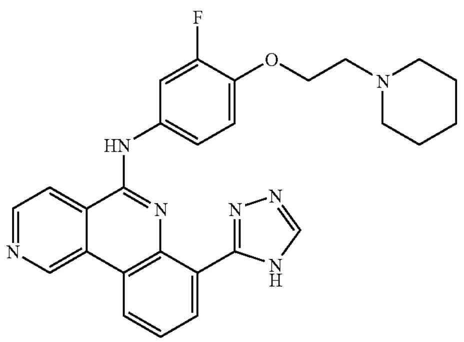

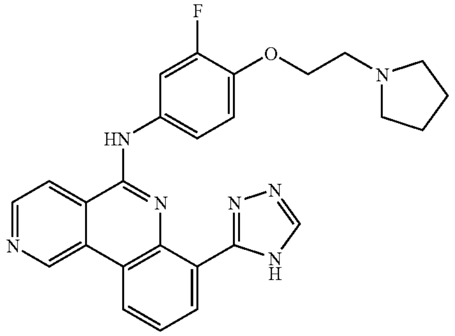

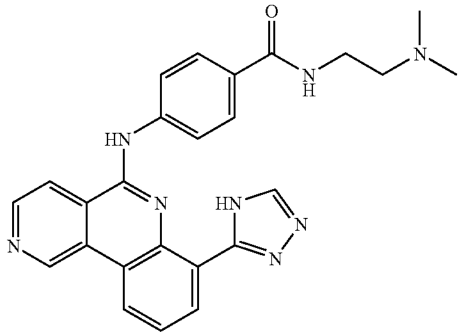

Further methods for preparing certain compounds of the invention, including compounds of Formula IA, IB and IC, are provided.

Process 45

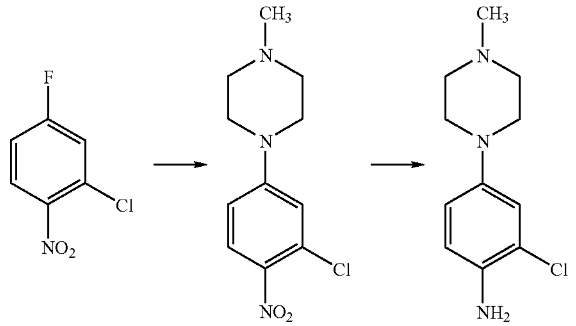

2-chloro-4-fluoronitrobenzene (1.0 eq, 1 g, 5.7 mmol), N-methyl piperazine (1.2 eq, 1.18 g, 6.84 mmol), potassium carbonate (2.0 eq, 1.6 g, 11.6 mmol) were stirred at 100° C. in DMF for 3 hours. The mixture was cooled down and diluted with water. The material was extracted with ethyl acetate. The organic layer was washed with brine, dried over $Na_2SO_4$ and the solvent evaporated in vacuo. After trituration in diethylether and filtration, 1-(3-chloro-4-nitrophenyl)-4-methylpiperazine was isolated as a solid (0.9 g, 62%). LCMS (ES): m/z 256 $[M+1]^+$. This material was suspended in MeOH (20 ml) with Raney Nickel (0.2 g) and stirred under hydrogen atmosphere overnight. The catalyst was filtered off through celite. Evaporation of the solvents provided 2-chloro-4-(4-methylpiperazin-1-yl)aniline as a dark brown oil (0.68 g, 86%). LCMS (ES): m/z 226 $[M+1]^+$.

Process 46

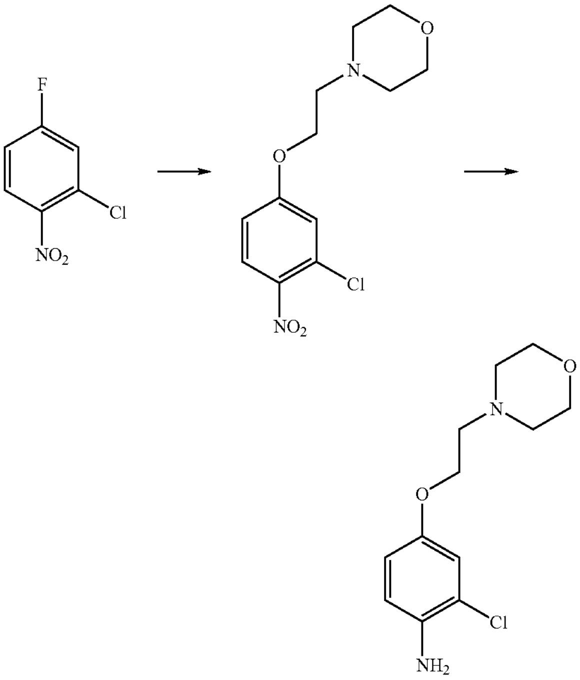

2-chloro-4-(2-morpholinoethoxy) aniline was obtained in two steps from 2-chloro-4-fluoronitrobenzene and 4-(2-hydroxyethyl) morphine using a protocol described in patent application WO2008/42282.

Process 47

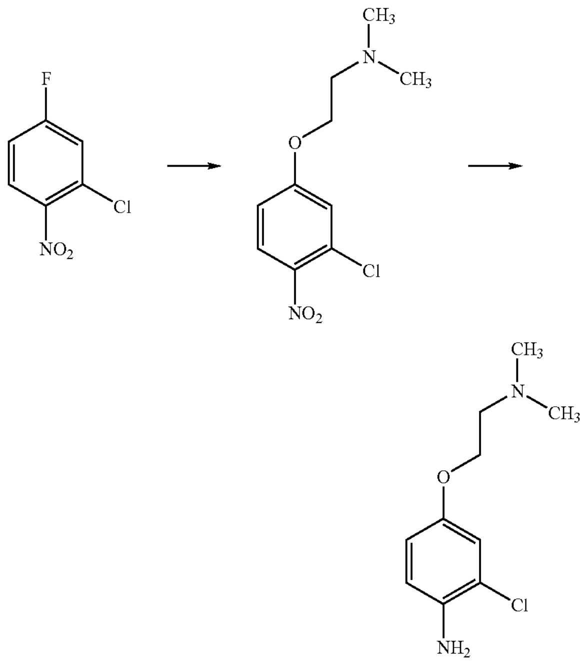

2-chloro-4-(2-(dimethylamino)ethoxy)aniline was prepared according to the procedure described in General Process 2.

Process 48

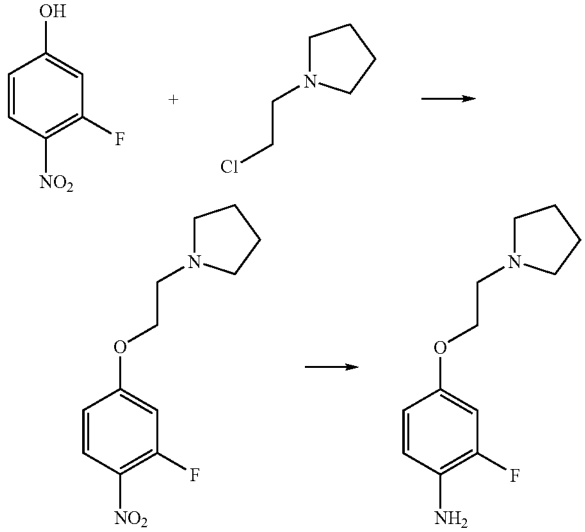

2-fluoro-4-(2-(pyrrolidin-1-yl)ethoxy)aniline was prepared in two steps using a procedure described in patent application WO2007/7152.

Process 49

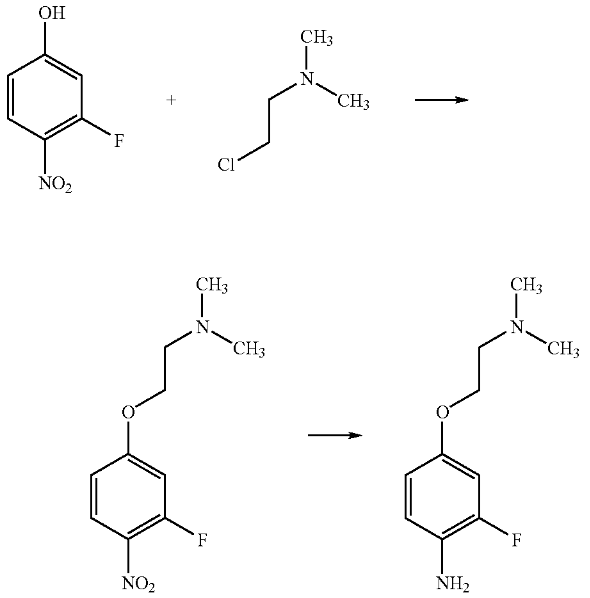

4-(2-(dimethylamino)ethoxy)-2-fluoroaniline was prepared in two steps using the procedure described in Process 46.

Process 50

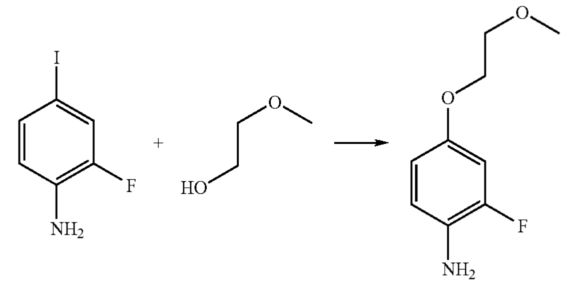

2-fluoro-4-(2-methoxyethoxy)aniline was prepared in one step using a procedure described in patent application US2006/155128.

Process 51

Step A:

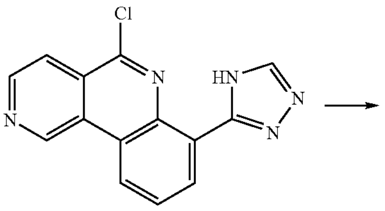

-continued

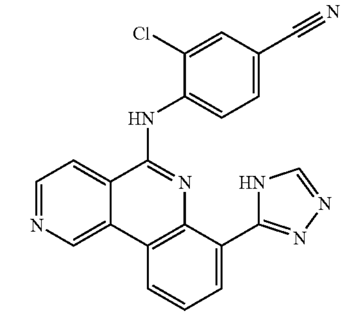

4 amino-3-chlorobenzonitrile was charged in a vial. NaHMDS (1 M solution in THF, 0.2 ml) was added and the solution stirred at 80° C. for 5 min. A suspension of 5-chloro-7-(4H-1,2,4-triazol-3-yl)benzo[c][2,6]naphthyridine (30 mg) in NMP (0.5 ml) was added and the solution stirred at 80° C. for 30 min. The mixture was cooled down, a few drops of HCl and NMP (1 ml) were added and mixture was purified by preparative HPLC to provide 4-(7-(4H-1,2,4-triazol-3-yl)benzo[c][2,6]naphthyridin-5-ylamino)-3-chlorobenzonitrile (25 mg).

Step B:

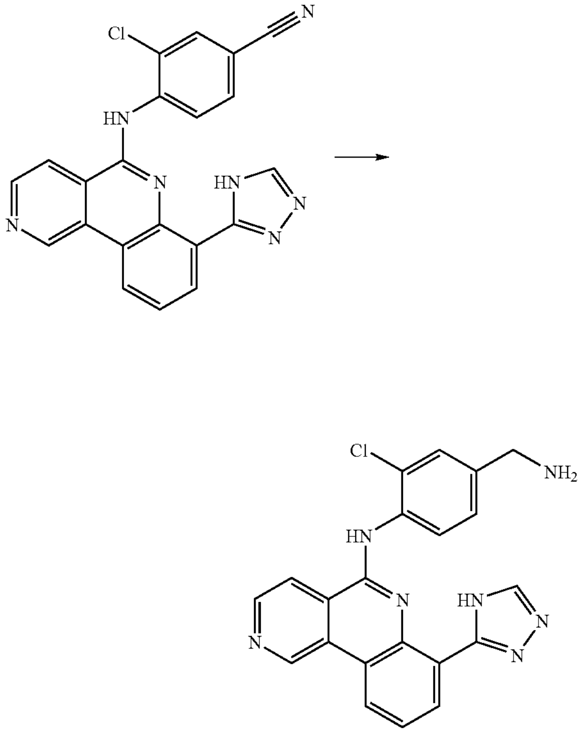

The material from step A was treated with $LiAlH_4$ (20 mg) in dry THF (1 ml) and the solution stirred at 60° C. for several hours. The reaction was then treated with $Na_2SO_4.10.H_2O$ and filtered. The residue was purified by preparative HPLC to afford N-(4-(aminomethyl)-2-chlorophenyl)-7-(4H-1,2,4-triazol-3-yl)benzo[c][2,6]naphthyridin-5-amine as a TFA salt (3 mg). LCMS (ES): >85% pure, m/z 402 $[M+1]^+$, 385 $[M+1-NH_3]^+$.

Process 52

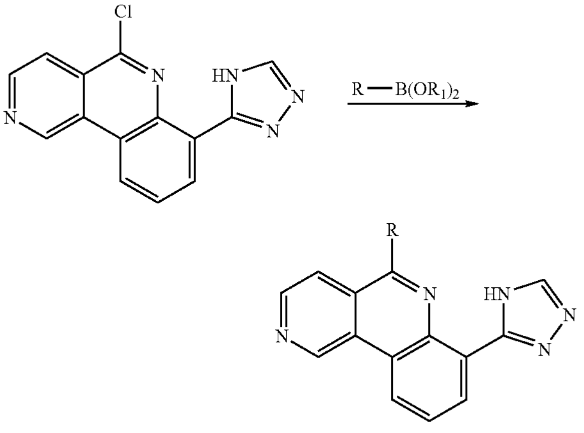

m

Reaction of 5-chloro-7-(4H-1,2,4-triazol-3-yl)benzo[c][2,6]naphthyridine with organoboranes under conditions of the Suzuki reaction affords compound m.

The following are examples of organoboranes that can be used in the Suzuki coupling reaction with 5-chloro-7-(4H-1,2,4-triazol-3-yl)benzo[c][2,6]naphthyridine.

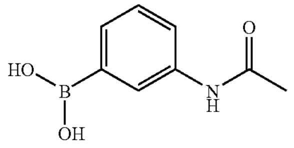
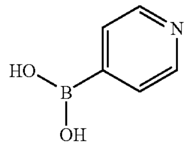
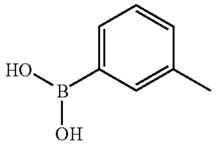
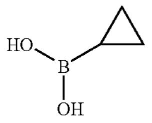
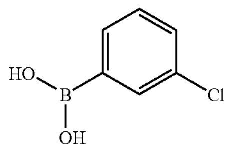
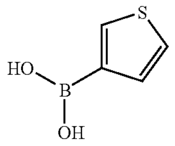
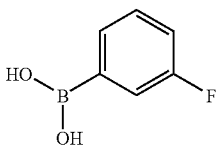
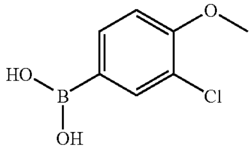
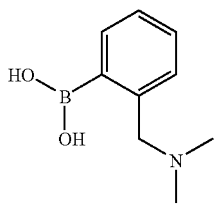
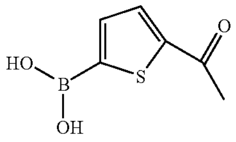

-continued
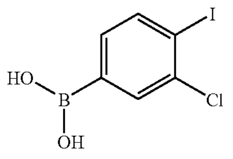
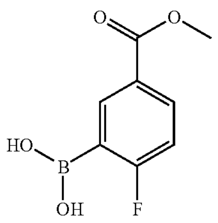
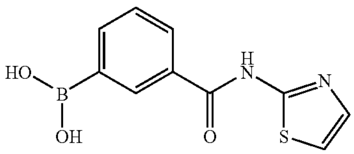
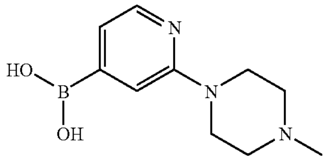
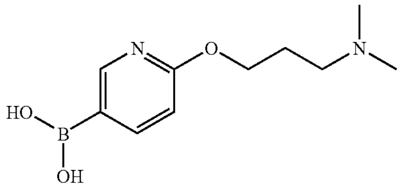
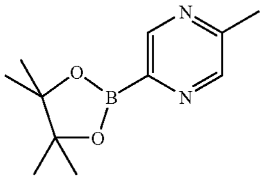
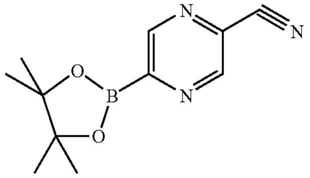
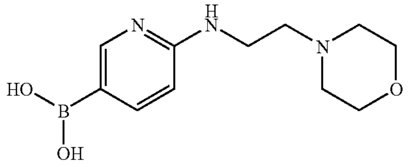
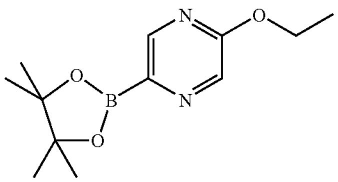
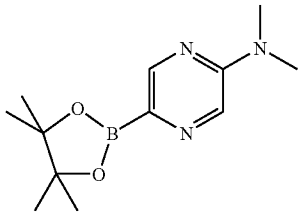
-continued
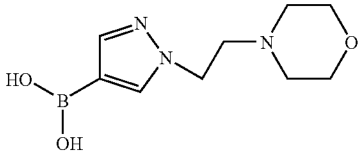
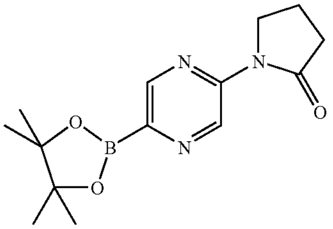
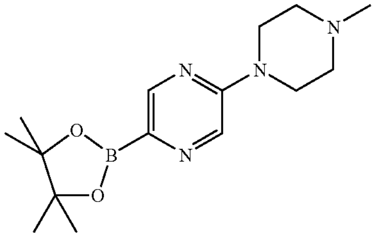
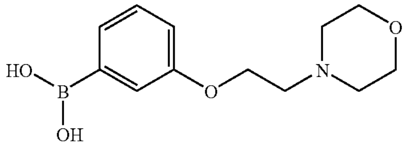
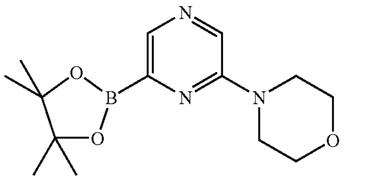
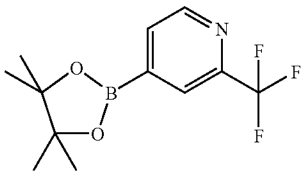
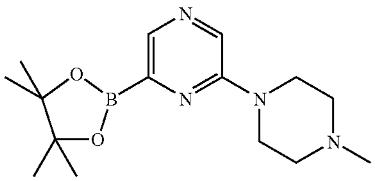

Process 57:

Synthesis of 5-phenyl-7-(4H-1,2,4-triazol-3-yl)benzo[c][2,6]naphthyridine

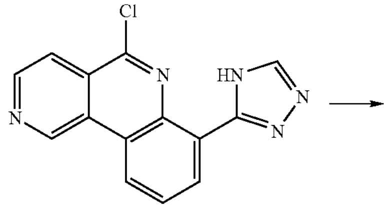

-continued

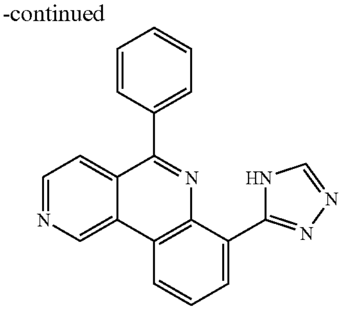

To 5-chloro-7-(4H-1,2,4-triazol-3-yl)benzo[c][2,6]naphthyridine (21.3 mg), cesium carbonate (49 mg) and phenylboronic acid (19 mg) in dioxane (1 mL) was added $PdCl_2$(dppf) under nitrogen atmosphere. The mixture stirred at 120° C. at 300 W (microwave) for 10 min. Water was added and residue obtained after extraction with dichloromethane was purified by preparative HPLC. LCMS (ES) m/z $[M+1]^+$ 324.

Biological data for representative compounds of the invention is provided in Tables 45 and 46:

TABLE 45

Biological data.

| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 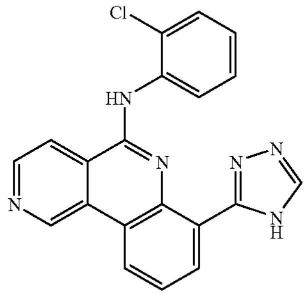 | <0.1 | <0.1 | <0.1 | <0.1 | <5 | <0.5 | <0.5 |
| 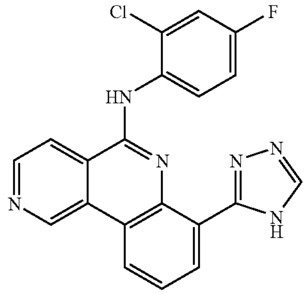 | <0.1 | <0.1 | <0.5 | <0.5 | <0.5 | >10 | |
| 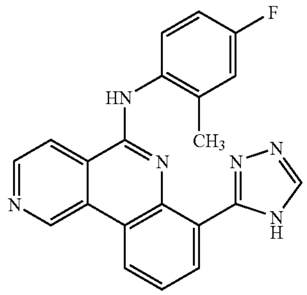 | <0.1 | <0.1 | <0.1 | <0.1 | <0.5 | <5 | >10 |

TABLE 45-continued
Biological data.
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 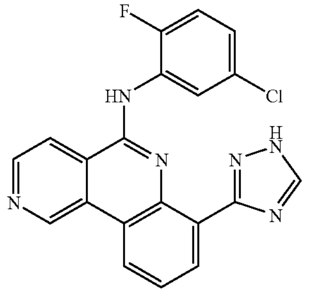 | <0.1 | <0.1 | <1 | <0.1 | <5 | <1 | <1 |
| 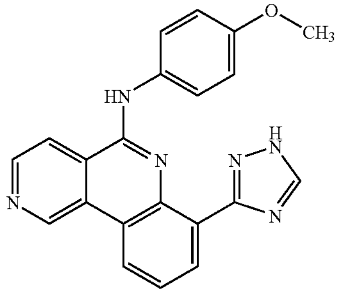 | <0.1 | <0.1 | <0.1 | <0.1 | <0.5 | <0.5 | |
| 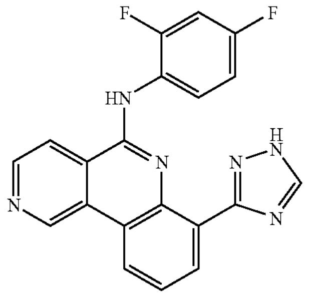 | <0.1 | <0.1 | <0.1 | <0.1 | <5 | <5 | <5 |
| 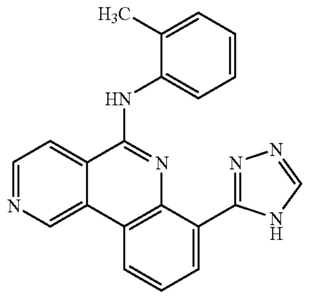 | <0.1 | <0.1 | <0.1 | <0.1 | <1 | <1 | >10 |
| 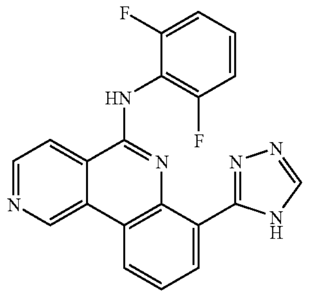 | <0.1 | <0.1 | <0.1 | <0.1 | <0.5 | <1 | <5 |

TABLE 45-continued
| Biological data. | | | | | | | |
|---|---|---|---|---|---|---|---|
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
| 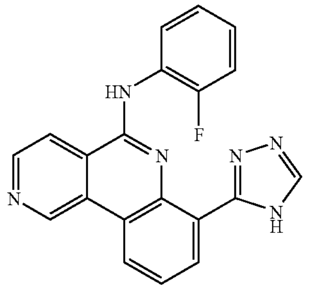 | <0.1 | <0.1 | <5 | <0.1 | <0.5 | <1 | |
| 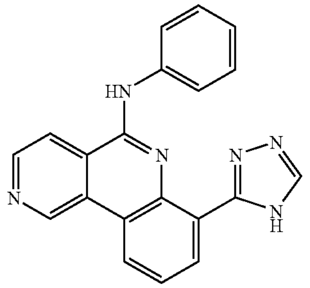 | <0.1 | <1 | <0.1 | <0.1 | <5 | <1 | >10 |
| 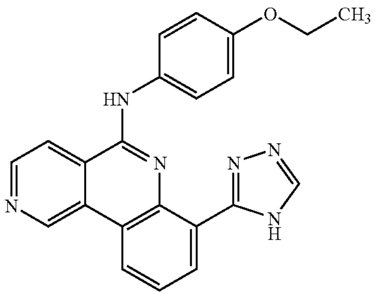 | <0.1 | <0.5 | <0.1 | <0.1 | <5 | <1 | >10 |
| 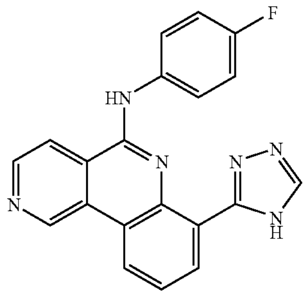 | <0.1 | <0.5 | <0.5 | <0.5 | >10 | <5 | <5 |
| 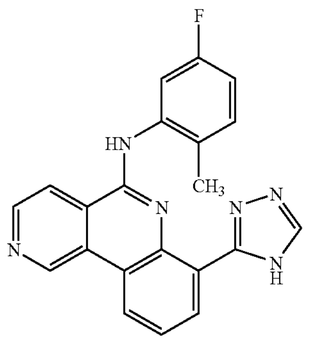 | <0.1 | <0.1 | <5 | <0.1 | >10 | | >10 |

TABLE 45-continued
| Biological data. | | | | | | | |
|---|---|---|---|---|---|---|---|
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
| 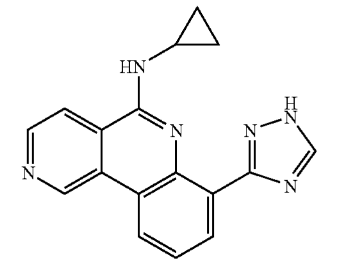 | <0.1 | <0.1 | <0.1 | <0.1 | <0.1 | <1 | <1 |
| 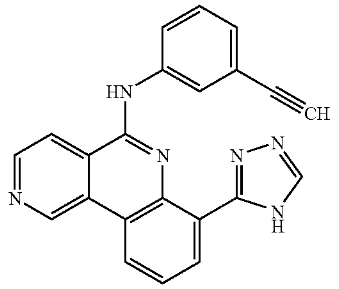 | <0.1 | <0.1 | <0.1 | <0.1 | <5 | <0.5 | <0.5 |
| 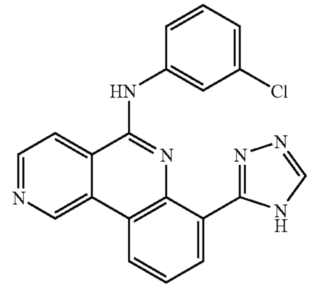 | <0.1 | <0.1 | <1 | <0.5 | <1 | <1 | <5 |
| 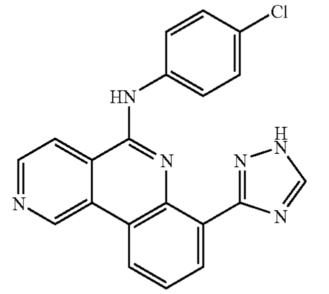 | <0.1 | <0.5 | <5 | <0.5 | <0.5 | >10 | >10 |
| 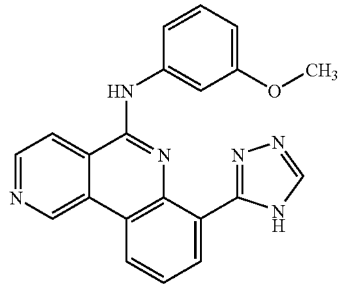 | <0.1 | <1 | <0.1 | <0.5 | <5 | <1 | <1 |

TABLE 45-continued
| Biological data. | | | | | | | |
|---|---|---|---|---|---|---|---|
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
| 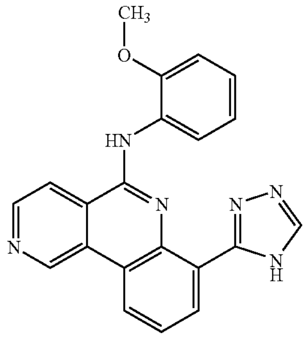 | <0.1 | <1 | <0.1 | <0.1 | <5 | v | <5 |
| 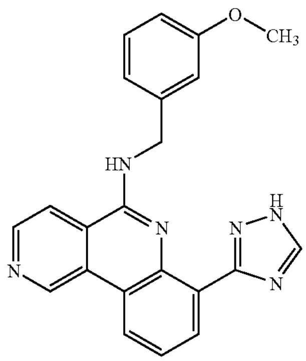 | <0.1 | <0.5 | <5 | <0.5 | <0.5 | >10 | >10 |
| 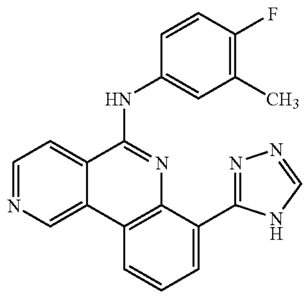 | <0.1 | <0.5 | <5 | <0.1 | >10 | <0.5 | >10 |
| 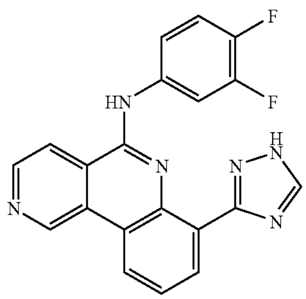 | <0.1 | <0.5 | <5 | <0.1 | >10 | <5 | <1 |

TABLE 45-continued
Biological data.
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 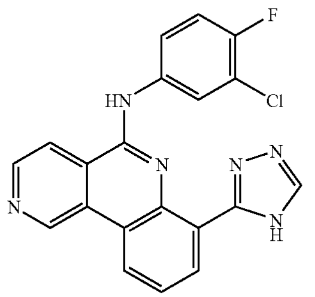 | <0.1 | <0.5 | <1 | <0.1 | <5 | <5 | <5 |
| 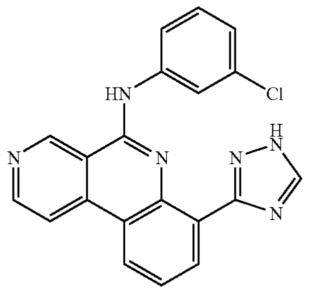 | <0.1 | <0.5 | | >10 | >10 | >10 | >10 |
| 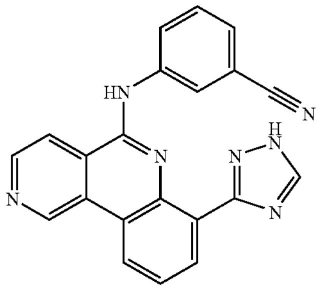 | <0.1 | >1.1 | <5 | <0.1 | >10 | >10 | |
| 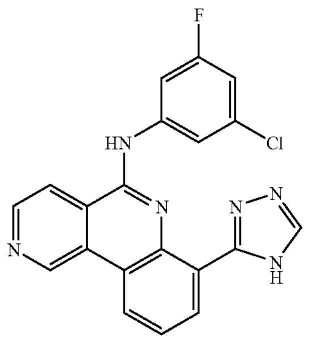 | <0.1 | >1.1 | <0.5 | <0.1 | <5 | <0.5 | <1 |

TABLE 45-continued
| Biological data. | | | | | | | |
|---|---|---|---|---|---|---|---|
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
| 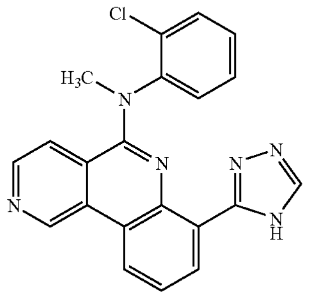 | <0.1 | <1 | <5 | <0.1 | <5 | | >10 |
| 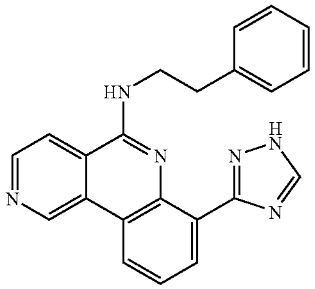 | <0.1 | <0.5 | <1 | <0.5 | >10 | >10 | <10 |
| 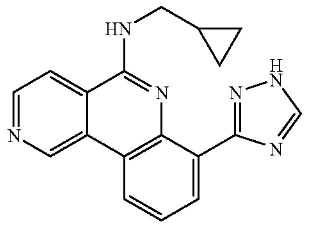 | <0.1 | <0.5 | <0.1 | <0.1 | >10 | <10 | v |
| 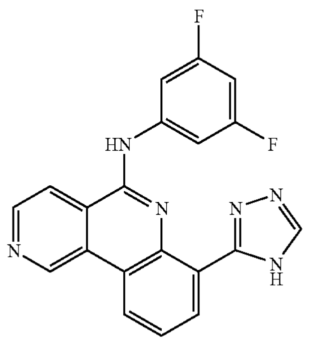 | <0.1 | <0.5 | <1 | <0.5 | <5 | <1 | >10 |

TABLE 45-continued
| Biological data. | | | | | | | |
|---|---|---|---|---|---|---|---|
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
| 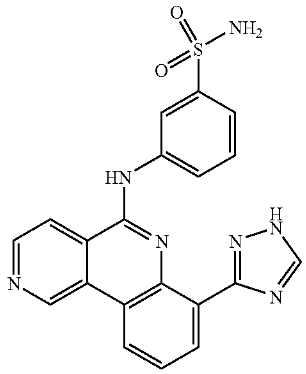 | <0.1 | <0.5 | <1 | <0.5 | >10 | >10 | >10 |
| 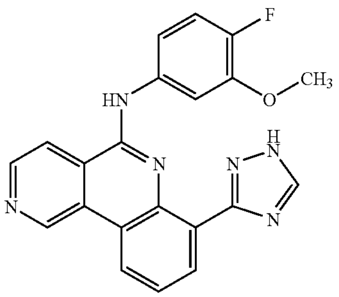 | <0.1 | <0.5 | <5 | <0.5 | <5 | <10 | >10 |
| 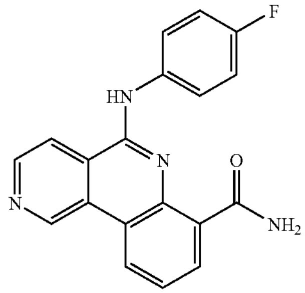 | <0.1 | <0.5 | <0.1 | <0.1 | <5 | <1 | >30 |
| 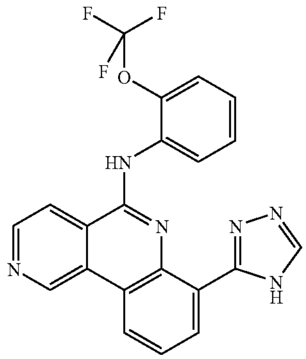 | <0.1 | <0.1 | <0.1 | <0.5 | >10 | >10 | >10 |

TABLE 45-continued
Biological data.
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 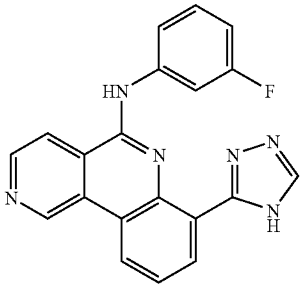 | <0.1 | | <0.5 | <0.5 | v | <1 | v |
| 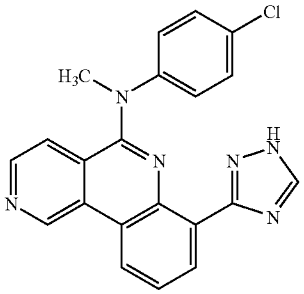 | <0.1 | <5 | | <1 | <0.5 | <5 | >10 |
| 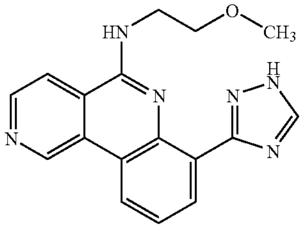 | <0.1 | <0.5 | <0.1 | <0.1 | <10 | <5 | <10 |
| 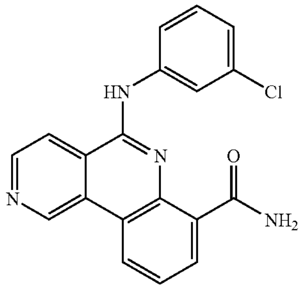 | <0.1 | | <5 | <0.1 | <0.5 | <1 | <10 |
| 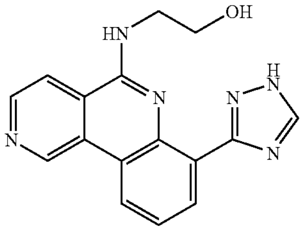 | <0.5 | <1 | <0.5 | <0.1 | >10 | <0.5 | >10 |

TABLE 45-continued
Biological data.
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 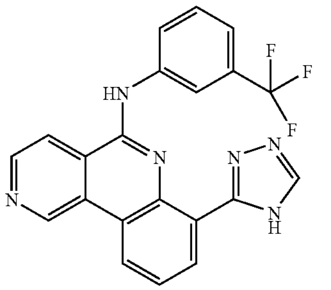 | <0.5 | >1.1 | <1 | <0.5 | <5 | <5 | |
| 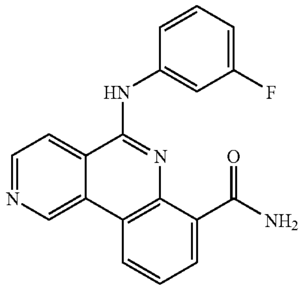 | <0.5 | | <0.1 | <0.12 | <1 | <1 | <1 |
| 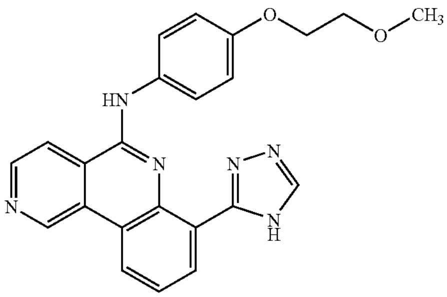 | <0.5 | <1 | <0.5 | <0.1 | >10 | <1 | <10 |
| 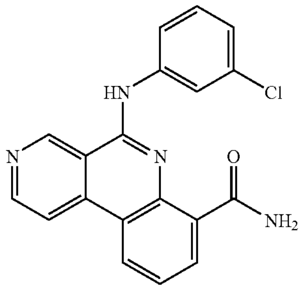 | <0.5 | | | >10 | >10 | >10 | >10 |
| 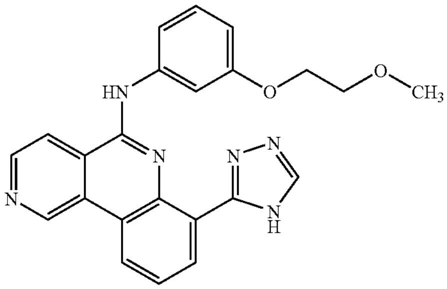 | <0.5 | | <0.1 | <0.1 | >10 | >10 | >10 |

TABLE 45-continued
| Biological data. | | | | | | | |
|---|---|---|---|---|---|---|---|
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
| 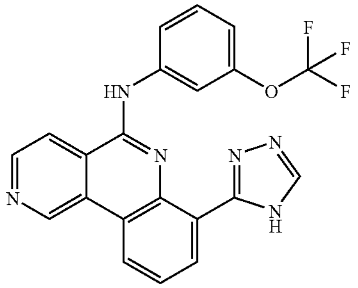 | <0.5 | <1 | <5 | <0.5 | <0.5 | <5 | >10 |
| 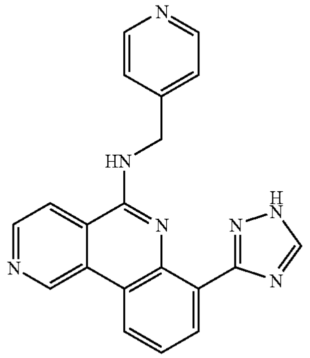 | <0.5 | <1 | | | | | |
| 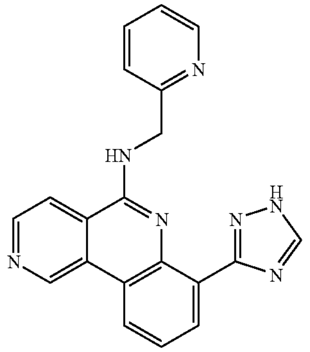 | <0.5 | <0.5 | | | | | |
| 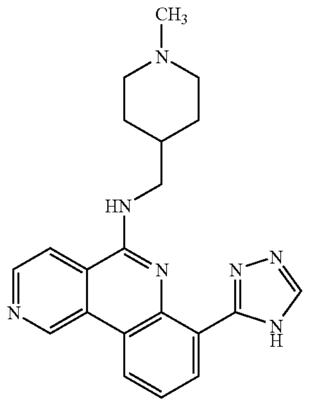 | <0.5 | >1.1 | | | | | |

TABLE 45-continued
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| Biological data. | | | | | | | |
| 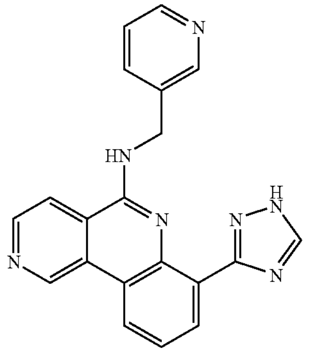 | <0.5 | >1.1 | | | | | |
| 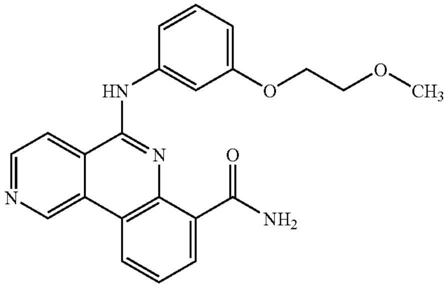 | <0.5 | | | | | | |
| 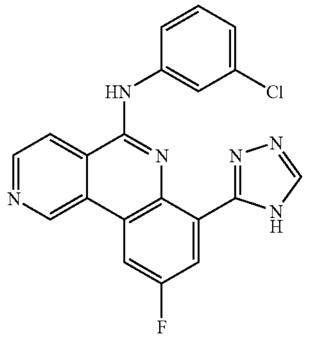 | <1 | <1 | | | | | |
| 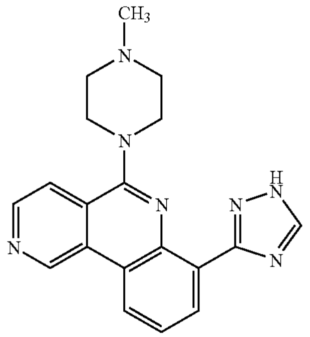 | <1 | >1.1 | | | | | |

TABLE 45-continued
Biological data.
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 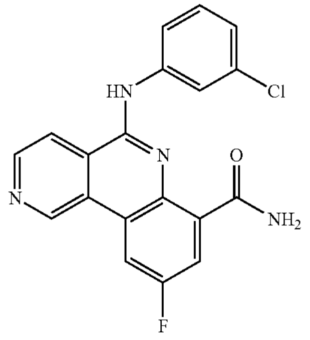 | <1 | >1.1 | | | | | |
| 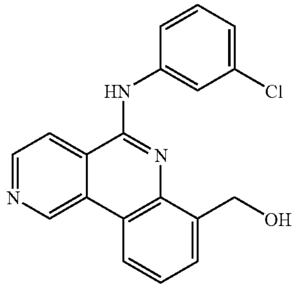 | <1 | | | | | | |
| 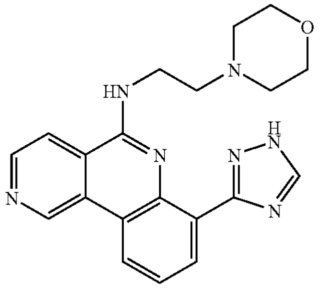 | <5 | >1.1 | | | | | |
| 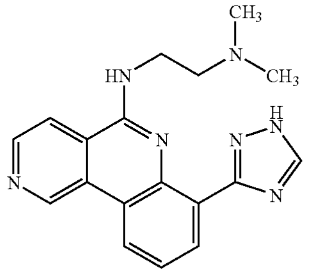 | <5 | >1.1 | | | | | |
| 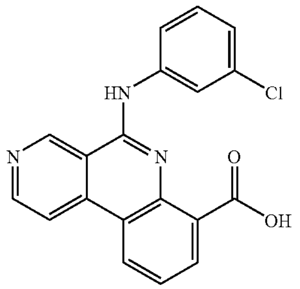 | >1.1 | | | | | | |

TABLE 45-continued
| Biological data. | | | | | | | |
|---|---|---|---|---|---|---|---|
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
| 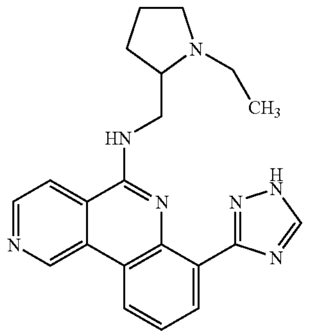 | >1.1 | >1.1 | | | | | |
| 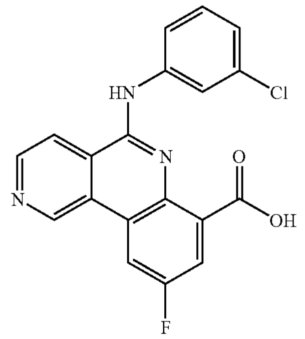 | >1.1 | >1.1 | | | | | |
| 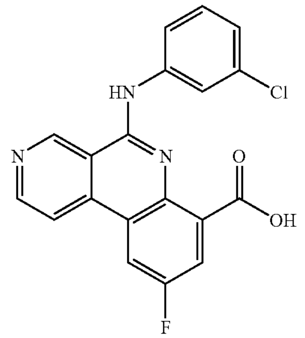 | >1.1 | >1.1 | | | | | |
| 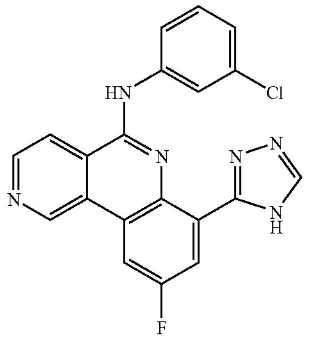 | >1.1 | >1.1 | | | | | |

TABLE 45-continued
| Biological data. | | | | | | | |
|---|---|---|---|---|---|---|---|
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
| 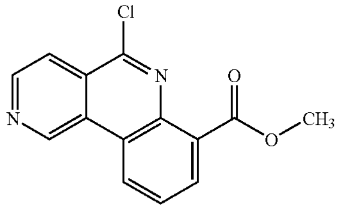 | >1.1 | | | | | | |
| 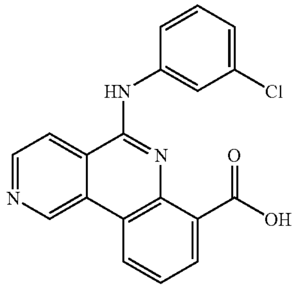 | >1.1 | | | | | | |
| 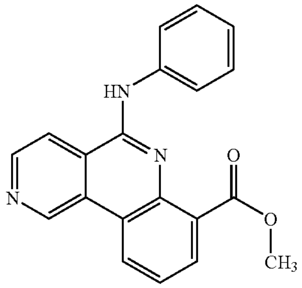 | >1.1 | | | | | | |
| 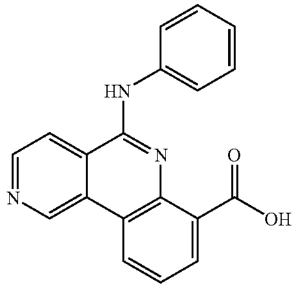 | >1.1 | | | | | | |
| 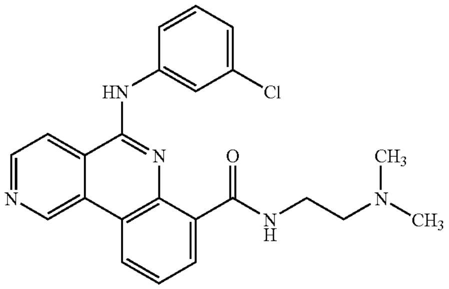 | >1.1 | | | | | | |

TABLE 45-continued
Biological data.
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 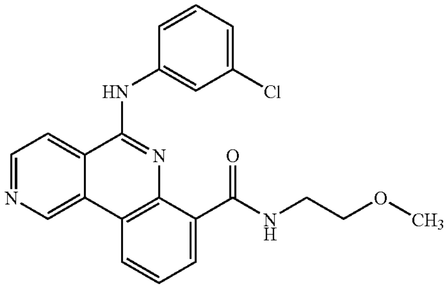 | >1.1 | | | | | | |
| 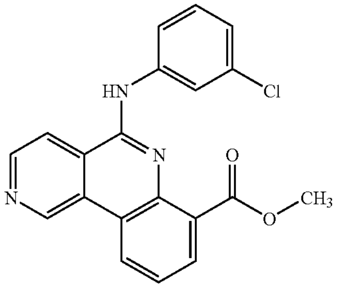 | >1.1 | | | | | | |
| 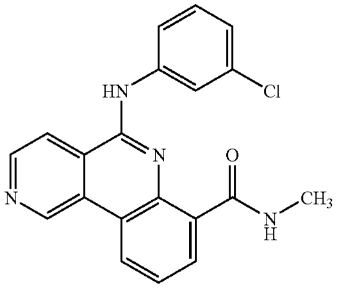 | >1.1 | | | | | | |
| 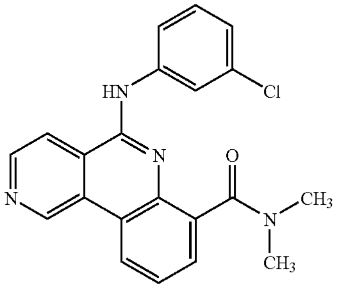 | >1.1 | | | | | | |
| 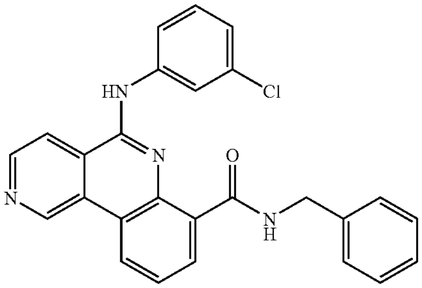 | >1.1 | | | | | | |

TABLE 45-continued
Biological data.
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 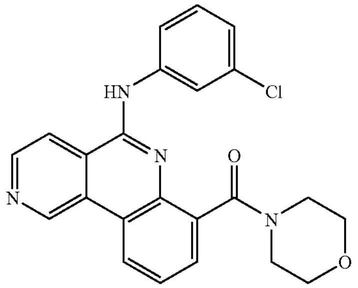 | >1.1 | | | | | | |
| 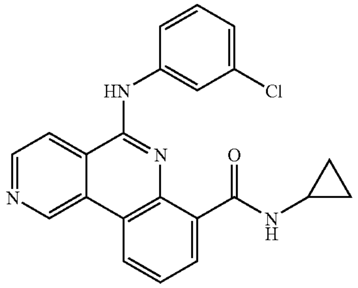 | >1.1 | | | | | | |
| 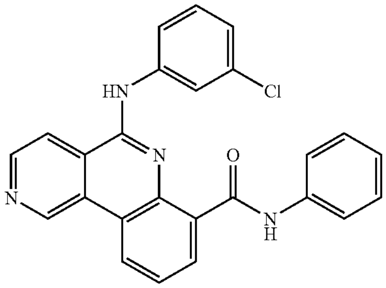 | >1.1 | | | | | | |
| 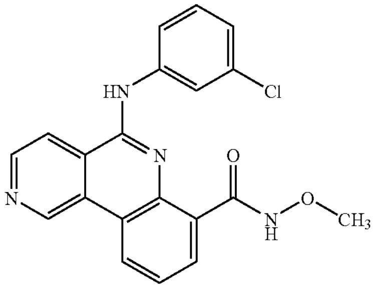 | >1.1 | | | | | | |
| 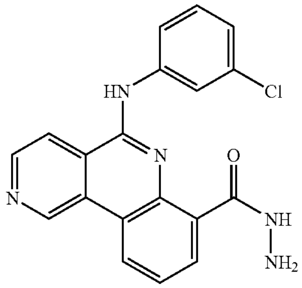 | <5 | | | | | | |

TABLE 45-continued
Biological data.
| Structure | PIM1: IC50 (uM) | PIM2: IC50 (uM) | phosphoBAD ser 112 IC50 (uM) | MV-4-11 IC50 (uM) | K-562 IC50 (uM) | MiaPaCa IC50 (uM) | MDAMB231 IC50 (uM) |
|---|---|---|---|---|---|---|---|
| 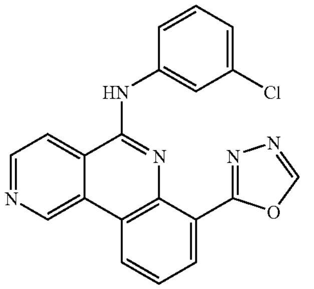 | >1.1 | | | | | | |
| 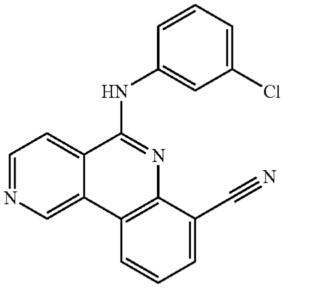 | >1.1 | | | | | | |
TABLE 46
Biological data.
| Structure | PIM1 $IC_{50}$ (uM) | FLT3 autophos $IC_{50}$ (uM) | phospho-BAD ser112 $IC_{50}$ (uM) | K-562 $IC_{50}$ (uM) | MV-411 $IC_{50}$ (uM) | MDA MB231 $IC_{50}$ (uM) | Mia-PaCa $IC_{50}$ (uM) | PC3 $IC_{50}$ (uM) |
|---|---|---|---|---|---|---|---|---|
| 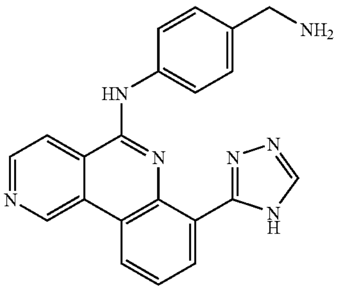 | <0.1 | | | >10 | <0.1 | 9.638 | | >30 |
| 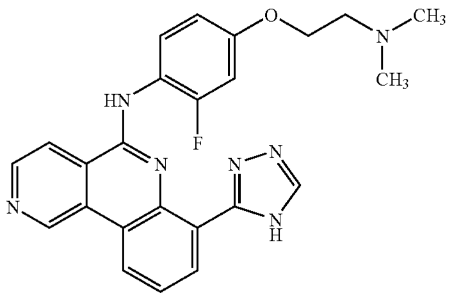 | <0.1 | | | <1 | <0.1 | 2.179 | | 11.983 |

TABLE 46-continued
Biological data.
| Structure | PIM1 IC$_{50}$ (uM) | FLT3 autophos IC$_{50}$ (uM) | phospho-BAD ser112 IC$_{50}$ (uM) | K-562 IC$_{50}$ (uM) | MV-411 IC$_{50}$ (uM) | MDA MB231 IC$_{50}$ (uM) | Mia-PaCa IC$_{50}$ (uM) | PC3 IC$_{50}$ (uM) |
|---|---|---|---|---|---|---|---|---|
| 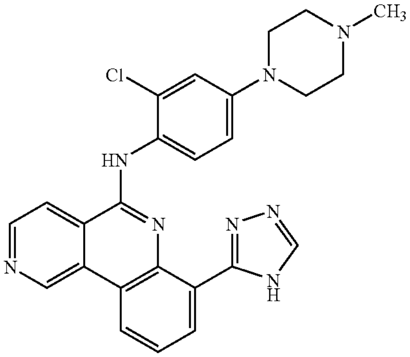 | <0.1 | | | <1 | <0.1 | 2.936 | 1.498 | 3.658 |
| 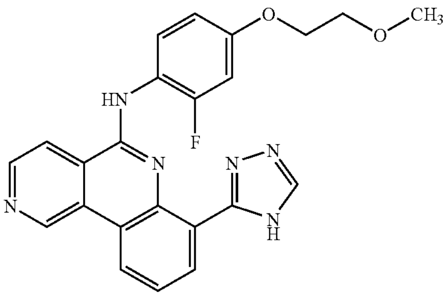 | <0.1 | | | <0.5 | <0.1 | <1 | <1 | |
| 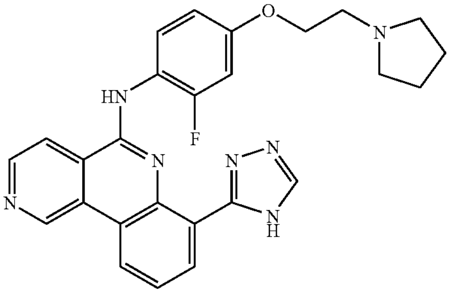 | <0.1 | >10 | <0.1 | <0.5 | <0.1 | <1 | | |
| 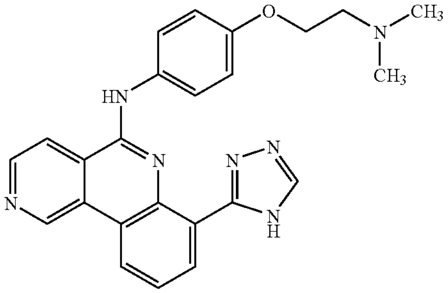 | <0.1 | >10 | <0.1 | <0.1 | <0.1 | 2.555 | | 1.765 |

TABLE 46-continued
Biological data.
| Structure | PIM1 IC$_{50}$ (uM) | FLT3 autophos IC$_{50}$ (uM) | phospho-BAD ser112 IC$_{50}$ (uM) | K-562 IC$_{50}$ (uM) | MV-411 IC$_{50}$ (uM) | MDA MB231 IC$_{50}$ (uM) | Mia-PaCa IC$_{50}$ (uM) | PC3 IC$_{50}$ (uM) |
|---|---|---|---|---|---|---|---|---|
| 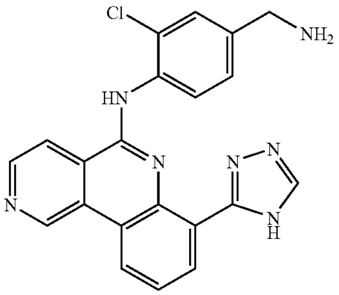 | <0.1 | | | | | | | |
| 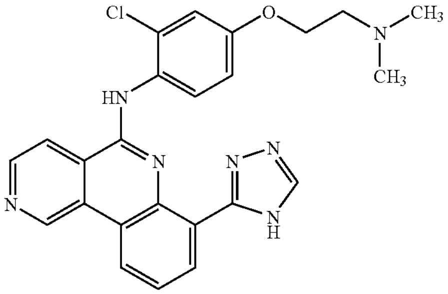 | <0.1 | 5.41 | <0.1 | 6.939 | <0.1 | 1.231 | | |
| 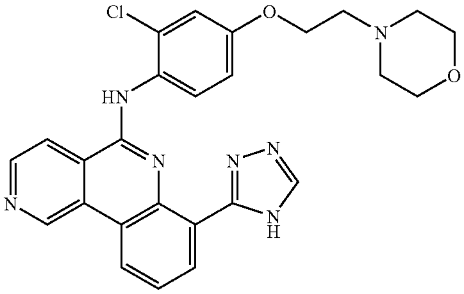 | <0.1 | 6.011 | <0.1 | >10 | <0.1 | >10 | | >30 |
| 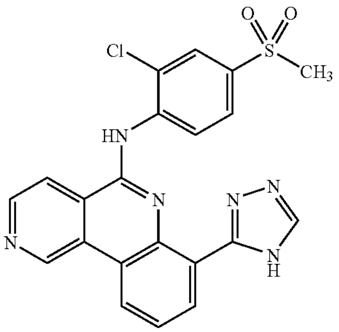 | <0.1 | | | 2.655 | <0.1 | 2.73 | | 1.507 |

TABLE 46-continued
Biological data.
| Structure | PIM1 $IC_{50}$ (uM) | FLT3 autophos $IC_{50}$ (uM) | phospho-BAD ser112 $IC_{50}$ (uM) | K-562 $IC_{50}$ (uM) | MV-411 $IC_{50}$ (uM) | MDA MB231 $IC_{50}$ (uM) | Mia-PaCa $IC_{50}$ (uM) | PC3 $IC_{50}$ (uM) |
|---|---|---|---|---|---|---|---|---|
| 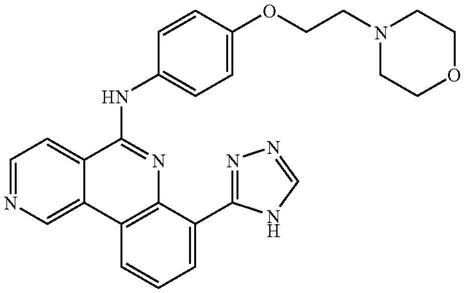 | <0.1 | >10 | <0.5 | <0.5 | <0.1 | 2.036 | 0.268 | <1 |
| 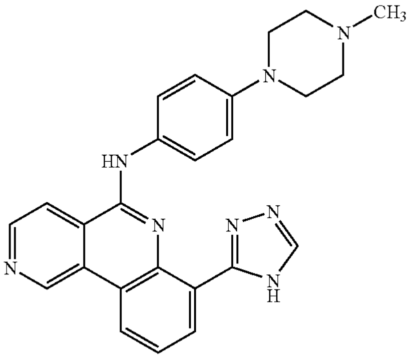 | <0.5 | | | | | | | |
| 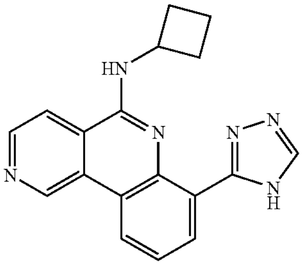 | <0.1 | >10 | <0.1 | <0.5 | <0.1 | >10 | 7.625 | <0.5 |
| 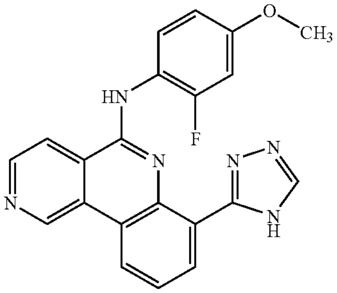 | <0.1 | >10 | 0.51 | <1 | <0.1 | 6.859 | <0.5 | <0.5 |

TABLE 46-continued
Biological data.
| Structure | PIM1 IC$_{50}$ (uM) | FLT3 autophos IC$_{50}$ (uM) | phospho-BAD ser112 IC$_{50}$ (uM) | K-562 IC$_{50}$ (uM) | MV-411 IC$_{50}$ (uM) | MDA MB231 IC$_{50}$ (uM) | Mia-PaCa IC$_{50}$ (uM) | PC3 IC$_{50}$ (uM) |
|---|---|---|---|---|---|---|---|---|
| 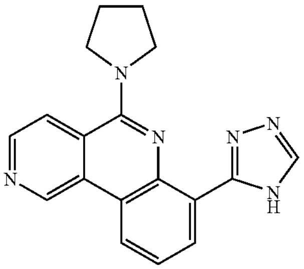 | <0.5 | >10 | 2.945 | 3.226 | <1 | >10 | <0.1 | >30 |
| 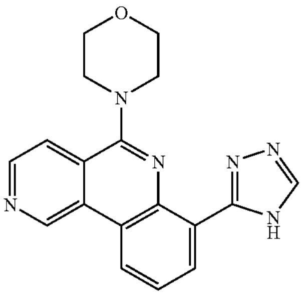 | 3.967 | | | | | | | |
| 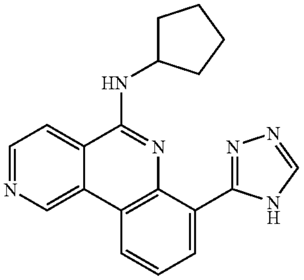 | <0.1 | >10 | <0.5 | 1.926 | <0.5 | >10 | | >30 |
| 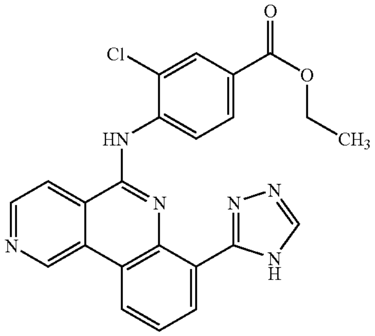 | <0.1 | | | >10 | <0.1 | >10 | >10 | >30 |

TABLE 46-continued
Biological data.
| Structure | PIM1 IC50 (uM) | FLT3 autophos IC50 (uM) | phospho-BAD ser112 IC50 (uM) | K-562 IC50 (uM) | MV-411 IC50 (uM) | MDA MB231 IC50 (uM) | Mia-PaCa IC50 (uM) | PC3 IC50 (uM) |
|---|---|---|---|---|---|---|---|---|
| 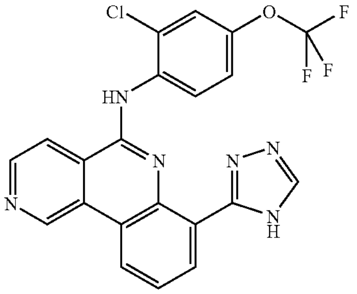 | <0.1 | >10 | 4.173 | >10 | <0.1 | >10 | >10 | >30 |
| 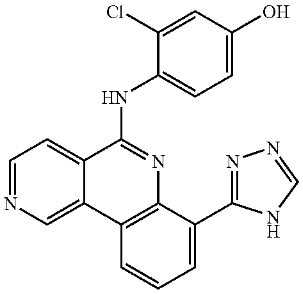 | <0.1 | | | <0.5 | >10 | 2.38 | <1 | <0.5 |
| 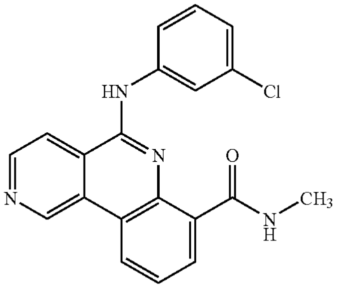 | <0.1 | | | >10 | <0.1 | >10 | <0.5 | >30 |
The following table is the %-activity data of compound A in different kinase enzymes at 0.5 μM of ATP.
TABLE 47
A
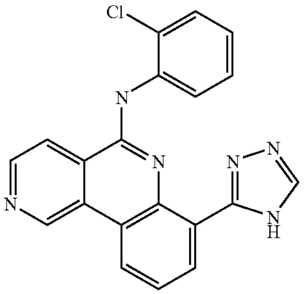
| Kinase | % Activity |
|---|---|
| DYRK2(h) | −4 |
| HIPK2(h) | −1 |
TABLE 47-continued
A
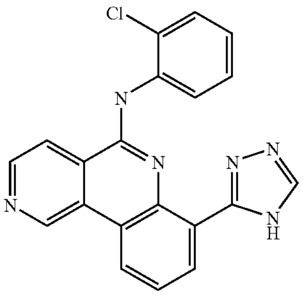
| Kinase | % Activity |
|---|---|
| Pim-1(h) | 1 |
| HIPK3(h) | 2 |
| Pim-2(h) | 2 |
| Flt3(h) | 5 |
| Rsk1(h) | 6 |
| TrkA(h) | 6 |

TABLE 47-continued

A

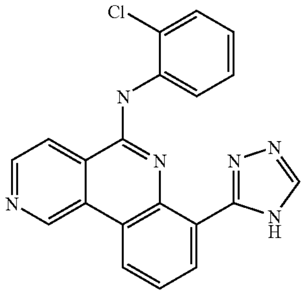

| Kinase | % Activity |
|---|---|
| Rsk3(h) | 7 |
| cKit(D816H)(h) | 8 |
| IRAK4(h) | 12 |
| Pim-3(h) | 12 |
| Rsk4(h) | 12 |
| MELK(h) | 13 |
| Rsk2(h) | 13 |
| CK1γ2(h) | 17 |
| Flt4(h) | 17 |
| Fms(h) | i7 |
| PDGFRα(D842V)(h) | 17 |
| EGFR(T790M,L858R)(h) | 20 |
| CK1γ3(h) | 21 |
| Lck(h) | 21 |
| Met(h) | 22 |
| GSK3β(h) | 23 |
| Flt3(D835Y)(h) | 24 |
| MLK1(h) | 24 |
| Yes(h) | 26 |
| TAK1(h) | 28 |
| CK1γ1(h) | 30 |
| FAK(h) | 30 |
| CDK2/cyclinA(h) | 31 |
| CDK1/cyclinB(h) | 37 |
| CDK9/cyclin T1 (h) | 37 |
| cKit(V560G)(h) | 38 |
| Mer(h) | 38 |
| ARK5(h) | 39 |
| JAK2(h) | 39 |
| PKCθ(h) | 39 |
| PKG1α(h) | 40 |
| Aurora-A(h) | 43 |
| KDR(h) | 43 |
| Ret(h) | 43 |
| MST1(h) | 44 |
| Fyn(h) | 49 |
| CDK7/cyclinH/MAT1(h) | 50 |
| MSK2(h) | 51 |
| EGFR(T790M)(h) | 53 |
| Mnk2(h) | 54 |
| EGFR(L858R)(h) | 56 |
| CK2(h) | 58 |
| EGFR(L861Q)(h) | 60 |
| Hck(h) | 61 |
| Flt1(h) | 62 |
| LOK(h) | 63 |
| cSRC(h) | 64 |
| c-RAF(h) | 66 |
| MEK1(h) | 72 |
| CK2α2(h) | 73 |
| DRAK1(h) | 75 |
| Lyn(h) | 75 |
| ErbB4(h) | 77 |
| MAPK1(h) | 77 |
| p70S6K(h) | 77 |
| Snk(h) | 79 |
| MKK7β(h) | 81 |
| Fes(h) | 84 |
| PKD2(h) | 86 |
| Abl(h) | 87 |
| EphB4(h) | 87 |
| cKit(h) | 89 |

TABLE 47-continued

A

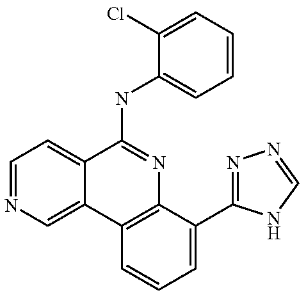

| Kinase | % Activity |
|---|---|
| CaMKI(h) | 90 |
| DDR2(h) | 90 |
| Fer(h) | 90 |
| Ros(h) | 90 |
| ASK1(h) | 92 |
| FGFR2(h) | 93 |
| PDGFRβ(h) | 94 |
| ROCK-I(h) | 94 |
| EphA5(h) | 95 |
| EphA7(h) | 96 |
| Plk1(h) | 96 |
| PDGFRα(h) | 97 |
| PKA(h) | 97 |
| PRAK(h) | 97 |
| ZAP-70(h) | 97 |
| PKBα(h) | 98 |
| mTOR(h) | 99 |
| PKCα(h) | 99 |
| Ron(h) | 99 |
| FGFR1(h) | 100 |
| ZIPK(h) | 100 |
| IGF-1R(h) | 101 |
| PDK1(h) | 101 |
| PAK2(h) | 106 |
| SRPK1(h) | 107 |
| CHK1(h) | 108 |
| IKKα(h) | 108 |
| Tie2(h) | 108 |
| Rse(h) | 109 |
| eEF-2K(h) | 111 |
| EGFR(h) | 111 |
| IR(h) | 112 |

Estimated $IC_{50}$ values of compound A are as follows:

| Compound | Kinase | $IC_{50}$ (nM) |
|---|---|---|
| A | Flt3(h) | 104 |
| A | Pim-1(h) | 1 |
| A | Pim-2(h) | 6 |
| A | Pim-3(h) | 86 |
| A | Rsk1(h) | 41 |
| A | Rsk2(h) | 72 |
| A | Rsk3(h) | 73 |
| A | Rsk4(h) | 37 |

The following table is the %-activity data of compound B in different kinases at 0.5 μM of ATP.

TABLE 48

B

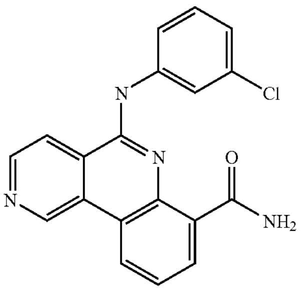

| Kinase | % activity |
|---|---|
| HIPK3(h) | −1 |
| Flt3(D835Y)(h) | 2 |
| HIPK2(h) | 2 |
| DYRK2(h) | 5 |
| Flt3(h) | 7 |
| cKit(D816H)(h) | 9 |
| Pim-1(h) | 9 |
| MELK(h) | 14 |
| DRAK1(h) | 15 |
| PDGFRα(D842V)(h) | 15 |
| CDK2/cyclinA(h) | 17 |
| CDK7/cyclinH/MAT1(h) | 17 |
| CDK1/cyclinB(h) | 18 |
| CDK9/cyclin T1(h) | 18 |
| ZIPK(h) | 19 |
| Rsk1(h) | 21 |
| TrkA(h) | 23 |
| Lck(h) | 24 |
| GSK3β(h) | 25 |
| cKit(V560G)(h) | 33 |
| Mnk2(h) | 33 |
| PKG1α(h) | 34 |
| CK1γ3(h) | 38 |
| Mer(h) | 39 |
| Rsk2(h) | 40 |
| Rsk3(h) | 40 |
| Flt4(h) | 41 |
| Rsk4(h) | 41 |
| Fms(h) | 42 |
| Yes(h) | 44 |
| Pim-2(h) | 46 |
| CK2(h) | 48 |
| Fyn(h) | 49 |
| CK2α2(h) | 51 |
| EGFR(L861Q)(h) | 54 |
| JAK2(h) | 55 |
| EGFR(L858R)(h) | 56 |
| GFR(T790M,L858R)(h | 59 |
| CaMKI(h) | 62 |
| Hck(h) | 62 |
| CDK6/cyclinD3(h) | 63 |
| CK1γ2(h) | 63 |
| MSK2(h) | 65 |
| Pim-3(h) | 65 |
| Flt1(h) | 66 |
| c-RAF(h) | 69 |
| CK1γ1(h) | 71 |
| Ret(h) | 73 |
| cSRC(h) | 74 |
| KDR(h) | 75 |
| Lyn(h) | 75 |
| MKK7β(h) | 75 |
| EGFR(T790M)(h) | 76 |
| Plk1(h) | 76 |
| Aurora-A(h) | 77 |
| ErbB4(h) | 77 |
| MLK1(h) | 77 |
| TAK1(h) | 79 |
| MST1(h) | 80 |
| IRAK4(h) | 81 |
| Snk(h) | 82 |
| PKCθ(h) | 83 |

TABLE 48-continued

B

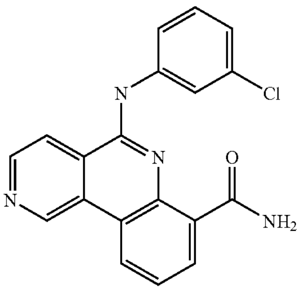

| Kinase | % activity |
|---|---|
| PRAK(h) | 84 |
| MAPK1(h) | 86 |
| PKD2(h) | 86 |
| LOK(h) | 87 |
| p70S6K(h) | 87 |
| Rse(h) | 87 |
| cKit(h) | 88 |
| MEK1(h) | 88 |
| PDK1(h) | 88 |
| EphA7(h) | 90 |
| IGF-1R(h) | 90 |
| CHK1(h) | 91 |
| SRPK1(h) | 91 |
| Abl(h) | 92 |
| ASK1(h) | 93 |
| eEF-2K(h) | 93 |
| EphA5(h) | 93 |
| FGFR1(h) | 93 |
| Tie2(h) | 93 |
| Fes(h) | 94 |
| FGFR2(h) | 94 |
| PDGFRβ(h) | 94 |
| IR(h) | 95 |
| NEK2(h) | 95 |
| Ron(h) | 95 |
| Met(h) | 96 |
| PKCα(h) | 97 |
| ROCK-I(h) | 97 |
| ARK5(h) | 98 |
| IKKα(h) | 99 |
| PKBα(h) | 90 |
| ALK(h) | 100 |
| PKA(h) | 100 |
| EGFR(h) | 101 |
| mTOR(h) | 101 |
| Plk3(h) | 102 |
| Fer(h) | 103 |
| MAPKAP-K2(h) | 104 |
| EphB4(h) | 105 |
| PDGFRα(h) | 105 |
| FAK(h) | 106 |
| ZAP-70(h) | 106 |
| PAK2(h) | 108 |

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention.

Representative embodiments of the invention are set forth in the following aspects and illustrate but do not limit the invention.

E1. A compound of Formula IA:

(IA)

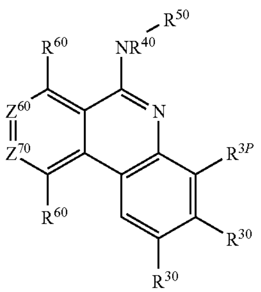

wherein:

$Z^{60}$ and $Z^{70}$ are independently N or $CR^{60}$, provided at least one of them is N;

each $R^{30}$ and each $R^{60}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^{30}$ and each $R^{60}$ can be halo, OR, $NR_2$, NROR, $NRNR_2$, SR, SOR, $SO_2R$, $SO_2NR_2$, $NRSO_2R$, $NRCONR_2$, $NRCSNR_2$, $NRC(=NR)NR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, $NR'C(=NR')NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, each $R^{40}$ is H or optionally substituted member selected from the group consisting of $C_1$-$C_6$ alkyl, C2-C6 heteroalkyl, and C1-C6 acyl;

each $R^{50}$ is independently an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic ring;

or $R^{50}$ can be a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring;

in each —$NR^{40}R^{50}$, $R^{40}$ and $R^{50}$ together with N may form an optionally substituted 3-8 membered ring, which may optionally contain an additional heteroatom selected from N, O and S as a ring member; and each $R^{3P}$ represents a polar substituent;

or a pharmaceutically acceptable salt thereof.

E2. The compound of embodiment E1, wherein $Z^{60}$ is N and $Z^{70}$ is CH.

E3. The compound of embodiment E1, wherein $Z^{70}$ is N and $Z^{60}$ is CH.

E4. The compound of embodiment E1, E2 or E3, wherein each $R^{60}$ and $R^{40}$ is H.

E5. The compound of any one of embodiments E1 to E4, wherein $R^{3P}$ is an optionally substituted imidazole or triazole ring.

E6. The compound of any one of embodiments E1 to E5, wherein $R^{50}$ is unsubstituted phenyl or phenyl substituted with 1-3 substituents selected from halo, cyano, $CF_3$, —$OCF_3$, $COOR^{40}$, and $SO_2NR^{40}R^{50}$, and one or more of these substituents can be an optionally substituted group selected from C1-C6 alkyl, C1-C6 alkoxy, C2-C6 alkenyl, and C2-C6 alkynyl.

E7. The compound of embodiment E1, which is a compound of Formula IB:

IB

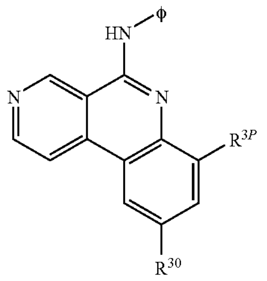

or a pharmaceutically acceptable salt thereof, wherein $R^{30}$ is as defined for embodiment 1, and $R^{3P}$ is an optionally substituted imidazole or triazole ring;

and each Φ independently represents an optionally substituted phenyl.

E8. The compound of embodiment E1, which is a compound of Formula IC:

IC

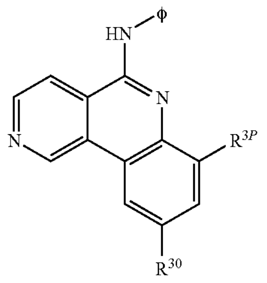

or a pharmaceutically acceptable salt thereof, wherein $R^{30}$ is as defined for embodiment 1, and $R^{3P}$ is an optionally substituted imidazole or triazole ring;

and each Φ independently represents an optionally substituted phenyl.

E9. The compound of embodiment E7 or E8, wherein Φ is unsubstituted phenyl or phenyl substituted with 1-3 substituents selected from halo, cyano, $CF_3$, $—OCF_3$, $COOR^{40}$, and $SO_2NR^{40}R^{50}$, and one or more of these substituents can be an optionally substituted group selected from C1-C6 alkyl, C1-C6 alkoxy, C2-C6 alkenyl, and C2-C6 alkynyl.

E10. The compound of any one of embodiments E1 to E5, wherein $R^{50}$ is an optionally substituted $C_{3-8}$ carbocyclic or $C_{3-8}$ heterocyclic ring, each of which may be optionally fused to an additional optionally substituted carbocyclic or heterocyclic ring.

E11. The compound of embodiment E10, wherein said optionally substituted $C_{3-8}$ carbocyclic or $C_{3-8}$ heterocyclic ring is an optionally substituted aromatic or heteroaromatic ring.

E12. A compound selected from the group consisting of:

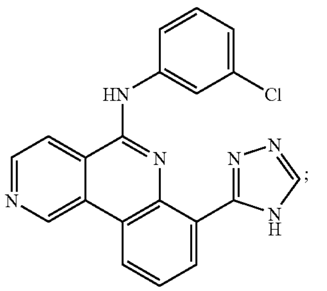

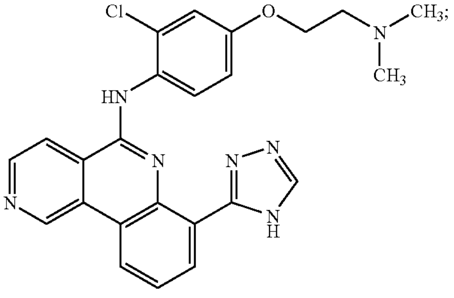

-continued

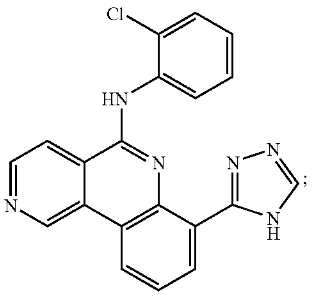

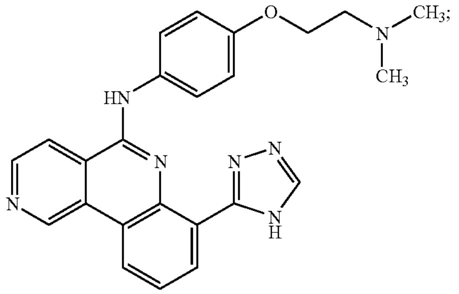

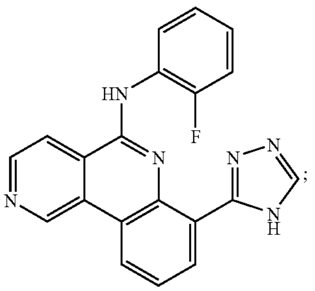

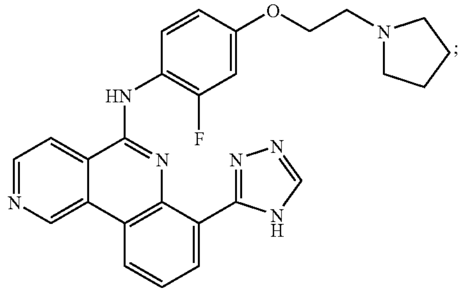

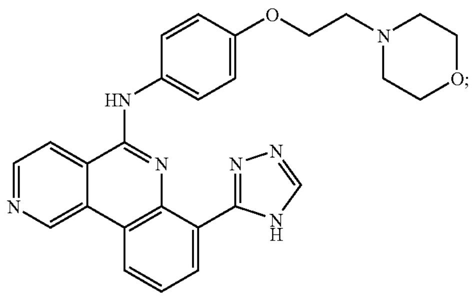

-continued

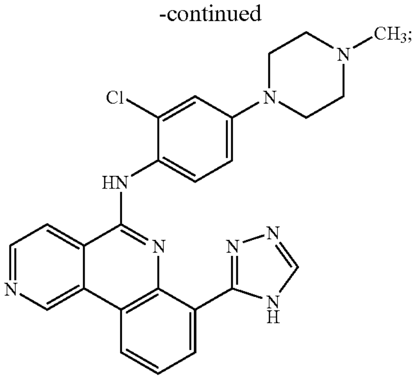

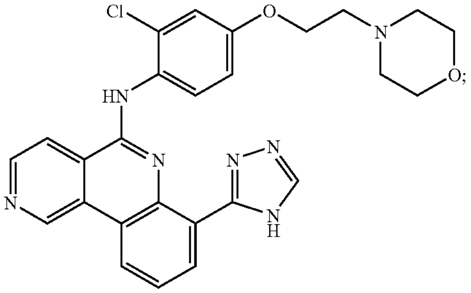

or

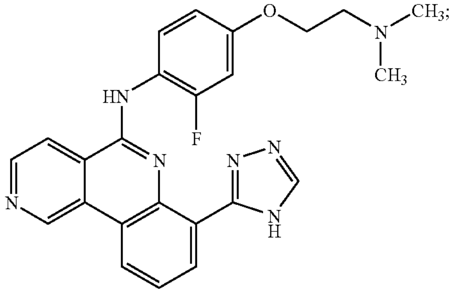

or a pharmaceutically acceptable salt thereof.

E13. A compound of Formula L:

(L)

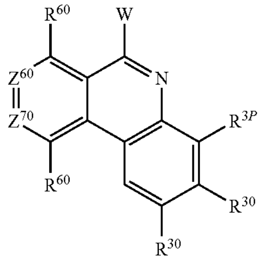

or a pharmaceutically acceptable salt thereof;

wherein:

$Z^{60}$ and $Z^{70}$ are independently N or $CR^{60}$, provided at least one of them is N;

each $R^{30}$ and each $R^{60}$ is independently H or an optionally substituted C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C12 heteroaryl, C7-C12 arylalkyl, or C6-C12 heteroarylalkyl group, or each $R^{30}$ and each $R^{60}$ can be halo, OR, $NR_2$, NROR, $NRNR_2$, SR, SOR, $SO_2R$, $SO_2NR_2$, $NRSO_2R$, $NRCONR_2$, $NRCSNR_2$, $NRC(=NR)NR_2$, NRCOOR, NRCOR, CN, COOR, $CONR_2$, OOCR, COR, or $NO_2$, wherein each R is independently H or C1-C8 alkyl, C2-C8 heteroalkyl, C2-C8 alkenyl, C2-C8 heteroalkenyl, C2-C8 alkynyl, C2-C8 heteroalkynyl, C1-C8 acyl, C2-C8 heteroacyl, C6-C10 aryl, C5-C10 heteroaryl, C7-C12 arylalkyl, or C6-C12 heteroarylalkyl, and wherein two R on the same atom or on adjacent atoms can be linked to form a 3-8 membered ring, optionally containing one or more N, O or S;

and each R group, and each ring formed by linking two R groups together, is optionally substituted with one or more substituents selected from halo, =O, =N—CN, =N—OR', =NR', OR', $NR'_2$, SR', $SO_2R'$, $SO_2NR'_2$, $NR'SO_2R'$, $NR'CONR'_2$, $NR'CSNR'_2$, $NR'C(=NR')NR'_2$, NR'COOR', NR'COR', CN, COOR', $CONR'_2$, OOCR', COR', and $NO_2$, wherein each R' is independently H, C1-C6 alkyl, C2-C6 heteroalkyl, C1-C6 acyl, C2-C6 heteroacyl, C6-C10 aryl, C5-C10 heteroaryl, C7-12 arylalkyl, or C6-12 heteroarylalkyl, each of which is optionally substituted with one or more groups selected from halo, C1-C4 alkyl, C1-C4 heteroalkyl, C1-C6 acyl, C1-C6 heteroacyl, hydroxy, amino, and =O;

and wherein two R' can be linked to form a 3-7 membered ring optionally containing up to three heteroatoms selected from N, O and S, each $R^{3P}$ represents a polar substituent; and each W represents an optionally substituted aryl, an optionally substituted heteroaryl, or an optionally substituted $C_{3-8}$ cycloalkyl ring.

E14. The compound of embodiment E13, which is a compound of Formula L-A or Formula L-B:

(L-A)

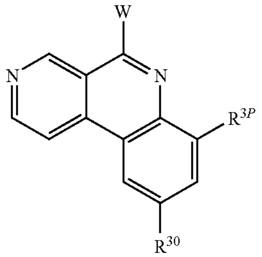

(L-B)

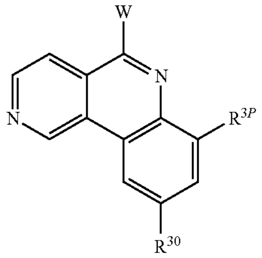

or a pharmaceutically acceptable salt thereof.

E15. The compound of embodiment E13 or E14, wherein $R^{3P}$ is an optionally substituted imidazole or triazole ring.

E16. A pharmaceutical composition comprising a compound of any one of embodiments E1 to E12 and a pharmaceutically acceptable excipient.

E17. A pharmaceutical composition comprising a compound of embodiment E13, E14 or E15 and a pharmaceutically acceptable excipient.

E18. A method for inhibiting cell proliferation, which comprises contacting cells with a compound or composition according to any one of embodiments E1 to E17, in an amount effective to inhibit proliferation of the cells.

E19. The method of embodiment E18, wherein the cells are in a cancer cell line.

E20. The method of embodiment E19, wherein the cancer cell line is a breast cancer, prostate cancer, pancreatic cancer, lung cancer, hemopoietic cancer, colorectal cancer, skin cancer, ovary cancer cell line.

E21. The method of embodiment E18 or E19, wherein the cells are in a tumor in a subject.

E22. The method of any one of embodiments E18 to E21, wherein contacting cells with a compound having a structure of any one of embodiments E1 to E17 induces cell apoptosis.

E23. A method for treating a condition related to aberrant cell proliferation, which comprises administering a compound or composition according to any one of embodiments E1 to E17 to a subject in need thereof in an amount effective to treat the cell proliferative condition.

E24. The method of embodiment E23, wherein the cell proliferative condition is a tumor-associated cancer.

E25. The method of embodiment E24, wherein the cancer is of the colorectum, breast, lung, liver, pancreas, lymph node, colon, prostate, brain, head and neck, skin, liver, kidney, blood and heart.

E26. The method of embodiment E23, wherein the cell proliferative condition is a non-tumor cancer.

E27. The method of embodiment E26, wherein the non-tumor cancer is a hematopoietic cancer.

E28. The method of embodiment E27, wherein the hematopoietic cancer is acute myelogenous leukemia.

E29. The method of embodiment E28, wherein the leukemia is refractory AML or wherein the AML is associated with a mutated Flt3.

E30. A method for treating pain or inflammation in a subject, which comprises administering a compound or composition according to any one of embodiments E1 to E17 to a subject in need thereof in an amount effective to treat the pain or the inflammation.

What is claimed:

1. A compound of Formula IA:

(IA)

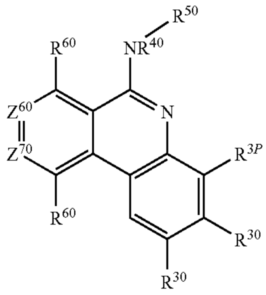

wherein:

$Z^{60}$ and $Z^{70}$ are independently N or $CR^{60}$, provided at least one of them is N;

$R^{30}$ and each $R^{60}$ is independently H or an optionally substituted C1-C8 alkyl or C2-C8 heteroalkyl, each $R^{40}$ is H or optionally substituted member selected from the group consisting of $C_1$-$C_6$ alkyl, C2-C6 heteroalkyl, and C1-C6 acyl;

each $R^{50}$ is independently an optionally substituted member selected from the group consisting of $C_{1-10}$ alkyl, $C_{2-10}$ alkenyl, $C_{2-10}$ heteroalkyl, $C_{3-8}$ carbocyclic ring, and $C_{3-8}$ heterocyclic ring optionally fused to an additional optionally substituted carbocyclic or heterocyclic ring;

or $R^{50}$ can be a $C_{1-10}$ alkyl, $C_{2-10}$ alkenyl, or $C_{2-10}$ heteroalkyl substituted with an optionally substituted $C_{3-8}$ carbocyclic ring or $C_{3-8}$ heterocyclic ring;

in each —$NR^{40}R^{50}$, $R^{40}$ and $R^{50}$ together with N may form an optionally substituted 3-8 membered ring, which may optionally contain an additional heteroatom selected from N, O and S as a ring member; and each $R^{3P}$ represents a polar substituent selected from the group consisting of tetrazole, triazole, imidazole, oxadiazole, oxothiadiazole, thiazole, aminothiazole, and hydroxythiazole;

or a pharmaceutically acceptable salt thereof.

2. The compound of claim 1, wherein $Z^{70}$ is N and $Z^{60}$ is CH.

3. The compound of claim 1, wherein each $R^{60}$ and $R^{40}$ is H.

4. The compound of claim 1, wherein $R^{3P}$ is an optionally substituted imidazole or triazole ring.

5. The compound of claim 1, wherein $R^{50}$ is unsubstituted phenyl or phenyl substituted with 1-3 substituents selected from halo, cyano, $CF_3$, —$OCF_3$, $COOR^{40}$, and $SO_2NR^{40}R^{50}$, and one or more of these substituents can be an optionally substituted group selected from C1-C6 alkyl, C1-C6 alkoxy, C2-C6 alkenyl, and C2-C6 alkynyl.

6. The compound of claim 1, which is a compound of Formula IC:

IC

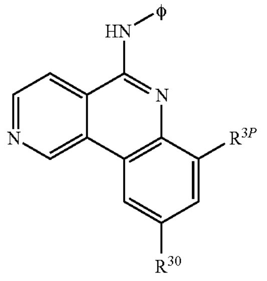

or a pharmaceutically acceptable salt thereof, wherein $R^{30}$ is as defined for claim 1, and $R^{3P}$ is an optionally substituted imidazole or triazole ring;

and each Φ independently represents an optionally substituted phenyl.

7. The compound of claim 6, wherein Φ is unsubstituted phenyl or phenyl substituted with 1-3 substituents selected from halo, cyano, $CF_3$, —$OCF_3$, $COOR^{40}$, and $SO_2NR^{40}R^{50}$, and one or more of these substituents can be an optionally substituted group selected from C1-C6 alkyl, C1-C6 alkoxy, C2-C6 alkenyl, and C2-C6 alkynyl.

8. The compound of claim 1, wherein $R^{50}$ is an optionally substituted $C_{3-8}$ carbocyclic or $C_{3-8}$ heterocyclic ring, each of which may be optionally fused to an additional optionally substituted carbocyclic or heterocyclic ring.

9. The compound of claim 8, wherein said optionally substituted $C_{3-8}$ carbocyclic or $C_{3-8}$ heterocyclic ring is an optionally substituted aromatic or heteroaromatic ring.

10. A compound selected from the group consisting of:

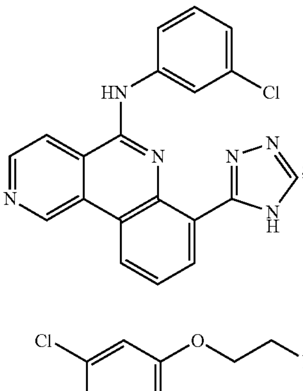

;

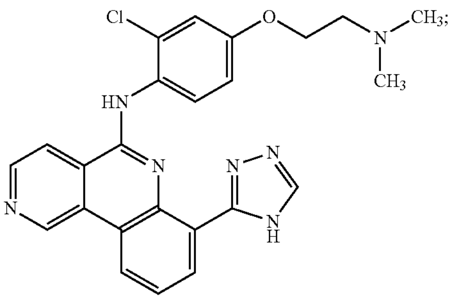

;

-continued
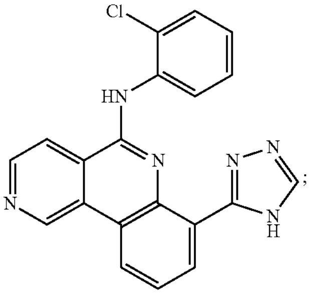
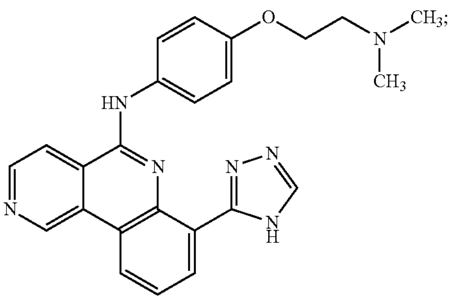
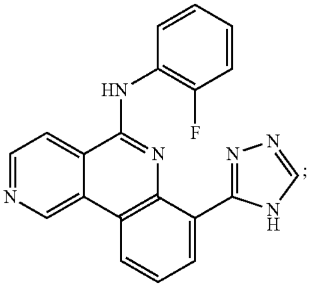
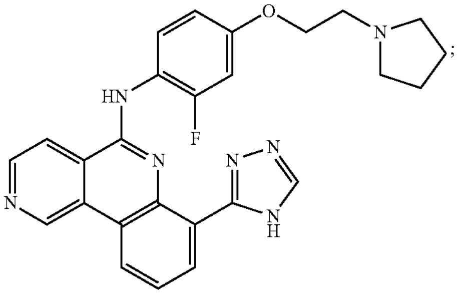
-continued
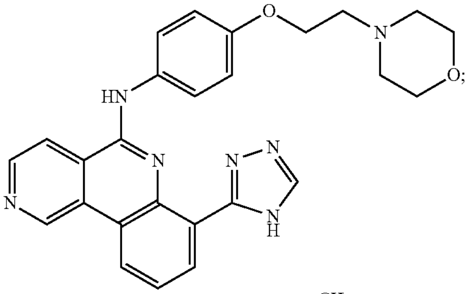
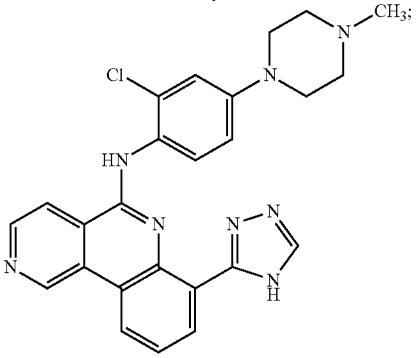
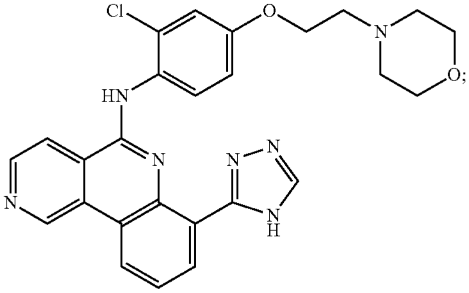
or
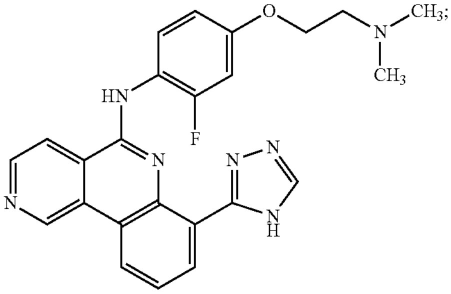
or a pharmaceutically acceptable salt thereof.
11. A pharmaceutical composition comprising a compound of claim 1 and a pharmaceutically acceptable excipient.
* * * * *

```
                          SEQUENCE LISTING


<160> NUMBER OF SEQ ID NOS: 6

<210> SEQ ID NO 1
<211> LENGTH: 391
<212> TYPE: PRT
<213> ORGANISM: Homo sapiens
<220> FEATURE:
<221> NAME/KEY: misc_feature
<222> LOCATION: (1)...(391)
<223> OTHER INFORMATION: casein kinase II alpha 1 subunit isoform a

<400> SEQUENCE: 1

Met Ser Gly Pro Val Pro Ser Arg Ala Arg Val Tyr Thr Asp Val Asn
 1               5                  10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175

Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205
```

```
Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
    290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Ala Asn Pro Leu Gly Met Pro Val Pro
    370                 375                 380

Ala Ala Ala Gly Ala Gln Gln
385                 390
```

<210> SEQ ID NO 2
<211> LENGTH: 391
<212> TYPE: PRT
<213> ORGANISM: Homo sapiens
<220> FEATURE:
<221> NAME/KEY: misc_feature
<222> LOCATION: (1)...(391)
<223> OTHER INFORMATION: casein kinase II alpha 1 subunit isoform a

<400> SEQUENCE: 2

```
Met Ser Gly Pro Val Pro Ser Arg Ala Arg Val Tyr Thr Asp Val Asn
 1               5                  10                  15

Thr His Arg Pro Arg Glu Tyr Trp Asp Tyr Glu Ser His Val Val Glu
            20                  25                  30

Trp Gly Asn Gln Asp Asp Tyr Gln Leu Val Arg Lys Leu Gly Arg Gly
        35                  40                  45

Lys Tyr Ser Glu Val Phe Glu Ala Ile Asn Ile Thr Asn Asn Glu Lys
    50                  55                  60

Val Val Val Lys Ile Leu Lys Pro Val Lys Lys Lys Lys Ile Lys Arg
65                  70                  75                  80

Glu Ile Lys Ile Leu Glu Asn Leu Arg Gly Gly Pro Asn Ile Ile Thr
                85                  90                  95

Leu Ala Asp Ile Val Lys Asp Pro Val Ser Arg Thr Pro Ala Leu Val
            100                 105                 110

Phe Glu His Val Asn Asn Thr Asp Phe Lys Gln Leu Tyr Gln Thr Leu
        115                 120                 125

Thr Asp Tyr Asp Ile Arg Phe Tyr Met Tyr Glu Ile Leu Lys Ala Leu
    130                 135                 140

Asp Tyr Cys His Ser Met Gly Ile Met His Arg Asp Val Lys Pro His
145                 150                 155                 160

Asn Val Met Ile Asp His Glu His Arg Lys Leu Arg Leu Ile Asp Trp
                165                 170                 175
```

```
Gly Leu Ala Glu Phe Tyr His Pro Gly Gln Glu Tyr Asn Val Arg Val
            180                 185                 190

Ala Ser Arg Tyr Phe Lys Gly Pro Glu Leu Leu Val Asp Tyr Gln Met
        195                 200                 205

Tyr Asp Tyr Ser Leu Asp Met Trp Ser Leu Gly Cys Met Leu Ala Ser
    210                 215                 220

Met Ile Phe Arg Lys Glu Pro Phe Phe His Gly His Asp Asn Tyr Asp
225                 230                 235                 240

Gln Leu Val Arg Ile Ala Lys Val Leu Gly Thr Glu Asp Leu Tyr Asp
                245                 250                 255

Tyr Ile Asp Lys Tyr Asn Ile Glu Leu Asp Pro Arg Phe Asn Asp Ile
            260                 265                 270

Leu Gly Arg His Ser Arg Lys Arg Trp Glu Arg Phe Val His Ser Glu
        275                 280                 285

Asn Gln His Leu Val Ser Pro Glu Ala Leu Asp Phe Leu Asp Lys Leu
    290                 295                 300

Leu Arg Tyr Asp His Gln Ser Arg Leu Thr Ala Arg Glu Ala Met Glu
305                 310                 315                 320

His Pro Tyr Phe Tyr Thr Val Val Lys Asp Gln Ala Arg Met Gly Ser
                325                 330                 335

Ser Ser Met Pro Gly Gly Ser Thr Pro Val Ser Ser Ala Asn Met Met
            340                 345                 350

Ser Gly Ile Ser Ser Val Pro Thr Pro Ser Pro Leu Gly Pro Leu Ala
        355                 360                 365

Gly Ser Pro Val Ile Ala Ala Ala Asn Pro Leu Gly Met Pro Val Pro
    370                 375                 380

Ala Ala Ala Gly Ala Gln Gln
385                 390


<210> SEQ ID NO 3
<211> LENGTH: 255
<212> TYPE: PRT
<213> ORGANISM: Homo sapiens
<220> FEATURE:
<221> NAME/KEY: misc_feature
<222> LOCATION: (1)...(255)
<223> OTHER INFORMATION: casein kinase II alpha 1 subunit isoform b

<400> SEQUENCE: 3

Met Tyr Glu Ile Leu Lys Ala Leu Asp Tyr Cys His Ser Met Gly Ile
 1               5                  10                  15

Met His Arg Asp Val Lys Pro His Asn Val Met Ile Asp His Glu His
            20                  25                  30

Arg Lys Leu Arg Leu Ile Asp Trp Gly Leu Ala Glu Phe Tyr His Pro
        35                  40                  45

Gly Gln Glu Tyr Asn Val Arg Val Ala Ser Arg Tyr Phe Lys Gly Pro
    50                  55                  60

Glu Leu Leu Val Asp Tyr Gln Met Tyr Asp Tyr Ser Leu Asp Met Trp
65                  70                  75                  80

Ser Leu Gly Cys Met Leu Ala Ser Met Ile Phe Arg Lys Glu Pro Phe
                85                  90                  95

Phe His Gly His Asp Asn Tyr Asp Gln Leu Val Arg Ile Ala Lys Val
            100                 105                 110

Leu Gly Thr Glu Asp Leu Tyr Asp Tyr Ile Asp Lys Tyr Asn Ile Glu
        115                 120                 125

Leu Asp Pro Arg Phe Asn Asp Ile Leu Gly Arg His Ser Arg Lys Arg
```

```
    130                 135                 140

Trp Glu Arg Phe Val His Ser Glu Asn Gln His Leu Val Ser Pro Glu
145                 150                 155                 160

Ala Leu Asp Phe Leu Asp Lys Leu Leu Arg Tyr Asp His Gln Ser Arg
                165                 170                 175

Leu Thr Ala Arg Glu Ala Met Glu His Pro Tyr Phe Tyr Thr Val Val
            180                 185                 190

Lys Asp Gln Ala Arg Met Gly Ser Ser Ser Met Pro Gly Gly Ser Thr
        195                 200                 205

Pro Val Ser Ser Ala Asn Met Met Ser Gly Ile Ser Ser Val Pro Thr
    210                 215                 220

Pro Ser Pro Leu Gly Pro Leu Ala Gly Ser Pro Val Ile Ala Ala Ala
225                 230                 235                 240

Asn Pro Leu Gly Met Pro Val Pro Ala Ala Ala Gly Ala Gln Gln
                245                 250                 255


<210> SEQ ID NO 4
<211> LENGTH: 10
<212> TYPE: PRT
<213> ORGANISM: Artificial Sequence
<220> FEATURE:
<223> OTHER INFORMATION: chemically synthesized substrate peptide

<400> SEQUENCE: 4

Arg Arg Arg Asp Asp Asp Ser Asp Asp Asp
 1               5                  10


<210> SEQ ID NO 5
<211> LENGTH: 9
<212> TYPE: PRT
<213> ORGANISM: Artificial Sequence
<220> FEATURE:
<223> OTHER INFORMATION: chemically synthesized substrate peptide

<400> SEQUENCE: 5

Lys Lys Arg Asn Arg Thr Leu Thr Val
 1               5


<210> SEQ ID NO 6
<211> LENGTH: 12
<212> TYPE: PRT
<213> ORGANISM: Artificial Sequence
<220> FEATURE:
<223> OTHER INFORMATION: chemically synthesized peptide

<400> SEQUENCE: 6

Glu Ala Ile Tyr Ala Ala Pro Phe Ala Lys Lys Lys
 1               5                  10
```